US006828314B2

(12) United States Patent
Frank et al.

(10) Patent No.: US 6,828,314 B2
(45) Date of Patent: Dec. 7, 2004

(54) SUBSTITUTED AZEPINO[4,5B]INDOLINE DERIVATIVES

(75) Inventors: Kristine E. Frank, Portage, MI (US); Brad A. Acker, Kalamazoo, MI (US); Michael D. Ennis, Mattawan, MI (US); Jed F. Fisher, Kalamazoo, MI (US); Jian-min Fu, Kalamazoo, MI (US); Eric Jon Jacobsen, Kalamazoo, MI (US); William W. McWhorter, Jr., Parchment, MI (US); Jeanette K. Morris, Kalamazoo, MI (US); Donald Joseph Rogier, Kalamazoo, MI (US)

(73) Assignee: Pfizer, Bridgewater, NJ (US)

( * ) Notice: Subject to any disclaimer, the term of this patent is extended or adjusted under 35 U.S.C. 154(b) by 0 days.

(21) Appl. No.: 10/394,676

(22) Filed: Mar. 20, 2003

(65) Prior Publication Data

US 2003/0225058 A1 Dec. 4, 2003

Related U.S. Application Data

(63) Continuation of application No. 09/957,319, filed on Sep. 20, 2001, now Pat. No. 6,586,421.
(60) Provisional application No. 60/234,376, filed on Sep. 20, 2000, provisional application No. 60/266,047, filed on Feb. 1, 2001, and provisional application No. 60/301,964, filed on Jun. 29, 2001.

(51) Int. Cl.[7] .................... C07D 487/04; A61K 31/407; A61K 31/55
(52) U.S. Cl. ........................ 514/215; 540/580
(58) Field of Search .......................... 514/215; 540/580

(56) References Cited

U.S. PATENT DOCUMENTS

| | | | |
|---|---|---|---|
| 3,525,750 A | 8/1970 | Renner | 260/326.5 |
| 3,553,232 A | 1/1971 | Hester, Jr. | 260/326.5 |
| 3,622,673 A | 11/1971 | Hester, Jr. | 424/274 |
| 3,652,588 A | 3/1972 | Hester, Jr. | 260/326.3 |
| 3,676,558 A | 7/1972 | Hester, Jr. | 424/274 |
| 3,776,922 A | 12/1973 | Epstein et al. | 260/326.5 B |
| 3,839,357 A | 10/1974 | Hester, Jr. | 260/326.5 |
| 6,221,866 B1 | 4/2001 | Brendel et al. | 514/237.8 |
| 6,503,899 B2 | 1/2003 | Fu | 514/215 |
| 2002/0022616 A1 | 2/2002 | Fu | 514/215 |

FOREIGN PATENT DOCUMENTS

| | | | | |
|---|---|---|---|---|
| AU | 636232 | 4/1993 | | C07D/471/10 |
| DE | 3315467 | 11/1983 | | C07D/487/04 |
| EP | 0028381 | 5/1981 | | C07D/487/04 |
| EP | 0377238 | 7/1990 | | C07D/471/16 |
| EP | 0466548 | 6/1991 | | C07D/471/04 |
| FR | 6699 | 2/1969 | | |
| GB | 1062840 | 3/1967 | | C07D/27/56 |
| GB | 1180615 | 2/1970 | | C07D/57/02 |
| GB | 2120662 | 12/1983 | | C07D/487/04 |
| JP | 63-163347 | 7/1988 | | G03C/7/26 |
| WO | WO-00/64899 | 11/2000 | | C07D/471/16 |
| WO | WO-00/77001 | 12/2000 | | C07D/471/16 |
| WO | WO-00/77002 | 12/2000 | | C07D/471/16 |
| WO | WO-00/77010 | 12/2000 | | C07D/513/16 |
| WO | WO-01/0573 A1 | 1/2001 | | C07D/487/04 |
| WO | WO-01/00573 | 1/2001 | | C07C/311/16 |

OTHER PUBLICATIONS

Baxter, G., et al., "5–HT$_2$ receptor subtypes: a family re–united?", *Trends in Pharmacological Reviews*, 16, (1995), pp. 105–110.

BOS, M., et al., "Novel Antagonists of 5HT$_{2C}$ Receptors. Synthesis and Biological Evaluation of Substituted 2–(Indol–1–yl)–1–methylethylamines and 2–(Indeno[1,2–b]pyrrol–1–yl)–1–methylethylamines. Improved Therapeutics for Obsessive Compulsive Disorder", *Journal of Medicinal Chemistry*, 40 (17), (1997), pp. 2762–2769.

Boullin, D. J., *Serotonin in Mental Abnormalities*, John Wiley & Sons, Ltd., (1978), pp. 1–316.

Bromidge, S. M., et al., "Novel and Selective 5–HT$_{2C/2B}$ Receptor Antagonists as Potential Anxiolytic Agents: Synthesis, Quantitative Structure–Activity Relationships, and Molecular Modeling of Substituted 1–(3–Pyridylcarbamoyl)indolines", *Journal of Medicinal Chemistry*, 41(10), (1998), pp. 1598–1612.

Dekeyne, A., et al., "Discriminative stimulus properties of the novel serotonin (5–HT)$_{2C}$ receptor agonist, RO 60–0175: a pharmacological analysis", *Neuropharmacology*, vol. 38, (1999), pp. 415–423.

Geigy, J R., "Azepino [4,5–b] indoles", *CAPLUS* abstract, (1966), 12 pages.

(List continued on next page.)

Primary Examiner—Bruck Kifle
(74) Attorney, Agent, or Firm—Schwegman, Lundberg, Woessner & Kluth, P.A.

(57) ABSTRACT

The invention provides compounds of Formula (I):

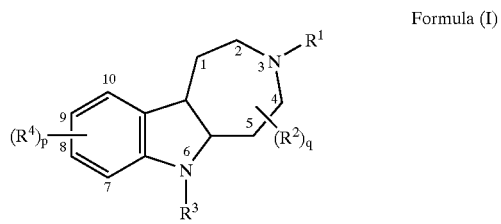

Figure 1:
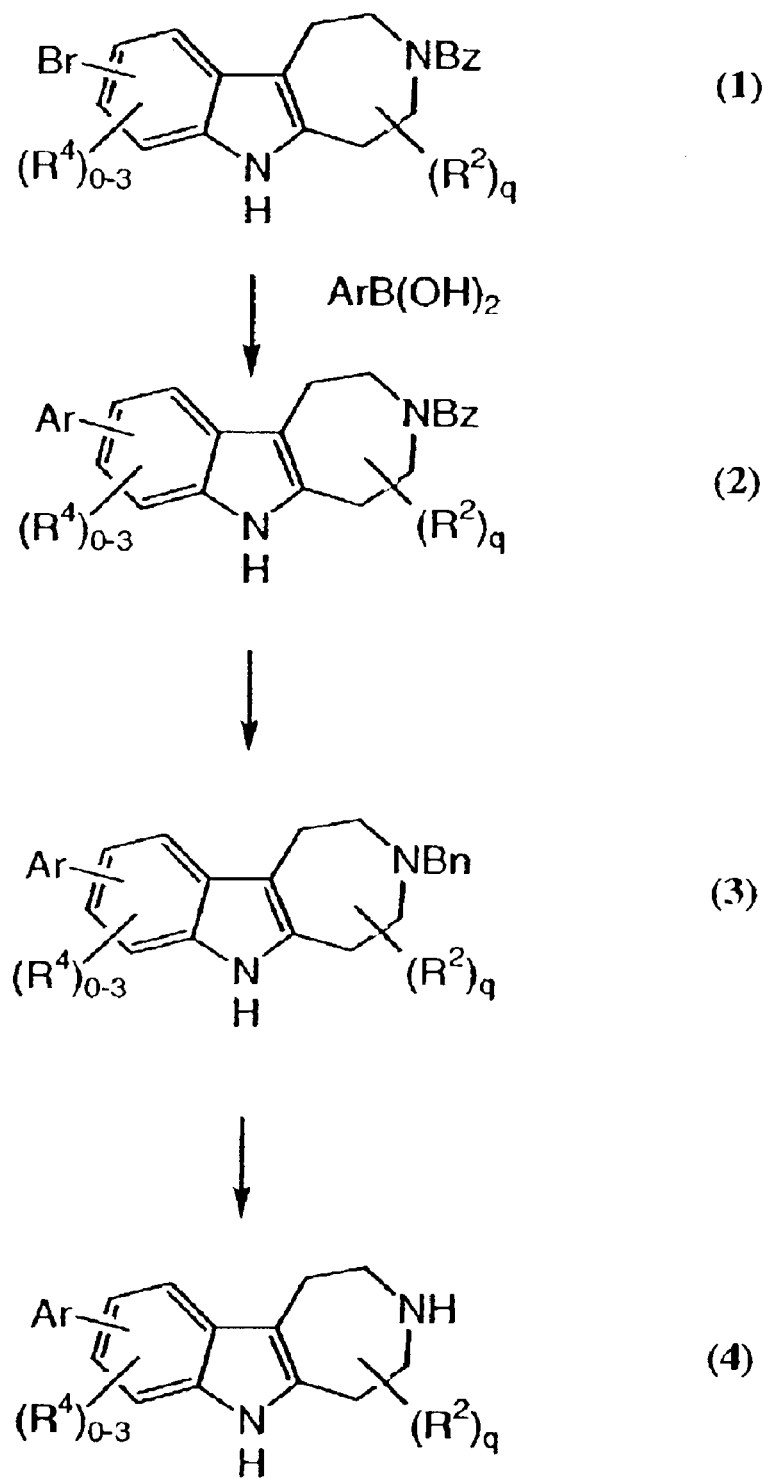

wherein $R^1$–$R^4$, p and q have any of the values described in the specification, as well as pharmaceutical salts thereof, and pharmaceutical compositions containing such compounds or salts. The compounds and salts are 5-HT ligands and are useful for treating diseases, disorders, and/or conditions in a mammal wherein activity of a 5-HT receptor is implicated. The compounds and salts are particularly useful for treating diseases of the central nervous system.

12 Claims, 32 Drawing Sheets

OTHER PUBLICATIONS

Gershon, M. D., et al., "5–Hydroxytryptamine and enteric neurones", *The peripheral actions of 5–hydroxytryptamine*, Chapter 11, Oxford University Press, (1989), pp. 247–273.

Glennon, R. A., "Serotonin Receptors: Clinical Implications", *Neuroscience & Behavioral Reviews*, vol. 14, (1990), pp. 35–47.

Harley–Mason, J., et al., "Hydroxytryptamines. III. Synthesis of an azepindole derivative by molecular rearrangement", *CAPLUS* abstract, (1955), 1 page.

Hester, J. B., et al., "Azepinoindoles. I. Hexahydroazepino(4,5–b) indoles", *J. Med. Chem*, 11, No. 1, (1968), pp. 101–106.

Hoyer, D., et al., "VII. International Union of Pharmacology Classification of Receptors for 5–Hydroxytryptamine (Serotonin)", *Pharmacological Reviews*, 46(2), (1994), pp. 157–203.

Jenck, F., et al., "The role of 5–$HT_{2C}$ receptors in affective disorders", *Expert Opinion on Investigational Drugs*, 7(10), (1998), pp. 1587–1599.

Kelley, J. M., et al., "Comparison of common interatomic distances in serotonin and some hallucinogenic drugs", *Pharmacology*, CAPLUS abstract, 10(1), (1973), 1 page.

Kennett, G. A., "5–HT drugs and eating disorders", *IDrugs*, 1(4), (1998), pp. 456–470.

Martin, J. R., et al., "5–$HT_{2C}$ Receptor Agonists: Pharmacological Characteristics and Therapeutic Poteintial", *The Journal of Pharmacology and Experimental Therapeutics*, 286(2), (1998), pp. 913–924.

Mash, D. C., et al., "Identification of a primary metabolite of ibogaine that targets serotonin transporters and elevates serotonin", *Life Sci.*, 57(3), CAPLUS Abstract, (1995) 1 page.

Robichaud, A. J., et al., "Recent Advances in Selective Serotonin Receptor Modulation", *Annual Reports in Medicinal Chemistry*, vol. 36, (2000), pp. 11–20.

Saxena, P. R., et al., "Cardiovascular Effects of Serotonin Agonists and Antagonists", *Journal of Cardiovascular Pharmacology*, 15(Suppl. 7), (1990), pp. S17–S34.

Saxena, P. R., "Serotonin Receptors: Subtypes, Functional Responses and Therapeutic Relevance", *Pharmac. Ther.*, vol. 66, (1995), pp. 339–368.

Sweetnam, P. M., et al., "Receptor binding profile suggests multiple mechanisms of action are responsible for ibogaine's putative anti–addictive activity", *Psychopharmacology*, vol. 118, (1995), pp. 369–376.

Zagorevskii, V. A., et al., "Synthesis and reactions of 2,2–dimethyl–4–chloromethyl–1,2,3,4–tetrahydro–.gamma.–carboline", *CAPLUS* Abstract, (1980), 1 page.

Artemenko, G. N., "Pharmacological activity spectra of some azepino– and benzoxepinoindole derivatives", *CAPLUS Abstract*, (1972), 1 pg.

Barkov, N. K., et al., "Pharamcological properties of carazedine", *Chemical Abstracts Service, Database accession No. 121:49905, XP002195043*, (1994).

Diker, K., et al., "Practical Syntheses of Hexahydroazepino [4,5–b]– and hexahydroazocino[4,5–b]indoles", *Tetrahedron Letters, 36*, Abstract Only, obtained from Chemical Abstracts, Accession No. 1995:597877, (1995), 1 p.

Kalaus, G., et al., "Synthesis of Vinca Alkaloids and Related Compounds. Part LXXXIX. Some Unexpected Reactions of Compounds Containing the D–seco–aspidospermane Ring System", *Heterocycles 47*, Abstract Only, Chemical Abstracts, Accession No. 1998:187118,(1998),2 p.

Kucherova, N. F., et al., "3,9–dimethyl–1,2,3,4,5,5a,6, 10b–octahydroazepino '4,5–b! indole", *Chemical Abstracts Service, Accession No. 69:59212 XP002195045*, (1968).

Sharkova, N. M., et al., "Indole Derivatives. XXIV. Synthesis of some new polycondensed indole systems", *CAPLUS Abstract*, (1969).

(21)
(22)
(23)
(24)
(25)
(26)

(23)

(31)

(32)

(33)

(32)

(34)

(35)

(31)

(36)

(37)

(31)

(38)

(39)

(31)

(40)

(22)

(43)

(44)

(49)

(51)

(52)

(88)

(95)

(90)

SUBSTITUTED AZEPINO[4,5B]INDOLINE DERIVATIVES

CROSS REFERENCE TO RELATED APPLICATIONS

This application is a continuation of U.S. patent application Ser. No. 09/957,319 filed Sep. 20, 2001, now U.S. Pat. No. 6,586,421 which claims priority from U.S. Provisional Application No. 60/234,376, filed 20 Sep. 2000; U.S. Provisional Application No. 60/266,047, filed 1 Feb. 2001; and U.S. Provisional Application No. 60/301,964, filed 29 Jun. 2001.

BACKGROUND OF THE INVENTION

1. Field of the Invention

The present invention generally relates to a series of compounds, to pharmaceutical compositions containing the compounds, and to use of the compounds and compositions as therapeutic agents. More specifically, compounds of the present invention are octahydroazepinoindole compounds. These compounds are serotonin receptor (5-HT) ligands and are useful for treating diseases, disorders, and conditions wherein modulation of the activity of serotonin receptors (5-HT) is desired (e.g. anxiety, depression or obesity).

2. Brief Description of Related Technology

Serotonin has been implicated in a number of diseases, disorders, and conditions that originate in the central nervous system, including diseases, disorders, and conditions related to, for example, sleeping, eating, perceiving pain, controlling body temperature, controlling blood pressure, depression, anxiety, and schizophrenia. Serotonin also plays an important role in peripheral systems, such as the gastrointestinal system, where it has been found to mediate a variety of contractile, secretory, and electrophysiologic effects.

Because of the broad distribution of serotonin within the body, a heightened interest exists for drugs that affect serotonergic systems. In particular, agonists, partial agonists, and antagonists of serotonergic systems are of interest for the treatment of a wide range of disorders, including anxiety, depression, hypertension, migraine, obesity, compulsive disorders, schizophrenia, autism, neurodegenerative disorders (e.g., Alzheimer's disease, Parkinsonism, and Huntington's chorea), and chemotherapy-induced vomiting.

The major classes of serotonin receptors ($5-HT_{1-7}$) contain fourteen to eighteen separate receptors that have been formally classified. See Glennon, et al., *Neuroscience and Behavioral Reviews*, 1990, 14, 35; and D. Hoyer, et al. *Pharmacol. Rev.* 1994, 46, 157–203.

For example, the $5-HT_2$ family of receptors contains $5-HT_{2A}$, $5-HT_{2B}$, and $5-HT_{2C}$ subtypes, which have been grouped together on the basis of primary structure, secondary messenger system, and operational profile. All three $5-HT_2$ subtypes are G-protein coupled, activate phospholipase C as a principal transduction mechanism, and contain a seven-transmembrane domain structure. There are distinct differences in the distribution of the three $5-HT_2$ subtypes in a mammal. The $5-HT_{2B}$ and $5-HT_{2A}$ receptors are widely distributed in the peripheral nervous system, while the $5-HT_{2C}$ receptor has been found only in the central nervous system, being highly expressed in many regions of the human brain. See G. Baxter, et al. *Trends in Pharmacol. Sci.* 1995, 16, 105–110.

Subtype $5-HT_{2A}$ has been associated with effects including vasoconstriction, platelet aggregation, and bronchoconstriction, while subtype $5-HT_{2C}$ has been associated with diseases that include depression, anxiety, obsessive compulsive disorder, panic disorders, phobias, psychiatric syndromes, and obesity. Very little is known about the pharmocologic role of the $5-HT_{2B}$ receptor. See F. Jenck, et al., *Exp. Opin. Invest. Drugs*, 1998, 7, 1587–1599; M. Bos, et al., *J. Med. Chem.*, 1997, 40, 2762–2769; J. R. Martin, et al., *The Journal of Pharmacology and Experimental Therapeutics*, 1998, 286, 913–924; S. M. Bromidge, et al., *J. Med. Chem.*, 1998, 41, 1598–1612; G. A. Kennett, *Drugs*, 1998, 1, 4, 456–470; and A. Dekeyne, et al., *Neuropharmacology*, 1999, 38, 415–423.

U.S. Pat. Nos. 3,553,232 and 3,622,673 disclose 4-(1,4,5,6-tetrahydroazepine[4,5-b]indole-3(2H)-yl) butyrophenones that are reported to be useful in the treatment of mental or emotional disorders.

N. M. Sharkova et al., *Khim. Geterotsikl. Soedin.*, 1969, 1, 88–90; report certain specific azepino[4,5-b]indoline compounds of the formula

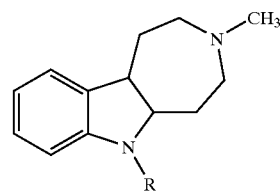

wherein R is hydrogen, nitroso, or amino. No biological activity was reported for the compounds.

G. N. Artemenko et al., *Farmakol. Toksikol*, 1972, 35, 3, 274–280 report certain specific azepino[4,5-b]indoline compounds of the formula

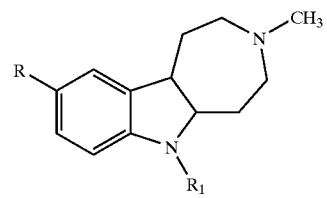

wherein $R_1$ is hydrogen or 3-(N,N-dimethylamino)propyl; and R is hydrogen or methyl. The compounds were reported to have antipressant activity similar to amitriptyline.

U.S. Pat. Nos. 3,652,588, 3,676,558, and 3,839,357 disclose 6-alkyl-1,2,3,4,5,6-hexahydroazepino[4,5-b]indoles and aneroxigenic compounds thereof that are reportedly useful to tranquilize and otherwise sedate mammals or suppress hunger in mammals.

JP Public Patent Disclosure Bulletin Number 63-163347 discloses compounds that are reported to prevent fading of organic coloring substances.

International Patent Application Publication Number WO 01/0573 A1 discloses 9-arylsulfone-1,2,3,4,5,6-hexahydroazepino[4,5-b]indoles that are reported to be useful for treating depression, obesity, and other CNS disorders.

Despite the teachings in the above-cited publications, there remains a need for pharmaceutical agents that are useful in treating a variety of diseases, disorders, and conditions that are associated with serotonin (5-HT) receptors.

SUMMARY OF THE INVENTION

Generally, the present invention is directed to methods and compositions useful in treating a disease, disorder, and/or condition in a mammal wherein a 5-HT receptor is implicated, and modulation of a 5-HT function is desired, by using a novel compound disclosed herein.

In accordance with the present invention, novel compounds which demonstrate useful biological activity, and particularly activity as 5-HT receptor ligands, are provided. More specifically, the invention provides a compound of Formula (I):

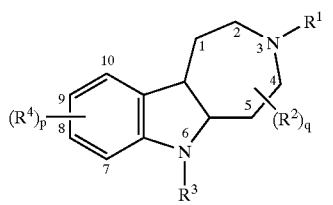

wherein:
R$^1$ is selected from the group consisting of hydrogen, C$_{1-8}$alkyl, and C$_{1-8}$hydrocarbylene Ar;
each R$^2$, independently, is selected from the group consisting of C$_{1-8}$alkyl, and OH;
R$^3$ is hydrogen, C$_{1-8}$alkyl, Ar, Het, R$^7$C(=O)—, R$^7$OC(=O)—, R$^5$R$^6$NC(=O)—, R$^7$C(=S)—, R$^7$SC(=O)—, R$^5$R$^6$NC(=S)—, R$^7$SO$_2$—, R$^5$R$^6$NSO$_2$—, R$^7$S(=O)—, R$^5$R$^6$NS(=O)—, R$^c$C$_{1-8}$hydrocarbylene-, or R$^c_{1-8}$hydrocarbyleneC(=O)—;
each R$^4$, independently, is selected from the group consisting of Ar, C$_{1-8}$alkyl, ArO—, C$_{1-8}$alkoxy, Het, halo, OH, CN, NO$_2$, CF$_3$, CF$_3$O, NR$^a$R$^b$, N=CR$^a$R$^b$, R$^7$S, C$_{1-8}$hydrocarbyleneAr, and C$_{1-8}$hydrocarbyleneOR$^a$;
each R$^5$ and R$^6$ is independently hydrogen, C$_{1-8}$alkyl, C$_{2-8}$alkenyl, C$_{2-8}$alkynyl, haloC$_{1-8}$alkyl, C$_{3-8}$cycloalkenyl, Ar, or —C$_{1-8}$hydrocarbyleneAr; or R$^5$ and R$^6$ together with the nitrogen to which they are attached form a pyrrolidino, piperidino, morpholino, or thiomorpholino ring;
each R$^7$ is independently hydrogen, C$_{1-8}$alkyl, C$_{2-8}$alkenyl, C$_{2-8}$alkynyl, haloC$_{1-8}$alkyl, C$_{3-8}$cycloalkenyl, Ar, or —C$_{1-8}$hydrocarbyleneAr;
R$^a$ and R$^b$, independently, are selected from the group consisting of hydrogen, C$_{1-8}$alkyl, Ar, C$_{1-3}$hydrocarbyleneAr, SO$_2$Ar, SO$_2$C$_{1-4}$ alkyl, (C$_{3-8}$cycloalkyl)C$_{1-8}$alkyl, and Het;
R$^c$ is Ar, Het, R$^7$CO$_2$—, R$^7$C(=O)—, R$^7$OC(=O)—, R$^7$O—, R$^7$C$_{1-8}$alkyleneO—, R$^7$S—, R$^7$C(=S)—, R$^7$S(=O)—, R$^7$S(=O)$_2$—, R$^7$SC(—O)—, R$^7$C(=O)N(R$^7$)—, R$^7$C(=S)N(R$^7$)—, R$^5$R$^6$N—, R$^5$R$^6$NC(=O)—, R$^5$R$^6$NC(=S)—, R$^5$R$^6$NS(=O)—, R$^5$R$^6$NSO$_2$—, R$^7$S(=O)N(R$^7$)—, R$^7$SO$_2$N(R$^7$)—, or R$^7$N(R$^7$)C(=O) N(R$^7$)—;
each Ar is independently aryl or heteroaryl;
p is 0, 1, 2, 3, or 4; and
q is 0, 1, 2, 3, 4, 5, 6, 7, 8, 9, or 10;
wherein any Ar of R$^1$, R$^3$–R$^7$, R$^a$, R$^b$ and R$^c$ is optionally substituted with one or more (e.g. 1, 2, 3, 4, or 5) substituents independently selected from halo, CN, NO$_2$, OR$^e$, methylenedioxy, ethylenedioxy, CF$_3$, OCF$_3$, SR$^e$, SO$_2$R$^e$, NR$^f$R$^g$, CONR$^f$R$^g$, COR$^e$, R$^e$, and C$_{1-8}$hydrocarbyleneR$^d$;
each R$^d$ is independently hydroxy, C$_{1-8}$alkoxy, cyano, SR$^h$, or C(=O)R$^h$;
each R$^e$ is independently selected from the group consisting of hydrogen, C$_{1-8}$alkyl, Ar, C$_{1-3}$hydrocarbyleneAr, SO$_2$Ar, SO$_2$C$_{1-4}$ alkyl, (C$_{3-8}$cycloalkyl)C$_{1-8}$alkyl, and Het; wherein any Ar of R$^e$ is optionally substituted with one or more (e.g. 1, 2, 3, 4, or 5) substituents independently selected from halo, CN, NO$_2$, OR$^d$, methylenedioxy, ethylenedioxy, CF$_3$, OCF$_3$, SR$^f$, SO$_2$R$^f$, NR$^f$R$^g$, CONR$^f$R$^g$, COR$^f$, R$^f$, and C$_{1-8}$hydrocarbyleneR$^d$;
each R$^f$ and R$^g$, is independently selected from the group consisting of hydrogen, C$_{1-8}$alkyl, Ar, C$_{1-3}$hydrocarbyleneAr, SO$_2$Ar, SO$_2$C$_{1-4}$ alkyl, (C$_{3-8}$cycloalkyl)C$_{1-8}$alkyl, and Het; and
each R$^h$ is independently hydrogen, C$_{1-8}$alkyl, C$_{2-8}$alkenyl, C$_{2-8}$alkynyl, haloC$_{1-8}$alkyl, C$_{3-8}$cycloalkenyl, phenyl, or —C$_{1-8}$hydrocarbylene (phenyl);

or a pharmaceutically acceptable salt thereof.

Preferably for a compound of Formula (I), when
(a) R$^1$ is methyl; and
(b) R$^3$ is hydrogen or —(CH$_2$)$_3$NR$^5$R$^6$, wherein R$^5$ and R$^6$, are each methyl;
then p and q are not each 0.

More preferably, for a compound of Formula (I), when
(a) R$^1$ is methyl; and
(b) R$^3$ is hydrogen or —(CH$_2$)$_3$NR$^5$R$^6$, wherein R$^5$ and R$^6$, are each methyl;
then either
(i) p is not 0 and at least one R$^4$ is Ar, ArO—, C$_{1-8}$alkoxy, Het, halo, OH, CN, NO$_2$, CF$_3$, CF$_3$O, NR$^a$R$^b$, N=CR$^a$R$^b$, R$^7$S, C$_{1-8}$hydrocarbyleneAr, and C$_{1-8}$hydrocarbyleneOR$^a$; or
(ii) q is not 0 and at least one R$^2$ is OH.

Even more preferably for a compound of Formula (I), when
(a) R$^1$ is hydrogen or C$_{1-8}$alkyl; and
(b) R$^3$ is hydrogen, C$_{1-8}$alkyl, or C$_{1-8}$hydrocarbyleneNR$^5$R$^6$, wherein R$^5$ and R$^6$, are each independently C$_{1-8}$alkyl;
then either
(i) p is not 0 and at least one R$^4$ is Ar, ArO—, C$_{1-8}$alkoxy, Het, halo, OH, CN, NO$_2$, CF$_3$, CF$_3$O, NR$^a$R$^b$, N=CR$^a$R$^b$, R$^7$S, C$_{1-8}$hydrocarbyleneAr, and C$_{1-8}$hydrocarbyleneOR$^a$; or
(ii) q is not 0 and at least one R$^2$ is OH.

Another embodiment of the present invention provides a pharmaceutical composition comprising a compound of Formula (I), or a pharmaceutically acceptable salt thereof, and a pharmaceutically acceptable carrier.

Still another embodiment of the present invention provides a method of treating a disease, disorder, and/or condition in a mammal (e.g., animal or human), wherein a 5-HT receptor is implicated and modulation of a 5-HT function is desired. The method comprises administering a therapeutically effective amount of a compound of Formula (I), or a pharmaceutically acceptable salt thereof, to the mammal.

Yet another embodiment of the present invention comprises a method of modulating 5-HT receptor function with an effective amount of a compound of Formula (I), or a pharmaceutically acceptable salt thereof.

A further embodiment of the present invention provides a method of treating or preventing diseases, disorders, and/or conditions of the central nervous system. The method comprises administering a therapeutically effective amount of a compound of Formula (I), or a pharmaceutically acceptable salt thereof, to the mammal.

Specific diseases, disorders, and/or conditions for which compounds of Formula (I) may have activity include, but are not limited to, obesity, depression, epilepsy, anxiety, Alzheimers disease, withdrawal from drug abuse, schizophrenia, schizophreniform disorder, schizoaffective disorder, delusional disorder, a stress related disease (e.g., general anxiety disorder), panic disorder, a phobia, obsessive compulsive disorder, post-traumatic-stress syndrome, immune system depression, a stress induced problem with the urinary, gastrointestinal or cardiovascular system (e.g., stress incontinence), neurodegenerative disorders, autism, chemotherapy-induced vomiting, hypertension, migraine headaches, cluster headaches, sexual dysfunction in a mammal (e.g., a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition, e.g., dementia, mental retardation or delirium), bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder (e.g., Huntington's disease or Tardive Dyskinesia), oppositional defiant disorder, peripheral neuropathy, post-traumatic stress disorder, premenstrual dysphoric disorder, a psychotic disorder (brief and long duration disorders and psychotic disorder due to medical condition), mood disorder (major depressive or bipolar disorder with psychotic features) seasonal affective disorder, a sleep disorder, a specific developmental disorder, agitation disorder, selective serotonin reuptake inhibition (SSRI) "poop out" syndrome or a Tic disorder (e.g., Tourette's syndrome).

Yet another embodiment of the present invention comprises the use of a compound of Formula (I), or a pharmaceutically acceptable salt thereof, in the preparation of a medicament for treating or preventing diseases, disorders, and conditions of the central nervous system. The activity of 5-HT receptors is implicated in the above diseases of the central nervous system.

The invention also provides synthetic intermediates and processes disclosed herein, which are useful for preparing compounds of the invention.

Compounds of formula (I) are 5-HT ligands. Thus, radiolabeled compounds of formula (I) are useful as imaging agents for medical therapy and diagnosis. Such radiolabeled compounds are also useful as pharmacological tools for studying 5-HT function and activity. Accordingly, the invention also provides a radiolabeled compound of formula (I), or a salt thereof.

Compounds of formula I can be labeled using techniques which are well known in the art. For example, a radioisotope can be incorporated into the compound or appended to the compound of formula I using techniques well known in the art. For example, see Arthur Murry III, D. Lloyd Williams; *Organic Synthesis with Isotopes*, vol. I and II, Interscience Publishers Inc., N.Y. (1958) and Melvin Calvin et al. *Isotopic Carbon* John Wiley and Sons Inc., N.Y. (1949). Any radioisotope capable of being detected can be employed as a label. For example, suitable radioisotopes include: carbon-11, fluorine-18, fluorine-19, iodine-123 and iodine-125. Preferably, a compound of formula I may be labeled by appending one or more radioisotopes of a halogen (e.g. iodine-123) to an aromatic ring, or by alkylating a nitrogen of a compound of formula (I) with a group comprising a phenyl group bearing a radioisotope.

The invention also provides a radiolabeled compound of formula (I) for use in medical diagnosis or therapy, as well as the use of a radiolabeled compound of formula (I) to prepare a medicamant useful for medical diagnosis or therapy.

Further aspects and embodiments of the invention may become apparent to those skilled in the art from a review of the following detailed description, taken in conjunction with the examples and the appended claims. While the invention is susceptible of embodiments in various forms, described hereafter are specific embodiments of the invention with the understanding that the present disclosure is intended as illustrative, and is not intended to limit the invention to the specific embodiments described herein.

BRIEF DESCRIPTION OF THE DRAWING FIGURES

FIGS. 1–32 depict reaction schemes for the preparation of compounds of the present invention.

DETAILED DESCRIPTION OF THE PREFERRED EMBODIMENTS

In describing the preferred embodiments, certain terminology has been utilized for the sake of clarity. Such terminology is intended to encompass the recited embodiments as well as all technical equivalents which operate in a similar manner for a similar purpose to achieve a similar result.

The following definitions are used, unless otherwise described:

As used herein, the term "alkyl" includes straight chained and branched hydrocarbon groups containing the indicated number of carbon atoms, typically methyl, ethyl, and straight chain and branched propyl and butyl groups. The term "alkyl" also encompasses cycloalkyl, i.e., a cyclic $C_3$–$C_8$ hydrocarbon group, such as cyclopropyl, cyclobutyl, cyclopentyl, and cyclohexyl. Reference to an individual group or moiety, such as "propyl," embraces only the straight chain group or moiety. A branched chain isomer, such as "isopropyl," is specifically referred to.

The term "alkoxy" is defined as —OR, wherein R is alkyl.

The term "halo" is defined herein to include fluoro, chloro, bromo, or iodo. Similarly, the term "halogen" is defined herein to include fluorine, chlorine, bromine, and iodine.

The term "haloalkyl" is defined herein as an alkyl group substituted with one or more halo substituents, either fluoro, chloro, bromo, iodo, or combinations thereof. Similarly, "halocycloalkyl" is defined as a cycloalkyl group having one or more halo substituents.

The term "aryl," alone or in combination, is defined herein as a monocyclic or bicyclic aromatic group (e.g., phenyl or naphthyl) that can be unsubstituted or substituted, for example, with one or more, and in particular one to three of the following substituents selected from the group consisting of halo, CN, $NO_2$, $CF_3$, $N_3$, $C_{1-6}$alkyl, OH, $NR^aR^b$, $OC_{1-6}$ alkyl, $OR^a$, $C(=O)NR^aR^b$, $C(=S)NR^aR^b$, tetrazoyl, triazoyl, amidinyl, guanidinyl, thioguanidinyl, cyanoguanadinyl, and aryl. Generally, "aryl" denotes a phenyl group, or an ortho-fused bicyclic carbocyclic group having nine to ten ring atoms in which at least one ring is aromatic (e.g. naphthyl or tetrahydronaphthyl). The term "aryl" also is abbreviated in the various chemical structures as "Ar."

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include, but are not limited to, 2H-pyrrolyl, 3H-indolyl, 4H-quinolizinyl, 4nH-carbazolyl, acridinyl, benzo[b]thienyl, benzothiazolyl, β-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group consisting of non-peroxide oxygen, sulfur, and N(Z) wherein Z is absent or is H, O, $C_{1-4}$alkyl, phenyl or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The term "Het" generally represents a heterocyclic group, saturated or partially unsaturated, containing at least one heteroatom selected from the group consisting of oxygen, nitrogen, and sulfur, and optionally substituted with $C_{1-6}$alkyl or $C(=O)OR^b$. Typically "Het" is a monocyclic, bicyclic, or tricyclic group containing one or more heteroatoms selected from the group consisting of oxygen, nitrogen, and sulfur. A "Het" group also can contain an oxo group (=O) attached to the ring. Nonlimiting examples of Het groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "alkanoyl" is defined as C(=O)R, wherein R is an alkyl group as previously defined.

The term "alkoxycarbonyl" is defined as C(=O)OR, wherein R is an alkyl group as previously defined.

The term "alkylene" refers to a divalent alkyl group having a substituent. For example, the term "$C_{1-3}$alkylenearyl" refers to an alkyl group containing one to three carbon atoms, and substituted with an aryl group. The term "alkenylene" as used herein is similarly defined, and contains the indicated number of carbon atoms and a carbon-carbon double bond, and includes straight chained and branched alkenylene groups, like ethyenylene. The term "alkynylene" as used herein is similary defined, and contains the indicated number of carbon atoms and a carbon-carbon triple bond, and includes straight chained and branched alkynylene groups, like propynylene.

The term "hydrocarbylene" refers to alkylene, alkenylene, and alkynylene. For example, the term "$C_{1-3}$hydrocarbylenearyl" refers to a hydrocarbylene group containing one to three carbon atoms, and substituted with an aryl group.

The term "amino" is defined as —NH$_2$, and the term "alkylamino" is defined as —NR$_2$, wherein at least one R is alkyl and the second R is alkyl or hydrogen. The term "acylamino" is defined as RC(=O)N, wherein R is alkyl or aryl.

The term "nitro" is defined as —NO$_2$.

The term "trifluoromethyl" is defined as —CF$_3$.

The term "trifluoromethoxy" is defined as —OCF$_3$.

The term "cyano" is defined as —CN.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, "$C_{1-6}$ alkyl" refers to alkyls having one to six carbon atoms, inclusive.

Also in the structures herein, for a bond lacking a substituent, the substituent is methyl, for example

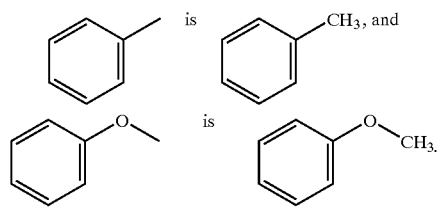

Where no substituent is indicated as attached to a carbon atom on a ring, it is understood that the carbon atom contains the appropriate number of hydrogen atoms.

Abbreviations which are well known to one of ordinary skill in the art also are used, e.g., "Boc" or "-Boc" for tert-butoxycarbamoyl, "Bz" for benzoyl, "Bn" for benzyl, "Ms" for mesyl, and "Ph" for phenyl.

Specific and preferred values listed below for groups or moieties, substituents, and ranges, are for purposes of illustration only and do not exclude other defined values or other values within the defined ranges.

One embodiment of the present invention provides a compound of Formula (I):

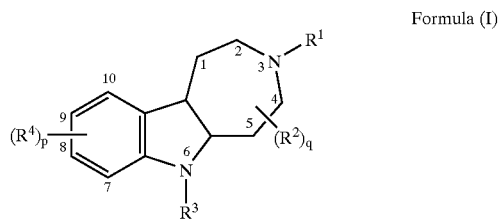

Formula (I)

wherein:
R$^1$ is selected from the group consisting of hydrogen, $C_{1-6}$alkyl, and $C_{1-6}$hydrocarbylenearyl;
R$^2$, independently, is selected from the group consisting of $C_{1-4}$alkyl, and OH;
R$^3$ is selected from the group consisting of hydrogen, alkyl, aryl, heteroaryl, C(=O)R$^a$, C(=O)OR$^a$, C(=O)NR$^a$R$^b$, C(=O)SR$^a$, C(=S)NR$^a$R$^b$, SO$_2$R$^a$, SO$_2$NR$^a$R$^b$, S(=O)R$^a$, S(=O)NR$^a$R$^b$, C(=O)NR$^a$C$_{1-6}$hydrocarbyleneOR$^a$, C(=O)NR$^a$C$_{1-6}$hydrocarbyleneHet, C(=O)C$_{1-6}$hydrocarbylenearyl, C(=O)C$_{1-6}$-hydrocarbyleneheteroaryl, C$_{1-6}$hydrocarbylenearyl, C$_{1-6}$-hydrocarbyleneheteroaryl, $C_{1-6}$hydrocarbyleneHet, $C_{1-6}$-hydrocarbyleneC(=O)$C_{1-6}$hydrocarbylenearyl, $C_{1-6}$hydrocarbyleneC(=O)$C_{1-6}$-hydrocarbyleneheteroaryl, $C_{1-6}$hydrocarbyleneC(=O)Het, $C_{1-6}$-hydrocarbyleneC(=O)NR$^a$R$^b$, $C_{1-6}$hydrocarblyneneOR$^a$, $C_{1-6}$-hydrocarbyleneNR$^a$C(=O)R$^a$, $C_{1-6}$hydrocarbyleneOC$_{1-6}$hydrocarbyleneOR$^a$, $C_{1-6}$hydrocarbyleneNR$^a$R$^b$, $C_{1-6}$hydrocarbyleneC(=O)OR$^a$, $C_{1-6}$-hydrocarbylene-O—$C_{1-6}$hydrocarbyleneC(=O)OR$^a$, $C_{1-6}$hydrocarbyleneSR$^a$, $C_{1-6}$hydrocarbyleneSO$_2$R$^a$, and $C_{1-6}$hydrocarbyleneS(=O)R$^a$; $C_{1-6}$-hydrocarbyleneSO$_2$NR$^a$R$^b$; $C_{1-6}$hydrocarbyleneNSO$_2$R$^a$;

R$^4$ is selected from the group consisting of aryl, aryloxy, alkoxy, heteroaryl, halo, OH, CN, NO$_2$, CF$_3$, CF$_3$O, NR$^a$R$^b$, N=CR$^a$R$^b$, $C_{1-3}$-hydrocarbylene-O-aryl, $C_{1-3}$hydrocarbylene-O-heteroaryl, $C_{1-3}$-hydrocarbyleneOR$^a$,

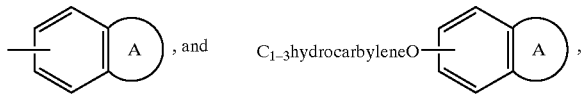

wherein A is a 5- or 6-membered ring, either saturated or partially or fully unsaturated, containing carbon atoms and one to three heteroatoms selected from oxygen, nitrogen, and sulfur;

or R$^3$ and R$^4$ can be taken together to form a 5-, 6-, or 7-membered saturated or partially unsaturated ring;

R$^a$ and R$^b$, independently, are selected from the group consisting of hydrogen, $C_{1-6}$alkyl, $C_{3-8}$cycloalkyl, aryl, heteroaryl, arylC$_{1-3}$alkyl, heteroarylC$_{1-3}$alkyl, $C_{1-3}$hydrocarbylenearyl, $C_{1-3}$hydrocarbyleneheteroaryl, SO$_2$aryl, SO$_2$C$_{1-4}$-alkyl, and Het;

p=0–4; and q=0–8;

or a pharmaceutically acceptable salt thereof;

wherein when R$^3$ and R$^4$ are aryl and/or heteroaryl, each can be substituted with one to five groups selected from OR$^a$, alkyl, aryl, aryloxy, alkoxy, halo, SR$^a$, C(=O)R$^a$, CN, CF$_3$, OCF$_3$, $C_{1-3}$hydrocarbyleneCN, $C_{1-3}$hydrocarbyleneOR$^a$, heteroaryl (optionally substituted with OR$^a$), and NO$_2$, or the two substitutents can be taken together to form a 3-, 4-, or 5-membered component of a 5-, 6-, or 7-membered saturated or partially unsaturated ring. In other words, substituents R$^3$ and R$^4$ can be taken together with the carbon atoms to which they are attached to form a 5-, 6-, or 7-membered saturated or partially unsaturated ring.

Another embodiment of the present invention provides a compound of Formula (I) wherein:

R$^1$ is selected from the group consisting of $C_{1-6}$ alkyl, and $C_{1-6}$hydrocarbylenearyl;

R$^2$, independently, is selected from the group consisting of $C_{1-4}$alkyl, and OH;

R$^3$ is selected from the group consisting of hydrogen, alkyl, aryl, heteroaryl, C(=O)R$^a$, C(=O)OR$^a$, C(=O)NR$^a$R$^b$, C(=O)SR$^a$, C(=S)NR R$^b$, SO$_2$R$^a$, SO$_2$NR$^a$R$^b$, S(=O)R$^a$, S(=O)NR$^a$R$^b$, C(=O)NR$^a$C$_{1-6}$hydrocarbyleneOR$^a$, C(=O)NR$^a$C$_{1-6}$hydrocarbyleneHet, C(=O)C$_{1-6}$hydrocarbylenearyl, C(=O)C$_{1-6}$-hydrocarbyleneheteroaryl, $C_{1-6}$hydrocarbylenearyl, $C_{1-6}$-hydrocarbyleneheteroaryl, $C_{1-6}$hydrocarbyleneHet, $C_{1-6}$hydrocarbyleneC(=O)$C_{1-6}$hydrocarbylenearyl, $C_{1-6}$hydrocarbyleneC(=O)$C_{1-6}$hydrocarbyleneheteroaryl, $C_{1-6}$hydrocarbyleneC(=O)Het, $C_{1-6}$-hydrocarbyleneC(=O)NR$^a$R$^b$, $C_{1-6}$hydrocarbyleneOR$^a$, $C_{1-6}$-hydrocarbyleneNR$^a$C(=O)R$^a$, $C_{1-6}$-hydrocarbyleneOC$_{1-6}$hydrocarbyleneOR$^a$, $C_{1-6}$hydrocarbyleneNR$^a$R$^b$, $C_{1-6}$hydrocarbyleneC(=O)OR$^a$, $C_{1-6}$-hydrocarbylene-O-$C_{1-6}$hydrocarbyleneC(=O)OR$^a$, $C_{1-6}$-hydrocarbyleneSR$^a$, $C_{1-6}$hydrocarbyleneSO$_2$R$^a$, and $C_{1-6}$hydrocarbyleneS(=O)R$^a$; $C_{1-6}$-hydrocarbyleneSO$_2$NR$^a$R$^b$; $C_{1-6}$hydrocarbyleneNSO$_2$R$^a$;

R$^4$ is selected from the group consisting of aryl, aryloxy, alkoxy, heteroaryl, halo, OH, CN, NO$_2$, CF$_3$, CF$_3$O, NR$^a$R$^b$, N=CR$^a$R$^b$, $C_{1-3}$-hydrocarbylene-O-aryl, $C_{1-3}$hydrocarbylene-O-heteroaryl, $C_{1-3}$-hydrocarbyleneOR$^a$,

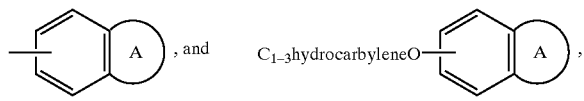

wherein A is a 5- or 6-membered ring, either saturated or partially or fully unsaturated, containing carbon atoms and one to three heteroatoms selected from oxygen, nitrogen, and sulfur;

or R$^3$ and R$^4$ can be taken together to form a 5-, 6-, or 7-membered saturated or partially unsaturated ring;

R$^a$ and R$^b$, independently, are selected from the group consisting of hydrogen, $C_{1-6}$alkyl, $C_{3-8}$cycloalkyl, aryl, heteroaryl, arylC$_{1-3}$alkyl, heteroarylC$_{1-3}$alkyl, $C_{1-3}$hydrocarbylenearyl, $C_{1-3}$hydrocarbyleneheteroaryl, SO$_2$aryl, SO$_2$C$_{1-4}$-alkyl, and Het;

p=0–4; and q=0–8;

or a pharmaceutically acceptable salt thereof;

wherein when R$^3$ and R$^4$ are aryl and/or heteroaryl, each can be substituted with one to five groups selected from OR$^a$, alkyl, aryl, aryloxy, alkoxy, halo, SR$^a$, C(=O)R$^a$, CN, CF$_3$, OCF$_3$, $C_{1-3}$hydrocarbyleneCN, $C_{1-3}$hydrocarbyleneOR$^a$, heteroaryl (optionally substituted with OR$^a$), and NO$_2$, or the two substitutents can be taken together to form a 3-, 4-, or 5-membered component of a 5-, 6-, or 7-membered saturated or partially unsaturated ring. In other words, substituents R$^3$ and R$^4$ can be taken together with the carbon atoms to which they are attached to form a 5-, 6-, or 7-membered saturated or partially unsaturated ring.

Compounds of Formula (I) are serotonin (5-HT) receptor ligands, and as such are useful in treating animals (including humans, farm animals, pets, and other animals) against diseases, disorders, and conditions of the central nervous system.

In one of the preferred embodiments, R$^1$ is hydrogen.

In another one of the preferred embodiments, p is 0, 1, or 2.

In yet another one of the preferred embodiments p is 1, 2, or 3.

In yet another one of the preferred embodiments p is 0.

In yet another one of the preferred embodiments, q is 0–4.

In yet another one of the preferred embodiments q is 2, 3, or 4.

In yet another one of the preferred embodiments q is 1.

In yet another one of the preferred embodiments q is 0.

In yet another one of the preferred embodiments $R^3$ is hydrogen, $C_{1-8}$alkyl, $R^5R^6NC(=O)CH_2-$, $R^7S$ $C_{1-8}$alkylene, or aryloxy(CH$_2$)$_2-$.

In yet another one of the preferred embodiments $R^3$ is hydrogen.

In yet another one of the preferred embodiments $R^3$ is $C_{1-8}$alkyl, $R^5R^6NC(=O)CH_2-$ or aryloxy(CH$_2$)$_2-$.

In yet another one of the preferred embodiments $R^3$ is: 2-(3-methoxyphenoxy)ethyl, 2-(3-nitrophenoxy)ethyl, 2-(3-isopropylphenoxy)ethyl, 2-(4-pyridyloxy)ethyl, 3-phenoxypropyl, 3-(3-chlorophenoxy)propyl, 3-(4-fluorophenoxy)propyl, 2-phenoxyethyl, N-(2,3-dimethylphenyl)amino-carbonylmethyl, N-(3-methylphenyl)aminocarbonylmethyl, N-(2-fluoro-4-methylphenyl)aminocarbonylmethyl, N-mesitylaminocarbonylmethyl, N-(4-methoxyphenyl)aminocarbonylmethyl, N-(phenyl)aminocarbonylmethyl, N-(4-fluorophenyl)aminocarbonylmethyl, N-(3-nitrophenyl)aminocarbonylmethyl, N-(3-methoxyphenyl)aminocarbonylmethyl, N-(4-cyanophenyl)aminocarbonylmethyl, N-(3,5-dimethoxyphenyl)aminocarbonylmethyl, N-(2,4-dimethoxyphenyl)aminocarbonylmethyl, N-(3-chloro-4-fluorophenyl)aminocarbonylmethyl, 2-anilinoethyl, 1H-benzimidazol-2-ylmethyl, isobutoxycarbonylmethyl, carboxymethyl, N,N-dimethylaminocarbonylmethyl, aminocarbonylmethyl, 2-(phenylsulfinyl)ethyl, 2-(phenylsulfonyl)ethyl, 2-hydroxyethyl, 2-(4-chlorophenoxy)ethyl, 2-(4-fluorophenoxy)ethyl, 2-(phenylthio)ethyl, 2-aminoethyl, 2-(anilinocarbonylamino)-ethyl, 2-(benzoylamino)ethyl, 2-(phenylsulfonylamino)ethyl, N-(4-methoxyphenyl)aminocarbonylethyl, N-phenylaminocarbonylmethyl, N-(2-pyridyl)aminocarbonylmethyl, N-(4-methoxyphenyl)aminocarbonylmethyl, N-(2,3-dimethylphenyl)aminocarbonylmethyl, N-(5,6,7,8-tetrahydro-1-naphthalenyl)aminocarbonylmethyl, 3-ethylanilinocarbonylmethyl, 3-isopropylanilinocarbonylmethyl, N-(3-tert-butylphenyl)aminocarbonylmethyl, N-(1,3-benzothiazol-2-yl)aminocarbonylmethyl, N-(4-methyl-1,3-thiazol-2-yl)aminocarbonylmethyl, N-(5-methyl-1,3-thiazol-2-yl)aminocarbonylmethyl, N-(4-tert-butyl-1,3-thiazol-2-yl)aminocarbonylmethyl, N-(4-phenyl-1,3-thiazol-2-yl)aminocarbonylmethyl, 3-phenylpropyl, 2-phenoxyethyl, 2-(4-chlorophenoxy)ethyl, 2-(4-fluorophenoxy)ethyl, 2-(5,7-dibromo-8-quinolinyloxy)ethyl, 2-(8-quinolinyloxy)ethyl, 2-(5-isoquinolinyloxy)ethyl, 2-(5-quinolinyloxy)ethyl, 2-(5,6,7,8-tetrahydro-1-naphthalenyloxy)ethyl, 2-(1,3-benzodioxol-5-yloxy)ethyl, 2-(1H-indol-4-yloxy)ethyl, 2-(5,6,7,8-tetrahydro-2-naphthalenyloxy)ethyl, 2-(7-quinolinyloxy)ethyl, 2-[(5,5-dimethyl-5,6,7,8-tetrahydronaphthalen-1-yl)oxy]ethyl, N-(3-chloro-2-methylphenyl)aminocarbonylmethyl, N-[2-methyl-3-(trifluoromethyl)phenyl]aminocarbonylmethyl, N-(5,6,7,8-tetrahydronaphthalen-1-yl)aminocarbonylmethyl, N-(4-methyl-1,3-thiazol-2-yl)aminocarbonylmethyl, N-(1,3-dihydro-2-benzofuran-4-yl)aminocarbonylmethyl, N-(4-methoxyphenyl)aminocarbonylmethyl, N-(3-pyridyl)aminocarbonylmethyl, N-(4-methyl-1,3-thiazol-2-yl)aminocarbonylmethyl, or 2-(5,6,7,8-tetrahydronaphthalen-1-yloxy)ethyl.

In yet another one of the preferred embodiments $R^4$ is phenyl, optionally substituted at the 2-position of the phenyl.

In yet another one of the preferred embodiments $R^4$ is 2-ethoxyphenyl, 2-($C_{3-8}$cycloalkyloxy)phenyl, or 2-chlorophenyl.

In yet another one of the preferred embodiments $R^4$ is aryl, substituted at the 10-position of formula (I).

In yet another one of the preferred embodiments $R^4$ is: 5-pyrimidinyl, 3,4-dimethoxyphenyl, 3,5-difluorophenyl, 4-n-butyloxyphenyl, 4-trifluoromethoxyphenyl, 3,4-dichlorophenyl, 2-naphthyl, 4-pyridinyl, bromo, benzhydrilideneamino, amino, N-(phenylsulfonyl)amino, phenoxy, 3-(phenoxy)propyl, 3-(2-naphthyloxy)propyl, 3-(1-naphthyloxy)propyl, 3-([1,1'-biphenyl]-4-yloxy)propyl, 3-(3-methoxyphonoxy)propyl, 3-(4-methoxyphenoxy)propyl, 3-(4-chlorophenoxy)propyl, 3-(3-chlorophenoxy)propyl, 3-(2-chlorophenoxy)propyl, 3-(2,4-dichlorophenoxy)propyl, 3-(2,5-dichlorophenoxy)propyl, 3-(4-fluorophenoxy)propyl, 3-(4-methylphenoxy)propyl, 3-(4-cyanophenoxy)propyl, 3-(pyridin-2-yloxy)propyl, 3-(2-bromophenoxy)propyl, 3-(2-iodophenoxy)propyl, 3-(2-ethylphenoxy)propyl, 3-(2-isopropylphenoxy)propyl, 3-(2-cyanophenoxy)propyl, 3-(pyridin-3yloxy)propyl, 3-(3-fluorophenoxy)propyl, 3-(3-bromophenoxy)propyl, 3-(3-iodophenoxy)propyl, 3-(3-isopropylphenoxy)propyl, 3-[3-(trifluoromethyl)phenoxy]propyl, 3-[3-(trifluoromethoxy)phenoxy]propyl, 3-(3-ethylphenoxy)propyl, 3-(3-tert-butylphenoxy)propyl, 3-(pyridin-4yloxy)propyl, 3-(4-methoxyphenoxy)propyl, 3-[4-(benzyloxy)phenoxy]propyl, 3-(4-bromophenoxy)propyl, 3-(4-iodophenoxy)propyl, 3-(4-ethylphenoxy)propyl, 3-(4-tert-butylphenoxy)propyl, 3-[4'-(bromo[1,1'-biphenyl]-4-yl)oxy]propyl, 3-(2,3-difluorophenoxy)propyl, 3-(2,4-dibromophenoxy)propyl, 3-(2,4-difluorophenoxy)propyl, 3-(2-methoxy-4-methylphenoxy)propyl, 3-(4-iodo-2-methylphenoxy)propyl, 3-(2,5-difluorophenoxy)propyl, 3-(2-chloro-5-methylphenoxy)propyl, 3-(2-isopropyl-5-methylphenoxy)propyl, 3-(2,6-difluorophenoxy)propyl, 3-(2,6-dichlorophenoxy)propyl, 3-(2,6-dimethylphenoxy)propyl, 3-(2-fluoro-6-methylphenoxy)propyl, 3-hydroxypropyl, 3-(2,3,6-trimethylphenoxy)propyl, 3-(mesityloxy)propyl, 3-(2,6-dibromo-4-fluorophenoxy)propyl, 3-(4-chloro-3-fluorophenoxy)propyl, 3-(4-chloro-3-methylphenoxy)propyl, 3-(3-chloro4-fluorophenoxy)propyl, 3-(1,3-benzodioxol-5-yloxy)propyl, 3-(3,5-dichlorophenoxy)propyl, 3-(3,5-dimethylphenoxy)propyl, 3-(3,5-dimethoxyphenoxy)propyl, 3-(5,6,7,8-tetrahydro-1-naphthalenyloxy)propyl, 3-[(2,4-dichloro-1-naphthyl)oxy]propyl, 3-[4-methoxy-1-naphthyl)oxy]propyl, 3-[4-chloro-1-naphthyl)oxy]propyl, 3-[1,6-dibromo-2-naphthyl)oxy]propyl, 3-[1-bromo-2-naphthyl)oxy]propyl, 3-(2,3,4,5,6-pentafluorophenoxy)propyl, 3-(5-isoquinolinyloxy)propyl, 2-methyl-4-methoxyphenyl, 2-ethoxyphenyl, phenyl, phenoxy, 4-pyridinyl, 4-methoxyphenyl, 3,5-difluorophenyl, 3-[1,1'-biphenyl]-2-yloxypropyl, chloro, 2,6-difluorophenyl, bromo, 2-methylphenyl, 2-methoxyphenyl, 2-propoxyphenyl, 2-fluorophenyl, 2,4-dichlorophenyl, 3-(2,4-dibromophenoxy)propyl, 3-(5-chloro-8-quinolinyloxy)propyl, fluoro, 2,6-difluorophenyl, 4-methoxy-2-methylphenyl, or 2,4-dichlorophenyl.

In yet another one of the preferred embodiments $R^4$ is 10-(2-ethoxyphenyl).

In still another embodiment, $R^4$ is an optionally substituted bicyclic ring system

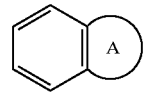

wherein the bicyclic ring can represent, for example, benzoxazole, benzothiazole, benzisoxazole, benzimidazole, quinoline, indole, benzothiophene, or benzofuran.

In still another embodiment, $R^4$ is an optionally substituted bicyclic ring system,

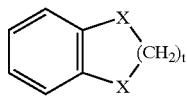

wherein t is an integer 1 or 2, and each X, independently is $C(R^a)_2$, O, S, or $NR^a$. The bicyclic ring comprising the $R^4$ subsituent typically is attached to the rest of the molecule by a phenyl ring carbon atom.

In another embodiment $R^4$ is represented by an optionally substituted bicyclic ring

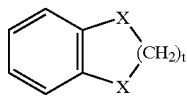

wherein t is 1 or 2, and X, independently, $CH_2$ or O. Especially preferred substituents include:

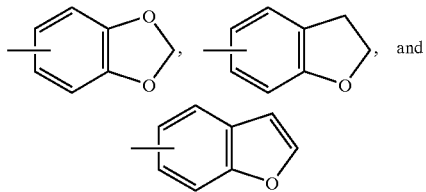

Within this particular group of compounds, nonlimiting examples of substituents for the bicyclic ring include halogen (e.g., chlorine), $C_{1-3}$alkyl (e.g., methyl, ethyl, or isopropyl), $OR^a$, (e.g., methoxy, ethoxy, or hydroxy), $CO_2R^a$, halomethyl or halomethoxy (e.g., trifluoromethyl or trifluoromethyoxy), cyano, nitro, and $N(R^a)_2$.

Another particularly preferred compound of the invention is a compound of formula (I), which is a compound of Formula (II):

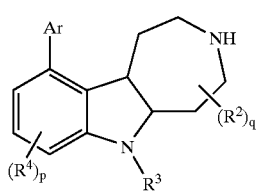

(II)

wherein p is 0, 1, 2, or 3; and $R^2$, $R^3$, $R^4$, Ar, and q are as defined above with respect to Formula (I).

Another particularly preferred compound of the invention is a compound of formula (I), which is a compound of Formula (III):

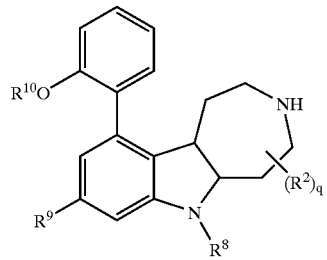

(III)

wherein $R^2$ and q are as defined above with respect to Formula (I); $R^8$ is H or $C_{1-6}$alkyl, $R^9$ is H, $C_{1-6}$alkyl, $C_{1-6}$alkyl S—, or halo, and $R^{10}$ is $C_{1-6}$alkyl or $C_{3-8}$cycloalkyl.

More specific diseases, disorders, and/or conditions for which compounds of Formula (I) may have activity include, but are not limited to, obesity, depression, schizophrenia, schizophreniform disorder, schizoaffective disorder, delusional disorder, a stress related disease (e.g., general anxiety disorder), panic disorder, a phobia, obsessive compulsive disorder, post-traumatic-stress syndrome, immune system depression, a stress induced problem with the urinary, gastrointestinal or cardiovascular system (e.g., stress incontinence), neurodegenerative disorders, autism, chemotherapy-induced vomiting, hypertension, migraine headaches, cluster headaches, sexual dysfunction in a mammal (e.g., a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition, e.g., dementia, mental retardation or delirium), bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder (e.g., Huntington's disease or Tardive Dyskinesia), oppositional defiant disorder, peripheral neuropathy, post-traumatic stress disorder, premenstrual dysphoric disorder, a psychotic disorder (brief and long duration disorders and psychotic disorder due to medical condition), mood disorder (major depressive or bipolar disorder with psychotic features) seasonal affective disorder, a sleep disorder, a specific developmental disorder, agitation disorder, selective serotonin reuptake inhibition (SSRI) "poop out" syndrome or a Tic disorder (e.g., Tourette's syndrome).

Preferred diseases, disorders, and/or conditions for which compounds of Formula (I) have activity include anxiety, depression, schizophrenia, epilepsy, migraine, Alzheimers disease, sleep disorders, obesity, a stress related disease, and withdrawal from drug abuse.

More preferred diseases, disorders, and/or conditions for which compounds of Formula (I) have activity include anxiety, depression, epilepsy, migraine, obesity, a stress related disease, and withdrawal from drug abuse.

FIGS. 1–26 illustrate the preparation of intermediate indole compounds of Formula (IV):

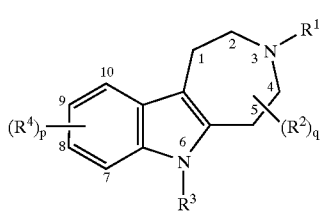

Formula (IV)

that can be used to prepare indoline compounds of the invention.

The compounds of the invention can be prepared as illustrated in FIGS. 27–32, using synthetic methods similar to those described herein, or using synthetic methods known in the art.

Intermediate (7, 8, 9, or 10-) arylazepinoindoles (Formula (IV) wherein $R^4$=Ar), can be prepared by the reactions depicted in FIG. 1. As shown in FIG. 1, a (7, 8, 9, or 10-) bromoazepinoindole (1) is coupled with an arylboronic acid under Suzuki reaction conditions to afford an arylated azepinoindole (2). The final product (4) is generated either by direct basic hydrolysis of compound (2), or by hydrogenation of benzyl compound (3), which are obtained from compound (2) by reduction with a suitable reducing agent such as lithium aluminum hydride (LAH or $LiAlH_4$).

Figure 2:
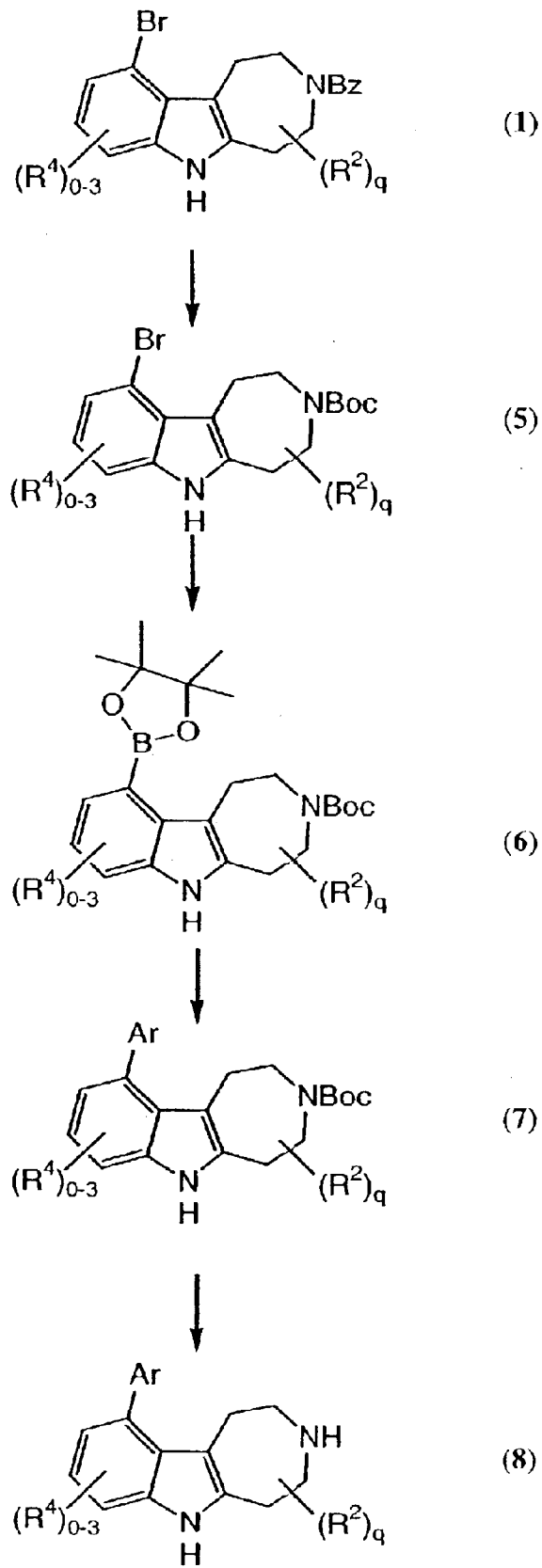

Intermediate 10-arylazepinoindole compounds of Formula (IV) can be prepared by the reactions depicted in FIG. 2. As shown in FIG. 2, the benzoyl group of compound (1) is removed under basic conditions and a Boc group is introduced to afford compound (5). Coupling with bis(pinacolato)diboron under palladium catalysis gives the boron compound (6), which is used for the synthesis. A mixture of boron compound (6), an aryl bromide, palladium catalyst (e.g., $Pd_2(dba)_3$), and a base (e.g., $Cs_2CO_3$) in methanol and dioxane is shaken for about 48 hours at about 90° C. to generate compound (7). The mixtures are cooled overnight, treated with acidic resin at about 65° C., and then washed successively with suitable solvents such as water, methanol, tetrahydrofuran, methylene chloride, and mixtures thereof. The resin is treated with ammonia and filtered. The filtrate is taken up to the vacuum and dried. The residue can be treated with a suitable acid solution, such as methanol/HCl solution, to give the salt form and/or purified by HPLC to yield the final product, a 10-arylazepinoindole (8).

Figure 3:
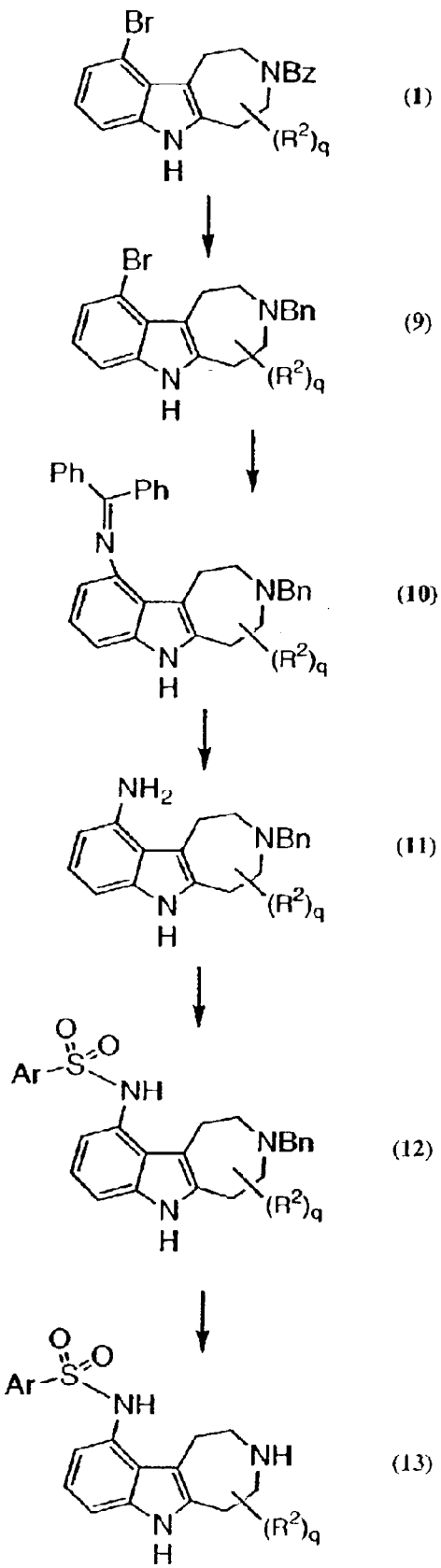

Intermediate indole compounds of formula (IV) (wherein $R^4$=$ArSO_2NH$) can be prepared by the reaction scheme depicted in FIG. 3. Compound (1) is reduced with a suitable reducing agent such as LAH or aluminum chloride to yield a benzyl compound (9). Under Buchwald/Hartwig amination conditions, compound (9) is reacted with benzophenone imine to afford compound (10), which is treated with a suitable acid solution, such as THF/HCl solution, to generate the 10-aminoazepinoindole (11). Subsequent sulphonylation and reduction, e.g., hydrogenation, yields the final product (13).

Figure 4:
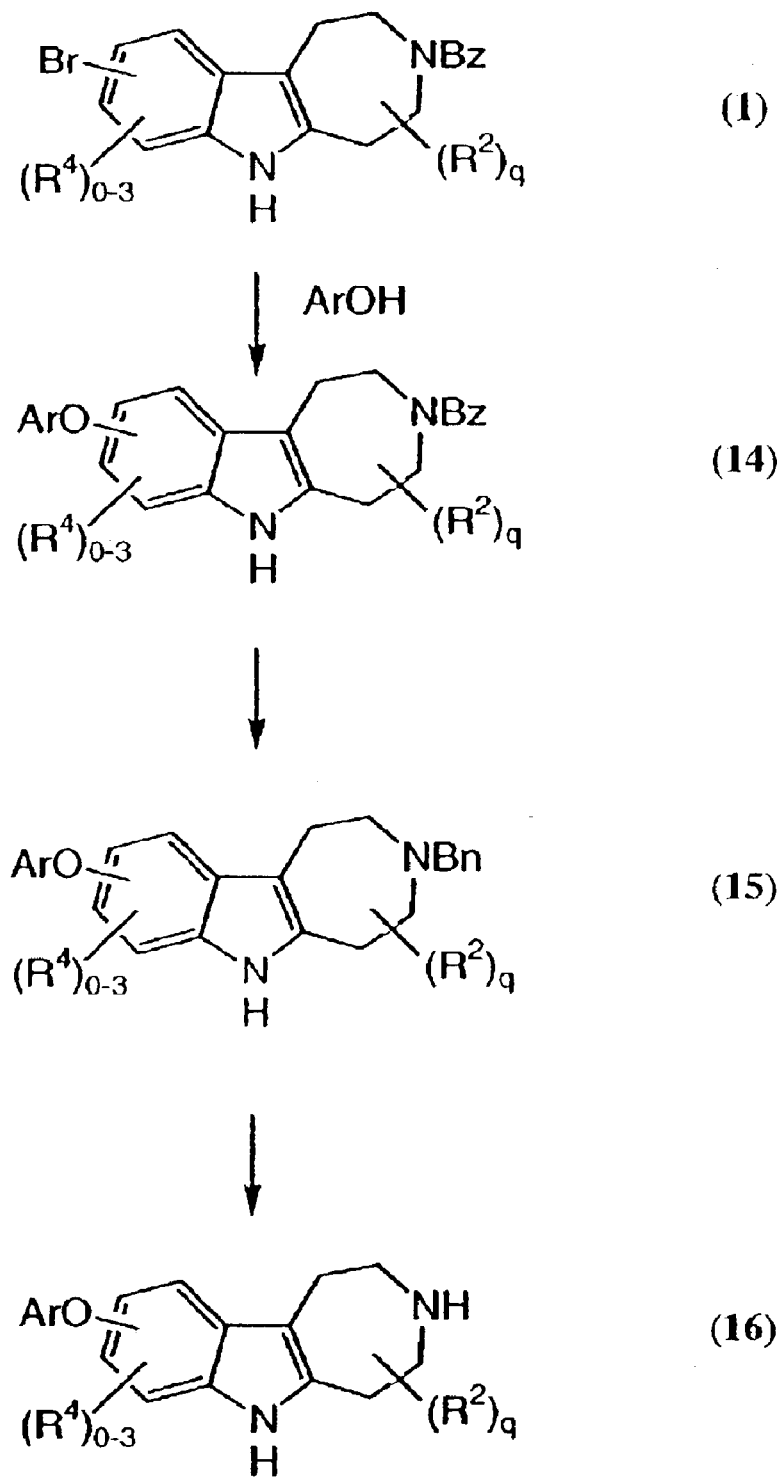

Intermediate compounds of Formula (IV) (wherein $R^4$=ArO) can be prepared by the reaction scheme depicted in FIG. 4. The aryloxy group is introduced on the indole ring by treating compound (1) with a substituted phenol in the presence of copper (I) oxide and cesium carbonate to generate compound (14). Reduction with a reducing agent, such as lithium aluminum hydride and hydrogenation yields the final product (16).

Figure 5:
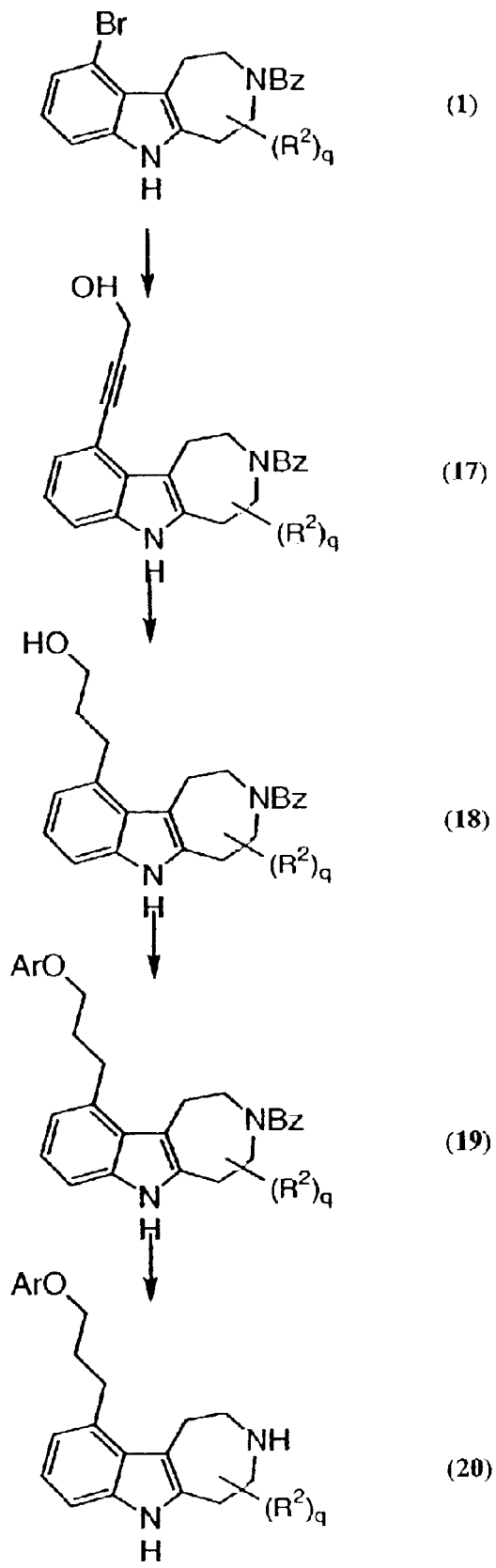

Intermediate compounds of Formula (IV) (wherein $R^4$=$ArO(CH_2)_nCH_2$) can be prepared by the reaction scheme depicted in FIG. 5. Sonogashira coupling of the aryl bromide (1) with propargyl alcohol, in pyrrolidine, using a suitable catalyst such as tetrakistriphenylphosphine palladium (0) and copper (1) iodide affords the aryl alkyne (17). Exhaustive hydrogenation of the alkyne leads to the alkane (18). Using standard Mitsunobu reaction conditions, various phenols are reacted to provide the corresponding aryl ethers (19). Removal of the benzamide functionality is accomplished through basic hydrolysis to give the final products (20) which can be trapped as their hydrochloride salts.

Figure 6:
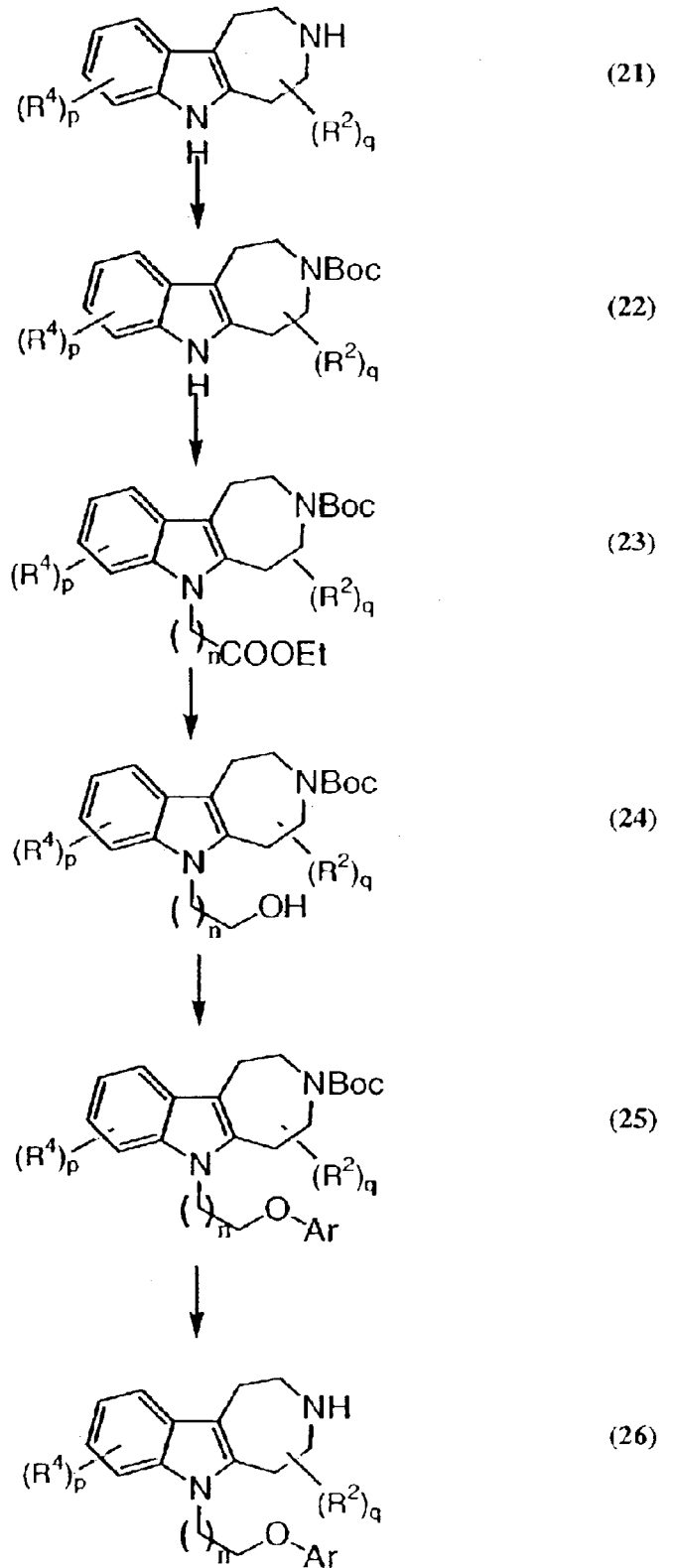

Intermediate compounds of Formula (IV) (wherein $R^3$=$ArO(CH_2)_n$) can be prepared by the reaction scheme depicted in FIG. 6 (wherein n=1–3). Protection of 1,2,3,4,5,6-hexahydroazepino[4,5-b]indole (21) as the tert-butyl carbamate (22), followed by alkylation with a suitable alkylating agent, such as a haloester, leads to the protected ester (23). Reduction of the ester (23) affords the primary alcohol (24). Standard Mitsunobu reaction conditions leads to the aryl ether (25), which is deprotected and isolated as the appropriate salt of compound (26) using suitable acids.

Figure 7:
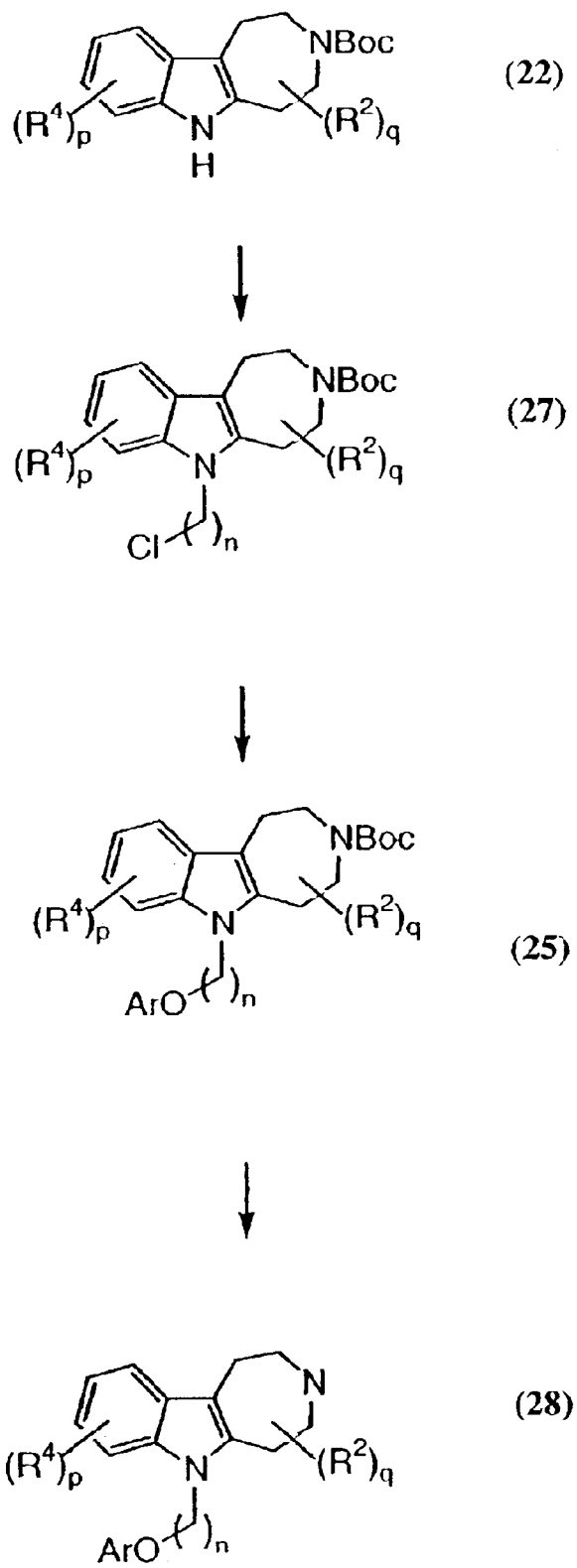

Intermediate compounds of Formula (IV) (wherein $R^3$=$ArO(CH_2)_n$) also can be prepared by the reaction scheme depicted in FIG. 7 (where n is 2 or 3). The tert-butyl carbamate protected azepinoindole (22) is alkylated with a suitable alkylating agent, such as bromochloropropane. Displacement with a substituted phenol affords compound (25), which then can be deprotected with acid to yield (28) as appropriate salts.

Figure 8:
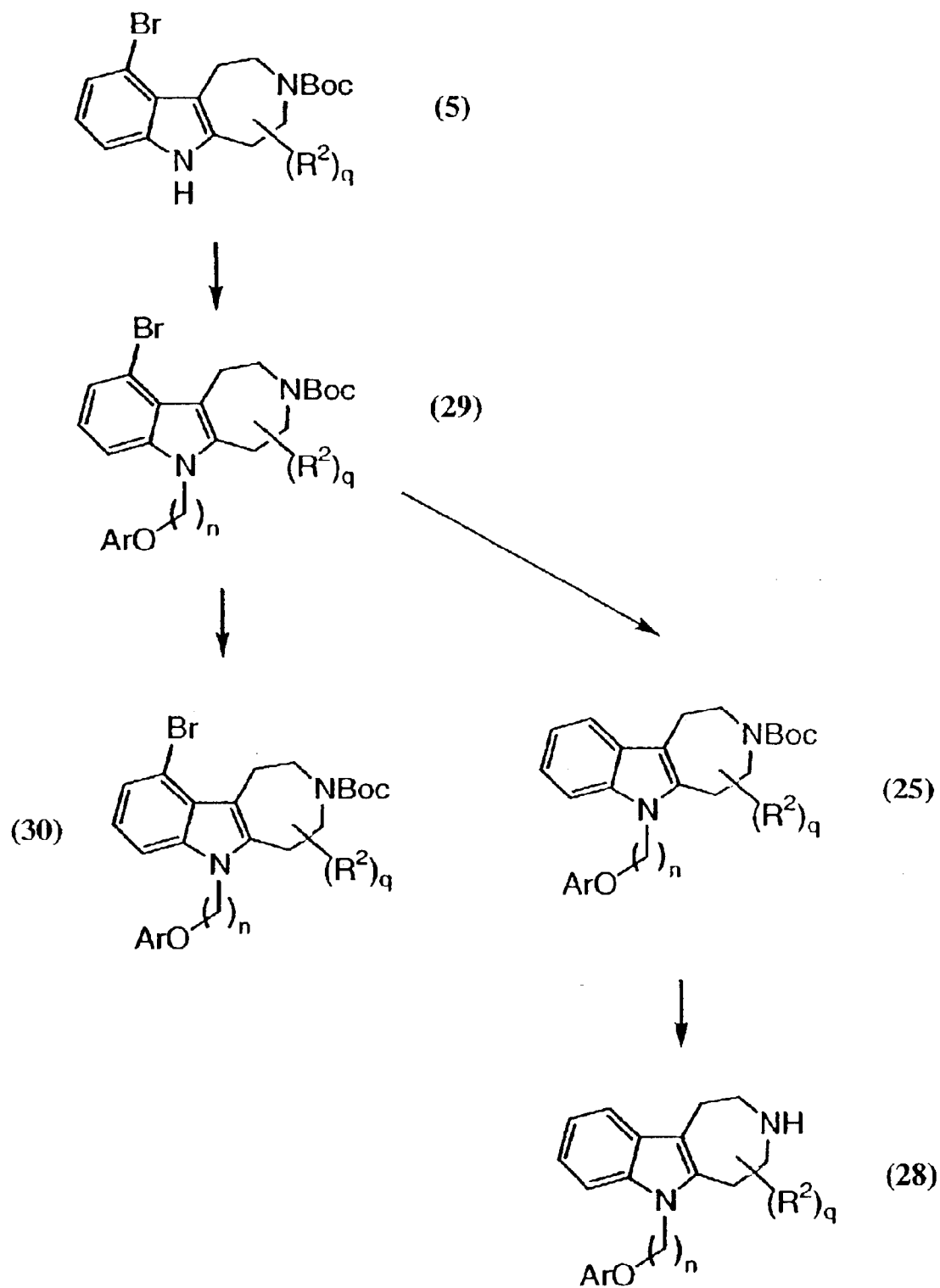

Intermediate compounds of Formula (IV) (wherein $R^3$=$ArO(CH_2)_n$, $R^4$=Br, H) also can be prepared by the reaction scheme depicted in FIG. 8 (where n is 2 or 3). The tert-butyl carbamate protected 10-bromoazepinoindole (5) is alkylated with a suitable alkylating agent such as phenoxybromoalkane. Deprotection with acid affords compound (30) as appropriate salts. Hydrogenolysis of (29) generates the dehalogenated compound (25), which is deprotected with acid to generate (28) as appropriate salts.

Figure 9:
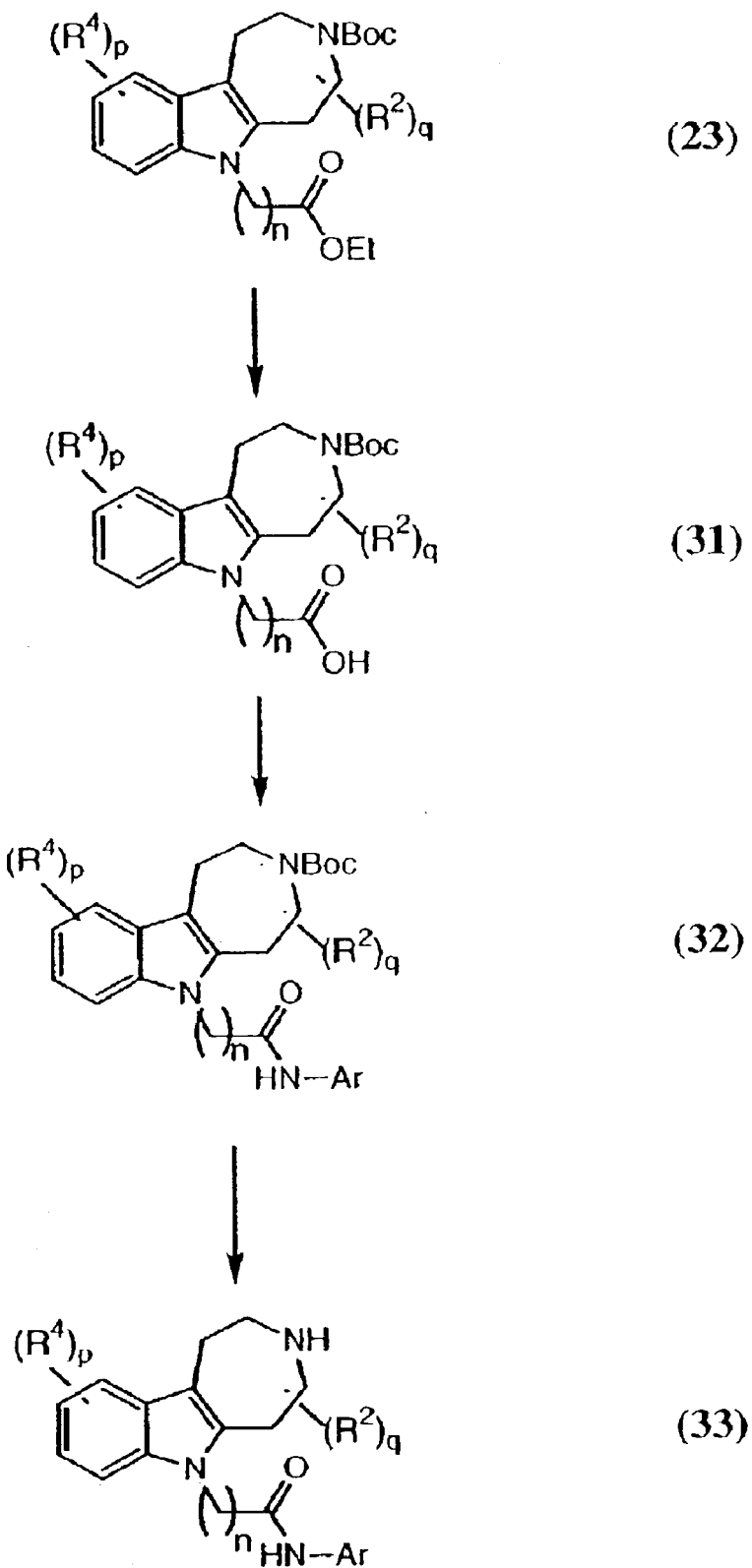

Intermediate compounds of Formula (IV) (wherein $R^3$=$(CH_2)_nCONHAr$) can be prepared by the reaction scheme depicted in FIG. 9. The ester (23) is hydrolyzed, for example, with 1N NaOH in methanol, and the resulting acid (31) is condensed with a suitable aniline using coupling conditions such as diisopropylcarbodiimde and dimethylaminopyridine (DMAP) in THF or EEDQ in THF or EtOH, to yield amide (32). The Boc protecting group is cleaved from the amide using a suitable acid solution, such as TFA in $CH_2Cl_2$, and the crude product can be treated with HCl in ether to yield the hydrochloride salt of (33).

Figure 10:
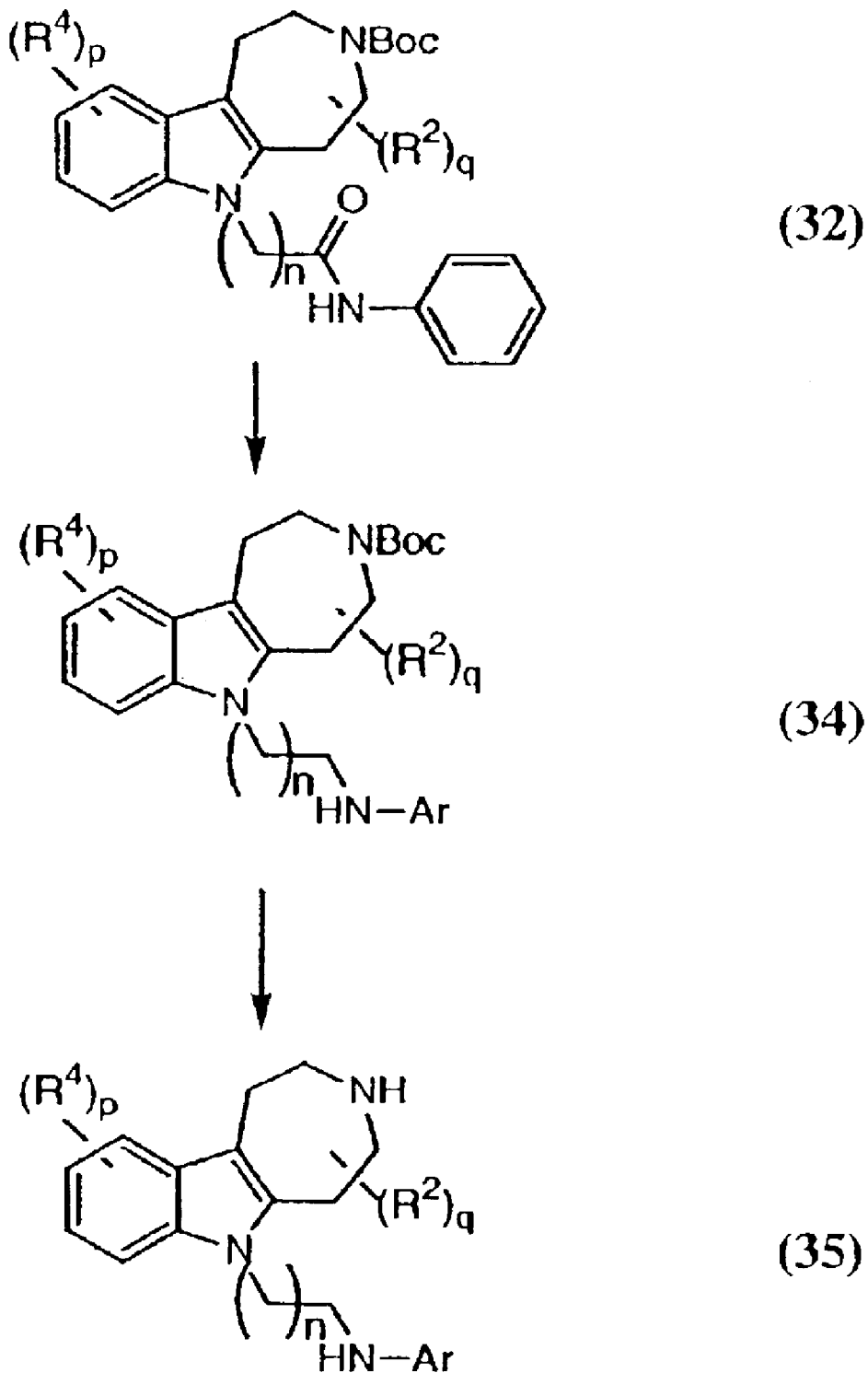

Intermediate compounds of Formula (IV) (wherein $R^3$=$(CH_2)_nNHAr$) can be prepared by the reaction scheme depicted in FIG. 10. Amide (32) is reduced with a suitable reducing agent, such as LAH in THF, to yield the corresponding secondary amine (34), which is in turn deprotected with an acid like TFA in $CH_2Cl_2$, to yield diamine (35).

Figure 11:
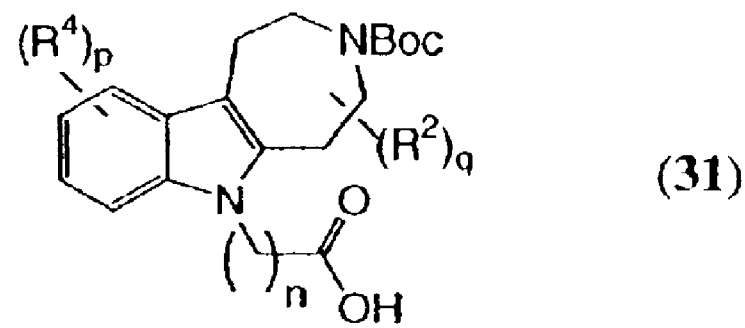
Figure 11:
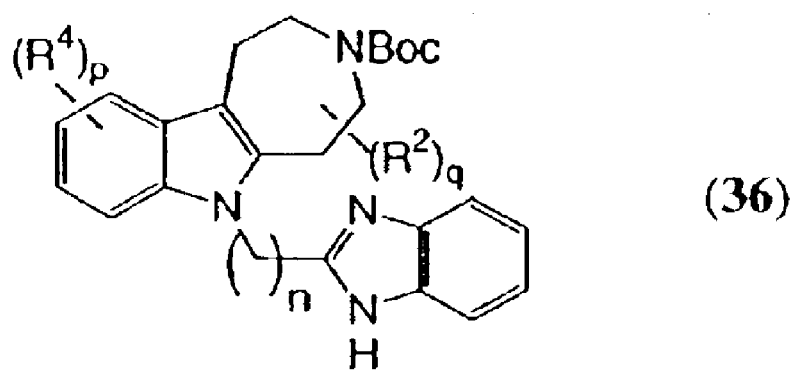
Figure 11:
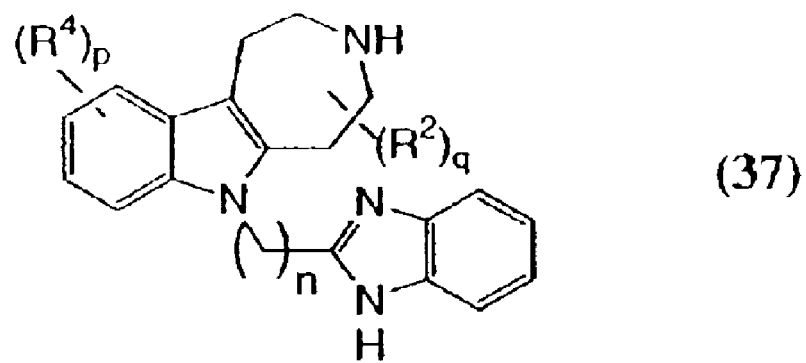

Intermediate compounds of Formula (IV) (wherein $R^3$=$(CH_2)_n$benzimidazole) can be prepared by the reaction scheme depicted in FIG. 11. Acid (31) is condensed with a substituted o-phenylenediamines using isobutyl chloroformate, triethylamine, and acetic acid in THF. Benzimidazole (36) is deprotected with a suitable acid solution, such as TFA in $CH_2Cl_2$, and the crude product may be converted to the hydrochloride salt of (37) using a suitable acid solution, such as HCl in ethyl ether.

Figure 12:
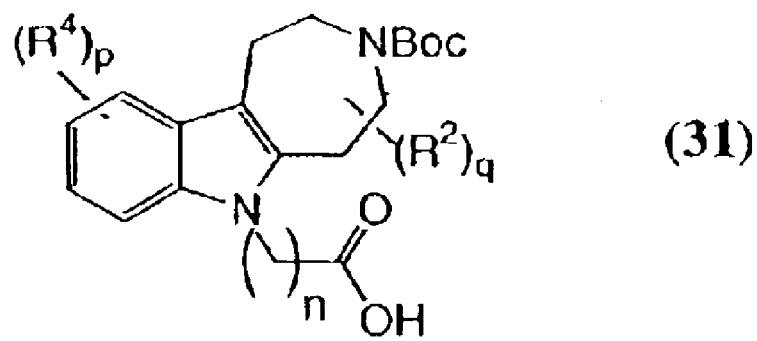
Figure 12:
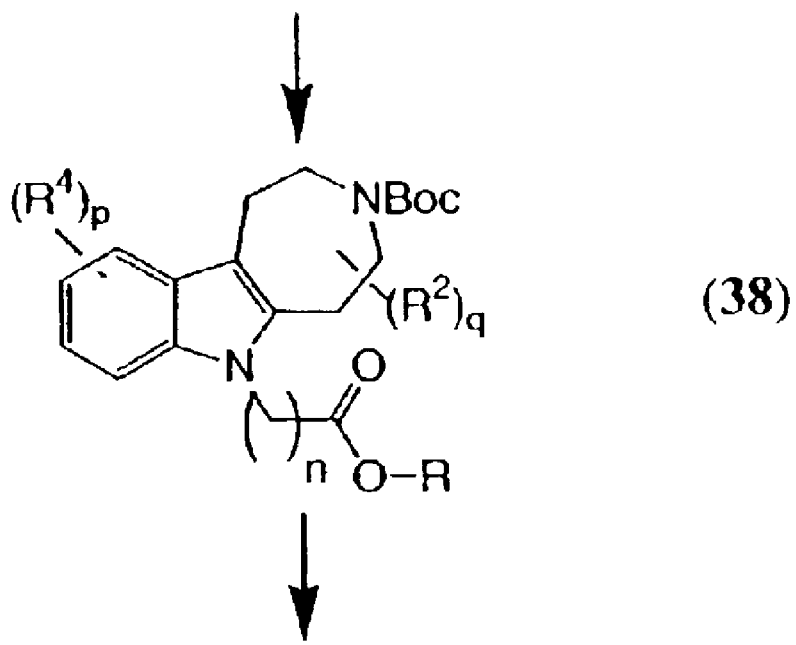
Figure 12:
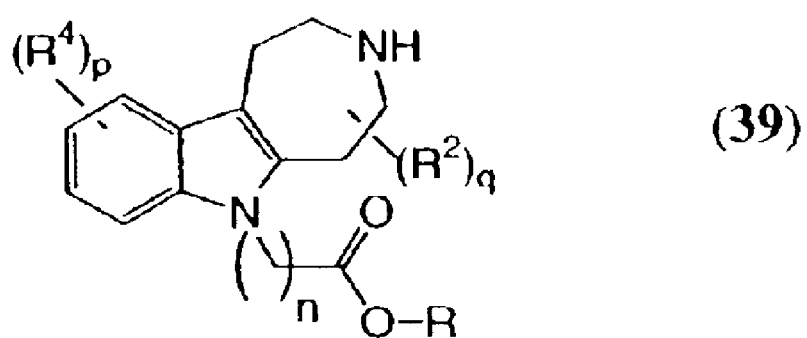

Intermediate compounds of Formula (IV) (wherein $R^3$=$(CH_2)_nCOOR^a$) can be prepared by the reaction scheme depicted in FIG. 12. The acid (31) is condensed with an alcohol and the resulting ester (38) is deprotected using a suitable acid solution, such as TFA in CH$_2$Cl$_2$, to yield the amino ester (39).

Figure 13:
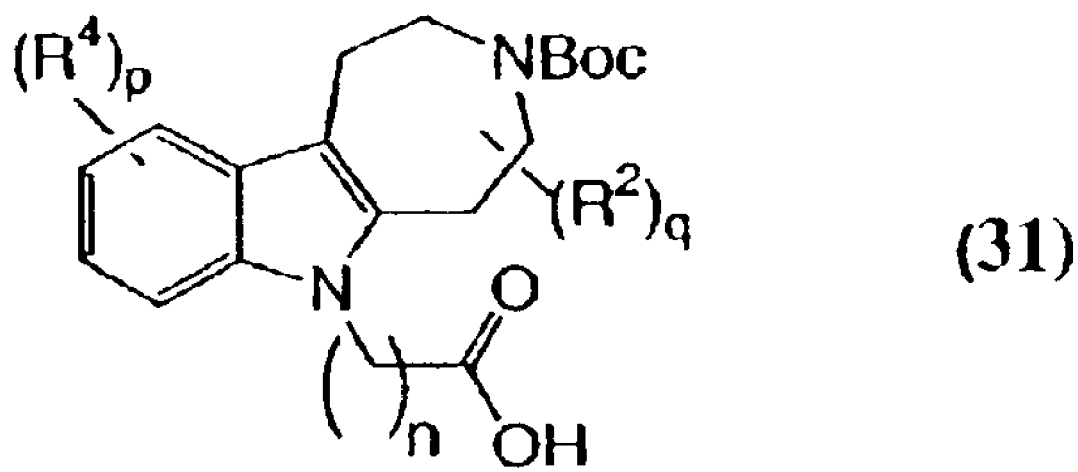
Figure 13:
Figure 13:
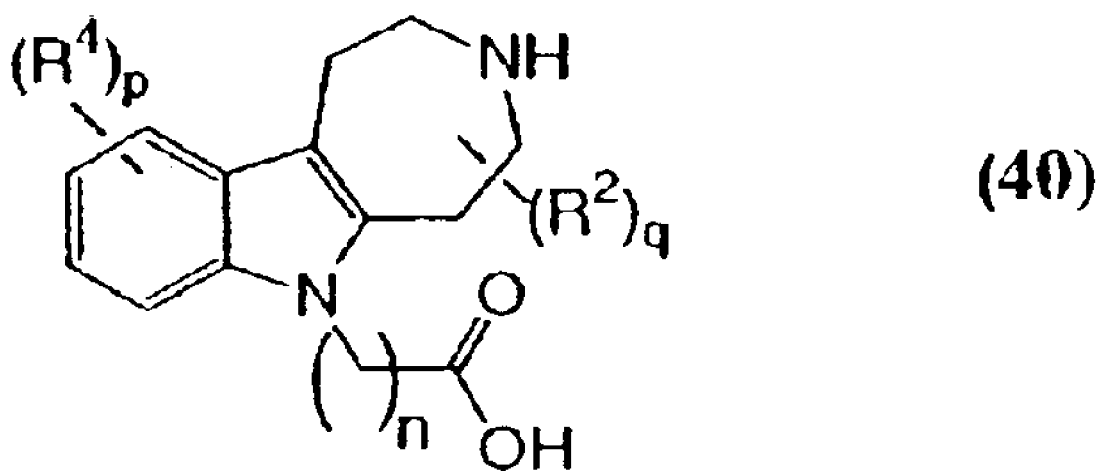

Intermediate compounds of Formula (IV) (wherein R$^3$=(CH$_2$)$_n$COOH) can be prepared by the reaction scheme depicted in FIG. 13. The acid (31) is treated with a suitable acid solution, such as TFA in CH$_2$Cl$_2$, and the crude product may be combined with a suitable acid solution, such as HCl in ethyl ether, to yield hydrochloride salt of (40).

Figure 14:
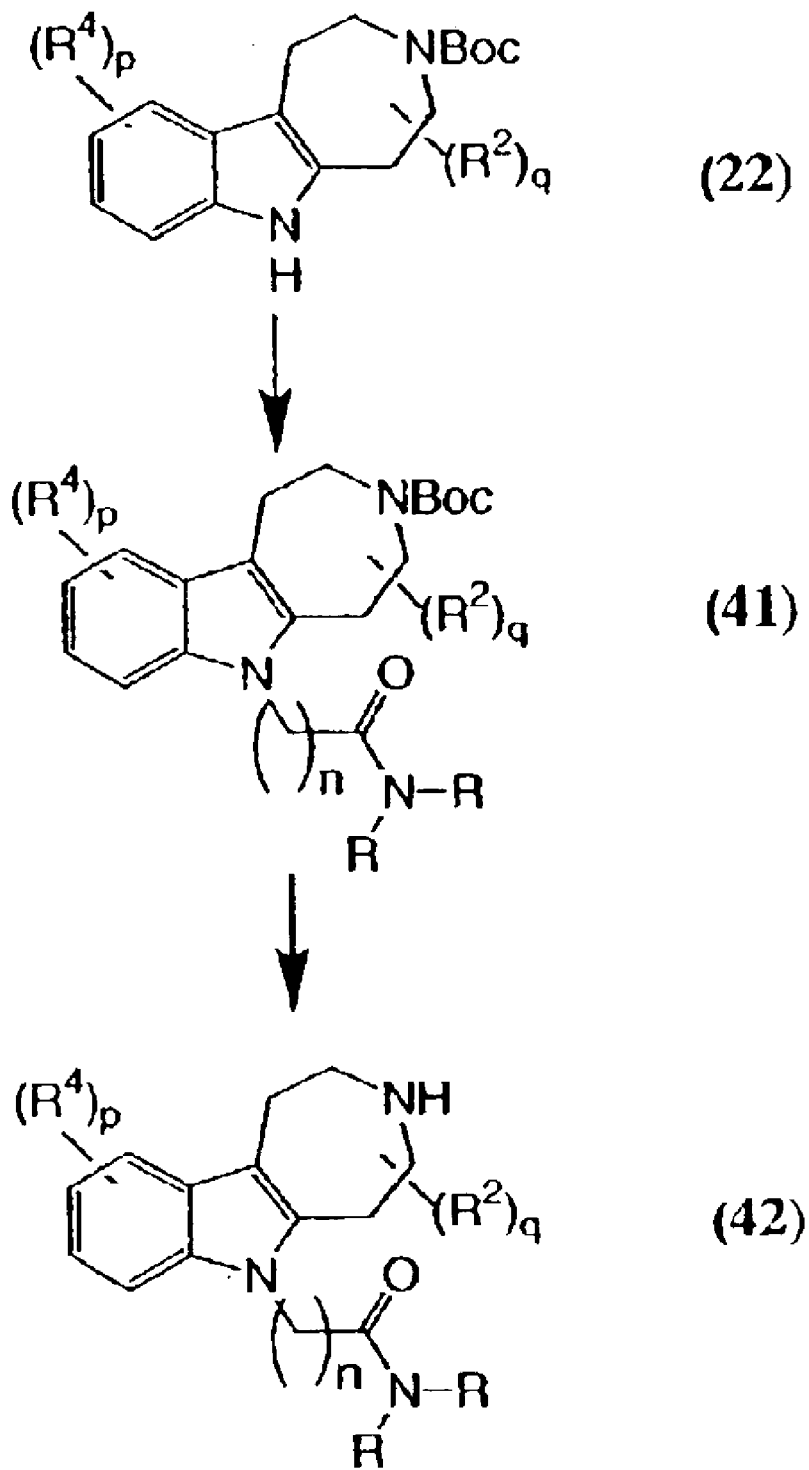

Intermediate compounds of Formula (IV) (wherein R$^3$=(CH$_2$)$_n$CONR$^a$R$^b$) can be prepared by the reaction scheme depicted in FIG. 14. N-Boc azepinoindole (22) is alkylated with an N-substituted haloacetamide (e.g., iodoacetamide or 2-chloro-N,N-dimethylacetamide) using NaH in DMF. The resulting substituted azepinoindoles is deprotected with a suitable acid solution, such as TFA in CH$_2$Cl$_2$, and the crude product may be treated with a suitable acid solution, such as HCl in ethyl ether, to form the hydrochloride salt of (42).

Figure 15:
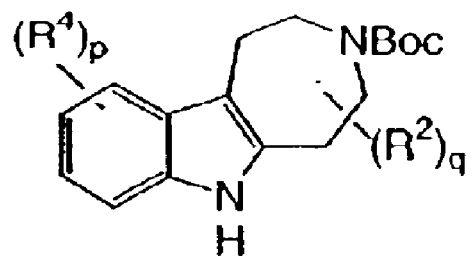
Figure 15:
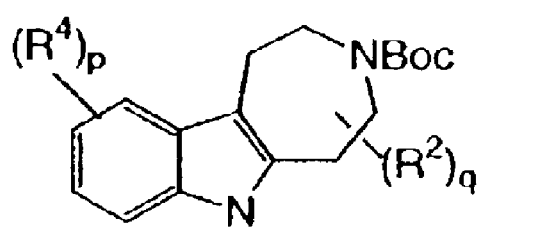
Figure 15:
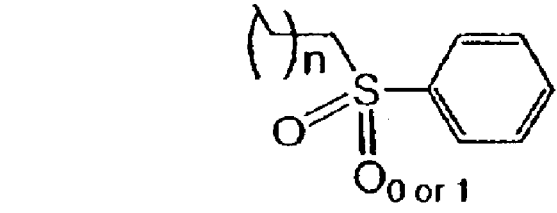

Intermediate compounds of Formula (IV) (wherein R$^3$=(CH$_2$)$_n$SO$_2$Ar) can be prepared by the reaction scheme depicted in FIG. 15. N-Boc azepinoindole (22) is alkylated with a suitable alkylating agent such as chloroalkyl phenyl sulfone or chloroalkyl phenyl sulfoxide, in the presence of either a suitable basic solution, such as NaH in DMF, or under phase transfer conditions (e.g., Bu$_4$NHSO$_4$, KOH, H$_2$O, CH$_2$Cl$_2$) to yield an alkylated azepinoindole (43). The Boc protecting group is removed by treating the alkylated azepinoindole (43) with a suitable acid solution such as TFA in CH$_2$Cl$_2$, to yield free amines (44).

Figure 16:
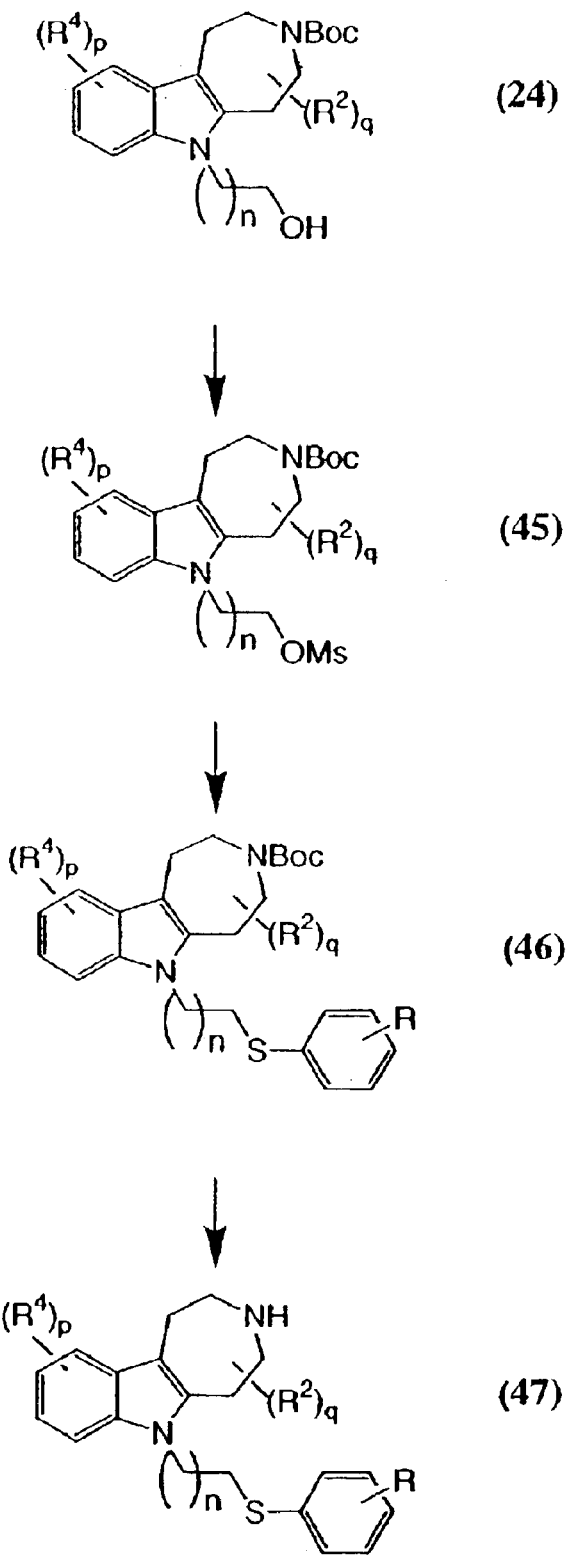

Intermediate compounds of Formula (IV) (wherein R$^3$=(CH$_2$)$_n$SAr) can be prepared by the reaction scheme depicted in FIG. 16. Alcohol (24) is treated with a suitable leaving group-containing compound such as methanesulfonyl chloride, in the presence of a suitable basic solution, such as triethylamine in CH$_2$Cl$_2$, to yield a mesylate (45). The mesylate (45) is treated with thiophenol, under phase transfer conditions (e.g., Bu$_4$NHSO$_4$, NaOH, H$_2$O, CH$_2$Cl$_2$) to yield a phenyl thioether (46). The phenyl thioether (46) is treated with a suitable acid solution, such as TFA in CH$_2$Cl$_2$, to remove the Boc protecting group to give (47).

Figure 17:
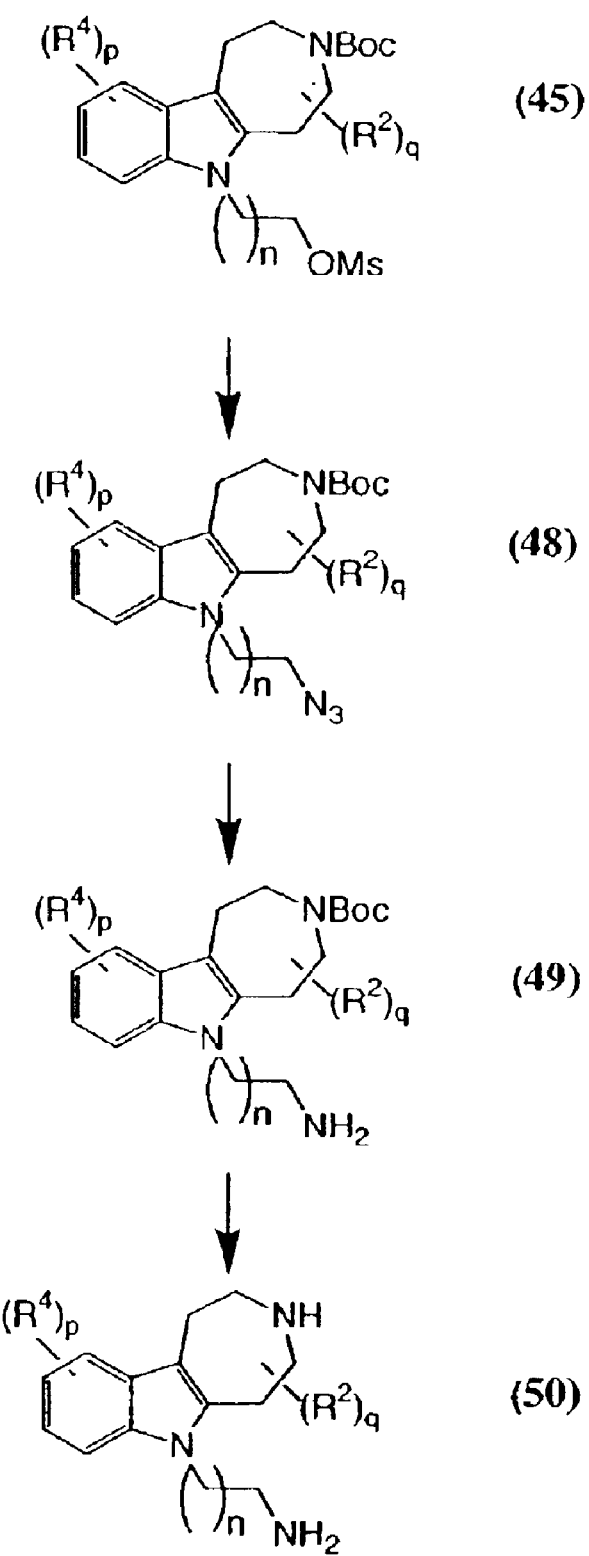

Intermediate compounds of Formula (IV) (wherein R$^3$=(CH$_2$)$_n$NH$_2$) can be prepared by the reaction scheme depicted in FIG. 17. The mesylate (45) is treated with a suitable azide such as sodium azide in DMF, to yield an azide (48). This azide is reduced by catalytic hydrogenolysis (e.g., H$_2$, 10% Pd/C, ethyl acetate, ethanol) to yield an amine (49). The amine (49) is treated with a suitable acid solution, such as TFA in CH$_2$Cl$_2$, and the resulting crude diamine can be treated with a suitable acid solution, such as HCl in ethyl ether, to yield the dihydrochloride salt of (50).

Figure 18:
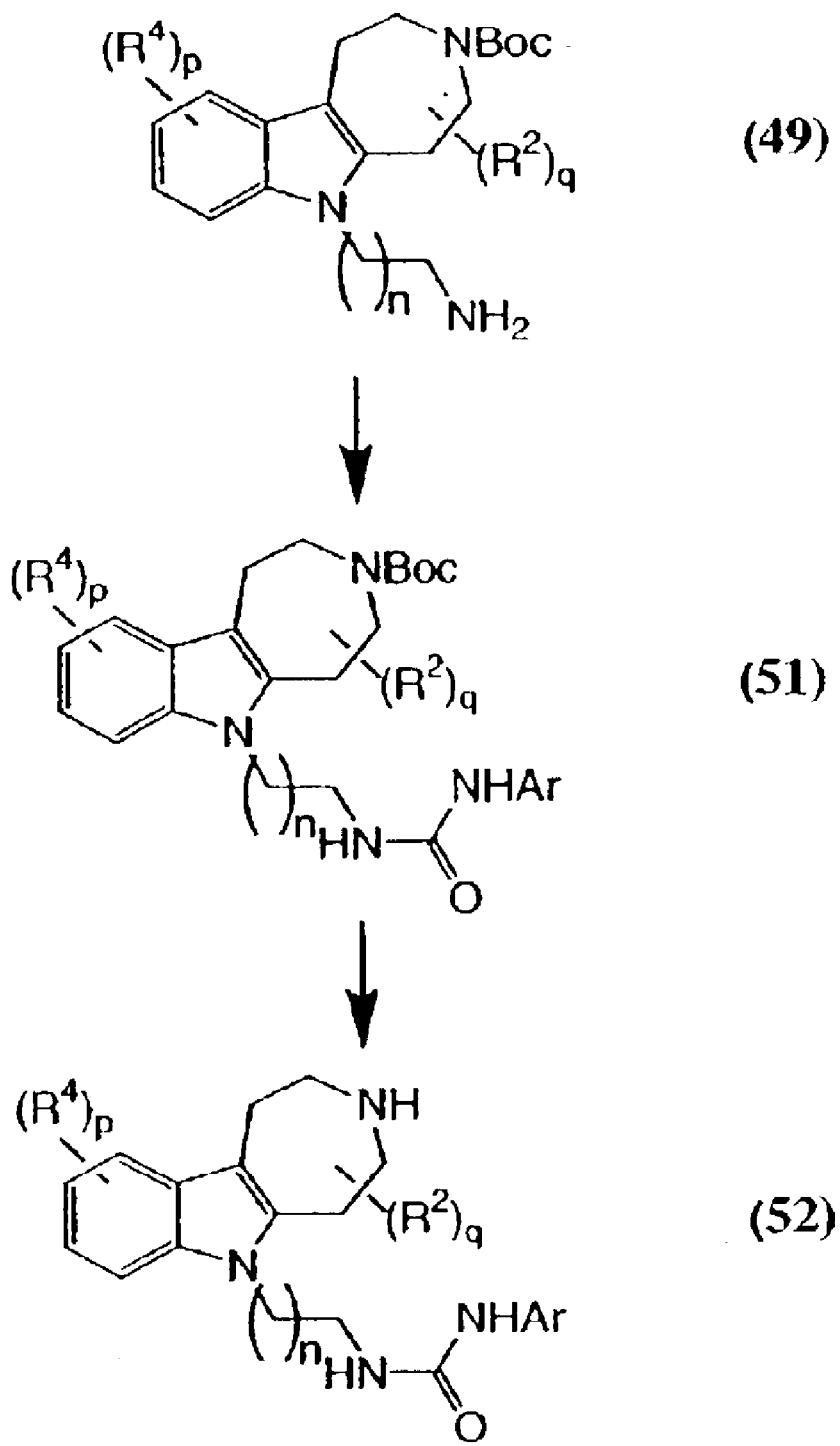

Intermediate compounds of Formula (IV) (wherein R$^3$=(CH$_2$)$_n$NHCONHAr) can be prepared by the reaction scheme depicted in FIG. 18. The amine (49) is treated with aryl isocyanate in CH$_2$Cl$_2$ to yield urea (51). The urea (51) is treated with a suitable acid solution, such as TFA in CH$_2$Cl$_2$, and the resulting crude amine ccan be treated with a suitable acid solution, such as HCl in ethyl ether, to yield hydrochloride salt of (52).

Figure 19:
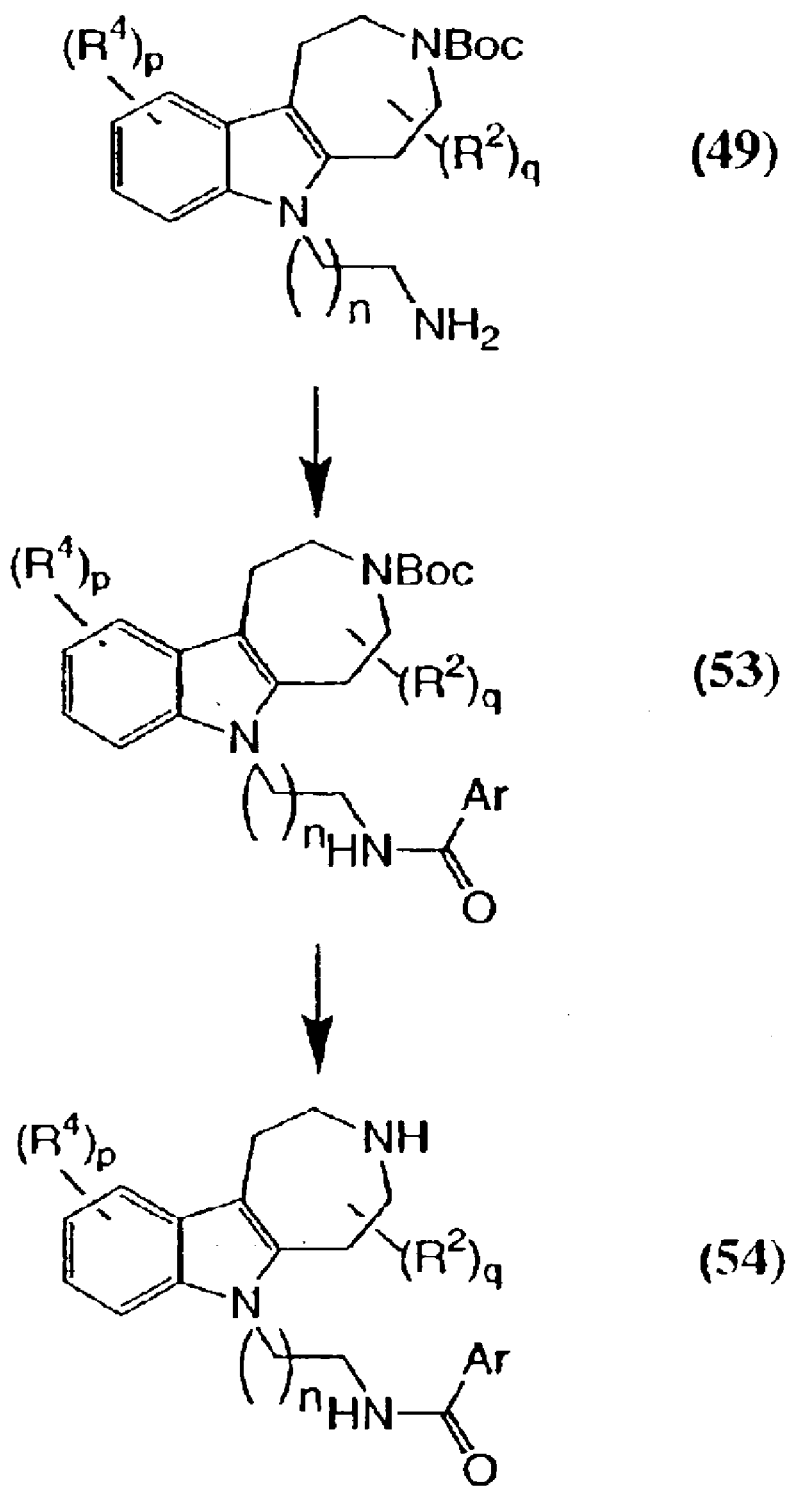

Intermediate compounds of Formula (IV) (wherein R$^3$=(CH$_2$)$_n$NHCOAr) can be prepared by the reaction scheme depicted in FIG. 19. The amine (49) is treated with a suitable aroyl chloride, in the presence of a suitable basic solution, such as diisopropylethylamine in CH$_2$Cl$_2$, to yield an amide (53). The amide (53) is treated with a suitable acid solution, such as TFA in CH$_2$Cl$_2$, and the resulting crude amine may be treated with a suitable acid solution, such as HCl in ethyl ether, to yield hydrochloride salt of (54).

Figure 20:
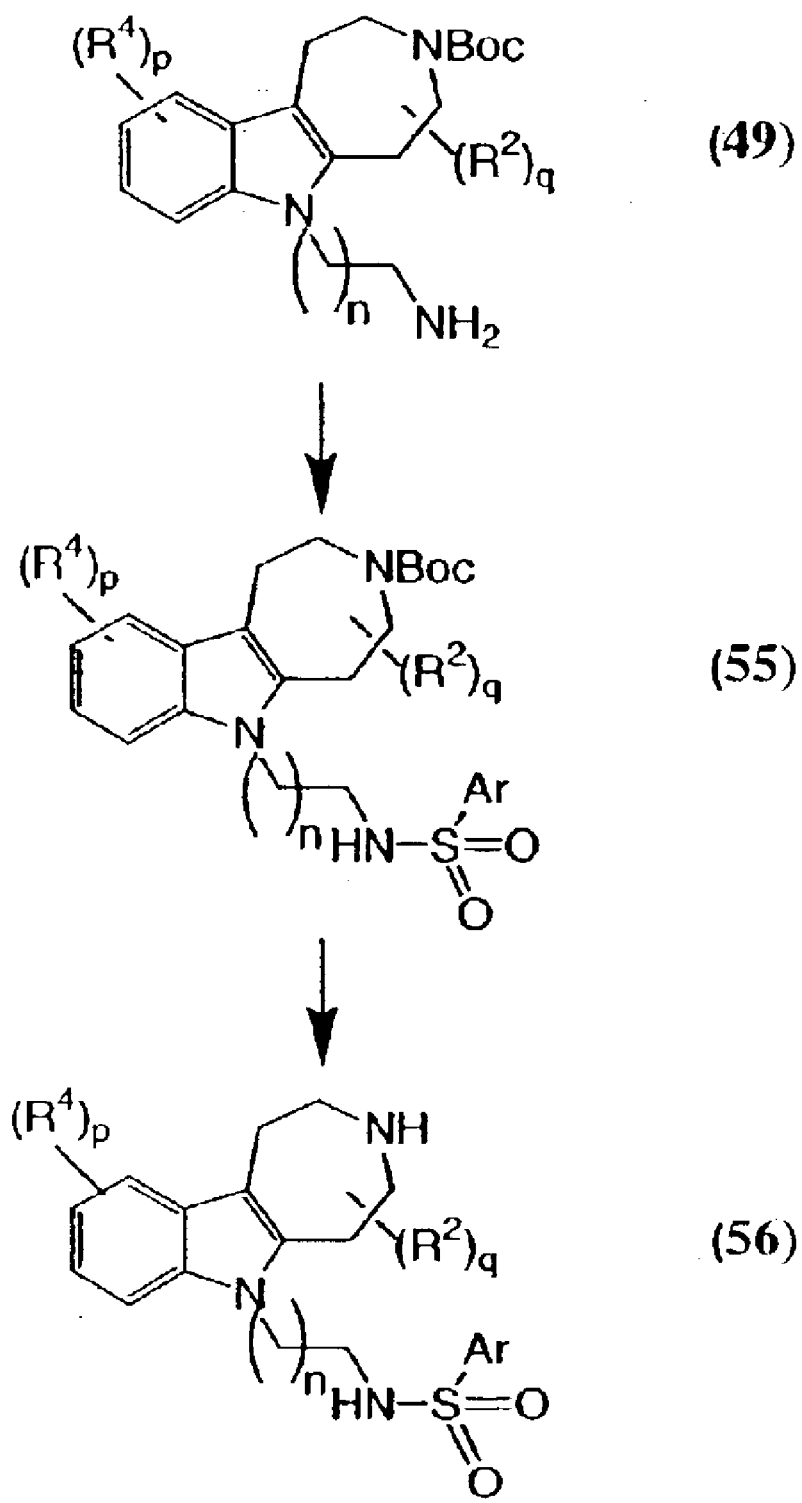

Intermediate compounds of Formula (IV) (wherein R$^3$=(CH$_2$)$_n$NHSO$_2$Ar) can be prepared by the reaction scheme depicted in FIG. 20. The amine (49) is treated with a suitable arylsulfonyl chloride, in the presence of a suitable basic solution, such as diisopropylethylamine in CH$_2$Cl$_2$, to yield sulfonamide (55). The sulfonamide (55) is treated with a suitable acid solution, such as TFA in CH$_2$Cl$_2$, and the resulting crude amine may be treated with a suitable acid solution, such as HCl in ethyl ether, to yield hydrochloride salt of (56).

Figure 21:
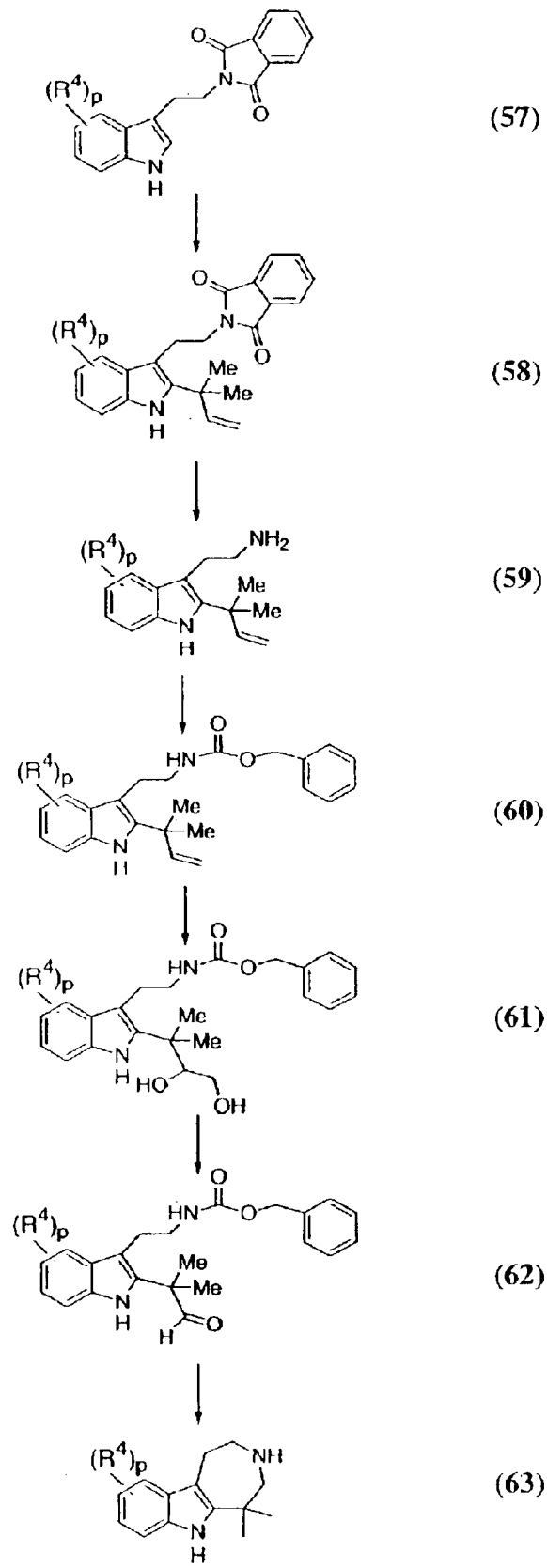

Intermediate compounds of Formula (IV) (wherein R$^2$=5,5-di-Me) can be prepared by the reaction scheme depicted in FIG. 21. The phthalimido-protected tryptamine (57) is reverse prenylated, using the procedures described by Depew et al. (*J. Am. Chem. Soc.* 1996, 118, 12463) and Schkeryantz et al. (*J. Am. Chem. Soc.* 1999, 121, 11964), to provide (58). Standard deprotection of (58) (e.g., NH$_2$NH$_2$, EtOH) provides (59). The amine group of (59) is re-protected (e.g., CbzCl) to provide (60). Oxidation of the vinyl group of (60) (e.g., OsO$_4$, NMO) provides diol (61), that is oxidatively cleaved (e.g., NaIO$_4$) to aldehyde (62). Mild catalytic hydrogenation of (62) accomplishes Cbz deprotection, that is followed by in situ intramolecular cyclization to the imine and imine reduction, to provide an amine (63), which may be formulated as the hydrochloride salt.

Figure 22:
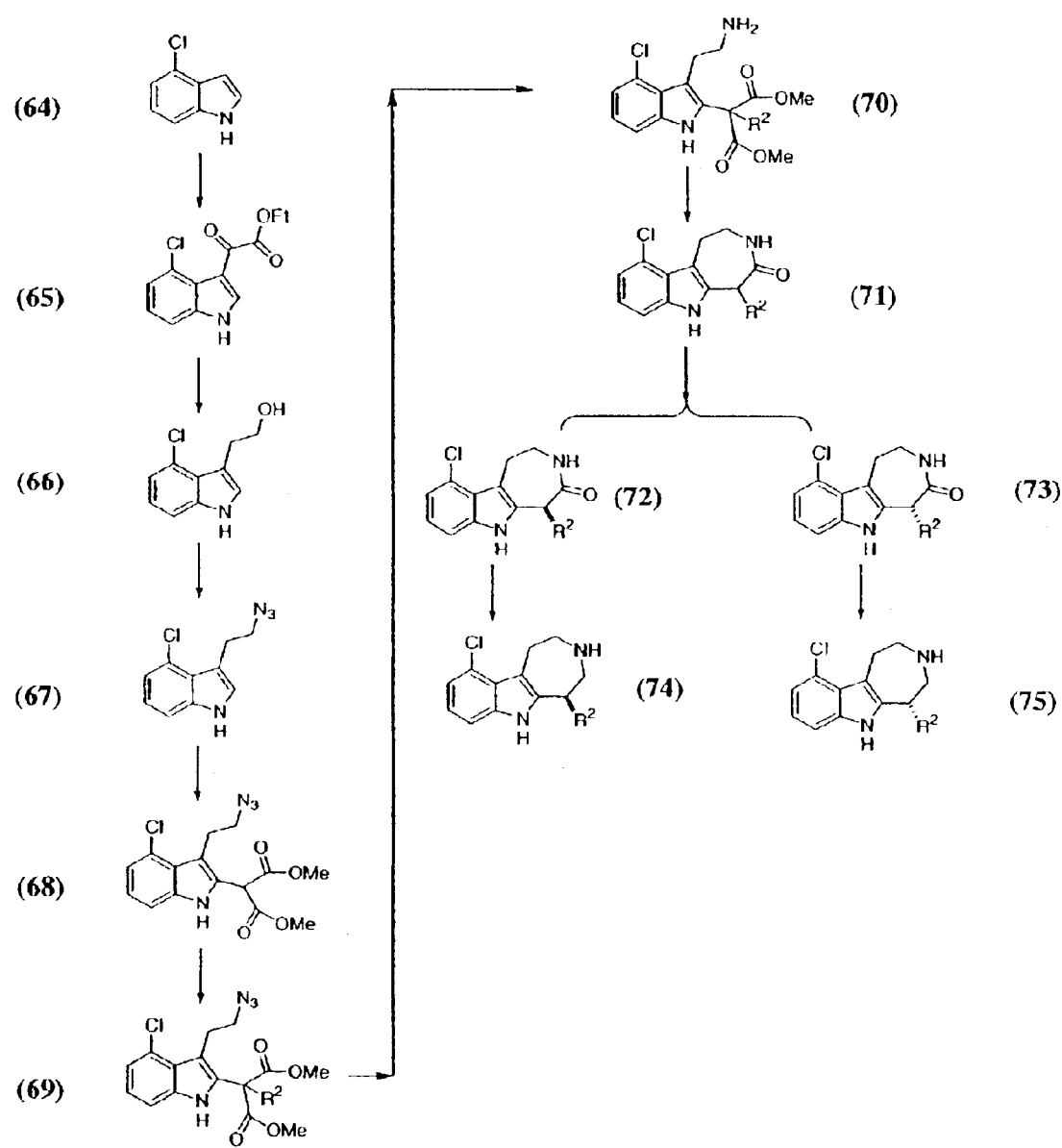

Intermediate compounds of Formula (IV) can be prepared by the reaction scheme depicted in FIG. 22. Acylation of 4-chloroindole (64) (oxalyl chloride, followed by an EtOH quench) provides an ethyl 4-chloroindole glyoxalate (65), which is reduced (e.g., LiAlH$_4$) to the 4-chloroindole-3-ethanol (66). Substitution of the alcohol (66) is achieved using a suitable azide, such as Zn(N$_3$)$_2$, under Mitsunobu reaction conditions to provide (67). Malonate addition to (67) is accomplished as described by Kuehne *J. Org. Chem.*, 63, 9427 (1998), to provide a malonyl enolate (68). Alkylation of the malonyl enolate (68) with a suitable alkylating agent such as NaOMe and MeI, provides (69). The azide group of (69) is reduced (sequential addition of PMe$_3$ and H$_2$O) to provide an aminoester (70). The aminoester (70) undergoes intramolecular cyclization, providing lactam (71) upon reflux as a solution in MeOH. Racemate (71) is separated into the enantiomers (72) and (73) by chiral support chromatography. The assignment of the absolute configurations to (72) and (73) is made by x-ray crystallographic analysis. The lactam group of each enantiomer is separately reduced (BH$_3$) to provide amines (74) (from reduction of (72)) and (75) (from reduction of (73)), which may be formulated as the fumarate salts.

Figure 23:
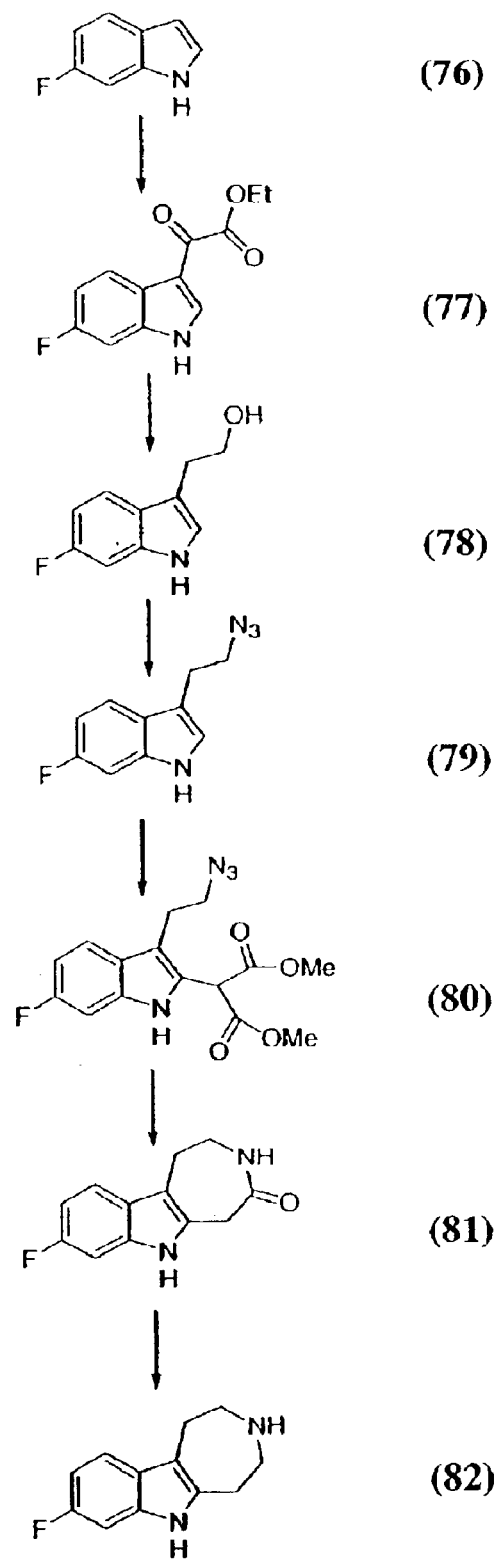

Intermediate compounds of Formula (IV) (wherein R$^4$=7-F) can be prepared by the reaction scheme depicted in FIG. 23. Beginning with 6-fluoroindole (76), the preparation of intermediates (77), (78), (79), and (80) follows the methods described respectively for (65), (66), (67), and (68) (FIG. 22). The azido group of (80) is reduced by catalytic hydrogenation, and the resulting aminoester is subjected (without isolation) to thermal cyclization to provide (81). Reduction (e.g., BH$_3$) of the lactam of (81) provides an amine (82), which may be formulated as the fumarate salt.

Figure 24:
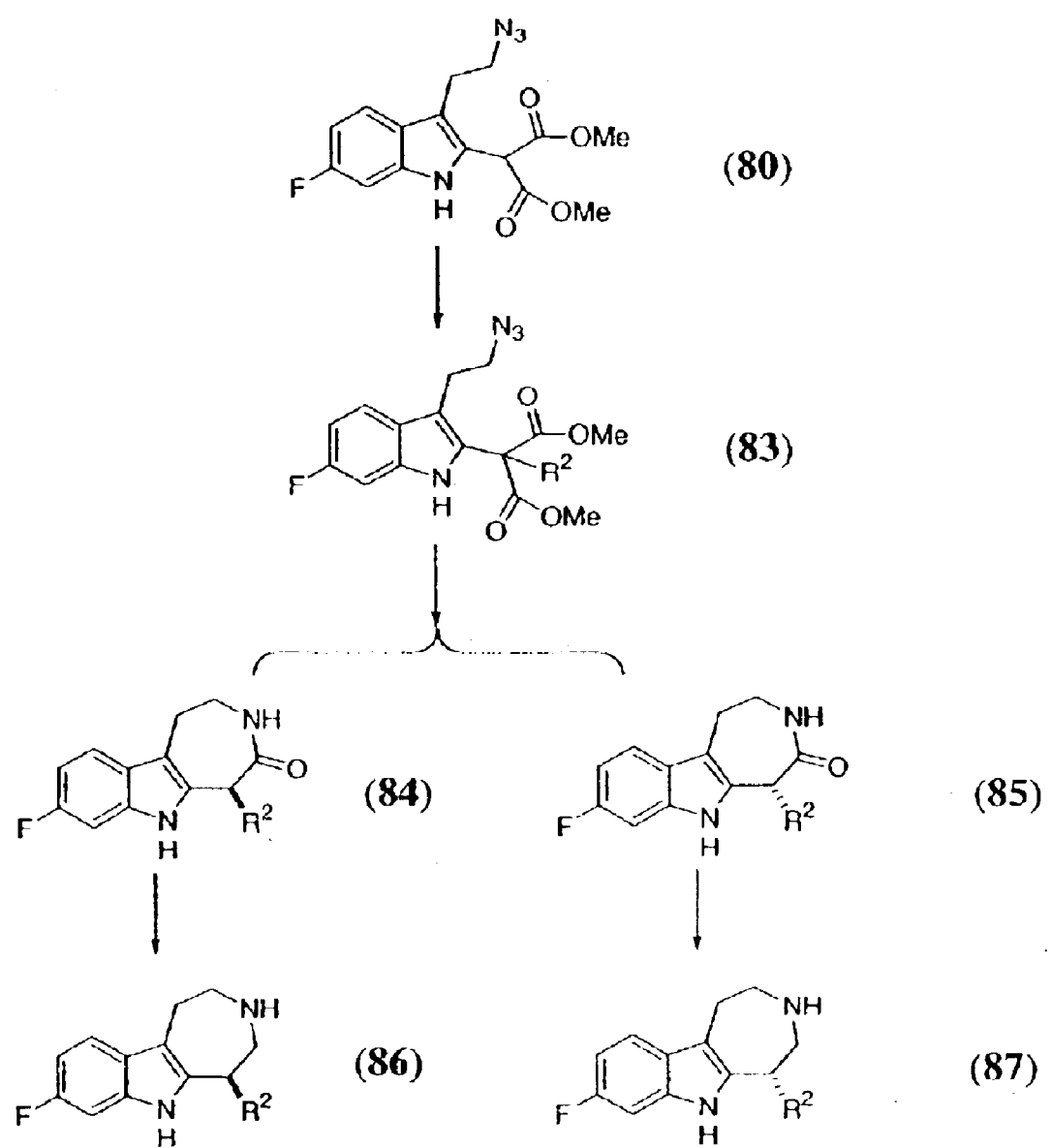

Intermediate compounds of Formula (IV) (R$^4$=7-F) can be prepared by the reaction scheme depicted in FIG. 24. According to the reaction sequence of FIG. 23, alkylation of the malonyl enolate of (80), as described previously for the preparation of (69), provides (83). Racemate (83) is separated into the enantiomers (84) and (85) by chiral support chromatography. The assignment of the absolute configurations to (84) and (85) is made by correlation of their CD spectra to those of (72) and (73). The lactam group of each enantiomer is separately reduced with a suitable reducing agent such as $BH_3$, to provide amines (86) (from reduction of (84)) and (87) (from reduction of (85)), which may be formulated as the fumarate salts.

Figure 25:
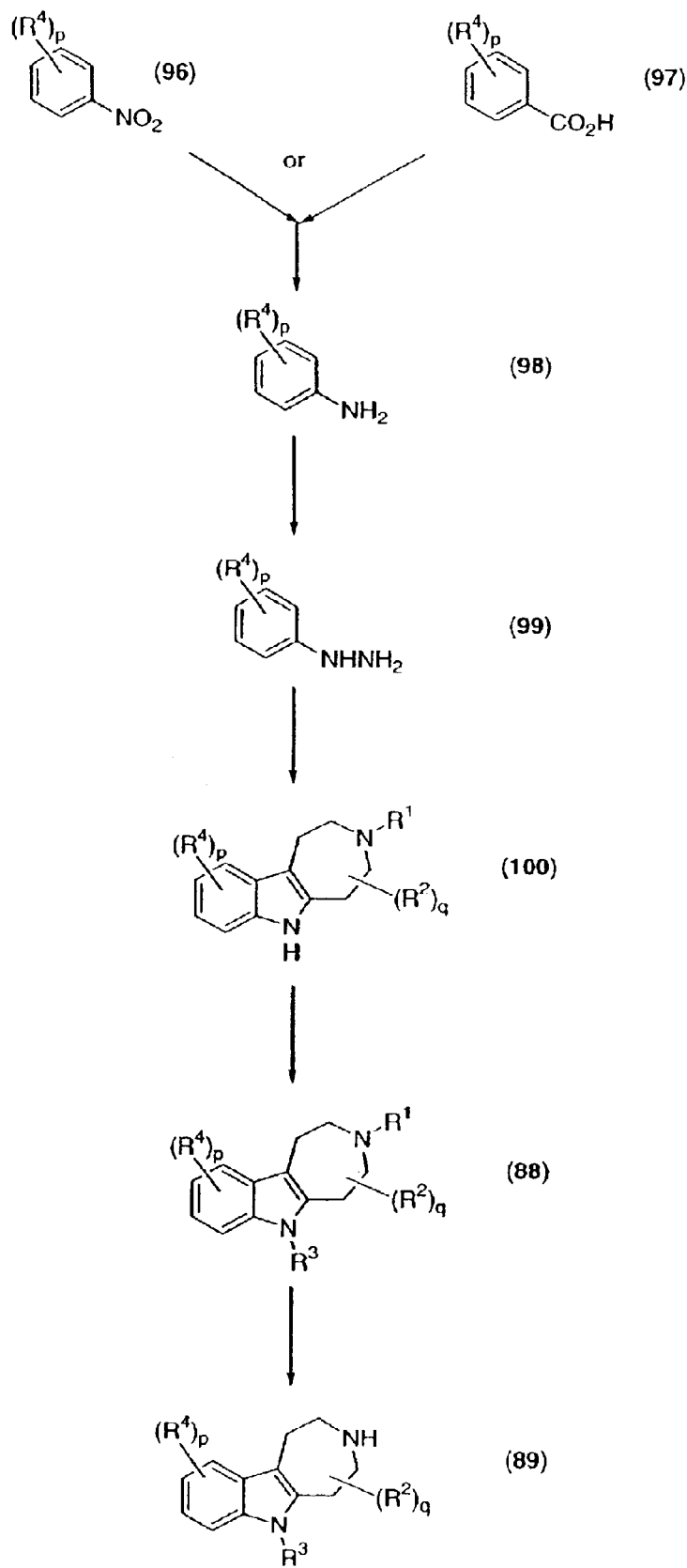

As shown in FIG. 25, compounds of Formula (IV) may also be prepared starting with the corresponding nitrobenzenes (96), benzoic acids (97) or anilines (98), many of which are commercially available or known in the scientific literature, or can be prepared by general procedures known to those skilled in the art (for examples, see Larock, R. C., *Comprehensive Organic Transformations*, $2^{nd}$ edition, 1999, Wiley-VCH Publishers, New York). For example, reduction of the nitro group using a variety of conditions or reagents such as $SnCl_2$ in acid, LAH, sodium borohydride, hydrazine, or hydrogen in the presence of appropriate catalysts such as palladium, platinum, nickel, etc (see Hudlicky, M. *"Reductions in Organic Chemistry"*, 1984, Ellis Horwood, Ltd., Chichester, UK) gives the corresponding anilines (98). Alternatively, benzoic acids (97) can be converted to the corresponding anilines (98) via reactions known to those in the art, such as the Curtius reaction, (for examples, see Larock, R. C., *Comprehensive Organic Transformations*, $2^{nd}$ edition, 1999, Wiley-VCH Publishers, New York, 868–869). Conversion of these anilines to the corresponding phenylhydrazines (99) can be accomplished through the well-known nitrosation/reduction sequence (e.g., treatment of (98) with $NaNO_2$ under acidic conditions, such as HOAc, followed by reduction of the resulting N-nitrosoamine with agents such as lithium aluminum hydride or zinc and an organic acid such as acetic or trifluoroacetic acid). Reaction of (99) with ketones, such as 1-benzoylazepan-4-one, under Fisher-indole cyclization conditions as described, for example, in *"Indoles, Best Synthetic Methods"* (Academic Press, 1999, San Diego, Calif.) produces azepinoindoles (100). These compounds can be treated as described above to give azepinoindoles (88) and (89).

Figure 26:
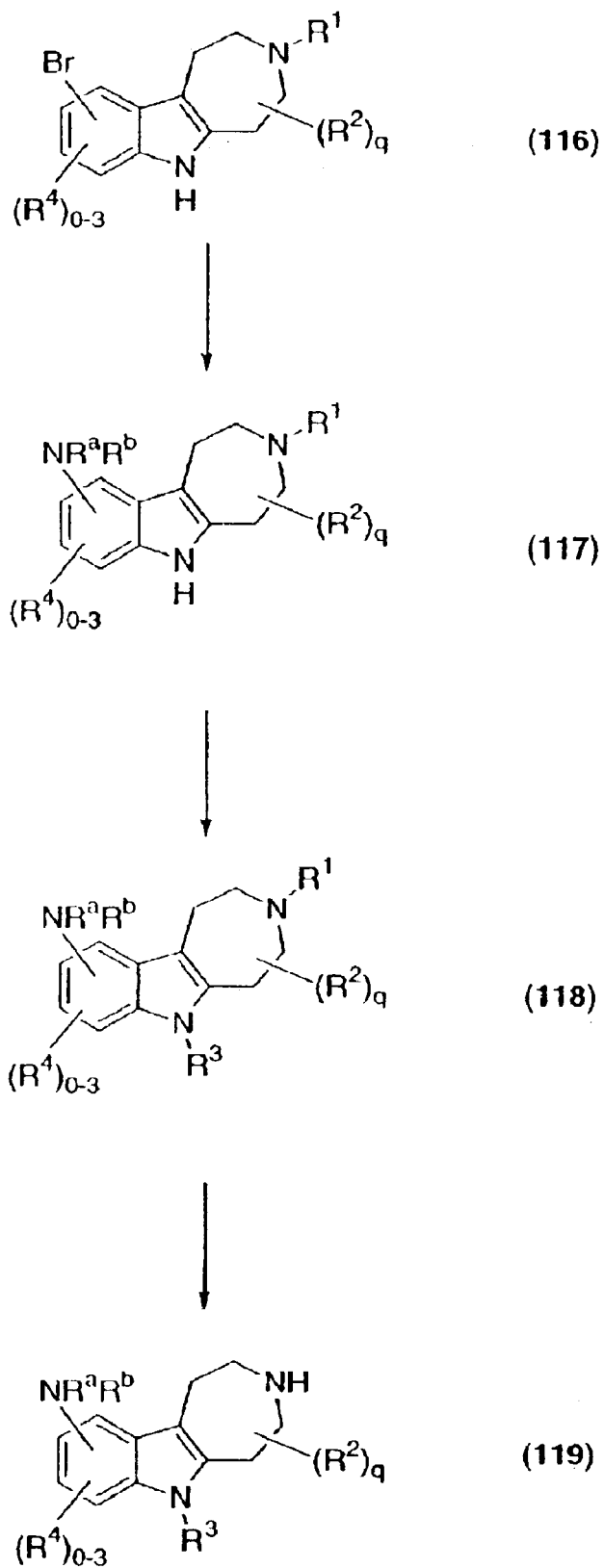

Intermediate (7, 8, 9, or 10-) aminoazepinoindoles (Formula (IV) wherein $R^4=NR^aR^b$), can be prepared by the reactions depicted in FIG. 26. As shown in FIG. 26, a (7, 8, 9, or 10-) bromoazepinoindole (116) is coupled with an amine via palladium catalysis (for example, see Buchwald et al, *J. Org. Chem.* 2000, 65, 1158–1174). When $R^3=H$, the final product (119) can then be generated by deprotection of compound (117) using the methods found in Green, T. W.; Wuts, P. G. M. Protective Groups in Organic Synthesis, $3^{rd}$ edition, 1999, John Wiley & Sons, Inc., New York. Alternatively, an $R^3$ group can be installed using the methods described above to give compound (118), which is then deprotected.

Figure 27:
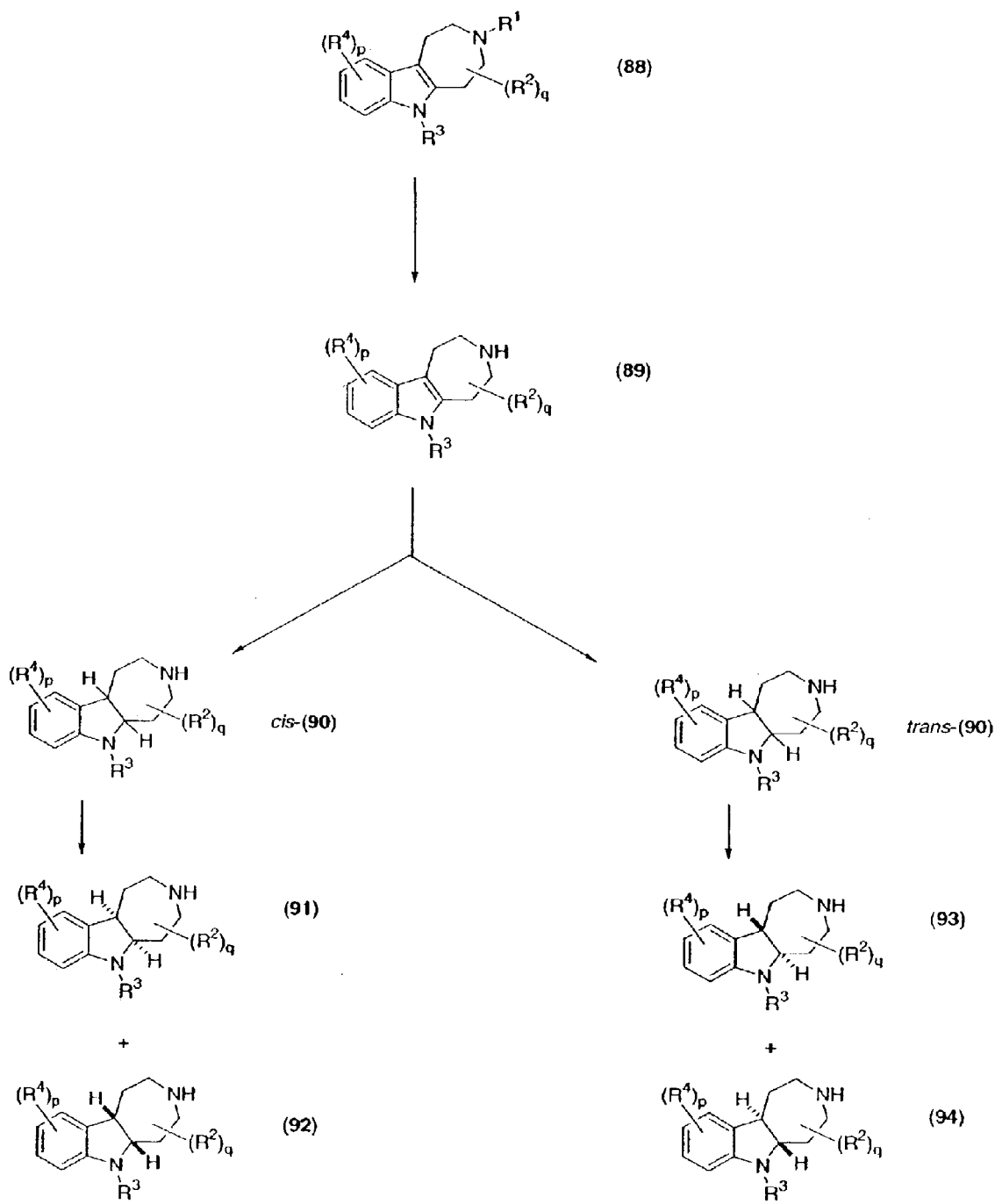

Compounds of Formula (I) can be prepared by the reaction scheme depicted in FIG. 27. Azepinoindoles (88) are known in the literature for $R^3=H$ (See *J. Med. Chem.*, 1968, 11, 101–106) or can be prepared as described herein. When $R^1$ is benzoyl, amines (89) can be obtained from basic hydrolysis (e.g., potassium hydroxide in ethylene glycol). Alternatively, when $R^1$ is Boc, amines (89) can be obtained under acidic conditions such as TFA in $CH_2Cl_2$. Reduction of (89) under conditions such as sodium cyanoborohydride (or sodium triacetoxyborohydride) in acidic solvents such as trifluoroacetic acid gives cis-azepinoindolines (90). Separation of cis-enantiomers (91) and (92) is carried out through resolution techniques know in the art, such as chromatographic resolution using a chiral stationary phase (normal or reverse phase) or using a traditional fractional crystallization of diastereomeric salts derived using readily-available chiral acids such as (d)- or (l)-tartaric acid or their derivatives (see for example Kinbara, et al, *J. Chem. Soc., Perkin Trans.*, 2, 1996, 2615 and Tomori, et al *Bull. Chem. Soc. Jpn.*, 1996, 3581). Reduction of (89) under conditions such as treatment with borane-tetrahydrofuran complex followed by water and trifluoroacetic acid (see for example *Tetrahedron Letters*, 1982, 23, 1983–1984) gives trans-azepinoindolines (90). Resolution of trans-enantiomers (93) and (94) is carried out as described above for the cis-isomers.

Figure 28:
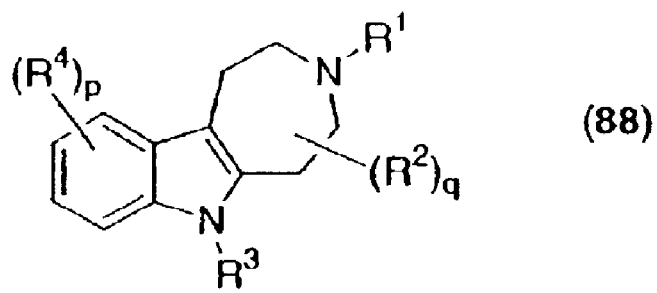
Figure 28:
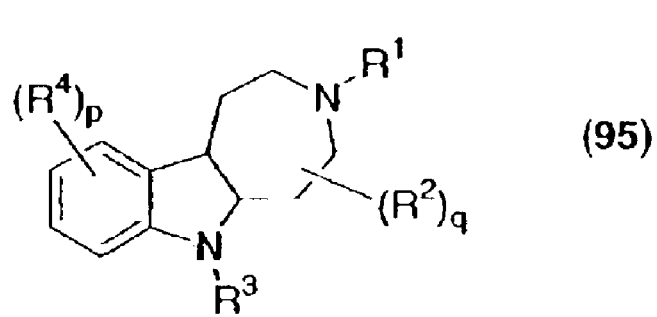
Figure 28:
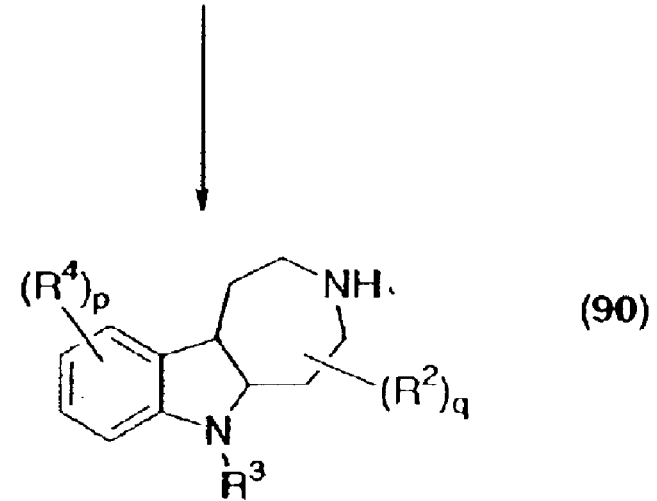

Compounds of Formula (I) also can be prepared by the reaction scheme depicted in FIG. 28. Reduction of the azepinoindoles (88) with suitable reducing agents, such as sodium cyanoborohydride in TFA/MeOH, yields a separable mixture of cis-and trans-azepinoindolines (95). When $R^1$ is benzoyl, deprotected azepinoindolines (90) can be obtained from basic hydrolysis (e.g., potassium hydroxide in ethylene glycol). Alternatively, when $R^1$ is Boc, deprotected azepinoindolines (90) can be obtained under acidic conditions such as TFA in $CH_2Cl_2$. If desired, resolution of (90) or (95) may be carried out as described above.

Figure 29:
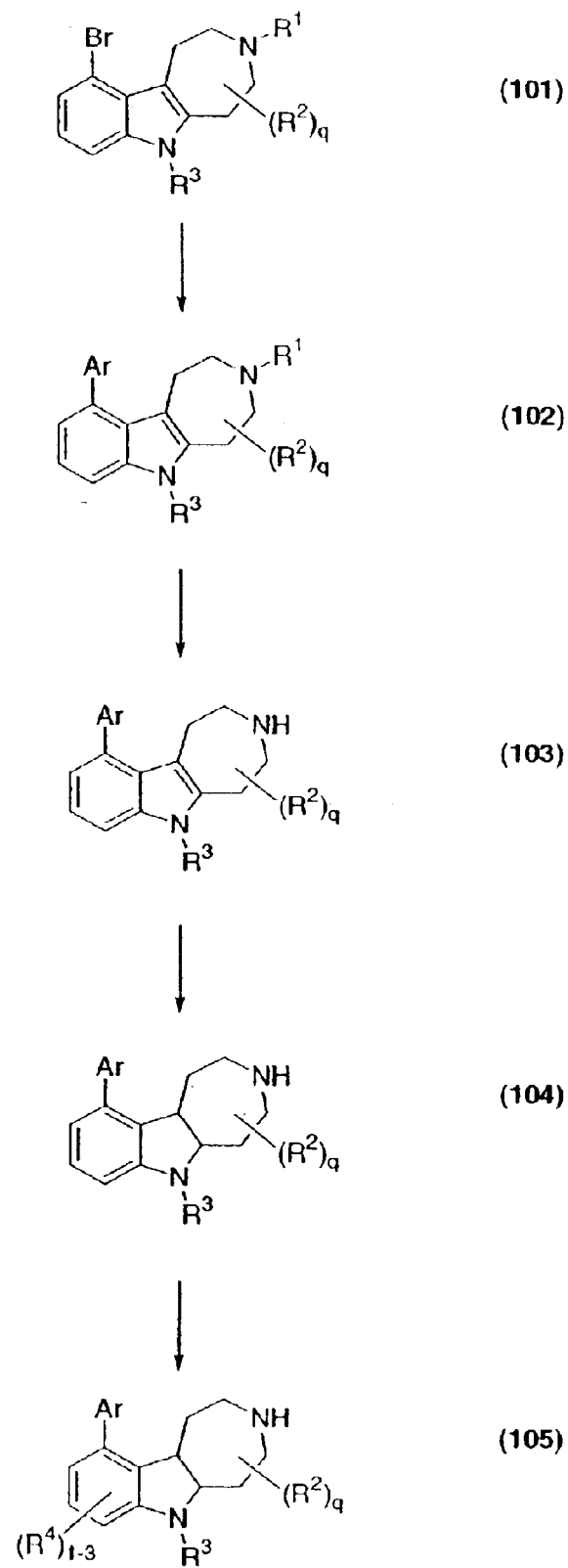

FIG. 29 shows yet another method for obtaining compounds of Formula (I). Bromoazepinoindoles (101) are competent partners for transition metal catalyzed coupling reactions with aryl boronic acids to give azepinoindoles (102) (for examples of the Suzuki reaction; see Miyaura, N., et al, *Chem. Rev.*, 1995, 2457 and referenced therein). Typically, the Suzuki reaction is carried out using a palladium catalyst (such as $Pd(PPh_3)_4$, $Pd(PPh_3)_2Cl_2$, $Pd(OAc)_2$, $Pd_2(dba)_3$, etc), a suitable ligand (such as $PPh_3$, $Pt-Bu_3$, $Pcy_3$, etc), a base (such as $Na_2CO_3$, $Cs_2CO_3$, amines, etc) in a solvent such as DMF, toluene, dioxane, or the like. Removal of the $R^1$ protecting group by the methods described above gives amines (103). Reduction of (103) with suitable reducing agents, such as sodium cyanoborohydride in TFA/MeOH, yields azepinoindolines (104). Further elaboration of (104), such as chloronation using NCS (for examples, see Larock, R. C., *Comprehensive Organic Transformations*, $2^{nd}$ edition, 1999, Wiley-VCH Publishers, New York), can be done to give more highly substituted azepinoindolines (105).

Figure 30:
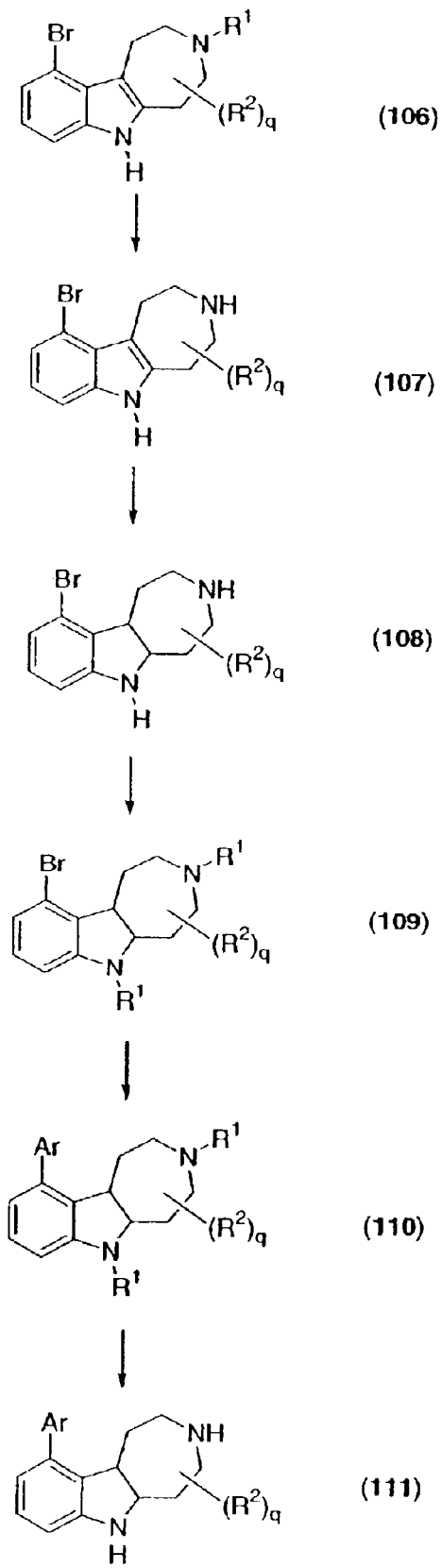

Compounds of Formula (I) can also be prepared as shown in FIG. 30. Bromoazepinoindolines (106) where $R^1$ is benzoyl are deprotected via basic hydrolysis (e.g., potassium hydroxide in ethylene glycol) to give amines (107). The reduction of (107) is accomplished with suitable reducing agents as described above to give azepinoindolines (108) which can then be protected to give (109) using, for example, excess di-tert-butyl dicarboxylate in THF/aqueous base (such as sodium hydroxide or potassium carbonate). Subjection of (109) to Suzuki reaction conditions as described above leads to azepinoindolines (110), which are deprotected to give amines (111). When $R^1$ is Boc, the deprotection can be accomplished via acidic conditions such as $TFA/CH_2Cl_2$ or treatment with acidic resin (for example, Dowex® 50WX2-400 ion-exchange resin).

Figure 31:
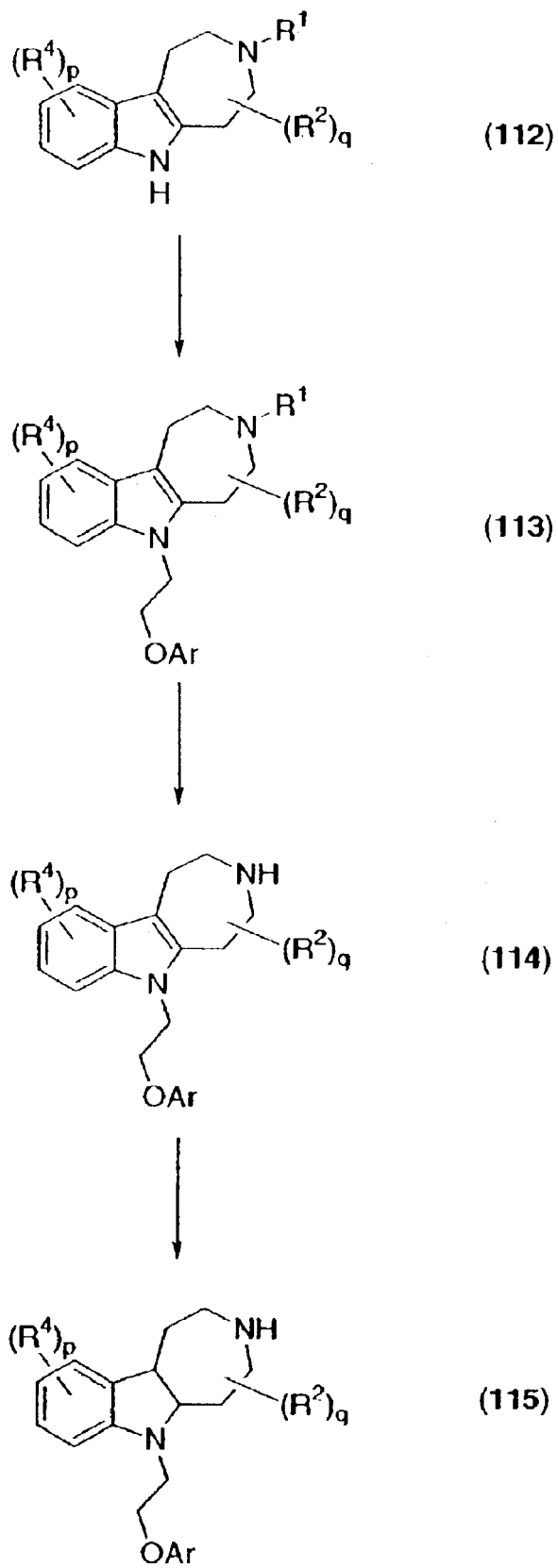

Compounds of Formula (I) can also be prepared following the sequence in FIG. 31. Azepinoindoles (112) are alkylated (for example, NaH and β-bromophenetole in DMF) to give 6-substituted azepinoindoles (113). These compounds are deprotected using the methods described above to give amines (114). Reduction of (114) with suitable reducing agents as described above leads to azepinoindolines (115).

Figure 32:
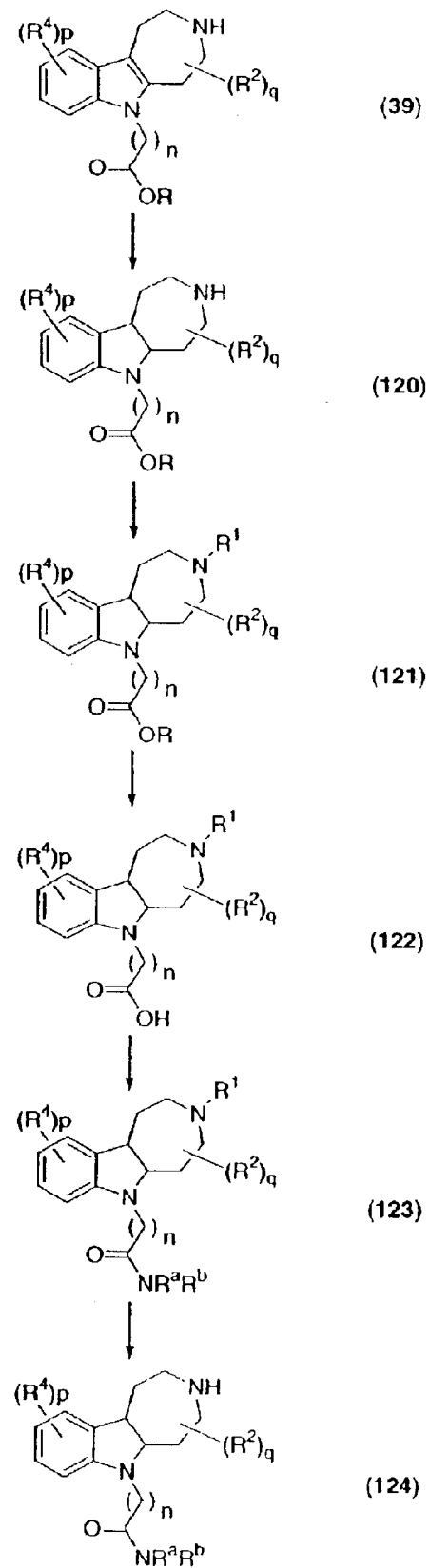

Compounds of Formula (1) can also be prepared as shown in FIG. 32. Ester-containing azepinoindole (39) is reduced to azepinoindoline (120) using suitable agents, such as sodium cyanoborohydride in TFA/MeOH. The protecting group $R^1$ is introduced to give compound (121) using standard conditions (such as those described in Green, T. W.; Wuts, P. G. M. Protective Groups in Organic Synthesis, $3^{rd}$ edition, 1999, John Wiley & Sons, Inc., New York). The ester is hydrolyzed to the acid (122) using basic conditions such as KOH in THF/H$_2$O. Amide (123) is prepared from acid (122) and an amine under coupling conditions such as EEDQ in THF or a carbodiimide with base in THF. Finally, removal of R$^1$ (using the methods such as those found in Green, T. W.; Wuts, P. G. M. Protective Groups in Organic Synthesis, 3$^{rd}$ edition, 1999, John Wiley & Sons, Inc., New York) gives amide-containing azepinoindoline (124).

The phrases "pharmaceutically acceptable salts" or "a pharmaceutically acceptable salt thereof" refer to salts prepared from pharmaceutically acceptable acids or bases, including organic and inorganic acids and bases. Salts can be prepared from pharmaceutically acceptable acids. Pharmaceutically acceptable salts can be obtained using standard procedures known by those skilled in the art, for example by reacting a sufficiently basic compound, such as an amine, with a suitable acid affording a physiologically acceptable anion. Suitable pharmaceutically acceptable acids include acetic, benzenesulfonic (besylate), benzoic, p-bromophenylsulfonic, camphorsulfonic, carbonic, citric, ethanesulfonic, fumaric, gluconic, glutamic, hydrobromic, hydrochloric, hydroiodic, isethionic, lactic, maleic, malic, mandelic, methanesulfonic (mesylate), mucic, nitric, oxalic, pamoic, pantothenic, phosphoric, succinic, sulfuric, tartaric, p-toluenesulfonic, and the like. Examples of such pharmaceutically acceptable salts, thus, include, but are not limited to, acetate, benzoate, β-hydroxybutyrate, bisulfate, bisulfite, bromide, butyne-1,4-dioate, carpoate, chloride, chlorobenzoate, citrate, dihydrogenphosphate, dinitrobenzoate, fumarate, glycollate, heptanoate, hexyne-1,6-dioate, hydroxybenzoate, iodide, lactate, maleate, malonate, mandelate, metaphosphate, methanesulfonate, methoxybenzoate, methylbenzoate, monohydrogenphosphate, naphthalene-1-sulfonate, naphthalene-2-sulfonate, oxalate, phenylbutyrate, phenylproionate, phosphate, phthalate, phylacetate, propanesulfonate, propiolate, propionate, pyrophosphate, pyrosulfate, sebacate, suberate, succinate, sulfate, sulfite, sulfonate, tartrate, xylene sulfonate, and the like. The compounds of the Formula (I) also can provide pharmaceutically acceptable metal salts, in particular alkali metal (e.g., sodium, potassium, magnesium, or lithium) salts and alkaline earth metal (e.g., calcium) salts, with bases.

Compounds of Formula (I) are useful in treating diseases, disorders, and conditions of the central nervous system occurring in mammals. Typically, the mammal is a human being, but the compounds can be used to treat other animals such as livestock, pets, or other animals.

It is to be understood that "a compound of Formula (I)," or a pharmaceutically acceptable (acidic or basic) salt or solvate (i.e., hydrate) thereof, can be administered as the neat compound, or as a pharmaceutical composition containing the compound in combination with a suitable excipient. Such pharmaceutical compositions can be prepared by methods and contain excipients which are known by those skilled in the art. A generally recognized compendium of such methods and ingredients is *Remington's Pharmaceutical Sciences* by E. W. Martin (Mark Publ. Co., 15th Ed., 1975), the disclosure of which is incorporated herein by reference. In cases where a compound is sufficiently basic or acidic to form a stable pharmaceutically acceptable salt, administration of the compounds as a salt may be preferred.

The compounds of this invention can be administered in oral unit dosage forms, such as aerosol sprays, buccal tablets, capsules, elixirs, pills, sachets, suspensions, syrups, tablets, troches, wafers, and the like. The compounds also can be administered parenterally, (e.g., subcutaneously, intravenously, intramuscularly, or by intraperitoneal injection), using forms known in the pharmaceutical art. The compounds further can be administered rectally or vaginally, in such forms as suppositories or bougies, transdermally, such as with a "patch" containing active ingredient, or nasally (i.e., by inhalation).

In general, the preferred route of administration of a present compound is oral. For oral administration, the active compound can be combined with one or more excipients and used in the form of ingestible aerosol sprays, buccal tablets, capsules, elixirs, pills, sachets, suspensions, syrups, tablets, troches, wafers, and the like. Such compositions and preparations typically contain at least 0.1% of active compound. The percentage of the compounds in these preparations can be varied, e.g., about 0.01 to about 60% of the weight of a given unit dosage form. The amount of active compound in such orally administered compositions is sufficient to provide an effective dosage level.

The aerosol sprays, buccal tablets, capsules, elixirs, pills, sachets, suspensions, syrups, tablets, troches, wafers, and the like also can contain one or more binders, diluents disintegrating agents, excipients, lubricants, sweetening agents, or flavoring agents. Suitable binders include, for example, gum arabic, tragacanth, acacia, polyvinylpyrrolidone, corn starch, methylcellulose, or gelatin. Suitable diluents include, for example, lactose, dextrose, sucrose, mannitol, sorbitol, and cellulose. Suitable disintegrating agents include, for example, starches, alginic acid, and alginates. Suitable excipients include dicalcium phosphate. Suitable lubricants include, for example, silica, talc, stearic acid, magnesium or calcium stearate, and/or polyethylene glycols. Suitable wetting agents include, for example, lecithin, polysorbates, and laurylsulfates. Generally, any effervescing agents, dyestuffs, and/or sweeteners known by those of ordinary skill in the art can be used in the preparation of a pharmaceutical composition. For example, suitable sweetening agents include sucrose, fructose, lactose or aspartame, and suitable flavoring agents include peppermint, oil of wintergreen, or cherry flavoring. The aforementioned ingredients are merely representative and one skilled in the art can envision other binders, excipients, sweetening agents, and the like.

When the unit dosage form is a capsule, it can contain, in addition to ingredients of the above type, a liquid carrier (e.g., vegetable oil or a polyethylene glycol). Various other ingredients can be present as coatings or to otherwise modify the physical form of the solid unit dosage form. For instance, tablets, pills, or capsules may be coated with gelatin, wax, shellac, or sugar, and the like. A syrup or elixir can contain the active compound, sucrose or fructose as a sweetening agent, methyl and propyl parabens as preservatives, a dye and flavoring, such as cherry or orange flavor. Any material used in preparing any unit dosage form should be pharmaceutically acceptable and substantially non-toxic in the amounts employed. In addition, the active compound can be incorporated into sustained-release preparations and devices including, but not limited to, those relying on osmotic pressures to obtain a desired release profile (e.g., the OROS drug delivery devices as designed and developed by Alza Corporation, Mountain View, Calif.).

Orally administered compositions can be prepared by any method that includes the step of bringing the active compound into intimate association with a carrier, which constitutes one or more necessary or desirable ingredients. Generally, the compositions are prepared by uniformly and intimately admixing the active ingredient with liquid carriers, finely divided solid carriers, or both, and then, if necessary, shaping the product into a desired form.

For example, a tablet can be prepared by compression or molding techniques, optionally, using one or more accessory ingredients. Compressed tablets can be prepared by compressing the active ingredient in a suitable machine into a free-flowing form, such as a powder or granules. Thereafter, the compressed, free-flowing form optionally can be mixed with binders, diluents, lubricants, disintegrating agents, effervescing agents, dyestuffs, sweeteners, wetting agents, and non-toxic and pharmacologically inactive substances typically present in pharmaceutical compositions. The pharmaceutical composition can contain about 5 to about 95%, and preferably about 25 to about 90%, of a compound of the present invention. Molded tablets can be made by molding a mixture of the powdered compound moistened with an inert liquid diluent in a suitable machine.

Oral administration is the most convenient route of administration and avoids the disadvantages associated with other routes of administration. For patients suffering from a swallowing disorder or from impairment of drug absorption after oral administration, the drug can be administered by other methods, such as parenterally, rectally or vaginally, transdermally, and nasally.

Parenteral administration is performed by preparing the composition containing the active compound. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for parenteral administration (e.g., subcutaneously, intravenously, intramuscularly, or by intraperitoneal injection or infusion) can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage.

The liquid carrier or vehicle can be a solvent or liquid dispersion medium comprising, for example, water, ethanol, a polyol (e.g., glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be achieved by various antibacterial and antifungal agents, for example, parabens, chlorobutanol, phenol, sorbic acid, thimerosal, and the like. In many cases, it is preferable to include isotonic agents, for example, sugars, buffers, or sodium chloride. Prolonged absorption of the injectable compositions can be achieved by use of agents that delay absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions. Sterilization of the powders also can be accomplished through irradiation and aseptic crystallization methods known to persons skilled in the art.

For parenteral administration, the active compounds are presented in aqueous solution in a concentration of about 0.1 to about 10%, more preferably about 0.1 to about 7%, by weight. The solution can contain other ingredients, such as emulsifiers, antioxidants, or buffers.

For topical administration, the present compounds can be applied in neat form, e.g., when the compound is a liquid. However, it is desirable to administer the compounds to the skin as compositions in combination with a dermatologically acceptable carrier, which can be a solid, semi-solid, or a liquid. Useful solid carriers include, but are not limited to, finely divided solids such as talc, clay, microcrystalline cellulose, silica, alumina, and the like. Useful liquid carriers include, but are not limited to, water, alcohols, glycols, and water-alcohol/glycol blends, in which the present compounds can be dissolved or dispersed at effective levels, optionally with the aid of a surfactant. Adjuvants, such as fragrances and additional antimicrobial agents, can be added to optimize the properties for a given use. The resultant liquid compositions can be applied topically by absorbent pads, used to impregnate bandages and other dressings, or sprayed onto the affected area using pump-type or aerosol sprayers.

For administration by inhalation, compounds of the present invention can be delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges for use in an inhaler or insufflator can be formulated containing a powder mix of the compound and a suitable powder base, such as lactose or starch.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Generally, compounds of the invention are serotonin receptor (5-HT) ligands. The ability of a compound of the invention to act as a 5-HT receptor agonist, partial agonist, or antagonist can be determined using in vitro and in vivo assays that are known in the art. The invention provides compounds of Formula (I) that act as either agonists, partial agonists, or as antagonists of one or more 5-HT receptor subtypes.

As used herein, the terms "treat," "treatment," and "treating," extend to prophylaxis, in other words "prevent," "prevention," and "preventing," lowering, stopping, or reversing the progression or severity of the condition or symptoms being treated. As such, the term "treatment" includes both medical therapeutic and/or prophylactic administration, as appropriate. The terms "prevent," "prevention," and "preventing" refer to an administration of the pharmaceutical composition to a person who has in the past suffered from the aforementioned diseases, disorders, or conditions, such as migraine headaches, but is not suffering from the diseases, disorders, or conditions at the time of the composition's administration.

Compounds and pharmaceutical compositions suitable for use in the present invention include those wherein the active ingredient is administered in an effective amount to achieve its intended purpose. More specifically, a "therapeutically effective amount" means an amount effective to treat the disease, disorder, and/or condition. Determination of a therapeutically effective amount is well within the capability of persons skilled in the art, especially in light of the detailed disclosure provided herein.

A "therapeutically effective dose" refers to that amount of the compound that results in achieving the desired treatment (or effect). Therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary within this range depending upon the dosage form employed, and the route of administration utilized.

The dosage regimen and amount for treating patients with the compounds of this invention is selected in accordance with a variety of factors including, for example, the type, age, weight, sex, and medical condition of the patient, the severity of the condition, and the route of administration. An ordinarily skilled physician or psychiatrist can readily determine and prescribe an effective amount of the compound to prevent or arrest the progress of the condition. In so proceeding, the physician or psychiatrist can employ relatively low initial dosages and subsequently increasing the dose until a maximum response is obtained.

The compound is administered in unit dosage form, for example, containing about 0.05 to about 500 mg, preferably about 0.1 to about 250 mg, and more preferably about 1 to about 150 mg, of active ingredient per unit dosage form. The desired dose can be presented in a single dose, or as divided doses administered at appropriate intervals, for example, as two, three, four or more sub-doses per day. The sub-dose itself can be further divided, e.g., into a number of discrete loosely spaced administrations.

The compositions can be administered orally, sublingually, transdermally, or parenterally at dose levels of about 0.01 to about 150 mg/kg, preferably about 0.1 to about 50 mg/kg, and more preferably about 0.1 to about 10 mg/kg of mammal body weight.

The exact regimen for administration of the compounds and compositions disclosed herein necessarily depends upon the needs of the individual subject being treated, the patient type (i.e., human or animal), the type of treatment and, of course, the judgment of the attending practitioner or physician. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

Specifically, for administration to a human in the curative or prophylactic treatment of the diseases, disorders, and conditions identified above, oral dosages of a compound of Formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required.

For veterinary use, a compound of Formula (I), or a nontoxic salt thereof, is administered as a suitably acceptable formulation in accordance with normal veterinary practice. The veterinarian can readily determine the dosing regimen and route of administration that is most appropriate for a particular animal.

In a particular embodiment, the invention includes a pharmaceutical composition for the curative or prophylactic treatment of diseases, disorders, and conditions, where modulation of 5-HT receptor function is desired, the composition comprising a therapeutically effective amount of a compound of Formula (I), or a pharmaceutically acceptable salt thereof, together with a pharmaceutically acceptable diluent or carrier.

Another embodiment of the present invention provides a method of treating the above-noted diseases, disorders, and conditions in a human or mammal body which comprises administering to said body a therapeutically effective amount of a compound of Formula (I).

According to another embodiment of the present invention, there is provided a compound of Formula (I) or a pharmaceutically acceptable salt thereof for use in medical therapy or diagnosis.

According to another embodiment of the present invention, there is provided the use of a compound of Formula (I) for the manufacture of a medicament for the treatment of the above-noted diseases, conditions, and disorders.

EXAMPLES

The following examples and preparations are provided to illustrate the invention but are not intended to limit the scope of the invention.

The following abbreviations, and others known to those skilled in the art, are used hereafter in the accompanying examples: μM (micromolar), Bn (benzyl), Bz (benzoyl), cm (centimeter), $CH_2Cl_2$ (dichloromethane), DIC (diisopropylcarbodiimide), DMAP (4-dimethylaminopyridine), DMF (N,N-dimethylformamide), LAH (lithium aluminum hydride), DMSO (dimethyl sulfoxide), $Et_3N$ (triethylamine), EtOAc (ethyl acetate), g (gram), IR (infrared), KBr (potassium bromide), mp (melting point), MeOH (methanol), $MgSO_4$ (magnesium sulfate), MHz (megahertz), h (hour), min (minute), mL (milliliter), mmol (millimole), NMR (nuclear magnetic resonance), psi (pounds per square inch), and THF (tetrahydrofuran).

Examples 1–350 illustrate the preparation of intermediate compounds of formula (IV), which are useful for preparing compounds of Formula (I).

Examples 351–465 illustrate the preparation of representative compounds of Formula (I).

EXAMPLES 1–350

Preparation 1

Preparation of 3-benzoyl-7-phenyl-1,2,3,4,5,6-hexahydroazepino[4,5-b]indole

A mixture of 3-benzoyl-7-bromo-1,2,3,4,5,6-hexahydroazepino[4,5-b]indole (0.517 g, 1.40 mmol), potassium carbonate (0.77 g, 5.60 mmol), phenylboronic acid (0.194 g, 1.54 mmol), tetrakis(triphenylphosphine) palladium (0.16 g, 0.14 mmol) in tetrahydrofuran (7.0 mL) and N,N-dimethylacetamide (7.0 mL) was stirred at room temperature overnight. The mixture was filtered through Celite and the filtrate concentrated in vacuo to give an oil, which was subjected to column chromatography (silica gel, 10–50% EtOAc/heptane) to afford 0.44 g (86%) of the title compound as a solid: mp 198–200° C.; 1H NMR (400 MHz, $CDCl_3$) δ 8.10, 7.67–7.60, 7.55–7.4, 7.47–7.33, 7.18–7.14, 4.04–3.96, 3.72–3.63, 3.20–3.12, 2.93–2.80; IR (drift) 3258, 1602, 1464, 1430, 1327, 1295, 1239, 1185, 930, 761, 749, 740, 711, 703, 696 cm$^{-1}$; MS (EI) m/z 366 (M$^+$); HRMS (FAB) calcd for $C_{25}H_{22}N_2O$+H: 367.1810, found: 367.1805; Anal. Calcd. for $C_{25}H_{22}N_2O$: C, 81.94; H, 6.05; N, 7.64. Found: C, 81.37; H, 6.12; N, 7.57.

Preparation 2

Preparation of 3-benzoyl-8-phenyl-1,2,3,4,5,6-hexahydroazepino[4,5-b]indole

A mixture of 3-benzoyl-8-bromo-1,2,3,4,5,6-hexahydroazepino[4,5-b]indole (1.48 g, 4.00 mmol) and tetrakis(triphenylphosphine)palladium (0.46 g, 0.40 mmol) in dimethoxyethane (10.0 mL) and a solution of phenylboronic acid (0.60 g, 4.80 mmol) in dimethoxyethane (10.0 mL) and sodium carbonate (2 M, 12.0 mL) were reacted in a manner similar to Preparation 1 to give a brown foam. Column chromatography (silica gel, 20–50% EtOAc/heptane) afforded 0.53 g (36%) of the title compound as a solid: mp 213–232° C.; $^1$H NMR (400 MHz, CDCl$_3$) δ 8.13, 7.61, 7.44–7.40, 7.34–7.29, 4.07–3.98, 3.70–3.63, 3.21–3.13, 2.92–2.83; $^{13}$C NMR (100 MHz, CDCl$_3$) δ 171.7, 142.3, 137.0, 135.9, 135.3, 134.9, 129.3, 128.7, 128.6, 128.3, 127.3, 126.5, 126.4, 119.3, 117.7, 110.3, 109.0, 51.4, 45.8, 29.1, 26.2; IR (drift) 3262, 1602, 1466, 1432, 1323, 1291, 1243, 811, 781, 763, 751, 743, 707, 699, 627 cm$^{-1}$; MS (EI) m/z 366 (M$^+$); HRMS (FAB) calcd for $C_{25}H_{22}N_2O$+H: 367.1810, found: 367.1813; Anal. Calcd for $C_{25}H_{22}N_2O$: C, 81.94; H, 6.05; N, 7.64. Found: C, 81.43; H, 6.20; N, 7.42.

Preparation 3

Preparation of 3-benzoyl-9-phenyl-1,2,3,4,5,6-hexahydroazepino[4,5-b]indole

A mixture of 3-benzoyl-9-bromo-1,2,3,4,5,6-hexahydroazepino[4,5-b]indole (1.477 g, 4.00 mmol) and tetrakis(triphenylphosphine)palladium (0.462 g, 0.40 mmol) in dimethoxyethane (15.0 mL) and a solution of phenylboronic acid (0.585 g, 4.80 mmol) in dimethoxyethane (5.0 mL) and sodium carbonate (2 M, 12.0 mL) were reacted in a manner similar to Preparation 1. Column chromatography (silica gel, 60% EtOAc/hexane) afforded 0.817 g (56%) of the title compound as a solid: mp 78–79° C.; $^1$H NMR (300 MHz, CDCl$_3$) δ 8.10–7.85, 7.71–7.57, 7.43–7.29, 7.18–7.05, 4.16–4.04, 3.70–3.65, 3.20–3.05, 2.95–2.80; MS (ESI+) m/z 367 (M$^+$+H).

Preparation 4

Preparation of 3-benzoyl-9-(4-methoxyphenyl)-1,2,3,4,5,6-hexahydroazepino[4,5-b]indole A mixture of 3-benzoyl-9-bromo-1,2,3,4,5,6-hexahydroazepino[4,5-b]indole (0.738 g, 2.0 mmol) and tetrakis(triphenylphosphine)palladium (0.23 g, 0.20 mmol) in dimethoxyethane (5.0 mL) and a solution of 4-methoxyphenylboronic acid (0.365 g, 2.4 mmol) in dimethoxyethane (5.0 mL) and sodium carbonate solution (2 M, 7.0 mL) were reacted in a manner similar to Preparation 1. Column chromatography (silica gel, 20–60% EtOAc/heptane) afforded 0.29 g (37%) of the title compound as a yellow foam: mp 140–145° C.; $^1$H NMR (300 MHz, CDCl$_3$) δ 7.92, 7.59–7.49, 7.43, 7.37–7.30, 7.03–6.94, 4.09–3.98, 3.85, 3.75–3.65, 3.25–3.14, 2.95–2.85.

Preparation 5

Preparation of 3-benzoyl-10-phenyl-1,2,3,4,5,6-hexahydroazepino[4,5-b]indole

A mixture of 3-benzoyl-10-bromo-1,2,3,4,5,6-hexahydroazepino[4,5-b]indole (0.517 g, 1.40 mmol), potassium carbonate (0.77 g, 5.60 mmol), phenylboronic acid (0.194 g, 1.54 mmole), tetrakis(triphenylphosphine) palladium (0.16 g, 0.14 mmol) in tetrahydrofuran (7.0 mL) and N,N-dimethylacetamide (7.0 mL) reacted in a manner similar to Preparation 1. Column chromatography (silica gel, 10–50% EtOAc/heptane) afforded 0.49 g (95%) of the title compound as a solid: mp 223–226° C.; $^1$H NMR (400 MHz, CDCl$_3$) δ 8.25, 7.57–7.23, 7.18–7.12, 6.98–6.89, 4.02–3.93, 3.76–3.67, 3.65–3.56, 3.43–3.35, 3.18–3.12, 2.90–2.83, 2.66–2.58, 2.43–2.34; IR (drift) 3231, 3203, 1602, 1501, 1468, 1433, 1352, 1336, 1249, 786, 758, 746, 740, 706, 700 cm$^{-1}$; MS (EI) m/z 366 (M$^+$); Anal. Calcd for $C_{25}H_{22}N_2O$: C, 81.94; H, 6.05; N, 7.64. Found: C, 81.75; H, 6.07; N, 7.61.

Preparation 6

Preparation of 3-benzoyl-10-(2-fluorophenyl)-1,2,3,4,5,6-hexahydroazepino[4,5-b]indole A mixture of 3-benzoyl-10-bromo-1,2,3,4,5,6-hexahydroazepino[4,5-b]indole (0.738 g, 2.0 mmol) and tetrakis(triphenylphosphine)palladium (0.23 g, 0.20 mmol) in dimethoxyethane (5.0 mL) and a solution of 2-fluorophenylboronic acid (0.336 g, 2.4 mmol) in dimethoxyethane (5.0 mL) and sodium carbonate (2 M, 7.0 mL) were-reacted in a manner similar to Preparation 1. Column chromatography (silica gel, 20–50% EtOAc/heptane) afforded 0.33 g (43%) of the title compound as a solid: mp 241–244° C.; $^1$H NMR (400 MHz, CDCl$_3$) δ 8.20, 8.04, 7.31, 7.15, 7.04, 3.96, 3.83, 3.62, 3.42, 3.14, 2.84, 2.71–2.69, 2.47, 2.31; IR (drift) 3236, 1603, 1501, 1485, 1469, 1456, 1434, 1249, 1217, 795, 786, 759, 746, 733, 706 cm$^{-1}$; MS (EI) m/z 384 (M$^+$); HRMS (FAB) calcd for $C_{25}H_{21}FN_2O$+H: 385.1716, found: 385.1721; Anal. Calcd for $C_{25}H_{21}FN_2O$: C, 78.10; H, 5.51; N, 7.29. Found: C, 77.61; H, 5.60; N, 7.14.

Preparation 7

Preparation of 3-benzoyl-10-(3,5-difluorophenyl)-1,2,3,4,5,6-hexahydroazepino[4,5-b]indole A mixture of 3-benzoyl-10-bromo-1,2,3,4,5,6-hexahydroazepino[4,5-b]indole (0.923 g, 2.5 mmol) and tetrakis(triphenylphosphine)palladium (0.29 g, 0.25 mmol) in dimethoxyethane (10.0 mL) and a solution of 3,5-difluorophenylboronic acid (0.95 g of a 50% by weight solution in THF/H$_2$O, 3.0 mmol) and sodium carbonate (2 M, 12.0 mL) were reacted in a manner similar to Preparation 1. Column chromatography (silica gel, 1–5% MeOH/CHCl$_3$) afforded 1.03 g (100%) of a white solid: mp 198–201° C.; $^1$H NMR (400 MHz, CDCl$_3$) δ 8.32, 7.40–7.28, 7.14, 6.98–6.80, 6.80–6.70, 4.04–3.94, 3.83–3.73, 3.65–3.58, 3.60–3.50, 3.20–3.13, 2.94–2.84, 2.71–2.60, 2.45–2.36; R (drift) 3235, 3211, 1607, 1466, 1431, 1336, 1291, 1117, 984, 864, 789, 751, 737, 704, 698 cm$^{-1}$; MS (EI) m/z 402 (M$^+$); Anal. Calcd for $C_{25}H_{20}F_2N_2O$: C, 74.61; H, 5.01; N, 6.96. Found: C, 74.57; H, 5.05; N, 6.99.

EXAMPLE 1

Preparation of 3-benzyl-7-phenyl-1,2,3,4,5,6-hexahydroazepino[4,5-b]indole

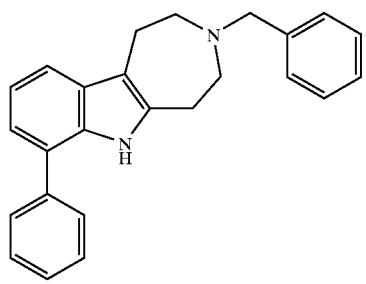

To a solution of lithium aluminum hydride (1.27 g, 33.5 mmol) in tetrahydrofuran (10.0 mL) was added a solution of 3-benzoyl-7-phenyl-1,2,3,4,5,6-hexahydroazepino[4,5-b]indole (1.27 g, 3.46 mmol) in tetrahydrofuran (25.0 mL) at 0° C. The mixture was stirred at room temperature overnight. Water (1.3 mL), 15% sodium hydroxide solution (1.3 mL) and water (3.9 mL) were added sequentially and the mixture was stirred for 30 min. Celite was added and the mixture was filtered through Celite. The filtrate was concentrated in vacuo to give 1.12 g (92%) of the title compound: mp 78–79° C.; $^1$H NMR (400 MHz, CDCl$_3$) δ 7.92, 7.62, 7.51–7.26, 7.19–7.11, 3.83, 3.00–2.90; $^{13}$C NMR(100 MHz, CDCl$_3$) δ 139.5, 139.3, 136.5, 132.4, 129.4, 129.1, 128.9, 128.3, 128.2, 127.2, 127.0, 124.8, 121.0, 119.8, 117.0, 113.3, 60.7, 55.7, 53.8, 28.6, 24.0; IR (drift) 2933, 2913, 2907, 2885, 2813, 1458, 1367, 1345, 1336, 1325, 796, 760, 745, 730, 700 cm$^{-1}$; MS (EI) m/z 352 (M$^+$); Anal. Calcd for C$_{25}$H$_{24}$N$_2$: C, 85.19; H, 6.86; N, 7.95. Found: C, 85.00; H, 6.89; N, 7.93.

EXAMPLE 2

Preparation of 3-benzyl-8-phenyl-1,2,3,4,5,6-hexahydroazepino[4,5-b]indole

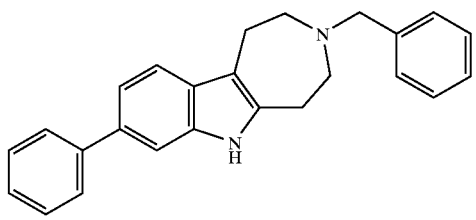

A solution of lithium aluminum hydride (1.40 g, 36.9 mmol) in tetrahydrofuran (15.0 mL) and a solution of 3-benzoyl-8-phenyl-1,2,3,4,5,6-hexahydroazepino[4,5-b]indole (1.40 g, 3.82 mmol) in tetrahydrofuran (30.0 mL) at 0° C. were reacted in a manner similar to Example 1 to give an oil. Column chromatography (silica gel, 20–30% EtOAc/heptane) afforded 1.22 g (90%) of the title compound as a white solid: mp 176–177° C.; $^1$H NMR (400 MHz, CDCl$_3$) δ 7.74, 7.63–7.61, 7.48, 7.45–7.40, 7.36, 3.84, 3.00–2.92; $^{13}$C NMR (100 MHz, CDCl$_3$) δ 142.5, 139.3, 136.9, 135.2, 134.5, 128.9, 128.6, 128.5, 128.3, 127.3, 127.0, 126.4, 119.1, 117.8, 112.8, 108.8, 60.7, 55.7, 53.8, 28.6, 23.9; IR (drift) 3385, 3371, 1467, 1344, 1328, 1120, 1027, 870, 820, 765, 756, 750, 735, 728, 698 cm$^{-1}$; MS (EI) m/z 352 (M$^+$); Anal. Calcd for C$_{25}$H$_{24}$N$_2$: C, 85.19; H, 6.86; N, 7.95. Found: C, 85.24; H, 6.89; N, 8.05.

EXAMPLE 3

Preparation of 3-benzyl-9-phenyl-1,2,3,4,5,6-hexahydroazepino[4,5-b]indole

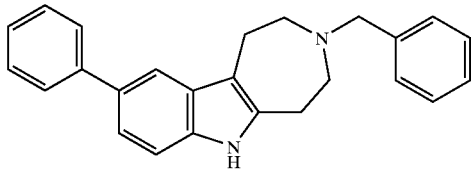

A solution of lithium aluminum hydride (0.17 g, 4.45 mmol) in tetrahydrofuran (3.0 mL) and a solution of 3-benzoyl-9-phenyl-1,2,3,4,5,6-hexahydroazepino[4,5-b]indole (0.17 g, 0.46 mmol) in tetrahydrofuran (5.0 mL) at 0° C. were reacted in a manner similar to Example 1 to give an oil. Column chromatography (silica gel, 10–50% EtOAc/heptane) afforded 0.113 g (71%) of the title compound as an oil. $^1$H NMR (300 MHz, CDCl$_3$) δ 8.05, 7.66–7.57, 7.49, 7.45–7.30, 7.13–7.04, 3.98, 3.18–2.97; MS (EI) m/z 366 (M$^+$); HRMS (FAB) calcd for C$_{25}$H$_{24}$N$_2$+H: 353.2018, found: 353.2021.

EXAMPLE 4

Preparation of 3-benzyl-9-(4-methoxyphenyl)-1,2,3,4,5,6-hexahydroazepino[4,5-b]indole

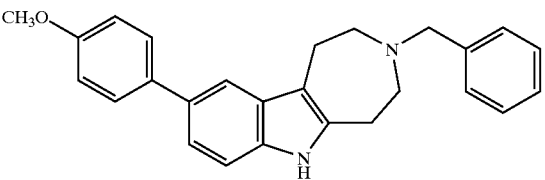

A solution of lithium aluminum hydride (0.26 g, 6.86 mmol) in tetrahydrofuran (5.0 mL) and a solution of 3-benzoyl-9-(4-methoxyphenyl)-1,2,3,4,5,6-hexahydroazepino[4,5-b]indole (0.257 g, 0.65 mmol) in tetrahydrofuran (5.0 mL) were reacted in a manner similar to Example 1 to give 0.26 g (100%) of the title compound as a white crystalline solid. $^1$H NMR (300 MHz, CDCl$_3$) δ 7.79, 7.58–7.54, 7.46–7.31, 6.97, 3.89, 3.85, 3.10–2.94.

EXAMPLE 5

Preparation of 3-benzyl-10-phenyl-1,2,3,4,5,6-hexahydroazepino[4,5-b]indole

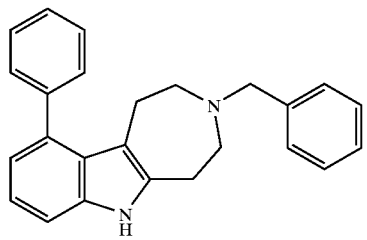

A solution of lithium aluminum hydride (0.73 g, 19.2 mmol) in tetrahydrofuran (10.0 mL) and a solution of 3-benzoyl-10-phenyl-1,2,3,4,5,6-hexahydroazepino[4,5-b]indole (0.73 g, 2.0 mmol) in tetrahydrofuran (20.0 mL) at 0° C. were reacted in a manner similar to Example 1 to give 0.67 g (96%) of the title compound as a white crystalline solid: mp 161–163° C.; $^1$H NMR (400 MHz, CDCl$_3$) δ 7.83, 7.43–7.23, 7.14–7.10, 6.91, 3.70, 2.93–2.90, 2.86–2.83, 2.65–2.62, 2.42–2.40; $^{13}$C NMR (100 MHz, CDCl$_3$) δ 142.0, 139.3, 137.2, 135.0, 134.7, 129.7, 128.9, 128.2, 127.6, 126.9, 126.6, 126.0, 121.6, 120.6, 113.6, 109.5, 61.8, 55.8, 53.4, 28.5, 25.9; IR (drift) 3407, 2810, 1454, 1377, 1347, 1334, 1319, 1175, 1120, 932, 785, 762, 754, 742, 700 cm$^{-1}$; MS (EI) m/z 352 (M$^+$); HRMS (FAB) calcd for C$_{25}$H$_{24}$N$_2$+H: 353.2018, found: 353.2039; Anal. Calcd for C$_{25}$H$_{24}$N$_2$: C, 85.19; H, 6.86; N, 7.95. Found: C, 84.83; H, 6.94; N, 7.83.

EXAMPLE 6

Preparation of 3-benzyl-10-(2-fluorophenyl)-1,2,3,4,5,6-hexahydroazepino[4,5-b]indole

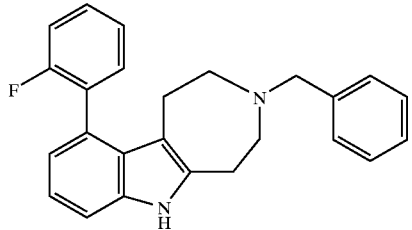

A solution of lithium aluminum hydride (0.25 g, 6.59 mmol) in tetrahydrofuran (5.0 mL) and a solution of 3-benzoyl-10-(2-fluorophenyl)-1,2,3,4,5,6-hexahydroazepino[4,5-b]indole (0.247 g, 0.642 mmol) in tetrahydrofuran (5.0 ml) were reacted in a manner similar to Example 1 to give 0.15 g (63%) of the title compound as pale yellow crystals: mp 157–159° C.; $^1$H NMR (400 MHz, CDCl$_3$) δ 7.86, 7.37–7.24, 7.18–7.10, 6.91, 3.72, 3.00–2.90, 2.75–2.61, 2.57–2.48, 2.42–2.33; $^{13}$C NMR (100 MHz, CDCl$_3$) δ 161.9, 159.4, 137.6, 135.3, 132.5, 130.0, 129.3, 128.7, 128.0, 127.5, 127.0, 124.1, 122.4, 121.0, 115.7, 115.4, 114.1, 110.7, 62.0, 56.1, 53.9, 28.8, 24.9; IR (drift) 3405, 2887, 2811, 1485, 1453, 1418, 1346, 1335, 1221, 1121, 924, 817, 782, 757, 740 cm$^{-1}$; MS (EI) m/z 370 (M$^+$); Anal. Calcd for C$_{25}$H$_{23}$FN$_2$: C, 81.05; H, 6.26; N, 7.56. Found: C, 80.82; H, 6.35; N, 7.47.

EXAMPLE 7

Preparation of 3-benzyl-10-(3,5-difluorophenyl)-1,2,3,4,5,6-hexahydroazepino[4,5-b]indole

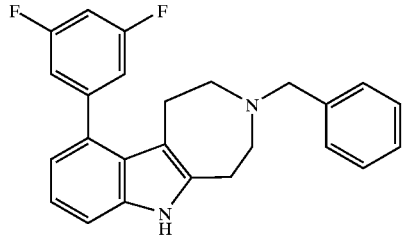

A solution of lithium aluminum hydride (0.60 g, 15.82 mmol) in tetrahydrofuran (5.0 mL) and a solution of 3-benzoyl-10-(3,5-difluoro)-1,2,3,4,5,6-hexahydroazepino[4,5-b]indole (0.64 g, 1.59 mmol) in tetrahydrofuran (5.0 mL) were reacted in a manner similar to Example 1 to give 0.20 g (32%) of the title compound as white crystals: mp 172–175° C.; 1H NMR (400 MHz, CDCl$_3$) δ 7.88, 7.37–7.23, 7.11, 6.95–6.93, 6.88, 6.81–6.75, 3.73, 2.95–2.92, 2.88–2.84, 2.70–2.67, 2.46–2.43; $^{13}$C NMR (100 MHz, CDCl$_3$) δ 163.3, 161.1, 145.4, 139.2, 137.8, 135.0, 132.2, 128.9, 128.7, 128.3, 127.0, 125.7, 121.3, 120.6, 113.2, 112.8, 112.5, 110.4, 61.9, 55.8, 53.4, 28.6, 26.0; IR (drift) 3405, 1619, 1590, 1455, 1350, 1334, 1117, 983, 865, 841, 793, 775, 755, 734, 700 cm$^{-1}$; Anal. Calcd for C$_{25}$H$_{22}$F$_2$N$_2$: C, 77.30; H, 5.71; N, 7.21. Found: C, 77.29; H, 5.81; N, 7.18.

EXAMPLE 8

Preparation of 7-phenyl-1,2,3,4,5,6-hexahydroazepino[4,5-b]indole

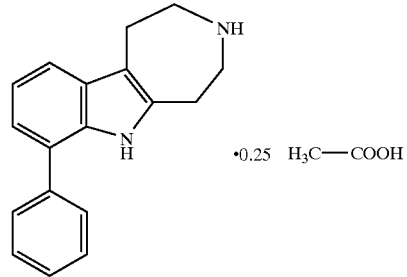

A mixture of 3-benzyl-7-phenyl-1,2,3,4,5,6-hexahydroazepino[4,5-b]indole (1.02 g, 2.89 mmol), glacial acetic acid (2 drops) and Pd/C (10%, 0.6 g) in ethanol (150 mL) was placed on a Parr hydrogenator under 50 psi of hydrogen and shaken for 10 h. The reaction mixture was then filtered through Celite and concentrated in vacuo to give 0.97 g of a brown oil. Column chromatography (silica gel, 10% MeOH/CHCl$_3$+1% NH$_4$OH) gave 0.58 g (76%) of a brown foam: mp 143–174° C.; $^1$H NMR (400 MHz, CDCl$_3$) δ 7.99, 7.64–7.61, 7.52–7.44, 7.40–7.36, 7.19–7.12, 3.12–3.06, 2.95–2.90; $^{13}$C NMR (100 MHz, CDCl$_3$) δ 139.5, 136.6, 132.4, 129.5, 129.1, 128.3, 127.3, 124.9, 121.0, 119.8, 117.0, 113.4, 50.4, 48.7, 32.9, 28.1; IR (drift) 3052, 3028, 2923, 2827, 1485, 1460, 1430, 1409, 1332, 1320, 1180, 795, 760, 743, 702 cm$^{-1}$; MS (EI) m/z 262 (M$^+$); HRMS (FAB) calcd for C$_{18}$H$_{18}$N$_2$+H: 263.1548, found: 263.1543; Anal. Calcd for C$_{18}$H$_{18}$N$_2$.0.25C$_2$H$_4$O$_2$: C, 80.11; H, 6.90; N, 10.10. Found: C, 79.80; H, 6.97; N, 10.17.

EXAMPLE 9

Preparation of 8-phenyl-1,2,3,4,5,6-hexahydroazepino[4,5-b]indole

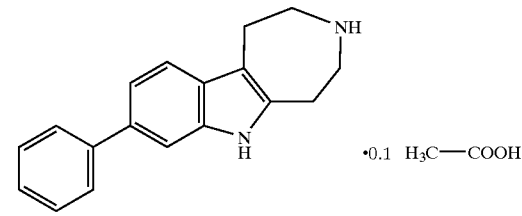

A mixture of 3-benzyl-8-phenyl-1,2,3,4,5,6-hexahydroazepino[4,5-b]indole (1.07 g, 3.0 mmol), glacial acetic acid (2 drops) and Pd/C (10%, 0.6 g) in ethanol (150 mL) was reacted in a manner similar to Example 8 to give 0.40 g (51%) of the title compound as a tan crystalline solid: mp 220–222° C.; $^1$H NMR (400 MHz, DMSO-d$_6$) δ 10.41, 7.61–7.59, 7.46, 7.42–7.38, 7.28–7.22, 3.04–3.01, 2.96–2.94, 2.87–2.84; $^{13}$C NMR (100 MHz, DMSO-d$_6$) δ 142.4, 138:2, 135.3, 133.0, 128.5, 128.4, 126.8, 126.0, 117.9, 117.5, 111.8, 108.8, 50.5, 48.8, 32.5, 28.0; IR (drift) 3305, 2929, 2918, 2893, 2827, 1468, 1324, 1242, 869, 814, 787, 762, 753, 743, 700 cm$^{-1}$; MS (EI) m/z 262 (M$^+$); HRMS (FAB) calcd for C$_{18}$H$_{18}$N$_2$+H: 263.1548, found: 263.1543; Anal. Calcd for C$_{18}$H$_{18}$N$_2$.0.1 C$_2$H$_4$O$_2$: C, 81.46; H, 6.91; N, 10.44. Found: C, 81.11; H, 7.01; N, 10.35.

EXAMPLE 10
Preparation of 9-phenyl-1,2,3,4,5,6-hexahydroazepino[4,5-b]indole

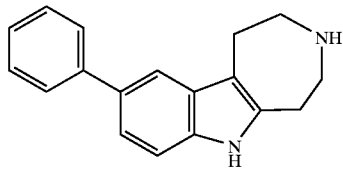

A mixture of 3-benzyl-9-phenyl-1,2,3,4,5,6-hexahydroazepino[4,5-b]indole (0.22 g, 0.62 mmol), glacial acetic acid-(2 drops) and Pd/C (10%, 0.15 g) in ethanol (50.0 mL) was reacted in a manner similar to Example 8 to give 0.13 g of an oil. Column chromatography (silica gel, 10–20% MeOH/CHCl$_3$+1% NH$_4$OH) gave an oil which precipitated from chloroform as a solid. Filtration gave 0.019 g (12%) of the title compound as a yellow-orange solid: mp >250° C.; $^1$H NMR (300 MHz, DMSO-d$_6$) δ 7.69–7.63, 7.41, 7.34, 7.29–7.23, 3.38–3.24, 3.20–3.07; MS (EI) m/z 262 (M$^+$); HRMS (FAB) calcd for C$_{18}$H$_{18}$N$_2$+H: 263.1548, found: 263.1550.

EXAMPLE 11
Preparation of 9-(4-methoxyphenyl)-1,2,3,4,5,6-hexahydroazepino[4,5-b]indole hydrochloride

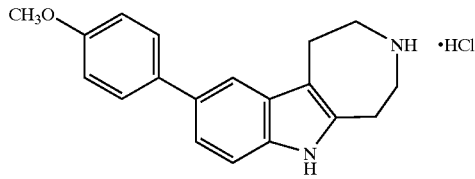

A mixture of 3-benzyl-9-(4-methoxyphenyl)-1,2,3,4,5,6-hexahydroazepino[4,5-b]indole (0.22 g, 0.62 mmol), 1 N hydrochloric acid (0.65 mL, 0.65 mmol) and Pd/C (10%, 0.24 g) in ethanol (50.0 mL) was reacted in a manner similar to Example 8 to give 0.168 g (80%) of a greenish solid: mp 258–260° C.; $^1$H NMR (400 MHz, DMSO-d$_6$) δ 11.08, 9.62, 7.64, 7.59, 7.31, 6.99, 3.79, 3.37–3.27, 3.22–3.12; IR (drift) 2986, 2957, 2921, 2893, 2829, 2752, 1514, 1476, 1456, 1273, 1250, 1239, 1180, 836, 800 cm$^{-1}$; MS (EI) m/z 292 (M$^+$); HRMS (FAB) calcd for C$_{19}$H$_{20}$N$_2$O+H: 293.1654, found: 293.1651; Anal. Calcd for C$_{19}$H$_{20}$N$_2$O. HCl: C, 69.40; H, 6.44; N, 8.52; Found: C, 68.37; H, 6.53; N, 8.27.

EXAMPLE 12
Preparation of 10-phenyl-1,2,3,4,5,6-hexahydroazepino[4,5-b]indole

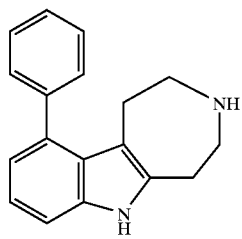

A mixture of 3-benzyl-10-phenyl-1,2,3,4,5,6-hexahydroazepino[4,5-b]indole (0.22 g, 0.62 mmol), glacial acetic acid (2 drops) and Pd/C (10%, 0.11 g) in ethanol (50.0 mL) was reacted in a manner similar to Example 8 to give 0.198 g (90%) of a brown foam. Crystallization from ethyl acetate gave 0.030 g of the title compound as a beige solid: mp >250° C.; $^1$H NMR (300 MHz, CDCl$_3$) δ 7.97, 7.48–7.36, 7.16, 6.94, 3.12–3.08, 3.02–2.98, 2.87–2.83, 2.47–2.43; IR (drift) 3053, 3025, 2927, 2895, 2833, 1458, 1428, 1415, 1335, 1292, 1262, 790, 760, 751, 703 cm$^{-1}$; MS (EI) m/z 262 (M$^+$); HRMS (FAB) calcd for C$_{18}$H$_{18}$N$_2$+H: 263.1548, found 263.1550.

EXAMPLE 13
Preparation of 10-(2-fluorophenyl)-1,2,3,4,5,6-hexahydroazepino[4,5-b]indole hydrochloride

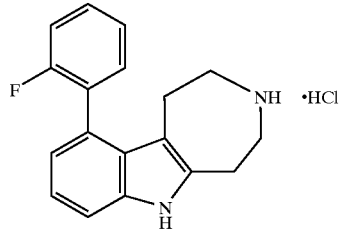

A mixture of 3-benzyl-10-(2-fluorophenyl)-1,2,3,4,5,6-hexahydroazepino[4,5-b]indole (0.11 g, 0.30 mmol), 1 N hydrochloric acid (0.3 mL, 0.3 mmol) and Pd/C (10%, 0.2 g) in ethanol (50.0 mL) was reacted in a manner similar to Example 8 to give 0.017 g of the title compound as a pale green solid: mp >259° C. (dec.); $^1$H NMR (300 MHz, DMSO-d$_6$) δ 11.29, 9.29, 7.51–7.41, 7.39–7.25, 7.08, 6.77, 3.33–3.20, 3.20–3.09, 3.09–2.99, 2.63–2.50; MS (EI) m/z 294 (M$^+$).

EXAMPLE 14
Preparation of 10-(3,5-difluorophenyl)-1,2,3,4,5,6-hexahydroazepino[4,5-b]indole hydrochloride

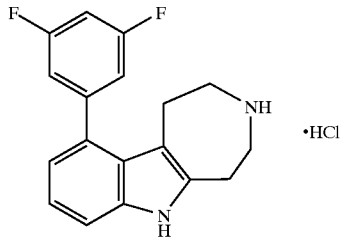

A mixture of 3-benzyl-10-(3,5-difluorophenyl)-1,2,3,4,5,6-hexahydroazepino[4,5-b]indole (0.35 g, 0.90 mmol), 1 N hydrochloric acid (0.9 mL, 0.9 mmol) and Pd/C (10%, 0.5 g) in ethanol (50 mL) was reacted in a manner similar to Example 8 to give 0.14 g of the title compound as a cream-colored solid: mp >267° C. (dec.); $^1$H NMR (400 MHz, DMSO-d$_6$) δ 11.42, 9.57, 7.37, 7.30–7.25, 7.11–7.07, 6.84, 6.78–6.76, 3.35–3.27, 3.25–3.18, 3.16–3.08, 2.63–2.56; IR (drift) 3259, 2956, 2861, 2811, 2778, 2699, 2641, 2455, 1622, 1591, 1458, 1332, 1113, 985, 749 cm$^{-1}$; HRMS (FAB) calcd for C$_{18}$H$_{16}$F$_2$N$_2$+H: 299.1360, found: 299.1369.

Preparation 8
Preparation of 3-tert-butyloxycarbonyl-10-bromo-1,2,3,4,5,6-hexahydroazepino[4,5-b]indole In a 500 mL round-bottomed flask, a mixture of 3-benzoyl-10-bromo-1,2,3,4,5,6-hexahydroazepino[4,5-b]

indole (13.59 g, 36.80 mmol), potassium hydroxide (10.32 g, 184.0 mmol), and ethylene glycol (200.0 mL) were heated at 140° C. overnight. The mixture was cooled to 0° C., then dioxane (500.0 mL) and di-tert-butyl dicarbonate (9.64 g, 44.16 mmol) were added and stirred at room temperature overnight. Dioxane was removed under reduced pressure and the resulting mixture was partitioned between chloroform and water. The aqueous layer was extracted with chloroform (2×) and the combined organic layers was dried (MgSO$_4$) and filtered. The filtrate was concentrated in vacuo to dryness. The residue was subjected to column chromatography (silica gel, 20–30% EtOAc/hexane) to give 12.74 g (95%) of a yellow solid: mp 223–225° C.; $^1$H NMR (400 MHz, CDCl$_3$) δ 7.99, 7.23–7.19, 6.92, 3.77–3.65, 3.56–3.47, 3.05–2.96; IR (drift) 3263, 1664, 1468, 1439, 1416, 1367, 1352, 1332, 1300, 1190, 1170, 1162, 1115, 769, 737 cm$^{-1}$; MS (EI) m/z 364 (M$^+$); HRMS (EI) calcd for C$_{17}$H$_{21}$BrN$_2$O$_2$: 364.0787, found: 364:0794; Anal. Calcd for C$_{17}$H$_{21}$BrN$_2$O$_2$: C, 55.90; H, 5.80; N, 7.67. Found: C, 55.93; H, 5.81; N, 7.66.

Preparation 9

Preparation of 3-(tert-butyloxycarbonyl)-10-(4,4,5,5-tetramethyl-1,3,2-dioxaborolan-2-yl)-1,2,3,4,5,6-hexahydroazepino[4,5-b]indole A mixture of dicloro[1,1'-bis(diphenylphosphino) ferrocene]-palladium (II) dichloromethane adduct (4.83 g, 6.6 mmol), acetic acid potassium salt (6.5 g, 66.0 mmol), and bis(pinacolato)diboron (6.14 g, 24.2 mmol) was flushed with nitrogen, and then dimethyl sulfoxide (125.0 mL) and 3-tert-butyloxycarbonyl-10-bromo-1,2,3,4,5,6-tetrahydroazepino[4,5-b]indole (8.03 g, 22.0 mmol) were added. The mixture was heated at 80° C. for 18 h. After cooling to room temperature, the mixture was partitioned between ethyl acetate and water. The aqueous layer was extracted with ethyl acetate (2×). The combined ethyl acetate solution was concentrated in vacuo to dryness. The residue was subjected to column chromatography (silica gel, 1–3% MeOH/CHCl$_3$) to give 5.58 g (62%) of the title compound as a white solid: mp 186–188° C.; $^1$H NMR (300 MHz, CDCl$_3$) δ 7.85, 7.49, 7.34, 7.10, 3.75–3.60, 3.33–3.20, 3.06–2.95.

Compounds identified in Examples 15–46 were prepared according to the following protocol (See FIG. 2):

1. Pinacol boronate (5.10 g, 12.4 mmol)) and 1,1'-bisdiphenylphosphine ferrocene (DPPF, 0.05 eq, 0.35 g, 0.62 mmol) were dissolved in 10% methanol in dioxane (degassed with argon) to a 100 mL volume.
2. Similarly, tris(dibenzylideneacetone)dipalladium (Pd$_2$dba$_3$, 0.03 eq, 0.34 g, 0.37 mmol) was dissolved in 10% methanol in dioxane (degassed with argon) to a 50 mL volume.
3. Cesium carbonate (1.5 eq, 0.12 g, 0.34 mmol) was weighed into labeled, 20 mL vials, and stored at room temperature overnight. A 4 mm glass bead and the appropriate aryl bromides (~3 eq) were added to the vials.
4. The pinacol boronate/DPPF solution above was added (1.8 mL to each vial) and the vials were purged with nitrogen and fitted with a Teflon-lined cap.
5. In an argon-filled glove-box, the palladium solution was added (0.9 mL to each vial). The tightly-capped vials were then placed in a heater block (90° C.) and shaken at 250 RPM overnight.
6. After cooling to ambient temperature, sulfonic acid resin (BioRad Ag®50W-X2, washed and dried, 5.2 meq/g dry weight) was added, 18 eq to each vial (0.85 g) and also 1.8 mL of methanol. The vials then were capped and agitated at 250 RPM with heating at 60° C. for 2 hours.
7. The vials then were cooled to ambient temperature and emptied into 25 mL fritted plastic syringe barrels affixed to a wash receiver tank. The resin was washed into the syringe barrels with water and methanol as required to have all the reagents in solution. A battery of washings then was used to ensure that all excess reagent was removed from the resin: 2×3 mL each of water, methanol, tetrahydrofuran, and methylene chloride. The methanol and tetrahydrofuran washes can be alternated to swell and then shrink the resin to help expel reagents from inside the resin. The vials that contained basic reagents (e.g., pyridines) were also washed with 2M pyridine in methanol after the methanol washes.
8. The syringe barrels then were racked above tared (using the Bohdan weighing station) and labeled 20 mL vials, and the resin was washed with 4M ammonium hydroxide in methanol (4×2 mL) and tetrahydrofuran (2×2 mL), gravity elution. Positive nitrogen pressure was applied after the final elution (needle through a tight-fitting septum).

Solvent was removed under vacuum with centrifugation to prevent bumping (Genevac apparatus) and the masses were recorded (Bohdan).

9. Hydrochloric acid (4N) in dioxane (excess) was added and they were capped and shaken at ambient temperature overnight. Solvent was removed again under vacuum with centrifugation, and masses were recorded (using the Bohdan weighing station).
10. Further purification was achieved through preparative HPLC separation, and samples with >80% purity were reevaluated for CNS binding activity as the formate salts.

EXAMPLE 15

Preparation of 10-(2-methoxyphenyl)-1,2,3,4,5,6-hexahydroazepino[4,5-b]indole hydrochloride

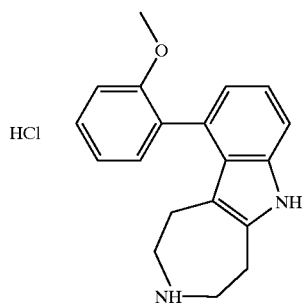

Following the protocol (Steps 1–10), above, making non-critical variations, the title compound was obtained. MS (EI) m/z 292.4 (MH$^+$).

EXAMPLE 16

Preparation of 10-(3-methoxyphenyl)-1,2,3,4,5,6-hexahydroazepino[4,5-b]indole hydrochloride

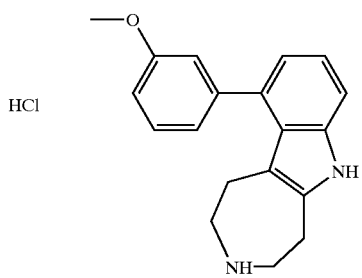

Following the protocol (Steps 1–10), above, making non-critical variations, the title compound was obtained. MS (EI) m/z 292.5 (MH$^+$).

EXAMPLE 17

Preparation of 10-(1,1'-biphenyl)-3-yl-1,2,3,4,5,6-hexahydroazepino[4,5-b]indole hydrochloride

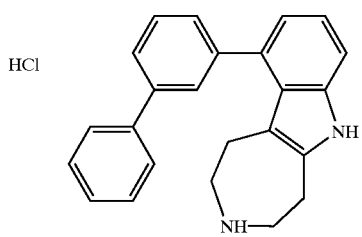

Following the protocol (Steps 1–10), above, making non-critical variations, the title compound was obtained. MS (EI) m/z 338.8 (MH$^+$).

EXAMPLE 18

Preparation of 10-(4-phenoxyphenyl)-1,2,3,4,5,6-hexahydroazepino[4,5-b]indole hydrochloride

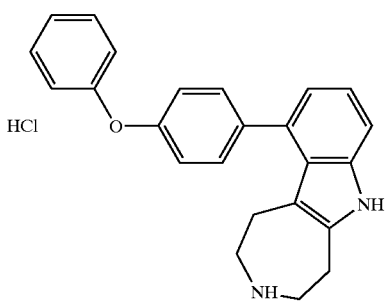

Following the protocol (Steps 1–10), above, making non-critical variations, the title compound was obtained. MS (EI) m/z 354.8 (MH$^+$).

EXAMPLE 19

Preparation of 10-(4-methoxyphenyl-1,2,3,4,5,6-hexahydroazepino[4,5-b]indole hydrochloride

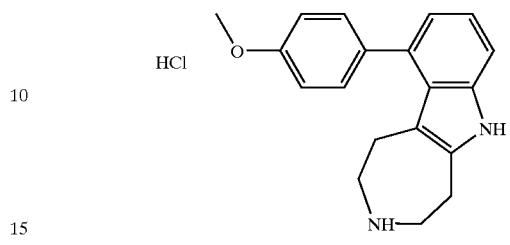

Following the protocol (Steps 1–10), above, making non-critical variations, the title compound was obtained. MS (EI) m/z 292.5 (MH$^+$).

EXAMPLE 20

Preparation of 10-(1,1'-biphenyl-)-4-yl-1,2,3,4,5,6-hexahydroazepino[4,5-b]indole hydrochloride

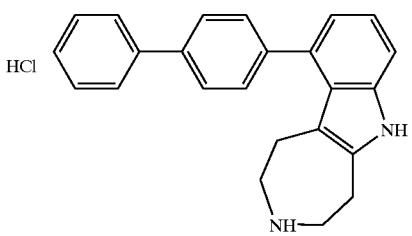

Following the protocol (Steps 1–10), above, making non-critical variations, the title compound was obtained. MS (EI) m/z 338.9 (MH$^+$).

EXAMPLE 21

Preparation of 10-(4-methylsulfanylphenyl)-1,2,3,4,5,6-hexahydroazepino[4,5-b]indole hydrochloride

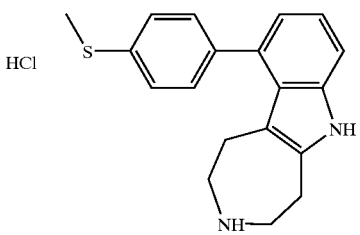

Following the protocol (Steps 1–10), above, making non-critical variations, the title compound was obtained. MS (EI) m/z 308.6 (MH$^+$).

EXAMPLE 22

Preparation of [4-(1,2,3,4,5,6-hexahydroazepino[4,5-b]indol-10-yl)phenyl](phenyl)methanone hydrochloride

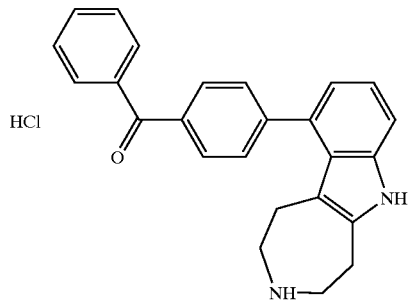

Following the protocol (Steps 1–10), above, making non-critical variations, the title compound was obtained. MS (EI) m/z 367.0 (MH$^+$).

EXAMPLE 23

Preparation of 10-(4-tert-butylphenyl)-1,2,3,4,5,6-hexahydroazepino[4,5-b]indole hydrochloride

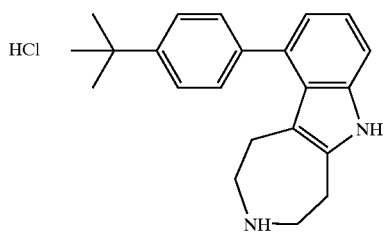

Following the protocol (Steps 1–10), above, making non-critical variations, the title compound was obtained MS (EI) m/z 318.8 (MH$^+$).

EXAMPLE 24

Preparation of 10-(2-fluorophenyl)-1,2,3,4,5,6-hexahydroazepino[4,5-b]indole hydrochloride

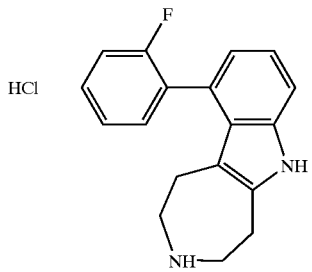

Following the protocol (Steps 1–10), above, making non-critical variations, the title compound was obtained. MS (EI) m/z 280.5 (MH$^+$).

EXAMPLE 25

Preparation of 10-(3,4-difluorophenyl)-1,2,3,4,5,6-hexahydroazepino[4,5-b]indole hydrochloride

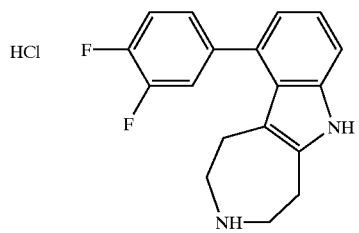

Following the protocol (Steps 1–10), above, making non-critical variations, the title compound was obtained. MS (EI) m/z 298.7 (MH$^+$).

EXAMPLE 26

Preparation of 10-(3-fluorophenyl)-1,2,3,4,5,6-hexahydroazepino[4,5-b]indole hydrochloride.

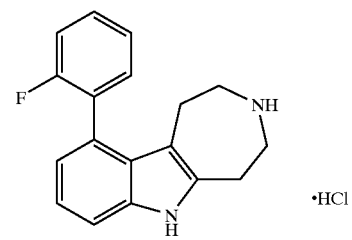

Following the protocol (Steps 1–10), above, making non-critical variations, the title compound was obtained. MS (EI) m/z 280.8 (MH$^+$).

EXAMPLE 27

Preparation of 10-(3-trifluoromethylphenyl)-1,2,3,4,5,6-hexahydroazepino[4,5-b]indole hydrochloride

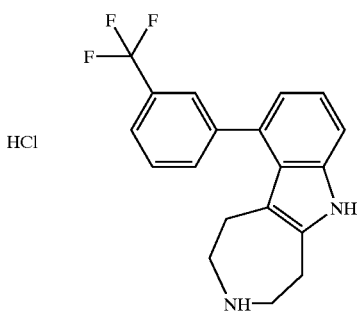

Following the protocol (Steps 1–10), above, making non-critical variations, the title compound was obtained. MS (EI) m/z 330.9 (MH$^+$).

EXAMPLE 28

Preparation of 10-(4-trifluoromethylphenyl)-1,2,3,4,5,6-hexahydroazepino[4,5-b]indole hydrochloride

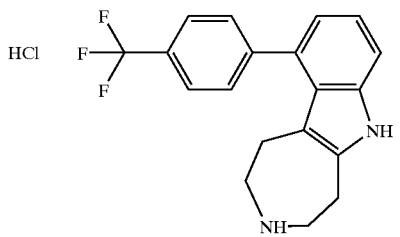

Following the protocol (Steps 1–10), above, making non-critical variations, the title compound was obtained. MS (EI) m/z 330.9 (MH$^+$).

EXAMPLE 29

Preparation of 10-(3-chlorophenyl)-1,2,3,4,5,6-hexahydroazepino[4,5-b]indole hydrochloride

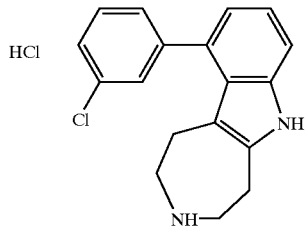

Following the protocol (Steps 1–10), above, making non-critical variations, the title compound was obtained. MS (EI) m/z 296.5/298.4 (MH$^+$).

EXAMPLE 30

Preparation of 10-(3,5-dichlorophenyl)-1,2,3,4,5,6-hexahydroazepino[4,5-b]indole hydrochloride

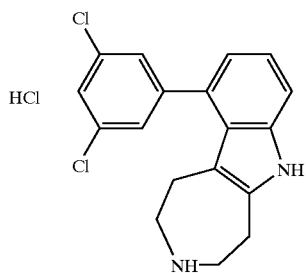

Following the protocol (Steps 1–10), above, making non-critical variations, the title compound was obtained. MS (EI) m/z 330.6/332.5 (MH$^+$).

EXAMPLE 31

Preparation of 10-(4-chlorophenyl)-1,2,3,4,5,6-hexahydroazepino[4,5-b]indole hydrochloride

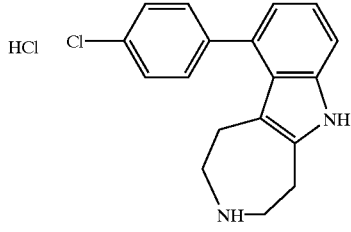

Following the protocol (Steps 1–10), above, making non critical variations, the title compound was obtained. MS (EI) m/z 296.6/298.4 (MH$^+$).

EXAMPLE 32

Preparation of 10-(3-cyanophenyl)-1,2,3,4,5,6-hexahydroazepino[4,5-b]indole hydrochloride

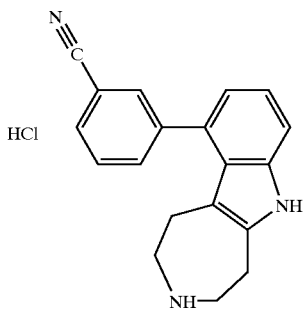

Following the protocol (Steps 1–10), above, making non-critical variations, the title compound was obtained. MS (EI) m/z 287.9 (MH$^+$).

EXAMPLE 33

Preparation of 10-(4-cyanophenyl)-1,2,3,4,5,6-hexahydroazepino[4,5-b]indole hydrochloride

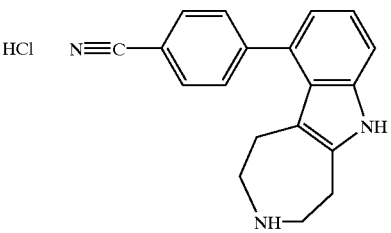

Following the protocol (Steps 1–10), above, making non-critical variations, the title compound was obtained. MS (EI) m/z 287.8 (MH$^+$).

EXAMPLE 34

Preparation of [3-(1,2,3,4,5,6-hexahydroazepino[4,5-b]indol-10-yl)phenyl]acetonitrile hydrochloride

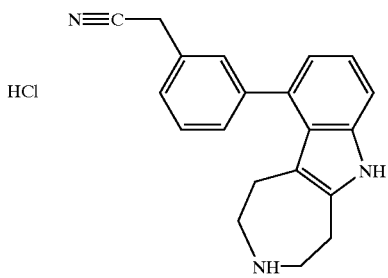

Following the protocol (Steps 1–10), above, making non-critical variations, the title compound was obtained. MS (EI) m/z 301.5 (MH$^+$).

EXAMPLE 35

Preparation of 10-(1-naphthyl)-1,2,3,4,5,6-hexahydroazepino[4,5b]indole hydrochloride

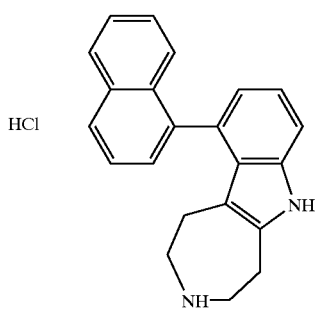

Following the protocol (Steps 1–10), above, making non-critical variations, the title compound was obtained. MS (EI) m/z 312.8 (MH$^+$).

EXAMPLE 36

Preparation of 10-(2-hydroxymethylphenyl)-1,2,3,4,5,6-hexahydroazepino[4,5-b]indole hydrochloride

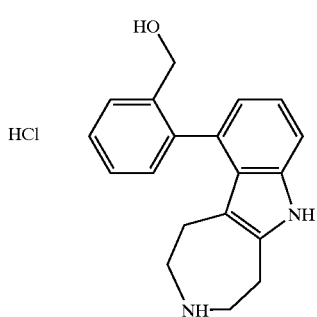

Following the protocol (Steps 1–10), above, making non-critical variations, the title compound was obtained. MS (EI) m/z 292.5 (MH$^+$).

EXAMPLE 37

Preparation of 10-(4-hydroxymethylphenyl)-1,2,3,4,5,6-hexahydroazepino[4,5-b]indole hydrochloride

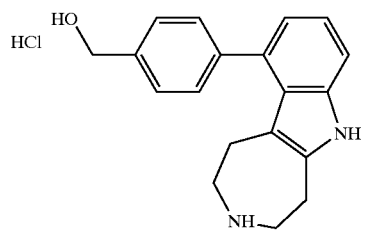

Following the protocol (Steps 1–10), above, making non-critical variations, the title compound was obtained. MS (EI) m/z 292.5 (MH$^+$).

EXAMPLE 38

Preparation of 10-(1,3-benzodioxol-5-yl)-1,2,3,4,5,6-hexahydroazepino[4,5-b]indole hydrochloride

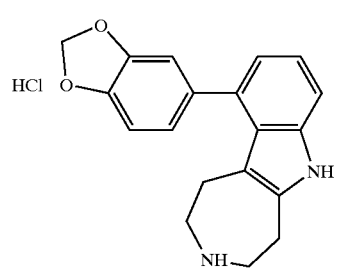

Following the protocol (Steps 1–10), above, making non-critical variations, the title compound was obtained. MS (EI) m/z 306.6 (MH$^+$).

EXAMPLE 39

Preparation of 10-(5-pyrimidinyl)-1,2,3,4,5,6-hexahydroazepino[4,5-b]indole hydrochloride

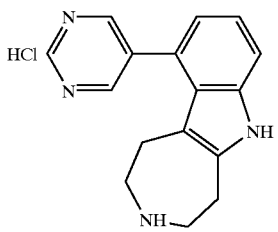

Following the protocol (Steps 1–10), above, making non-critical variations, the title compound was obtained. MS (EI) m/z 264.5 (MH$^+$).

EXAMPLE 40

Preparation of 10-(3,4-dimethoxyphenyl)-1,2,3,4,5,6-hexahydroazepino[4,5-b]indole hydrochloride

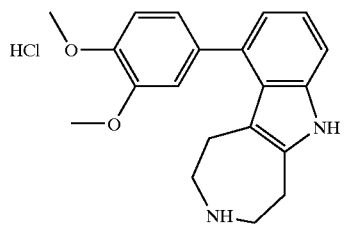

Following the protocol (Steps 1–10), above, making non-critical variations, the title compound was obtained. MS (EI) m/z 322.5 (MH$^+$).

EXAMPLE 41

Preparation of 10-(3,5-difluorophenyl)-1,2,3,4,5,6-hexahydroazepino[4,5-b]indole hydrochloride

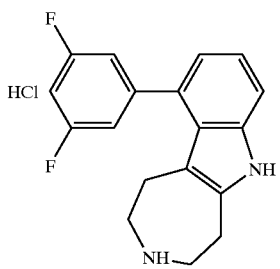

Following the protocol (Steps 1–10), above, making non-critical variations, the title compound was obtained. MS (EI) m/z 298.8 (MH$^+$).

EXAMPLE 42

Preparation of 10-(4-n-butyloxyphenyl)-1,2,3,4,5,6-hexahydroazepino[4,5-b]indole hydrochloride

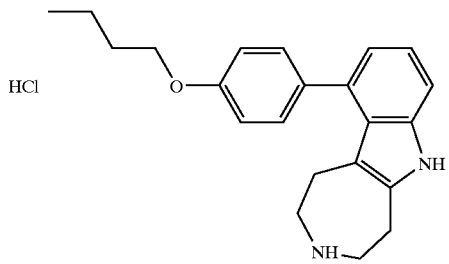

Following the protocol (Steps 1–10), above, making non-critical variations, the title compound was obtained. MS (EI) m/z 335.0 (MH$^+$).

EXAMPLE 43

Preparation of 10-(4-trifluoromethoxyphenyl)-1,2,3,4,5,6-hexahydroazepino[4,5-b]indole hydrochloride

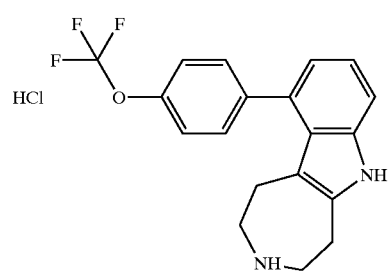

Following the protocol (Steps 1–10), above, making non-critical variations, the title compound was obtained. MS (EI) m/z 346.9 (MH$^+$).

EXAMPLE 44

Preparation of 10-(3,4-dichlorophenyl)-1,2,3,4,5,6-hexahydroazepino[4,5-b]indole hydrochloride

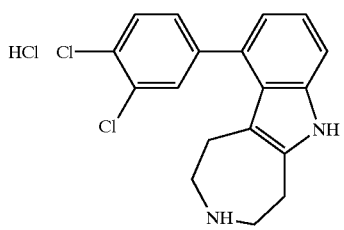

Following the protocol (Steps 1–10), above, making non-critical variations, the title compound was obtained. MS (EI) m/z 330.5/332.5 (MH$^+$).

EXAMPLE 45

Preparation of 10-(2-naphthyl)-1,2,3,4,5,6-hexahydroazepino[4,5-b]indole hydrochloride

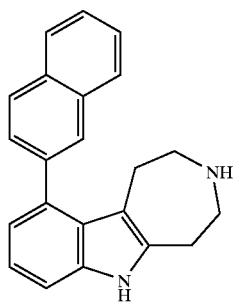

Following the protocol (Steps 1–10), above, making non-critical variations, the title compound was obtained. MS (EI) m/z 313.3 (MH+).

EXAMPLE 46

Preparation of 10-(4-pyridinyl)-1,2,3,4,5,6-hexahydroazepino[4,5-b]indole

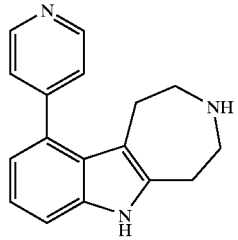

Following the protocol (Steps 1–10), above, making non-critical variations, the title compound was obtained. MS (EI) m/z 264.2 (MH+).

EXAMPLE 47

Preparation of 3-benzyl-10-bromo-1,2,3,4,5,6-hexahydro-azepino[4,5-b]indole

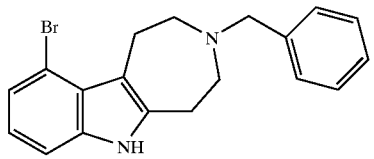

To a suspension of lithium aluminum hydride (4.63 g, 121.9 mmol) in tetrahydrofuran (500.0 mL) was added aluminum chloride (16.3 g, 121.9 mmol) at −20° C. followed by the addition of the suspension of 3-benzoyl-10-bromo-1,2,3,4,5,6-hexahydro-azepino[4,5-b]indole (15.0 g, 40.6 mmol) in tetrahydrofuran (100.0 mL). The mixture then was stirred at room temperature for 16 h and treated with 20% sodium hydroxide solution (about 150 mL) until pH>13. After water was added, the aqueous mixture was extracted with ethyl acetate (3×). The combined ethyl acetate solution was dried ($MgSO_4$) and filtered. The filtrate was concentrated in vacuo to dryness to give 13.6 g (94%) of colorless solid as the desired product: mp 179–180° C. (EtOAc/hexane); IR (KBr) 3410 $cm^{-1}$; $^1$H NMR (400 MHz, DMSO-$d_6$) δ 11.12, 7.32–7.40, 7.23–7.27, 7.08, 6.86, 3.75, 3.29–3.26, 2.92–2.89, 2.82–2.77; $^{13}$C NMR (100.6 MHz, DMSO-$d_6$) δ 139.5, 139.2, 135.8, 128.5, 128.1, 126.7, 125.2, 122.8, 120.7, 111.9, 111.7, 110.4, 60.5, 55.0, 53.0, 27.5, 24.1; MS (EI) m/z 354 (M+), 356 (M+); HRMS cacld for $C_{19}H_{19}BrN_2$+H: 355.0810, found: 355.0803; Anal. Calcd. for $C_{19}H_{19}BrN_2$: C, 64.23; H, 5.39; N, 7.89. Found: C, 64.28; H, 5.47; N, 7.87.

EXAMPLE 48

Preparation of benzhydrylidene-(3-benzyl-1,2,3,4,5,6-hexahydro-azepino[4,5-b]indol-10-yl)amine

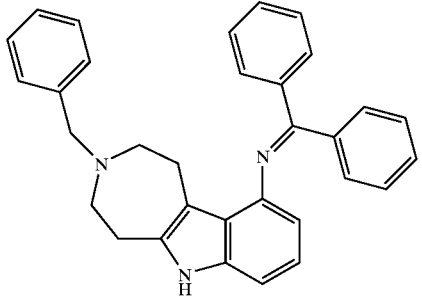

A mixture of 3-benzyl-10-bromo-1,2,3,4,5,6-hexahydro-azepino[4,5-b]indole (0.71 g, 2.00 mmol), benzophenone imine (0.44 g, 0.40 mL, 2.40 mmol), tris(dibenzylideneacetone)dipalladium(0) (0.037 g, 0.040 mmol), (S)-(−)-2,2'-bis(diphenylphosphino)-1,1'-binaphthyl (0.075 g, 0.120 mmol), and sodium tert-butoxide (0.269 g, 2.80 mmol) in toluene (20.0 mL) was refluxed for 16 h. After cooling to room temperature, water and ethyl acetate were added, and the pahases separated. The aqueous layer was extracted with ethyl acetate (2×). The combined ethyl acetate solution was dried ($MgSO_4$) and filtered. The filtrate was concentrated in vacuo to dryness and the residue was subjected to column chromatography (silica gel, 30% EtOAc/hexane, 1% $Et_3N$) to afford a yellow fluffy solid as the title compound (0.855 g, 94%): mp >71° C. (dec.); $^1$H NMR (300 MHz, $CDCl_3$) δ 7.82–7.80, 7.65, 7.66–7.11, 6.82–6.79, 6.73, 5.95, 3.78, 3.20–3.16, 2.90–2.78; MS (ESI+) m/z 456 (M++H).

EXAMPLE 49

Preparation of 3-benzyl-10-amino-1,2,3,4,5,6-hexahydro-azepino[4,5-b]indole

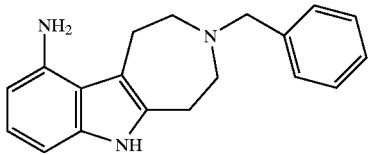

To a solution of benzhydrylidene-(3-benzyl-1,2,3,4,5,6-hexahydro-azepino[4,5-b]indol-10-yl)amine (0.794 g, 1.74 mmol) in tetrahydrofuran was added 1 M hydrochloric acid (10.0 mL). The mixture was stirred at room temperature for 10 min, and then tetrahydrofuran was removed in vacuo. The aqueous mixture was extracted with ethyl acetate (2×). The acidic residue was basified with ammonia and extracted with dichloromethane (3×). The combined dichloromethane solution was dried ($MgSO_4$) and filtered. The filtrate was concentrated in vacuo to dryness to give 0.416 g (82%) of the title compound: mp 164–165° C.; $^1$H NMR (300 MHz, $CDCl_3$) δ 7.76, 7.45–7.26, 6.88, 6.74, 6.29, 3.86, 3.27–3.23, 3.06–2.97; MS (ESI+) m/z 292 (M++H).

EXAMPLE 50
Preparation of N-(3-benzyl-1,2,3,4,5,6-hexahydro-azepino[4,5-b]indol-10-yl)-benzenesulfonamide

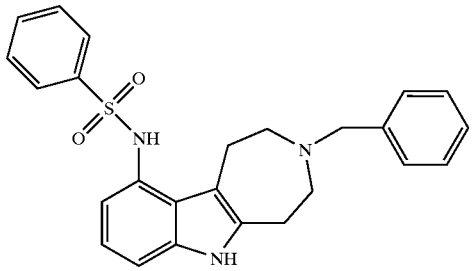

To a solution of 3-benzyl-10-amino-1,2,3,4,5,6-hexahydro-azepino[4,5-b]indole (1.05 g, 3.60 mmol) in pyridine (7.00 mL) was added benzenesulfonyl chloride (0.77 g, 4.40 mmol) at 0° C. After ten minutes at 0° C., the mixture was stirred at room temperature for 16 h, and then poured into ice water. The mixture was filtered to give a sticky solid, which was dissolved in ethyl acetate, washed successively with saturated ammonium chloride, saturated sodium bicarbonate, and brine, dried over magnesium sulphate and concentrated in vacuo to give a brown oil. The addition of dichloromethane gave a brown solid which was recrystallized from dichloromethane to give 0.62 g (40%) of yellow solid as the title compound: mp 164–165° C.; $^1$H NMR (400 MHz, acetone-$d_6$) δ 10.00, 8.40, 7.70–7.67, 7.64–7.59 (m, 1 H), 7.51–7.48 (m, 2 H), 7.43–7.41 (m, 2 H), 7.36–7.32 (t, 2 H), 7.27–7.24, 7.17, 6.79, 6.45, 3.75, 3.15–3.13, 2.95–2.92, 2.80–2.77, 2.72–2.69; $^{13}$C NMR (100.6 MHz, acetone-$d_6$) δ 142.1, 140.7, 139.1, 139.0, 137.5, 137.4, 133.2, 129.6, 129.0, 128.1, 127.6, 126.5, 120.4, 119.5, 113.3, 110.9, 62.5, 56.9, 54.7, 29.2, 26.4; IR (KBr) 3403, 1341, 1325, 1178, 1168 cm$^{-1}$; HRMS (FAB) calcd for $C_{25}H_{25}N_3O_2S$+H: 432.1746, found: 432.1747; Anal. Calcd for $C_{25}H_{25}N_3O_2S$: C, 69.58; H, 5.84; N. 9.74. Found: C, 69.41; H, 5.91; N, 9.64.

EXAMPLE 51
Preparation of N-(1,2,3,4,5,6-hexahydro-azepino[4,5-b]indol-10-yl)-benzenesulfonamide

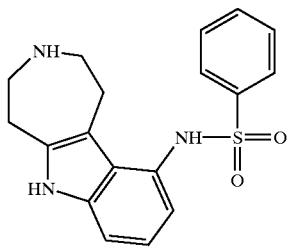

A solution of N-(3-benzyl-1,2,3,4,5,6-hexahydro-azepino[4,5-b]indol-10-yl)-benzenesulfonamide (0.26 g, 0.60 mmol) in ethanol (60.0 mL) was hydrogenated in the presence of palladium on carbon (0.14 g) and 2 N hydrochloric acid (0.30 mL, 0.60 mmol) at 50 psi for 24 h. More palladium on carbon (0.28 g) was added and hydrogenation was continued for 5 days. After filtration through a pad of Celite, the filtrate was concentrated in vacuo to dryness. The residue was subjected to column chromatography (10% MeOH/CHCl$_3$, 1% Et$_3$N) to give 0.037 g (18%) of yellowish solid as the title compound: mp 250–252° C.; IR (KBr) 3347, 1335, 1329, 1317, 1153 cm$^{-1}$; $^1$H NMR (300 MHz, MeOH-$d_4$) δ 7.66–7.60, 7.57–47, 7.22, 6.79, 6.14, 3.66–3.57, 3.45–3.38, 3.28–3.24; MS (ESI+) m/z 342 (M$^+$+H); HRMS cacld for $C_{18}H_{18}N_2O$+H: 342.1276, found: 342.1284; Anal. Calcd. for $C_{18}H_{19}N_3O_2S$: C, 63.32; H, 5.61; N, 12.31. Found: C, 62.99; H, 5.93; N, 11.90.

Preparation 10

Preparation of 3-benzoyl-9-phenoxy-1,2,3,4,5,6-hexahydroazepino[4,5-b]indole

A mixture of 3-benzoyl-9-bromo-1,2,3,4,5,6-hexahydroazepino[4,5-b]indole (1.00 g, 2.71 mmol), phenol (0.51 g, 5.42 mmol), copper (I) oxide (0.019 g, 0.14 mmol), and cesium carbonate (2.65 g, 8.12 mmol) in o-xylene was refluxed for 24 h. After cooling to room temperature, the mixture was filtered and washed with ethyl acetate. The filtrate was concentrated in vacuo to dryness, and the residue was subjected to column chromatography (silica gel, 60% EtOAc/hexane) to afford 0.11 g (10%) of a colorless solid as the title compound: $^1$H NMR (300 MHz, CDCl$_3$) δ 7.42, 7.29–7.19, 7.03–6.86, 4.12–3.91, 3.72–3.61, 3.20–3.04, 2.90–2.76; MS (ESI+) m/z 383 (M$^+$+1).

Preparation 11

Preparation of 3-benzoyl-10-phenoxy-1,2,3,4,5,6-hexahydroazepino[4,5-b]indole

A mixture of 3-benzoyl-10-bromo-1,2,3,4,5,6-hexahydroazepino[4,5-b]indole (1.85 g, 5.00 mmol), phenol (0.94 g, 10.0 mmol), copper (I) oxide (0.036 g, 0.25 mmol), and cesium carbonate (4.89 g, 15.0 mmol) in o-xylene was reacted in a similar manner to Preparation 10 to afford 0.55 g (29%) of colorless solid as the title compound: mp 179–182° C. (CH$_2$Cl$_2$/hexane); IR (KBr) 1601, 3226 cm$^{-1}$; $^1$H NMR (300 MHz, CDCl$_3$) δ 8.40–8.24, 7.43–7.34, 7.05–6.90, 6.55–6.50, 4.00–3.90, 3.64–3.55, 3.29–2.84; $^{13}$C NMR (75.5 MHz, CDCl$_3$) δ 171.8, 158.1, 150.1, 137.0, 136.9, 135.0, 129.7, 129.3, 128.6, 126.5, 122.6, 122.0, 118.1, 117.6, 110.1, 109.4, 106.5, 51.2, 45.2, 28.9, 27.2; MS (EI) m/z 382 (M$^+$); HRMS cacld for $C_{25}H_{22}N_2O_2$+H: 383.1759, found: 383.1749; Anal. Calcd. for $C_{25}H_{22}N_2O_2$·1/2H$_2$O: C, 76.70; H, 5.92; N, 7.17. Found: C, 76.72; H, 5.79; N, 7.15.

EXAMPLE 52
Preparation of 3-benzyl-9-phenoxy-1,2,3,4,5,6-hexahydro-azepino[4,5-b]indole

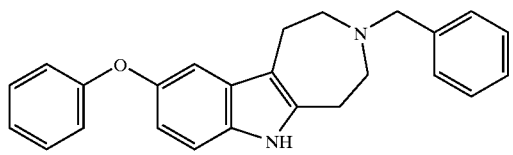

To a solution of 3-benzoyl-9-phenoxy-1,2,3,4,5,6-hexahydroazepino[4,5-b]indole (0.10 g, 0.26 mmol) in tetrahydrofuran (5.0 mL) was added lithium aluminum hydride (0.10 g, 2.61 mmol). The resulted mixture was stirred at room temperature for 16 h. Water (0.10 mL), 15% sodium hydroxide solution (0.10 mL) and water (0.30 mL) were added sequentially. The mixture was filtered through a pad of Celite and the filtrate was concentrated in vacuo to dryness. The residue was subjected to column chromatography (silica gel, 50% EtOAc/hexane with 1% Et$_3$N) to afford 0.093 g (99%) of colorless solid as the desired product. $^1$H NMR (300 MHz, CDCl$_3$) δ 7.77, 7.21–7.44, 7.12, 6.95–7.04, 6.87, 3.00–2.91, 2.89–2.83.

EXAMPLE 53

Preparation of 3-benzyl-10-phenoxy-1,2,3,4,5,6-hexahydro-azepino[4,5-b]indole

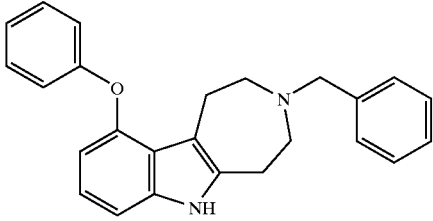

A solution of 3-benzoyl-10-phenoxy-1,2,3,4,5,6-hexahydroazepino[4,5-b]indole (0.55 g, 1.45 mmol) in tetrahydrofuran (30.0 mL) and lithium aluminum hydride (0.56 g, 14.5 mmol) was reacted in a manner similar to Preparation 11 to afford 0.47 g (87%) of colorless solid as the desired product: mp 168–170° C.(CH$_2$Cl$_2$/hexane); $^1$H NMR (400 MHz, DMSO-d$_6$) δ 11.0; 7.34–7.21, 7.10, 7.01, 6.94, 6.84, 6.47, 3.69, 2.89–2.87, 2.84–2.81, 2.78–2.75, 2.65–2.62; $^{13}$C NMR (100.6 MHz, DMSO-d$_6$) δ 158.5, 147.8, 139.2, 137.4, 136.9, 129.6, 128.4, 128.1, 126.7, 121.8, 120.5, 120.3, 116.4, 110.2, 109.3, 107.4, 60.2, 55.4, 53.3, 27.6, 24.8; MS (EI) m/z 368 (M$^+$); HRMS calcd for C$_{25}$H$_{24}$N$_2$O+H: 369.1967, found: 369.1961; Anal. Calcd. for C$_{25}$H$_{24}$N$_2$O: C, 81.49; H, 6.57; N, 7.60. Found: C, 81.12; H, 6.70; N, 7.53.

EXAMPLE 54

Preparation of 9-phenoxy-1,2,3,4,5,6-hexahydro-azepino[4,5-b]indole hydrochloride

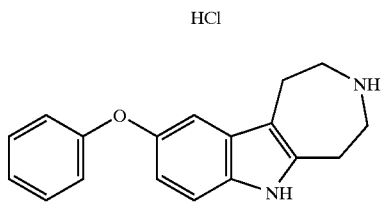

A solution of 3-benzyl-9-phenoxy-1,2,3,4,5,6-hexahydro-azepino[4,5-b]indole (0.092 g, 0.26 mmol) in ethanol (20.0 mL) was hydrogenated in the presence of palladium on carbon (0.04 g) and 2 N hydrochloric acid (0.13 mL, 0.26 mmol,) at 50 psi for 16 h. After filtration through a pad of Celite, the filtrate was concentratec in vacuo to dryness. The residue was recrystalized from EtOAc/MeOH to give 0.071 g (99%) of colorless solid as the desired product: mp >227° C. (dec.); $^1$H NMR (400 MHz, DMSO-d$_6$) δ 11.10, 9.60, 7.32–7.28, 7.11, 7.01, 6.88, 6.77, 3.36–3.27, 3.21–3.19, 3.05–3.01; $^{13}$C NMR (100.6 MHz, DMSO-d$_6$) δ 159.1, 148.5, 136.4, 131.5, 129.6, 128.5, 121.7, 116.6, 114.0, 111.8, 109.7, 108.1, 46.6, 44.8, 24.7, 20.8; MS (EI) m/z 278 (M$^+$); HRMS cacld for C$_{18}$H$_{18}$N$_2$O+H: 279.1497, found: 279.1508; Anal. Calcd. for C$_{18}$H$_{18}$H$_2$O.HCl: C, 68.67; H, 6.08; N, 8.90. Found: C, 67.95; H, 6.14; N, 8.99.

EXAMPLE 55

Preparation of 10-phenoxy-1,2,3,4,5,6-hexahydroazepino[4,5-b]indole hydrochloride

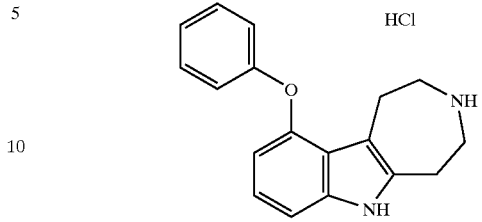

A solution of 3-benzyl-10-phenoxy-1,2,3,4,5,6-hexahydro-azepino[4,5-b]indole (0.28 g, 0.75 mmol) in ethanol (20.0 mL) was hydrogenated reacted in a manner similar to Example 54 to give 0.23 g (98%) of colorless solid as the desired product: mp >245° C. (dec.); $^1$H NMR (400 MHz, DMSO-d$_6$) δ 11.28, 9.45, 7.34, 7.14, 7.06, 6.99, 6.91, 6.49, 3.29–3.27, 3.18–3.14; $^{13}$C NMR (100.6 MHz, DMSO-d$_6$) δ 158.1, 148.3, 136.8, 135.2, 129.8, 122.3, 121.2, 119.7, 116.9, 109.1, 108.5, 107.5, 46.3, 44.4, 24.4, 21.9; MS (EI) m/z 278 (M$^+$); HRMS cacld for C$_{18}$H$_{18}$N$_2$O+H: 279.1497, found: 279.1502; Anal. Calcd. for C$_{18}$H$_{18}$H$_2$O.HCl. 1/2H$_2$O: C, 66.76; H, 5.91; N, 8.65. Found: C, 67.39; H, 5.98; N, 8.80.

Preparation 12

Preparation of 3-(3-benzoyl-1,2,3,4,5,6-hexahydroazepino[4,5-b]indol-10-yl)-2-propyn-1-ol A mixture of 3-benzoyl-10-bromo-1,2,3,4,5,6-hexahydroazepino[4,5-b]indole (11.68 g, 31.63 mmol), propargyl alcohol (3.25 mL, 60.20 mmol), tetrakistriphenylphosphine palladium(0) (1.83 g, 1.58 mmol), copper(I) iodide (0.151 g, 0.79 mmol), and pyrrolidine (100 mL) was allowed to stir under N$_2$. The mixture was warmed in a 93° C. oil bath and stirred under reflux for 2.5 h. The mixture was cooled, concentrated and absorbed onto SiO$_2$. Column chromatography (130 g SiO$_2$, 2.5% MeOH/CH$_2$Cl$_2$) provided 6.40 g of a brown foam. A second purification (Biotage 90 g, 2.5% MeOH/CH$_2$Cl$_2$) provided pure product fractions which were collected and evaporated. Crystallization from dichloromethane, methanol, ethyl acetate, and hexanes provided 4.97 g of the title compound (mp 162–165° C.). $^1$H NMR (CDCl$_3$) δ 8.05–8.35, 7.35–7.50, 7.15–7.25, 6.95–7.10, 7.40–7.60, 3.90–4.05, 3.55–3.70, 3.48, 3.25–3.40, 3.05–3.20, 2.75–2.85.

Preparation 13

Preparation of 3-(3-benzoyl-1,2,3,4,5,6-hexahydroazepino[4,5-b]indol-10-yl)-1-propanol A mixture of 3-(3-benzoyl-1,2,3,4,5,6-hexahydroazepino[4,5-b]indol-10-yl)-2-propyn-1-ol (4.715 g, 13.69 mmol) and 10% Pd/C (0.548 g) in ethanol (75 mL) was hydrogenated under 35 p.s.i. H$_2$ for 3.5 h. The mixture was filtered through celite, rinsed both ethanol, dichloromethane and evaporated. Crystallization from ethyl acetate/hexanes provided 4.230 g of the title compound (mp 144–147° C.). $^1$H NMR (CDCl$_3$) δ 8.20–8.55, 7.30–7.50, 7.05–7.15, 6.95–7.05, 6.75–6.90, 3.90–4.10, 3.55–3.80, 3.35–3.45, 2.90–3.20, 2.80–2.90, 1.75–2.00.

Preparation 14

Preparation of 3-benzoyl-10-(3-phenoxypropyl)-1,2,3,4,5,6-hexahydroazepino[4,5-b]indole A dry flask was charged with 3-(3-benzoyl-1,2,3,4,5,6-hexahydroazepino[4,5-b]indol-10-yl)-1-propanol (0.214 g, 0.61 mmol), triphenylphosphine (0.178 g, 0.68 mmol), phenol (0.064 g, 0.68 mmol) and tetrahydrofuran (5.0 mL). Under a N$_2$ atmosphere, diethylazodicarboxylate (0.11 mL, 0.68 mmol) was added. The mixture stirred for 0.5 hours at room temperature and was evaporated in vacuo. The ether product was purified by flash chromatography (90 g SiO$_2$, 1% MeOH/CH$_2$Cl$_2$) providing 0.145 g of the title compound (mp 121–124° C.). IR (drift) 3236, 3210, 2940, 1604, 1496, 1466, 1430, 1298, 1258, 1238, 1046, 928, 751, 739, 704 cm$^{-1}$.

EXAMPLE 56

Preparation of 3-(1,2,3,4,5,6-hexahydroazepino[4,5-b]indol-10-yl)propyl phenyl ether hydrochloride

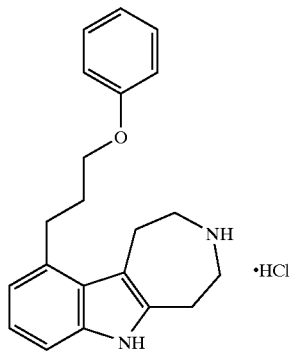

A mixture of 3-benzoyl-10-(3-phenoxypropyl)-1,2,3,4,5,6-hexahydroazepino[4,5-b]indole (0.265 g, 0.61 mmol) and potassium hydroxide (0.175 g, 3.12 mmol) in ethylene glycol (10.0 mL) was heated under N$_2$ at 130° C. for 16 h. The mixture was cooled to rt, poured into water (50 mL) and extracted with dichloromethane (3×75 mL). The combined organics were washed with water, brine, dried over anhydrous sodium sulfate and evaporated in vacuo. The residue was treated with methanolic hydrochloric acid and evaporated in vacuo. Recrystallization from ethyl acetate and hexanes provided 0.132 g of the title compound (mp 215–218° C.). $^1$H NMR (DMSO-d$_6$) δ 11.05, 7.27, 7.10, 6.80–7.00, 6.70, 4.00, 2.95–3.50, 1.85–2.08.

EXAMPLE 57

Preparation of 3-(1,2,3,4,5,6-hexahydroazepino[4,5-b]indol-10-yl)propyl 2-naphthyl ether hydrochloride

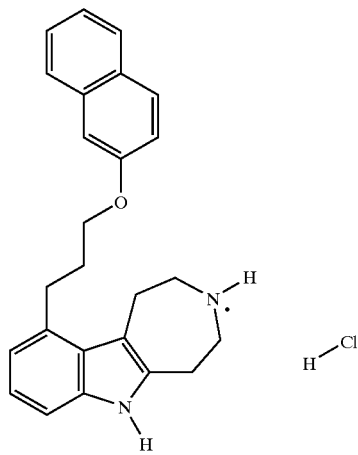

Following the procedures of Preparation 14 and Example 56, making non-critical variations, and using 2-naphthol, the title compound was obtained. HRMS (FAB) calcd for C$_{25}$H$_{26}$N$_2$O(MH$^+$) 371.2123, found 371.2123.

EXAMPLE 58

Preparation of 3-(1,2,3,4,5,6-hexahydroazepino[4,5-b]indol-10-yl)propyl 1-naphthyl ether hydrochloride

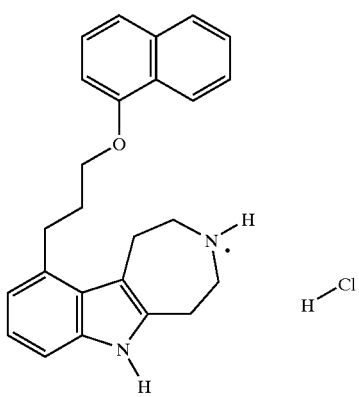

Following the procedures of Preparation 14 and Example 56, making non-critical variations, and using 1-naphthol, the title compound was obtained. HRMS (FAB) calcd for C$_{25}$H$_{26}$N$_2$O(MH$^+$) 371.2123, found 371.2134.

EXAMPLE 59

Preparation of 10-[3-([1,1'-biphenyl]-4-yloxy)propyl]-1,2,3,4,5,6-hexahydroazepino[4,5-b]indole hydrochloride

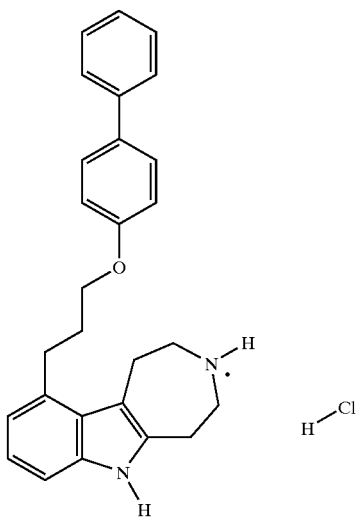

Following the procedures of Preparation 14 and Example 56, making non-critical variations, starting with the appropriate phenol, the title compound was obtained. HRMS (FAB) calcd for $C_{27}H_{28}N_2O(MH^+)$ 397.2280, found 397.2288.

EXAMPLE 60

Preparation of 10-[3-(3-methoxyphenoxy)propyl]-1,2,3,4,5,6-hexahydroazepino[4,5-b]indole hydrochloride

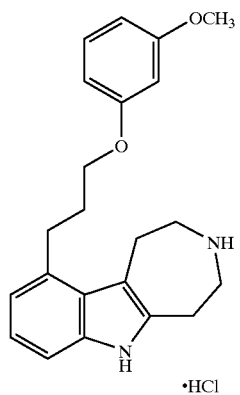
·HCl

Following the procedures of Preparation 14 and Example 56, making non-critical variations, starting with the appropriate phenol, the title compound was obtained. HRMS (FAB) calcd for $C_{22}H_{26}N_2O_2$ $(MH^+)$ 351.2072, found 351.2073.

EXAMPLE 61

Preparation of 10-[3-(4-methoxyphenoxy)propyl]-1,2,3,4,5,6-hexahydroazepino[4,5-b]indole hydrochloride

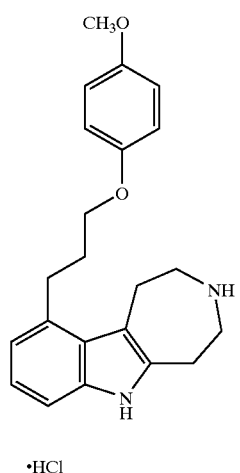
·HCl

Following the procedures of Preparation 14 and Example 56, making non-critical variations, starting with the appropriate phenol, the title compound was obtained. HRMS (FAB) calcd for $C_{22}H_{26}N_2O_2$ $(MH^+)$ 351.2072, found 351.2077.

EXAMPLE 62

Preparation of 10-[3-(4-chlorophenoxy)propyl]-1,2,3,4,5,6-hexahydroazepino[4,5-b]indole hydrochloride

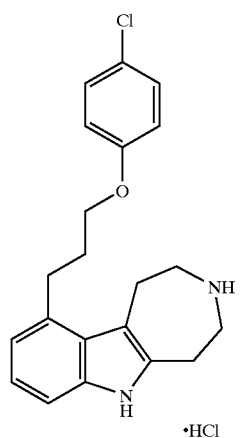
·HCl

Following the procedures of Preparation 14 and Example 56, making non-critical variations, starting with the appropriate phenol, the title compound was obtained. HRMS (FAB) calcd for $C_{21}H_{23}ClN_2O(MH^+)$ 355.1577, found 355.1584.

EXAMPLE 63

Preparation of 10-[3-(3-chlorophenoxy)propyl]-1,2,3,4,5,6-hexahydroazepino-[4,5-b]indole hydrochloride

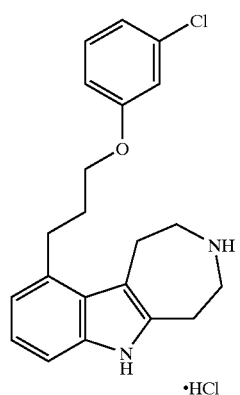
·HCl

Following the procedures of Preparation 14 and Example 56, making non-critical variations, starting with the appropriate phenol, the title compound was obtained. HRMS (FAB) calcd for $C_{21}H_{23}ClN_2O(MH^+)$ 355.1577, found 355.1581.

EXAMPLE 64

Preparation of 10-[3-(2-chlorophenoxy)propyl]-1,2,3,4,5,6-hexahydroazepino[4,5-b]indole hydrochloride

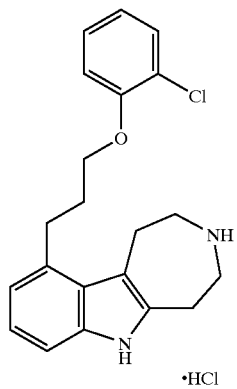

Following the procedures of Preparation 14 and Example 56, making non-critical variations, starting with the appropriate phenol, the title compound was obtained. HRMS (FAB) calcd for $C_{21}H_{23}ClN_2O$ $(MH^+)$ 355.1577, found 355.1570.

EXAMPLE 65

Preparation of 10-[3-(2,4-dichlorophenoxy)propyl]-1,2,3,4,5,6-hexahydroazepino[4,5-b]indole hydrochloride

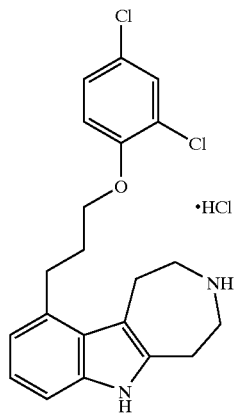

Following the procedures of Preparation 14 and Example 56, making non-critical variations, starting with the appropriate phenol, the title compound was obtained. MS (EI) m/z 389 $(MH^+)$.

EXAMPLE 66

Preparation of 10-[3-(2,5-dichlorophenoxy)propyl]-1,2,3,4,5,6-hexahydroazepino[4,5-b]indole hydrochloride

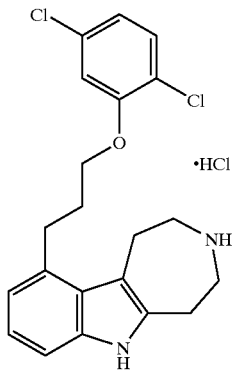

Following the procedures of Preparation 14 and Example 56, making non-critical variations, starting with the appropriate phenol, the title compound was obtained. MS (EI) m/z 389 $(MH^+)$.

EXAMPLE 67

Preparation of 10-[3-(4-fluorophenoxy)propyl]-1,2,3,4,5,6-hexahydroazepino[4,5-b]indole hydrochloride

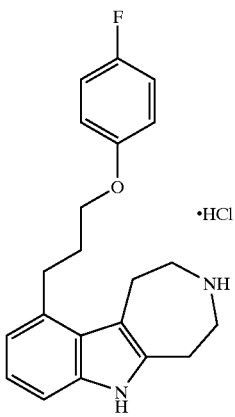

Following the procedures of Preparation 14 and Example 56, making non-critical variations, starting with the appropriate phenol, the title compound was obtained. MS (EI) m/z 339 $(MH^+)$.

EXAMPLE 68

Preparation of 10-[3-(4-methylphenoxy)propyl]-1,2,3,4,5,6-hexahydroazepino[4,5-b]indole hydrochloride

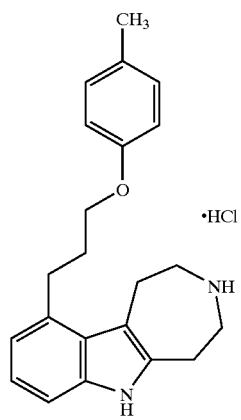

Following the procedures of Preparation 14 and Example 56, making non-critical variations, starting with the appropriate phenol, the title compound was obtained. MS (EI) m/z 335 (MH+).

Parallel Synthesis

A modified version of the above mentioned scheme was utilized for the parallel synthesis. The Sonogashira coupling and reduction to the alkane followed as previously mentioned to obtain 3-(3-benzoyl-1,2,3,4,5,6-hexahydroazepino [4,5-b]indol-10-yl)-1-propanol. Hydrolysis of the amide functionality under basic conditions led to the free base. Protection in situ as the tert-butyl carbamate and standard Mitsunobu reaction conditions using various aryl alcohols provided the corresponding aryl ethers. Immediate deprotection of the tert-butyl carbamate using DOWEXO® ion exchange resin (5.2 meq/g), removal of the reaction byproducts and excess reagents through successive washing, release from the resin through addition of excess base, and trapping the freebase as the hydrochloride salt led to the desired compounds.

Preparation 15

Preparation of tert-butyl 10-(3-hydroxypropyl)-1,4,5,6-tetrahydroazepino[4,5-b]indole-3(2H)-carboxylate A mixture of 3-(3-benzoyl-1,2,3,4,5,6-hexahydroazepino [4,5-b]indol-10-yl)-1-propanol (1.515 g, 4.35 mmol), potassium hydroxide (2.440 g, 43.47 mmol), and ethylene glycol (50 mL) was allowed to stir under $N_2$ in an oil bath. The bath temperature was raised to 158° C. and stirred for 16 h. The mixture was then cooled to rt, diluted with $H_2O$ (25 mL), dioxane (25 mL) and cooled further in an ice bath. Di-tert-butyldicarbonate (1.218 g 5.581 mmol) was added in two portions and the ice bath was removed. After 2 h, the room temperature mixture was poured into $H_2O$ (about 300 mL) and extracted with ethyl acetate (3×50 mL). Evaporation of the combined organic layers provided a brown oil. Crystallization from ethyl acetate and hexanes provided the title compound 0.825 as a tan solid (mp 166–168° C.): IR (drift) 3242, 3218, 2974, 2943, 2930, 2873, 1667, 1484, 1452, 1417, 1365, 1239, 1171, 1037, 749 cm$^{-1}$.

EXAMPLE 69

Preparation of 4-[3-(1,2,3,4,5,6-hexahydroazepino[4,5-b] indol-10-yl)propoxy]benzonitrile hydrochloride

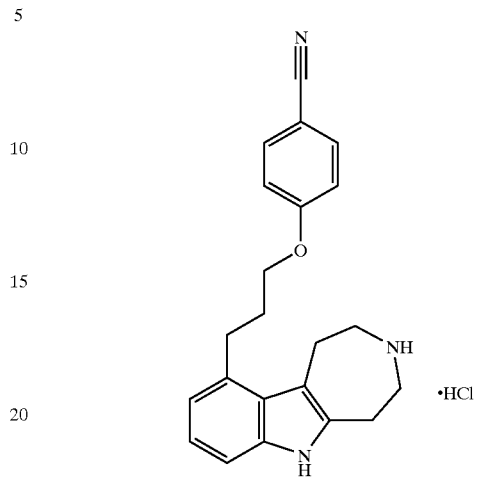

To a 25 mL scintillation vial containing a glass bead was added 4-cyanophenol (0.033 g, 0.277 mmol), a solution (0.250 M) of tert-butyl 10-(3-hydroxypropyl)-1,4,5,6-tetrahydroazepino[4,5-b]indole-3 (2H)-carboxyl ate (1.0 mL, 0.250 mmol) in tetrahydrofuran, a solution (0.275 M) of triphenylphosphine (1.0 mL, 0.275 mmol) in tetrahydrofuran, and diethylazodicarboxylate (43.5 µl, 0.275 mmol). The vial was capped and orbitally shaken for 30 h. The mixture then was diluted with dichloromethane (1 mL) and methanol (1 mL). DOWEX® ion exchange resin (5.2 meq/gram, 0.5–0.75 g) was added and the mixtures were capped and shaken orbitally at 40° C. for 3 h. The mixture was filtered and the resin was washed (2× each) with dichloromethane, methanol, water, and tetrahydrofuran. The product then was eluted using a 4 N solution of ammonium hydroxide in methanol. Evaporation provided a residue which upon treatment with methanolic hydrochloric acid and evaporation led to the title compound. MS (EI) for m/z 346 (MH+).

EXAMPLE 70

Preparation of 3-(1,2,3,4,5,6-hexahydroazepino[4,5-b] indol-10-yl)propyl 2-pyridinyl ether dihydrochloride

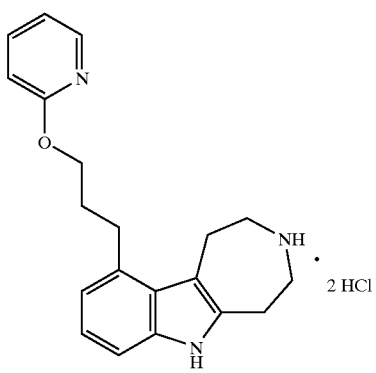

EXAMPLE 71

Preparation of 2-bromophenyl 3-(1,2,3,4,5,6-hexahydroazepino[4,5-b]indol-10-yl)propyl ether hydrochloride

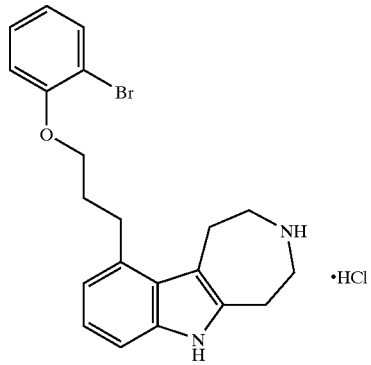

Following the procedure of Example 69, making non-critical variations, starting with the appropriate phenol, the title compound was obtained. MS (EI) m/z 322 (MH⁺).

Following the procedure of Example 69, making non-critical variations, starting with the appropriate phenol, the title compound was obtained. MS (EI) m/z 399 (MH⁺).

EXAMPLE 72

Preparation of 3-(1,2,3,4,5,6-hexahydroazepino[4,5-b]indol-10-yl)propyl 2-iodophenyl ether hydrochloride

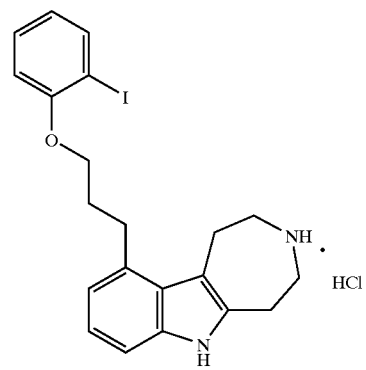

Following the procedure of Example 69, making non-critical variations, starting with the appropriate phenol, the title compound was obtained. MS (EI) m/z 447 (MH⁺).

EXAMPLE 73

Preparation of 2-ethylphenyl 3-(1,2,3,4,5,6-hexahydroazepino[4,5-b]indol-10-yl)propyl ether hydrochloride

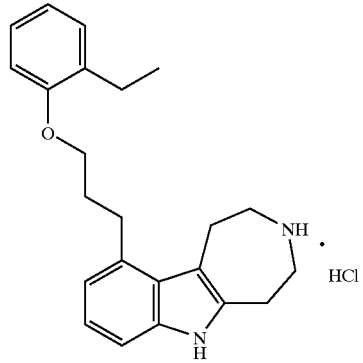

Following the procedure of Example 69, making non-critical variations, starting with the appropriate phenol, the title compound was obtained. MS (EI) m/z 349 (MH⁺).

EXAMPLE 74

Preparation of 10-[3-(2-isopropylphenoxy)propyl]-1,2,3,4,5,6-hexahydroazepino[4,5-b]indole hydrochloride

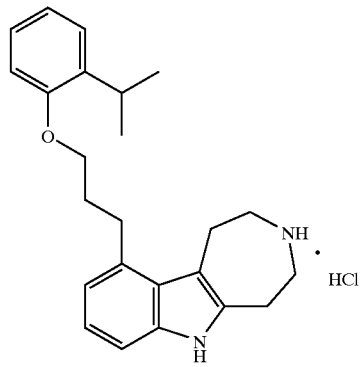

Following the procedure of Example 69, making non-critical variations, starting with the appropriate phenol, the title compound was obtained. MS (EI) m/z 363 (MH⁺).

EXAMPLE 75

Preparation of 2-[3-(1,2,3,4,5,6-hexahydroazepino[4,5-b]indol-10-yl)propoxy]benzonitrile hydrochloride

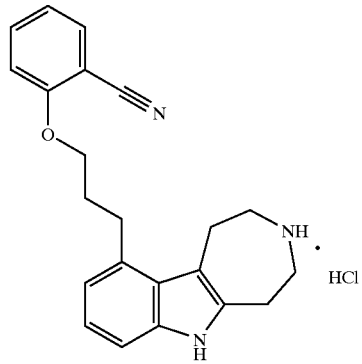

Following the procedure of Example 69, making non-critical variations, starting with the appropriate phenol, the title compound was obtained. MS (EI) m/z 346 (MH⁺).

EXAMPLE 76

Preparation of 3-(1,2,3,4,5,6-hexahydroazepino[4,5-b]indol-10-yl)propyl 3-pyridinyl ether dihydrochloride

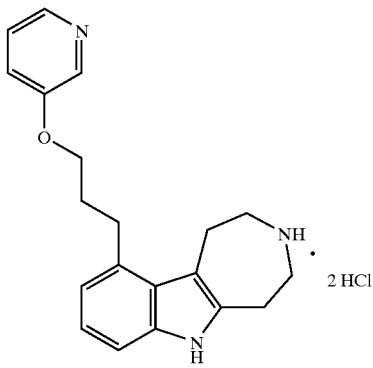

Following the procedure of Example 69, making non-critical variations, starting with the appropriate phenol, the title compound was obtained. MS (EI) m/z 322 (MH⁺).

EXAMPLE 77

Preparation of 10-[³-(3-fluorophenoxy)propyl]-1,2,3,4,5,6-hexahydroazepino[4,5-b]indole hydrochloride

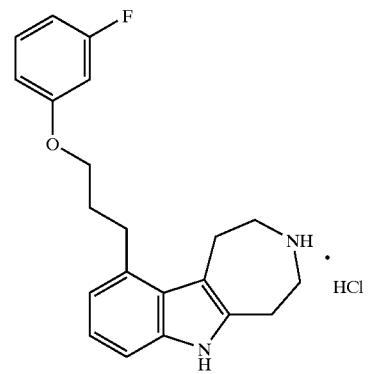

Following the procedure of Example 69, making non-critical variations, starting with the appropriate phenol, the title compound was obtained. MS (EI) m/z 339 (MH⁺).

EXAMPLE 78

Preparation of 3-bromophenyl 3-(1,2,3,4,5,6-hexahydroazepino[4,5-b]indol-10-yl)propyl ether hydrochloride

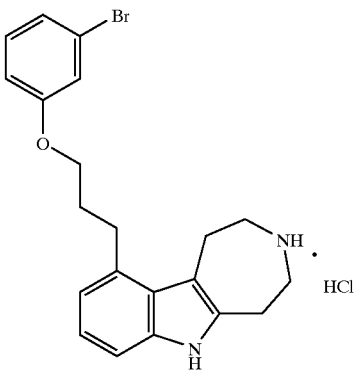

Following the procedure of Example 69, making non-critical variations, starting with the appropriate phenol, the title compound was obtained. MS (EI) m/z 399 (MH⁺).

EXAMPLE 79

Preparation of 3-(1,2,3,4,5,6-hexahydroazepino[4,5-b]indol-10-yl)propyl 3-iodophenyl ether hydrochloride

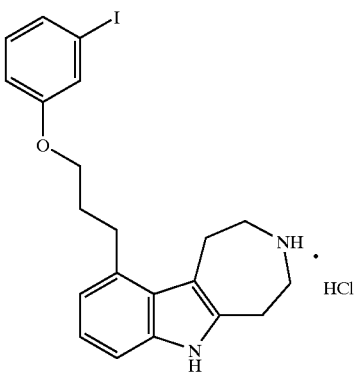

Following the procedure of Example 69, making non-critical variations, starting with the appropriate phenol, the title compound was obtained. MS (EI) m/z 447 (MH⁺).

EXAMPLE 80

Preparation of 10-[3-(3-isopropylphenoxy)propyl]-1,2,3,4,5,6-hexahydroazepino[4,5-b]indole hydrochloride

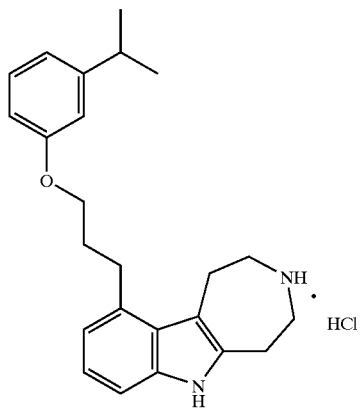

Following the procedure of Example 69, making non-critical variations, starting with the appropriate phenol, the title compound was obtained. MS (EI) m/z 363 (MH$^+$).

EXAMPLE 81

Preparation of 10-{3-[3-(trifluoromethyl)phenoxy]propyl}-1,2,3,4,5,6-hexahydroazepino[4,5-b]indole hydrochloride

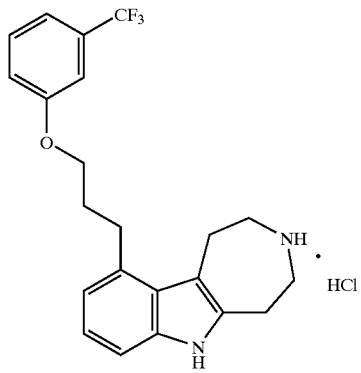

Following the procedure of Example 69, making non-critical variations, starting with the appropriate phenol, the title compound was obtained. MS (EI) m/z 389 (MH$^+$).

EXAMPLE 82

Preparation of 10-{3-[3-(trifluoromethoxy)phenoxy]propyl}-1,2,3,4,5,6-hexahydroazepino[4,5-b]indole hydrochloride.

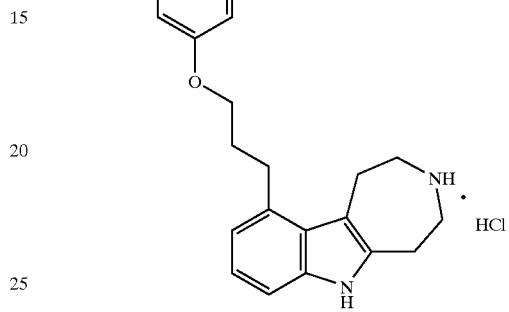

Following the procedure of Example 69, making non-critical variations, starting with the appropriate phenol, the title compound was obtained. MS (EI) m/z 405 (MH$^+$).

EXAMPLE 83

Preparation of 3-ethylphenyl 3-(1,2,3,4,5,6-hexahydroazepino[4,5-b]indol-10-yl)propyl ether hydrochloride

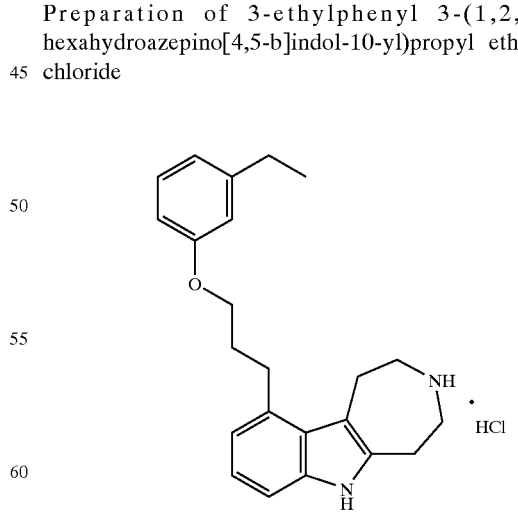

Following the procedure of Example 69, making non-critical variations, starting with the appropriate phenol, the title compound was obtained. MS (EI) m/z 349 (MH$^+$).

EXAMPLE 84
Preparation of 10-[3-(3-tert-butylphenoxy)propyl]-1,2,3,4,5,6-hexahydroazepino[4,5-b]indole hydrochloride

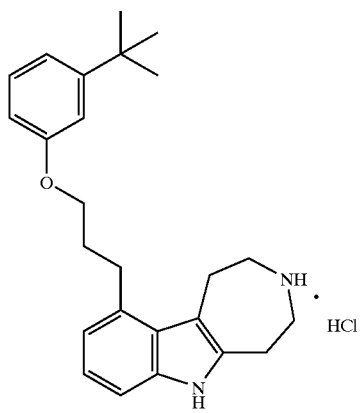

Following the procedure of Example 69, making non-critical variations, starting with the appropriate phenol, the title compound was obtained. MS (EI) m/z 377 (MH$^+$).

EXAMPLE 85
Preparation of 3-(1,2,3,4,5,6-hexahydroazepino[4,5-b]indol-10-yl)propyl 4-pyridinyl ether dihydrochloride

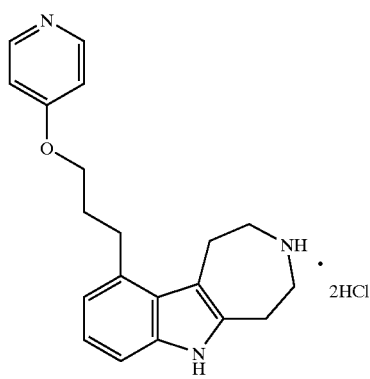

Following the procedure of Example 69, making non-critical variations, starting with the appropriate phenol, the title compound was obtained. MS (EI) m/z 322 (MH$^+$).

EXAMPLE 86
Preparation of 10-[3-(4-methoxyphenoxy)propyl]-1,2,3,4,5,6-hexahydroazepino[4,5-b]indole hydrochloride

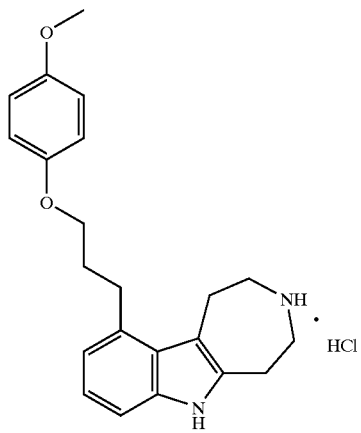

Following the procedure of Example 69, making non-critical variations, starting with the appropriate phenol, the title compound was obtained. MS (EI) m/z 351 (MH$^+$).

EXAMPLE 87
Preparation of 10-{3-[4-(benzyloxy)phenoxy]propyl}-1,2,3,4,5,6-hexahydroazepino[4,5-b]indole hydrochloride

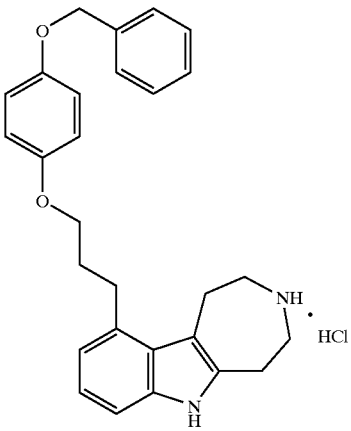

Following the procedure of Example 69, making non-critical variations, starting with the appropriate phenol, the title compound was obtained. MS (EI) m/z 427 (MH$^+$).

EXAMPLE 88
Preparation of 4-bromophenyl 3-(1,2,3,4,5,6-hexahydroazepino[4,5-b]indol-10-yl)propyl ether hydrochloride

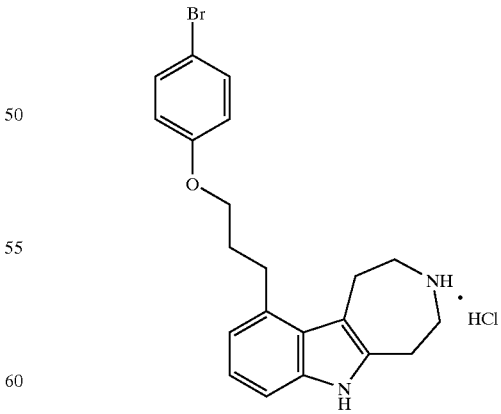

Following the procedure of Example 69, making non-critical variations, starting with the appropriate phenol, the title compound was obtained. MS (EI) m/z 399 (MH$^+$).

EXAMPLE 89

Preparation of 3-(1,2,3,4,5,6-hexahydroazepino[4,5-b]indol-10-yl)propyl 4-iodophenyl ether hydrochloride

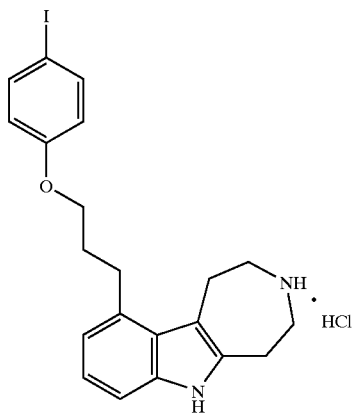

Following the procedure of Example 69, making non-critical variations, starting with the appropriate phenol, the title compound was obtained. MS (EI) m/z 447 (MH+).

EXAMPLE 90

Preparation of 4-ethylphenyl 3-(1,2,3,4,5,6-hexahydroazepino[4,5-b]indol-10-yl)propyl ether hydrochloride

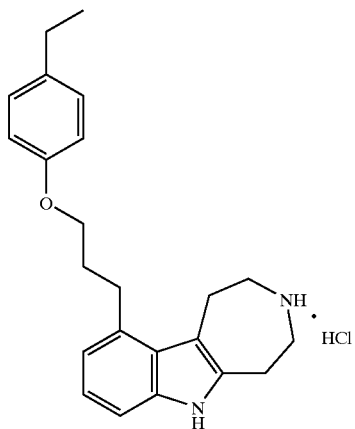

Following the procedure of Example 69, making non-critical variations, starting with the appropriate phenol, the title compound was obtained. MS (EI) m/z 349 (MH+).

EXAMPLE 91

Preparation of 10-[3-(4-isopropylphenoxy)propyl]-1,2,3,4,5,6-hexahydroazepino[4,5-b]indole hydrochloride

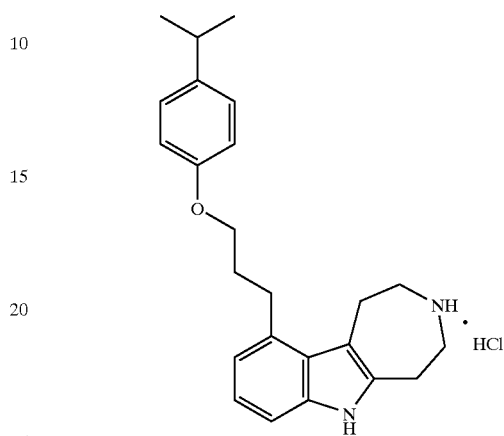

Following the procedure of Example 69, making non-critical variations, starting with the appropriate phenol, the title compound was obtained. MS (EI) m/z 363 (MH+).

EXAMPLE 92

Preparation of 10-{3-[(4'-bromo[1,1'-biphenyl]-4-yl)oxy]propyl}-1,2,3,4,5,6-hexahydroazepino[4,5-b]indole hydrochloride

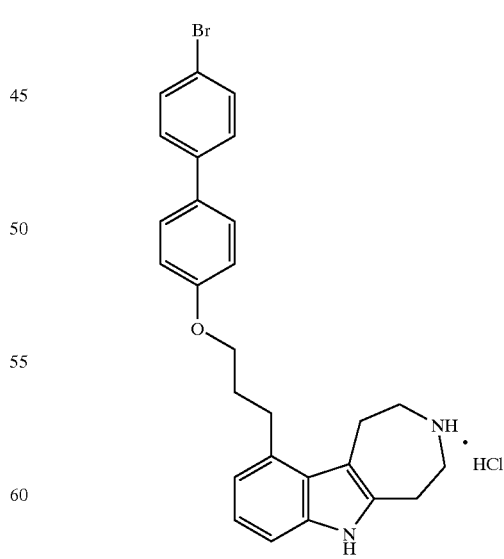

Following the procedure of Example 69, making non-critical variations, starting with the appropriate phenol, the title compound was obtained. MS (EI) m/z 477 (MH+).

EXAMPLE 93

Preparation of 10-[3-(2,3-difluorophenoxy)propyl]-1,2,3,4,5,6-hexahydroazepino[4,5-b]indole hydrochloride

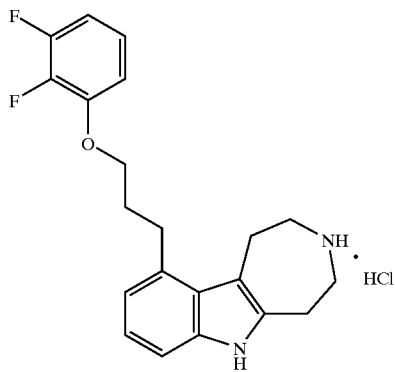

Following the procedure of Example 69, making non-critical variations, starting with the appropriate phenol, the title compound was obtained. MS (EI) m/z 357 (MH$^+$).

EXAMPLE 94

Preparation of 10-[3-(2,4-dibromophenoxy)propyl]-1,2,3,4,5,6-hexahydroazepino[4,5-b]indole hydrochloride

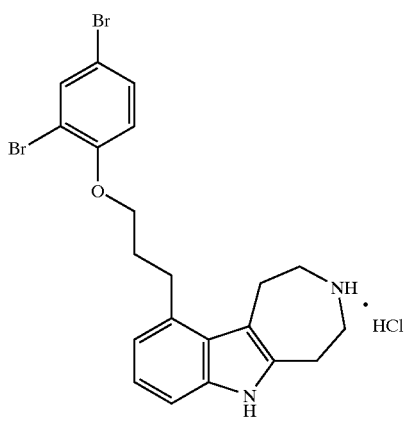

Following the procedure of Example 69, making non-critical variations, starting with the appropriate phenol, the title compound was obtained. MS (EI) m/z 479 (MH$^+$).

EXAMPLE 95

Preparation of 10-[3-(2,4-difluorophenoxy)propyl]-1,2,3,4,5,6-hexahydroazepino[4,5-b]indole hydrochloride

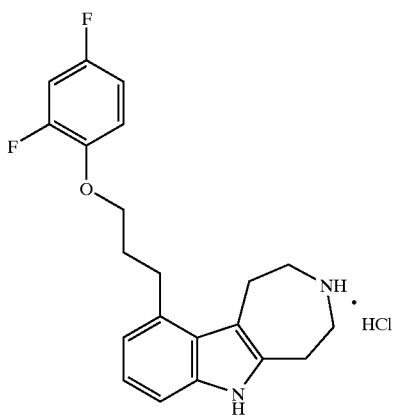

Following the procedure of Example 69, making non-critical variations, starting with the appropriate phenol, the title compound was obtained. MS (EI) m/z 357 (MH$^+$).

EXAMPLE 96

Preparation of 10-[3-(2-methoxy-4-methylphenoxy)propyl]-1,2,3,4,5,6-hexahydroazepino[4,5-b]indole hydrochloride

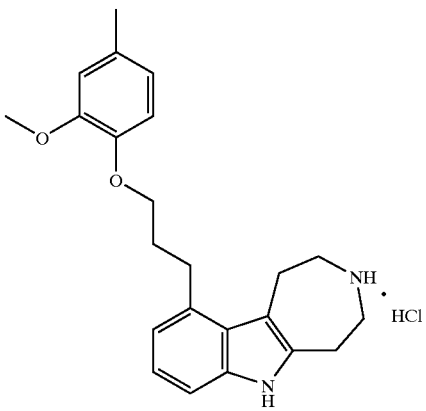

Following the procedure of Example 69, making non-critical variations, starting with the appropriate phenol, the title compound was obtained. MS (EI) m/z 365 (MH$^+$).

EXAMPLE 97

Preparation of 10-[3-(4-iodo-2-methylphenoxy)propyl]-1,2,3,4,5,6-hexahydroazepino[4,5-b]indole hydrochloride

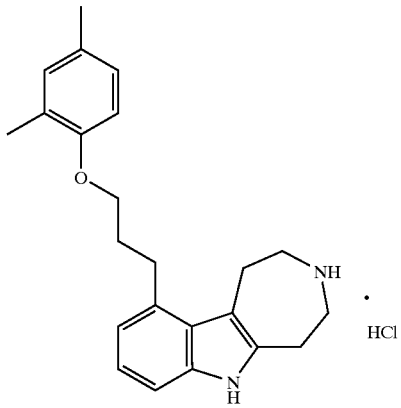

Following the procedure of Example 69, making non-critical variations, starting with the appropriate phenol, the title compound was obtained. MS (EI) m/z 461 (MH$^+$).

EXAMPLE 98

Preparation of 10-[3-(2,5-difluorophenoxy)propyl]-1,2,3,4,5,6-hexahydroazepino[4,5-b]indole hydrochloride

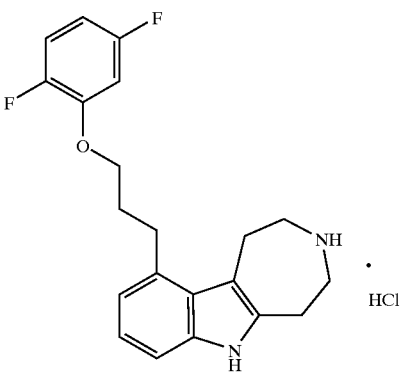

Following the procedure of Example 69, making non-critical variations, starting with the appropriate phenol, the title compound was obtained. MS (EI) m/z 357 (MH$^+$).

EXAMPLE 99

Preparation of 10-[3-(2-chloro-5-methylphenoxy)propyl]-1,2,3,4,5,6-hexahydroazepino[4,5-b]indole hydrochloride

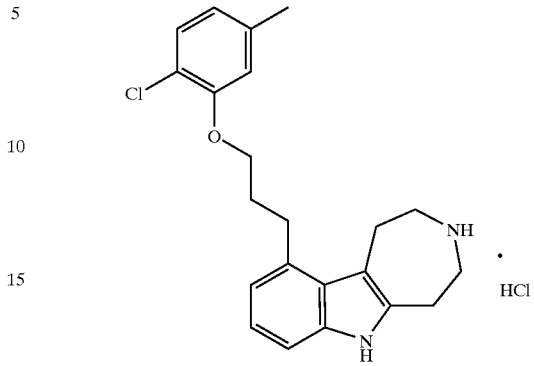

Following the procedure of Example 69, making non-critical variations, starting with the appropriate phenol, the title compound was obtained. MS (EI) m/z 369 (MH$^+$)

EXAMPLE 100

Preparation of 10-[3-(2-isopropyl-5-methylphenoxy)propyl]-1,2,3,4,5,6-hexahydroazepino[4,5-b]indole hydrochloride

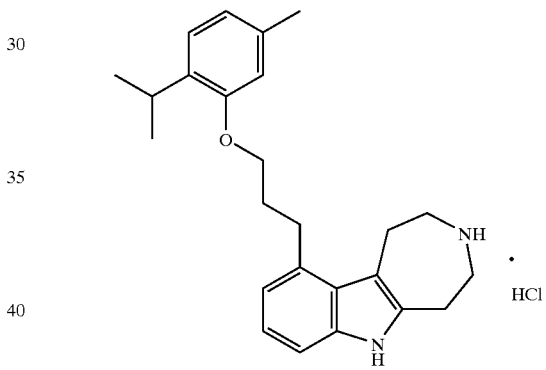

Following the procedure of Example 69, making non-critical variations, starting with the appropriate phenol, the title compound was obtained. MS (EI) m/z 377 (MH$^+$).

EXAMPLE 101

Preparation of 10-[3-(2,6-difluorophenoxy)propyl]-1,2,3,4,5,6-hexahydroazepino[4,5-b]indole hydrochloride

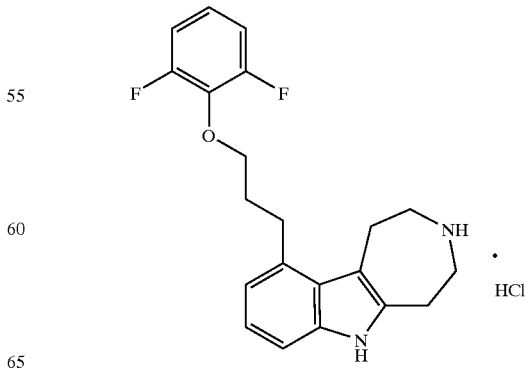

Following the procedure of Example 69, making non-critical variations, starting with the appropriate phenol, the title compound was obtained. MS (EI) m/z 357 (MH⁺).

EXAMPLE 102

Preparation of 10-[3-(2,6-dichlorophenoxy)propyl]-1,2,3,4,5,6-hexahydroazepino[4,5-b]indole hydrochloride

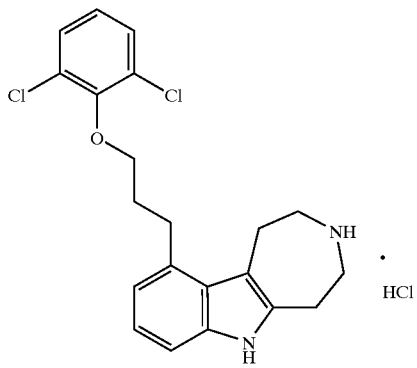

Following the procedure of Example 69, making non-critical variations, starting with the appropriate phenol, the title compound was obtained. MS (EI) m/z 389 (MH⁺).

EXAMPLE 103

Preparation of 10-[3-(2,6-dimethylphenoxy)propyl]-1,2,3,4,5,6-hexahydroazepino[4,5-b]indole hydrochloride

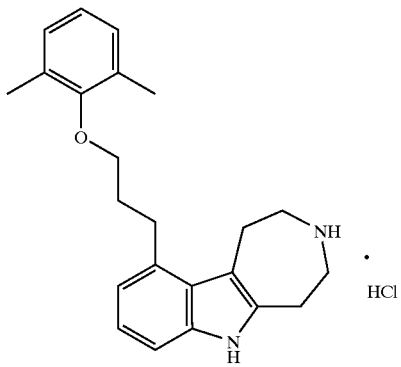

Following the procedure of Example 69, making non-critical variations, starting with the appropriate phenol, the title compound was obtained. MS (EI) m/z 349 (MH⁺).

EXAMPLE 104

Preparation of 10-[3-(2-fluoro-6-methylphenoxy)propyl]-1,2,3,4,5,6-hexahydroazepino[4,5-b]indole hydrochloride

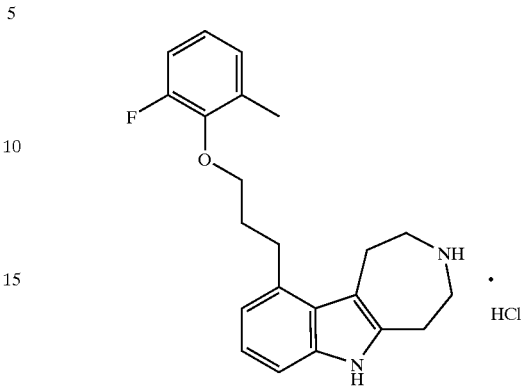

Following the procedure of Example 69, making non-critical variations, starting with the appropriate phenol, the title compound was obtained. MS (EI) m/z 369 (MH⁺).

EXAMPLE 105

Preparation of 3-(1,2,3,4,5,6-hexahydroazepino[4,5-b]indol-10-yl)-1-propanol hydrochloride

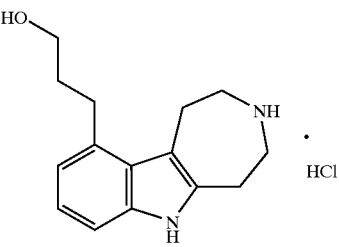

Following the procedure of Example 69, except using no phenol, the title compound was obtained. MS (EI) m/z 245 (MH⁺).

EXAMPLE 106

Preparation of 10-[3-(2,3,6-trimethylphenoxy)propyl]-1,2,3,4,5,6-hexahydroazepino[4,5-b]indole hydrochloride

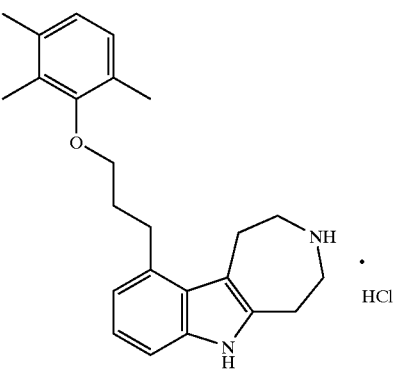

Following the procedure of Example 69, making non-critical variations, starting with the appropriate phenol, the title compound was obtained. MS (EI) m/z 363 (MH⁺).

EXAMPLE 107

Preparation of 10-[3-(mesityloxy)propyl]-1,2,3,4,5,6-hexahydroazepino[4,5-b]indole hydrochloride

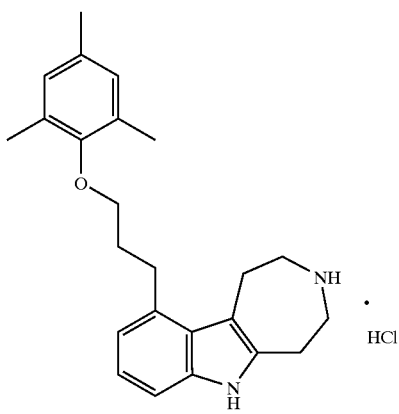

Following the procedure of Example 69, making non-critical variations, starting with the appropriate phenol, the title compound was obtained. MS (EI) m/z 363 (MH⁺).

EXAMPLE 108

Preparation of 10-[3-(2,6-dibromo-4-methylphenoxy)propyl]-1,2,3,4,5,6-hexahydroazepino[4,5-b]indole hydrochloride

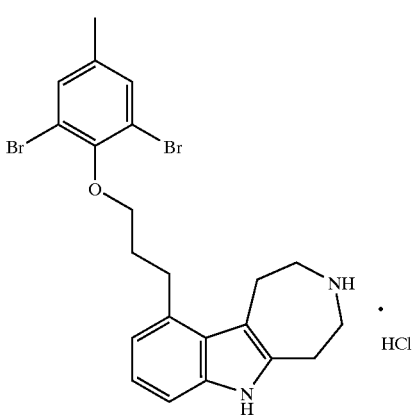

Following the procedure of Example 69, making non-critical variations, starting with the appropriate phenol, the title compound was obtained. MS (EI) m/z 493 (MH⁺).

EXAMPLE 109

Preparation of 10-[3-(4-chloro-3-fluorophenoxy)propyl]-1,2,3,4,5,6-hexahydroazepino[4,5-b]indole hydrochloride

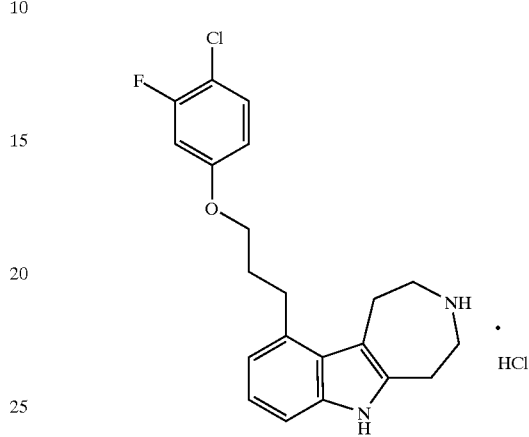

Following the procedure of Example 69, making non-critical variations, starting with the appropriate phenol, the title compound was obtained. MS (EI) m/z 373 (MH⁺).

EXAMPLE 110

Preparation of 10-[3-(4-chloro-3-methylphenoxy)propyl]-1,2,3,4,5,6-hexahydroazepino[4,5-b]indole hydrochloride

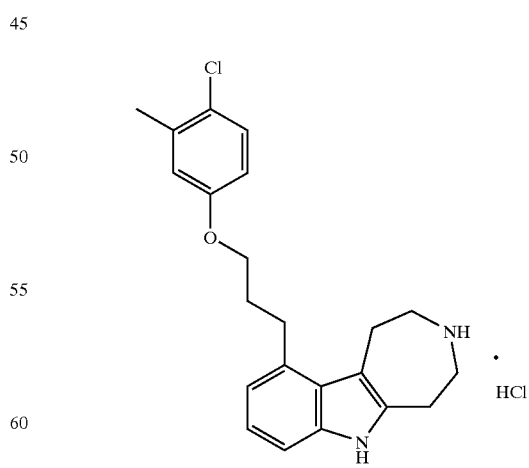

Following the procedure of Example 69, making non-critical variations, starting with the appropriate phenol, the title compound was obtained. MS (EI) m/z 369 (MH⁺).

EXAMPLE 111
Preparation of 10-[3-(3-chloro-4-fluorophenoxy)propyl]-1,2,3,4,5,6-hexahydroazepino[4,5-b]indole hydrochloride

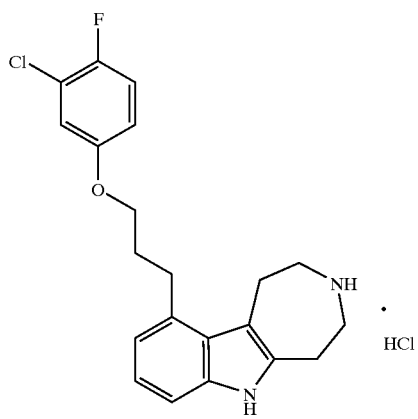

Following the procedure of Example 69, making non-critical variations, starting with the appropriate phenol, the title compound was obtained. MS (EI) m/z 373 (MH⁺).

EXAMPLE 112
Preparation of 10-[3-(1,3-benzodioxol-5-yloxy)propyl]-1,2,3,4,5,6-hexahydroazepino[4,5-b]indole hydrochloride

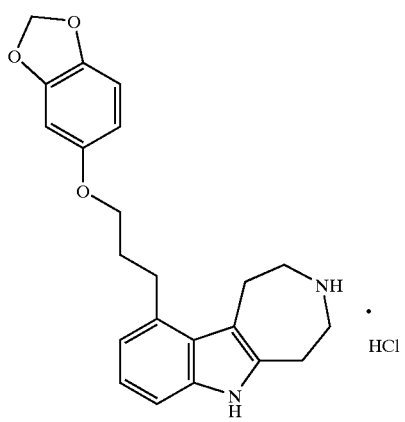

Following the procedure of Example 69, making non-critical variations, starting with the appropriate phenol, the title compound was obtained. MS (EI) m/z 365 (MH⁺).

EXAMPLE 113
Preparation of 10-[3 (3,5-dichlorophenoxy)propyl]-1,2,3,4,5,6-hexahydroazepino[4,5-b]indole hydrochloride

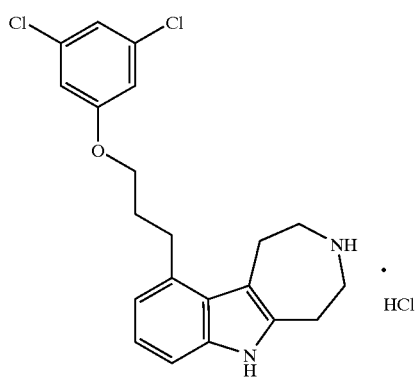

Following the procedure of Example 69, making non-critical variations, starting with the appropriate phenol, the title compound was obtained. MS (EI) m/z 389 (MH⁺).

EXAMPLE 114

Preparation of 10-[3-(3,5-dimethylphenoxy)propyl]-1,2,3,4,5,6-hexahydroazepino[4,5-b]indole hydrochloride

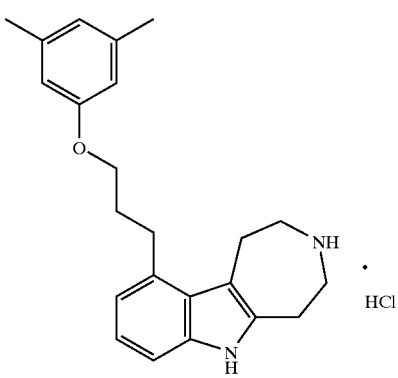

Following the procedure of Example 69, making non-critical variations, starting with the appropriate phenol, the title compound was obtained. MS (EI) m/z 349 (MH⁺).

EXAMPLE 115

Preparation of 10-[3-(3,5-dimethoxyphenoxy)propyl]-1,2,3,4,5,6-hexahydroazepino[4,5-b]indole hydrochloride.

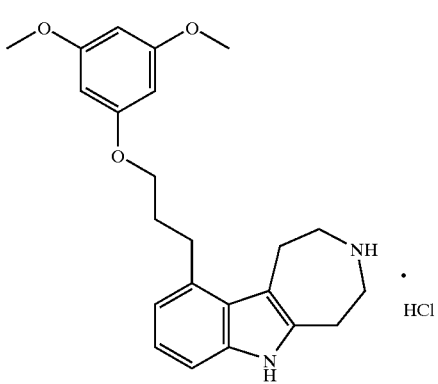

Following the procedure of Example 69, making non-critical variations, starting with the appropriate phenol, the title compound was obtained. MS (EI) m/z 381 (MH⁺).

EXAMPLE 116

Preparation of 10-[3-(5,6,7,8-tetrahydro-1-naphthalenyloxy)propyl]-1,2,3,4,5,6-hexahydroazepino[4,5-b]indole hydrochloride

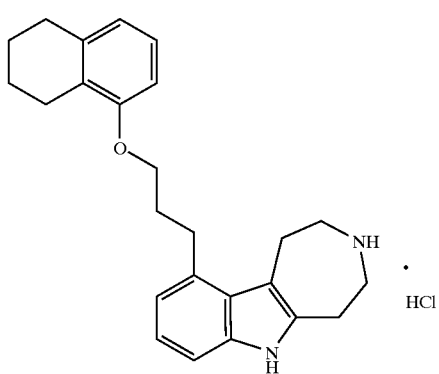

Following the procedure of Example 69, making non-critical variations, starting with the appropriate phenol, the title compound was obtained. MS (EI) m/z 375 (MH$^+$).

EXAMPLE 117

Preparation of 10-{3-[(2,4-dichloro-1-naphthyl)oxy]propyl}-1,2,3,4,5,6-hexahydroazepino[4,5-b]indole hydrochloride

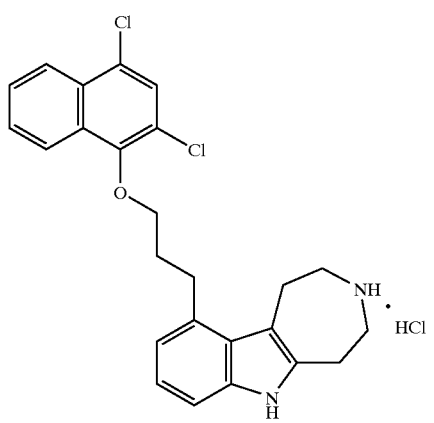

Following the procedure of Example 69, making non-critical variations, starting with the appropriate phenol, the title compound was obtained. MS (EI) m/z 439 (MH$^+$).

EXAMPLE 118

Preparation of 10-{3-[(4-methoxy-1-naphthyl)oxy]propyl}-1,2,3,4,5,6-hexahydroazepino[4,5-b]indole hydrochloride

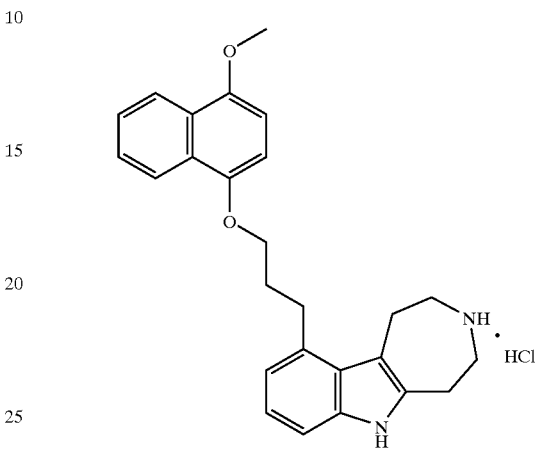

Following the procedure of Example 69, making non-critical variations, starting with the appropriate phenol, the title compound was obtained. MS (EI) m/z 401 (MH$^+$).

EXAMPLE 119

Preparation of 10-{3-[(4-chloro-1-naphthyl)oxy]propyl}-1,2,3,4,5,6-hexahydroazepino[4,5-b]indole hydrochloride

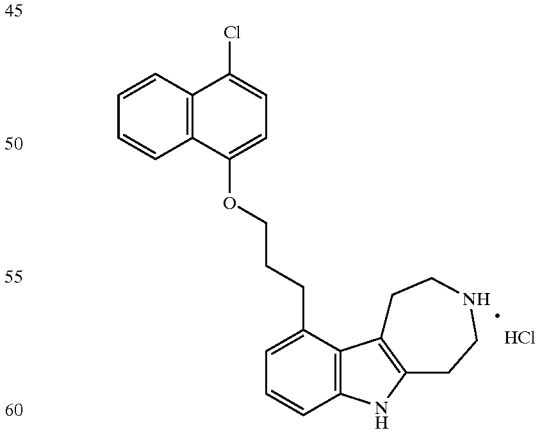

Following the procedure of Example 69, making non-critical variations, starting with the appropriate phenol, the title compound was obtained. MS (EI) m/z 405 (MH$^+$).

EXAMPLE 120

Preparation of 10-{3-[(1,6-dibromo-2-naphthyl)oxy]propyl}-1,2,3,4,5,6-hexahydroazepino[4,5-b]indole hydrochloride

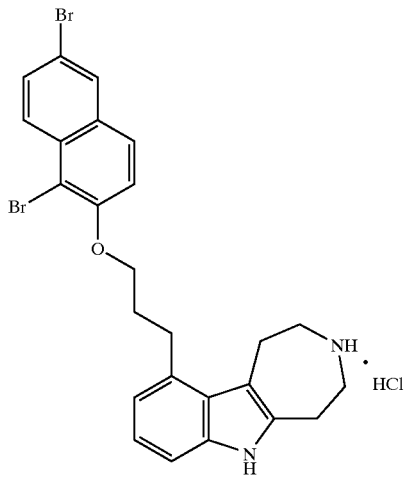

Following the procedure of Example 69, making non-critical variations, starting with the appropriate phenol, the title compound was obtained. MS (EI) m/z 529 (MH$^+$).

EXAMPLE 121

Preparation of 10-{3-[(1-bromo-2-naphthyl)oxy]propyl}-1,2,3,4,5,6-hexahydroazepino[4,5-b]indole hydrochloride

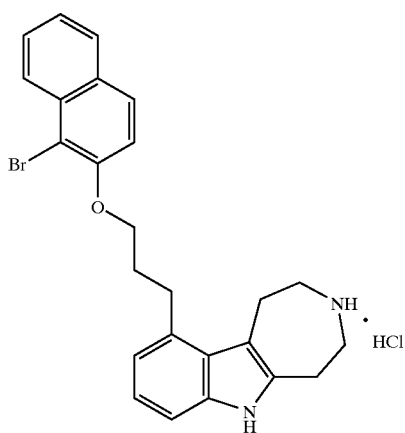

Following the procedure of Example 69, making non-critical variations, starting with the appropriate phenol, the title compound was obtained. MS (EI) m/z 449 (MH$^+$).

EXAMPLE 122

Preparation of 10-[3-(2,3,4,5,6-pentafluorophenoxy)propyl]-1,2,3,4,5,6-hexahydroazepino[4,5-b]indole hydrochloride

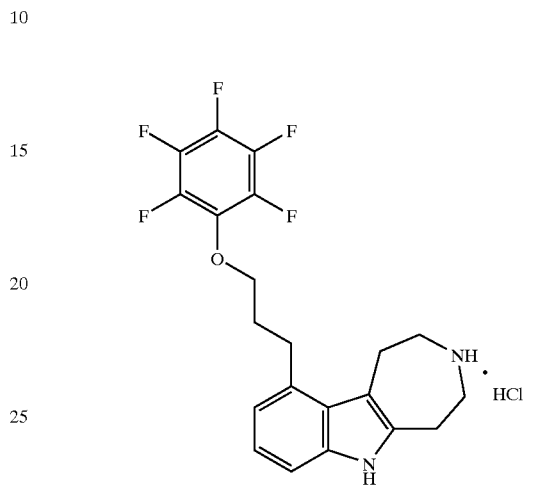

Following the procedure of Example 69, making non-critical variations, starting with the appropriate phenol, the title compound was obtained. MS (EI) m/z 411 (MH$^+$).

EXAMPLE 123

Preparation of 10-[3-(5-isoquinolinyloxy)propyl]-1,2,3,4,5,6-hexahydroazepino[4,5-b]indole dihydrochloride

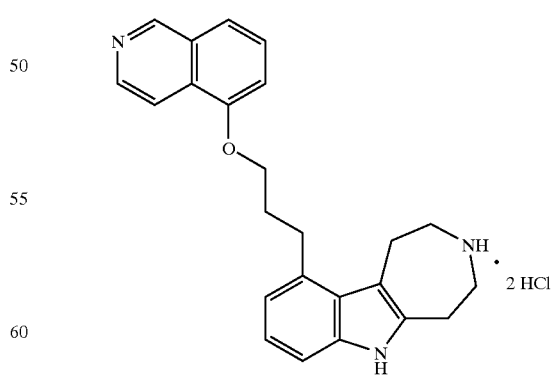

Following the procedure of Example 69, making non-critical variations, starting with the appropriate phenol, the title compound was obtained. MS (EI) m/z 372 (MH$^+$).

EXAMPLE 124
Preparation of 10-[3-([1,1'-biphenyl]-2-yloxy)propyl]-1,2,3,4,5,6-hexahydroazepino[4,5-b]indole hydrochloride

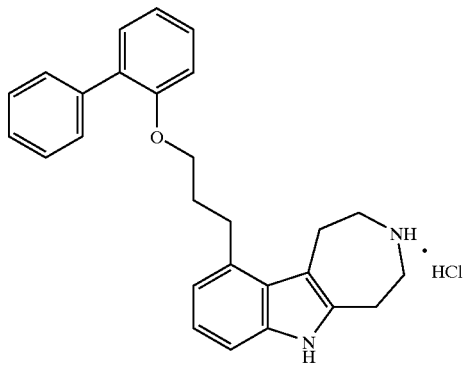

Following the procedure of Example 69, making non-critical variations, starting with the appropriate phenol, the title compound was obtained. MS (EI) m/z 397 (MH+).

EXAMPLE 125
Preparation of 10-{3-[(5-chloro-8-quinolinyl)oxy]propyl}-1,2,3,4,5,6-hexahydroazepino[4,5-b]indole dihydrochloride

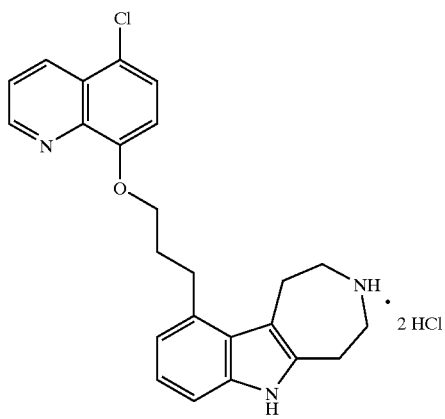

Following the procedure of Example 69, making non-critical variations, starting with the appropriate phenol, the title compound was obtained. MS (EI) m/z 406 (MH+).

Preparation 16
Preparation of tert-butyl 1,4,5,6-tetrahydroazepino[4,5-b]indole-3(2H)-carboxylate Di-tert-butyldicarbonate (6.33 g, 29.0 mmol) was added to a mixture of 1,2,3,4,5,6-hexahydroazepino[4,5-b]indole (5.40 g, 29.0 mmol) in dichloromethane (20 mL). The mixture was stirred for 48 h, then poured into water (50 mL), and extracted with dichloromethane (3×40 mL). The combined organics were dried over sodium sulfate, evaporated in vacuo and crystallized from ethyl acetate to provide 5.71 g of the title compound, the structure of which is shown in FIG. 6 as (22).

Preparation 17
Preparation of tert-butyl 6-(2-ethoxy-2-oxoethyl)-1,4,5,6-tetrahydroazepino[4,5-b]indole-3(2H)-carboxylate To a mixture of tert-butyl 1,4,5,6-tetrahydroazepino[4,5-b]indole-3(2H)-carboxylate (3.557 g, 12.42 mmol) and N,N-dimethylformamide (30 mL) was added 60% sodium hydride (0.596 g, 14.90 mmol). The mixture stirred for 1 h, and then cooled in a 0° C. bath. Ethyl bromoacetate was added, and the mixture warmed to room temperature. Water then was added and the mixture was evaporated in vacuo. The residue was taken up in ethyl acetate and washed with water. Evaporation and trituration with hexanes provided 3.289 g of the title compound, the structure of which is shown in FIG. 6 as (23) (where n=1).

Preparation 18
Preparation of tert-butyl 6-(2-hydroxyethyl)-1,4,5,6-tetrahydroazepino[4,5-b]indole-3(2H)-carboxylate A chilled (0° C.) mixture of tert-butyl 6-(2-ethoxy-2-oxoethyl)-1,4,5,6-tetrahydroazepino[4,5-b]indole-3(2H)-carboxylate in tetrahydrofuran (30 mL) was treated over 1 h with 1 M diisobutylaluminum hydride (19.0 mL, 19.0 mmol) in dichloromethane. After 1.5 h, ice was added and the mixture was allowed to warn to rt. The mixture was evaporated in vacuo and the residue was partitioned between ethyl acetate and water. The organic phase was filtered through celite, dried, and evaporated in vacuo to provide 2.479 g of the title compound, the structure of which is shown in FIG. 6 as (24) (where n=1).

Preparation 19
Preparation of tert-butyl 6-[2-(3-methoxyphenoxy)ethyl]-1,4,5,6-tetrahydroazepino[4,5-b]indole-3(2H)-carboxylate A mixture of tert-butyl 6-(2-hydroxyethyl)-1,4,5,6-tetrahydroazepino[4,5-b]indole-3(2H)-carboxylate (0.459 g, 1.39 mmol), 3-methoxyphenol (0.170 g, 1.39 mmol) and triphenylphosphine (0.364 g, 1.39 mmol) in tetrahydrofuran (15 mL) was treated with diethylazodicarboxylate (0.243 g, 1.39 mmol). The mixture stirred for 24 h, and then was evaporated in vacuo. Column chromatography (90 g SiO₂, 70% hexanes/30% ethyl acetate) provided an oil which was extracted into ethyl acetate and washed with 1 N sodium hydroxide. The organic phase was dried and evaporated to provide the title compound and was used without isolation. The structure of the title compound is shown in FIG. 6 as (25), where n=1 and Ar=3-MeOphenyl.

EXAMPLE 126
Preparation of 6-[2-(3-methoxyphenoxy)ethyl]-1,2,3,4,5,6-hexahydroazepino[4,5-b]indole maleate

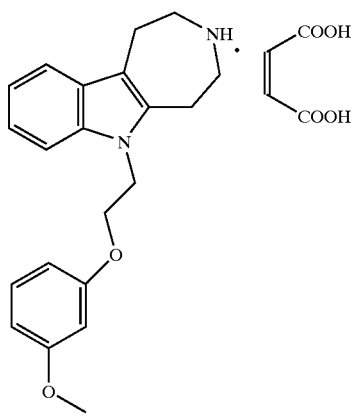

A mixture of tert-butyl 6-[2-(3-methoxyphenoxy)ethyl]-1,4,5,6-tetrahydroazepino[4,5-b]indole-3(2H)-carboxylate (0.447 g, 1.02 mmol) in methanolic hydrochloric acid was warmed in a 50° C. bath for 1.5 h. The mixture was evaporated, taken up in ethyl acetate, then washed with 1 N sodium hydroxide. The organic phase was dried and evaporated to provide an oil. The oil was diluted with methanol

EXAMPLE 127

Preparation of 3-nitrophenyl 2-(2,3,4,5-tetrahydroazepino[4,5-b]indol-6(1H)-yl)ethyl ether hydrochloride

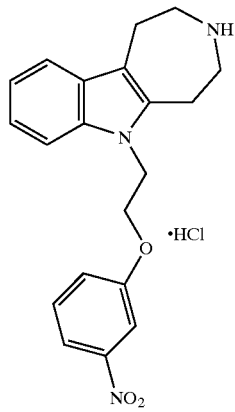

Following the procedure of Example 126, making non-critical variations, starting with the appropriate phenol, and trapping as the hydrochloride salt, the title compound was obtained. HRMS (FAB) calcd for $C_{20}H_{21}N_3O_3$ (MH$^+$) 352.1661, found 352.1681.

EXAMPLE 128

Preparation of 6-[2-(3-isopropylphenoxy)ethyl]-1,2,3,4,5,6-hexahydroazepino[4,5-b]indole maleate

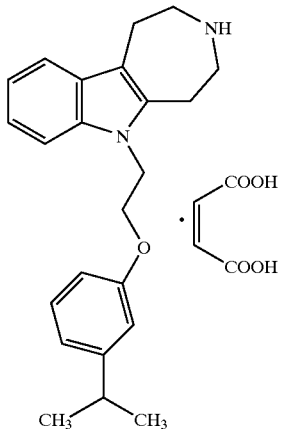

Following the procedure of Example 126, making non-critical variations, starting with the appropriate phenol, and trapping as the maleate salt, the title compound was obtained. HRMS (FAB) calcd for $C_{23}H_{28}N_2O$ (MH$^+$) 349.2280, found 349.2272.

EXAMPLE 129

Preparation of 4-pyridinyl 2-(2,3,4,5-tetrahydroazepino[4,5-b]indol-6(1H)-yl)ethyl ether dihydrochloride

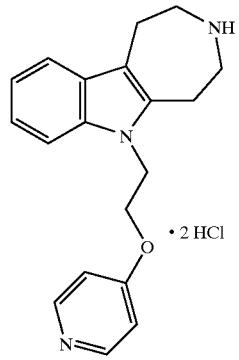

Following the procedure of Example 126, making non-critical variations, starting with the appropriate phenol, and trapping as the dihydrochloride salt, the title compound was obtained. HRMS (FAB) calcd for $C_{19}H_{21}N_3O$ (MH$^+$) 308.1763, found 308.1759.

Preparation 20

Preparation of 3-tert-butyloxycarbonyl-6-(3-chloropropyl)-1,2,3,4,5,6-hexahydroazepino[4,5-b]indole Sodium hydride (335 mg, 60%) was added to a solution of 3-tert-butyloxycarbonyl-1,2,3,4,5,6-hexahydroazepino[4,5-b]indole (1.99 g) and DMF (21.0 mL) at 0° C. The solution was stirred at 0° C. for 30 min and then 1-bromo-3-chloropropane (0.74 mL) was added. The solution was stirred at 0° C. for 1 h and 16 h at room temperature. The solution was diluted with EtOAc, which was washed with water (3×20 mL). The combined aqueous layers were extracted with EtOAc (2×20 mL). The combined organic layers were dried (MgSO$_4$), filtered, and concentrated. The crude material was purified by chromatography (Biotage, silica gel, 4:1–1:1 hexane:EtOAc) to give 1.38 g of the title compound as an oil: $^1$H NMR (300 MHz, CDCl$_3$) δ 7.50, 7.10–7.40, 4.28, 3.55–3.82, 3.52, 2.95–3.10, 2.15–2.30, 1.51; MS (ESI) m/z 363 (M$^+$).

Preparation 21

Preparation of 3-tert-butyloxycarbonyl-6-(3-phenoxypropyl)-1,2,3,4,5,6-hexahydroazepino[4,5-b]indole A mixture of 3-tert-butyloxycarbonyl-6-(3-chloropropyl)-1,2,3,4,5,6-hexahydroazepino[4,5-b]indole (213 mg), phenol (90 mg), DMF (2.0 mL), and K$_2$CO$_3$ (81 mg) was heated at 100° C. for 16 h, then allowed to cool to room temperature. The mixture was diluted with EtOAc (50 mL), then washed with water (3×10 mL). The organic layer was dried (MgSO$_4$), filtered, and concentrated. Purification by flash chromatography (silica gel, 3:1 hexane:EtOAc) gave 205 mg of the title compound as an oil: $^1$H NMR (300 MHz, CDCl$_3$) δ 7.45–7.55, 6.8–7.35, 4.33, 3.90, 3.55–3.75, 2.90–3.10, 2.12–2.28, 1.49; MS (ESI) m/z 421 (M$^+$).

EXAMPLE 130

Preparation of 6-(3-phenoxypropyl)-1,2,3,4,5,6-hexahydroazepino[4,5-b]indole maleate

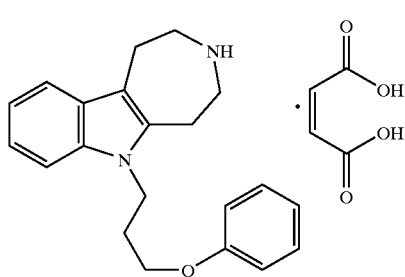

A solution of 3-tert-butyloxycarbonyl-6-(3-phenoxypropyl)-1,2,3,4,5,6-hexahydroazepino[4,5-b]indole (205 mg), CH$_2$Cl$_2$ (4.0 mL), and TFA (2.0 mL) was stirred at 0° C. for 1.5 h, then concentrated. The residue was partitioned between CH$_2$Cl$_2$ and aq. NaHCO$_3$. The organic layers were dried (MgSO$_4$), filtered, and concentrated to give 70 mg of the desired product. The maleic acid salt was prepared in ether, and the crude product triturated with ether to provide the title compound: $^1$H NMR (300 MHz, CDCl$_3$) δ 7.40–7.50, 7.20–7.35, 7.00–7.15, 6.95, 6.80–6.90, 4.33, 3.87, 2.85–3.10, 2.10–2.25.

EXAMPLE 131

Preparation of 6-[3-(3-chlorophenoxy)propyl]-1,2,3,4,5,6-hexahydroazepino[4,5-b]indole maleate

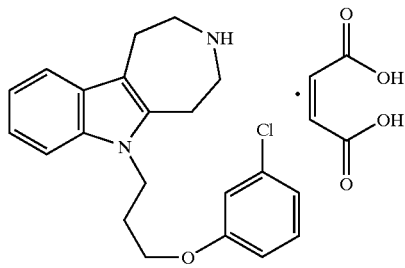

Following Example 130, but starting with 3-chlorophenol, and making non-critical variations, the title compound was obtained: $^1$H NMR (300 MHz, CDCl$_3$) δ 7.41–7.51, 7/05–7.30, 6.65–6.95, 4.31, 3.84, 2.90–3.15, 2.05–2.45; MS (ESI) m/z 357, 355.

EXAMPLE 132

Preparation of 6-[3-(4-fluorophenoxy)propyl]-1,2,3,4,5,6-hexahydroazepino[4,5-b]indol-6(1H)-yl]propyl ether maleate Following Example 130, but starting with 4-fluorophenol and making non-critical variations, the title compound was obtained: $^1$H NMR (300 MHz, CDCl$_3$) δ 7.40–7.50, 6.90–7.30, 6.85–6.95, 4.32, 3.81, 2.85–3.15, 2.10–2.25, 1.83; MS (ESI) m/z 339 (M$^+$).

EXAMPLE 133

Preparation of 10-bromo-6-(2-phenoxyethyl)-1,2,3,4,5,6-hexahydroazepino[4,5-b]indole oxalate

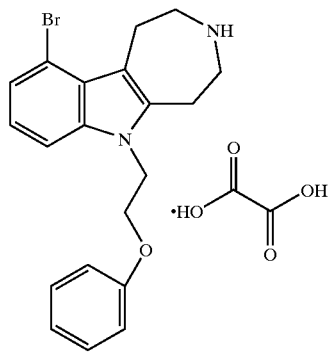

Starting with 3-tert-butyloxycarbonyl-10-bromo-1,2,3,4,5,6-tetrahydroazepino[4,5-b]indole, and β-bromophenetole, the title compound was obtained: $^1$H NMR (300 MHz, CDCl$_3$) δ 7.20–7.35, 6.90–7.10, 6.75–6.90, 4.49, 4.18, 3.40–3.65, 3.00–3.30; MS (ESI) m/z 387, 385.

EXAMPLE 134

Preparation of 6-(2-phenoxyethyl)-1,2,3,4,5,6-hexahydroazepino[4,5-b]indole oxalate

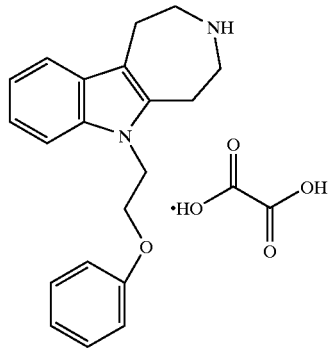

Hydrogenolysis of 10-bromo-6-(2-phenoxyethyl)-1,2,3,4,5,6-hexahydroazepino[4,5-b]indole oxalate gave the title compound: $^1$H NMR (300 MHz, CDCl$_3$) δ 6.70–7.35, 4.40–4.55, 4.10–4.25, 3.45–3.55, 3.00–3.20; MS (ESI) m/z 307 (M$^+$).

Preparation 22

Preparation of tert-butyl 10-bromo-6-(2-ethoxy-2-oxoethyl)-1,4,5,6-tetrahydroazepino[4,5-b]indole-3(2H)-carboxylate Prepared according to the procedure used to prepare tert-butyl 6-(2-ethoxy-2-oxoethyl)-1,4,5,6-tetrahydroazepino[4,5-b]indole-3(2H)-carboxylate in 82% yield. $^1$H NMR (300 MHz, CDCl$_3$) δ 1.28, 1.50, 2.90–2.99, 3.54–3.63, 3.66–3.82, 4.22, 4.79, 6.98, 7.12, 7.27; MS (ESI+) for C$_{21}$H$_{27}$BrN$_2$O$_4$ m/z 451.1 (M+H)$^+$.

Preparation 23

Preparation of (3-(tert-butoxycarbonyl)-2,3,4,5-tetrahydroazepino[4,5-b]indol-6(1H)-yl)acetic acid tert-Butyl 6-(2-ethoxy-2-oxoethyl)-1,4,5,6-tetrahydroazepino[4,5-b]indole-3(2H)-carboxylate (0.606 g, 1.63 mmol) is dissolved in MeOH (20 mL) and 1N NaOH (2.44 mL, 2.44 mmol, 1.5 equiv.) is added. The resulting solution is stirred at rt for 3 h. The reaction mixture is concentrated and the residue is partitioned between EtOAc (50 mL) and 10% aqueous citric acid (30 mL). The layers are separated and the aqueous layer is extracted with EtOAc (25 mL). The combined organic layers are washed with water (2×15 mL) and brine (15 mL), dried over MgSO$_4$, filtered and concentrated. Crude (3-(tert-butoxycarbonyl)-2,3,4,5-tetrahydroazepino[4,5-b]indol-6(1H)-yl)acetic acid (0.566 g) is obtained in quantitative yield. $^1$H NMR (300 MHz, CDCl$_3$) δ 1.49, 2.92–2.96, 3.00–3.04, 3.67–3.79, 4.83, 7.14, 7.19–7.20, 7.49; MS (ESI–) for C$_{19}$H$_{24}$N$_2$O$_4$ m/z 343.1 (M–H)$^-$.

Preparation 24

Preparation of (10-bromo-3-(tert-butoxycarbonyl)-2,3,4,5-tetrahydroazepino[4,5-b]indol-6(1H)-yl)acetic acid Prepared according to the procedure used to prepare (3-(tert-butoxycarbonyl)-2,3,4,5-tetrahydroazepino[4,5-b]indol-6(1H)-yl)acetic acid.

Preparation 25

Preparation of tert-butyl 6-[2-(2,3-dimethylanilino)-2-oxoethyl]-1,4,5,6-tetrahydroazepino[4,5-b]indole-3(2H)-carboxylate (3-(tert-butoxycarbonyl)-2,3,4,5-tetrahydroazepino[4,5-b]indol-6(1H)-yl)acetic acid (3.38 mmol) was dissolved in THF (20 mL) and 2,3-dimethylaniline (0.43 mL, 0.43 g, 3.6 mmol, 1.05 equiv.), dimethylaminopyridine (0.415 g, 3.40 mmol, 1.01 equiv.), and diisopropylcarbodiimide (0.60 mL, 0.48 g, 3.8 mmol, 1.13 equiv.) were added. The reaction mixture was stirred at rt under N$_2$ for 18 h. The reaction mixture was taken up in EtOAc (100 mL) and this solution was washed with 10% aqueous citric acid (2×50 mL), 5% aqueous NaHCO$_3$ (2×50 mL), and brine (50 mL). The organic layer was dried over MgSO$_4$, filtered, and concentrated. The crude product (1.7223 g) was chromatographed (SiO$_2$ 187 g, eluted with 10:1 toluene:acetone followed by 9:1 toluene:acetone) to give tert-butyl 6-[2-(2,3-dimethylanilino)-2-oxoethyl]-1,4,5,6-tetrahydroazepino[4,5-b]indole-3(2H)-carboxylate (1.1066 g) in 67% yield. $^1$H NMR (300 MHz, CD$_3$OD) δ 1.50, 2.01–2.03, 2.27, 2.29–3.12, 3.66–3.75, 3.75–3.83, 5.03, 7.04–7.19, 7.37, 7.49; MS (ESI+) for C$_{27}$H$_{33}$N$_3$O$_3$ m/z 448.1 (M+H)$^+$.

EXAMPLE 135

Preparation of N-(2,3-dimethylphenyl)-2-(2,3,4,5-tetrahydroazepino[4,5-b]indol-6(1H)-yl)acetamide hydrochloride

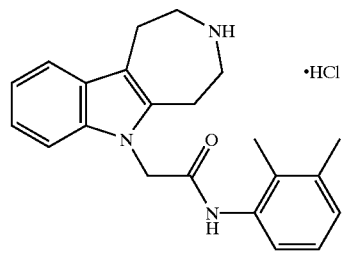

tert-Butyl 6-[2-(2,3-dimethylanilino)-2-oxoethyl]-1,4,5,6-tetrahydroazepino[4,5-b]indole-3(2H)-carboxylate (1.02 g, 2.27 mmol) was disolved in CH$_2$Cl$_2$ (15 mL), then trifluoroacetic acid (3.0 mL, 4.44 g, 38.9 mmol, 17.2 equiv.) was added. The resulting solution was stirred at rt for 1.5 h. The reaction mixture was concentrated to dryness, then the residue was partitioned between EtOAc (100 mL) and 1N NaOH (50 mL). The layers were separated, and the aqueous layer was extracted with EtOAc (50 mL). The combined organic layers were washed with brine (25 mL), dried over MgSO$_4$, filtered, and concentrated. The residue was combined with EtOAc (20 mL) and 1M HCl in Et$_2$O (20 mL), then the salt was collected by filtration. The salt was dried under vacuum over P$_2$O$_5$. N-(2,3-dimethylphenyl)-2-(2,3,4,5-tetrahydroazepino[4,5-b]indol-6(1H)-yl)acetanide hydrochloride (0.7739 g) was obtained in 89% yield. $^1$H NMR (300 MHz, CD$_3$OD) δ 2.11, 2.29, 3.23–3.26, 3.32–3.35, 3.47–3.56, 5.12, 7.06–7.15, 7.22, 7.44, 7.53; MS (ESI+) for C$_{22}$H$_{25}$N$_3$O m/z 348.3 (M+H)$^+$.

Preparation 26

Preparation of tert-butyl 6-[2-oxo-2-(3-toluidino)ethyl]-1,4,5,6-tetrahydroazepino[4,5-b]indole-3(2H)-carboxylate Prepared according to the procedure used to prepare tert-butyl 6-[2-(2,3-dimethylanilino)-2-oxoethyl]-1,4,5,6-tetrahydroazepino[4,5-b]indole-3(2H)-carboxylate in 92% yield. $^1$H NMR (300 MHz, CD$_3$OD) δ 1.50–1.51, 2.31, 3.00–3.06, 3.69–3.80, 4.98, 6.95, 7.06, 7.13, 7.19, 7.30, 7.34, 7.38, 7.47; MS (ESI+) for C$_{26}$H$_{31}$N$_3$O$_3$ m/z 434.1 (M+H)$^+$.

EXAMPLE 136

Preparation of N-(3-methylphenyl)-2-(2,3,4,5-tetrahydroazepino[4,5-b]indol-6(1H)-yl)acetamide hydrochloride

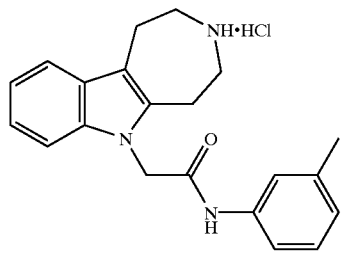

Prepared according to the procedure used to prepare N-(2,3-dimethylphenyl)-2-(2,3,4,5-tetrahydroazepino[4,5-b]indol-6(1H)-yl)acetamide hydrochloride in 91% yield. $^1$H NMR (300 MHz, DMF) δ 2.47, 3.46–3.51, 3.63–3.68, 3.73–3.83, 5.41, 7.08–7.11, 7.25, 7.33, 7.39, 7.66–7.75; MS (ESI+) for $C_{21}H_{23}N_3O$ m/z 334.2 (M+H)$^+$.

Preparation 27

Preparation of tert-butyl 6-[2-(2-fluoro-4-methylanilino)-2-oxoethyl]-1,4,5,6-tetrahydroazepino[4,5-b]indole-3(2H)-carboxylate Prepared according to the procedure used to prepare tert-butyl 6-[2-(2,3-dimethylanilino)-2-oxoethyl]-1,4,5,6-tetrahydroazepino[4,5-b]indole-3(2H)-carboxylate in 77% yield. $^1$H NMR (300 MHz, CDCl$_3$) δ 1.50, 2.29, 2.97–3.10, 3.71–3.81, 4.89, 6.80, 6.92, 7.03, 7.20, 7.23–7.30, 7.55–7.59, 7.97; MS (ESI+) for $C_{26}H_{30}FN_3O_3$ m/z 452.1 (M+H)$^+$

EXAMPLE 137

Preparation of N-(2-fluoro-4-methylphenyl)-2-(2,3,4,5-tetrahydroazepino[4,5-b]indol-6(1H)-yl)acetamide hydrochloride

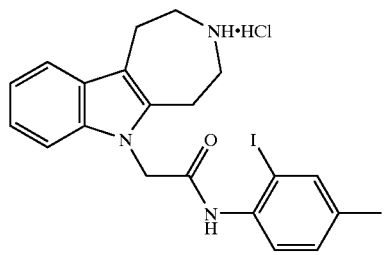

Prepared according to the procedure used to prepare N-(2,3-dimethylphenyl)-2-(2,3,4,5-tetrahydroazepino[4,5-b]indol-6(1H)-yl)acetamide hydrochloride in 88% yield. $^1$H NMR (300 MHz, DMF) δ 2.48, 3.48–3.51, 3.62–3.68, 3.69–3.81, 5.51, 7.17, 7.24–7.36, 7.72, 7.73, 8.04; MS (ESI+) for $C_{21}H_{22}FN_3O$ m/z 352.1 (M+H)$^+$.

Preparation 28

Preparation of tert-butyl 6-[2-(mesitylamino)-2-oxoethyl]-1,4,5,6-tetrahydroazepino[4,5-b]indole-3(2H)-carboxylate Prepared according to the procedure used to prepare tert-butyl 6-[2-(2,3-dimethylanilino)-2-oxoethyl]-1,4,5,6-tetrahydroazepino[4,5-b]indole-3(2H)-carboxylate in 76% yield. $^1$H NMR (300 MHz, CDCl$_3$) δ 1.50, 2.01, 2.23, 3.03–3.12, 3.70–3.85, 4.93, 6.36, 6.83, 7.20, 7.28, 7.34, 7.53–7.57; MS (ESI+) for $C_{28}H_{35}N_3O_3$ m/z 462.1 (M+H)$^+$.

EXAMPLE 138

Preparation of N-mesityl-2-(2,3,4,5-tetrahydroazepino[4,5-b]indol-6(1H)-yl)acetamide hydrochloride

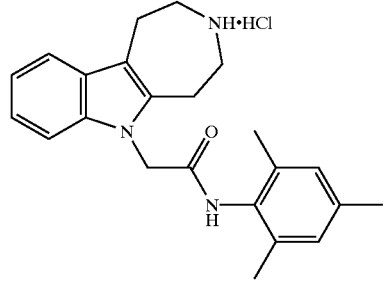

Prepared according to the procedure used to prepare N-(2,3-dimethylphenyl)-2-(2,3,4,5-tetrahydroazepino[4,5-b]indol-6(1H)-yl)acetamide hydrochloride in 99% yield. $^1$H NMR (300 MHz, DMF) δ 2.18, 2.23, 3.29–3.33, 3.49–3.66, 5.28, 6.89, 7.10, 7.20, 7.55, 7.62; MS (ESI+) for $C_{23}H_{27}N_3O$ m/z 362.2 (M+H)$^+$.

Preparation 29

Preparation of tert-butyl 6-[2-(4-methoxyanilino)-2-oxoethyl]-1,4,5,6-tetrahydroazepino[4,5-b]indole-3(2H)-carboxylate Prepared according to the procedure used to prepare tert-butyl 6-[2-(2,3-dimethylanilino)-2-oxoethyl]-1,4,5,6-tetrahydroazepino[4,5-b]indole-3(2H)-carboxylate in 86% yield. $^1$H NMR (300 MHz, CDCl$_3$) δ 1.49, 2.96–3.11, 3.71–3.81, 4.85, 6.81, 6.86, 7.21, 7.21–7.31, 7.57; MS (ESI+) for $C_{26}H_{31}N_3O_4$ m/z 450.1 (M+H)$^+$.

EXAMPLE 139

Preparation of N-(4-methoxyphenyl)-2-(2,3,4,5-tetrahydroazepino[4,5-b]indol-6(1H)-yl)acetamide hydrochloride

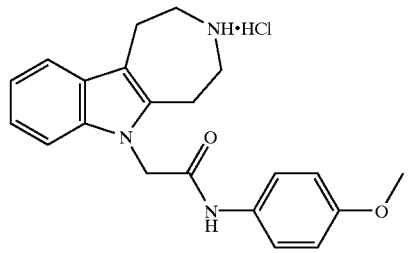

Prepared according to the procedure used to prepare N-(2,3-dimethylphenyl)-2-(2,3,4,5-tetrahydroazepino[4,5-b]indol-6(1H)-yl)acetamide hydrochloride in 96% yield. $^1$H NMR (300 MHz, CD$_3$OD) δ 3.23–3.30, 3.48–3.56, 3.78, 5.05, 6.89, 7.11, 7.19, 7.37, 7.45, 7.52; MS (ESI+) for $C_{21}H_{23}N_3O_2$ m/z 350.1 (M+H)$^+$.

Preparation 30

Preparation of tert-butyl 6-(2-anilino-2-oxoethyl)-1,4,5,6-tetrahydroazepino[4,5-b]indole-3(2H)-carboxylate Prepared according to the procedure used to prepare tert-butyl 6-[2-(2,3-dimethylanilino)-2-oxoethyl]-1,4,5,6-tetrahydroazepino[4,5-b]indole-3(2H)-carboxylate. $^1$H NMR (300 MHz, CDCl$_3$) δ 1.46, 2.99, 3.06, 3.71–3.77, 4.84, 7.01, 7.09, 7.17–7.31, 7.55; MS (ESI+) for $C_{25}H_{29}N_3O_3$ m/z 420.1 (M+H)$^+$.

EXAMPLE 140
Preparation of N-phenyl-2-(2,3,4,5-tetrahydroazepino[4,5-b]indol-6(1H)-yl)acetamide trifluoroacetate

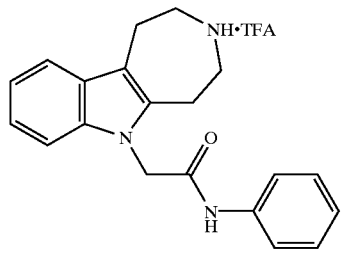

Prepared according to a procedure closely related to that used to prepare N-(2,3-dimethylphenyl)-2-(2,3,4,5-tetrahydroazepino[4,5-b]indol-6(1H)-yl)acetamide hydrochloride of Example 135. $^1$H NMR (300 MHz, CD$_3$OD) δ 3.21–3.27, 3.46–3.54, 5.06, 7.09, 7.10, 7.17, 7.28–7.35, 7.50, 7.54, 7.54; MS (ESI+) for C$_{20}$H$_{21}$N$_3$O m/z 320.2 (M+H)$^+$.

EXAMPLE 141
Preparation of N-(4-fluorophenyl)-2-(2,3,4,5-tetrahydroazepino[4,5-b]indol-6(1H)-yl)acetamide hydrochloride

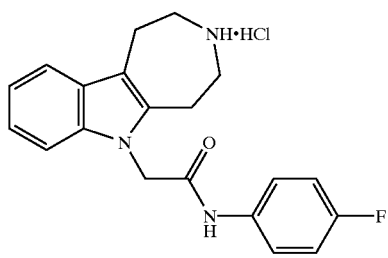

Prepared according to the procedure used to prepare N-(2,3-dimethylphenyl)-2-(2,3,4,5-tetrahydroazepino[4,5-b]indol-6(1H)-yl)acetamide hydrochloride of Example 135. $^1$H NMR (300 MHz, CD$_3$OD) δ 3.20–3.29, 3.44–3.52, 5.05, 7.04, 7.08, 7.16, 7.34, 7.49, 7.56; MS (ESI+) for C$_{20}$H$_{20}$FN$_3$O m/z 338.1 (M+H)$^+$.

EXAMPLE 142
Preparation of N-(3-nitrophenyl)-2-(2,3,4,5-tetrahydroazepino[4,5-b]indol-6(1H)-yl)acetamide hydrochloride

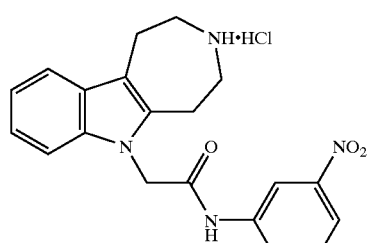

Prepared according to the procedure used to prepare N-(2,3-dimethylphenyl)-2-(2,3,4,5-tetrahydroazepino[4,5-b]indol-6(1H)-yl)acetamide hydrochloride of Example 135. $^1$H NMR (300 MHz, CD$_3$OD) δ 3.22–3.30, 3.47–3.55, 5.11, 7.10, 7.17, 7.34, 7.51, 7.57, 7.88, 7.98, 8.64; MS (ESI+) for C$_{20}$H$_{20}$N$_4$O$_3$ m/z 365.1 (M+H)$^+$.

EXAMPLE 143
Preparation of N-(3-methoxyphenyl)-2-(2,3,4,5-tetrahydroazepino[4,5-b]indol-6(1H)-yl)acetamide hydrochloride

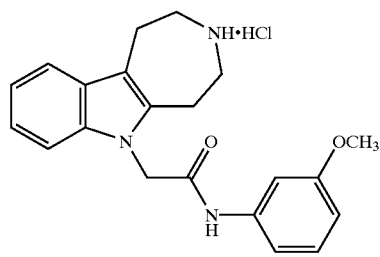

Prepared according to the procedure used to prepare N-(2,3-dimethylphenyl)-2-(2,3,4,5-tetrahydroazepino[4,5-b]indol-6(1H)-yl)acetamide hydrochloride of Example 135. $^1$H NMR (300 MHz, CD$_3$OD) δ 3.19–3.28, 3.42–3.51, 3.75, 5.06, 6.68, 7.09, 7.11, 7.17, 7.21, 7.30, 7.36, 7.50; MS (ESI+) for C$_{21}$H$_{23}$N$_3$O$_2$ m/z 350.3 (M+H)$^+$.

EXAMPLE 144
Preparation of N-(4-cyanophenyl)-2-(2,3,4,5-tetrahydroazepino[4,5-b]indol-6(1H)-yl)acetamide hydrochloride

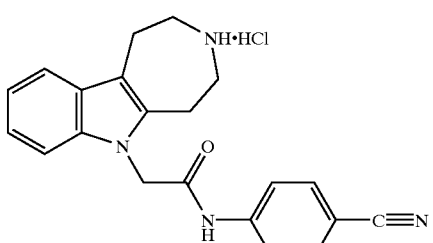

Prepared according to the procedure used to prepare N-(2,3-dimethylphenyl)-2-(2,3,4,5-tetrahydroazepino[4,5-b]indol-6(1H)-yl)acetamide hydrochloride of Example 135. $^1$H NMR (300 MHz, CD$_3$OD) δ 3.22–3.30, 3.46–3.53, 5.13, 7.10, 7.17, 7.35, 7.51, 7.66, 7.80; MS (ESI+) for C$_{21}$H$_{20}$N$_4$O m/z 345.2 (M+H)$^+$.

EXAMPLE 145
Preparation of N-(3,5-dimethoxyphenyl)-2-(2,3,4,5-tetrahydroazepino[4,5-b]indol-6(1H)-yl)acetamide hydrochloride

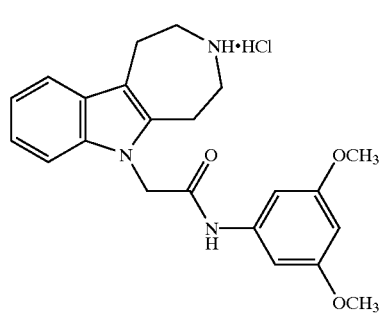

Prepared according to the procedure used to prepare N-(2,3-dimethylphenyl)-2-(2,3,4,5-tetrahydroazepino[4,5-b]indol-6(1H)-yl)acetamide hydrochloride of Example 135. $^1$H NMR (300 MHz, CD$_3$OD) δ 3.19–3.28, 3.43–3.51, 3.73, 5.05, 6.26, 6.84, 7.09, 7.17, 7.35, 7.49; MS (ESI+) for $C_{22}H_{25}N_3O_3$ m/z 380.2 (M+H)+.

EXAMPLE 146
Preparation of N-(2,4-dimethoxyphenyl)-2-(2,3,4,5-tetrahydroazepino[4,5-b]indol-6(1H)-yl)acetamide hydrochloride

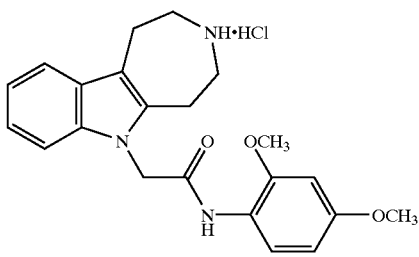

Prepared according to the procedure used to prepare N-(2,3-dimethylphenyl)-2-(2,3,4,5-tetrahydroazepino[4,5-b]indol-6(1H)-yl)acetamide hydrochloride. $^1$H NMR (300 MHz, CD$_3$OD) δ 3.22–3.30, 3.45–3.52, 3.77, 3.79, 5.09, 6.45, 6.57, 7.12, 7.21, 7.40, 7.53, 7.70; MS (ESI+) for $C_{22}H_{25}N_3O_3$ m/z 380.2 (M+H)+.

EXAMPLE 147
Preparation of N-(3-chloro-4-fluorophenyl)-2-(2,3,4,5-tetrahydroazepino[4,5-b]indol-6(1H)-yl)acetamide hydrochloride

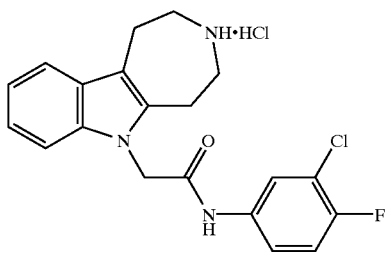

Prepared according to the procedure used to prepare N-(2,3-dimethylphenyl)-2-(2,3,4,5-tetrahydroazepino[4,5-b]indol-6(1H)-yl)acetamide hydrochloride of Example 135. $^1$H NMR (300 MHz, CD$_3$OD) δ 3.23–3.31, 3.47–3.55, 5.08, 7.10, 7.18, 7.21, 7.35, 7.46, 7.52, 7.86; MS (ESI+) for $C_{20}H_{19}ClFN_3O$ m/z 372.0 (M+H)+.

EXAMPLE 148
Preparation of N-[2-(2,3,4,5-tetrahydroazepino[4,5-b]indol-6(1H)-yl)ethyl]aniline

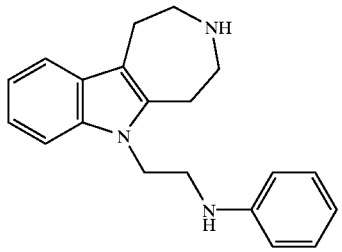

tert-Butyl 6-(2-anilino-2-oxoethyl)-1,4,5,6-tetrahydroazepino [4,5-b]indole-3(2H)-carboxylate (0.059 g, 0.14 mmol) was dissolved in THF (5 mL) and LAH (0.0080 g, 0.21 mmol, 1.5 equiv.) was added. The reaction mixture was refluxed for 6 h under N$_2$. The reaction mixture was quenched with water and extracted with EtOAc. The extracts were treated with TFA, and the resulting mixture was concentrated. THF and excess LAH were added and the reaction mixture was refluxed for 2 h. The reaction mixture was quenched by the addition of acetone, methanol, and water. The resulting mixture was extracted with EtOAc (4×) and the reaction mixture was concentrated. The crude product was purified by PTLC (1 mm×20 cm×20 cm plate, developed with 10% MeOH:CH$_2$Cl$_2$, eluted with MeOH) to yield N-[2-(2,3,4,5-tetrahydroazepino[4,5-b]indol-6(1H)-yl)ethyl]aniline (0.0093 g) in 22% yield. $^1$H NMR (400 MHz, CDCl$_3$) δ 2.87–2.89, 2.93–2.96, 3.03, 3.09, 3.49–3.53, 4.31, 6.57, 6.74, 7.07–7.28, 7.50.

Preparation 31
Preparation of tert-butyl 6-(1H-benzimidazol-2-ylmethyl)-10-bromo-1,4,5,6-tetrahydroazepino[4,5-b]indole-3(2H)-carboxylate A solution (10-bromo-3-(tert-butoxycarbonyl)-2,3,4,5-tetrahydroazepino[4,5-b]indol-6(1H)-yl)acetic acid (0.152 g, 0.359 mmol) and triethylamine (0.052 mL, 0.038 g, 0.372 mmol, 1.04 equiv.) in THF (2 mL) was cooled to 0° C. under N$_2$. Isobutyl chloroformate (0.048 mL, 0.051 g, 0.372 mmol, 1.04 equiv.) was added and the reaction mixture was stirred for 2.3 h. o-Phenylenediamine (0.0406 g, 0.375 mmol, 1.04 equiv.) and acetic acid (0.24 mL, 0.26 g, 4.25 mmol, 11.8 equiv.) were added, and the reaction mixture was heated to 50° C. The temperature of the reaction mixture gradually was increased to 64° C. over 3 h. After 19 h, the reaction mixture was cooled to rt. The reaction mixture was taken up in EtOAc, and the resulting solution was washed with water, saturated aq. NaHCO$_3$, and brine. The organic layer was dried over MgSO$_4$, filtered and concentrated. The crude product (0.1865 g) was chromatographed (SiO$_2$ 22 g, eluted with 5:1 toluene:acetone) to give tert-butyl 6-(1H-benzimidazol-2-ylmethyl)-10-bromo-1,4,5,6-tetrahydroazepino[4,5-b]indole-3(2H)-carboxylate (0.105 g) in 59% yield. $^1$H NMR (300 MHz, CDCl$_3$) δ 1.12, 3.20, 3.54, 3.68–3.74, 5.54, 5.58, 6.88, 7.20, 7.23–7.30.

EXAMPLE 149
Preparation of 6-(1H-benzimidazol-2-ylmethyl)-10-bromo-1,2,3,4,5,6-hexahydroazepino[4,5-b]indole hydrochloride

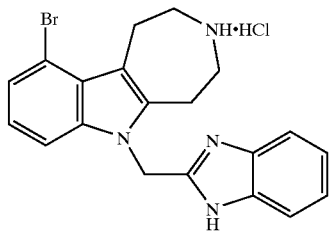

tert-Butyl 6-(1H-benzimidazol-2-ylmethyl)-10-bromo-1,4,5,6-tetrahydroazepino[4,5-b]indole-3(2H)-carboxylate (0.105 g, 0.212 mmol) was dissolved in CH$_2$Cl$_2$ (5 mL) and trifluoroacetic acid (2.0 mL, 2.96 g, 26.0 mmol, 122 equiv.) was added. This mixture was stirred at rt in a capped vessel for 2.5 h. The reaction mixture was concentrated to dryness. The residue was taken up in EtOAc (2 mL), and 1M HCl in Et$_2$O was added. The hydrochloride salt was collected by filtration and dried under vacuum. 6-(1H-benzimidazol-2-ylmethyl)-10-bromo-1,2,3,4,5,6-hexahydroazepino[4,5-b]indole hydrochloride (0.943 g) was produced in quantitative yield. $^1$H NMR (300 MHz, DMF) δ 3.61–3.70, 3.83–3.86, 6.12, 7.06, 7.31, 7.36–7.42, 7.66–7.74, 7.74; $^1$H NMR (300

MHz, CD$_3$OD) δ 3.33–3.36, 3.54–3.59, 3.83–3.86, 6.04, 7.09, 7.35, 7.41, 7.54–7.57, 7.71–7.74; MS (ESI+) for C$_{20}$H$_{19}$BrN$_4$ m/z 395, 396.9 (M+H)$^+$.

Preparation 32

Preparation of tert-butyl 10-bromo-6-(2-isobutoxy-2-oxoethyl)-1,4,5,6-tetrahydroazepino[4,5-b]indole-3(2H)-carboxylate Obtained as a by-product in the formation of tert-butyl 6-(1H-benzimidazol-2-ylmethyl)-10-bromo-1,4,5,6-tetrahydroazepino[4,5-b]indole-3(2H)-carboxylate. $^1$H NMR (300 MHz, CDCl$_3$) δ 0.87, 1.50, 1.90, 2.93–2.99, 3.56–3.62, 3.68–3.82, 3.93, 4.80, 6.98, 7.13, 7.27; MS (ESI+) for C$_{23}$H$_{31}$BrN$_2$O$_4$ m/z 479 (M+H)$^+$.

EXAMPLE 150

Preparation of isobutyl (10-bromo-2,3,4,5-tetrahydroazepino[4,5-b]indol-6(1H)-yl)acetate

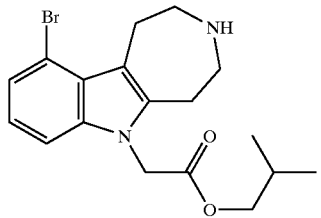

tert-butyl 10-bromo-6-(2-isobutoxy-2-oxoethyl)-1,4,5,6-tetrahydroazepino[4,5-b]indole-3(2H)-carboxylate (0.0412 g, 0.0859 mmol) was dissolved in CH$_2$Cl$_2$ (2 mL) and trifluoroacetic acid (1.0 mL, 1.48 g, 13.0 mmol, 151 equiv.) was added. The resulting solution was stirred at rt for 2.5 h. The reaction mixture was concentrated to dryness. The residue was taken up in EtOAc (2 mL), then treated with 1N HCl in Et$_2$O. Hydrochloride salt formation did not occur and the resulting solution were concentrated to dryness. The residue was partitioned between EtOAc and 1N NaOH. The layers were separated, and the aqueous layer was extracted with EtOAc. The combined organic layers were washed with brine, dried over MgSO$_4$, filtered and concentrated. The crude isobutyl (10-bromo-2,3,4,5-tetrahydroazepino[4,5-b]indol-6(1H)-yl)acetate (0.0260 g) was obtained in 80% yield. $^1$H NMR (300 MHz, CD$_3$OD) δ 0.85, 1.86, 2.98–3.03, 3.11–3.14, 3.53–3.56, 3.91, 5.02, 6.94, 7.18, 7.25; MS (ESI+) for C$_{18}$H$_{23}$BrN$_2$O$_2$ m/z 379.0 (M+H)$^+$.

EXAMPLE 151

Preparation of 2,3,4,5-tetrahydroazepino[4,5-b]indol-6(1H)-ylacetic acid hydrochloride

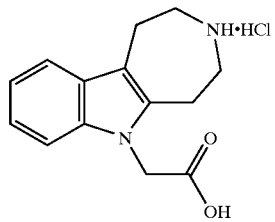

tert-Butyl 6-(2-ethoxy-2-oxoethyl)-1,4,5,6-tetrahydroazepino[4,5-b]indole-3(2H)-carboxylate (0.122 g, 0.328 mmol) was dissolved in methanol (5 mL). Strongly acidic cation exchange resin (Bio-Rad AG 50W-2×200–400 mesh, 0.424 g) was added and the reaction mixture was stirred overnight at rt. The resin was collected by filtration, then washed with methanol. The resin was combined with 1:17M aqueous NH$_4$OH and methanol, and the resin was removed by filtration. The filtrate was concentrated to dryness, and the residue was taken up in methanol and concentrated to dryness to remove excess NH$_3$. The free amino acid was treated with concentrated aqueous HCl (11.6 M, 3 drops) in methanol and the mixture was concentrated to give 2,3,4,5-tetrahydroazepino[4,5-b]indol-6(1H)-ylacetic acid hydrochloride (0.088 g) in 96% yield as a white solid. $^1$H NMR (300 MHz, CD$_3$OD) δ 3.21–3.25, 3.45–3.51, 5.05, 7.10, 7.18, 7.29, 7.50; MS (ESI–) for C$_{14}$H$_{16}$N$_2$O$_3$ m/z 243.1 (M–H)$^-$.

Preparation 33

Preparation of tert-butyl 6-[2-(dimethylamino)-2-oxoethyl]-1,4,5,6-tetrahydroazepino[4,5-b]indole-3(2H)-carboxylate tert-Butyl 1,4,5,6-tetrahydroazepino[4,5-b]indole-3(2H)-carboxylate (0.100 g, 0.349 mmol) was dissolved in DMF (1.0 mL) under N$_2$ at rt. NaH (0.0450 g, 1.13 mmol, 3.22 equiv., 60% dispersion) was added and the mixture was stirred at rt for 30 min. 2-Chloro-N,N-dimethylacetamide (86 μL, 0.102 g, 0.838 mmol, 2.4 equiv.) was added, and the reaction mixture was stirred at rt for 24 h. The reaction mixture was poured over ice, thenextracted with EtOAc (2×). The organic extracts was washed first with water, then with brine and dried over MgSO$_4$. The organic extracts was filtered and concentrated to yield a crude product (0.148 g). The crude product was chromatographed (SiO$_2$ 18 g, eluted with 3:1 toluene:acetone) to give tert-butyl 6-[2-(dimethylamino)-2-oxoethyl]-1,4,5,6-tetrahydroazepino[4,5-b]indole-3(2H)-carboxylate (0.116 g) in 90% yield. $^1$H NMR (300 MHz, CDCl$_3$) δ 1.50, 2.87–2.95, 3.01, 3.00–3.07, 3.13, 3.68–3.80, 4.85, 7.07–7.19, 7.47–7.51; MS (ESI+) for C$_{21}$H$_{29}$N$_3$O$_3$ m/z 372.2 (M+H)$^+$.

EXAMPLE 152

Preparation of N,N-dimethyl-2-(2,3,4,5-tetrahydroazepino[4,5-b]indol-6(1H)-yl)acetamide hydrochloride

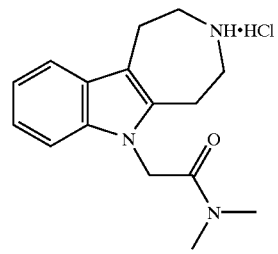

tert-Butyl 6-[2-(dimethylamino)-2-oxoethyl]-1,4,5,6-tetrahydroazepino[4,5-b]indole-3(2H)-carboxylate (0.113 g, 0.305 mmol) was dissolved in CH$_2$Cl$_2$ (3 mL) at rt. CF$_3$CO$_2$H (1 mL) was added and the reaction mixture was stirred for 40 min. The reaction mixture was concentrated to give a crude product (0.145 g). The crude product was dissolved in EtOAc (3 mL), then 1 N HCl in Et$_2$O (6 mL) was added and the precipitated salt was collected by filtration. N,N-Dimethyl-2-(2,3,4,5-tetrahydroazepino[4,5-b]indol-6(1H)-yl)acetamide hydrochloride (0.0896 g) was obtained in 95% yield. $^1$H NMR (300 MHz, CD$_3$OD) δ 2.99, 3.14–3.17, 3.21–3.24, 3.26, 3.47–3.50, 5.16, 7.08, 7.15, 7.30, 7.50; MS (ESI+) for C$_{16}$H$_{21}$N$_3$O m/z 272.2 (M+H)$^+$.

Preparation 34

Preparation of tert-butyl 6-(2-amino-2-oxoethyl)-1,4,5,6-tetrahydroazepino[4,5-b]indole-3(2H)-carboxylate tert-Butyl 1,4,5,6-tetrahydroazepino[4,5-b]indole-3(2H)-carboxylate (0.0994 g, 0.347) and iodoacetamide (0.0704 g, 0.381 mmol, 1.10 equiv.) was dissolved in DMF (1 mL) at rt under N$_2$. NaH (0.033 g, 0.825 mmol, 2.38 equiv., 60% dispersion) was added, and the reaction mixture was stirred for 16 h. Additional NaH (0.039 g) was added and the reaction mixture was stirred for 1.5 h. The reaction mixture was poured over ice, and the resulting mixture was extracted with EtOAc. The organic extracts was washed with water and then with brine. The organic extracts was dried over MgSO$_4$, filtered, and concentrated. The crude product (0.124 g) was purified by PTLC (2×1 mm×20 cm×20 cm SiO$_2$ plates, developed with 3:1 EtOAc:hexane, eluted with 10% MeOH in CH$_2$Cl$_2$) to give tert-butyl 6-(2-amino-2-oxoethyl)-1,4,5,6-tetrahydroazepino[4,5-b]indole-3(2H)-carboxylate (0.0233 g) in 19% yield. $^1$H NMR (300 MHz, CDCl$_3$) δ 1.50, 2.93–3.07, 3.68–3.79, 4.71, 5.33, 5.90–5.94, 7.15–7.24, 7.50–7.54; MS (ESI+) for C$_{19}$H$_{25}$N$_3$O$_3$ m/z 344.1 (M+H)$^+$.

EXAMPLE 153

Preparation of 2-(2,3,4,5-tetrahydroazepino[4,5-b]indol-6 (1H)-yl)acetamide hydrochloride

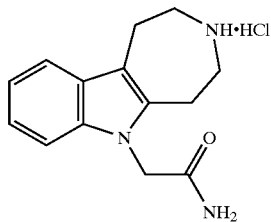

tert-Butyl 6-(2-amino-2-oxoethyl)-1,4,5,6-tetrahydroazepino[4,5-b]indole-3(2H)-carboxylate (0.0233 g, 0.0678 mmol) was dissolved in CH$_2$Cl$_2$ (2 mL) at rt. CF$_3$CO$_2$H (0.8 mL) was added, then the reaction mixture was stirred for 30 min. The reaction mixture was concentrated to give a crude product (0.0288 g). The crude product was dissolved in EtOAc (1 mL), 1 N HCl in Et$_2$O (2 mL) was added, and the precipitated salt was collected by filtration. 2-(2,3,4,5-Tetrahydroazepino[4,5-b]indol-6(1H)-yl) acetamide hydrochloride (0.0151 g) was obtained in 80% yield. $^1$H NMR (300 MHz, DMF-d$_7$) δ 3.29–3.33, 3.40–3.43, 3.50–3.58, 4.97, 7.07, 7.15, 7.45, 7.53; MS (ESI+) for C$_{14}$H$_{17}$N$_3$O m/z 244.1 (M+H)$^+$.

Preparation 35

Preparation of tert-butyl 6-[2-(phenylsulfinyl)ethyl]-1,4,5,6-tetrahydroazepino[4,5-b]indole-3(2H)-carboxylate tert-Butyl 1,4,5,6-tetrahydroazepino[4,5-b]indole-3(2H)-carboxylate (0.170 g, 0.594 mmol) and 2-chloroethyl phenyl sulfoxide (0.225 g, 1.20 mmol, 2.0 equiv.) was dissolved in DMF (10 mL) at rt. NaH (0.100 mg, 2.5 mmol, 4.21 equiv., 60% dispersion) was added, then the reaction mixture was stirred for 3 h. The reaction was quenched with a saturated aqueous NH$_4$Cl solution and partitioned between water and CH$_2$C$_2$. The aqueous layer was extracted with CH$_2$Cl$_2$ (3×). The combined organic layers were concentrated and the residue was dissolved in EtOAc, dried over MgSO$_4$, filtered, and concentrated. The crude product was chromatographed (Biotage 12 m SiO$_2$ column, eluted with a 20% to 30% EtOAc in hexane gradient) to give tert-butyl 6-[2-(phenylsulfinyl)ethyl]-1,4,5,6-tetrahydroazepino[4,5-b]indole-3(2H)-carboxylate.

EXAMPLE 154

Preparation of 6-[2-(phenylsulfinyl)ethyl]-1,2,3,4,5,6-hexahydroazepino[4,5-b]indole

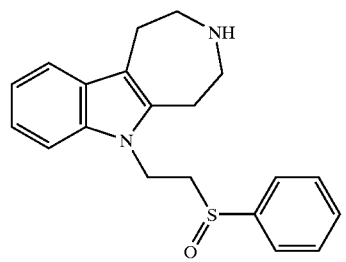

tert-Butyl 6-[2-(phenylsulfinyl)ethyl]-1,4,5,6-tetrahydroazepino[4,5-b]indole-3(2H)-carboxylate was dissolved in trifluoroacetic acid and stirred for 5 min. The reaction mixture was concentrated to dryness, and the residue was dissolved in 10% aqueous acetic acid. This aqueous solution was extracted with CH$_2$Cl$_2$ (3×). The aqueous layer was adjusted to pH 10 with NaOH, then extracted with EtOAc (3×). The combined EtOAc extracts was dried over MgSO$_4$, filtered, and concentrated. The product was chromatographed (SiO$_2$, 10% methanol in CH$_2$Cl$_2$) to give 6-[2-(phenylsulfinyl)ethyl]-1,2,3,4,5,6-hexahydroazepino [4,5-b]indole (0.116 g) in 70% yield as a white solid. $^1$H NMR (300 MHz, CD$_3$OD) δ 3.09–3.24, 3.28–3.44, 4.40, 4.62, 7.05, 7.13, 7.25, 7.43, 7.50–7.59; $^{13}$C NMR (75 MHz, CD$_3$OD) δ 22.79, 24.84, 37.04, 46.77, 48.66, 56.93, 110.42, 112.81, 116.30, 118.82, 120.17, 120.93, 122.91, 125.18, 128.93, 130.72, 132.72, 136.17, 136.92, 143.37.

Preparation 36

Preparation of tert-butyl 6-[2-(phenylsulfonyl)ethyl]-1,4,5,6-tetrahydroazepino[4,5-b]indole-3(2H)-carboxylate tert-Butyl 1,4,5,6-tetrahydroazepino[4,5-b]indole-3(2H)-carboxylate (0.111 g, 0.388 mmol) was dissolved in CH$_2$Cl$_2$ (10 mmol) and this solution was added to a mixture of 50% aqueous KOH (5 mL) and tetrabutylammonium hydrogen sulfate (0.100 g). The biphasic mixture was stirred vigorously at rt. 2-Chloroethyl phenyl sulfone (0.318 g, 1.55 mmol) was added, then the reaction mixture was stirred for 4 h. The organic phase was separated and the aqueous phase was extracted with CH$_2$Cl$_2$. The combined organic layers was concentrated. The crude product was chromatographed (Biotage 40s SiO$_2$ column, eluted with a 10% to 40% EtOAc in hexane gradient) to give tert-butyl 6-[2-(phenylsulfonyl) ethyl]-1,4,5,6-tetrahydroazepino[4,5-b]indole-3(2H)-carboxylate (0.154 g) in 87% as a clear solid. $^1$H NMR (300 MHz, CDCl$_3$) δ 1.48, 2.87–2.93, 3.38–3.42, 3.63, 3.69, 4.52, 7.04–7.17, 7.42, 7.53–7.59, 7.63–7.70, 7.88.

EXAMPLE 155

Preparation of 6-[2-(phenylsulfonyl)ethyl]-1,2,3,4,5,6-hexahydroazepino[4,5-b]indole

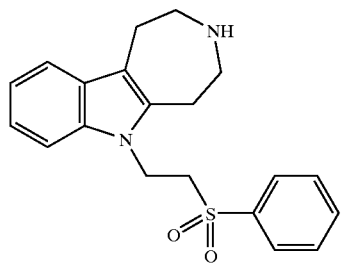

tert-Butyl 6-[2-(phenylsulfonyl)ethyl]-1,4,5,6-tetrahydroazepino[4,5-b]indole-3(2H)-carboxylate (0.139 g, 0.306 mmol) was treated with trifluoroacetic acid (1 mL) for 5 min. $CH_2Cl_2$ was added and the reaction mixture was concentrated to dryness. The salt was partitioned between $CH_2Cl_2$ and a mixture of 1M KOH and brine. The organic layer was dried over $MgSO_4$, filtered and concentrated. The crude product was chromatographed ($SiO_2$, eluted with 1:1 EtOAc:hexane) to give 6-[2-(phenylsulfonyl)ethyl]-1,2,3,4,5,6-hexahydroazepino[4,5-b]indole (0.0123 g) as a white solid. $^1$H NMR (300 MHz, $CD_3OD$) δ 3.13, 3.29–3.33, 3.42, 3.50, 3.71, 4.65, 7.07, 7.14, 7.22, 7.42, 7.51, 7.66, 7.70.

Preparation 37

Preparation of tert-butyl 6-(2-hydroxyethyl)-1,4,5,6-tetrahydroazepino[4,5-b]indole-3(2H)-carboxylate tert-Butyl 6-(2-ethoxy-2-oxoethyl)-1,4,5,6-tetrahydroazepino[4,5-b]indole-3(2H)-carboxylate (0.602 g, 1.62 mmol) was dissolved in THF (15 mL), and the resulting solution was cooled to –10° C. under $N_2$. $LiBH_4$ (0.0756 g, 3.47 mmol, 2.14 equiv.) was added and the reaction mixture was allowed to warm to rt. After 19.5 h, the reaction mixture was cooled to 0° C., and $LiBH_4$ (0.0250 g, 1.15 mmol, 0.71 equiv.) was added and the reaction mixture was allowed to warm up for 3.5 h. The reaction mixture was combined with water and was extracted with EtOAc (2×). The combined organic layers was washed with brine, dried over $MgSO_4$, filtered, and concentrated to give tert-butyl 6-(2-hydroxyethyl)-1,4,5,6-tetrahydroazepino[4,5-b]indole-3(2H)-carboxylate (0.533 g) in acceptable purity and essentially quantitative yield. $^1$H NMR (300 MHz, $CD_3OD$) δ 1.48–1.51, 3.00–3.11, 3.66–3.79, 3.87–3.95, 4.27, 7.12, 7.19, 7.32, 7.50; MS (ESI+) for $C_{19}H_{26}N_2O_3$ m/z 331.2 (M+H)$^+$.

EXAMPLE 156

Preparation of 2-(2,3,4,5-tetrahydroazepino[4,5-b]indol-6(1H)-yl)ethanol hydrochloride

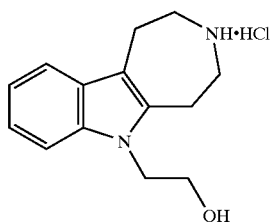

2-(2,3,4,5-Tetrahydroazepino[4,5-b]indol-6(1H)-yl)ethanol hydrochloride was prepared from tert-butyl 6-(2-hydroxyethyl)-1,4,5,6-tetrahydroazepino[4,5-b]indole-3(2H)-carboxylate by the procedure used to prepare 2,3,4,5-tetrahydroazepino[4,5-b]indol-6(1H)-ylacetic acid hydrochloride in 48% yield. $^1$H NMR (300 MHz, $CDCl_3$) δ 3.22, 3.37, 3.44–3.52, 3.80, 4.30, 7.07, 7.15, 7.37, 7.48; MS (ESI+) for $C_{14}H_{18}N_2O$ m/z 231.3 (M+H)$^+$.

Preparation 38

Preparation of tert-butyl 6-[2-(4-chlorophenoxy)ethyl]-1,4,5,6-tetrahydroazepino[4,5-b]indole-3(2H)-carboxylate tert-Butyl 6-(2-hydroxyethyl)-1,4,5,6-tetrahydroazepino[4,5-b]indole-3(2H)-carboxylate (0.533 g, 1.61 mmol), p-chlorophenol (0.224 g, 1.74 mmol, 1.08 equiv.) and triphenylphosphine (0.445 g, 1.70 mmol, 1.05 equiv.) was dissolved in THF (10 mL) and stirred at rt under $N_2$. Diethyl azodicarboxylate (0.30 mL, 0.337 g, 1.93 mmol, 1.2 equiv.) was added, and the reaction mixture was stirred for 2.5 h. The reaction mixture was concentrated to give crude product (1.85 g), which was chromatographed ($SiO_2$ 175 g, eluted with 4:1 hexane:EtOAc) to give tert-butyl 6-[2-(4-chlorophenoxy)ethyl]-1,4,5,6-tetrahydroazepino[4,5-b]indole-3(2H)-carboxylate (0.622 g) in 88% yield. $^1$H NMR (300 MHz, $CD_3OD$) δ 1.48, 2.96–3.03, 3.05–3.14, 3.63–3.78, 4.15, 4.48, 6.70, 7.11, 7.15–7.20, 7.17, 7.27–7.31, 7.46–7.51; MS (ESI+) for $C_{25}H_{29}ClN_2O_3$ m/z 440.9 (M+H)$^+$.

EXAMPLE 157

Preparation of 4-chlorophenyl 2-(2,3,4,5-tetrahydroazepino[4,5-b]indol-6(1H)-yl)ethyl ether hydrochloride

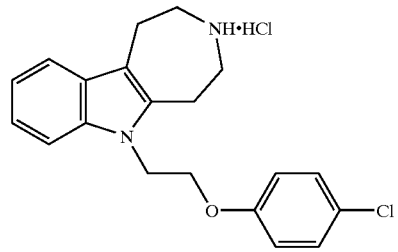

tert-Butyl 6-[2-(4-chlorophenoxy)ethyl]-1,4,5,6-tetrahydroazepino[4,5-b]indole-3(2H)-carboxylate (0.622 g, 1.41 mmol) was dissolved in $CH_2Cl_2$ (10 mL) at rt. $CF_3CO_2H$ (4 mL) was added, then the reaction mixture was stirred for 1 h. The reaction mixture was concentrated and the residue was taken up in EtOAc and washed with 1 N NaOH. The aqueous layer was extracted with EtOAc, and the combined organic layers were washed with brine, dried over $MgSO_4$, filtered, and concentrated. The crude product (0.541 g) was dissolved in EtOAc (2 mL) and 1 N HCl in $Et_2O$ (2 mL) was added. The solvents were removed under vacuum and $Et_2O$ (10 mL) was added to the residue. The resulting mixture was sonicated and the finely powdered salt was collected by filtration. 4-Chlorophenyl 2-(2,3,4,5-tetrahydroazepino[4,5-b]indol-6(1H)-yl)ethyl ether hydrochloride (0.503 g) was obtained in 94% yield. $^1$H NMR (300 MHz, $CD_3OD$) δ 3.16–3.20, 3.35–3.50, 4.22, 4.59, 6.76, 7.07, 7.18, 7.18, 7.43, 7.48; MS (ESI+) for $C_{20}H_{21}ClN_2O$ m/z 341.0 (M+H)$^+$.

EXAMPLE 158

Preparation of 4-fluorophenyl 2-(2,3,4,5-tetrahydroazepino [4,5-b]indol-6(1H)-yl)ethyl ether hydrochloride

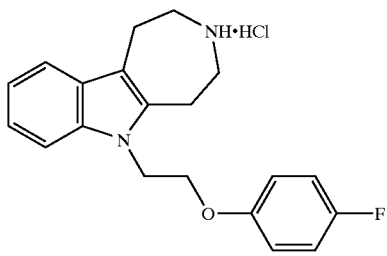

Prepared according to the procedure used to prepare 4-chlorophenyl 2-(2,3,4,5-tetrahydroazepino[4,5-b]indol-6 (1H)-yl)ethyl ether hydrochloride of Example 157. $^1$H NMR (300 MHz, CD$_3$OD) δ 3.17–3.21, 3.39–3.50, 4.18, 4.56, 6.75, 6.92, 7.08, 7.18, 7.42, 7.48; MS (ESI+) for C$_{20}$H$_{21}$FN$_2$O m/z 325.1 (M+H)$^+$.

Preparation 39

Preparation of tert-butyl 6-{2-[(methylsulfonyl)oxy]ethyl}-1,4,5,6-tetrahydroazepino[4,5-b]indole-3(2H)-carboxylate tert-Butyl 6-(2-hydroxyethyl)-1,4,5,6-tetrahydroazepino [4,5-b]indole-3(2H)-carboxylate (0.181 g, 0.549 mmol) and triethylamine (0.115 mL, 0.0833 g, 0.824 mmol, 1.5 equiv.) were dissolved in CH$_2$Cl$_2$ at -10° C. under N$_2$. MsCl (0.0510 mL, 0.0755g, 0.659 mmol, 1.2 equiv.) was added and the reaction mixture was stirred for 30 min. The reaction mixture was taken up in EtOAc (25 mL) and was washed sequentially with 10% citric acid (10 mL), 5% NaHCO$_3$ (10 mL), and brine (10 mL). The organic layer was dried over MgSO$_4$, filtered, and concentrated. The crude tert-butyl 6-{2-[(methylsulfonyl)oxy]ethyl}-1,4,5,6-tetrahydroazepino[4,5-b]indole-3(2H)-carboxylate was used directly in the next reaction.

Preparation 40

Preparation of tert-butyl 6-[2-(phenylsulfanyl)ethyl]-1,4,5, 6-tetrahydroazepino[4,5-b]indole-3(2H)-carboxylate tert-Butyl 6-(2-hydroxyethyl)-1,4,5,6-tetrahydroazepino [4,5-b]indole-3(2H)-carboxylate, (0.0488 g, 0.148 mmol) was dissolved in CH$_2$Cl$_2$ (5 mL) and stirred at rt. Triethylamine (5 mL) was added, followed by methanesulfonyl chloride (0.017 mL, 0.221 mmol, 1.50 equiv.). The reaction mixture was stirred for 2 h, and additional methanesulfonyl chloride (0.015 mL) was added. After 30 min, a mixture of thiophenol (0.065 mL, 0.592 mmol, 4.0 equiv.) and KOH (12 equiv.) in DMF (5 mL) was added, and the resulting mixture was stirred for 30 min. The reaction mixture was quenched with saturated aqueous NH$_4$Cl, then the resulting mixture was extracted with CH$_2$Cl$_2$ (3×). The combined organic extracts were dried over MgSO$_4$, filtered, and concentrated. The crude product was purified by PTLC (1 mm×20 cm×20 cm SiO$_2$ plates, developed with 1:4 EtOAc:hexane) to give tert-butyl 6-[2-(phenylsulfanyl) ethyl]-1,4,5,6-tetrahydroazepino[4,5-b]indole-3(2H)-carboxylate (0.017 g) in 28% yield as a white solid. $^1$H NMR (300 MHz, CDCl$_3$) δ 1.52, 2.92, 2.99, 3.17, 3.66–3.73, 4.28, 7.10–7.20, 7.25–7.41, 7.48; MS (ESI+) for C$_{25}$H$_{30}$N$_2$O$_2$S m/z 423 (M+H)$^+$.

EXAMPLE 159

Preparation of phenyl 2-(2,3,4,5-tetrahydroazepino[4,5-b] indol-6(1H)-yl)ethyl sulfide trifluoroacetate

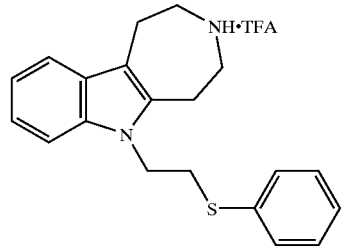

tert-Butyl 6-[2-(phenylsulfanyl)ethyl]-1,4,5,6-tetrahydroazepino[4,5-b]indole-3(2H)-carboxylate (0.0532 g, 0126 mmol) was dissolved in trifluoroacetic acid (2 mL), and the solution was stirred for 5 min. The reaction mixture was concentrated to dryness to give phenyl 2-(2,3,4,5-tetrahydroazepino[4,5-b]indol-6(1H)-yl)ethyl sulfide trifluoroacetate (0.70 g) as a tan solid. $^1$H NMR (300 MHz, CD$_3$OD) δ 3.12, 3.18, 3.30, 3.34–3.41, 4.41, 7.08, 7.15, 7.17–7.26, 7.45; MS (ESI+) for C$_{20}$H$_{22}$N$_2$S m/z 323.2 (M+H)$^+$.

Preparation 41

Preparation of tert-butyl 6-(2-azidoethyl)-1,4,5,6-tetrahydroazepino[4,5-b]indole-3(2H)-carboxylate tert-Butyl 6-{2-[(methylsulfonyl)oxy]ethyl}-1,4,5,6-tetrahydroazepino[4,5-b]indole-3(2H)-carboxylate (0.224 g, 0.549 mmol) and NaN$_3$ (0.357 g, 5.49 mmol, 10.0 equiv.) were dissolved in DMF (2.5 mL) and the solution was stirred at 60° C. under N$_2$ for 14.5 h. The reaction mixture was taken up in EtOAc and washed with water (2×15 mL). The aqueous layers were back extracted with EtOAc (25 mL). The combined organic layers were washed with brine (10 mL), dried over MgSO$_4$, filtered and concentrated. The crude product (0.214 g) was chromatographed (SiO$_2$ 25 g, eluted with 3:1 hexane:EtOAc) to give tert-butyl 6-(2-azidoethyl)-1,4,5,6-tetrahydroazepino[4,5-b]indole-3(2H)-carboxylate (0.184 g) in 94% yield. $^1$H NMR (300 MHz, CDCl$_3$) δ 1.51, 2.99–3.10, 3.60, 3.66–3.84, 4.26, 7.14, 7.21, 7.27, 7.51; MS (ESI+) for C$_{19}$H$_{25}$N$_5$O$_2$ m/z 356.2 (M+H)$^+$.

Preparation 42

Preparation of tert-butyl 6-(2-aminoethyl)-1,4,5,6-tetrahydroazepino[4,5-b]indole-3(2H)-carboxylate tert-Butyl 6-(2-azidoethyl)-1,4,5,6-tetrahydroazepino[4, 5-b]indole-3(2H)-carboxylate (0.174 g, 0.490 mmol) was dissolved in 1:1 EtOAc:EtOH (4 mL). 10% Pd/C (0.0543 g) was added, then the reaction mixture was stirred at rt under H$_2$ for 2 h. The reaction mixture was filtered through celite and the celite pad was carefully washed with EtOAc. The filtrate was concentrated to give tert-butyl 6-(2-aminoethyl)-1,4,5,6-tetrahydroazepino[4,5-b]indole-3(2H)-carboxylate (0.153 g) in 95% crude yield. $^1$H NMR (300 MHz, CDCl$_3$) δ 1.51, 2.99–3.10, 3.67–3.80, 4.17, 7.12, 7.19, 7.32, 7.50.

EXAMPLE 160
Preparation of 2-(2,3,4,5-tetrahydroazepino[4,5-b]indol-6 (1H)-yl)ethanamine dihydrochloride

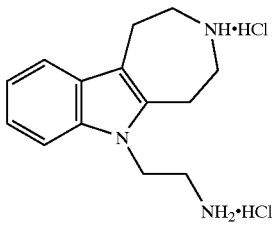

tert-Butyl 6-(2-aminoethyl)-1,4,5,6-tetrahydroazepino[4,5-b]indole-3(2H)-carboxylate (0.0336 g, 0.102 mmol) was dissolved in $CH_2Cl_2$ (2 mL) at rt. $CF_3CO_2H$ (1 mL) was added and the reaction mixture was stirred for 4 h. The reaction mixture was concentrated and the residue was taken up in EtOAc (2 mL). HCl in $Et_2O$ (1 N) and MeOH were added and the mixture was concentrated to give crude 2-(2,3,4,5-tetrahydroazepino[4,5-b]indol-6(1H)-yl)ethanamine dihydrochloride (0.0339 g). $^1$H NMR (300 MHz, DMF-$d_7$) δ 3.48–3.51, 3.53–3.59, 3.65–3.70, 3.75–3.79, 4.94, 7.27, 7.35, 7.72, 7.91; MS (ESI+) for $C_{14}H_{19}N_3$ m/z 230.2 (M+H)$^+$.

Preparation 43
Preparation of tert-butyl 6-{2-[(anilinocarbonyl)amino]ethyl}-1,4,5,6-tetrahydroazepino[4,5-b]indole-3(2H)-carboxylate tert-Butyl 6-(2-aminoethyl)-1,4,5,6-tetrahydroazepino[4,5-b]indole-3(2H)-carboxylate (0.0399 g, 0.121 mmol) was dissolved in THF (2 mL) at rt under $N_2$. Phenyl isocyanate (0.016 g mL, 0.0173 g, 0.145 mmol, 1.20equiv.) was added, then the reaction mixture was stirred for 2.5 h. The reaction mixture was concentrated and the crude product (0.0598 g) was chromatographed ($SiO_2$ 25 g, eluted with 3:2 hexane:EtOAc) to give tert-butyl 6-{2-[(anilinocarbonyl)amino]ethyl}-1,4,5,6-tetrahydroazepino[4,5-b]indole-3(2H)-carboxylate (0.0390 g) in 72% yield. $^1$H NMR (300 MHz, CDCl$_3$) δ 1.36, 1.44, 2.96–3.08, 3.42–3.51, 3.65–3.72, 4.17, 4.23, 5.14, 5.23, 6.94–7.30, 7.43–7.49; MS (ESI+) for $C_{26}H_{32}N_4O_3$ m/z 449.1 (M+H)$^+$.

EXAMPLE 161
Preparation of N-phenyl-N'-[2-(2,3,4,5-tetrahydroazepino[4,5-b]indol-6(1H)-yl)ethyl]urea hydrochloride

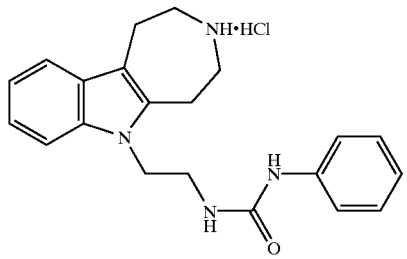

tert-Butyl 6-{2-[(anilinocarbonyl)amino]ethyl}-1,4,5,6-tetrahydroazepino[4,5-b]indole-3(2H)-carboxylate (0.0390 g, 0.0869 mmol) was dissolved in $CH_2Cl_2$ (2 mL) at rt. $CF_3CO_2H$ (1 mL) was added, then the reaction mixture was stirred for 45 min. The reaction mixture was concentrated and the residue was taken up in EtOAc (2 mL). 1 N HCl in $Et_2O$ (2 mL) was added and the precipitated salt was collected by filtration. N-Phenyl-N'-[2-(2,3,4,5-tetrahydroazepino[4,5-b]indol-6(1H)-yl)ethyl]urea hydrochloride (0.0296 g) was obtained in 88% yield. $^1$H NMR (300 MHz, CD$_3$OD) δ 3.19–3.22, 3.35–3.38, 3.43–3.53, 4.35, 6.97–7.03, 7.07, 7.17, 7.25–7.27, 7.44, 7.48; MS (ESI+) for $C_{21}H_{24}N_4O$ m/z 349.2 (M+H)$^+$.

Preparation 44
Preparation of tert-butyl 6-[2-(benzoylamino)ethyl]-1,4,5,6-tetrahydroazepino[4,5-b]indole-3(2H)-carboxylate tert-Butyl 6-(2-aminoethyl)-1,4,5,6-tetrahydroazepino[4,5-b]indole-3(2H)-carboxylate (0.0401 g, 0.122 mmol) was dissolved in THF (2 mL) at rt under $N_2$. Diisopropylethylamine (0.028 mL, 0.0205 g, 0.158 mmol, 1.30 equiv.) and benzoyl chloride (0.017 mL, 0.0205 g, 0.146 mmol, 1.20 equiv.) were added, then the reaction mixture was stirred for 19 h. Citric acid (10%) was added and the reaction mixture was stirred for 15 min. The reaction mixture was extracted with EtOAc and the organic layer was washed sequentially with 10% citric acid, saturated aqueous NaHCO$_3$, and brine. The organic layer was dried over MgSO$_4$, filtered and concentrated. The crude product (0.056 g) was chromatographed ($SiO_2$ 25 g, eluted with 1:1 hexane:EtOAc) to give tert-butyl 6-[2-(benzoylamino)ethyl]-1,4,5,6-tetrahydroazepino[4,5-b]indole-3(2H)-carboxylate (0.0398 g) in 75% yield. $^1$H NMR (300 MHz, CDCl$_3$) δ 1.45, 1.48, 2.96–3.05, 3.60–3.70, 3.74, 4.36–4.42, 6.29, 7.10–7.19, 7.31–7.43, 7.46–7.53, 7.63; MS (ESI+) for $C_{26}H_{31}N_3O_3$ m/z 434.1 (M+H)$^+$.

EXAMPLE 162
Preparation of N-[2-(2,3,4,5-tetrahydroazepino[4,5-b]indol-6(1H)-yl)ethyl]benzamide hydrochloride

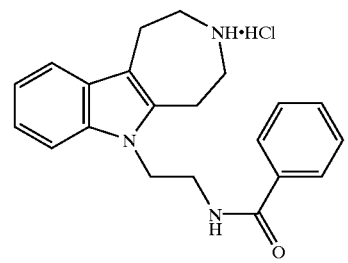

tert-Butyl 6-[2-(benzoylamino)ethyl]-1,4,5,6-tetrahydroazepino[4,5-b]indole-3(2H)-carboxylate (0.0398 g, 0.0918 mmol) was dissolved in $CH_2Cl_2$ (2 mL) at rt. $CF_3CO_2H$ (1 mL) was added, then the reaction mixture was stirred for 2 h. The reaction mixture was concentrated and the residue was taken up in EtOAc (2 mL). HCl (1N) in $Et_2O$ (2 mL) was added and the precipitated salt was collected by filtration. N-[2-(2,3,4,5-tetrahydroazepino[4,5-b]indol-6(1H)-yl)ethyl]benzamide hydrochloride (0.0271 g) was obtained in 79% yield. $^1$H NMR (300 MHz, CD$_3$OD) δ 3.18–3.21, 3.33–3.38, 3.42–3.49, 3.69, 4.44, 7.05, 7.15, 7.38–7.54, 7.60, 7.60, 8.55–8.59; MS (ESI+) for $C_{21}H_{23}N_3O$ m/z 334.2 (M+H)$^+$.

Preparation 45
Preparation of tert-butyl 6-{2-[(phenylsulfonyl)amino]ethyl}-1,4,5,6-tetrahydroazepino[4,5-b]indole-3(2H)-carboxylate tert-Butyl 6-(2-aminoethyl)-1,4,5,6-tetrahydroazepino[4,5-b]indole-3(2H)-carboxylate (0.0403 g, 0.122 mmol) was dissolved in THF (2 mL) at rt under $N_2$. Diisopropylethylamine (0.043 mL, 0.0316 g, 0.245 mmol, 2.00 equiv.) and benzenesulfonyl chloride (0.023 mL, 0.0324 g, 0.183 mmol, 1.50 equiv.) were added, then the reaction mixture was stirred for 19 h. Citric acid (10%) was added and the reaction mixture was stirred for 15 min. The reaction mixture was extracted with EtOAc, and the organic layer was washed sequentially with 10% citric acid, saturated aqueous NaHCO₃ and brine. The organic layer was dried over MgSO₄, filtered, and concentrated. The crude product (0.0649 g) was chromatographed (SiO₂ 25 g, eluted with 2:1 hexane:EtOAc) to give tert-butyl 6-{2-[(phenylsulfonyl)amino]ethyl}-1,4,5,6-tetrahydroazepino[4,5-b]indole-3(2H)-carboxylate (0.0430 g) in 75% yield. $^1$H NMR (300 MHz, CDCl₃) δ 1.46, 1.52, 2.95–3.02, 3.22–3.30, 3.63–3.75, 4.24–4.31, 4.63, 4.79, 7.09–7.26, 7.45–7.51, 7.48, 7.58, 7.79; MS (ESI+) for $C_{25}H_{31}N_3O_4S$ m/z 470.0 (M+H)⁺.

EXAMPLE 163
Preparation of N-[2-(2,3,4,5-tetrahydroazepino[4,5-b]indol-6(1H)-yl)ethyl]benzenesulfonamide hydrochloride

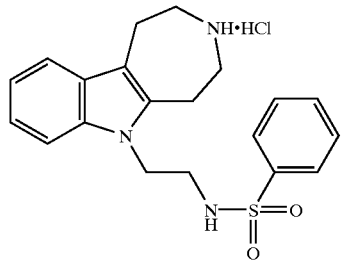

tert-Butyl 6-{2-[(phenylsulfonyl)amino]ethyl}-1,4,5,6-tetrahydroazepino[4,5-b]indole-3(2H)-carboxylate (0.0430 g, 0.0916 mmol) was dissolved in CH₂Cl₂ (2 mL) at rt. CF₃CO₂H (1 mL) was added, then the reaction mixture was stirred for 2 h. The reaction mixture was concentrated and the residue was taken up in EtOAc (2 mL). HCl in Et₂O (1N) (2 mL) was added and the precipitated salt was collected by filtration. N-[2-(2,3,4,5-tetrahydroazepino[4,5-b]indol-6(1H)-yl)ethyl]benzenesulfonamide hydrochloride (0.0335 g) was obtained in 90% yield. $^1$H NMR (300 MHz, CD₃OD) δ 3.16, 3.19–3.23, 3.37–3.41, 3.44–3.47, 3.53–3.57, 4.34, 7.08, 7.15, 7.32, 7.49, 7.52, 7.61, 7.77; MS (ESI+) for $C_{20}H_{23}N_3O_2S$ m/z 370.1 (M+H)⁺.

Preparation 46
Preparation of 3-(3-(tert-butoxycarbonyl)-2,3,4,5-tetrahydroazepino[4,5-b]indol-6(1H)-yl)propanoic acid Sodium hydride (0.302 g, 7.55 mmol, 2.16 equiv., 60% dispersion) was added to a solution of tert-butyl 1,4,5,6-tetrahydroazepino[4,5-b]indole-3(2H)-carboxylate (1.00 g, 3.49 mmol) in DMF (15 mL) at rt under N₂ and the mixture was stirred for 1.66 h. β-Propiolactone (0.55 mL, 0.629g, 8.73 mmol, 2.5 equiv.) was added in four portions over 1 h, then the reaction mixture was stirred for 72 h at rt. The reaction mixture was partitioned between EtOAc (50 mL) and 10% citric acid (25 mL), and the layers were separated. The organic layer was washed with 10% citric acid. The combined aqueous layers were extracted with EtOAc (25 mL). The combined organic layers were washed with brine (25 mL), dried over MgSO₄, filtered, and concentrated. The crude product (2.27 g) was dissolved in CH₃OH (30 mL), then water (5 mL) and K₂CO₃ (2.10 g. 15.2 mmol) was added, and the reaction mixture was stirred overnight. The reaction mixture was concentrated, and the residue was partitioned between EtOAc (100 mL) and water (100 mL). The organic layer was extracted with 10% aq. Na₂CO₃ (2×50 mL) and 1N NaOH (2×50 mL). The combined aqueous layers were made acidic (pH=2) by the addition of 2.9 M HCl and 10% aq. citric acid. The acidified aqueous mixture was extracted with EtOAc (3×100 mL). The organic extracts were washed with water (50 mL) followed by brine (50 mL), dried over MgSO₄, filtered, and concentrated. The crude product (1.06 g) was chromatographed (SiO₂ 109 g, eluted with 4% MeOH in CH₂Cl₂ followed by 10% MeOH in CH₂Cl₂) to give 3-(3-(tert-butoxycarbonyl)-2,3,4,5-tetrahydroazepino[4,5-b]indol-6(1H)-yl)propanoic acid (0.796 g) in 63% yield. $^1$H NMR (300 MHz, CDCl₃) δ 1.51 (s, 9H), 2.78, 2.99–3.08, 3.67–3.81, 4.42, 7.13, 7.20, 7.31, 7.49, 10.48; MS (ESI+) for $C_{20}H_{26}N_2O_4$ m/z 359.3 (M+H)⁺.

Preparation 47
Preparation of tert-butyl 6-[3-(4-methoxyanilino)-3-oxopropyl]-1,4,5,6-tetrahydroazepino[4,5-b]indole-3(2H)-carboxylate 3-(3-(tert-butoxycarbonyl)-2,3,4,5-tetrahydroazepino[4,5-b]indol-6(1H)-yl)propanoic acid (0.105 g, 0.292 mmol), p-anisidine (0.0377 g, 0.306 mmol, 1.05 equiv.) and dimethylaminopyridine (0.0357 g, 0.292 mmol, 1.00 equiv.) were dissolved in THF at rt under N₂. Diisopropylcarbodiimide (0.0503 mL, 0.0405 g, 0.321 mmol, 1.00 equiv.) was added, then the reaction mixture was stirred for 29 h. The reaction mixture was taken up in EtOAc and washed with 10% aq. citric acid (2×), saturated aq. NaHCO₃ (2×) and brine (1×). The organic layer was dried over MgSO₄, filtered, and concentrated. The crude product (0.1686 g) was chromatographed (SiO₂ 25 g, eluted with 9:1 toluene:acetone) to give tert-butyl 6-[3-(4-methoxyanilino)-3-oxopropyl]-1,4,5,6-tetrahydroazepino[4,5-b]indole-3(2H)-carboxylate (0.113 g) in 84% yield. $^1$H NMR (300 MHz, CDCl₃) δ 1.47, 2.68–2.76, 2.95–3.08, 3.56–3.70, 3.79, 4.53, 6.83, 7.12–7.54; MS (ESI+) for $C_{27}H_{33}N_3O_4$ m/z 464.0 (M+H)⁺.

EXAMPLE 164
Preparation of N-(4-methoxyphenyl)-3-(2,3,4,5-tetrahydroazepino[4,5-b]indol-6(1H)-yl)propanamide hydrochloride

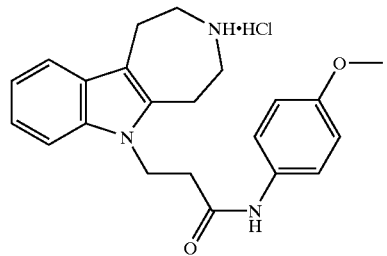

tert-butyl 6-[3-(4-methoxyanilino)-3-oxopropyl]-1,4,5,6-tetrahydroazepino[4,5-b]indole-3(2H)-carboxylate (0.110 g, 0.238 mmol) was disolved in CH₂Cl₂ (5 mL) and trifluoroacetic acid (2.0 mL, 2.96 g, 26.0 mmol, 109 equiv.) was added. The resulting solution was stirred at rt for 2.5 h. The reaction mixture was concentrated to dryness, and the residue was partitioned between EtOAc and 1N NaOH. The layers were separated, and the aqueous layer was extracted with EtOAc. The combined organic layers were washed with brine, dried over MgSO₄, filtered, and concentrated. The crude product (0.0805 g) was combined with EtOAc (2 mL), and 1M HCl in Et₂O (2 mL) and the salt was collected by filtration. The salt was dried under vacuum over P₂O₅. N-(4-methoxyphenyl)-3-(2,3,4,5-tetrahydroazepino[4,5-b]indol-6(1H)-yl)propanamide hydrochloride (0.0796 g) was obtained in 84% yield. $^1$H NMR (300 MHz, CD₃OD) δ 2.76, 3.13–3.17, 3.28–3.39, 3.74, 4.55, 6.82, 7.08, 7.18, 7.26, 7.44, 7.47; MS (ESI+) for $C_{22}H_{25}N_3O_2$ m/z 364.1 (M+H)⁺.

Preparation 48
Preparation of 2-[2-(1H-indol 3-yl)ethyl]-1H-isoindole-1,3 (2H)-dione This compound was prepared by the reaction of tryptamine and N-carboethoxyphthalimide: TLC $R_f$=0.36 ($CH_2Cl_2$); MS (ESI+) m/z 291.0.

Preparation 49
Preparation of 2-[2-[2-(1,1-dimethyl-2-propenyl)-1H-indol-3-yl]ethyl]-1H-isoindole-1,3(2H)-dione To a solution of 2-[2-(1H-indol-3-yl)ethyl]-1H-isoindole-1,3(2H)-dione (3.77 g, 13.0 mmol) in dry THF (0.13 L) under argon was added $NEt_3$ (1.84 mL, 13.0 mmol). This mixture was cooled to -78° C., and neat t-BuOCl (1.54 mL, 13.0 mmol) was added. The reaction mixture was stirred for 30 min at -78° C. A solution of 9-(3-methyl-2-butenyl)-9-bora-bicyclo[3.3.1]nonane (40 mmol) in hexanes was added. The reaction mixture was stirred for 6 h at -78° C. It was quenched with 1 M aq HCl, and permitted to warm to rt overnight. The reaction mixture was extracted with $CH_2Cl_2$. The $CH_2Cl_2$ extracts were dried, filtered, and concentrated to give an oil. The oil was purified by silica chromatography to give the title compound: TLC $R_f$=0.36 ($CH_2Cl_2$); MS (ESI+) m/z 381.2, 359.2; $^1$H NMR (300 MHz, $CDCl_3$) δ 7.91 (1H), 7.88–7.69 (5H), 7.29 (1H), 7.10 (2H), 6.18 (1H), 5.25 (2H), 3.95 (2H), 3.16 (2H), 1.61 (6H).

Preparation 50
Preparation of 2-(1,1-dimethyl-2-propenyl)-1H-indole-3-ethanamine To a solution of 2-[2-[2-(1,1-dimethyl-2-propenyl)-1H-indol-3-yl]ethyl]-1H-isoindole-1,3(2H)-dione (1.10 g, 3.07 mmol) in 3:1 MeOH/$CH_2Cl_2$ (20 mL) at rt under argon was added $N_2H_4H_2O$ (0.52 mL). The reaction mixture was stirred overnight, concentrated in vacuo, diluted with $CHCl_3$, then extracted with $H_2O$. The $CHCl_3$ layer was separated. The $H_2O$ layer was extracted further with $CHCl_3$. The combined $CHCl_3$ extracts were washed, dried, filtered, and concentrated to give the title compound: MS (ESI+) m/z 229.2.

Preparation 51
Preparation of N-[2-[2-(1,1-dimethyl-2-propenyl)-1H-indol-3-yl]ethyl]-carbamic acid phenylmethyl ester To a solution of 2-(1,1-dimethyl-2-propenyl)-1H-indole-3-ethanamine (0.707 g, 3.07 mmol) in dry $CH_2Cl_2$ (30 mL) at 0° C. under argon was added $NEt_3$ (0.98 mL, 6.93 mmol) and BnOC(O)Cl (1.10 mL, 7.32 mmol). The reaction was permitted to warm to rt while stirring overnight. It was diluted with $CH_2Cl_2$, and extracted with cold $H_2O$. The $CH_2Cl_2$ layer was separated. The $H_2O$ layer was re-extracted with $CH_2Cl_2$. The combined $CH_2Cl_2$ extracts were washed with satd aq $NaHCO_3$ and brine, dried, filtered and concentrated to give an oil. This oil was purified by silica chromatography to provide the title compound: TLC $R_f$=0.34 ($CH_2Cl_2$); MS (EI) m/z 362.3, 254, 211, 198, 182. 168, 167, 108, 91, 77, 65, 51; $^1$H NMR (300 MHz, $CDCl_3$) δ 7.89 (1H), 7.56 (1H), 7.33–7.26 (6H), 7.10 (2H), 6.12 (1H), 5.18–5.12 (2H), 5.12 (2H), 4.87 (1H), 3.47 (2H), 3.07 (2H), 1.53 (6H).

Preparation 52
Preparation of (±)-N-[2-[2-(2,3-dihydroxy-1,1-dimethylpropyl)-1H-indol-3-yl]ethyl]-carbamic acid phenylmethyl ester To a solution of N-[2-[2-(1,1-dimethyl-2-propenyl)-1H-indol-3-yl]ethyl]-carbamic acid phenylmethyl ester (0.511 g, 1.41 mmol) and 4-methylmorpholine-N-oxide (0.187 g, 1.59 mmol) in 1:1 acetone/$H_2O$ (14.2 mL) was added $OSO_4$ as a 39 mM solution in tBuOH (2.5 mL). The reaction mixture was stirred for 18 h at rt. The reaction mixture was quenched by the addition of 7.1 mL of an aqueous slurry of $Na_2S_2O_4$ (0.088 g) and Florisl® (0.881 g). The mixture was filtered. The filtrate was acidified to pH 4 with dilute aq $H_2SO_4$, and concentrated. The pH of the filtrate was adjusted to pH 2 with $H_2SO_4$. The mixture was extracted with EtOAc. The combined EtOAc extracts were washed with brine, dried, filtered, and concentrated to give an oil. The oil was purified by silica chromatography to give the title compound: TLC $R_f$=0.21 (4:1 EtOAc/hexanes); MS (ESI+) m/z 419.2, 397.2; $^1$H NMR (300 MHz, $CDCl_3$) δ 8.80 (1H), 7.52 (1H), 7.33–7.26 (6H), 7.16–7.06 (2H), 5.04 (1H), 5.04 (2H), 4.11 (1H), 3.85 (1H), 3.69 (1H), 3.46 (1H), 3.31 (2H), 3.10 (2H), 2.04 (1H), 1.47 (6H).

Preparation 53
Preparation of N-[2-[2-(1,1-dimethyl-2-oxoethyl)-1H-indol-3-yl]ethyl]-carbamic acid phenylmethyl ester To a solution of (±)-N-[2-[2-(2,3-dihydroxy-1,1-dimethylpropyl)-1H-indol-3-yl]ethyl]-carbamic acid phenylmethyl ester (0.323 g, 0.81 mol) in 1:1 acetone/$CH_2Cl_2$ (19.5 mL) was added $NaIO_4$ (0.350 g, 1.64 mmol) in $H_2O$ (2.2 mL). The reaction mixture was stirred for 3 h at rt. Solid $Na_2SO_4$ was added. The mixture was filtered. The filtrate was extracted with $CH_2Cl_2$. The $CH_2Cl_2$ extracts were dried, filtered, and concentrated to an oil. This oil was purified by silica chromatography to give the title compound: TLC $R_f$=0.31 (1:1 heptane/EtOAc); MS (ESI+) m/z 365.2; $^1$H NMR (300 MHz, $CDCl_3$) δ 9.56 (1H), 8.11 (1H), 7.64 (1H), 7.37 (5H), 7.21 (1H), 7.13 (1H), 5.14 (2H), 4.92 (1H), 3.45 (2H), 2.95 (2H), 1.60 (6H).

EXAMPLE 165
Preparation of 5,5-dimethyl-1,2,3,4,5,6-hexahydroazepino[4,5-b]indole hydrogen chloride salt

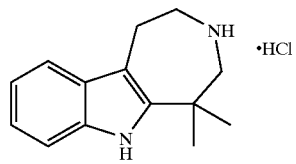

A suspension of N-[2-[2-(1,1-dimethyl-2-oxoethyl)-1H-indol-3-yl]ethyl]-carbamic acid phenylmethyl ester (0.200 g, 0.55 mol) and 10% Pd/C (0.080 g) in MeOH (40 mL) was hydrogenated at atmospheric pressure for 2 h. The mixture was filtered. The filtrate was concentrated. The residue was taken up in MeOH (2 mL), and a solution of HCl in $Et_2O$ was added. The precipitate was collected and triturated with $Et_2O$. The solid was dried to give the title compound: MS (FAB) m/z 216.2, 215.2, 214.2, 213.1, 186.1, 184.1, 177.0, 172.1; $^1$H NMR (300 MHz, $CD_3SOCD_3$) δ 10.88 (1H), 9.54 (1H), 7.42 (1H), 7.32 (1H), 7.04 (1H), 6.97 (1H), 3.61 (2H), 3.39 (4H), 3.10 (2H), 1.44 (6H); Anal. C 62.92, H 7.34, N 10.11.

Preparation 54
Preparation of 4-chloro-3-(1H)-indoleglyoxylic acid ethyl ester

To a solution of 4-chloroindole (5.00 g, 33.0 mmol) in dry THF (0.2 L), at 0° C. under argon was added $(COCl)_2$ (3.6 mL, 40.4 mmol). The reaction mixture was stirred overnight while warming to rt, cooled to 0° C., and EtOH (4 mL, 69 mmol) was added. The reaction mixture was stirred at rt overnight, then partitioned between cold 0.2 M aq HCl and EtOAc. The aqueous layer was separated and re-extracted with EtOAc. The EtOAc extracts were washed with saturated aqueous $NaHCO_3$ and brine. The extracts were dried, filtered, and concentrated to give a solid. The solid was purified by silica chromatography to give the title compound: TLC $R_f$=0.40 (19:1 $CH_2Cl_2/Me_2CO$); MS (ESI+) m/z 274.0; $^1$H NMR (300 MHz, $CDCl_3$) δ 9.22 (1H), 8.26 (1H), 7.36 (1H ), 7.31 (1H ), 7.22 (1H ), 4.71 (2H), 1.41 (3H).

Preparation 55
Preparation of 2-(4-chloro-1H-indol-3-yl)-ethanol

To a solution of 4-chloro-3-(1H)-indoleglyoxylic acid ethyl ester (7.04 g, 30.0 mmol) in dry THF (0.4 L), at 0° C. under argon was added portionwise $LiAlH_4$ (5.4 g, 135.2 mmol). The suspension was stirred at 0° C. for 20 min and at reflux for 3.5 h, cooled to 0° C., and water (17.6 mL) was added. It was stirred for 10 min, and then diluted with EtOAc. The reaction mixture was filtered. The solid was washed with EtOAc. The combined EtOAc portions were washed with water and brine, dried, filtered, and concentrated to give the title compound: TLC $R_f$=0.38 (9:1 $CH_2Cl_2$/$Me_2CO$); MS (ESI–) m/z 194.0; $^{13}C$ NMR (75 MHz, $CDCl_3$) δ 138.02, 126.42, 124.21, 124.12, 122.70, 120.61, 112.63, 110.06, 63.59, 29.78.

Preparation 56
Preparation of 3 (2-azidoethyl)-4-chloro-1H-indole

To a mixture of 2-(4-chloro-1H-indol-3-yl)-ethanol (5.35 g, 27.3 mmol), $PPh_3$ (14.35 g, 54.7 mmol), and $Zn(N_3)_2$; $pyr_2$ (12.1 g, 41.0 mmol) in $PhCH_3$ (0.14 L) was added $iPrO_2CNNCO_2iPr$ (10.78 mL, 54.7 mmol). The reaction mixture was stirred for 3.5 h at rt, then concentrated. The residue was purified by silica chromatography to give the title compound: TLC $R_f$=0.64 ($CH_2Cl_2$); MS (ESI–) m/z 219.0; $^{13}C$ NMR (75 MHz, $CDCl_3$) δ 137.80, 126.16, 124.07, 123.90, 122.78, 120.64, 112.73, 110.07, 52.74, 26.21.

Preparation 57
Preparation of 2-[3-(2-azidoethyl)-4-chloro-1H-indol-2-yl]-propanedioic acid dimethyl ester To a solution of 3-(2-azidoethyl)-4-chloro-1H-indole (4.25 g, 19.3 mmol) and $NEt_3$ (3.00 mL, 21.3 mmol) in THF (0.11 L) at –78° C. under argon was added dropwise tBuOCl (2.51 mL, 21.2 mmol). The solution was stirred for 30 min at –78° C. A solution of 1 M $ZnCl_2$ in $Et_2O$ (4.1 mL) was added. The reaction mixture was stirred for 20 min at –78° C. A solution of lithiodimethyl malonate (23.1 mmol) in THF/hexanes (50 mL) was added at –78 ° C. The reaction mixture was stirred for 60 min. at -78° C., stirred at rt overnight, then diluted with cold $H_2O$. The mixture was extracted with $Et_2O$. The combined $Et_2O$ extracts were washed with $H_2O$ , dried, filtered, and concentrated to give the title compound: TLC $R_f$=0.44 ($CH_2Cl_2$); MS (ESI–) 349.0; $^1$H NMR (300 MHz, $CDCl_3$) δ 9.14 (1H), 7.25 (1H), 7.07 (2H), 5.10 (1H), 3.81 (6H), 3.57 (2H), 3.23 (2H).

Preparation 58
Preparation of 2-[3-(2-azidoethyl)-4-4-chloro-1H-indol-2-yl]-2-methylpropanedioic acid dimethyl ester To a solution of 2-[3-(2-azidoethyl)-4-chloro-1H-indol-2-yl]-propanedioic acid dimethyl ester (19.3 mmol) in dry MeOH (0.1 L) at 0° C. under argon was added a 25% NaOMe in MeOH (4.37 mL, 19.11 mmol). The reaction mixture was stirred for 30 min, and MeI (1.82 mL, 29.2 mmol) was added. The mixture was stirred briefly at rt, and then was refluxed overnight. The reaction mixture was concentrated. The residue was taken up with cold $H_2O$. This mixture was extracted with $Et_2O$. The combined $Et_2O$ extracts were washed with $H_2O$, dried, filtered, and concentrated to an oil. This oil was purified by silica chromatography to give the title compound: TLC $R_f$=0.50 ($CH_2Cl_2$), MS (ESI+) 387.0; $^1$H NMR (300 MHz $CDCl_3$) δ 9.95 (1H), 7.27 (1H), 7.07 (2H), 3.83 (6H), 3.48 (2H), 3.15 (2H), 1.94 (3H).

Preparation 59
Preparation of (±)-10-chloro-5-methyl-2,3,5,6-tetrahydroazepino[4,5-b]indol-4(1H)-one To a solution of 2-[3-(2-azidoethyl)-4-chloro-1H-indol-2-yl]-2-methylpropanedioic acid dimethyl ester (2.07 g, 5.67 mmol) in dry THF (50 mL) under argon at rt was added 1 M $PMe_3$ in THF (9.7 mL). The reaction mixture was stirred for 1.5 h at rt. Water (9.7 mL) was added. After 1.5 h at rt, the reaction mixture was concentrated. The residue was partitioned between $CH_2Cl_2$ and saturated aqueous $NaHCO_3$. The $CH_2Cl_2$ extracts were combined, dried, filtered, and concentrated to give the amine as an oil. This oil was dissolved in MeOH. This solution was refluxed under $N_2$ for 42 h. The reaction mixture was cooled, and 1 M aq LiOH (28.5 mL) was added. The reaction mixture was refluxed for 47 h. It was concentrated, and the residue was taken up in EtOAc. The EtOAc solution was extracted with $H_2O$, dried, filtered, and concentrated to give the title compound: TLC $R_f$=0.25 (4:1 $CH_2Cl_2$/acetone); MS (ESI–) 247.0; $^1$H NMR (300 MHz, $CDCl_3$) δ 8.16 (1H), 7.18 (1H), 6.99 (2H), 6.12 (1H), 4.29 (1H), 3.83 (1H), 3.55 (1H), 3.36 (2H), 1.64 (3H).

Preparation 60
Preparation of (R)-10-chloro-5-methyl-2,3,5,6-tetrahydroazepino[4,5-b]indol-4(1H)-one The racemate (0.70 g) was resolved by chiral support chromatography. Portions of the racemate (0.35 g dissolved in 20 mL of 3:1 iPrOH/THF) were injected onto a preparative Chiralcel OD™ column equilibrated at 30° C. with 800:200:1 heptane/iPrOH/$Et_3N$. From the injections were recovered the faster eluting S-enantiomer and the R-enantiomer. Analytical HPLC analysis ($t_R$=11.9 min on a Chiralcel™ OD-H at a 0.4 mL min$^{-1}$ flow rate of 1000:1 EtOH/$Et_2NH$) gave an ee of 91%: UV $\lambda_{max}$ nm (ϵ, L.mol$^{-1}$.cm$^{-1}$) 284 (6840); CD $\lambda_{max}$ nm (θ, deg.cm$^2$ dmol$^{-1}$) 300 (6700), 289 (7000), 279 (6500).

Preparation 61
Preparation of (S)-10-Chloro-5-methyl-2,3,5,6-tetrahydroazepino[4,5-b]indol-4(1H)-one Analytical HPLC analysis ($t_R$=11.2 min on a Chiralcel™ OD-H at a 0.4 ML min$^{-1}$ flow rate of 1000:1 EtOH/$Et_2NH$) gave an ee of >99%: UV $\lambda_{max}$ nm (ϵ, L.mol$^{-1}$.cm$^{-1}$) 284 (7560); CD $\lambda_{max}$ nm (θ, deg.cm$^2$.dmol$^{-1}$) 300 (–8200), 289 (–8800), 279 (–8500).

EXAMPLE 166
Preparation of (R)-10-chloro-5-methyl-1,2,3,4,5,6-hexahydroazepino[4,5-b]indole (E)-butenedioic acid salt

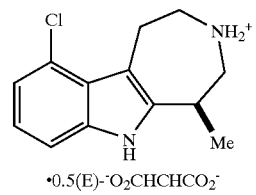

•0.5(E)-$^-O_2$CHCHCO$_2^-$

A solution of 1 M $iBu_2AlH$ in $CH_2Cl_2$ (15.3 mL) was mixed with dry THF (10 mL) at –78° C. After stirring this mixture for 5 min, a solution of (R)-10-chloro-5-methyl-2,3,5,6-tetrahydroazepino[4,5-b]indol-4(1H)-one (0.251 g, 1.01 mmol) in THF (15 mL) was added. The reaction mixture was allowed to warm to rt, stirred at rt for 7 days, cooled to 0° C., then quenched by the addition of MeOH (4.5 mL). The reaction mixture was diluted with $CH_2Cl_2$ and 1 M aq $KO_2CCH(OH)CH(OH)CO_2Na$. This mixture was stirred for 1 h. The $CH_2Cl_2$ layer was separated. The aqueous mixture was extracted further with $CH_2Cl_2$. The combined $CH_2Cl_2$ extracts were washed with brine, dried, filtered, and concentrated to give an oil. This oil was purified by silica chromatography to give the amine. A solution of this amine (0.087 g, 0.37 mmol) in anhydrous MeOH (4 mL) was mixed at rt with a solution of fumaric acid (0.021 g, 0.185 mmol) in MeOH (2 mL). The mixture was stirred at rt for 18 h, then concentrated. The solid residue was taken up in hot MeOH (14 mL), that upon standing at rt for 3 days yielded 0.048 g (0.164 mmol, 38%) of the title compound as a crystalline tan-colored solid: MS (EI) m/z 234, 205, 204, 199, 194, 192, 190, 155, 154, 77; $^1$H NMR (300 MHz, $CD_3SOCD_3$) δ 11.14 (1H), 7.23 (1H), 6.94 (2H), 6.43 (1H), 3.52–2.83 (8H), 1.31 (3H); Anal. C 60.62, H 6.02, N 9.27.

EXAMPLE 167

Preparation of (S)-10-chloro-5-methyl-1,2,3,4,5,6-hexahydroazepino[4,5-b]indole (E)-butenedioic acid salt

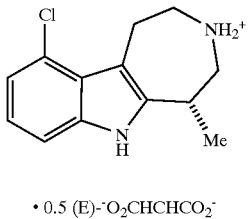

• 0.5 (E)-$^-O_2CHCHCO_2^-$

The crystalline salt was prepared as described for (R)-10-chloro-5-methyl-2,3,5,6-tetrahydroazepino[4,5-b]indol-4(1H)-one in Example 166. These crystals occupy the monoclinic space group P21 with Z=4. The absolute configuration was determined as S by single crystal x-ray analysis. Intensity data from a 0.50∞0.22∞0.08 mm pale yellow plate crystal were measured at 153° K., on a Brucker SMART 6000™ area detector using graphite monochromatized copper radiation [λ(CuKα)=1.5418 Å]. All reflections to a resolution of 0.90, and their Freidel equivalents, were measured (3533 reflections total) and face-indexed absorption corrections were applied. The structure was solved, and the data were refined, using the SHELXTL™ computer program. The final agreement index R was 0.0508 for all reflections. The Flack parameter was −0.030 (0.016). A Flack parameter within 3 standard deviations of zero indicates the correct assignment of absolute configuration (the opposite enantiomer should have a Flack value of one). Refinement of the coordinates for the other enantiomer gave an R value of 0.065 and a Flack value of 0.973(0.025), verifying the assignment of absolute configurations: mp 276–278° C.; MS (ESI) m/z 237.0, 235.0; Anal. C 61.05, H 5.95, N 9.41.

Preparation 62

Preparation of 6-fluoro-3-indoleglyoxylic acid ethyl ester

To a solution of 6-fluoroindole (1.18 g, 8.56 mmol) in dry THF (65 mL) at 0° C. under argon was added $(COCl)_2$ (0.93 mL, 10.7 mmol). The reaction mixture was stirred at 0° C. for 2 h and at rt for 15 h. The reaction mixture was cooled to 0° C. and EtOH (0.90 mL, 15.5 mmol) was added. The reaction mixture was stirred at rt for 24 h, then poured into cold satd $NaHCO_3$. The mixture was extracted with EtOAc. The combined EtOAc extracts were washed with satd aq $NaHCO_3$ and brine, dried, and evaporated to give the title compound: TLC $R_f$=0.48 (19:1 $CH_2Cl_2/Me_2CO$); MS (ESI-) m/z 234.0; $^1$H NMR ($CDCl_3$, 300 MHz) δ 10.95 (1H), 8.38 (1H), 8.31 (1H), 7.07 (1H), 4.37 (2H), 1.39 (3H).

Preparation 63

Preparation of 2-(6-fluoro-1H-indol-3-yl)-ethanol

To a solution of 6-fluoro-3-indoleglyoxylic acid ethyl ester (2.01 g, 8.55 mmol) in dry THF (0.11 L) at 0° C. under argon was added $LiAlH_4$ (1.68 g, 44.2 mmol). The reaction mixture was refluxed for 3 h, cooled to 0° C., and treated with $H_2O$ (1.7 mL), 15% aq KOH (1.7 mL), and $H_2O$ (5 mL). The mixture was filtered. The filtrate was diluted with EtOAc, and washed with $H_2O$ and brine. The EtOAc solution was dried, filtered, and concentrated to give the title compound: TLC $R_f$=0.33 (9:1 $CH_2Cl_2/Me_2CO$); MS (ESI-) m/z 178.0; $^1$H NMR ($CDCl_3$, 300 MHz) δ 8.38 (1H), 7.49 (1H), 7.01–6.63 (3H), 3.90 (2H), 2.99 (2H), 2.23 (1H).

Preparation 64

Preparation of 3-(2-azidoethyl)-6-fluoro-1H-indole

To a mixture of 2-(6-fluoro-1H-indol-3-yl)-ethanol (3.16 g, 17.6 mmol), $PPh_3$ (9.26 g, 35.3 mmol), and $Zn(N_3)_2$·(pyridine)$_2$ (7.80 g, 26.5 mmol) in dry $PhCH_3$ (0.08 L) at rt was added $iPrO_2CNNCO_2iPr$ (7.0 mL, 35.3 mmol). The reaction mixture was stirred at rt for 4 h, concentrated to a residue, then purified by silica chromatography to give the title compound: TLC $R_f$=0.63 ($CH_2Cl_2$); MS (ESI-) m/z 203.0; $^1$H NMR ($CDCl_3$, 300 MHz) δ 8.03 (1H), 7.50 (1H), 7.06 (2H), 6.91 (1H), 3.56 (2H), 3.04 (2H).

Preparation 65

Preparation of 2-[3-(2-azidoethyl)-6-fluoro-1H-indol-2-yl]-propanedioic acid dimethyl ester To a solution of 3-(2-azidoethyl)-6-fluoro-1H-indole (4.77 g, 23.3 mmol) and $NEt_3$ (3.63 mL, 25.8 mmol) in dry THF (0.13 L) at −78° C. under argon was added tBuOCl (3.04 mL, 26.9 mmol). The reaction mixture was stirred for 30 min at −78° C. A solution of 1 M $ZnCl_2$ in $Et_2O$ (5.0 mL) was added. After 15 min a solution of dimethyl lithiomalonate (28.1 mmol in THF/hexanes) was added. The mixture was stirred at −78° C. for 1 h and at rt overnight, diluted with cold water, then extracted with $Et_2O$. The $Et_2O$ extracts were dried, filtered, and concentrated to give the title compound: TLC $R_f$=0.46 ($CH_2Cl_2$); MS (ESI-) m/z 333.1; $^1$H NMR ($CDCl_3$, 300 MHz) δ 8.97 (1H), 7.45 (1H), 7.05 (1H), 6.89 (1H), 5.02 (1H), 3.80 (6H), 3.50 (2H), 2.97 (2H).

Preparation 66

Preparation of 8-fluoro-2,3,5,6-tetrahydroazepino[4,5-b]indol-4(1H)-one

A suspension of 2-[3-(2-azidoethyl)-6-fluoro-1H-indol-2-yl]-propanedioic acid dimethyl ester (2.05 g, 6.13 mmol) and 10% Pd/C (0.69 g) in MeOH (0.15 L) was hydrogenated at atmospheric pressure for 2 h. The mixture was filtered. The MeOH solution was refluxed overnight. The reaction mixture was cooled, and most of the MeOH solvent was evaporated. The mixture was purified by silica chromatography (steps of 4:1 to 7:3 $CH_2Cl_2/Me_2CO$) to give the carboxylactam. To a solution of the carboxylactam (1.37 g, 4.11 mmol) in MeOH (0.2 L) at rt under $N_2$ was added a solution of 1 M aq $LiOH·H_2O$ (21 mL). The mixture was refluxed overnight, and then concentrated. The residue was partitioned between EtOAc and $H_2O$. The EtOAc extracts were filtered and concentrated to give a solid, that was purified by silica chromatography to give the title compound: TLC $R_f$=0.14 (9:1 $CH_2Cl_2$/satd $NH_3$ in MeOH); MS (ESI-) m/z 217.0 [M−H]$^-$; $^1$H NMR ($CDCl_3$, 300 MHz) δ 9.53 (1H), 7.24 (1H), 6.94 (1H), 6.74 (1H), 6.35 (1H), 3.79 (2H), 3.60 (2H), 2.85 (2H).

EXAMPLE 168
Preparation of 8-Fluoro 1,2,3,4,5,6-hexahydroazepino[4,5-b]indole 0.5 (E)-butenedioic acid salt

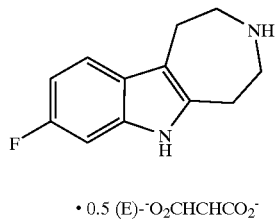

• 0.5 (E)-$^-O_2CHCHCO_2^-$

To a flask containing THF (10 mL) at −78° C. under argon was added a 1 M solution of iBU$_2$AlH in CH$_2$Cl$_2$ (16.3 mL). After 5 min, a solution of 8-fluoro-2,3,5,6-tetrahydroazepino[4,5-b]indol-4(1H)-one (0.175 g, 0.80 mmol) in THF (16 mL) was added. The reaction mixture was allowed to warm to rt, stirred for 48 h, cooled to 0° C., then quenched with MeOH (4.5 mL). It was partitioned between CH$_2$Cl$_2$ and aqueous 1 M KO$_2$CC(OH)C(OH)CO$_2$Na. The CH$_2$Cl$_2$ extracts were washed with brine, dried, filtered, and concentrated to give a solid. The solid was purified by silica chromatography (92.5:7.5 CH$_2$Cl$_2$/satd NH$_3$ in MeOH) to give the free amine. A solution of this amine (0.094 g, 0.46 mmol) in dry MeOH (4.0 mL) at rt under argon was mixed with a solution of fumaric acid (0.027 g, 0.23 mmol) in dry MeOH (2.2 mL). The turbid solution was stirred overnight at rt. The MeOH was evaporated. The residue was dissolved in hot MeOH, and the salt was permitted to crystallize. The crystalline salt was collected: mp 266° C.; MS (ESI+) m/z 205.1; $^1$H NMR (CD$_3$SOCD$_3$, 300 MHz) δ 10.94 (1H), 7.34 (1H), 7.00 (1H), 6.77 (1H), 6.40 (1H), 3.11 (4H), 2.91 (4H); Anal. C 63.90, H 5.83, N 10.63.

Preparation 67
Preparation of 2-[3-(2-azidoethyl)-6-fluoro-1H-indol-2-yl]-2-methylpropanedioic acid dimethyl ester To a solution of 2-[3-(2-azidoethyl)-6-fluoro-1H-indol-2-yl]-propanedioic acid dimethyl ester (37 mmol) in dry MeOH (0.25 L) at 0° C. under argon was added a solution of 25% NaOMe in MeOH (8.56 mL, 37.4 mmol). The mixture was stirred for 30 min at 0° C. MeI (3.56 mL, 56.6 mmol) was added. The mixture was refluxed for 42 h, cooled, and concentrated. The residue was partitioned between H$_2$O and Et$_2$O. The Et$_2$O extracts were washed with H$_2$O, dried, and concentrated to an oil. This oil was purified by silica chromatography to give the title compound: TLC R$_f$=0.50 (CH$_2$Cl$_2$); MS (ESI+) m/z 371.1; $^1$H NMR (CDCl$_3$, 300 MHz) δ 9.63 (1H), 7.44 (1H), 7.05 (1H), 6.97 (1H), 3.82 (6H), 3.44 (2H), 2.94 (2H), 1.93 (3H).

Preparation 68
Preparation of (±)-8-fluoro-5-methyl-2,3,5,6-tetrahydroazepino[4,5-b]indol-4(1H)-one A mixture of 2-[3-(2-azidoethyl)-6fluoro-1H-indol-2-yl]-2-methylpropanedioic acid dimethyl ester (3.10 g, 8.90 mmol) and 10% Pd/C (0.87 g) in MeOH (0.2 L) was hydrogenated at atmospheric pressure for 2.5 h. The reaction mixture was filtered. The filtrate was refluxed for 18 h. The reaction mixture was concentrated to give the carboxylactam. A solution of the carboxylactam (2.08 g, 5.96 mmol) in MeOH (0.27 L), and a 1 M LiOH.H$_2$O in MeOH solution (0.030 L), were combined at rt. The mixture was refluxed for 42 h, cooled, and concentrated. The MeOH solution was diluted with H$_2$O, and the aqueous solution was extracted with EtOAc. The EtOAc extracts were concentrated to give the title compound: MS (ESI−) m/z 231.0; $^1$H NMR (300 MHz, CDCl$_3$) δ 8.04 (1H), 7.31 (1H), 7.10 (1H), 6.86 (1H), 6.16 (1H), 4.24 (1H), 3.86 (1H), 3.58 (1H), 2.96 (2H), 1.64 (3H).

Preparation 69
Preparation of (R)-8-fluoro-5-methyl-2,3,5,6-tetrahydroazepino[4,5-b]indol-4(1H)-one The racemate was resolved by chiral support chromatography. Portions of the racemate (0.2 g dissolved in 10 mL of 3:1 iPrOH/THF) were injected onto a preparative Chiralcel OD™ column equilibrated at 30° C. with 800:200:1 heptane/iPrOH/Et$_3$N. Assignment of absolute configurations to the separated enantiomers was made by comparison of the CD spectra to those of the 10-chloro strictures. Analytical HPLC analysis (t$_R$=17.2 min on a Chiralcel™ OD-H at a 0.5 mL min$^{-1}$ flow rate of 800:200:1 hepane/iPrOH/Et$_2$NH) gave an ee of 97%: UV λ$_{max}$ nm (ε, L.mol$^{-1}$.cm$^{-1}$) 284 (4740); CD λ$_{max}$ nm (θ, deg.cm$^2$.dmol$^{-1}$) 298 (3700), 273 (4400).

Preparation 70
Preparation of (S)-8-fluoro-5-methyl-2,3,5,6-tetrahydroazepino[4,5-b]indol-4(1H)-one Analytical HPLC analysis (t$_R$=15.2 min on a Chiralcel™ OD-H at a 0.5 mL min$^{-1}$ flow rate of 800:200:1 hepane/iPrOH/Et$_2$NH) gave an ee of >99%: UV λ$_{max}$ nm (ε, L.mol$^{-1}$.cm$^{-1}$) 292 (4540); CD λ$_{max}$ nm (θ, deg.cm$^2$.dmol$^{-1}$) 297 (−3000), 273 (−4000).

EXAMPLE 169

Preparation of (R)-8-fluoro-5-methyl-1,2,3,4,5,6-hexahydroazepino[4,5-b]indole 0.5 (E)-butenedioic acid salt

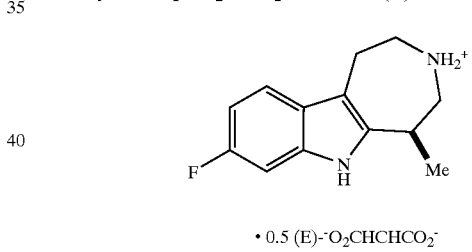

• 0.5 (E)-$^-O_2CHCHCO_2^-$

To an oven dried flask containing dry THF (10 mL) under argon at −78° C. was added a 1 M solution of (iBu)$_2$AlH in CH$_2$Cl$_2$ (16.3 mL). This mixture was stirred at −78° C. for 5 min. To this was (R)-8-fluoro-5-methyl-2,3,5,6tetrahydroazepino[4,5-b]indol-4(1H)-one (0.236 g, 1.02 mmol) in dry THF (16 mL). The reaction mixture was stirred at rt for 72 h, cooled to 0° C., then quenched by the addition of MeOH (4.5 mL). The mixture was partitioned between CH$_2$Cl$_2$ and 1 M aq NaO$_2$CCH(OH)CH(OH)CO$_2$K. The CH$_2$Cl$_2$ extracts were washed with brine, and dried, filtered and concentrated to give an oil. The oil was purified by silica chromatography to give the amine. To a solution of this amine (0.105 g, 0.48 mmol) in dry MeOH (4 mL) was added fumaric acid (0.028 g, 0.24 mmol) in MeOH (2.2 mL). The mixture was stirred overnight, concentrated, and the residue was dissolved in hot MeOH from which crystalline product was recovered: mp 256–258° C.; MS (ESI+) m/z 219.1; $^1$H NMR (CD$_3$SOCD$_3$, 300 MHz) δ 10.83 (1H), 9.3–8.5 (2H), 7.35 (1H), 7.01 (1H), 6.78 (1H), 6.43 (1H), 3.22–2.70 (8H), 1.30 (3H); Anal. C 64.94, H 6.27, N 10.07.

EXAMPLE 170

Preparation of (S)-8-fluoro-5-methyl-1,2,3,4,5,6-hexahydroazepino[4,5-b]indole 0.5 (E)-butenedioic acid salt

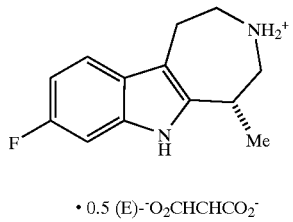

• 0.5 (E)-⁻O₂CHCHCO₂⁻

This salt was prepared by the method taught for the R-enantiomer in Example 169: mp 254–256° C.; MS (ESI+) m/z 219.1; Anal. C 64.83, H 6.23, N 10.05.

EXAMPLE 171

Preparation of 2-(7-bromo-2,3,4,5-tetrahydroazepino[4,5-b]indol-6(1H)-yl)-N-(4-methoxyphenyl)acetamide hydrochloride

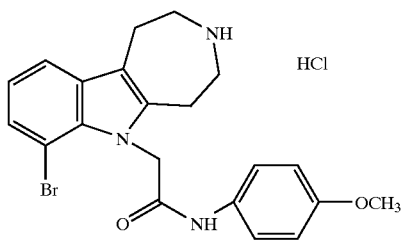

Prepared according to the procedure used to prepare N-(2,3-dimethylphenyl)-2-(2,3,4,5-tetrahydroazepino[4,5-b]indol-6(1H)-7yl)acetamide hydrochloride. $^1$H NMR (CD$_3$OD) δ 7.51, 7.47, 7.34, 6.98, 7.90, 5.53, 3.78, 3.51, 3.24. MS (ESI+) for C$_{21}$H$_{22}$BrN$_3$O$_2$ m/z 428.1 (M+H)$^+$.

EXAMPLE 172

Preparation of N-pyridin-2-yl-2-(2,3,4,5-tetrahydroazepino[4,5-b]indol-6(1H)-yl)acetamide

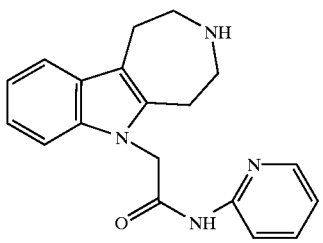

Prepared according to the procedure used to prepare N-(2,3-dimethylphenyl)-2-(2,3,4,5-tetrahydroazepino[4,5-b]indol-6(1H)-yl)acetamide hydrochloride. $^1$H NMR (CD$_3$OD) δ 8.30, 8.05, 7.76, 7.49, 7.32, 7.16–7.06, 5.10, 3.27–3.23, 3.11–3.04. MS (ESI+) for C$_{19}$H$_{20}$N$_4$O m/z 321.2 (M+H)$^+$.

EXAMPLE 173

Preparation of N-pyridin-3-yl-2-(2,3,4,5-tetrahydroazepino[4,5-b]indol-6(1H)-yl)acetamide

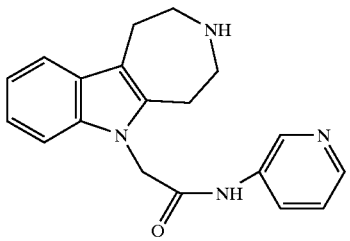

Prepared according to the procedure used to prepare N-(2,3-dimethylphenyl)-2-(2,3,4,5-tetrahydroazepino[4,5-b]indol-6(1H)-yl)acetamide hydrochloride in 30% yield. $^1$H NMR (CD$_3$OD) δ 8.74, 8.28, 8.11, 7.46, 7.40, 7.29, 7.13, 7.05, 5.04, 3.16–3.10, 3.05–2.99; MS (ESI+) for C$_{19}$H$_{20}$N$_4$O m/z 321.2 (M+H)$^+$.

Preparation 71

Preparation of tert-Butyl 8,9-dichloro-6-(2-ethoxy-2-oxoethyl)-1,4,5,6-tetrahydroazepino[4,5-b]indole-3(2H)-carboxylate Sodium hydride (60% dispersion in mineral oil, 0.34 g, 8.5 mmol) was added to a solution of tert-butyl 8,9-dichloro-1,4,5,6-tetrahydroazepino[4,5-b]indole-3(2H)-carboxylate (2.00 g, 5.63 mmol) in DMF (30 mL). After 20 min, ethyl bromoacetate (1.25 mL, 11.3 mmol) was added. The reaction was quenched with saturated aqueous NH$_4$Cl after 4 h and extracted with EtOAc (3×50 mL). The combined organic extracts were washed with brine, dried over Na$_2$SO$_4$, decanted, and concentrated. The crude product was purified by column chromatography with heptane/EtOAc (3:1) to give 2.10 g (84%) of a pale yellow solid: mp 137.5–139.5° C.; IR (diffuse reflectance) 2985, 1742, 1687, 1473, 1411, 1377, 1367, 1341, 1318, 1249, 1218, 1193, 1167, 1118, 922 cm$^{-1}$; MS (CI) m/z 441 (M+H$^+$), 404, 402, 387, 385, 343, 341, 339, 307, 52, 51; Anal. Calcd for C$_{21}$H$_{26}$Cl$_2$N$_2$O$_4$: C, 57.15; H, 5.94; N, 6.35; found: C, 57.13; H, 6.05; N, 6.24.

Preparation 72

Preparation of [3-(tert-Butoxycarbonyl)-8,9-dichloro-2,3,4,5-tetrahydroazepino[4,5-b]indol-6(1H)-yl]acetic acid A solution of KOH (0.17 g, 3.0 mmol) in H$_2$O (10 mL) was added to a solution of tert-butyl 8,9-dichloro-6-(2-ethoxy-2-oxoethyl)-1,4,5,6-tetrahydroazepino[4,5-b]indole-3(2H)-carboxylate (1.00 g, 2.27 mmol) in THF (15 mL). The mixture was heated at 60° C. for 2 h. The reaction was then cooled to rt, acidified with 10% aqueous HCl, and extracted with EtOAc (3×30 mL). The combined organic extracts were washed with brine, dried over Na$_2$SO$_4$, decanted, and concentrated to give crude acid (1.03 g, 110%): $^1$H NMR (300 MHz, CDCl$_3$) δ 7.50 (s, 1H), 7.26 (s, 1H), 4.73 (s, 2H), 3.74 (m, 2H), 3.67 (m, 2H), 2.89 (m, 4H), 1.47 (s, 9H); MS(ESI+) m/z 410.9.

Preparation 73

Preparation of tert-Butyl 6-(2-anilino-2-oxoethyl)-8,9-dichloro-1,4,5,6-tetrahydroazepino[4,5-b]indole-3(2H)-carboxylate DMAP (60 mg, 0.49 mmol), aniline (0.050 mL, 0.55 mmol) and DIC (0.084 mL, 0.54 mmol) were added to the solution of crude [3-(tert-butoxycarbonyl)-8,9-dichloro-2,3,4,5-tetrahydroazepino[4,5-b]indol-6(1H)-yl]acetic acid (0.20 g, 0.48 mmol) in dry THF (2.5 mL). After 18 h, the reaction was diluted with EtOAc followed by washing with 10% aqueous citric acid, saturated aqueous NaHCO$_3$, and

EXAMPLE 174
Preparation of 2-(8,9-Dichloro-2,3,4,5-tetrahydroazepino[4,5-b]indol-6(1H)-yl)-N-phenylacetamide hydrochloride

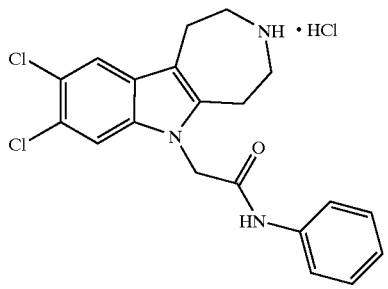

TFA (0.10 mL, 1.3 mmol) was added to a solution of tert-butyl 6-(2-anilino-2-oxoethyl)-8,9-dichloro-1,4,5,6-tetrahydroazepino[4,5-b]indole-3(2H)-carboxylate (60 mg, 0.12 mmol) in $CH_2Cl_2$ (2 mL). The reaction was quenched with 10% aqueous NaOH (5 mL) after 2 h and extracted with $CH_2Cl_2$ (3×10 mL). The combined organic layers were washed with brine, dried over $Na_2SO_4$, decanted, and concentrated to give 46 mg of crude solid. The hydrochloride salt was prepared to give 32 mg (62%) of a pale yellow solid: mp 292–297.5° C. (dec); IR (diffuse reflectance) 2960, 2883, 2817, 2805, 2769, 2715, 1682, 1601, 1550, 1498, 1466, 1447, 1313, 869, 759 $cm^{-1}$; MS (EI) m/z 387 ($M^+$), 347, 345, 188, 166, 92, 78, 76, 74, 66, 51; HRMS (FAB) calcd for $C_{20}H_{19}Cl_2N_3O+H$ 388.0983, found 388.0973; Anal. Calcd for $C_{20}H_{19}Cl_2N_3O \cdot HCl$: C, 56.55; H, 4.75; N, 9.89; found: C, 56.78; H, 5.04; N, 9.50.

Preparation 74
Preparation of tert-Butyl 8,9-dichloro-6-[2-(4-methoxyanilino)-2-oxoethyl]-1,4,5,6-tetrahydroazepino[4,5-b]indole-3(2H)-carboxylate DMAP (60 mg, 0.49 mmol), p-anisidine (66 mg, 0.54 mmol) and DIC (0.084 mL, 0.54 mmol) were added to the solution of crude [3-(tert-butoxycarbonyl)-8,9-dichloro-2,3,4,5-tetrahydroazepino[4,5-b]indol-6(1H)-yl]acetic acid (0.20 g, 0.48 mmol) in dry THF (2.5 mL). After 18 h, the reaction was diluted with EtOAc and washed with 10% aqueous citric acid, saturated aqueous $NaHCO_3$, and brine. The organic layer was then dried over $Na_2SO_4$, decanted, and concentrated. The crude product was first purified by column chromatography (Biotage, 40S, SIM) with $CH_2Cl_2$/EtOAc (gradient, 99:1 to 95:5) to give 81 mg of impure product. Then, crystallization from EtOAc/heptane gave 73 mg (29%) of a white solid: mp 151–151.5° C.; IR (diffuse reflectance) 3288, 1695, 1661, 1550, 1513, 1473, 1422, 1367, 1318, 1269, 1250, 1172, 1161, 1118, 831 $cm^{-1}$; MS (CI) m/z 518 ($M+H^+$), 222, 221, 220, 167, 166, 124, 59, 58, 52, 51; Anal. Calcd for $C_{26}H_{29}Cl_2N_3O_4$: C, 60.24; H, 5.64; N, 8.10; found: C, 60.23; H, 5.73; N, 8.10.

EXAMPLE 175
Preparation of 2-(8,9-Dichloro-2,3,4,5-tetrahydroazepino[4,5-b]indol-6(1H)-yl)-N-(4-methoxyphenyl)acetamide hydrochloride

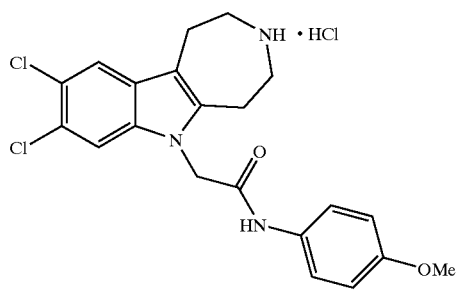

TFA (0.25 mL, 3.2 mmol) was added to a solution of tert-butyl 8,9-dichloro-6-[2-(4-methoxyanilino)-2-oxoethyl]-1,4,5,6-tetrahydroazepino[4,5-b]indole-3(2H)-carboxylate (50 mg, 0.096 mmol) in $CH_2Cl_2$ (3.0 mL). After 1.5 h, the reaction was quenched with 10% aqueous NaOH and extracted with $CH_2Cl_2$ and EtOAc. The combined organic layers were washed with brine, dried over $Na_2SO_4$, decanted, and concentrated to 39 mg of a crude solid. The hydrochloride salt was prepared to give 22 mg (50%) of off-white crystals: mp 294–299° C. (dec); IR (diffuse reflectance) 3248, 2964, 2959, 2907, 2883, 2855, 2840, 2820, 2772, 1676, 1549, 1511, 1466, 1251, 823 $cm^{-1}$; MS (EI) m/z 417 ($M^+$), 389, 387, 375, 238, 224, 162, 136, 134, 127, 108; Anal. Calcd for $C_{21}H_{21}Cl_2N_3O_2 \cdot HCl$: C, 55.46; H, 4.88; N, 9.24; found: C, 55.37; H, 4.80; N, 9.15.

Preparation 75

Preparation of tert-Butyl 8,9-dichloro-6-[2-(2,3-dimethylanilino)-2-oxoethyl]-1,4,5,6-tetrahydroazepino[4,5-b]indole-3(2H)-carboxylate DMAP (60 mg, 0.49 mmol), 2,3-dimethylaniline (0.065 mL, 0.53 mmol) and DIC (0.084 mL, 0.54 mmol) were added to the solution of crude [3-(tert-butoxycarbonyl)-8,9-dichloro-2,3,4,5-tetrahydroazepino[4,5-b]indol-6(1H)-yl] acetic acid (0.20 g, 0.48 mmol) in dry THF (2.5 mL). After 18 h, the reaction was diluted with EtOAc followed by washing with 10% aqueous citric acid, saturated aqueous $NaHCO_3$, and brine. The organic layer was then dried over $Na_2SO_4$, decanted, and concentrated. The crude product was first purified by column chromatography (Biotage, 40S, SIM) with $CH_2Cl_2$/EtOAc (98:2) to give 0.13 g of impure product. Then, crystallization from EtOAc/heptane gave 96 mg (38%) of a white solid: mp 186–187.5° C.; IR (diffuse reflectance) 3290, 2977, 2939, 1692, 1681, 1662, 1538, 1471, 1450, 1412, 1366, 1338, 1282, 1235, 1163 $cm^{-1}$; MS (EI) m/z 515 ($M^+$), 375, 373, 226, 225, 223, 120, 84, 76, 56, 51; Anal. Calcd for $C_{27}H_{31}Cl_2N_3O_3$: C, 62.79; H, 6.05; N, 8.14; found: C, 62.60; H, 6.04; N, 8.07.

EXAMPLE 176
Preparation of 2-(8,9-Dichloro-2,3,4,5-tetrahydroazepino[4,5-b]indol-6(1H)-yl)-N-(2,3-dimethylphenyl)acetamide hydrochloride

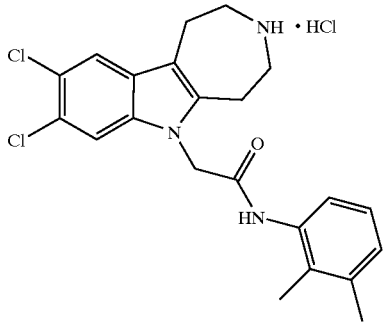

TFA (0.25 mL, 3.2 mmol) was added to a solution of tert-butyl 8,9-dichloro-6-[2-(2,3-dimethylanilino)-2-oxoethyl]-1,4,5,6-tetrahydroazepino[4,5-b]indole-3(2H)-carboxylate (50 mg, 0.097 mmol) in $CH_2Cl_2$ (3.0 mL). After 1.5 h, the reaction was quenched with 10% aqueous NaOH and extracted with $CH_2Cl_2$. The combined organic layers were washed with brine, dried over $Na_2SO_4$, decanted, and concentrated to give 41 mg of a crude solid. The hydrochloride salt was prepared to give 25 mg (56%) of pale yellow needles: mp 289–293° C. (dec); IR (diffuse reflectance) 3278, 2973, 2954, 2801, 2747, 2721, 2689, 2633, 1656, 1536, 1466, 1448, 1427, 1293, 870 $cm^{-1}$; MS (EI) m/z 415 ($M^+$), 374, 372, 224, 119, 84, 77, 73, 63, 61, 51; Anal. Calcd for $C_{22}H_{23}Cl_2N_3O\cdot HCl$: C, 58.35; H, 5.34; N, 9.28; found: C, 58.10; H, 5.36; N, 9.17.

Preparation 76
Preparation of tert-Butyl 9,10-dichloro-6-(2-ethoxy-2-oxoethyl)-1,4,5,6-tetrahydroazepino[4,5-b]indole-3(2H)-carboxylate To a solution of tert-butyl 9,10-dichloro-1,4,5,6-tetrahydroazepino[4,5-b]indole-3(2H)-carboxylate (0.10 g, 0.28 mmol) in DMF (2 mL), sodium hydride (60% dispersion in mineral oil, 17 mg, 0.42 mmol) was added. After 15 min, ethyl bromoacetate (0.060 mL, 0.56 mmol) was added. The reaction was quenched with saturated aqueous $NH_4Cl$ after 2.5 h and extracted with EtOAc (3×15 mL). The combined organic extracts were washed with brine, dried over $Na_2SO_4$, decanted, and concentrated. The crude product was purified by column chromatography (Biotage, 40S) with heptane/EtOAc (3:1) to give 85 mg (70%) of a white solid: mp 136.5–138.0° C.; $^1H$ NMR (300 MHz, $CDCl_3$) δ 7.19 (d, J=8.7 Hz, 1H), 6.99 (d, J=8.7 Hz, 1H), 4.74 (s, 2H), 4.21 (dd, J=7.1, 7.1 Hz, 2H), 3.75 (m, 4H), 3.53 (m, 2H), 2.93 (m, 2H), 1.48 (s, 9H), 1.26 (t, J=7.1 Hz, 3H); IR (diffuse reflectance) 2985, 2976, 1737, 1685, 1466, 1450, 1414, 1367, 1344, 1249, 1213, 1169, 1156, 1115, 926 $cm^{-1}$; MS (EI) m/z 440 ($M^+$), 307, 305, 301, 299, 298, 272, 225, 189, 58, 56; Anal. Calcd for $C_{21}H_{26}Cl_2N_2O_4$: C, 57.15; H, 5.94; N, 6.35, found: C, 57.16; H, 5.98; N, 6.27.

Preparation 77
Preparation of [3-(tert-Butoxycarbonyl)-9,10-dichloro-2,3,4,5-tetrahydroazepino[4,5-b]indol-6(1H)-yl]acetic acid To a solution of tert-butyl 9,10-dichloro-6-(2-ethoxy-2-oxoethyl)-1,4,5,6-tetrahydroazepino[4,5-b]indole-3(2H)-carboxylate (1.5 g, 3.4 mmol) in THF (15 mL), a solution of KOH (25 mg, 4.4 mmol) dissolved in $H_2O$ (10 mL) was added and heated to 60° C. The reaction was cooled to rt after 2 h. The reaction was made acidic with 10% aqueous HCl and extracted with EtOAc (3×30 mL). The combined organic extracts were washed with brine, dried over $Na_2SO_4$, decanted, and the crude acid was concentrated: $^1H$ NMR (300 MHz, DMSO) δ 13.11 (br s, 1H), 7.43 (d, J=8.8 Hz, 1H), 7.23 (d, J=8.7 Hz, 1H), 5.04 (s,2H), 3.62 (m, 4H), 2.93 (m, 2H), 1.41 (s, 9H); HRMS (FAB) calcd for $C_{19}H_{22}Cl_2N_2O_4+H$ 413.1035, found 413.1050.

Preparation 78
Preparation of tert-Butyl 6-(2-anilino-2-oxoethyl)-9,10-dichloro-1,4,5,6-tetrahydroazepino[4,5-b]indole-3(2H)-carboxylate DMAP (60 mg, 0.49 mmol), aniline (0.050 mL, 0.55 mmol) and DIC (0.084 mL, 0.54 mmol) were added to the solution of crude [3-(tert-butoxycarbonyl)-9,10-dichloro-2,3,4,5-tetrahydroazepino[4,5-b]indol-6(1H)-yl]acetic acid (0.20 g, 0.48 mmol) in dry THF (2.5 mL). After 24 h, the reaction was diluted with EtOAc followed by washing with 10% aqueous citric acid (20 mL), saturated aqueous $NaHCO_3$ (20 mL), and brine (20 mL). The organic layer was then dried over $Na_2SO_4$, decanted, and concentrated. The crude product was first purified by column chromatography (Biotage, 40S, SIM) with $CH_2Cl_2$/EtOAc and yielded 0.16 g of impure product. Then, crystallization from EtOAc/heptane gave 90 mg (37%) of a white solid; mp 208.5–210.0° C.; $^1H$ NMR (300 MHz, DMSO) δ 10.45 (s, 1H), 7.58 (d, J=8.3 Hz, 2H), 7.45 (d, J=9.0 Hz, 1H), 7.30 (m, 3H), 7.07 (m, 1H), 5.08 (br s, 2H), 3.63 (m, 4H), 3.40 (m, 2H), 2.99 (m, 2H), 1.40 (app d, 9H); IR (diffuse reflectance) 3275, 1693, 1671, 1602, 1554, 1449, 1409, 1365, 1319, 1312, 1302, 1254, 1166, 1113, 762 $cm^{-1}$; MS (EI) m/z 487 ($M^+$), 346, 345, 105, 94, 92, 76, 65, 62, 56, 52; MS (FAB) m/z 488 ($M+H^+$), 488, 487, 434, 433, 432, 431, 388, 57, 42, 41; HRMS (EI) calcd for $C_{25}H_{27}Cl_2N_3O_3$ 487.1429, found 487.1441; Anal. Calcd for $C_{25}H_{27}Cl_2N_3O_3$: C, 61.48; H, 5.57; N, 8.60; found: C, 61.41; H, 5.70; N, 8.48.

EXAMPLE 177
Preparation of 2-(9,10-Dichloro-2,3,4,5-tetrahydroazepino[4,5-b]indol-6(1H)-yl)-N-phenylacetamide hydrochloride

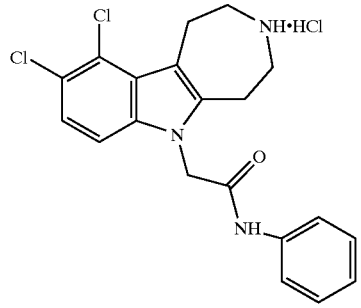

To a solution of tert-butyl 6-(2-anilino-2-oxoethyl)-9,10-dichloro-1,4,5,6-tetrahydroazepino[4,5-b]indole-3(2H)-carboxylate (40 mg, 0.082 mmol) in $CH_2Cl_2$ (3 mL), TFA (0.032 mL, 0.41 mmol) was added while stirring at rt. Additional TFA (0.032 mL, 0.41 mmol) was added after 3 h. After 69 h, TFA (0.25 mL, 3.2 mmol) was added along with additional $CH_2Cl_2$ (3 mL). The reaction was quenched with 10% aqueous NaOH (5 mL) after 70 h and extracted with $CH_2Cl_2$ (3×15 mL). The combined organic layers were washed with brine, dried over $Na_2SO_4$, decanted, and concentrated to give 30 mg of crude solid. The hydrochloride salt prepared to give 23 mg (67%) of a white solid: mp 274.0–276.0° C.; $^1H$ NMR (300 MHz, DMSO) δ 7.58 (d, J=7.9 Hz, 2H), 7.52 (d, J=8.7 Hz, 1H), 7.32 (m, 3H), 7.07 (t, J=7.2 Hz, 1H), 5.14 (s, 2H), 3.56 (m, 2H), 3.18 (m, 2H); IR (diffuse reflectance) 2995, 2983, 2967, 2948, 2940, 2936, 2809, 2767, 1680, 1600, 1549, 1448, 1314, 797, 759 cm$^{-1}$; MS (ES+) m/z 388 (M+H$^+$), 361, 359, 268, 266, 242, 241, 240, 238, 228, 226; Anal. Calcd for $C_{20}H_{19}Cl_2N_3O \cdot HCl$: C, 56.55; H, 4.75; N, 9.89; found: C, 56.25; H, 4.89; N, Preparation 79

Preparation of tert-Butyl 9,10-dichloro-6-[2-(4-methoxyanilino)-2-oxoethyl]-1,4,5,6-tetrahydroazepino[4,5-b]indole-3(2H)-carboxylate DMAP (89 mg, 0.73 mmol), p-anisidine (0.10 g, 0.81 mmol) and DIC (0.13 mL, 0.81 mmol) were added to the solution of crude [3-(tert-butoxycarbonyl)-9,10-dichloro-2,3,4,5-tetrahydroazepino[4,5-b]indol-6(1H)-yl]acetic acid (0.30 g, 0.73 mmol) in dry THF (3.5 mL). After 4 h, additional p-anisidine (45 mg, 0.37 mmol) was added. The reaction was diluted with EtOAc after another 17 h and washed with 10% aqueous citric acid (20 mL), saturated aqueous NaHCO$_3$ (20 mL), and brine (20 mL). The organic layer was then dried over Na$_2$SO$_4$, decanted, and concentrated impure product. It was then crystallized from EtOAc/heptane, triturated with pentane, and recrystallized from EtOAc/heptane to give 0.14 g (36%) of a white solid: mp 143.0–144.0° C.; $^1$H NMR (300 MHz, DMSO) δ 10.30 (s, 1H), 7.47 (m, 3H), 7.25 (d, J=8.7 Hz, 1H), 6.88 (d, J=9.0 Hz, 2H), 5.04 (br s, 2H), 3.71 (s, 3H), 3.63 (m, 4H), 3.39 (m, 2H), 2.99 (m, 2H), 1.40 (app d, 9H); IR (diffuse reflectance) 2975, 1666, 1545, 1514, 1474, 1451, 1414, 1365, 1253, 1239, 1222, 1173, 1158, 830, 784 cm$^{-1}$; MS (EI) m/z 517 (M$^+$), 377, 375, 227, 224, 212, 134, 124, 121, 55, 53; MS (FAB) m/z 518 (M+H$^+$), 520, 519, 518, 517, 464, 463, 462, 461, 418, 57; HRMS (EI) calcd for $C_{26}H_{29}Cl_2N_3O_4$ 517.1535, found 517.1537; Anal. Calcd for $C_{26}H_{29}Cl_2N_3O_4$: C, 60.24; H, 5.64; N, 8.10; found: C, 59.86; H, 5.68; N, 7.94.

EXAMPLE 178

Preparation of 2-(9,10-Dichloro-2,3,4,5-tetrahydroazepino[4,5-b]indol-6(1H)-yl)-N-(4-methoxyphenyl)acetamide hydrochloride

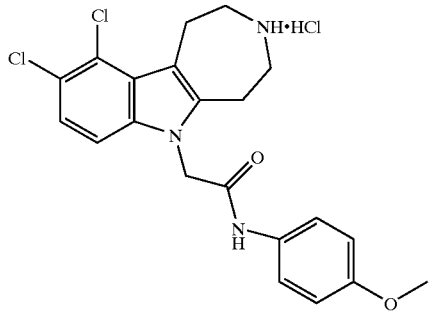

To a solution of tert-butyl 9,10-dichloro-6-[2-(4-methoxyanilino)-2-oxoethyl]-1,4,5,6-tetrahydroazepino[4,5-b]indole-3(2H)-carboxylate (90 mg, 0.17 mmol) in CH$_2$Cl$_2$ (6.0 mL), TFA (0.27 mL, 3.5 mmol) was added while stirring at rt. After 5 h, the reaction was made basic with 10% aqueous NaOH and extracted with CH$_2$Cl$_2$ (3×10 mL). The combined organic layers were washed with brine, dried over Na$_2$SO$_4$, decanted, and concentrated to 70 mg of a crude white solid. The hydrochloride salt was prepared to give 49 mg (62%) of a white solid: mp 262.0–263.0° C.; $^1$H NMR (300 MHz, DMSO) δ 10.39 (s, 1H), 9.08 (br s, 2H), 7.50 (m, 3H), 7.30 (d, J=8.7 Hz, 1H), 6.89 (d, J=9.1 Hz, 2H), 5.10 (s, 2H), 3.71 (s, 3H), 3.55 (m, 2H), 3.19 (m, 2H); $^{13}$C NMR (400 MHz, DMSO) δ 165.2, 155.3, 140.4, 135.6, 131.9, 123.9, 122.7, 122.0, 121.4, 120.6, 113.8, 110.6, 110.1, 55.0, 46.0, 45.3, 43.5, 22.3, 21.2; IR (diffuse reflectance) 3316, 2950, 2930, 2912, 2900, 2803, 2741, 1679, 1532, 1449, 1433, 1414, 1317, 1255, 837 cm$^{-1}$; MS (ES+) m/z 418 (M+H$^+$), 391, 389, 266, 241, 240, 240, 238, 228, 226, 226; Anal. Calcd for $C_{21}H_{21}Cl_2N_3O_2 \cdot HCl$: C, 55.46; H, 4.88; N, 9.24, found: C, 55.16; H, 4.97; N, 9.06.

Preparation 80

Preparation of tert-Butyl 9,10-dichloro-6-[2-(2,3-dimethylanilino)-2-oxoethyl]-1,4,5,6-tetrahydroazepino[4,5-b]indole-3(2H)-carboxylate DMAP (89 mg, 0.73 mmol), 2,3-dimethylaniline (98 mg, 0.81 mmol) and DIC (0.13 mL, 0.81 mmol) were added to the solution of crude [3-(tert-butoxycarbonyl)-9,10-dichloro-2,3,4,5-tetrahydroazepino[4,5-b]indol-6(1H)-yl] acetic acid (0.30 g, 0.73 mmol) in dry THF (3.5 mL). After 4 h, additional 2,3-dimethylaniline (0.049 mL, 0.40 mmol) and THF (2 mL) was added. The reaction was diluted with EtOAc after 25 h followed by washing with 10% aqueous citric acid (75 mL), saturated aqueous NaHCO$_3$ (40 mL), and brine (40 mL). A precipitate in the combined organic layers was filtered to yield 0.22 g (58%) white solid: mp 232.5–233.0° C.; $^1$H NMR (DMSO, 400 MHz) δ 9.77 (s, 1H), 7.49 (d, J=8.8 Hz, 1H), 7.28 (d, J=8.7 Hz, 1H), 7.13 (d, J=6.8 Hz, 1H), 7.03 (m, 2H), 5.11 (s, 2H), 3.64 (m, 4H), 3.39 (m, 2H), 3.03 (m, 2H), 2.24 (s, 3H), 2.09 (s, 3H), 1.41 (s, 9H); IR (diffuse reflectance) 2977, 1692, 1659, 1541, 1474, 1451, 1412, 1366, 1303, 1269, 1201, 1174, 1112, 791, 773 cm$^{-1}$; MS (EI) m/z 515 (M$^+$), 376, 226, 224, 212, 189, 149, 133, 119, 55, 52; HRMS (EI) calcd for $C_{27}H_{31}Cl_2N_3O_3$ 515.1743, found 515.1747.

EXAMPLE 179

Preparation of 2-(9,10-Dichloro-2,3,4,5-tetrahydroazepino[4,5-b]indol-6(1H)-yl)-N-(2,3-dimethylphenyl)acetamide hydrochloride

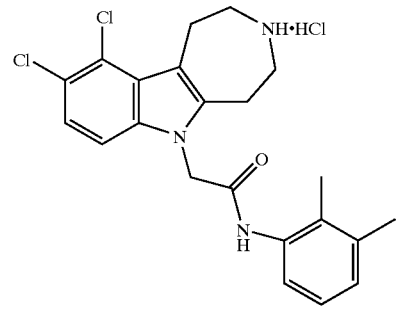

To a solution of tert-butyl 9,10-dichloro-6-[2-(2,3-dimethylanilino)-2-oxoethyl]-1,4,5,6-tetrahydroazepino[4,5-b]indole-3(2H)-carboxylate (0.15 g, 0.29 mmol) in CH$_2$Cl$_2$ (11 mL), TFA (0.45 mL, 5.8 mmol) was added while stirring at rt. After 5 h, the reaction was made basic with 10% aqueous NaOH and extracted with CH$_2$Cl$_2$ (7×15 mL). The combined organic layers were washed with brine, dried over Na$_2$SO$_4$, decanted, and concentrated to give 0.11 g of a crude solid. The hydrochloride salt was prepared to give 85 mg (65%) of a white solid: mp 248.0–249.5° C.; $^1$H NMR (300 MHz, DMSO) δ 9.83 (s, 1H), 9.07 (br s, 2H), 7.55 (d, J=8.7 Hz, 1H), 7.33 (d, J=8.6 Hz, 1H), 7.12 (m, 1H), 7.03 (m, 2H), 5.17 (s, 2H), 3.55 (m, 2H), 3.21 (m, 2H), 2.24 (s, 3H), 2.08 (s, 3H); $^{13}$C NMR (400 MHz, DMSO) δ 165.9, 140.4, 137.0, 135.6, 135.3, 130.9, 127.1, 125.1, 123.9, 123.2, 122.8, 122.0, 121.4, 110.7, 110.0, 45.8, 45.3, 43.5, 22.3, 21.2, 20.0, 14.0; IR (diffuse reflectance) 3301, 2966, 2941, 2916, 2878, 2851, 2813, 2767, 2737, 2692, 2633, 2438, 1668, 1534, 1451 cm$^{-1}$; MS (ES+) m/z 416 (M+H$^+$), 389, 389, 387, 266, 242, 240, 238, 228, 226; % Water (KF): 1.99; Anal. Calcd for $C_{22}H_{23}Cl_2N_3O·HCl·1.99\%\ H_2O$: C, 57.19; H, 5.46; N, 9.10; found: C, 56.97; H, 5.46; N, 8.92.

EXAMPLES 180–239

The compounds of Examples 180–239 were prepared using the following general procedure and the purification technique noted.

The appropriate aryl amine (0.29 mmol) was added to a 20 mL scintillation vial followed by the addition of a stock solution of the appropriate dichloroazepinoindole acid (5 mL, 0.053 M in THF). Next, a stock solution of EEDQ (3 mL, 0.097 M in THF) was added to each vial. The vials were capped, placed in a J-KEM® heater block attached to a Lab-Line® orbit shaker and shaken (250 RPM) at 40° C. overnight. A subset of the reactions was monitored by HPLC. After all the starting acid was consumed in these reactions, MeOH (3 mL) and Dowex® 50WX2-400 ion-exchange resin (0.75 g) was added to each vial. The reactions were then shaken (300 RPM) at 40° C. until the product was on the resin, based on HPLC monitoring. The vials were cooled to rt and transferred with 2×5 mL of CH$_2$Cl$_2$/MeOH (3:1) to disposable fritted syringe barrels on a syringe washing station. The resin was then rinsed with 2×5 mL of each of the following: pyridine/MeOH (3:7), CH$_2$Cl$_2$, and MeOH. The syringe barrels were then transferred to a vacuum manifold and the product was eluted off the resin into 40 mL scintillation vials with 5×5 mL of MeOH/NH$_4$OH (3:1). Three different methods were used to isolate products.

Method A consisted of removing the solvent in the vacuum oven overnight at 47° C.

Method B involved blowing the solvent down under nitrogen and then further drying in the vacuum oven overnight at 47° C.

Method C consisted of filtering the precipitate that formed upon being blown down under nitrogen. The products were then evaluated by HPLC and MS or LC/MS.

EXAMPLE 180

2-(8,9-Dichloro-2,3,4,5-tetrahydroazepino[4,5-b]indol-6 (1H)-yl)-N-(2,3-dimethylphenyl)acetamide;

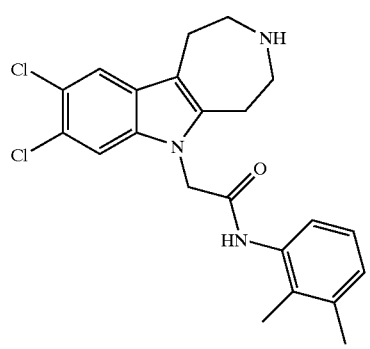

isolation method A; MS (ESI+) m/z 415.9 (MH$^+$).

EXAMPLE 181

2-(9,10-Dichloro-2,3,4,5-tetrahydroazepino[4,5-b]indol-6 (1H)-yl)-N-(2,3-dimethylphenyl)acetamide;

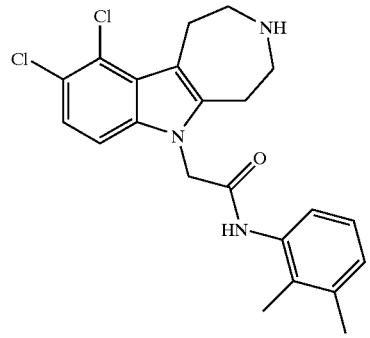

isolation method A, the title compound was obtained. MS (ESI+) m/z 415.9 (MH$^+$).

EXAMPLE 182

2-(7,8-Dichloro-2,3,4,5-tetrahydroazepino[4,5-b]indol-6 (1H)-yl)-N-(2,3-dimethylphenyl)acetamide;

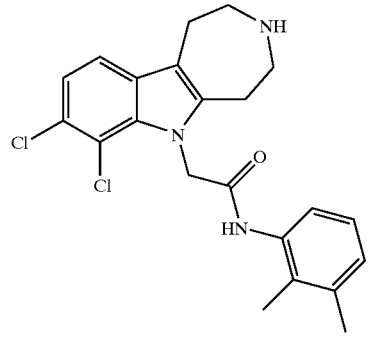

isolation method C; MS (ESI+) m/z 416.3 (MH$^+$).

EXAMPLE 183

2-(7,9-Dichloro-2,3,4,5-tetrahydroazepino[4,5-b]indol-6 (1H)-yl)-N-(2,3-dimethylphenyl)acetamide;

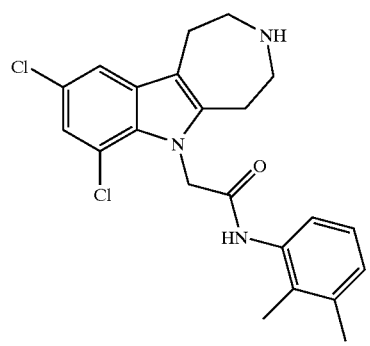

isolation method C; MS (ESI+) m/z 416.1 (MH$^+$).

EXAMPLE 184

2-(7,10-Dichloro-2,3,4,5-tetrahydroazepino[4,5-b]indol-6 (1H)-yl)-N-(2,3-dimethylphenyl)acetamide;

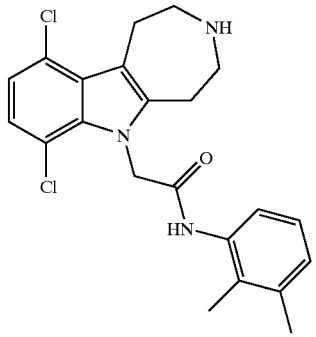

isolation method C; MS (ESI+) m/z 416.3 (MH+).

EXAMPLE 185

2-(8,10-Dichloro-2,3,4,5-tetrahydroazepino[4,5-b]indol-6 (1H)-yl)-N-(2,3-dimethylphenyl)acetamide;

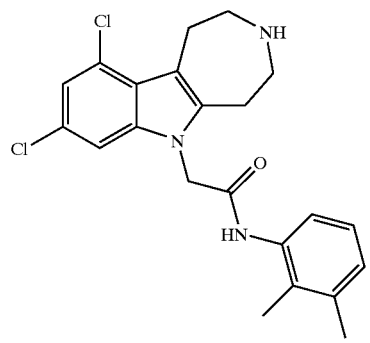

isolation method C; MS (ESI+) m/z 416.1 (MH+).

EXAMPLE 186

2-(8,9-Dichloro-2,3,4,5-tetrahydroazepino[4,5-b]indol-6 (1H)-yl)-N-(5,6,7,8-tetrahydro-1-naphthalenyl)acetamide;

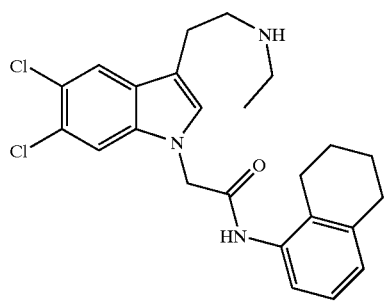

isolation method A; MS (ESI+) m/z 441.9 (MH+).

EXAMPLE 187

2-(9,10-Dichloro-2,3,4,5-tetrahydroazepino[4,5-b]indol-6 (1H)-yl)-N-(5,6,7,8-tetrahydro-1-naphthalenyl)acetamide;

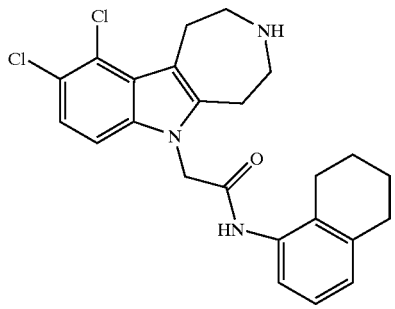

isolation method A; MS (ESI+) m/z 441.9 (MH+).

EXAMPLE 188

2-(7,8-Dichloro-2,3,4,5-tetrahydroazepino[4,5-b]indol-6 (1H)-yl)-N-(5,6,7,8-tetrahydro-1−1-naphthalenyl) acetamide;

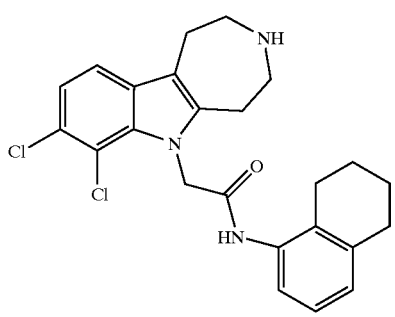

isolation method C; MS (ESI+) m/z 442.1 (MH+).

EXAMPLE 189

2-(7,9-Dichloro-2,3,4,5-tetrahydroazepino[4,5-b]indol-6 (1H)-yl)-N-(5,6,7,8-tetrahydro-1-naphthalenyl)acetamide;

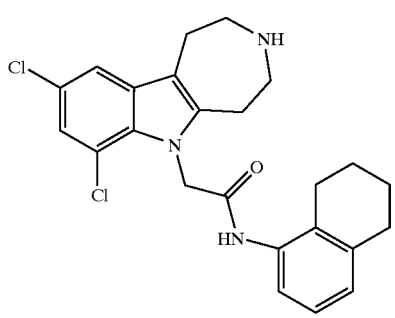

isolation method C; MS (ESI+) m/z 442.1 (MH+).

EXAMPLE 190

2-(7,10-Dichloro-2,3,4,5-tetrahydroazepino[4,5-b]indol-6(1H)-yl)-N-(5,6,7,8-tetrahydro-1-naphthalenyl)acetamide;

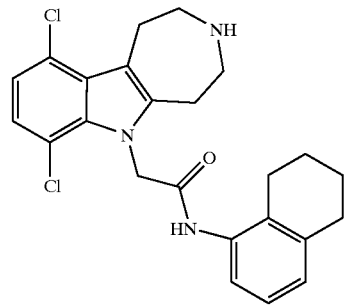

isolation method C; MS (ESI+) m/z 442.1 (MH+).

EXAMPLE 191

2-(8,10-Dichloro-2,3,4,5-tetrahydroazepino[4,5-b]indol-6(1H)-yl)-N-(5,6,7,8-tetrahydro-1-naphthalenyl)acetamide;

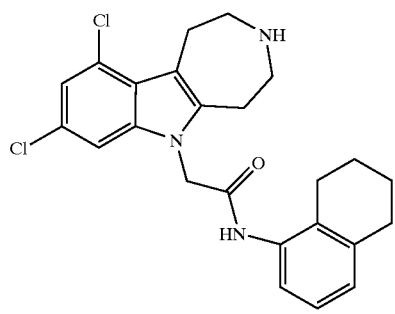

isolation method C; MS (ESI+) m/z 442.1 (MH+).

EXAMPLE 192

2-(8,9-Dichloro-2,3,4,5-tetrahydroazepino[4,5-b]indol-6(1H)-yl)-N-(3-ethylphenyl)acetamide;

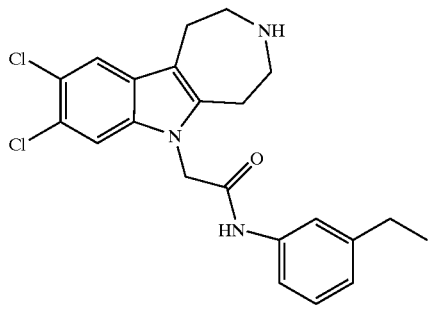

isolation method A; MS (ESI+) m/z 415.9 (MH+).

EXAMPLE 193

2-(9,10-Dichloro-2,3,4,5-tetrahydroazepino[4,5-b]indol-6(1H)-yl)-N-(3-ethylphenyl)acetamide;

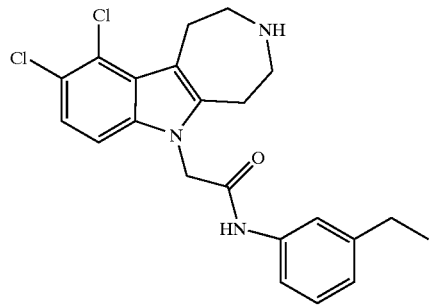

isolation method A; MS (ESI+) m/z 415.9 (MH+).

EXAMPLE 194

2-(7,8-Dichloro-2,3,4,5-tetrahydroazepino[4,5-b]indol-6(1H)-yl)-N-(3-ethylphenyl)acetamide;

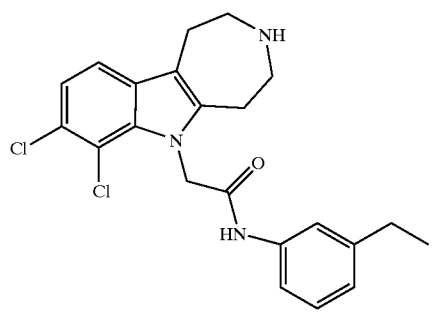

isolation method C; MS (ESI+) m/z 416.4 (MH+).

EXAMPLE 195

2-(7,9-Dichloro-2,3,4,5-tetrahydroazepino[4,5-b]indol-6(1H)-yl)-N-(3-ethylphenyl)acetamide;

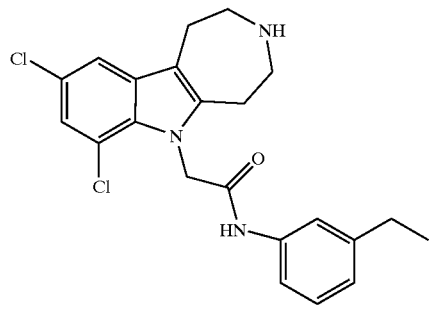

isolation method C; MS (ESI+) m/z 416.4 (MH+).

EXAMPLE 196

2-(7,10-Dichloro-2,3,4,5-tetrahydroazepino[4,5-b]indol-6(1H)-yl)-N-(3-ethylphenyl)acetamide;

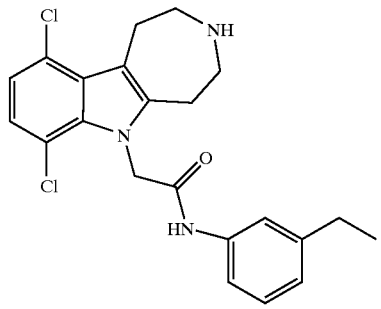

isolation method C; MS (ESI+) m/z 416.3 (MH+).

EXAMPLE 197

2-(8,10-Dichloro-2,3,4,5-tetrahydroazepino[4,5-b]indol-6(1H)-yl)-N-(3-ethylphenyl)acetamide;

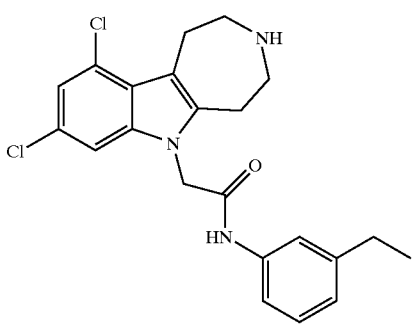

isolation method B; MS (ESI+) m/z 415.9 (MH+).

EXAMPLE 198

2-(8,9-Dichloro-2,3,4,5-tetrahydroazepino[4,5-b]indol-6(1H)-yl)-N-(3-isopropylphenyl)acetamide;

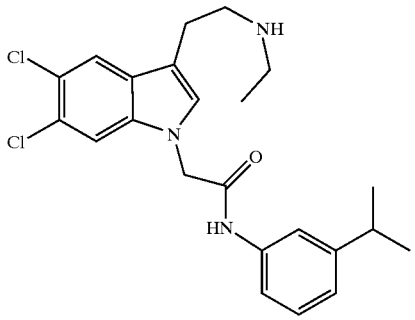

isolation method A; MS (ESI+) m/z 429.9 (MH+).

EXAMPLE 199

2-(9,10-Dichloro-2,3,4,5-tetrahydroazepino[4,5-b]indol-6(1H)-yl)-N-(3-isopropylphenyl)acetamide;

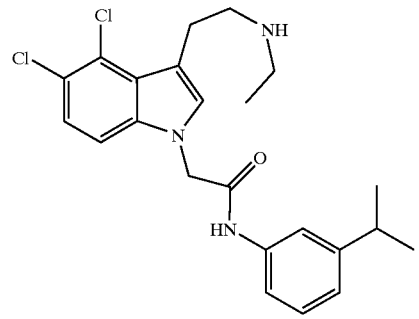

isolation method A; MS (ESI+) m/z 429.9 (MH+).

EXAMPLE 200

2-(7,8-Dichloro-2,3,4,5-tetrahydroazepino[4,5-b]indol-6(1H)-yl)-N-(3-isopropylphenyl)acetamide;

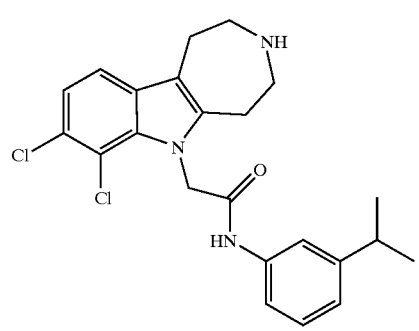

isolation method B; MS (ESI+) m/z 429.9 (MH+).

EXAMPLE 201

2-(7,9-Dichloro-2,3,4,5-tetrahydroazepino[4,5-b]indol-6(1H)-yl)-N-(3-isopropylphenyl)acetamide;

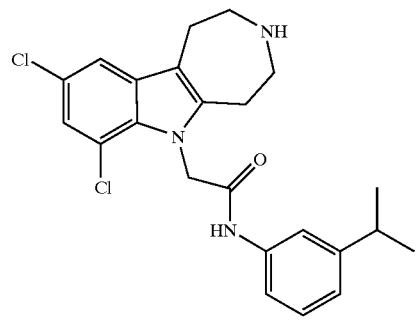

isolation method C; MS (ESI+) m/z 430.4 (MH+).

EXAMPLE 202

2-(7,10-Dichloro-2,3,4,5-tetrahydroazepino[4,5-b]indol-6(1H)-yl)-N-(3-isopropylphenyl)acetarmide;

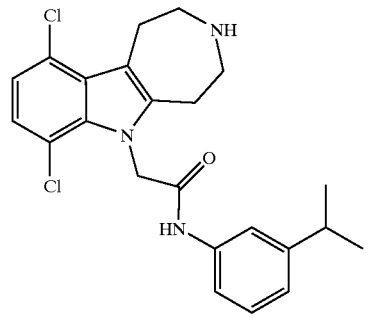

isolation method C; MS (ESI+) m/z 430.4 (MH$^+$).

EXAMPLE 203

2-(8,10-Dichloro-2,3,4,5-tetrahydroazepino[4,5-b]indol-6(1H)-yl)-N-(3-isopropylphenyl)acetamide;

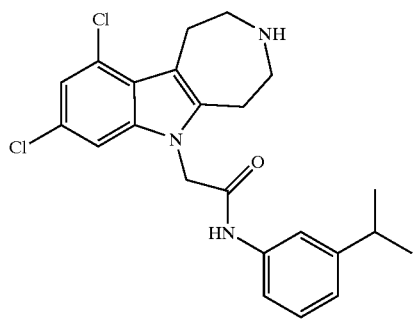

isolation method B; MS (ESI+) m/z 431.9 (MH$^+$).

EXAMPLE 204

N-(3-tert-Butylphenyl)-2-(8,9-dichloro-2,3,4,5-tetrahydroazepino[4,5-b]indol-6(1H)-yl)acetamide;

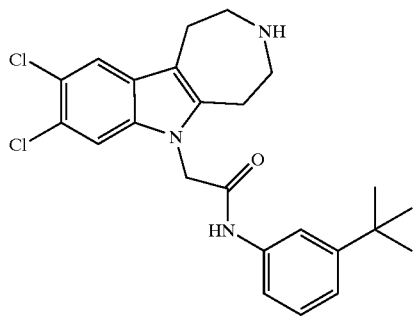

isolation method A; MS (ESI+) m/z 443.9 (MH$^+$).

EXAMPLE 205

N-(3-tert-Butylphenyl)-2-(9,10-dichloro-2,3,4,5-tetrahydroazepino[4,5-b]indol-6(1H)-yl)acetamide;

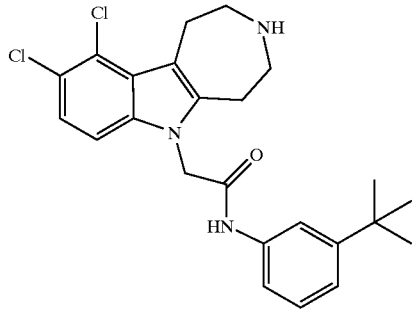

isolation method A; MS (ESI+) m/z 443.9 (MH$^+$).

EXAMPLE 206

N-(3-tert-Butylphenyl)-2-(7,8-dichloro-2,3,4,5-tetrahydroazepino[4,5-b]indol-6(1H)-yl)acetamide;

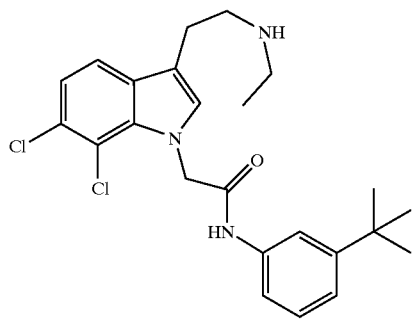

isolation method B; MS (ESI+) m/z 443.9 (MH$^+$).

EXAMPLE 207

N-(3-tert-Butylphenyl)-2-(7,9-diclhloro-2,3,4,5-tetrahydroazepino[4,5-b]indol-6(1H)-yl)acetarmde;

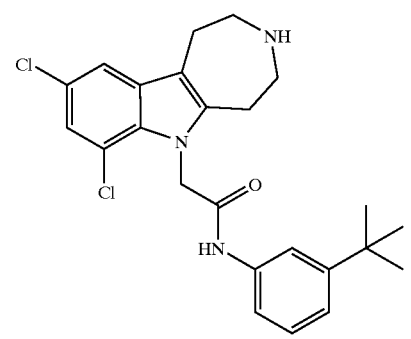

isolation method C; MS (ESI+) m/z 443.9 (MH$^+$).

EXAMPLE 208

N-(3-tert-Butylphenyl)-2-(7,10-dichloro-2,3,4,5-tetrahydroazepino[4,5-b]indol-6(1H)-yl)acetamide;

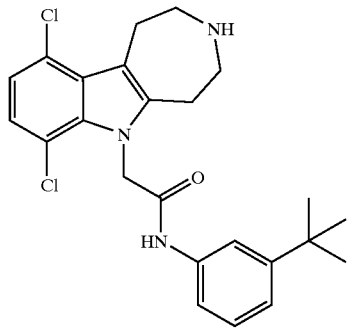

isolation method C; MS (ESI+) m/z 444.4 (MH$^+$).

EXAMPLE 209

N-(3-tert-Butylphenyl)-2-(8,10-dichloro-2,3,4,5-tetrahydroazepino[4,5-b]indol-6(1H)-yl)acetamide;

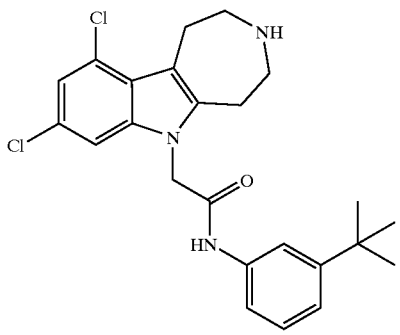

isolation method B; MS (ESI+) m/z 443.9 (MH$^+$).

EXAMPLE 210

N-(1,3-Benzothiazol-2-yl)-2-(8,9-dichloro-2,3,4,5-tetrahydroazepino[4,5-b]indol-6(1H)-yl)acetamide;

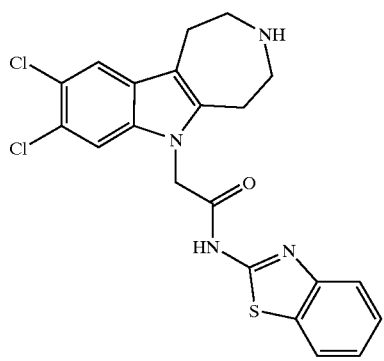

isolation method A; MS (ESI+) m/z 444.8 (MH$^+$).

EXAMPLE 211

N-(1,3-Benzothiazol-2-yl)-2-(9,10-dichloro-2,3,4,5-tetrahydroazepino[4,5-b]indol-6(1H)-yl)acetamide;

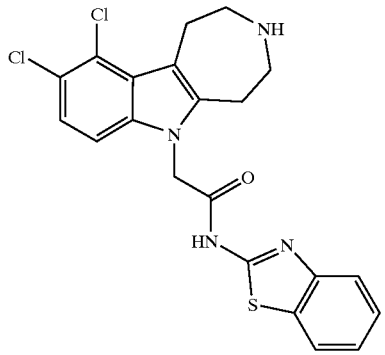

isolation method A; MS (ESI+) m/z 444.8 (MH$^+$).

EXAMPLE 212

N-(1,3-Benzothiazol-2-yl)-2-(7,8-dichloro-2,3,4,5-tetrahydroazepino[4,5-b]indol-6(1H)-yl)acetamide;

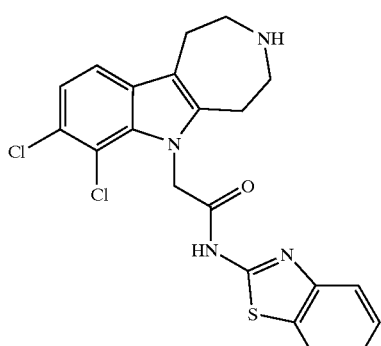

isolation method C; MS (ESI+) m/z 445.1 (MH$^+$).

EXAMPLE 213

N-(1,3-Benzothiazol-2-yl)-2-(7,9-dichloro-2,3,4,5-tetrahydroazepino[4,5-b]indol-6(1H)-yl)acetamide;

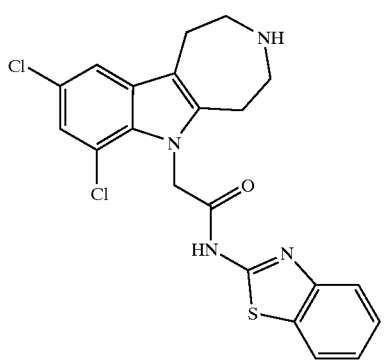

isolation method C; MS (ESI+) m/z 445.0 (MH$^+$).

EXAMPLE 214

N-(1,3-Benzothiazol-2-yl)-2-(7,10-dichloro-2,3,4,5-tetrahydroazepino[4,5-b]indol-6(1H)-yl)acetamide;

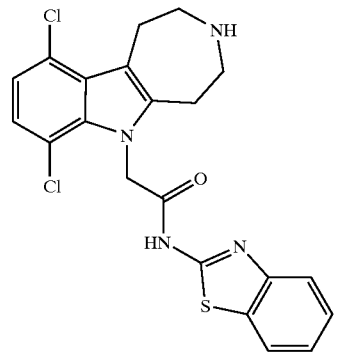

isolation method C; MS (ESI+) m/z 445.0 (MH⁺).

EXAMPLE 215

N-(1,3-Benzothiazol-2-yl)-2-(8,10-dichloro-2,3,4,5-tetrahydroazepino[4,5-b]indol-6(1H)-yl)acetamide;

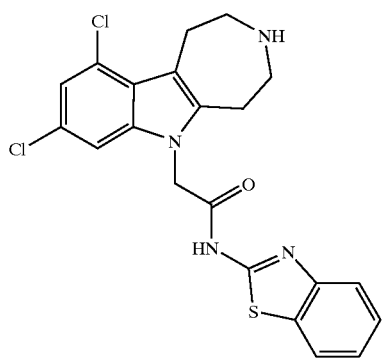

isolation method C; MS (ESI+) m/z 445.3 (MH⁺).

EXAMPLE 216

2-(8,9-Dichloro-2,3,4,5-tetrahydroazepino[4,5-b]indol-6(1H)-yl)-N-(4-methyl-1,3-thiazol-2-yl)acetamide;

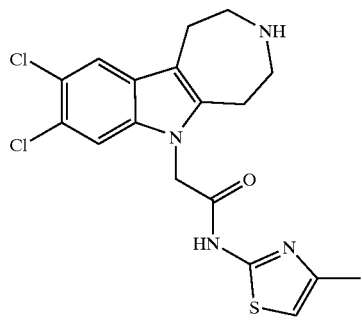

isolation method A; MS (ESI+) m/z 408.9 (MH⁺).

EXAMPLE 217

2-(9,10-Dichloro-2,3,4,5-tetrahydroazepino[4,5-b]indol-6(1H)-yl)-N-(4-methyl-1,3-thiazol-2-yl)acetamide;

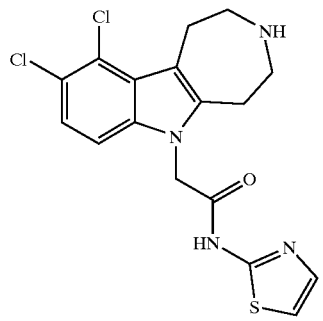

isolation method A; MS (ESI+) m/z 408.9 (MH⁺).

EXAMPLE 218

2-(7,8-Dichloro-2,3,4,5-tetrahydroazepino[4,5-b]indol-6(1H)-yl)-N-(4-methyl-1,3-thiazol-2-yl)acetamide;

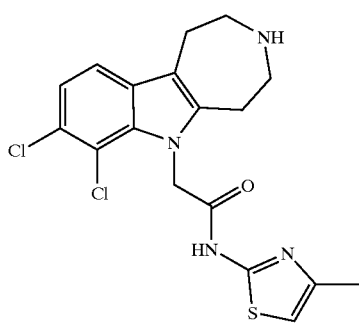

isolation method B; MS (ESI+) m/z 408.9 (MH⁺).

EXAMPLE 219

2-(7,9-Dichloro-2,3,4,5-tetrahydroazepino[4,5-b]indol-6(1H)-yl)-N-(4-methyl-1,3-thiazol-2-yl)acetamide;

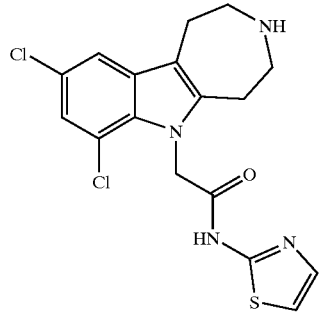

isolation method B; MS (ESI+) m/z 408.9(MH⁺).

EXAMPLE 220

2-(7,10-Dichloro-2,3,4,5-tetrahydroazepino[4,5-b]indol-6 (1H)-yl)-N-(4-methyl-1,3-thiazol-2-yl)acetamide;

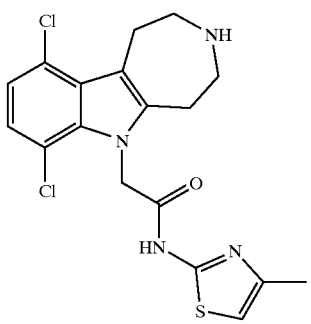

isolation method B; MS (ESI+) m/z 408.9 (MH$^+$).

EXAMPLE 221

2-(8,10-Dichloro-2,3,4,5-tetrahydroazepino[4,5-b]indol-6 (1H)-yl)-N-(4-methyl-1,3-thiazol-2-yl)acetamide;

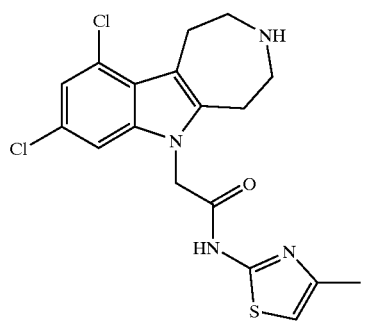

isolation method C; MS (ESI+) m/z 408.8 (MH$^+$).

EXAMPLE 222

2-(8,9-Dichloro-2,3,4,5-tetrahydroazepino[4,5-b]indol-6 (1H)-yl)-N-(5-methyl-1,3-thiazol-2-yl)acetanude;

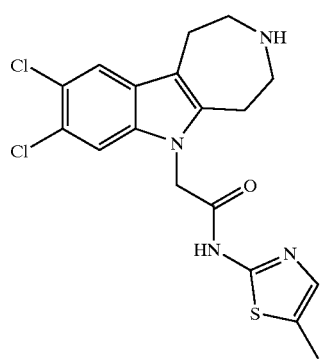

isolation method A; MS (ESI+) m/z 408.9 (MH$^+$).

EXAMPLE 223

2-(9,10-Dichloro-2,3,4,5-tetrahydroazepino[4,5-b]indol-6 (1H)-yl)-N-(5-methyl-1,3-thiazol-2-yl)acetamide;

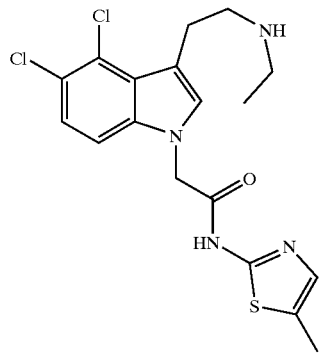

isolation method A; MS (ESI+) m/z 408.9 (MH$^+$).

EXAMPLE 224

2-(7,8-Dichloro-2,3,4,5-tetrahydroazepino[4,5-b]indol-6 (1H)-yl)-N-(5-methyl-1,3-thiazol-2-yl)acetamide;

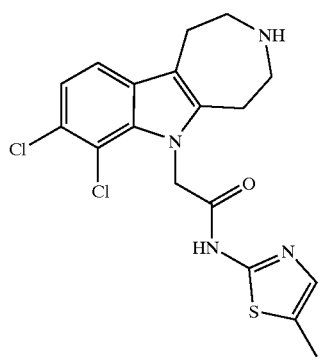

isolation method C; MS (ESI+) m/z 409.3 (MH$^+$).

EXAMPLE 225

2-(7,9-Dichloro-2,3,4,5-tetrahydroazepino[4,5-b]indol-6 (1H)-yl)-N-(5-methyl-1,3-thiazol-2-yl)acetamide;

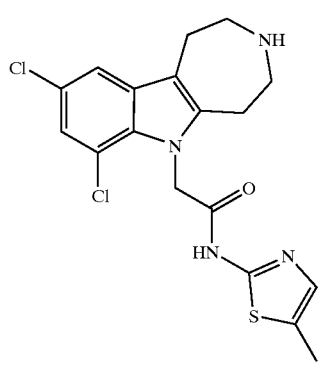

isolation method C; MS (ESI+) m/z 409.1 (MH$^+$).

EXAMPLE 226

2-(7,10-Dichloro-2,3,4,5-tetrahydroazepino[4,5-b]indol-6(1H)-yl)-N-(5-methyl-1,3-thiazol-2-yl)acetamide;

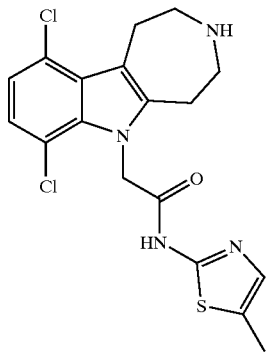

isolation method C; MS (ESI+) m/z 409.3 (MH$^+$).

EXAMPLE 227

2-(8,10-Dichloro-2,3,4,5-tetrahydroazepino[4,5-b]indol-6(1H)-yl)-N-(5-methyl-1,3-thiazol-2-yl)acetamide;

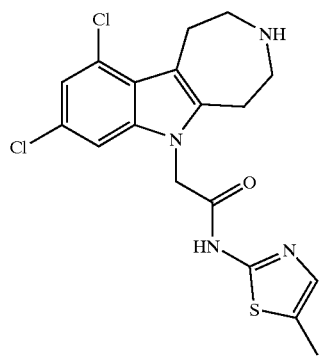

isolation method C; MS (ESI+) m/z 408.9 (MH$^+$).

EXAMPLE 228

N-(4-tert-Butyl-1,3-thiazol-2-yl)-2-(8,9-dichloro-2,3,4,5-tetrahydroazepino[4,5-b]indol-6(1H)-yl)acetaamide;

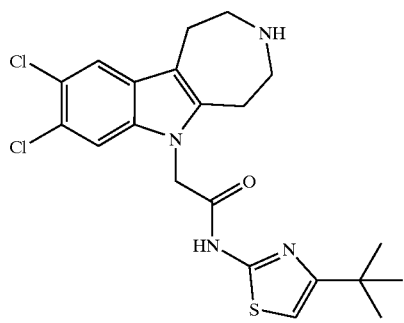

isolation method A; MS (ESI+) m/z 450.9 (MH$^+$).

EXAMPLE 229

N-(4-tert-Butyl-1,3-thiazol-2-yl)-2-(9,10-dichloro-2,3,4,5-tetrahydroazepino[4,5-b]indol-6(1H)-yl)acetamide;

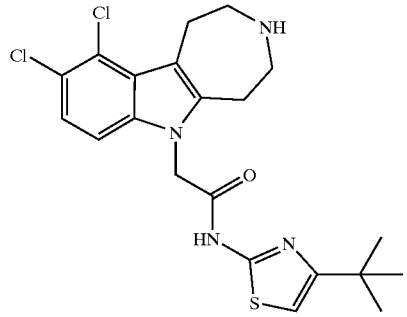

isolation method A; MS (ESI+) m/z 450.9 (MH$^+$).

EXAMPLE 230

N-(4-tert-Butyl-1,3-thiazol-2-yl)-2-(7,8-dichloro-2,3,4,5-tetrahydroazepino[4,5-b]indol-6(1H)-yl)acetamide;

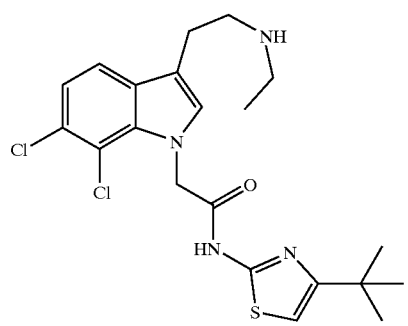

isolation method C; MS (ESI+) m/z 451.2 (MH$^+$).

EXAMPLE 231

N-(4-tert-Butyl-1,3-thiazol-2-yl)-2-(7,9-dichloro-2,3,4,5-tetrahydroazepino[4,5-b]indol-6(1H)-yl)acetamide;

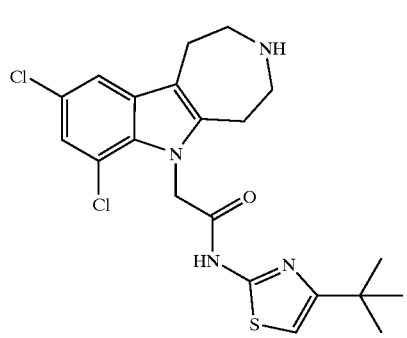

isolation method C; MS (ESI+) m/z 451.1 (MH$^+$).

EXAMPLE 232

N-(4-tert-Butyl-1,3-thiazol-2-yl)-2-(7,10-dichloro-2,3,4,5-tetrahydroazepino[4,5-b]indol-6(1H)-yl)acetamide;

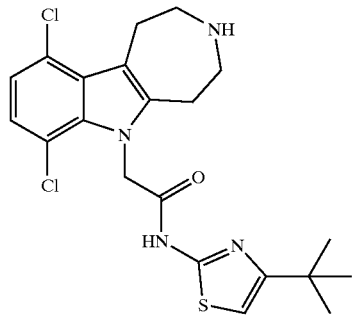

isolation method C; MS (ESI+) m/z 450.9 (MH$^+$).

EXAMPLE 233

N-(4-tert-Butyl-1,3-thiazol-2-yl)-2-(8, 10-dichloro-2,3,4,5-tetrahydroazepino[4,5-b]indol-6(1H)-yl)acetamide;

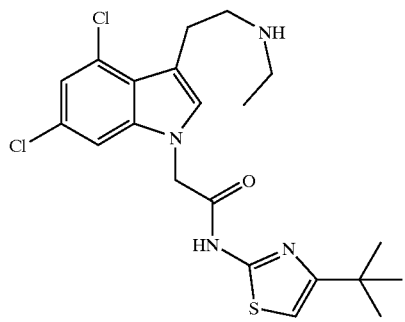

isolation method C; MS (ESI+) m/z 451.2 (MH$^+$).

EXAMPLE 234

2-(8,9-Dichloro-2,3,4,5-tetrahydroazepino[4,5-b]indol-6(1H)-yl)-N-(4-phenyl-1,3-thiazol-2-yl)acetamide;

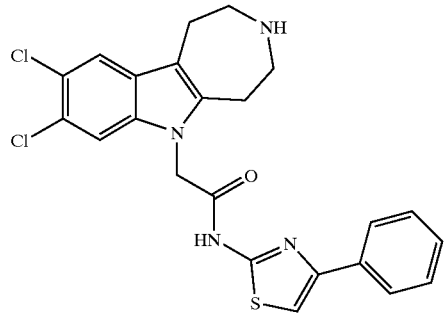

isolation method A; MS (ESI+) m/z 470.8 (MH$^+$).

EXAMPLE 235

2-(9,10-Dichloro-2,3,4,5-tetrahydroazepino[4,5-b]indol-6(1H)-yl)-N-(4-phenyl-1,3-thiazol-2-yl)acetanide;

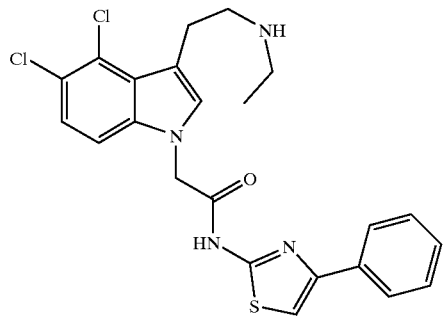

isolation method A; MS (ESI+) m/z 471.0 (MH$^+$).

EXAMPLE 236

2-(7,8-Dichloro-2,3,4,5-tetrahydroazepino[4,5-b]indol-6(1H)-yl)-N-(4-phenyl-1,3-thiazol-2-yl)acetamide;

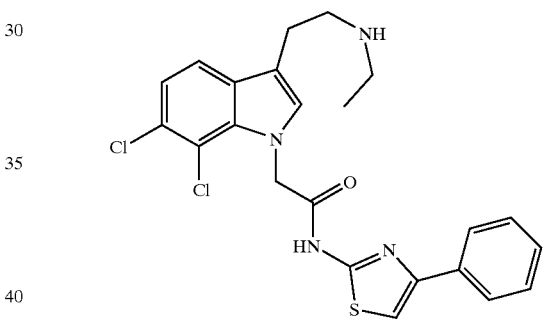

isolation method C; MS (ESI+) m/z 471.1 (MH$^+$).

EXAMPLE 237

2-(7,9-Dichloro-2,3,4,5-tetrahydroazepino[4,5-b]indol-6(1H)-yl)-N-(4-phenyl-1,3-thiazol-2-yl)acetamide;

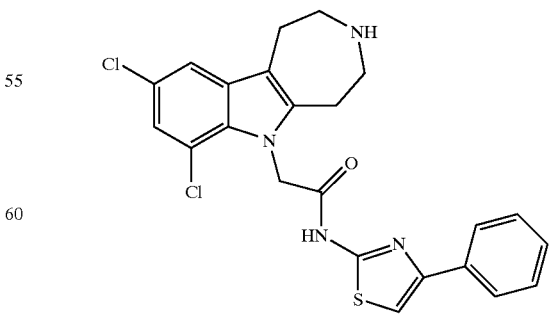

isolation method C; MS (ESI+) m/z 471.1 (MH$^+$).

EXAMPLE 238

2-(7,10-Dichloro-2,3,4,5-tetrahydroazepino[4,5-b]indol-6(11H)-yl)-N-(4-phenyl-1,3-thiazol-2-yl)acetamide;

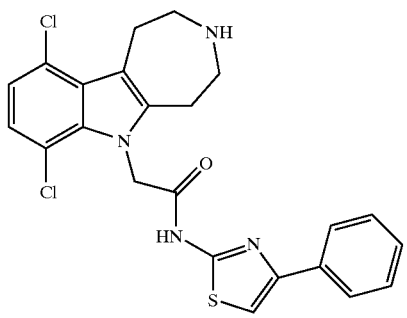

isolation method C; MS (ESI+) m/z 471.1 (MH+).

EXAMPLE 239

2-(8,10-Dichloro-2,3,4,5-tetrahydroazepino[4,5-b]indol-6(1H)-yl)-N-(4-phenyl-1,3-thiazol-2-yl)acetamide;

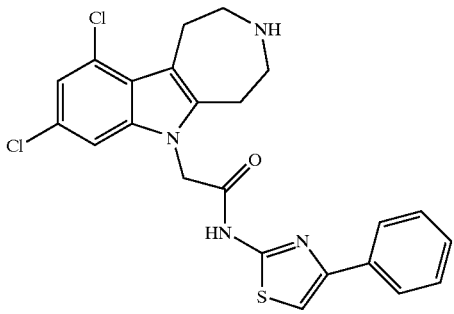

isolation method C; MS (ESI+) m/z 471.2 (MH+)

Preparation 81

Preparation of tert-Butyl 8,9-dichloro-6-(3-phenylpropyl)-1,4,5,6-tetrahydroazepino[4,5-b]indole-3(2H)-carboxylate Potassium hydride (45 mg, 1.1 mmol) was added to a solution of tert-butyl 8,9-dichloro-1,4,5,6-tetrahydroazepino[4,5-b]indole-3(2H)-carboxylate (0.20 g, 0.56 mmol) in DMF (1.0 mL). After 15 min, 1-bromo-3-phenylpropane (0.13 mL, 0.86 mmol) was added. After 5 h, the reaction was quenched with saturated aqueous NH$_4$Cl (10 mL) and extracted with CH$_2$Cl$_2$ (3×10 mL). The combined organic extracts were washed with brine, dried over Na$_2$SO$_4$, decanted, and concentrated. The crude product was purified by column chromatography (Biotage, 40S) with heptane/EtOAc (3:1) to give 0.21 g (78%) of a yellow solid: mp 119–124° C.; IR (diffuse reflectance) 2980, 2973, 2941, 2932, 1686, 1478, 1462, 1417, 1365, 1247, 1178, 1160, 1112, 855, 699 cm$^{-1}$; MS (EI) m/z 472 (M+), 416, 227, 226, 224, 211, 188, 153, 115, 90, 56; Anal. Calcd for C$_{26}$H$_{30}$Cl$_2$N$_2$O$_2$: C, 65.96; H, 6.39; N, 5.92; found: C, 66.01; H, 6.47; N, 5.82.

EXAMPLE 240

Preparation of 8,9-Dichloro-6-(3-phenylpropyl)-1,2,3,4,5,6-hexahydroazepino[4,5-b]indole hydrochloride

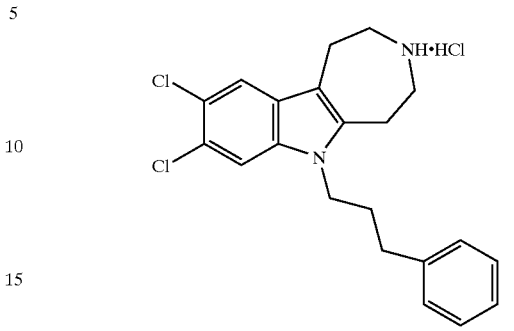

To a solution of tert-butyl 8,9-dichloro-6-(3-phenylpropyl)-1,4,5,6-tetrahydroazepino[4,5-b]indole-3(2H)-carboxylate (0.20 g, 0.42 mmol) in CH$_2$Cl$_2$ (5 mL), TFA (0.65 mL, 8.4 mmol) was added while stirring at rt. After 4 h, the reaction was made basic with 10% aqueous NaOH, then extracted with CH$_2$Cl$_2$ (3×15 mL). The combined organic layers were washed with brine, dried over Na$_2$SO$_4$, decanted, and concentrated to 0.12 g of crude material. After the hydrochloride salt was prepared, it was further purified by recrystallization from MeOH/EtOAc to give 99 mg (57%) of a white solid: mp 148.0–150.5° C.; $^1$H NMR (300 MHz, DMSO) δ 9.26 (br s, 2H), 7.75 (d, J=8.7 Hz, 2H), 7.28 (m, 2H), 7.20 (m, 3H), 4.19 (m, 2H), 3.19 (m, 2H), 3.08 (m, 2H), 2.61 (m, 2H), 1.89 (pentet, J=7.5 Hz, 2H); $^{13}$C NMR (400 MHz, DMSO) δ 141.0, 138.4, 134.0, 128.2, 128.1, 126.5, 125.8, 123.0, 121.4, 118.7, 111.3, 110.2, 45.8, 44.0, 42.3, 31.9, 31.5, 22.5, 20.2; IR (diffuse reflectance) 3021, 2997, 2970, 2953, 2888, 2850, 2825, 2812, 2760, 2709, 2632, 1473, 1421, 1106, 700 cm$^{-1}$; MS (EI) m/z 374, 372 (M+), 332, 331, 330, 228, 226, 91, 86, 84.

Preparation 82

Preparation of tert-Butyl 9,10-dichloro-6-(3-phenylpropyl)-1,4,5,6-tetrahydroazepino[4,5-b]indole-3(2H)-carboxylate To a solution of tert-butyl 9,10-dichloro-1,4,5,6-tetrahydroazepino[4,5-b]indole-3(2H)-carboxylate (0.40 g, 1.1 mmol) in DMF (6 mL), sodium hydride (60% dispersion in mineral oil, 68 mg, 1.7 mmol) was added. After 25 min, 1-bromo-3-phenyl propane (0.34 mL, 2.3 mmol) was added. The reaction was quenched with saturated aqueous NH$_4$Cl after 3 h and extracted with EtOAc (3×15 mL). The combined organic extracts were washed with brine, dried over Na$_2$SO$_4$, decanted, and concentrated. The crude product was purified by column chromatography (Biotage, 40M) with heptane/EtOAc (17:3) to give 0.33 g (62%) of a yellow solid: mp 113.5–115.5° C.; $^1$H NMR (300 MHz, CDCl$_3$) δ 7.14 (m, 3H), 6.93 (d, J=8.7 Hz, 1H), 4.02 (m, 2H), 3.70 (m, 4H), 3.50 (m, 2H), 2.93 (m, 2H), 2.65 (t, J=7.5 Hz, 2H), 1.99 (m, 2H), 1.48 (s, 9H); IR (diffuse reflectance) 2976, 1686, 1447, 1416, 1366, 1360, 1247, 1180, 1168, 1152, 1108, 930, 788, 747, 701 cm$^{-1}$; MS (FAB) m/z 473 (M+H+), 475, 474, 473, 472, 419, 418, 417, 416, 91, 57; HRMS (FAB) calcd for C$_{26}$H$_{30}$Cl$_2$N$_2$O$_2$+H 473.1762, found 473.1759; Anal. Calcd for C$_{26}$H$_{30}$Cl$_2$N$_2$O$_2$: C, 65.96; H, 6.39; N, 5.92, found: C, 66.00; H, 6.41; N, 5.85.

EXAMPLE 241

Preparation of 9,10-Dichloro-6-(3-phenylpropyl)-1,2,3,4,5,6-hexahydroazepino[4,5-b]indole hydrochloride

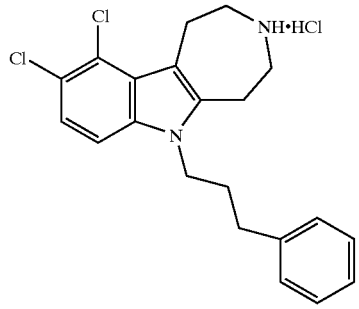

To a solution of tert-butyl 9,10-dichloro-6-(3-phenylpropyl)-1,4,5,6-tetrahydroazepino[4,5-b]indole-3(2H)-carboxylate (0.20 g, 0.42 mmol) in $CH_2Cl_2$ (10 mL), TFA (0.65 mL, 8.4 mmol) was added while stirring at rt. After 5 h, the reaction was made basic with 10% aqueous NaOH, then extracted with $CH_2Cl_2$ (3×15 mL). The combined organic layers were washed with brine, dried over $Na_2SO_4$, decanted, and concentrated to 0.15 g of a crude solid. After the hydrochloride salt was prepared, it was further purified by a recrystallization from MeOH/EtOAc to give 47 mg (27%) of a white solid: mp 214.0–216.0; $^1H$ NMR (300 MHz, DMSO) δ 9.29 (br s, 2H), 7.45 (d, J=8.8 Hz, 1H), 7.27 (m, 3H), 7.19 (m, 3H), 4.22 (t, J=7.2 Hz, 2H), 3.51 (m, 2H), 3.22 (m, 2H), 2.61 (m, 2H), 1.90 (pentet, J=7.5 Hz, 2H); $^{13}C$ NMR (400 MHz, DMSO) δ 141.0, 139.2, 134.8, 128.2, 128.0, 125.8, 123.6, 122.4, 121.8, 121.4, 110.5, 110.2, 45.1, 43.4, 42.3, 32.0, 31.4, 21.9, 21.1; IR (diffuse reflectance) 2972, 2951, 2885, 2824, 2796, 2747, 2722, 2671, 2652, 2443, 1448, 1423, 779, 746, 700 $cm^{-1}$; MS (ES+) m/z 373 (M+H+), 344, 232, 232, 228, 226, 205, 203, 191, 68; Anal. Calcd for $C_{21}H_{22}Cl_2N_2$·HCl·2.15% $H_2O$: C, 60.23; H, 5.78; N, 6.69, found: C, 60.37; H 5.68; N, 6.66.

Preparation 83

Preparation of tert-Butyl 8,9-dichloro-6-(2-phenoxyethyl)-1,4,5,6-tetrahydroazepino[4,5-b]indole-3(2H)-carboxylate To a solution of tert-butyl 8,9-dichloro-1,4,5,6-tetrahydroazepino[4,5-b]indole-3(2H)-carboxylate (0.40 g, 1.1 mmol) in DMF (5 mL), sodium hydride (60% dispersion in mineral oil, 68 mg, 1.7 mmol) was added. After 20 min, β-bromophenetole (0.31 mL, 2.3 mmol) was added. The reaction was quenched with saturated aqueous $NH_4Cl$ after 2 h and extracted with EtOAc (3×15 mL). The combined organic extracts were washed with brine, dried over $Na_2SO_4$, decanted, and concentrated. The crude product was purified by two column chromatographies (Biotage, 40S) with heptane/EtOAc (17:3) and (Biotage, 40M) with heptane/EtOAc (9:1) to give 0.41 g (76%) of a white solid: mp 135.5–137.5° C.; $^1H$ NMR (300 MHz, $CDCl_3$) δ 7.50 (d, J=4.5 Hz, 1H), 7.41 (d, J=7.5 Hz, 1H), 6.93 (m, 1H), 6.77 (d, J=7.9 Hz, 2H), 4.42 (m, 2H), 4.17 (t, J=5.3 Hz, 2H), 3.70 (m, 4H), 3.09 (m, 2H), 2.89 (m, 2H), 1.49 (s, 9H); IR (diffuse reflectance) 1678, 1494, 1469, 1406, 1364, 1297, 1245, 1233, 1172, 1119, 1106, 941, 875, 758, 691 $cm^{-1}$; MS (ES+) m/z 475 (M+H+), 498, 497, 348, 346, 255, 252, 169, 137, 121, 90; Anal. Calcd for $C_{25}H_{28}Cl_2N_2O_3$: C, 63.16; H, 5.94; N, 5.89; found: C, 63.22; H, 6.00; N, 5.88.

EXAMPLE 242

Preparation of 8,9-Dichloro-6-(2-phenoxyethyl)-1,2,3,4,5,6-hexahydroazepino[4,5-b]indole hydrochloride

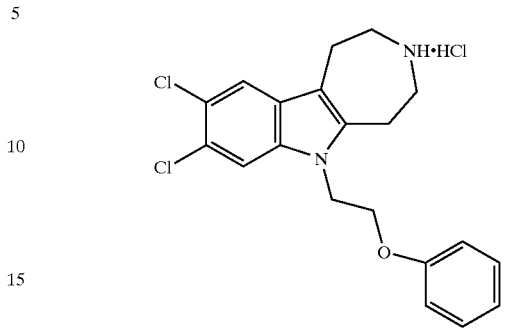

To a solution of tert-butyl 8,9-dichloro-6-(2-phenoxyethyl)-1,4,5,6-tetrahydroazepino[4,5-b]indole-3(2H)-carboxylate (0.20 g, 0.42 mmol) in $CH_2Cl_2$ (5 mL), TFA (0.65 mL, 8.5 mmol) was added while stirring at rt. After 3 h, the reaction was made basic with 10% aqueous NaOH and extracted with $CH_2Cl_2$ (3×15 mL). The combined organic layers were washed with brine, dried over $Na_2SO_4$, decanted, and concentrated to give 0.18 g of a crude solid. The hydrochloride salt was prepared to give 0.13 g (73%) of an off-white solid: mp 235.0–235.5° C.; $^1H$ NMR (300 MHz, DMSO) δ 9.20 (br s, 2H), 7.88 (s, 1H), 7.76 (s, 1H), 7.25 (m, 2H), 6.91 (t, J=7.2 Hz, 1H), 6.83 (d, J=7.5 Hz, 2H), 4.61 (m, 2H), 4.17 (t, J=4.5 Hz, 2H), 3.09 (m, 2H); $^{13}C$ NMR (400 MHz, DMSO) δ 157.8, 139.3, 134.2, 129.4, 126.7, 123.0, 121.6, 120.7, 118.7, 114.1, 111.8, 110.3, 66.7, 45.8, 44.2, 42.2, 22.9, 20.2; IR (diffuse reflectance) 2949, 2934, 2740, 2697, 2678, 1592, 1495, 1468, 1244, 1108, 886, 877, 754, 745, 687 $cm^{-1}$; MS (EI) m/z 376, 374 (M+), 334, 333, 332, 119, 91, 77, 65, 51; Anal. Calcd for $C_{20}H_{20}Cl_2N_2O$·HCl: C, 58.34; H, 5.14; N, 6.80; found: C, 57.99; H, 5.23; N, 6.66.

Preparation 84

Preparation of tert-Butyl 8,9-dichloro-6-[2-(4-chlorophenoxy)ethyl]-1,4,5,6-tetrahydroazepino[4,5-b]indole-3(2H)-carboxylate To a solution of tert-butyl 8,9-dichloro-1,4,5,6-tetrahydroazepino[4,5-b]indole-3(2H)-carboxylate (0.40 g, 1.1 mmol) in DMF (5 mL), sodium hydride (60% dispersion in mineral oil, 68 mg, 1.7 mmol) was added. After 20 min, 2-chlorophenyl 2-bromoethyl ether (0.34 mL, 2.3 mmol) was added. The reaction was quenched with saturated aqueous $NH_4Cl$ after 3 h and extracted with EtOAc (3×15 mL). The combined organic extracts were washed with brine, dried over $Na_2SO_4$, decanted, and concentrated. The crude product was purified by column chromatography (Biotage, 40M) with heptane/EtOAc (17:3) to give 0.47 g (82%) of a white foam: $^1H$ NMR (300 MHz, $CDCl_3$) δ 7.50 (d, J=4.5 Hz, 1H), 7.40 (d, J=6.0 Hz, 1H), 7.18 (d, J=9.0 Hz, 2H), 6.68 (m, 2H), 4.40 (t, J=5.3 Hz, 2H), 4.16 (t, J=5.3 Hz, 2H), 3.64 (m, 4H), 3.06 (m, 2H), 2.90 (m, 2H), 148 (s, 9H); IR (diffuse reflectance) 1691, 1687, 1491, 1467, 1413, 1365, 1297, 1285, 1268, 1242, 1221, 1169, 1114, 1104, 822 $cm^{-1}$; MS (ES+) m/z 509 (M+H+), 533, 531, 392, 292, 160, 155, 146, 118, 106, 91; Anal. Calcd for $C_{25}H_{27}Cl_3N_2O_3$: C, 58.89; H, 5.34; N, 5.49, found: C, 58.89; H, 5.44; N, 5.48.

EXAMPLE 243

Preparation of 8,9-Dichloro-6-[2-(4-chlorophenoxy)ethyl]-1,2,3,4,5,6-hexahydroazepino[4,5-b]indole hydrochloride

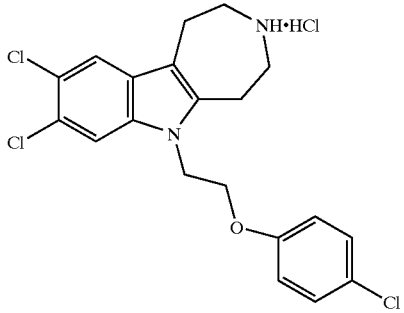

To a solution of tert-butyl 8,9-dichloro-6-[2-(4-chlorophenoxy)ethyl]-1,4,5,6-tetrahydroazepino[4,5-b]indole-3(2H)-carboxylate (0.30 g, 0.59 mmol) in $CH_2Cl_2$ (10.0 mL), TFA (0.91 mL, 12 mmol) was added while stirring at rt. After 3 h, the reaction was made basic with 10% aqueous NaOH and extracted with $CH_2Cl_2$ (3×15 mL). The combined organic layers were washed with brine, dried over $Na_2SO_4$, decanted, and concentrated to give 0.24 g of crude material. The hydrochloride salt was prepared to give 0.21 g (82%) of an off-white solid: mp 262.3–263.5° C.; $^1$H NMR (300 MHz, DMSO) δ 9.27 (br s, 2H), 7.86 (s, 1H), 7.76 (s, 1H), 7.30 (d, J=8.9 Hz, 2H), 6.86 (t, J=8.9 Hz, 2H), 4.61 (t, J=4.5 Hz, 2H), 4.17 (m, 2H), 3.08 (m, 2H); $^{13}$C NMR (400 MHz, DMSO) δ 156.8, 139.3, 134.2, 129.2, 126.7, 124.5, 123.1, 121.7, 118.7, 116.0, 111.8, 110.3, 67.2, 45.9, 44.2, 42.1, 22.9, 20.3; IR (diffuse reflectance) 2949, 2823, 2757, 2715, 2703, 2676, 1589, 1491, 1472, 1324, 1243, 1110, 868, 814, 666 cm$^{-1}$; MS (EI) m/z 408 (M$^+$), 111, 99, 86, 84, 78, 73, 63, 57, 51, 50; Anal. Calcd for $C_{20}H_{19}Cl_3N_2O\cdot HCl$: C, 53.84; H, 4.52; N, 6.28, found: C, 53.47; H, 4.56; N, 6.17.

Preparation 85

Preparation of tert-Butyl 8,9-dichloro-6-[2-(4-fluorophenoxy)ethyl]-1,4,5,6-tetrahydroazepino[4,5-b]indole-3(2H)-carboxylate To a solution of tert-butyl 8,9-dichloro-1,4,5,6-tetrahydroazepino[4,5-b]indole-3(2H)-carboxylate (0.40 g, 1.1 mmol) in DMF (5 mL), sodium hydride (60% dispersion in mineral oil, 68 mg, 1.7 mmol) was added. After 25 min, 4-fluorophenoxy ethyl bromide (0.34 mL, 2.3 mmol) was added. The reaction was quenched with saturated aqueous $NH_4Cl$ after 2 h and extracted with EtOAc (3×15 mL). The combined organic extracts were washed with brine, dried over $Na_2SO_4$, decanted, and concentrated. The crude product was purified by column chromatography (Biotage, 40M) with heptane/EtOAc (gradient, 9:1 to 17:3) to give 0.43 g (78%) of a white foam: $^1$H NMR (300 MHz, $CDCl_3$) δ 7.51 (d, J=3.8 Hz, 1H), 7.40 (d, J=6.0 Hz, 1H), 6.92 (t, J=8.7 Hz, 2H), 6.70 (m, 2H), 4.40 (t, J=5.3 Hz, 2H), 4.13 (t, J=5.3 Hz, 4H), 3.69 (m, 4H), 3.08 (m, 2H), 2.90 (m, 2H), 1.48 (s, 9H); IR (diffuse reflectance) 1687, 1505, 1468, 1414, 1366, 1296, 1268, 1248, 1218, 1169, 1114, 1105, 865, 827, 746 cm$^{-1}$; MS (ES+) m/z 493 (M+H$^+$), 516, 515, 366, 364, 265, 253, 138, 94, 91, 85; Anal. Calcd for $C_{25}H_{27}Cl_2FN_2O_3$: C, 60.86; H, 5.51; N, 5.68, found: C, 60.91; H, 5.61; N, 5.64.

EXAMPLE 244

Preparation of 8,9-Dichloro-6-[2-(4-fluorophenoxy)ethyl]-1,2,3,4,5,6-hexahydroazepino[4,5-b]indole hydrochloride

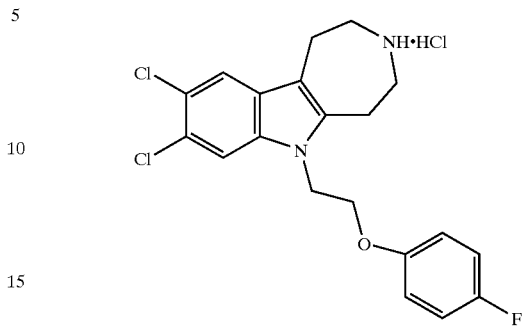

To a solution of tert-butyl 8,9-dichloro-6-[2-(4-fluorophenoxy)ethyl]-1,4,5,6-tetrahydroazepino[4,5-b]indole-3(2H)-carboxylate (0.20 g, 0.41 mmol) in $CH_2Cl_2$ (5.0 mL), TFA (0.63 mL, 8.1 mmol) was added while stirring at rt. After 5 h, the reaction was made basic with 10% aqueous NaOH, then extracted with $CH_2Cl_2$ (3×15 mL). The combined organic layers were washed with brine, dried over $Na_2SO_4$, decanted, and concentrated to 0.17 g of crude material. The hydrochloride salt was prepared to give 0.16 g (93%) of an off-white solid: mp 189.5–192.0° C.; $^1$H NMR (300 MHz, DMSO) δ 9.19 (br s, 2H), 7.86 (s, 1H), 7.77 (s, 1H), 7.09 (m, 2H), 6.84 (m, 2H), 4.60 (t, J=4.9 Hz, 2H), 4.15 (t, J=4.9 Hz, 2H), 3.09 (m, 2H); $^{13}$C NMR (400 MHz, DMSO) δ 157.6, 155.3, 154.1, 139.3, 134.2, 126.7, 123.0, 121.6, 118.7, 115.9, 115.6, 115.4, 115.3, 111.8, 110.3, 67.3, 45.8, 44.2, 42.2, 22.9, 20.2; IR (diffuse reflectance) 2950, 2937, 2834, 2757, 2741, 2664, 1508, 1466, 1246, 1225, 1208, 8719, 826, 816, 747 cm$^{-1}$; MS (ES+) m/z 393 (M+H$^+$), 366, 255, 238, 211, 191, 170, 168, 147, 74, 72; % Water (KF): 1.36; Anal. Calcd for $C_{20}H_{19}Cl_2FN_2O\cdot HCl\cdot .36\% H_2O$: C, 55.14; H, 4.78; N, 6.43, found: C, 54.83; H, 4.88; N, 6.30.

Preparation 86

Preparation of tert-Butyl 9,10-dichloro-6-(2-phenoxyethyl)-1,4,5,6-tetrahydroazepino[4,5-b]indole-3(2H)-carboxylate To a solution of tert-butyl 9,10-dichloro-1,4,5,6-tetrahydroazepino[4,5-b]indole-3(2H)-carboxylate (0.20 g, 0.56 mmol) in DMF (4 mL), sodium hydride (60% dispersion in mineral oil, 34 mg, 0.84 mmol) was added. After 25 min, β-bromophenetole (0.15 mL, 1.1 mmol) was added. The reaction was quenched with saturated aqueous $NH_4Cl$ after 2 h and extracted with EtOAc (3×15 mL). The combined organic extracts were washed with brine, dried over $Na_2SO_4$, decanted, and concentrated. The crude product was purified by column chromatography (Biotage, 40S) with heptane/EtOAc (17:3) and triturating with hexanes gave 35 mg (13%) of a white solid: mp 175.0–176.0° C.; $^1$H NMR (400 MHz, DMSO) δ 7.53 (d, J=8.8 Hz, 1H), 7.24 (m, 3H), 6.90 (t, J=7.6 Hz, 1H), 6.81 (d, J=7.6 Hz, 1H), 6.81 (d, J=7.9 Hz, 2H), 4.60 (m, 2H), 4.17 (m, 2H), 3.67 (m, 2H), 3.61 (m, 2H), 3.14 (t, J=5.3 Hz, 2H), 1.41 (s, 9H); IR (diffuse reflectance) 2967, 2931, 1676, 1493, 1448, 1422, 1406, 1363, 1298, 1245, 1221, 1167, 1118, 754, 690 cm$^{-1}$; MS (EI) m/z 474 (M$^+$), 333, 95, 92, 79, 78, 76, 67, 64, 57, 55; HRMS (FAB) calcd for $C_{25}H_{28}Cl_2N_2O_3$+H 475.1555, found 475.1559; Anal. Calcd for $C_{25}H_{28}Cl_2N_2O_3$: C, 63.16; H, 5.94; N, 5.89; found: C, 63.47; H, 6.11; N, 5.84.

EXAMPLE 245

Preparation of 9,10-Dichloro-6-(2-phenoxyethyl)-1,2,3,4,5,6-hexahydroazepino[4,5-b]indole hydrochloride

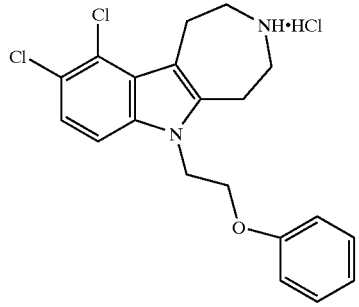

TFA (0.39 mL, 5.1 mmol) was added to a solution of tert-butyl 9,10-dichloro-6-(2-phenoxyethyl)-1,4,5,6-tetrahydroazepino[4,5-b]indole-3(2H)-carboxylate (0.12 g, 0.25 mmol) in $CH_2Cl_2$ (6.0 mL). After 4.5 h, the reaction was made basic with 10% aqueous NaOH and extracted with $CH_2Cl_2$ (3×10 mL). The combined organic layers were washed with brine, dried over $Na_2SO_4$, decanted, and concentrated to 90 mg of a light yellow crude oil. The hydrochloride salt was prepared to give 61 mg (59%) of a white solid: mp 194.0–196.5° C.; $^1H$ NMR (300 MHz, DMSO) δ 9.17 (br s, 2H), 7.59 (d, J=8.8 Hz, 1H), 7.28 (m, 3H), 6.91 (t, J=7.3 Hz, 1H), 6.83 (d, J=7.9 Hz, 2H), 4.63 (t, J=4.7 Hz, 2H), 4.17 (t, J=4.9 Hz, 2H), 3.53 (m, 2H); $^{13}C$ NMR (400 MHz, DMSO) δ 157.8, 140.1, 135.0, 129.4, 123.8, 122.7, 121.9, 121.3, 120.8, 114.1, 110.6, 66.5, 45.1, 43.6, 42.3, 22.3, 21.2; IR (diffuse reflectance) 2979, 2955, 2867, 2824, 2797, 2757, 2730, 2673, 2656, 1495, 1459, 1442, 1240, 1221, 758 $cm^{-1}$; MS (ES+) m/z 375 (M+H$^+$), 348, 346, 346, 255, 253, 240, 238, 227, 225, 121; % Water (KF): 2.99; Anal. Calcd for $C_{20}H_{20}Cl_2N_2O \cdot HCl \cdot 2.99\% H_2O$: C, 56.60; H, 5.32; N, 6.60; found: C, 56.53; H, 5.64; N, 6.53.

Preparation 87

Preparation of tert-Butyl 9,10-dichloro-6-[2-(4-chlorophenoxy)ethyl]-1,4,5,6-tetrahydroazepino[4,5-b]indole-3(2H)-carboxylate Sodium hydride (60% dispersion in mineral oil, 68 mg, 1.7 mmol) was added to a solution of tert-butyl 9,10-dichloro-1,4,5,6-tetrahydroazepino[4,5-b]indole-3(2H)-carboxylate (0.40 g, 1.1 mmol) in DMF (6 mL). After 25 min, 2-chlorophenyl 2-bromoethyl ether (0.34 mL, 2.3 mmol) was added. The reaction was quenched with saturated aqueous $NH_4Cl$ after 19 h and extracted with EtOAc (3×20 mL). The combined organic extracts were washed with brine, dried over $Na_2SO_4$, decanted, and concentrated. The crude product was purified by column chromatography (Biotage, 40M) with heptane/EtOAc (17:3) to give 0.46 g (76%) of a white foam: $^1H$ NMR (300 MHz, CDCl$_3$) δ 7.17 (m, 4H), 6.68 (d, J=9.0 Hz, 2H), 4.45 (t, J=5.3 Hz, 2H), 4.13 (t, J=3.5 Hz, 2H), 3.72 (m, 4H), 3.51 (m, 2H), 3.11 (m, 2H), 1.48 (s, 9H); IR (diffuse reflectance) 2975, 2930, 1691, 1492, 1448, 1414, 1392, 1365, 1300, 1285, 1269, 1244, 1169, 1114, 823 $cm^{-1}$; MS (FAB) m/z 509 (M+H$^+$), 510, 509, 508, 455, 454, 453, 452, 57, 42, 41; HRMS (EI) calcd for $C_{25}H_{27}Cl_3N_2O_3$ 508.1087, found 508.1089; Anal. Calcd for $C_{25}H_{27}Cl_3N_2O_3$: C, 58.89; H, 5.34; N, 5.49; found: C, 58.94; H, 5.38; N, 5.41.

EXAMPLE 246

Preparation of 9,10-Dichloro-6-[2-(4-chlorophenoxy)ethyl]-1,2,3,4,5,6-hexahydroazepino[4,5-b]indole hydrochloride

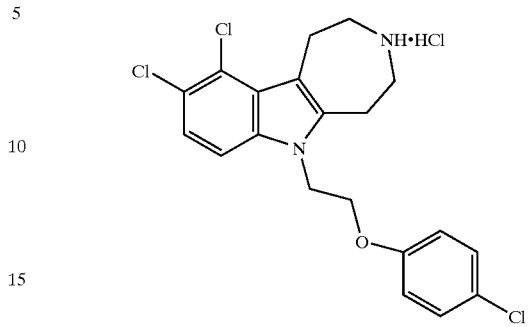

TFA (0.84 mL, 11 mmol) was added to a solution of tert-butyl 9,10-dichloro-6-[2-(4-chlorophenoxy)ethyl]-1,4,5,6-tetrahydroazepino[4,5-b]indole-3(2H)-carboxylate (0.30 g, 0.55 mmol) in $CH_2Cl_2$ (10.0 mL). After 3 h, the reaction was made basic with 10% aqueous NaOH and $CH_2Cl_2$ was added to dissolve the pink precipitate that had formed. The layers were separated and the aqueous layer was extracted with additional $CH_2Cl_2$. The combined organic layers were washed with brine, dried over $Na_2SO_4$, decanted, and concentrated to 0.27 g of a crude solid. The hydrochloride salt was prepared to give 0.19 g (80%) of a white solid: mp 203.5–205.0; $^1H$ NMR (300 MHz, DMSO) δ 9.32 (br s, 2H), 7.58 (d, J=8.8 Hz, 1H), 7.30 (m, 3H), 6.86 (d, J=9.0 Hz, 2H), 4.63 (t, J=4.9 Hz, 2H), 4.17 (m, 2H), 3.52 (m, 2H); $^{13}C$ NMR (400 MHz, DMSO) δ 156.6, 140.1, 135.0, 129.1, 124.5, 123.8, 122.7, 121.9, 121.3, 115.9, 110.7, 110.6, 67.1, 45.1, 43.5, 42.2, 22.2, 21.1; IR (diffuse reflectance) 2977, 2953, 2823, 2796, 2749, 2727, 2672, 2653, 2442, 1491, 1460, 1442, 1242, 826, 774 $cm^{-1}$; MS (ES+) m/z 409 (M+H$^+$), 253, 225, 217, 169, 169, 137, 123, 97, 84, 74; % Water (KF): 1.48; Anal. Calcd for $C_{20}H_{19}Cl_3N_2O \cdot HCl \cdot 1.48\% H_2O$: C, 53.04; H, 4.62; N, 6.19, found: C, 52.90; H, 4.64; N, 6.12.

Preparation 88

Preparation of tert-Butyl 9,10-dichloro-6-[2-(4-fluorophenoxy)ethyl]-1,4,5,6-tetrahydroazepino[4,5-b]indole-3(2H)-carboxylate Sodium hydride (60% dispersion in mineral oil, 68 mg, 1.7 mmol) was added to a solution of tert-butyl 9,10-dichloro-1,4,5,6-tetrahydroazepino[4,5-b]indole-3(2H)-carboxylate (0.40 g, 1.1 mmol) in DMF (6 mL). After 25 min, 4-fluorophenoxy ethyl bromide (0.34 mL, 2.3 mmol) was added. The reaction was quenched with saturated aqueous $NH_4Cl$ after 22 h and extracted with EtOAc (3×15 mL). The combined organic extracts were washed with brine, dried over $Na_2SO_4$, decanted, and concentrated. The crude product was purified by column chromatography (Biotage, 40M) with heptane/EtOAc (17:3) to give 0.46 g (82%) of a white solid: mp 163.5–165.5° C.; $^1H$ NMR (300 MHz, CDCl$_3$) δ 7.16 (m, 2H), 6.92 (m, 2H), 6.70 (m, 2H), 4.44 (m, 2H), 4.12 (m, 2H), 3.73 (m, 4H), 3.51 (m, 2H), 3.12 (m, 2H), 1.48 (s, 9H); IR (diffuse reflectance) 1675, 1507, 1449, 1405, 1365, 1354, 1298, 1249, 1242, 1221, 1209, 1170, 1120, 835, 828 $cm^{-1}$; MS (FAB) m/z 493 (M+H$^+$), 494, 493, 492, 439, 438, 437, 436, 435, 57,42; HRMS (EI) calcd for $C_{25}H_{27}Cl_2FN_2O_3$ 492.1383, found 492.1385; Anal. Calcd for $C_{25}H_{27}Cl_2FN_2O_3$: C, 60.86; H, 5.51; N, 5.68, found: C, 60.93; H, 5.60; N, 5.69.

EXAMPLE 247

Preparation of 9,10-Dichloro-6-[2-(4-fluorophenoxy)ethyl]-1,2,3,4,5,6-hexahydroazepino[4,5-b]indole hydrochloride

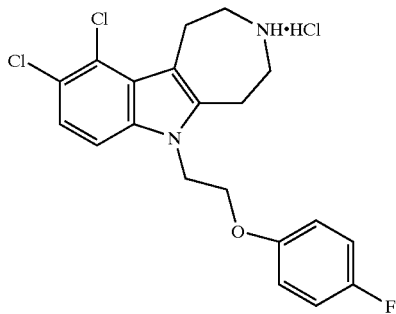

To a solution of tert-butyl 9,10-dichloro-6-[2-(4-fluorophenoxy)ethyl]-1,4,5,6-tetrahydroazepino[4,5-b]indole-3(2H)-carboxylate (0.20 g, 0.41 mmol) in $CH_2Cl_2$ (6.0 mL), TFA (0.63 mL, 8.1 minol) was added while stirring at rt. After 30 min, the reaction was made basic with 10% aqueous NaOH, then extracted with $CH_2Cl_2$ (3×15 mL). The combined organic layers were washed with brine, dried over $Na_2SO_4$, decanted, and concentrated to 0.17 g of a crude solid. After the hydrochloride salt was prepared, it was further purified by a recrystallization from MeOH/EtOAc to give 69 mg (40%) of a white solid: mp 214.0–216.0; $^1H$ NMR (300 MHz, DMSO) δ 7.58 (d, J=8.7 Hz, 1H), 7.31 (d, J=9.0 Hz, 1H), 7.09 (m, 2H), 6.84 (m, 2H), 4.63 (m, 2H), 4.15 (t, J=4.9 Hz, 2H), 3.53 (m, 2H), $^{13}C$ NMR (400 MHz, DMSO) δ 157.0, 154.7, 153.5, 153.5, 139.5, 134.4, 123.2, 122.0, 121.2, 120.7, 115.2, 115.0, 114.8, 114.7, 110.0, 109.9, 66.6, 44.5, 42.9, 41.6, 21.6, 20.5; IR (diffuse reflectance) 2965, 2838, 2823, 2794, 2770, 2745, 2714, 2697, 2651, 1506, 1442, 1249, 1222, 1206, 831 $cm^{-1}$; MS (ES+) m/z 393 (M+H$^+$), 364, 238, 221, 175, 79, 74, 66, 64, 62, 61. Anal. Calcd for $C_{20}H_{19}Cl_2FN_2O·HCl$: C, 55.90; H, 4.69; N, 6.52, found: C, 55.65; H, 4.72; N, 6.49.

Preparation 89

Preparation of tert-Butyl 7,8-dichloro-6-(2-phenoxyethyl)-1,4,5,6-tetrahydroazepino[4,5-b]indole-3(2H)-carboxylate Sodium hydride (60% dispersion in mineral oil, 51 mg, 1.3 mmol) was added to a solution of tert-butyl 7,8-dichloro-1,4,5,6-tetrahydroazepino[4,5-b]indole-3(2H)-carboxylate (0.30 g, 0.84 mmol) in DMF (5 mL). After 30 min, β-bromophenetole was added (0.31 mL). The reaction was quenched with saturated aqueous $NH_4Cl$ after 18 h and extracted with EtOAc (3×15 mL). The combined organic extracts were washed with brine, dried over $Na_2SO_4$, decanted, and concentrated. The crude product was purified by column chromatography (Biotage, 40S) with heptane/EtOAc (17:3) to give 0.22 g (55%) of a white solid: mp 138.4–139.7° C.; $^1H$ NMR (300 MHz, CDCl$_3$) δ 6.92 (m, 1H), 6.79 (m, 2H), 4.90 (m, 2H), 4.27 (m, 2H), 3.80 (m, 2H), 3.66 (m, 2H), 3.17 (m, 2H), 2.93 (m, 2H), 1.49 (s, 9H); IR (diffuse reflectance) 2979, 1687, 1467, 1443, 1416, 1365, 1253, 1239, 1223, 1172, 1165, 1156, 923, 808, 760 $cm^{-1}$; MS (EI) m/z 474 (M$^+$), 420, 418, 332, 86, 84, 57, 56, 55, 51; Anal. Calcd for $C_{25}H_{28}Cl_2N_2O_3$: C, 63.16; H, 5.94; N, 5.89; found: C, 63.15; H, 6.00; N, 5.89.

EXAMPLE 248

Preparation of 7,8-Dichloro-6-(2-phenoxyethyl)-1,2,3,4,5,6-hexahydroazepino[4,5-b]indole hydrochloride

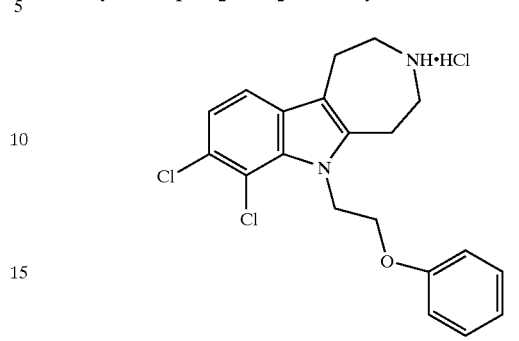

TFA (0.41 mL, 5.3 mmol) was added to a solution of tert-butyl 7,8-dichloro-6-(2-phenoxyethyl)-1,4,5,6-tetrahydroazepino[4,5-b]indole-3(2H)-carboxylate (0.13 g, 0.26 mmol) in $CH_2Cl_2$ (5 mL). After 4 h, the reaction was made basic with 10% aqueous NaOH and extracted with $CH_2Cl_2$ (3×15 mL). The combined organic layers were washed with brine, dried over $Na_2SO_4$, decanted, and concentrated to give a crude solid. The hydrochloride salt was prepared to give 61 mg (57%) of a white solid: mp 196.5–197.0° C.; $^1H$ NMR (300 MHz, DMSO) δ 9.11 (br s, 2H), 7.49 (d, J=8.5 Hz, 1H), 7.26 (m, 3H), 6.90 (m, 3H), 4.95 (m, 2H), 4.26 (m, 2H), 3.09 (m, 2H); $^{13}C$ NMR (300 MHz, DMSO) δ 157.8, 139.9, 130.7, 129.4, 128.7, 125.2, 121.0, 120.8, 117.5, 114.2, 113.5, 111.5, 67.8, 45.6, 44.0, 43.2, 23.0, 19.9; IR (diffuse reflectance) 2971, 2955, 2828, 2799, 2759, 2677, 2659, 2446, 1601, 1588, 1496, 1463, 1244, 811, 760 $cm^{-1}$; MS (EI) m/z 374 (M$^+$), 86, 84, 78, 77, 65, 64, 63, 62, 61, 51; Anal. Calcd for $C_{20}H_{20}Cl_2N_2O·HCl$: C, 58.34; H, 5.14; N, 6.80; found: C, 58.12; H, 5.42; N, 6.47.

Preparation 90

Preparation of tert-Butyl 7,9-dichloro-6-(2-phenoxyethyl)-1,4,5,6-tetrahydroazepino[4,5-b]indole-3(2H)-carboxylate Sodium hydride (60% dispersion in mineral oil, 51 mg, 1.3 mmol) was added to a solution of tert-butyl 7,9-dichloro-1,4,5,6-tetrahydroazepino[4,5-b]indole-3(2H)-carboxylate (0.30 g, 0.84 mmol) in DMF (5 mL). After 30 min, β-bromophenetole was added (0.23 mL). The reaction was quenched with saturated aqueous $NH_4Cl$ after 18 h and extracted with EtOAc (1×50 mL, 2×20 mL). The combined organic extracts were washed with brine, dried over $Na_2SO_4$, decanted, and concentrated. The crude product was purified by column chromatography (Biotage, 40S) with heptane/EtOAc (17:3) and crystallized from EtOAc/heptane to give 0.31 g (77%) of a white solid: mp 154.0–155.0° C.; $^1H$ NMR (300 MHz, DMSO) δ 7.54 (d, J=1.9 Hz, 1H), 7.20 (m, 3H), 6.85 (m, 3H), 4.86 (m, 2H), 4.24 (m, 2H), 3.69 (m, 2H), 3.54 (m, 2H), 3.12 (m, 2H), 2.91 (m, 2H), 1.42 (s, 9H); IR (diffuse reflectance) 1683, 1463, 1410, 1366, 1345, 1293, 1242, 1232, 1227, 1174, 1167, 1113, 857, 756, 693 $cm^{-1}$; MS (EI) m/z 474 (M$^+$), 474, 420, 419, 418, 334, 332, 311, 238, 84, 57; Anal. Calcd for $C_{25}H_{28}Cl_2N_2O_3$: C, 63.16; H, 5.94; N, 5.89; found: C, 63.19; H, 5.97; N, 5.86.

EXAMPLE 249

Preparation of 7,9-Dichloro-6-(2-phenoxyethyl)-1,2,3,4,5,6-hexahydroazepino[4,5-b]indole hydrochloride

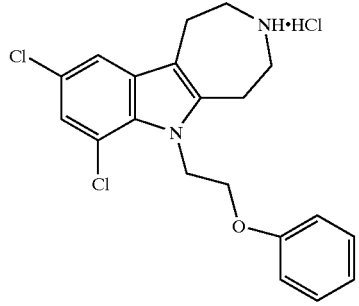

To a solution of tert-butyl 7,9-dichloro-6-(2-phenoxyethyl)-1,4,5,6-tetrahydroazepino[4,5-b]indole-3(2H)-carboxylate (0.20 g, 0.42 mmol) in CH$_2$Cl$_2$ (6 mL), TFA (0.65 mL, 8.4 mmol) was added while stirring at rt. After 5 h, the reaction was made basic with 10% aqueous NaOH and extracted with CH$_2$Cl$_2$ (3×15 mL). The combined organic layers were washed with brine, dried over Na$_2$SO$_4$, decanted, and concentrated to give a crude solid. The hydrochloride salt was prepared to give 0.10 g (60%) of a white solid: mp 204.0–204.5° C.; $^1$H NMR (300 MHz, DMSO) δ 9.35 (br s, 2H), 7.60 (d, J=1.9 Hz, 1H), 7.26 (m, 3H), 6.90 (m, 3H), 4.91 (m, 2H), 4.25 (m, 2H), 3.10 (m, 2H) $^{13}$C NMR (300 MHz, DMSO) δ 157.9, 141.0, 130.9, 129.5, 128.7, 123.7, 122.1, 120.9, 116.5, 115.9, 114.2, 111.5, 67.8, 45.6, 44.0, 43.2, 22.9, 20.0; IR (diffuse reflectance) 2969, 2941, 2924, 2847, 2832, 2809, 2734, 2691, 2664, 2632, 2430, 1493, 1464, 1250, 767 cm$^{-1}$; MS (EI) m/z 374 (M$^+$), 334, 332, 238, 224, 188, 94, 77, 65, 51; Anal. Calcd for C$_{20}$H$_{20}$Cl$_2$N$_2$O.HCl: C, 58.34; H, 5.14; N, 6.80; found: C, 58.15; H, 5.19; N, 6.72.

Preparation 91

Preparation of tert-Butyl 7,10-dichloro-6-(2-phenoxyethyl)-1,4,5,6-tetrahydroazepino[4,5-b]indole-3(2H)-carboxylate Sodium hydride (60% dispersion in mineral oil, 51 mg, 1.3 mmol) was added to a solution of tert-butyl 7,10-dichloro-1,4,5,6-tetrahydroazepino[4,5-b]indole-3(2H)-carboxylate (0.30 g, 0.84 mmol) in DMF (5 mL). After 25 min, β-bromophenetole was added (0.23 mL). The reaction was quenched with saturated aqueous NH$_4$Cl after 18 h and extracted with EtOAc (3×20 mL). The combined organic extracts were washed with brine, dried over Na$_2$SO$_4$, decanted, and concentrated. The crude product was purified by column chromatography (Biotage, 40S) with heptane/EtOAc (9:1) to give 0.32 g (79%) of a white solid: mp 131.5–133.0° C.; $^1$H NMR (300 MHz, CDCl$_3$) δ 6.96 (m, 3H), 6.81 (m, 2H), 4.92 (t, J=4.9 Hz, 2H), 4.27 (m, 2H), 3.80 (m, 2H), 3.67 (m, 2H), 3.52 (m, 2H), 3.18 (m, 2H), 1.49 (s, 9H); IR (diffuse reflectance) 1686, 1498, 1474, 1404, 1366, 1350, 1318, 1295, 1248, 1227, 1221, 1167, 1116, 788, 757 cm$^{-1}$; MS (EI) m/z 474 (M$^+$), 418, 376, 374, 339, 334, 332, 77, 57, 56, 55; Anal. Calcd for C$_{25}$H$_{28}$Cl$_2$N$_2$O$_3$: C, 63.16; H5.94; N, 5.89; found: C, 63.13; H, 6.00; N, 5.89.

EXAMPLE 250

Preparation of 7,10-Dichloro-6-(2-phenoxyethyl)-1,2,3,4,5,6-hexahydroazepino[4,5-b]indole hydrochloride

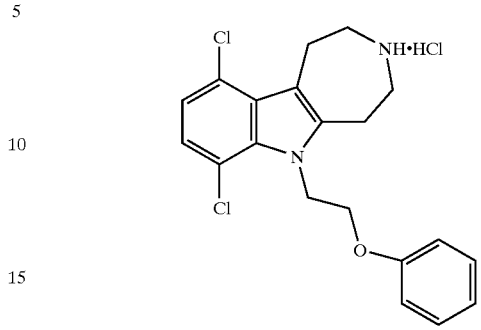

TFA (0.65 mL, 8.4 mmol) was added to a solution of tert-butyl 7,10-dichloro-6-(2-phenoxyethyl)-1,4,5,6-tetrahydroazepino[4,5-b]indole-3(2H)-carboxylate (0.20 g, 0.42 mmol) in CH$_2$Cl$_2$ (6 mL). After 5 h, the reaction was made basic with 10% aqueous NaOH and extracted with CH$_2$Cl$_2$ (3×15 mL). The combined organic layers were washed with brine, dried over Na$_2$SO$_4$, decanted, and concentrated to give a crude solid. After the hydrochloride salt was prepared, it was further purified by recrystallization from MeOH/EtOAc to give 51 mg (30%) of a white solid: mp 261.0–263.0° C.; $^1$H NMR (300 MHz, DMSO) δ 9.24 (br s, 2H), 7.26 (m, 2H), 7.16 (d, J=8.3 Hz, 1H), 7.06 (d, J=8.3 Hz, 1H), 6.90 (m, 3H), 4.97 (t, J=4.9 Hz, 2H), 4.26 (m, 2H), 3.53 (m, 2H); $^{13}$C NMR (300 MHz, DMSO) δ 157.8, 141.3, 131.1, 129.4, 125.5, 123.4, 123.2, 121.3, 120.8, 114.4, 114.1, 111.4, 67.7, 44.8, 43.2, 43.1, 22.2, 20.9; IR (diffuse reflectance) 2965, 2952, 2826, 2794, 2741, 2676, 2650, 2443, 1496, 1467, 1241, 1234, 1170, 804, 755 cm$^{-1}$; MS (EI) m/z 374 (M$^+$), 339, 334, 332, 84, 78, 77, 65, 63, 61; Anal. Calcd for C$_{20}$H$_{20}$Cl$_2$N$_2$O.HCl: C, 58.34; H, 5.14; N, 6.80; found: C, 58.25; H, 5.23; N, 6.80.

Preparation 92

Preparation of tert-Butyl 8,10-dichloro-6-(2-phenoxyethyl)-1,4,5,6-tetrahydroazepino[4,5-b]indole-3(2H)-carboxylate Sodium hydride (60% dispersion in mineral oil, 51 mg, 1.3 mmol) was added to a solution of tert-butyl 8,10-dichloro-1,4,5,6-tetrahydroazepino[4,5-b]indole-3(2H)-carboxylate (0.30 g, 0.84 mmol) in DMF (5 mL). After 25 min, β-bromophenetole was added (0.23 mL). The reaction was quenched with saturated aqueous NH$_4$Cl after 18 h and extracted with EtOAc (3×15 mL). The combined organic extracts were washed with brine, dried over Na$_2$SO$_4$, decanted, and concentrated. The crude product was purified by column chromatography (Biotage, 40S) with heptane/EtOAc (9:1) to give 0.36 g (90%) of a white solid: mp 131.5–133.0° C.; $^1$H NMR (300 MHz, CDCl$_3$) δ 7.04 (d, J=1.7 Hz, 1H), 6.94 (t, J=7.4 Hz, 1H), 6.77 (m, 2H), 4.41 (m, 2H), 4.16 (m, 2H), 3.76 (m, 2H), 3.65 (m, 2H), 3.45 (m, 2H), 3.11 (m, 2H), 1.48 (s, 9H); IR (diffuse reflectance) 2974, 2929, 1691, 1600, 1496, 1459, 1413, 1393, 1365, 1348, 1303, 1243, 1170, 1114, 754 cm$^{-1}$; MS (EI) m/z 474 (M$^+$), 420, 419, 418, 417, 344, 334, 332, 57, 56; Anal. Calcd for C$_{25}$H$_{28}$Cl$_2$N$_2$O$_3$: C, 63.16; H, 5.94; N, 5.89; found: C, 63.19; H, 5.99; N, 5.89.

EXAMPLE 251
Preparation of 8,10-Dichloro-6-(2-phenoxyethyl)-1,2,3,4,5,6-hexahydroazepino[4,5-b]indole hydrochloride

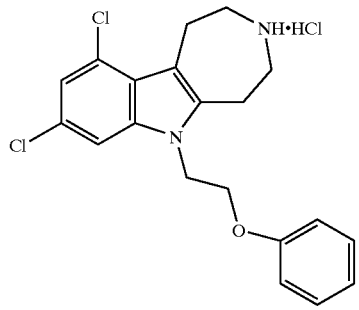

TFA (0.65 mL, 8.4 mmol) was added to a solution of tert-butyl 8,10-dichloro-6-(2-phenoxyethyl)-1,4,5,6-tetrahydroazepino[4,5-b]indole-3 (2H)-carboxylate (0.20 g, 0.42 mmol) in $CH_2Cl_2$ (6 mL). After 5 h, the reaction was made basic with 10% aqueous NaOH and extracted with $CH_2Cl_2$ (3×15 mL). The combined organic layers were washed with brine, dried over $Na_2SO_4$, decanted, and concentrated to give a crude solid. After the hydrochloride salt was prepared, it was further purified by recrystallization from MeOH/EtOAc to give 57 mg (33%) of a white solid: mp 242.0–243.0° C.; $^1H$ NMR (300 MHz, DMSO) δ 9.13 (br s, 2H), 7.72 (d, J=1.7 Hz, 1H), 7.26 (m, 2H), 7.13 (d, J=1.7 Hz, 1H), 6.92 (t, J=7.4 Hz, 1H), 6.84 (d, J=7.9 Hz, 2H), 4.64 (m, 2H), 4.17 (m, 2H), 3.49 (m, 2H); $^{13}C$ NMR (300 MHz, DMSO) δ 157.7, 139.8, 136.7, 129.4, 125.2, 124.4, 121.5, 120.8, 120.0, 114.1, 110.4, 109.6, 66.5, 45.2, 43.6, 42.3, 22.3, 21.0; IR (diffuse reflectance) 2843, 2718, 2688, 2666, 2633, 2440, 1601, 1497, 1460, 1244, 1238, 845, 827, 754, 694 cm$^{-1}$; MS (EI) m/z 376, 374 (M$^+$), 339, 334, 333, 332, 78, 77, 65, 63; Anal. Calcd for $C_{20}H_{20}Cl_2N_2O·HCl$: C, 58.34; H, 5.14; N, 6.80; found: C, 58.10; H, 5.20; N, 6.76.

Preparation 93
Preparation of tert-Butyl 8,9-dichloro-6-(2-hydroxyethyl)-1,4,5,6-tetrahydroazepino[4,5-b]indole-3(2H)-carboxylate A solution tert-butyl 8,9-dichloro-6-(2-ethoxy-2-oxoethyl)-1,4,5,6-tetrahydroazepino[4,5-b]indole-3(2H)-carboxylate (0.95 g, 2.15 mmol) in dry THF (10 mL) was cooled to 0° C. Then, $LiBH_4$ (0.14 g, 6.43 mmol) was added and the reaction was allowed to warm slowly to rt. After 17 h, the reaction was diluted with $H_2O$ (50 mL) followed by addition of 10% aqueous NaOH (10 mL) and extraction with EtOAc (3×50 mL). The combined organic extracts were washed with brine, dried over $Na_2SO_4$, decanted, and concentrated. The crude product was first purified by two column chromatographies (Biotage, 40M) with heptane/EtOAc (1:1) and (Biotage, 40S) with heptane/EtOAc (2:1) to give 0.51 g of impure product. Finally, crystallization from $Et_2O$/heptane gave 0.45 g (52%) of pale yellow crystals: mp 130.5–133° C.; IR (diffuse reflectance) 3469, 2976, 2937, 2869, 1676, 1477, 1449, 1415, 1366, 1342, 1240, 1219, 1172, 1164, 853 cm$^{-1}$; MS (EI) m/z 398 (M$^+$), 400, 398, 342, 341, 270, 268, 86, 84, 57, 51; Anal. Calcd for $C_{19}H_{24}Cl_2N_2O_3$: C, 57.15; H, 6.06; N, 7.01; found: C, 57.24; H, 6.19; N, 6.95.

Preparation 94
Preparation of tert-Butyl 9,10-dichloro-6-(2-hydroxyethyl)-1,4,5,6-tetrahydroazepino[4,5-b]indole-3(2H)-carboxylate A solution tert-butyl 9,10-dichloro-6-(2-ethoxy-2-oxoethyl)-1,4,5,6-tetrahydroazepino[4,5-b]indole-3(2H)-carboxylate (1.0 g, 2.3 mmol) in dry THF (10 mL) was cooled to 0° C. Then, $LiBH_4$ (0.15 g, 6.8 mmol) was added and the reaction was allowed to warm slowly to rt. After 4 h, the reaction was diluted with $H_2O$ followed by addition of 10% aqueous NaOH and extraction with EtOAc (3×50 mL). The combined organic extracts were washed with brine, dried over $Na_2SO_4$, decanted, and concentrated. The crude product was purified by column chromatography (Biotage, 40M, SIM) with heptane/EtOAc (1:1) followed by crystallization from EtOAc/heptane gave 0.19 g (21%) of a white solid: mp 174.5–176.0° C.; IR (diffuse reflectance) 3419, 1662, 1466, 1447, 1424, 1370, 1359, 1275, 1248, 1170, 1157, 1120, 1078, 933, 799cm$^{-1}$; MS (EI) m/z 398 (M$^+$), 400, 398, 344, 342, 341, 268, 86, 84, 57, 51; Anal. Calcd for $C_{19}H_{24}Cl_2N_2O_3$: C, 57.15; H, 6.06; N, 7.01; found: C, 57.13; H, 6.13; N, 6.9.

Preparation 95
Preparation of tert-Butyl 7,8-dichloro-6-(2-ethoxy-2-oxoethyl)-1,4,5,6-tetrahydroazepino[4,5-b]indole-3(2H)-carboxylate Sodium hydride (60% dispersion in mineral oil, 0.25 g, 6.3 mmol) was added to a solution of tert-butyl 7,8-dichloro-1,4,5,6-tetrahydroazepino[4,5-b]indole-3(2H)-carboxylate (1.5 g, 4.2 mmol) in DMF (15 mL). After 20 min, ethyl bromoacetate (0.94 mL, 8.4 mmol) was added. The reaction was quenched with saturated aqueous $NH_4Cl$ after 2.5 h and extracted with EtOAc (3×20 mL). The combined organic extracts were washed with brine, dried over $Na_2SO_4$, decanted, and concentrated. The crude product was purified by column chromatography (Biotage, 40M) with heptane/EtOAc (3:1) followed by crystallization from MeOH/EtOAc to give 1.5 g (81%) of a white solid: mp 132.5–135.0° C.; IR (diffuse reflectance) 2974, 1747, 1683, 1465, 1450, 1416, 1365, 1303, 1255, 1216, 1195, 1170, 1155, 1115, 803 cm$^{-1}$; MS (EI) m/z 440 (M$^+$), 442, 440, 386, 385, 384, 311, 300, 298, 57, 56; Anal. Calcd for $C_{21}H_{26}Cl_2N_2O_4$: C, 57.15; H, 5.94; N, 6.35; found: C, 57.13; H, 5.98; N, 6.36.

Preparation 96
Preparation of tert-Butyl 7,8-dichloro-6-(2-hydroxyethyl)-1,4,5,6-tetrahydroazepino[4,5-b]indole-3(2H)-carboxylate A solution tert-butyl 7,8-dichloro-6-(2-ethoxy-2-oxoethyl)-1,4,5,6-tetrahydroazepino[4,5-b]indole-3(2H)-carboxylate (3.0 g, 6.8 mmol) in dry THF (30 mL) was cooled to 0° C. Then, $LiBH_4$ (0.74 g, 34 mmol) was added and the reaction was allowed to warm slowly to rt. Additional $LiBH_4$ (0.30 g, 14 mmol) was added after 24 h. After another 7 h, the reaction was diluted with $H_2O$ (75 mL) followed by addition of 10% aqueous NaOH and extraction with EtOAc (3×100 mL). The combined organic extracts were washed with brine, dried over $Na_2SO_4$, decanted, and concentrated. The crude product was purified by column chromatography (Biotage, 40M, SIM) with heptane/EtOAc (1:1) followed by crystallization from EtOAc/heptane gave 1.7 g (64%) of a white solid: mp 149.0–149.5° C.; IR (diffuse reflectance) 3420, 2974, 1665, 1482, 1468, 1445, 1414, 1365, 1334, 1240, 1220, 1168, 1151, 1122, 900 cm$^{-1}$; MS (EI) m/z 398 (M$^+$), 398, 342, 298, 270, 268, 258, 256, 212, 57, 56; Anal. Calcd for $C_{19}H_{24}Cl_2N_2O_3$: C, 57.15; H, 6.06; N, 7.01; found: C, 57.31; H, 6.10; N, 6.98

Preparation 97
Preparation of tert-Butyl 7,9-dichloro-6-(2-ethoxy-2-oxoethyl)-1,4,5,6-tetrahydroazepino[4,5-b]indole-3(2H)-carboxylate Sodium hydride (60% dispersion in mineral oil, 0.25 g, 6.3 mmol) was added to a solution of tert-butyl 7,9-dichloro-1,4,5,6-tetrahydroazepino[4,5-b]indole-3(2H)-carboxylate (1.5 g, 4.2 mmol) in DMF (15 mL). After 20 min, ethyl bromoacetate (0.94 mL, 8.4 mmol) was added.

The reaction was quenched with saturated aqueous NH$_4$Cl after 2 h and extracted with EtOAc (3×20 mL). The combined organic extracts were washed with brine, dried over Na$_2$SO$_4$, decanted, and concentrated. The crude product was purified by column chromatography (Biotage, 40M) with heptane/EtOAc (3:1) to give 1.8 g (98%) of a white solid: mp 117.0–120.0° C.; IR (diffuse reflectance) 2972, 1744, 1690, 1464, 1409, 1377, 1366, 1349, 1294, 1222, 1204, 1190, 1167, 1111, 861 cm$^{-1}$; MS (EI) m/z 440 (M$^+$), 440, 386, 385, 384, 339, 311, 310, 300, 298, 57; Anal. Calcd for C$_{21}$H$_{26}$Cl$_2$N$_2$O$_4$: C, 57.15; H, 5.94; N, 6.35; found: C, 56.97; H, 5.97; N, 6.19.

Preparation 98

Preparation of tert-Butyl 7,9-dichloro-6-(2-hydroxyethyl)-1,4,5,6-tetrahydroazepino[4,5-b]indole-3(2H)-carboxylate A solution tert-butyl 7,9-dichloro-6-(2-ethoxy-2-oxoethyl)-1,4,5,6-tetrahydroazepino[4,5-b]indole-3(2H)-carboxylate (3.00 g, 6.80 mmol) in dry THF (30 mL) was cooled to 0° C. Then, LiBH$_4$ (0.44 g, 20.2 mmol) was added and the reaction was allowed to warm slowly to rt. After 18 h, additional LiBH$_4$ (0.44 g, 20.2 mmol) was added. After an additional 24 h, the reaction was diluted with H$_2$O followed by addition of 10% aqueous NaOH and extraction with EtOAc. The combined organic extracts were washed with brine, dried over Na$_2$SO$_4$, decanted, and concentrated. The crude product was first purified by column chromatography (Biotage 40M, SIM) with heptane/EtOAc (1:1) to give 2.37 g of impure product. Then, crystallization from EtOAc/heptane gave 2.21 g (82%) of ivory crystals: mp 183–184° C.; IR (diffuse reflectance) 1693, 1658, 1468, 1448, 1433, 1406, 1380, 1370, 1347, 1323, 1293, 1226, 1166, 1064, 771 cm$^{-1}$; MS (EI) m/z 398 (M$^+$), 344, 342, 270, 268, 258, 256, 63, 57, 56. Anal. Calcd for C$_{19}$H$_{24}$Cl$_2$N$_2$O$_3$: C, 57.15; H, 6.06; N, 7.01; found: C, 57.20; H, 6.11; N, 6.95.

Preparation 99

Preparation of tert-Butyl 7,10-dichloro-6-(2-ethoxy-2-oxoethyl)-1,4,5,6-tetrahydroazepino[4,5-b]indole-3(2H)-carboxylate Sodium hydride (60% dispersion in mineral oil, 0.85 g, 21 mmol) was added to a solution of tert-butyl 7,10-dichloro-1,4,5,6-tetrahydroazepino[4,5-b]indole-3(2H)-carboxylate (5.0 g, 14 mmol) in DMF (75 mL). After 25 min, ethyl bromoacetate(3.1 mL, 28 mmol) was added. The reaction was quenched with saturated aqueous NH$_4$Cl after 3 h and extracted with EtOAc (3×100 mL). The combined organic extracts were washed with brine, dried over Na$_2$SO$_4$, decanted, and concentrated. The crude product was purified by column chromatography with heptane/EtOAc (3:1) to give 6.0 g (96%) of a white foam: mp 118.5–119.5° C.; IR (diffuse reflectance) 2976, 1747, 1674, 1477, 1457, 1420, 1405, 1370, 1366, 1344, 1254, 1200, 1165, 1111, 930 cm$^{-1}$; MS (EI) m/z 440 (M$^+$), 386, 384, 339, 310, 305, 300, 298, 224, 57, 56; Anal. Calcd for C$_{21}$H$_{26}$Cl$_2$N$_2$O$_4$: C, 57.15; H, 5.94; N, 6.35; found: C, 57.27; H, 6.01; N, 6.22.

Preparation 100

Preparation of tert-Butyl 7,10-dichloro-6-(2-hydroxyethyl)-1,4,5,6-tetrahydroazepino[4,5-b]indole-3(2H)-carboxylate A solution tert-butyl 7,10-dichloro-6-(2-ethoxy-2-oxoethyl)-1,4,5,6-tetrahydroazepino[4,5-b]indole-3(2H)-carboxylate (3.0 g, 6.8 mmol) in dry THF (30 mL) was cooled to 0° C. Then, LiBH$_4$ (0.74 g, 34 mmol) was added and the reaction was allowed to warm slowly to rt. Additional LiBH$_4$ (0.30 g, 14 mmol) was added after 24 h. After another 7 h, the reaction was diluted with H$_2$O (75 mL) followed by addition of 10% aqueous NaOH and extraction with EtOAc (3×100 mL). The combined organic extracts were washed with brine, dried over Na$_2$SO$_4$, decanted, and concentrated. The crude product was purified by column chromatography (Biotage, 40M, SIM) with heptane/EtOAc (1:1) followed by crystallization from EtOAc/heptane gave 1.8 g (65%) of a white solid: mp 156.0–158.5° C.; IR (diffuse reflectance) 1686, 1652, 1476, 1433, 1414, 1400, 1364, 1353, 1319, 1302, 1229, 1178, 1156, 1063, 972 cm$^{-1}$; MS (EI) m/z 398 (M$^+$), 398, 342, 270, 268, 263, 258, 256, 212, 57, 56; Anal. Calcd for C$_{19}$H$_{24}$Cl$_2$N$_2$O$_3$: C, 57.15; H, 6.06; N, 7.01; found: C, 57.23; H, 6.10; N, 7.00.

Preparation 101

Preparation of tert-Butyl 8,10-dichloro-6-(2-ethoxy-2-oxoethyl)-1,4,5,6-tetrahydroazepino[4,5-b]indole-3(2H)-carboxylate Sodium hydride (60% dispersion in mineral oil, 0.25 g, 6.3 mmol) was added to a solution of tert-butyl 8,10-dichloro-1,4,5,6-tetrahydroazepino[4,5-b]indole-3(2H)-carboxylate (1.5 g, 4.2 mmol) in DMF (15 mL). After 20 min, ethyl bromoacetate(0.94 mL, 8.4 mmol) was added. The reaction was quenched with saturated aqueous NH$_4$Cl after 1.5 h and extracted with EtOAc (3×20 mL). The combined organic extracts were washed with brine, dried over Na$_2$SO$_4$, decanted, and concentrated. The crude product was purified by column chromatography (Biotage, 40M) with heptane/EtOAc (3:1) followed by crystallization from MeOH/EtOAc to give 1.4 g (78%) of a white solid: mp 144.5–147.0° C.; IR (diffuse reflectance) 2982, 2972, 1748, 1690, 1456, 1411, 1373, 1366, 1352, 1252, 1222, 1202, 1159, 1115, 824 cm$^{-1}$; MS (EI) m/z 440 (M$^+$), 442, 440, 386, 384, 310, 300, 298, 86, 84, 57; Anal. Calcd for C$_{21}$H$_{26}$Cl$_2$N$_2$O$_4$: C, 57.15; H, 5.94; N, 6.35; found: C, 57.15; H, 6.04; N, 6.37

Preparation 102

Preparation of tert-Butyl 8,10-dichloro-6-(2-hydroxyethyl)-1,4,5,6-tetrahydroazepino[4,5-b]indole-3(2H)-carboxylate A solution of tert-butyl 8,10-dichloro-6-(2-ethoxy-2-oxoethyl)-1,4,5,6-tetrahydroazepino[4,5-b]indole-3(2H)-carboxylate (3.0 g, 6.8 mmol) in dry THF (30 mL) was cooled to 0° C. Then, LiBH$_4$ (0.74 g, 34 mmol) was added and the reaction was allowed to warm slowly to rt. After 24 h, the reaction was diluted with H$_2$O (75 mL) followed by addition of 10% aqueous NaOH (30 mL) and extraction with EtOAc (3×100 mL). The combined organic extracts were washed with brine, dried over Na$_2$SO$_4$, decanted, and concentrated. The crude product was purified by column chromatography (Biotage, 40M, SIM) with heptane/EtOAc (1:1) followed by crystallization from EtOAc/heptane gave 1.6 g (58%) of a white solid: mp 166.5–167.0° C.; IR (diffuse reflectance) 3462, 1665, 1458, 1426, 1367, 1362, 1342, 1264, 1249, 1165, 1115, 1081, 931, 828, 820cm$^{-1}$; MS (EI) m/z 398 (M$^+$), 398, 342, 341, 298, 270, 268, 258, 256, 57, 56; Anal. Calcd for C$_{19}$H$_{24}$Cl$_2$N$_2$O$_3$: C, 57.15; H, 6.06; N, 7.01; found: C, 57.08; H, 6.08; N, 6.97.

EXAMPLES 252–307

Using the following general procedure the compounds of Examples 251–306 were prepared.

The appropriate aryl alcohol (0.50 mmol) was added to a 20 mL scintillation vial followed by the addition of a stock solution of the appropriate dichloroazepinoindole alcohol (0.10 g, 0.25 mmol) and PPh$_3$ (99 mg, 0.38 mmol) in THF (5 mL). Next, a stock solution of DBAD (87 mg, 0.38 mmol) in THF (3 mL) was added to each vial. The vials were capped, placed in a J-KEM® heater block attached to a Lab-Line® orbit shaker and shaken (250 RPM) at 40° C. overnight. A subset of the reactions was monitored by LC/MS. After all the starting alcohol was consumed in these reactions, MeOH (3 mL) and Dowex® 50WX2-400 ion-exchange resin (0.75 g) was added to each vial. The reactions were then shaken (300 RPM) at 40° C. until the product was on the resin, based on LC/MS monitoring. The vials were cooled to rt and transferred with 2×5 mL of CH$_2$Cl$_2$/MeOH (3:1) to disposable fritted syringe barrels on a syringe washing station. The resin was then rinsed with 3×10 mL of pyridine/MeOH (3:7), 1×10 mL of CH$_2$Cl$_2$, and 3×10 mL of MeOH. The syringe barrels were then transferred to a vacuum manifold and the product was eluted off the resin with a total of 10×5 mL of MeOH/NH$_4$OH (3:1) into two 40 mL scintillation vials for each compound. The vials were blown down under nitrogen and followed by further drying in the vacuum oven overnight at 47° C. to give product. The products were evaluated by HPLC and MS or LC/MS.

EXAMPLE 252

8,9-Dichloro-6-{2-[(5,7-dibromo-8-quinolinyl)oxy]ethyl}-1,2,3,4,5,6-hexahydroazepino[4,5-b]indole;

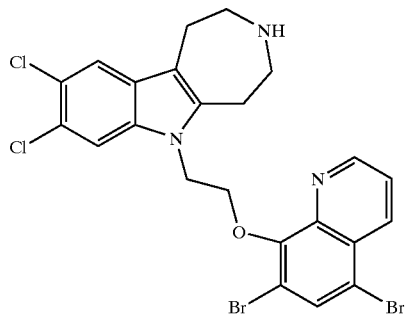

MS (ESI+) 583.3 m/z (MH$^+$).

EXAMPLE 253

9,10-Dichloro-6-{2-[(5,7-dibromo-8-quinolinyl)oxy]ethyl}-1,2,3,4,5,6-hexahydroazepino[4,5-b]indole;

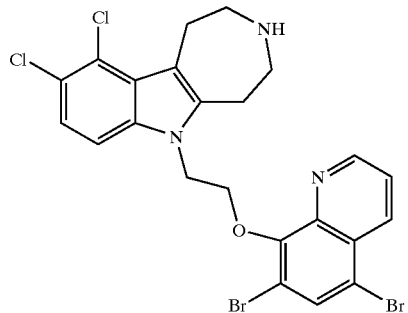

MS (ESI+) 583.8 m/z (MH$^+$).

EXAMPLE 254

7,8-Dichloro-6-{2-[(5,7-dibromo-8-quinolinyl)oxy]ethyl}-1,2,3,4,5,6-hexahydroazepino[4,5-b]indole:

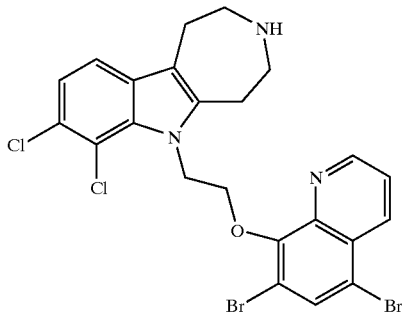

MS (ESI+) 583.8 m/z (MH$^+$).

EXAMPLE 255

7,9-Dichloro-6-{2-[(5,7-dibromo-8-quinolinyl)oxy]ethyl}-1,2,3,4,5,6-hexahydroazepino[4,5-b]indole:

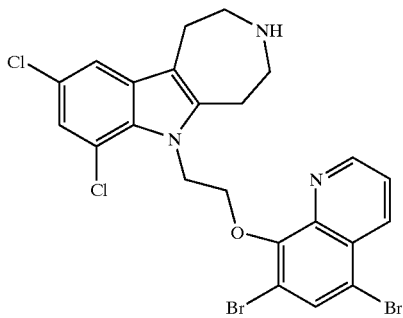

MS (ESI+) 583.8 m/z (MH$^+$).

EXAMPLE 256

7,10-Dichloro-6-{2-[(5,7-dibromo-8-quinolinyl)oxy]ethyl}-1,2,3,4,5,6-hexahydroazepino[4,5-b]indole:

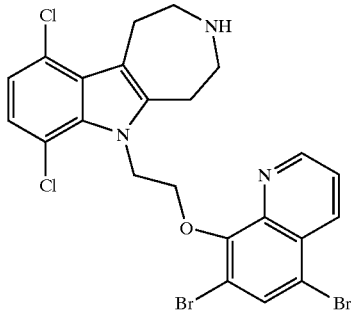

MS (ESI+) 583.8 mz (MH$^+$).

EXAMPLE 257

8,10-Dichloro-6-{2-[(5,7-dibromo-8-quinolinyl)oxy]ethyl}-1,2,3,4,5,6-hexahydroazepino[4,5-b]indole:

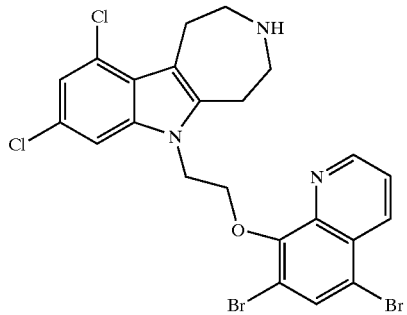

MS (ESI+) 583.8 m/z (MH+).

EXAMPLE 258

8,9-Dichloro-6-{2-(8-quinolinyloxy)ethyl}-1,2,3,4,5,6-hexahydroazepino[4,5-b]indole:

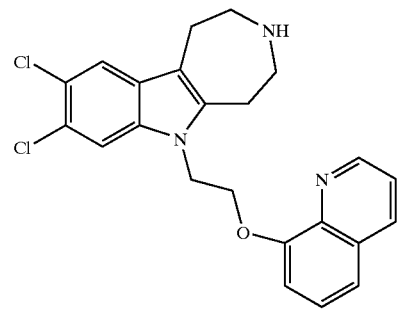

MS (ESI+) 425.8 m/z (MH+).

EXAMPLE 259

9,10-Dichloro-6-[2-(8-quinolinyloxy)ethyl]-1,2,3,4,5,6-hexahydroazepino[4,5-b]indole:

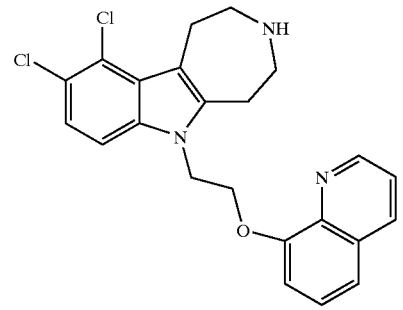

MS (ESI+) 426.0 m/z (MH+).

EXAMPLE 260

7,8-Dichloro-6-[2-(8-quinolinyloxy)ethyl]-1,2,3,4,5,6-hexahydroazepino[4,5-b]indole:

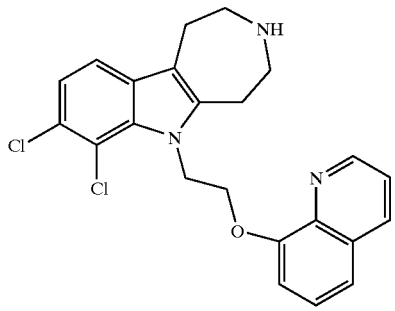

MS (ESI+) 426.0 m/z (MH+).

EXAMPLE 261

7,9-Dichloro-6-[2-(8-quinolinyloxy)ethyl]-1,2,3,4,5,6-hexahydroazepino[4,5-b]indole:

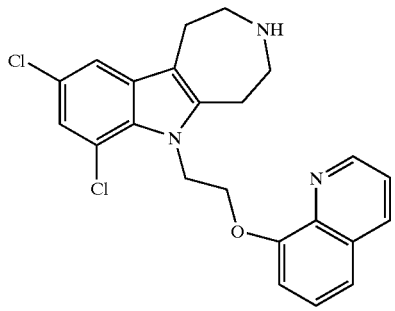

MS (ESI+) 426.1 m/z (MH+).

EXAMPLE 262

7,10-Dichloro-6-[2-(8-quinolinyloxy)ethyl]-1,2,3,4,5,6-hexahydroazepino[4,5-b]indole:

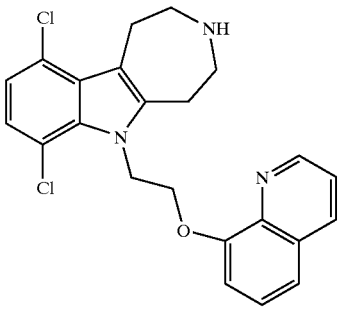

MS (ESI+) 425.9 m/z (MH+).

EXAMPLE 263

8,10-Dichloro-6-[2-(8-quinolinyloxy)ethyl]-1,2,3,4,5,6-hexahydroazepino[4,5-b]indole:

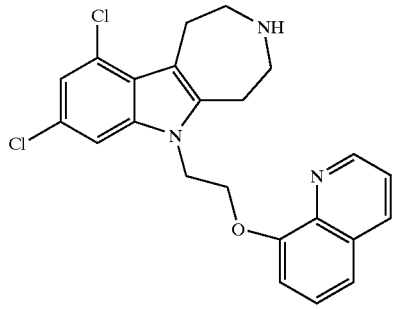

MS (ESI+) 426.0 m/z (MH$^+$).

EXAMPLE 264

8,9-Dichloro-6-[2-(5-isoquinolinyloxy)ethyl]-1,2,3,4,5,6-hexahydroazepino[4,5-b]indole:

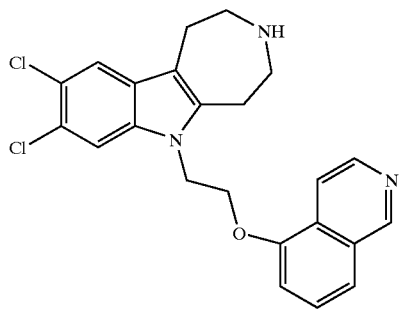

MS (ESI+) 425.8 m/z (MH$^+$).

EXAMPLE 265

7,8-Dichloro-6-[2-(5-isoquinolinyloxy)ethyl]-1,2,3,4,5,6-hexahydroazepino[4,5-b]indole:

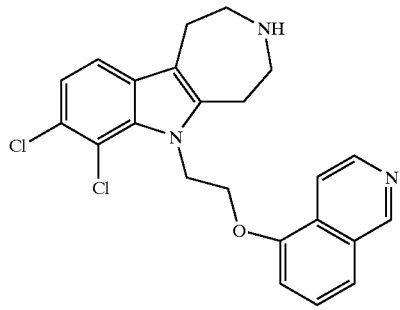

MS (ESI+) 425.9 m/z (MH$^+$).

EXAMPLE 266

7,9-Dichloro-6-[2-(5-isoquinolinyloxy)ethyl]-1,2,3,4,5,6-hexahydroazepino[4,5-b]indole:

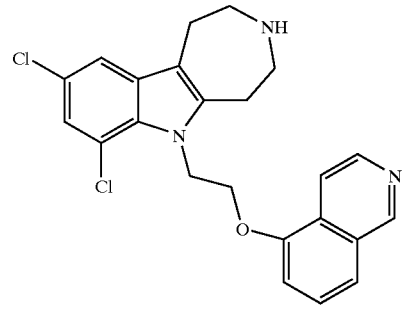

MS (ESI+) 426.1 m/z (MH$^+$).

EXAMPLE 267

8,10-Dichloro-6-[2-(5-isoquinolinyloxy)ethyl]-1,2,3,4,5,6-hexahydroazepino[4,5-b]indole:

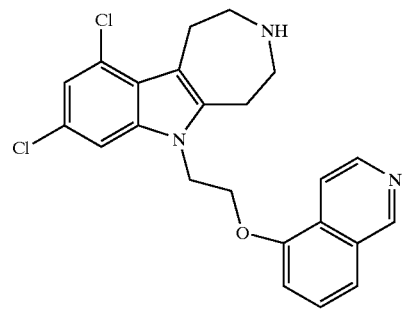

MS (ESI+) 426.1 m/z (MH$^+$).

EXAMPLE 268

8,9-Dichloro-6-[2-(5-quinolinyloxy)ethyl]-1,2,3,4,5,6-hexahydroazepino[4,5-b]indole:

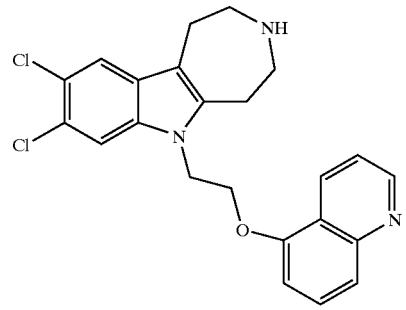

MS (ESI+) 425.8 m/z (MH$^+$).

EXAMPLE 269

9,10-Dichloro-6-[2-(5-quinolinyloxy)ethyl]-1,2,3,4,5,6-hexahydroazepino[4,5-b]indole:

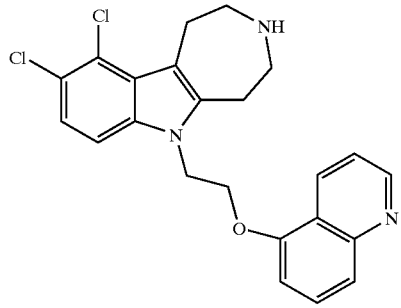

MS (ESI+) 426.0 m/z (MH$^+$).

EXAMPLE 270

7,8-Dichloro-6-[2-(5-quinolinyloxy)ethyl]-1,2,3,4,5,6-hexahydroazepino[4,5-b]indole:

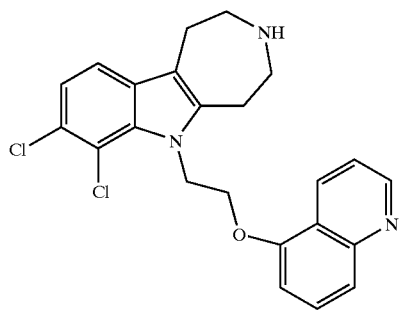

MS (ESI+) 426.1 m/z (MH$^+$).

EXAMPLE 271

7,9-Dichloro-6-[2-(5-quinolinyloxy)ethyl]-1,2,3,4,5,6-hexahydroazepino[4,5-b]indole:

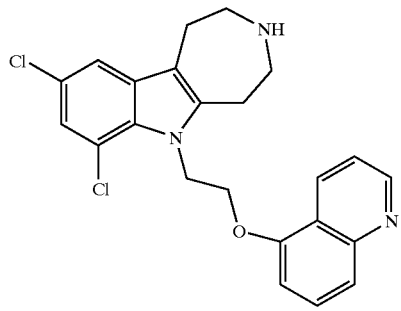

MS (ESI+) 426.1 m/z (MH$^+$).

EXAMPLE 272

7,10-Dichloro-6-[2-(5-quinolinyloxy)ethyl]-1,2,3,4,5,6-hexahydroazepino[4,5-b]indole:

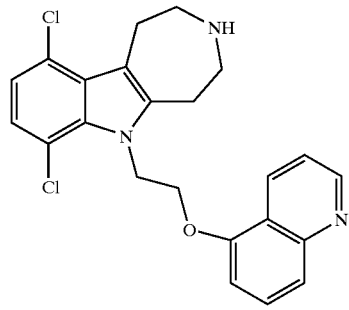

MS (ESI+) 425.9 m/z (MH$^+$).

EXAMPLE 273

8,10-Dichloro-6-[2-(5-quinolinyloxy)ethyl]-1,2,3,4,5,6-hexahydroazepino[4,5-b]indole:

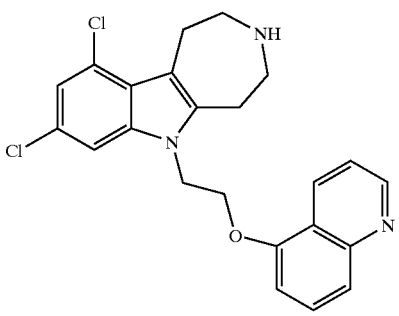

MS (ESI+) 426.0 m/z (MH$^+$).

EXAMPLE 274

8,9-Dichloro-6-[2-(5,6,7,8-tetrahydro-1-naphthalenyloxy)ethyl]-1,2,3,4,5,6-hexahydroazepino[4,5-b]indole:

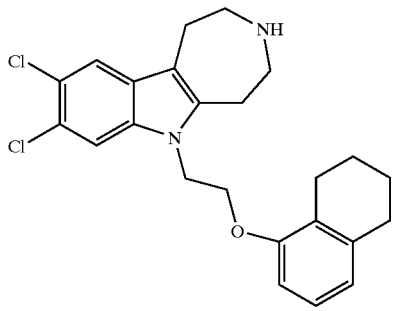

MS (ESI+) 428.8 m/z (MH$^+$).

EXAMPLE 275

9,10-Dichloro-6-[2-(5,6,7,8-tetrahydro-1-naphthalenyloxy)ethyl]-1,2,3,4,5,6-hexahydroazepino[4,5-b]indole:

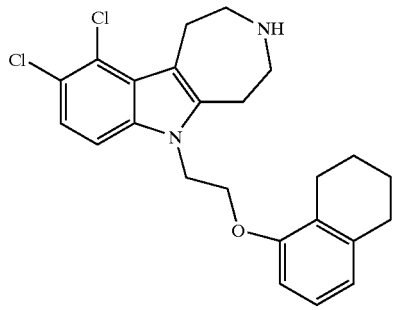

MS (ESI+) 429.1 m/z (MH+).

EXAMPLE 276

7,8-Dichloro-6-[2-(5,6,7,8-tetrahydro-1-naphthalenyloxy)ethyl]-1,2,3,4,5,6-hexahydroazepino[4,5-b]indole:

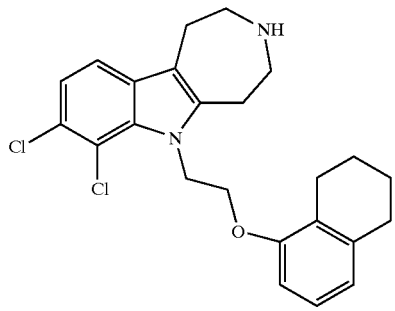

MS (ESI+) 429.1 m/z (MH+).

EXAMPLE 277

7,9-Dichloro-6-[2-(5,6,7,8-tetrahydro-1-naphthalenyloxy)ethyl]-1,2,3,4,5,6-hexahydroazepino[4,5-b]indole:

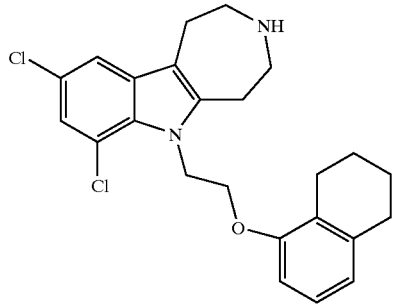

MS (ESI+) 429.1 m/z (MH+).

EXAMPLE 278

7,10-Dichloro-6-[2-(5,6,7,8-tetrahydro-1-naphthalenyloxy)ethyl]-1,2,3,4,5,6-hexahydroazepino[4,5-b]indole:

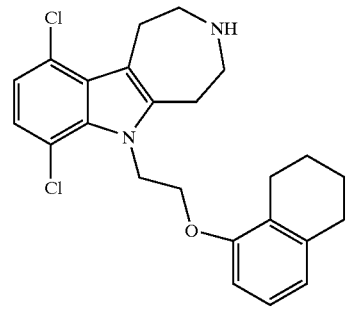

MS (ESI+) 429.0 m/z (MH+).

EXAMPLE 279

8,10-Dichloro-6-[2-(5,6,7,8-tetrahydro-1-naphthalenyloxy)ethyl]-1,2,3,4,5,6-hexahydroazepino[4,5-b]indole:

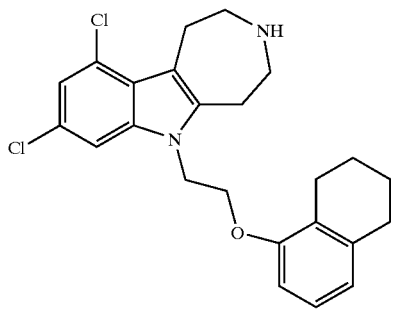

MS (ESI+) 429.1 m/z (MH+).

EXAMPLE 280

6-[2-(1,3-Benzodioxol-5-yloxy)ethyl]-8,9-dichloro-1,2,3,4,5,6-hexahydroazepino[4,5-b]indole:

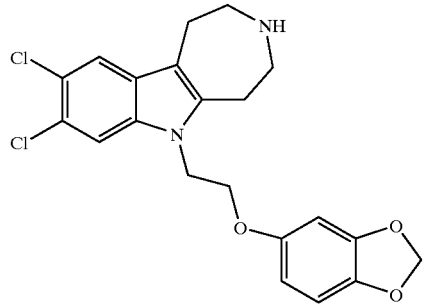

MS (ESI+) 418.7 m/z (MH+).

EXAMPLE 281

6-[2-(1,3-Benzodioxol-5-yloxy)ethyl]-9,10-dichloro-1,2,3,4,5,6-hexahydroazepino[4,5-b]indole:

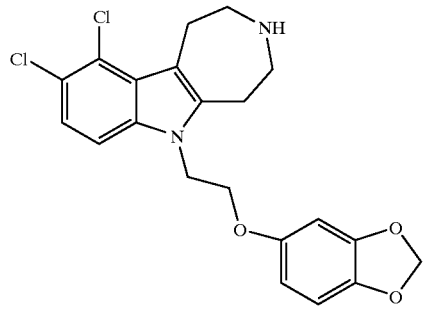

MS (ESI+) 419.0 m/z (MH+).

EXAMPLE 282

6-[2-(1,3-Benzodioxol-5-yloxy)ethyl]-7,8-dichloro-1,2,3,4,5,6-hexahydroazepino[4,5-b]indole:

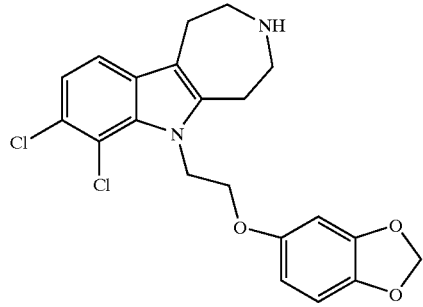

MS (ESI+) 419.0 m/z (MH+).

EXAMPLE 283

6-[2-(1,3-Benzodioxol-5-yloxy)ethyl]-7,9-dichloro-1,2,3,4,5,6-hexahydroazepino[4,5-b]indole:

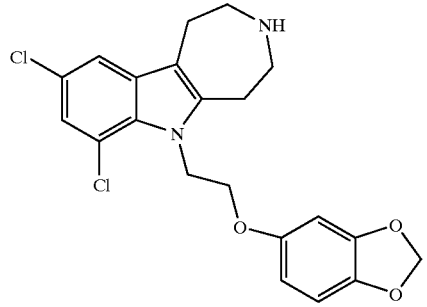

MS (EST+) 419.1 m/z (MH+).

EXAMPLE 284

6-[2-(1,3-Benzodioxol-5-yloxy)ethyl]-7,10-dichloro-1,2,3,4,5,6-hexahydroazepino[4,5-b]indole:

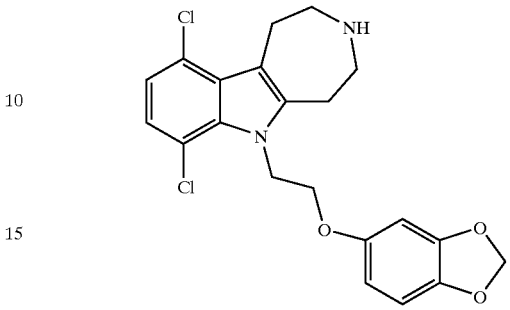

MS (ESI+) 419.0 m/z (MH+).

EXAMPLE 285

6-[2-(1,3-Benzodioxol-5-yloxy)ethyl]-8,10-dichloro-1,2,3,4,5,6-hexahydroazepino[4,5-b]indole:

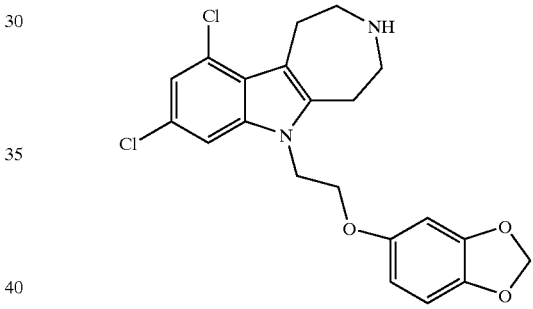

MS (ESI+) 419.0 m/z (MH+).

EXAMPLE 286

8,9-Dichloro-6-[2-(1H-indol-4-yloxy)ethyl]-1,2,3,4,5,6-hexahydroazepino[4,5-b]indole:

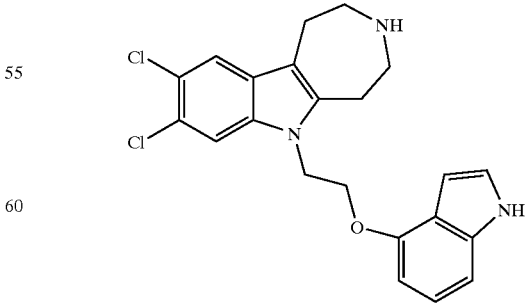

MS (ESI+) 414.1 m/z (MH+).

EXAMPLE 287

9,10-Dichloro-6-[2-(1H-indol-4-yloxy)ethyl]-1,2,3,4,5,6-hexahydroazepino[4,5-b]indole:

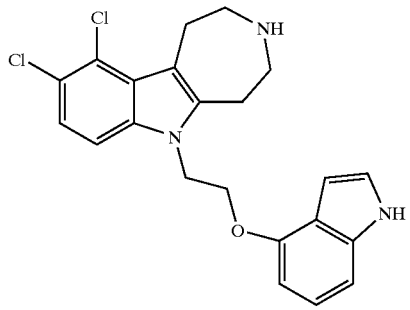

MS (ESI+) 414.1 n/z (MH+).

EXAMPLE 288

7,8-Dichloro-6-[2-(1H-indol-4-yloxy)ethyl]-1,2,3,4,5,6-hexahydroazepino[4,5-b]indole:

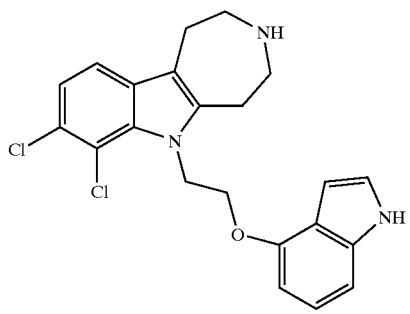

MS (ESI+) 414.1 m/z (MH+).

EXAMPLE 289

8,10-Dichloro-6-[2-(1H-indol-4-yloxy)ethyl]-1,2,3,4,5,6-hexahydroazepino[4,5-b]indole:

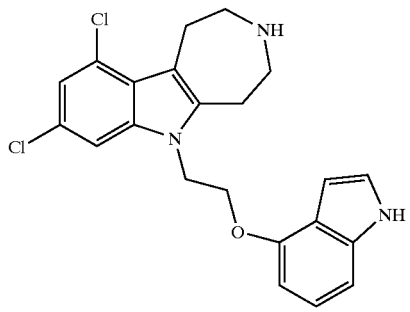

MS (ESI+) 414.1 m/z (MH+).

EXAMPLE 290

8,9-Dichloro-6-[2-(5,6,7,8-tetrahydro-2-naphthalenyloxy)ethyl]-1,2,3,4,5,6-hexahydroazepino[4,5-b]indole:

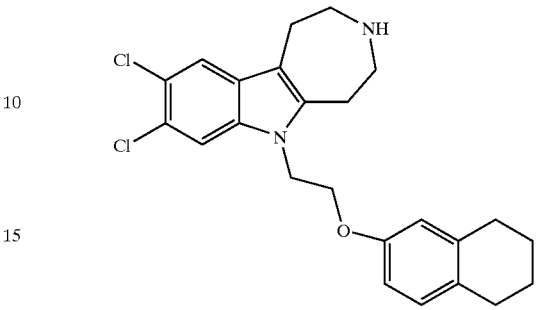

MS (ESI+) 429.3 m/z (MH+).

EXAMPLE 291

9,10-Dichloro-6-[2-(5,6,7,8-tetrahydro-2-naphthalenyloxy)ethyl]-1,2,3,4,5,6-hexahydroazepino[4,5-b]indole:

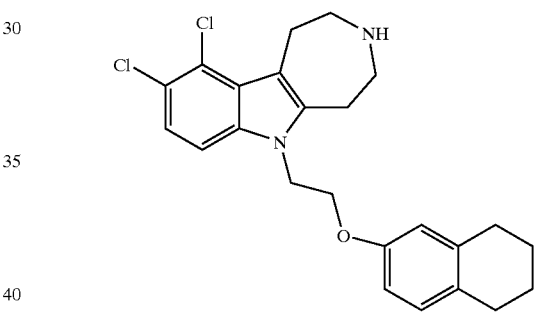

MS (ESI+) 429.1 m/z (MH+).

EXAMPLE 292

7,8-Dichloro-6-[2-(5,6,7,8-tetrahydro-2-naphthalenyloxy)ethyl]-1,2,3,4,5,6-hexahydroazepino[4,5-b]indole:

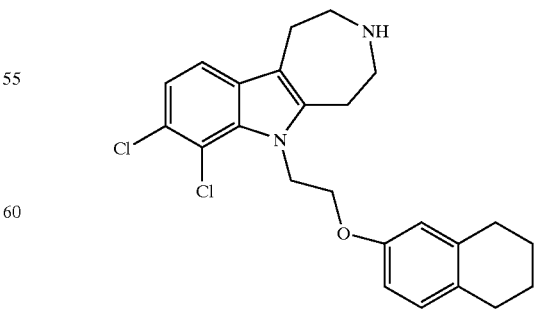

MS (ESI+) 429.1 m/z (MH+).

EXAMPLE 293

7,9-Dichloro-6-[2-(5,6,7,8-tetrahydro-2-naphthalenyloxy)ethyl]-1,2,3,4,5,6-hexahydroazepino[4,5-b]indole:

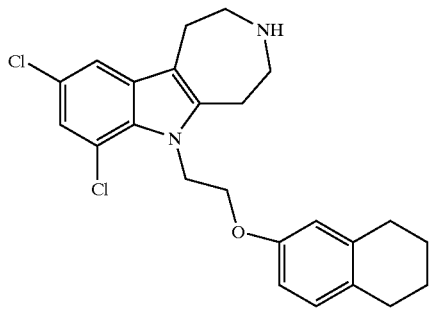

MS (ESI+) 429.1 m/z (MH$^+$).

EXAMPLE 294

7,10-Dichloro-6-[2-(5,6,7,8-tetrahydro-2-naphthalenyloxy)ethyl]-1,2,3,4,5,6-hexahydroazepino[4,5-b]indole:

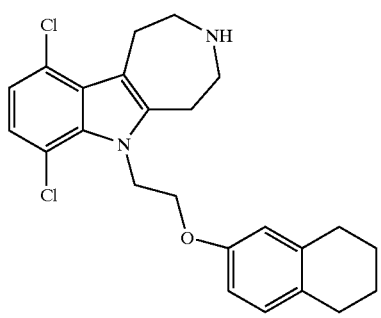

MS (ESI+) 429.0 m/z (MH$^+$).

EXAMPLE 295

8,10-Dichloro-6-[2-(5,6,7,8-tetrahydro-2-naphthalenyloxy)ethyl]-1,2,3,4,5,6-hexahydroazepino[4,5-b]indole:

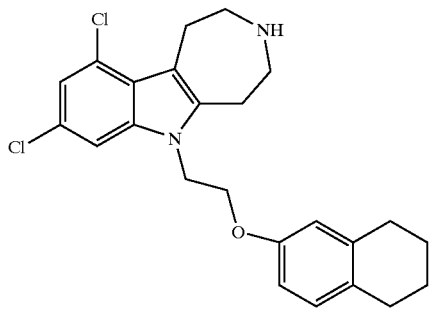

MS (ESI+) 429.1 m/z (MH$^+$).

EXAMPLE 296

8,9-Dichloro-6-[2-(7-quinolinyloxy)ethyl]-1,2,3,4,5,6-hexahydroazepino[4,5-b]indole:

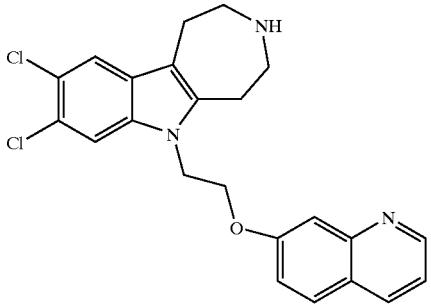

MS (ESI+) 426.2 m/z (MH$^+$).

EXAMPLE 297

9,10-Dichloro-6-[2-(7-quinolinyloxy)ethyl]-1,2,3,4,5,6-hexahydroazepino[4,5-b]indole:

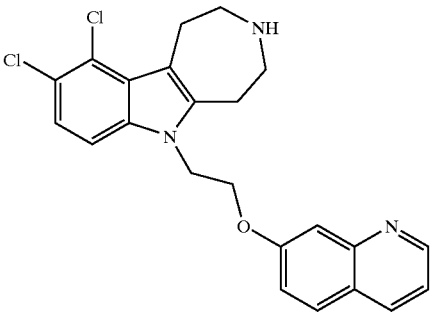

MS (ESI+) 426.1 m/z (MH$^+$).

EXAMPLE 298

7,8-Dichloro-6-[2-(7-quinolinyloxy)ethyl]-1,2,3,4,5,6-hexahydroazepino[4,5-b]indole:

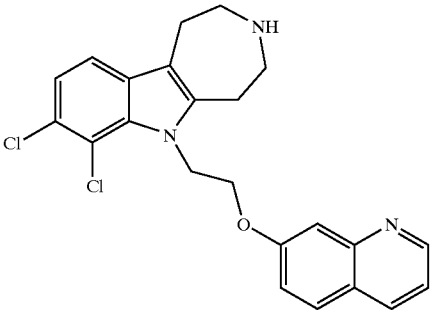

MS (ESI+) 426.1 m/z (MH$^+$).

EXAMPLE 299

7,9-Dichloro-6-[2-(7-quinolinyloxy)ethyl]-1,2,3,4,5,6-hexahydroazepino[4,5-b]indole:

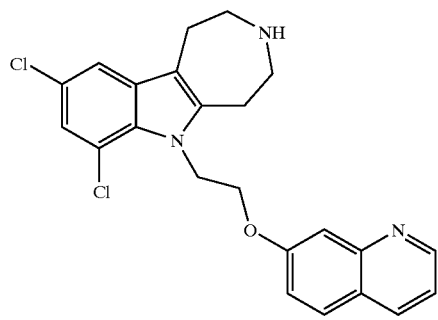

MS (ESI+) 426.1 m/z (MH+).

EXAMPLE 300

7,10-Dichloro-6-[2-(7-quinolinyloxy)ethyl]-1,2,3,4,5,6-hexahydroazepino[4,5-b]indole:

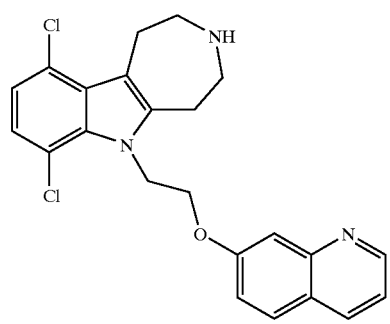

MS (ESI+) 426.0 m/z (MH+).

EXAMPLE 301

8,10-Dichloro-6-[2-(7-quinolinyloxy)ethyl]-1,2,3,4,5,6-hexahydroazepino[4,5-b]indole:

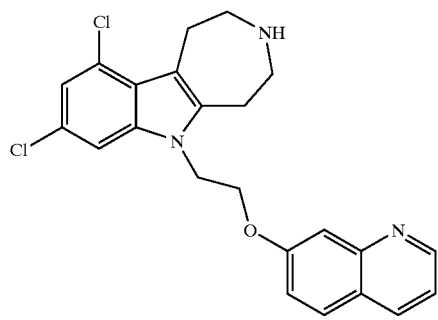

MS (ESI+) 426.0 m/z (MH+).

EXAMPLE 302

8,9-Dichloro-6-{2-[(5,5-dimethyl-5,6,7,8-tetrahydronaphthalen-1-yl)oxy]ethyl}1,2,3,4,5,6-hexahydroazepino[4,5-b]indole:

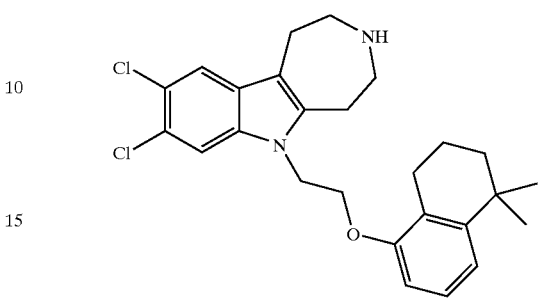

MS (ESI+) 457.2 m/z (MH+).

EXAMPLE 303

9,10-Dichloro-6-{2-[(5,5-dimethyl-5,6,7,8-tetrahydronaphthalen-1-yl)oxy]ethyl}1,2,3,4,5,6-hexahydroazepino[4,5-b]indole:

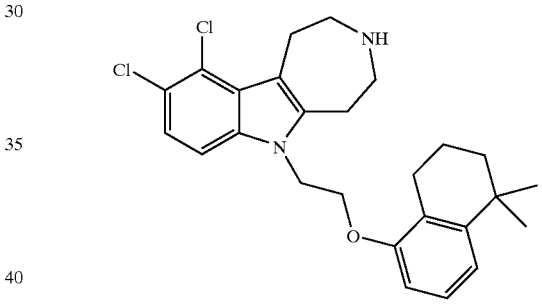

MS (ESI+) 457.2 m/z (MH+).

EXAMPLE 304

7,8-Dichloro-6-{2-[(5,5-dimethyl-5,6,7,8-tetrahydronaphthalen-1-yl)oxy]ethyl}-1,2,3,4,5,6-hexahydroazepino[4,5-b]indole:

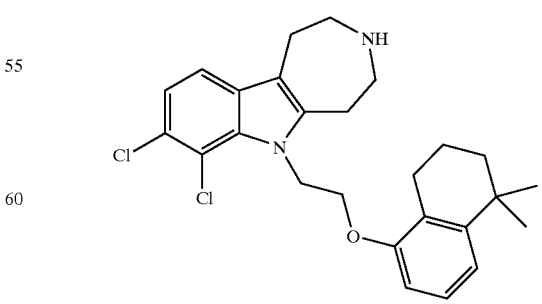

MS (ESI+) 457.2 m/z (MH+).

EXAMPLE 305

7,9-Dichloro-6-{2-[(5,5-dimethyl-5,6,7,8-tetrahydronaphthalen-1-yl)oxy]ethyl}-1,2,3,4,5,6-hexahydroazepino[4,5-b]indole:

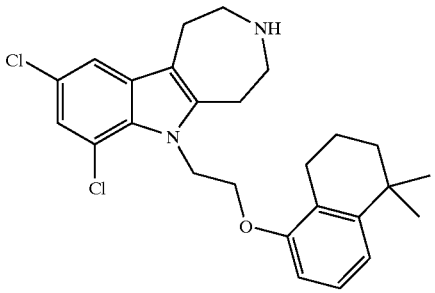

MS (ESI+) 457.2 m/z (MH+).

EXAMPLE 306

7,10-Dichloro-6-{2-[(5,5-dimethyl-5,6,7,8-tetrahydronaphthalen-1-yl)oxy]ethyl}1,2,3,4,5,6-hexahydroazepino[4,5-b]indole:

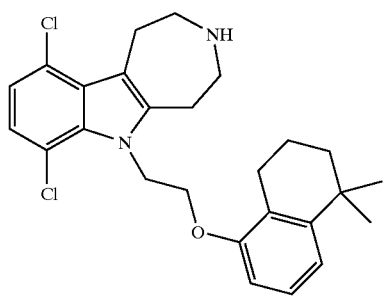

MS (ESI+) 457.2 m/z (MH+).

EXAMPLE 307

8,10-Dichloro-6-{2-[(5,5-dimethyl-5,6,7,8-tetrahydronaphthalen-1-yl)oxy]ethyl}-1,2,3,4,5,6-hexahydroazepino[4,5-b]indole:

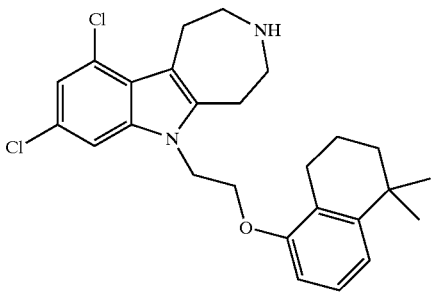

MS (ESI+) 457.2 m/z (MH+).

Preparation 103

Preparation of 3-tert-butyloxycarbonyl-9-bromo-1,2,3,4,5,6-hexahydroazepino[4,5-b]indole In a 500 mL round-bottomed flask a mixture of 3-benzoyl-9-bromo-1,2,3,4,5,6-hexahydroazepino[4,5-b]indole (12.9 g, 35.0 mmol), KOH (9.8 g, 175 mmol), and ethylene glycol (250 mL) was heated at 140° C. overnight. The mixture was cooled to 0° C. and dioxane (150 mL) and Boc$_2$O (8.4 g, 38.5 mmol) were added and stirred for 1 h. The bath was removed and the mixture was stirred at room temperature for 18 h, and then heated at 100° C. for 6 h. Heat was removed and the mixture was allowed to stir at room temperature for 72 h. Dioxane was removed under reduced pressure and the resulting mixture was partitioned between CHCl$_3$ and water. The aqueous layer was extracted a second time with CHCl$_3$ and the combined organic layers were washed with water and concentrated to give 12.5 g of an oily brown foam. A precipitate formed upon dissolution in CHCl$_3$ and was filtered to give 3.21 g (25%) of title compound as an off-white solid. 3.65 g of additional material obtained from a second precipitation contained 20% impurity. Column chromatography of the second lot of mother liquors (elution with 20–50% EtOAc/heptane) gave an additional 1.3 g (10%) of the title compound as a yellow solid. The mixture was resubmitted to the reaction conditions and the resulting 3.27 g (25%) of the title compound obtained as an off-white solid was submitted for analysis: mp 200–203° C. (dec); $^1$H NMR (400 MHz, CDCl$_3$) δ 7.96 (br s, 1 H), 7.56 (s, 1 H), 7.19 (dd, J=1.7, 8.5 Hz, 1 H), 7.12 (d, J=8.5 Hz, 1 H), 3.73–3.62 (m, 4 H), 3.03–2.95 (m, 2 H), 2.95–2.86 (m, 2 H), 1.49 (s, 9 H); IR (drift) 3294, 1667, 1478, 1423, 1366, 1326, 1286, 1266, 1249, 1238, 1169, 1118, 927, 857, 790 cm$^{-1}$.

Preparation 104

Preparation of 3-(tert-Butyloxycarbonyl)-9-(4,4,5,5-tetramethyl-1,3,2-dioxaborolan-2-yl)-1,2,3,4,5,6-hexahydroazepino[4,5-b]indole.

Following the general procedure of

Preparation 9, but starting with 3-(tert-butyloxycarbonyl)-9-bromo-1,2,3,4,5,6-hexahydroazepino[4,5-b]indole (6.50 g, 17.8 mmol), the title compound was obtained as a yellow solid (2.70 g, 37%): mp 234–237° C.; $^1$H NMR (300 MHz, CDCl$_3$) δ 7.99 (s, 1 H), 7.82 (br s, 1 H), 7.57 (d, J=8 Hz, 1 H), 7.26–7.24 (m, 1 H), 3.75–3.60 (m, 4 H), 3.07–2.93 (m, 4 H), 1.48 (s, 9 H), 1.36 (s, 12 H). MS (FAB) m/z 413 (M+H$^{30}$), 412, 411, 358, 357, 356, 355, 354, 282, 57; HRMS (EI) calcd for C$_{23}$H$_{33}$BN$_2$O$_4$ 412.2533, found 412.2541.

Preparation 105

Preparation of tert-Butyl 9-(2,6-difluorophenyl)-1,4,5,6-tetrahydroazepino-[4,5-b]indole-3(2H)-carboxylate.

A solution 1-bromo-2,6-difluorobenzene (0.28 g, 1.5 mmol) in dioxane (12 mL) was added to a flask charged with 3-(tert-butyloxycarbonyl)-9-(4,4,5,5-tetramethyl-1,3,2-dioxaborolan-2-yl)-1,2,3,4,5,6-hexahydroazepino[4,5-b]indole (0.50 g, 1.2 mmol), Pd$_2$(dba)$_3$ (0.11 g, 0.12 mmol) and potassium phosphate(0.59 g, 2.8 mmol). Next, trimethylphosphite (0.045 mL, 0.38 mmol) was added and the mixture was heated to 95° C. After 28.5 h, the reaction was cooled to rt, diluted with H$_2$O, and extracted with EtOAc (3×50 mL). The combined organic extracts were washed with brine, dried over Na$_2$SO$_4$, decanted, and concentrated. The crude product was purified by column chromatography (Biotage, 40M, SIM) with heptane/EtOAc (4:1) to give 0.38 g (80%) of a pale yellow solid: mp 225.5–226° C.; % water (KF): 0.10; melt solvate: 1.46% CH$_2$Cl$_2$; 0.19% EtOAc; Anal. Calcd for C$_{23}$H$_{24}$F$_2$N$_2$O$_2$.0.10% H$_2$O.1.46% CH$_2$Cl$_2$.0.19% EtOAc: C, 68.34; H, 6.19; N, 6.91; found: C, 68.34; H, 6.19; N, 6.81.

EXAMPLE 308

9-(2,6-Difluorophenyl)-1,2,3,4,5,6-hexahydroazepino[4,5-b]indole hydrochloride

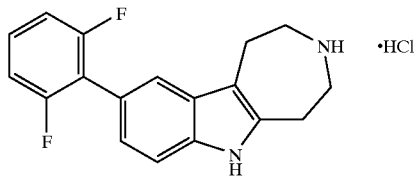

TFA (1.9 mL, 25 mmol) was added to a mixture of tert-butyl 9-(2,6-difluorophenyl)-1,4,5,6-tetrahydroazepino[4,5-b]indole-3(2H)-carboxylate (0.48 g, 1.2 mmol) in $CH_2Cl_2$ (25 mL). After 1 h, the reaction was quenched with 10% aqueous NaOH and diluted with $H_2O$. The layers were separated and the aqueous layer was extracted with $CH_2Cl_2$ (3×25 mL). The combined organic extracts were washed with brine, dried over $Na_2SO_4$, decanted, and concentrated. The crude product was purified by column chromatography (Biotage, 40S, SIM) with $CH_2Cl_2$/MeOH/$NH_4OH$ (976:21:3) to give 0.30 g (85%) of the free base. The HCl salt was prepared from 100 mg of free base as a gray-brown solid (73 mg): mp 285.5–287.5° C.; IR (diffuse reflectance) 3226, 2949, 2827, 2800, 2753, 1589, 1468, 1449, 1425, 1268, 1228, 995, 802, 780, 731 $cm^{-1}$; MS (EI) m/z 298 ($M^+$), 269, 268, 257, 256, 255, 78, 64, 63, 62; Anal. Calcd for $C_{18}H_{16}F_2N_2 \cdot HCl$: C, 64.57; H, 5.12; N, 8.37; found: C, 64.51; H, 5.22; N, 8.29.

Preparation 106

Preparation of 3-Benzoyl-9-(4-methoxy-2-methylphenyl)-1,2,3,4,5,6-hexahydroazepino[4,5-b]indole.

A solution of 3-benzoyl-9-bromo-1,2,3,4,5,6-hexahydroazepino[4,5-b]indole (1.50 g, 4.06 mmol) in DME (50 mL) was degassed via sonication and vacuum/$N_2$ purge. Then, $(PhP_3)_4Pd$ (0.235 g, 0.203 mmol) was added and the mixture was stirred for 20 min prior to the addition of a solution of tris(4-methoxy-2-methylphenyl)boroxin (0.900 g, 2.03 mmol) in DME (10 mL) and MeOH (2.5 mL). Next, 2M $Na_2CO_3$ (12 mL) was added and the reaction was heated to reflux. After 7 h, additional $(PhP_3)_4Pd$ (0.235 g, 0.203 mmol) was added. The reaction was cooled to rt after an additional 15 h. The reaction was partitioned between $H_2O$ and EtOAc and the layers were separated. The aqueous layer was extracted with additional EtOAc (2×100 mL). The combined organic extracts were washed with brine, dried over $Na_2SO_4$, decanted, and concentrated. The crude product was purified by column chromatography (Biotage, 40M) with heptane/EtOAc (gradient, 2:1 to 1:1) to give 0.61 (37%) of the title compound. An analytical sample was prepared, via crystallization from heptane/EtOAc, as an off-white solid: mp 268.5–271.5° C.; IR (diffuse reflectance) 3297, 3250, 3243, 3202, 1608, 1500, 1467, 1430, 1300, 1289, 1276, 1233, 786, 740, 706 $cm^{-1}$; MS (EI) m/z 410 ($M^+$), 290, 289, 288, 276, 105, 86, 77, 51, 50; HRMS (FAB) calcd for $C_{27}H_{26}N_2O_2+H$ 411.2072, found 411.2073; % water (KF): 0.23; melt solvate: 1.91% EtOAc, 0.15% heptane; Anal. Calcd for $C_{27}H_{26}N_2O_2 \cdot 0.23\%$ $H_2O \cdot 1.91\%$ EtOAc-0.15% heptane: C, 78.36; H, 6.46; N, 6.67; found: C, 78.16; H, 6.47; N, 6.91.

EXAMPLE 309

9-(4-Methoxy-2-methylphenyl)-1,2,3,4,5,6-hexahydroazepino[4,5-b]indole hydrochloride

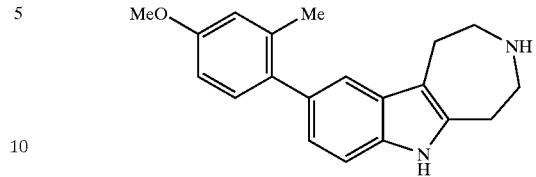

A mixture of 3-benzoyl-9-(4-methoxy-2-methylphenyl)-1,2,3,4,5,6-hexahydroazepino[4,5-b]indole (0.40 g, 0.97 mmol), potassium hydroxide (1.0 g, 18 mmol) and ethylene glycol (10 mL) was heated to 170° C. After 3 h, the reaction was cooled to rt, diluted with $H_2O$, and extracted with $CH_2Cl_2$. The combined organic extracts were washed with brine, dried over $K_2CO_3$, decanted, and concentrated to give 0.26 g (87%) of crude product. The HCl salt was prepared from 100 mg of free base as a light brown solid (39 mg): mp 276.5–277° C.; IR (diffuse reflectance) 3226, 3004, 2986, 2958, 2938, 2832, 2798, 2752, 1609, 1468, 1449, 1420, 1292, 1235, 800 $cm^{-1}$; MS (EI) m/z 306 ($M^+$), 277, 264, 86, 84, 78, 63, 62, 61, 51 HRMS (FAB) calcd for $C_{20}H_{22}N_2O+H$ 307.1810, found 307.1806.

Preparation 107

Preparation of 3-Benzoyl-9-(2,4-dichlorophenyl)-1,2,3,4,5,6-hexahydroazepino[4,5-b]indole.

A solution of 3-benzoyl-9-bromo-1,2,3,4,5,6-hexahydroazepino[4,5-b]indole (2.00 g, 5.42 mmol) in DME (50 mL) was degassed via vacuum/$N_2$ purge. Then, $(PhP_3)_4Pd$ (0.63 g, 0.54 mmol) was added and the mixture was stirred for 20 min prior to the addition of a degassed solution of 2,4-dichlorophenylboronic acid (1.55 g, 8.12 mmol) in DME (10 mL) and MeOH (0.5 mL). Next, 2M $Na_2CO_3$ (16 mL) was added and the reaction was heated to reflux. After 2 h, the reaction was cooled to rt and partitioned between $H_2O$ and EtOAc. The layers were separated and the aqueous layer was extracted with additional EtOAc (2×75 mL). The combined organic extracts were washed with brine, dried over $Na_2SO_4$, decanted, and concentrated. The crude product was purified by column chromatography with heptane/EtOAc (gradient, 1:1 to 1:2) to give 2.15 g of impure product. Triturating with ether and extended drying under vacuum gave 1.42 g (60%) of gray-brown solid: mp 235.5–237° C.; IR (diffuse reflectance) 3294, 1601, 1468, 1434, 1374, 1330, 1295, 1246, 933, 873, 821, 796, 785, 743, 708 $cm^{-1}$; MS (EI) m/z 434 ($M^+$), 315, 313, 300, 105, 78, 77, 64, 63, 51; HRMS (FAB) calcd for $C_{25}H_{20}CL_2N_2O+H$ 435.1031, found 435.1017; % Water (KF): 0.10; melt solvate: 0.84% EtOAc.

EXAMPLE 310

9-(2,4-Dichlorophenyl)-1,2,3,4,5,6-hexahydroazepino[4,5-b]indole hydrochloride

A mixture of 3-benzoyl-9-(2,4-dichlorophenyl)-1,2,3,4,5,6-hexahydroazepino[4,5-b]indole (1.00 g, 2.30 mmol), potassium hydroxide (2.00 g, 35.6 mmol) and ethylene glycol (20 mL) was heated to 170° C. After 3 h, the reaction was cooled to rt, diluted with $H_2O$, and extracted with $CH_2Cl_2$. The combined organic extracts were washed with brine, dried over $K_2CO_3$, decanted, and concentrated to give 0.74 g (97%) of crude product. The HCl salt was prepared from 100 mg of free base as a beige solid (57 mg): mp 273–274.5° C.; IR (diffuse reflectance) 3230, 2952, 2827, 2799, 2753, 2679, 2576, 1594, 1469, 1454, 1421, 1330, 827, 813, 799 $cm^{-1}$; MS (EI) m/z 332, 330 ($M^+$), 303, 301, 300, 292, 290, 289, 288, 287; Anal. Calcd for $C_{18}H_{16}Cl_2N_2 \cdot HCl$: C, 58.80; H, 4.66; N, 7.62; found: C, 58.76; H, 4.76; N, 7.53.

EXAMPLE 311

N-(3-chloro-2-methylphenyl)-2-(2,3,4,5-tetrahydroazepino [4,5-b]indol-6(1H)-yl)acetamide hydrochloride

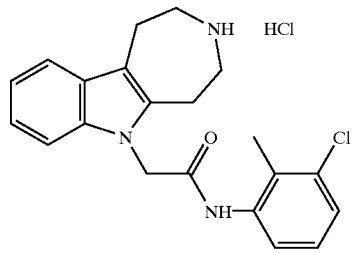

Prepared according to the procedure used to prepare N-(2, 3-dimethylphenyl)-2-(2,3,4,5-tetrahydroazepino[4,5-b] indol-6(1H)-yl)acetamide hydrochloride. 1H NMR ($CD_3OD$) δ 7.52, 7.42, 7.29, 7.23–7.11, 5.13, 3.52, 3.47, 3.32, 3.23, 2.25. MS (ESI+) for $C_{21}H_{20}ClN_3O$ m/z 368.0 $(M+H)^+$.

EXAMPLE 312

N-[2-methyl-3-(trifluoromethyl)phenyl]-2-(2,3,4,5-tetrahydroazepino[4,5-b]indol-6(1H)-yl)acetamide hydrochloride

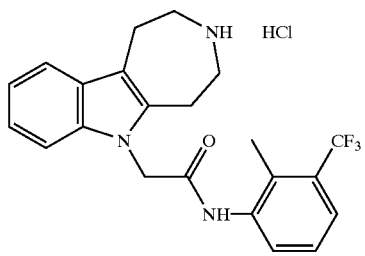

Prepared according to the procedure used to prepare N-(2, 3-dimethylphenyl)-2-(2,3,4,5-tetrahydroazepino[4,5-b] indol-6(1H)-yl)acetamide hydrochloride. $^1$H NMR ($CD_3OD$) δ 7.56, 7.44, 7.35, 7.22, 7.12, 5.17, 3.53, 3.47, 3.33, 3.23, 2.32. MS (ESI+) for $C_{22}H_{22}F_3N_3O$ m/z 402.0 $(M+H)^+$.

EXAMPLE 313

2-(2,3,4,5-tetrahydroazepino[4,5-b]indol-6(1H)-yl)-N-(5,6, 7,8-tetrahydronaphthalen-1-yl)acetamide hydrochloride

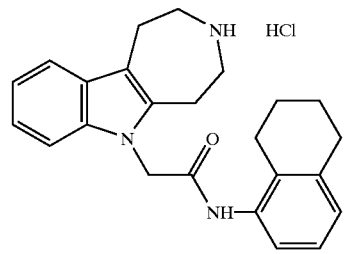

Prepared according to the procedure used to prepare N-(2, 3-dimethylphenyl)-2-(2,3,4,5-tetrahydroazepino[4,5-b] indol-6(1H)-yl)acetamide hydrochloride. $^1$H NMR ($CD_3OD$) δ 7.52, 7.43, 7.21, 7.14, 7.06, 6.97, 5.10, 3.51, 3.45, 3.32, 3.22, 2.76, 2.55, 1.76. MS (ESI+) for $C_{24}H_{27}N_3O$ m/z 374.1 $(M+H)^+$.

EXAMPLE 314

N-(4-methyl-1,3-thiazol-2-yl)-2-(2,3,4,5-tetrahydroazepino [4,5-b]indol-6(1H)-yl)acetamide hydrochloride

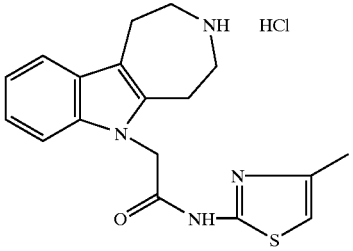

Prepared according to the procedure used to prepare N-(2, 3-dimethylphenyl)-2-(2,3,4,5-tetrahydroazepino[4,5-b] indol-6(1H)-yl)acetamide hydrochloride. 1H NMR ($CDCl_3$) δ 7.53, 7.35, 7.18, 7.11, 6.94, 5.83, 3.51, 3.32, 3.26, 2.41. MS (ESI+) for $C_{18}H_{20}N_4OS$ m/z 341.1 $(M+H)^+$.

EXAMPLE 315

N-(1,3-dihydro-2-benzofuran-4-yl)-2-(2,3,4,5-tetrahydroazepino[4,5-b]indol-6(1H)-yl)acetamide hydrochloride

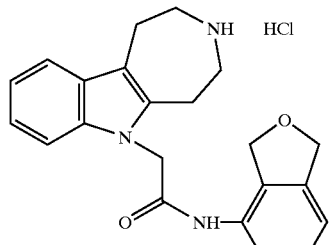

Prepared according to the procedure used to prepare N-(2, 3-dimethylphenyl)-2-(2,3,4,5-tetrahydroazepino[4,5-b] indol-6(1H)-yl)acetamide hydrochloride. $^1$H NMR ($CD_3OD$) δ 7.51, 7.37, 7.27, 7.20, 7.11, 5.10, 5.06, 4.98, 3.51, 3.46, 3.29, 3.22. MS (ESI+) for $C_{22}H_{23}NO_2$ m/z 362.2 $(M+H)^+$.

EXAMPLE 316

2-(7-bromo-2,3,4,5-tetrahydroazepino[4,5-b]indol-6(1H)-yl)-N-(4-methyl-1,3-thiazol-2-yl)acetamide hydrochloride

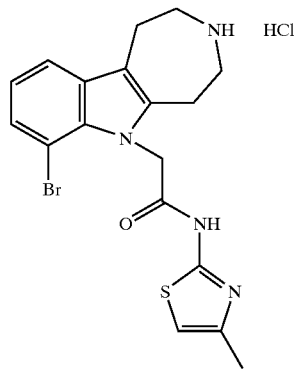

tert-Butyl 7-bromo-6-{2-[(4-methyl-1,3-thiazol-2-yl)amino]-2-oxoethyl}-1,4,5,6-tetrahydroazepino[4,5-b]indole-3(2H)-carboxylate (0.280 g, 0.52 mmol) was dissolved in EtOAc (15 mL). 4N HCl in dioxane (5 mL) was added and the reaction mixture was stirred at rt under $N_2$. After 1 h, a white solid precipitated from the solution. The precipitate was collected by filtration. Pure 2-(7-bromo-2,3,4,5-tetrahydroazepino[4,5-b]indol-6(1H)-yl)-N-(4-methyl-1,3-thiazol-2-yl)acetamide hydrochloride was obtained after recrystallization from 3:1 $CH_3OH:Et_2O$ (20 mL), as a white solid (0.220 g) in 94% yield. $^1H$ NMR (400 MHz, $CD_3OD$) δ 2.4, 3.22–3.28, 3.49–3.59, 5.7–5.78, 6.88, 7.02, 7.35, 7.54; MS (ESI+) for $C_{18}H_{19}BrN_4OS$ m/z 420.8 (M+H)$^+$.

EXAMPLE 317

2-(8-bromo-2,3,4,5-tetrahydroazepino[4,5-b]indol-6(1H)-yl)-N-(4-methyl-1,3-thiazol-2-yl)acetamide hydrochloride

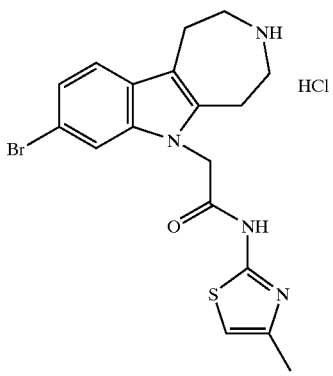

Prepared according to the procedure used to prepare 2-(7-bromo-2,3,4,5-tetrahydroazepino[4,5-b]indol-6(1H)-yl)-N-(4-methyl-1,3-thiazol-2-yl)acetamide hydrochloride in 53% yield. 1H NMR (400 MHz, $CD_3OD$) δ 2.38, 3.21–3.29, 3.46–3.56, 5.24, 6.83, 7.25, 7.46, 7.58; MS (ESI+) for $C_{18}H_{19}BrN_4OS$ m/z 420.8 (M+H)$^+$.

EXAMPLE 318

2-(9-bromo-2,3,4,5-tetrahydroazepino[4,5-b]indol-6(1H)-yl)-N-(4-methyl-1,3-thiazol-2-yl)acetamide hydrochloride

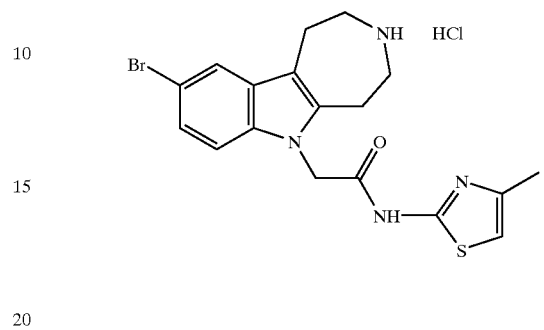

Prepared according to the procedure used to prepare N-(2,3-dimethylphenyl)-2-(2,3,4,5-tetrahydroazepino[4,5-b]indol-6(1H)-yl)acetamide hydrochloride in 14% yield. $^1H$ NMR (400 MHz, $CD_3OD$) δ 2.33, 3.18–3.29, 3.46–3.55, 5.19, 6.69, 7.28, 7.69; MS (ESI+) for $C_{18}H_{19}BrN_4OS$ m/z 420.9 (M+H)$^+$.

EXAMPLE 319

2-(10-bromo-2,3,4,5-tetrahydroazepino[4,5-b]indol-6(1H)-yl)-N-(4-methyl-1,3-thiazol-2-yl)acetamide

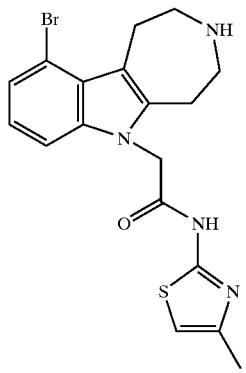

tert-Butyl 10-bromo-6-{2-[(4-methyl-1,3-thiazol-2-yl)amino]-2-oxo ethyl}-1,4,5,6-tetrahydroazepino[4,5-b]indole-3(2H)-carboxylate (0.13 g, 0.24 mmol) was dissolved in $CH_2Cl_2$ (5 mL). $CF_3CO_2H$ (0.5 mL, 0.74 g, 6.5 mmol) was added. The reaction mixture was stirred at rt under $N_2$ for 46 h. The reaction mixture was partitioned between 1N NaOH (60 mL) and EtOAc (350 mL). The aqueous layer was back extracted with EtOAc (100 mL). The combined organic layers were washed with brine (25 mL), dried over $MgSO_4$, filtered and concentrated under reduced pressure. The crude product was flash chromatographed (10% $CH_3OH/CH_2Cl_2$ containing 0.05% 7N $NH_3/CH_3OH$) and 2-(10-bromo-2,3,4,5-tetrahydroazepino[4,5-b]indol-6(1H)-yl)-N-(4-methyl-1,3-thiazol-2-yl)acetamide was obtained in 28% yield. ¹H NMR (400 MHz, CD₃OD) δ 2.33, 3.02–3.09, 3.14–3.21, 3.55–3.63, 5.16, 6.67, 6.97, 7.21, 7.30; MS (ESI+) for C₁₈H₁₉BrN₄OS m/z 420.8 (M+H)⁺.

EXAMPLE 320

6-[2-(5,6,7,8-tetrahydronaphthalen-1-yloxy)ethyl]-1,2,3,4,5,6-hexahydroazepino[4,5-b]indole hydrochloride

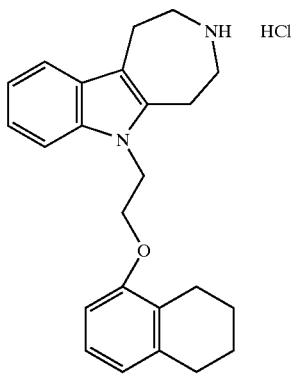

tert-Butyl 6-(2-hydroxyethyl)-1,4,5,6-tetrahydroazepino[4,5-b]indole-3(2H)-carboxylate (0.100 g, 0.302 mmol) was dissolved in THF (6 mL). 5,6,7,8-Tetrahydronaphthalen-1-ol (0.067 g, 0.454 mmol) was added, and after 25 min di-tert-butyl azodicarboxylate (0.105 g, 0.454 mmol) was added. The reaction mixture was stirred at 40° C. for 5 h. The solvent was removed in vacuo. The crude product was flash chromatographed (9:1 hexane:EtOAc) and tert-butyl 6-[2-(5,6,7,8-tetrahydronaphthalen-1-yloxy)ethyl]-1,4,5,6-tetrahydroazepino[4,5-b]indole-3(2H)-carboxylate was obtained in 22% yield. tert-Butyl 6-[2-(5,6,7,8-tetrahydronaphthalen-1-yloxy)ethyl]-1,4,5,6-tetrahydroazepino[4,5-b]indole-3(2H)-carboxylate (0.028 g, 0.061 mmol) was dissolved in EtOAc (5 mL). 4N HCl in dioxane (2 mL) was added. The reaction mixture was stirred at rt under N₂ for 20 h. The solvent was removed in vacuo. The crude product was dissolved in EtOAc (2 mL) and Et₂O (3 mL) was added dropwise. The precipitate was collected by filtration, wash with Et₂O and dried in vacuo at reduced pressure to yield 6-[2-(5,6,7,8-tetrahydronaphthalen-1-yloxy)ethyl]-1,2,3,4,5,6-hexahydroazepino[4,5-b]indole hydrochloride in 73% yield. ¹H NMR (400 MHz, CD₃OD) δ 1.66–1.72, 2.35–2.39, 2.65–2.72, 3.20–3.23, 3.36–3.50, 4.23–4.28, 4.61–4.64, 6.51, 6.63, 6.93, 7.10, 7.18, 7.44, 7.50; MS (ESI+) for C₂₄H₂₈N₂O m/z 361.1 (M+H)⁺.

EXAMPLE 321

6-{2-[(5,5-dimethyl-5,6,7,8-tetrahydronaphthalen-1-yl)oxy]ethyl}-1,2,3,4,5,6-hexahydroazepino[4,5-b]indole hydrochloride

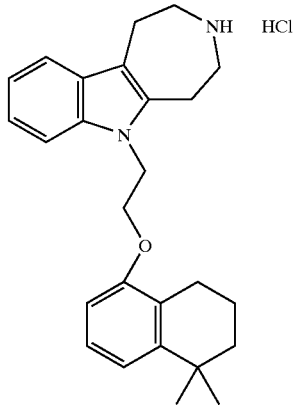

Prepared according to the procedure used to prepare 6-[2-(5,6,7,8-tetrahydronaphthalen-1-yloxy)ethyl]-1,2,3,4,5,6-hexahydroazepino[4,5-b]indole hydrochloride in 69% yield. ¹H NMR (400 MHz, CD₃OD) δ 1.20–1.26, 1.53–1.61, 1.63–1.73, 2.34–2.40, 3.21–3.26, 3.37–3.53, 4.22–4.28, 4.59–4.66, 6.53, 6.93, 6.99, 7.10, 7.18, 7.42, 7.50; MS (ESI+) for C₂₆H₃₂N₂O m/z 389.1 (M+H)⁺.

Preparation 108

Preparation of 3-benzoyl-10-(2-chlorophenyl)-1,2,3,4,5,6-hexahydroazepino[4,5-b]indole Prepared according to the procedure used to prepare 3-benzoyl-10-[2-(trifluoromethoxy)phenyl]-1,2,3,4,5,6-hexahydroazepino[4,5-b]indole. ¹H NMR (400 MHz, CD₃OD) δ 2.15, 2.27, 2.39, 2.53, 2.92, 3.19, 3.42, 3.65, 3.71, 3.95, 6.72, 7.08, 7.26–7.35, 7.36–7.55; MS (ESI+) for C₂₅H₂₁ClN₂O m/z 401.0 (M+H)⁺.

EXAMPLE 322

10-(2-chlorophenyl)-3-methyl-1,2,3,4,5,6-hexahydroazepino[4,5-b]indole

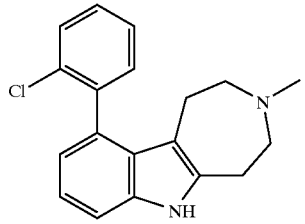

Obtained as a minor product, in 21% yield, from the deprotection reaction of 3-benzoyl-10-(2-chlorophenyl)-1,2,3,4,5,6-hexahydroazepino[4,5-b]indole with KOH in ethylene glycol at 170° C. for 26 h. ¹H NMR (400 MHz, CD₃OD) δ 2.26, 2.35–2.46, 2.53–2.60, 2.77–2.84, 2.97–3.02, 6.72, 7.06, 7.29, 7.32–7.40, 7.48; MS (ESI+) for C₁₉H₁₉ClN₂ m/z 311.1 (M+H)⁺.

EXAMPLE 323
10-(2-chlorophenyl)-1,2,3,4,5,6-hexahydroazepino[4,5-b]indole

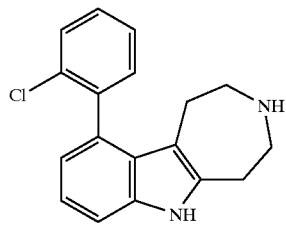

Prepared according to the procedure used to prepare 10-[2-(trifluoromethoxy)phenyl]-1,2,3,4,5,6-hexahydroazepino[4,5-b]indole in 96% yield. $^1$H NMR (400 MHz, CD$_3$OD) δ 2.31, 2.45, 2.86–2.93, 3.04–3.10, 3.12–3.18, 6.73, 7.08, 7.31, 7.33–7.40, 7.48; MS (ESI+) for C$_{18}$H$_6$ClN$_2$ m/z 297.1 (M+H)$^+$.

Preparation 109
Preparation of tert-butyl 10-(2-methylphenyl)-1,4,5,6-tetrahydroazepino[4,5-b]indole-3(2H)-carboxylate
tert-Butyl 10-bromo-1,4,5,6-tetrahydroazepino[4,5-b]indole-3(2H)-carboxylate (1.17g, 3.2 mmol), Pd(PPh$_3$)$_4$ (0.39 g, 0.34 mmol), and dimethoxyethane (25 mL) were stirred at room temperature for 10 minutes then treated with 2-methylboronic acid (0.52 g, 3.8 mmol) and a 2 M solution of Na$_2$CO$_3$ (12 mL). The reaction was heated to reflux for 15.25 hours then cooled to room temperature and partitioned between ethyl acetate and water. The aqueous layer was extracted with ethyl acetate (2×) and the organic layers were combined, washed with brine, dried over MgSO$_4$ and concentrated in vacuo to give a brown oil which was passed through a column of silica gel with 1:5 ethyl acetate/hexane to give 0.53 g (44%) of a brown oil as the title compound.

EXAMPLE 324
10-(2-methylphenyl)-1,2,3,4,5,6-hexahydroazepino[4,5-b]indole hydrochloride

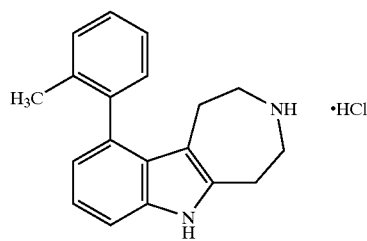

The tert-butyl 10-(2-methylphenyl)-1,4,5,6-tetrahydroazepino[4,5-b]indole-3(2H)-carboxylate (0.53 g, 1.40 mmol) from above was treated with a solution of 4 N HCl in dioxane (10 mL) and stirred at room temperature for 3.7 hours. After the reaction mixture was concentrated in vacuo CH$_2$Cl$_2$ was added and the solution was concentrated in vacuo to give a green solid (475 mg) which was recrystallized from CH$_3$OH/ethyl acetate to give 0.362 g (82%) of a light brown solid as the title compound: mp 278.5–281° C. $^1$H NMR (400 MHz, DMSO-d$_6$) δ 11.20 (s, 1 H), 9.40 (br s, 1 H), 7.32–7.22 (m, 4 H), 7.15 (d, J=7.2 Hz, 1H), 7.09–7.05 (m, 1 H), 6.68 (d, J=7.1 Hz, 1 H), 3.26 (m, 2 H), 3.17–3.16 (m, 2 H). 2.98 (m, 2 H), 2.37–2.27 (m, 2 H), 1.98 (s, 3 H); $^{13}$C NMR (100 MHz, DMSO-d$_6$) δ 140.9, 135.8, 135.5, 134.5, 132.7, 129.4, 129.2, 127.2, 125.3, 125.0, 120.2, 119.7, 110.0, 109.7, 45.9, 44.2, 24.3, 21.1, 19.6; IR (diffuse reflectance) 3257 (s), 2992 (s), 2946 (s,b), 2906 (s,b), 2849 (s), 2831 (s), 2801 (s), 2774 (s), 2676, 2572, 2446, 1463, 1336, 766, 744 (s) cm$^{-1}$; HRMS (FAB) calcd for C-$_{19}$H$_{20}$N$_2$+H$_1$277.1704, found 277.1702. Anal. Calcd for C$_{19}$H$_{20}$N$_2$.HCl.0.5 EtOAc: C, 72.69; H, 6.80; N, 8.83. Found: C, 72.60; H, 6.82; N, 8.94.

Preparation 110
Preparation of 3-benzoyl-10-(2-methoxyphenyl)-1,2,3,4,5,6-hexahydroazepino[4,5-b]indole
tert-Butyl 10-bromo-1,4,5,6-tetrahydroazepino[4,5-b]indole-3(2H)-carboxylate (4.40g, 11.9 mmol), Pd(PPh$_3$)$_4$ (1.40 g, 1.21 mmol), and dimethoxyethane (60 mL) were stirred at room temperature for 15 minutes then treated with 2-methoxyboronic acid (2.18 g, 14.3 mmol) and a 2 M solution of Na$_2$CO$_3$ (36 mL). The reaction was heated to reflux for 17.0 hours then cooled to room temperature and partitioned between ethyl acetate and water. The aqueous layer was extracted with ethyl acetate (2×) and the organic layers were combined, washed with brine, dried over MgSO$_4$ and concentrated in vacuo to give a brown foam which was passed through a column of silica gel with 40% ethyl acetate/hexane to give 3.87 g (82%) of a white solid as the title compound: mp 218.9–221.6° C. $^1$H NMR (400 MHz, DMSO-d$_6$) δ 10.95–10.85 (m, 1 H), 7.43–7.38 (m, 4 H), 7.27–7.23 (m, 2 H), 7.17–6.97 (m, 4 H), 6.67–6.61 (m, 3.82 (m, 1 H), 3.66–3.53 (m, 5 H), 3.27 (m, 1 H), 3.09–3.06 (m, 1 H), 2.85 (m, 1 H), 2.39–2.32 (m, 1 H), 2.17–2.13 (m, 1 H); $^{13}$C NMR (100 MHz, DMSO-d$_6$) δ 170.1, 169.8, 156.8, 156.7, 137.1, 135.7, 134.8, 134.6, 130.8, 130.5, 130.4, 130.2, 130.0, 128.9, 128.5, 128.3, 128.2, 126.1, 126.0, 120.5, 119.9, 119.8, 119.7, 111.2, 110.5, 110.2, 109.7, 109.5, 54.9, 54.7, 49.6, 48.3, 46.1, 44.2, 29.4, 27.5, 25.7, 24.6; IR (diffuse reflectance) 3202, 3181 (b), 1602 (s), 1500, 1489, 1466, 1434, 1299, 1266, 1249, 1241, 786, 759 (s), 748, 707 cm$^{-1}$; HRMS (FAB) calcd for C$_{26}$H$_{24}$N$_2$O$_2$+H$_1$ 397.1916, found 397.1910. Anal. Calcd for C$_{26}$H$_{24}$N$_2$O$_2$: C, 78.76; H, 6.10; N, 7.07. Found: C, 78.40; H, 6.22; N, 6.97.

EXAMPLE 325
10-(2-Methoxyphenyl)-1,2,3,4,5,6-hexahydroazepino[4,5-b]indole hydrochloride

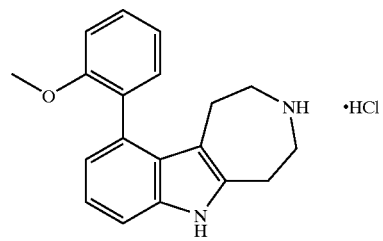

The 3-benzoyl-10-(2-methoxyphenyl)-1,2,3,4,5,6-hexahydroazepino[4,5-b]indole (1.10 g, 2.8 mmol), potassium hydroxide (3.71 g, 57.5 mmol), and ethylene glycol (30 mL) were heated to 170° C. for 4 hours. The reaction was diluted with water and extracted with ethyl acetate (3×). The organic layers were combined, washed with brine, dried over MgSO$_4$ and concentrated in vacuo to give a brown oil (2.76 g) which was passed through a column of silica gel with 1:19 methanol/chloroform with 1% NH$_4$OH to give a yellow powder 381 mg (47%) which was treated with a solution of 4 N HCl in dioxane (5 mL) and stirred at room temperature for 2.3 hours. After the reaction mixture was concentrated in vacuo CH$_2$Cl$_2$ was added and the solution was concentrated in vacuo to give a white solid which was recrystallized from CH$_3$OH EtOAc to give 0.40 g (43%) of a white solid as the title compound: mp 281.4–283.9° C. $^1$H NMR (400 MHz, DMSO-d$_6$) δ 11.15 (s, 1 H), 9.40 (br s, 1 H), 7.41–7.36 (m, 1 H), 7.26 (d, J=8.0 Hz, 1 H), 7.15 (dd, J=7.4 Hz, 1.7 Hz, 1 H), 7.07–6.99 (m, 3 H), 6.69 (d, J=7.6Hz, 1 H), 3.65 (s, 3 H), 3.26 (m, 2 H), 3.17–3.14 (m, 2 H), 3.01 (m, 2 H), 2.56–2.39 (m, 2 H); $^{13}$C NMR (100 MHz, DMSO-d$_6$) δ 156.7, 135.2, 134.4, 130.9, 130.0, 129.9, 128.6, 125.5, 120.7, 120.0, 110.5, 110.3, 110.0, 54.9, 45.9, 44.3, 24.3, 21.2; IR (diffuse reflectance) 3373 (s), 2958, 2935, 2895, 2832, 2791, 2770, 2727, 1483, 1459 (s), 1415, 1230 (s), 1024, 762 (s), 757 (s) cm$^{-1}$; HRMS (FAB) calcd for C$_{19}$H$_{20}$N$_2$O$_1$+H$_1$ 293.1654, found 293.1658.

Preparation 111

Preparation of 2-(3-Benzoyl-1,2,3,4,5,6-hexahydroazepino[4,5-b]indol-10-yl)phenol A 0° C. solution of 3-benzoyl-10-(2-methoxyphenyl)-1,2,3,4,5,6-hexahydroazepino[4,5-b]indole (936 mg, 2.36 mmol) in CH$_2$Cl$_2$ (20 mL) was treated with BBr$_3$ (0.75 mL, 7.94 mmol). The reaction was stirred at room temperature under nitrogen for 16.5 hours. The reaction was cooled to 0°C. and slowly quenched with saturated NH$_4$Cl solution. After stirring at room temperature for 1.7 hours the reaction was extracted with CH$_2$Cl$_2$. The organic layer was dried over MgSO$_4$ and concentrated in vacuo to give 792 mg (88%) of a yellow foam as the title compound: MS m/z 383.3 (M$^+$+H).

Preparation 112

Preparation of 3-Benzoyl-10-(2-propoxyphenyl)-1,2,3,4,5,6-hexahydroazepino[4,5-b]indole A slurry of 2-(3-benzoyl-1,2,3,4,5,6-hexahydroazepino[4,5-b]indol-10-yl)phenol (357 mg, 0.93 mmol), CS$_2$CO$_3$ (1.24 g, 3.82 mmol) and 1-iodopropane (195 mg, 1.15 mmol) in acetone (10 mL) was stirred at room temperature under nitrogen for 15 hours. The reaction was filtered and the filtrate concentrated in vacuo. The residue was partitioned between ethyl acetate and water. The organic layer was washed with brine, dried over MgSO$_4$ and concentrated in vacuo to give a yellow oil which was passed through a column of silica gel with 50% ethyl acetate/hexane to give 276 mg (70%) of a white foam as the title compound: MS m/z 425.3 (M$^+$+H).

EXAMPLE 326

10-(2-Propoxyphenyl)-1,2,3,4,5,6-hexahydroazepino[4,5-b]indole

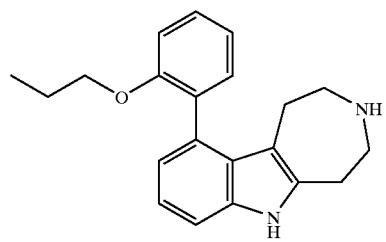

The 3-benzoyl-10-(2-propoxyphenyl)-1,2,3,4,5,6-hexahydroazepino[4,5-b]indole (1.32 g, 3.1 mmol), potassium hydroxide (4.01 g, 62.2 mmol), and ethylene glycol (30 mL) were heated to 170° C. for 3.25 hours. The reaction was diluted with water and extracted with ethyl acetate (2×). The organic layers were combined, washed with brine, dried over MgSO$_4$ and concentrated in vacuo to give a brown oil (2.79 g) which was passed through a column of silica gel with 1:19 methanol/chloroform with 1% NH$_4$OH to give 747 mg (75%) of a yellow foam as the title compound: $^1$H NMR (400 MHz, DMSO-d$_6$) δ 10.65 (s, 1 H), 7.33–7.28 (m, 1H), 7.17 (d, J=7.3 Hz, 1 H), 7.11 (dd, J=7.3 Hz, 1.7 Hz), 7.01 (d, J=8.1 Hz, 1 H), 6.97–6.92 (m, 2 H), 6.63 (d, J=7.1 Hz, 1 H), 3.88–3.76 (m, 2 H), 2.86–2.78 (m, 4 H), 2.59–2.53 (m, 2 H), 2.25–2.11 (m, 2 H), 1.47–1.40 (m, H), 0.69 (t, J=7.4 Hz, 3 H); $^{13}$C NMR (100 MHz, DMSO-d$_6$) δ 156.2, 137.6, 134.4, 131.0, 130.9, 130.0, 128.2, 126.5, 120.2, 119.7, 119.0, 112.6, 111.5, 109.4, 68.8, 49.8, 47.9, 32.0, 28.4, 21.9, 10.0; IR (diffuse reflectance) 3399, 3055, 2961, 2932, 2906 (b), 2877, 2834, 1484, 1466, 1449, 1416, 1334, 1259, 1234, 751 (s) cm$^{-1}$. HRMS (FAB) calcd for C$_{21}$H$_{24}$N$_2$O$_3$+H$_1$: 321.1967 found 321.1958.

EXAMPLE 327

10-(2-Fluorophenyl)-1,2,3,4,5,6-hexahydroazepino[4,5-b]indole

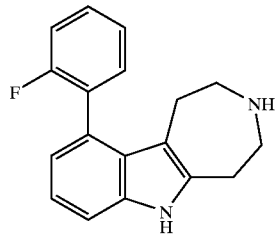

3-Benzoyl-10-(2-fluorophenyl)-1,2,3,4,5,6-hexahydroazepino[4,5-b]indole (3.50 g, 9.1 mmol), potassium hydroxide (11.80 g, 183 mmol), and ethylene glycol (80 mL) were heated to 170° C. for 6.6 hours. The reaction was diluted with water and extracted with ethyl acetate. The organic layers were combined, washed with brine, dried over MgSO$_4$ and concentrated in vacuo to give a red oil which was passed through a column of silica gel with 1:19 methanol/chloroform with 1% NH$_4$OH to give 2.43 g (95%) of a white solid as the title compound: mp 121.8–126.3° C. $^1$H NMR (400 MHz, CDCl$_3$) δ 8.02 (br s, 1 H), 7.42–7.34 (m, 3 H), 7.26–7.16 (m, 3 H), 6.98 (d, J=7.2 Hz, 1 H), 3.16–2.86 (m, 6 H), 2.58–2.53 (m, 1 H), 2.46–2.39 (m, 1 H); MS m/z 281.2 (M$^+$+H).

EXAMPLE 328

10-(2,4-dichlorophenyl)-1,2,3,4,5,6-hexahydroazepino[4,5-b]indole hydrochloride

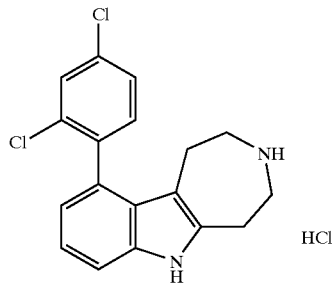

Prepared according to the procedure used to prepare 10-(2-methylphenyl)-1,2,3,4,5,6-hexahydroazepino[4,5-b]indole hydrochloride, the title compound was obtained: MS (ESI+) m/z 331.3 (MH$^+$).

EXAMPLE 329

3-benzyl-10-(2,4-dichlorophenyl)-1,2,3,4,5,6-hexahydroazepino[4,5-b]indole

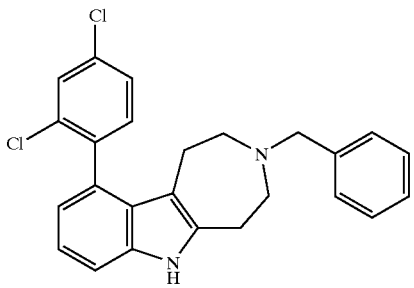

Prepared according to the procedure used to prepare 3-benzyl-7-phenyl-1,2,3,4,5,6-hexahydroazepino[4,5-b]indole, the title compound was obtained: 0.82 g (91%); mp 194–195.5° C.; IR (diffuse reflectance) 3404, 1465, 1455, 1419, 1374, 1346, 1334, 1122, 931, 923, 821, 808, 753, 738, 699 cm$^{-1}$; MS (EI) m/z 420 (M+), 420, 302, 300, 288, 217, 134, 133, 132, 91, 65; HRMS (FAB) calcd for $C_{25}H_{22}Cl_2N_2$+H 421.1238, found 421.1233; Anal. Calcd for $C_{25}H_{22}Cl_2N_2$: C, 71.26; H, 5.26; N, 6.65; Cl, 16.83, found: C, 71.62; H, 5.38; N, 6.56.

EXAMPLE 330

10-(4-methoxy-2-methylphenyl)-1,2,3,4,5,6-hexahydroazepino[4,5-b]indole hydrochloride

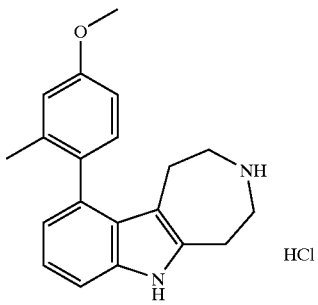

Prepared according to the procedure used to prepare 9-(4-methoxyphenyl)-1,2,3,4,5,6-haxahydroazepino[4,5-b]indole hydrochloride, the title compound was obtained: 0.60 g (100%); mp >262° C. (dec.); IR (diffuse reflectance) 3241, 3053, 2955, 2831, 2806, 2769, 2739, 2671, 2642, 1607, 1491, 1458, 1291, 1238, 753 cm$^{-1}$; MS (EI) m/z 306 (M+), 291, 277, 265, 264, 249, 248, 234, 218, 204; HRMS (FAB) calcd for $C_{20}H_{22}N_2O$+H 307.1810, found 307.1801; Anal. Calcd for $C_{20}H_{22}N_2O$.HCl: C, 70.06; H, 6.76; N, 8.17; Cl, 10.34; found: C, 70.09; H, 6.90; N, 8.17.

EXAMPLE 331

3-benzyl-10-(4-methoxy-2-methylphenyl)-1,2,3,4,5,6-hexahydroazepino[4,5-b]indole

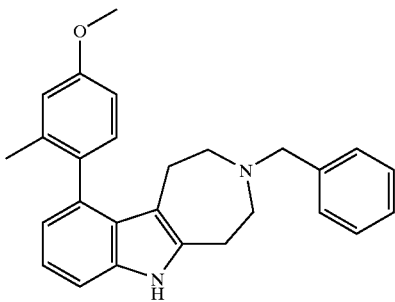

Prepared according to the procedure used to prepare 3-benzyl-7-phenyl-1,2,3,4,5,6-hexahydroazepino[4,5-b]indole, the title compound was obtained: 0.81 g (97%); mp 177–178° C.; IR (diffuse reflectance) 3406, 2813, 1607, 1513, 1490, 1454, 1346, 1332, 1318, 1237, 1175, 1121, 930, 754, 743 cm$^{-1}$; MS (EI) m/z 396 (M+), 276, 264, 134, 100, 91, 77, 60, 57, 55; HRMS (FAB) calcd for $C_{27}H_{28}N_2O$+H 397.2280, found 397.2282.

EXAMPLE 332

10-(2-ethoxyphenyl)-1,2,3,4,5,6-hexahydroazepino[4,5-b]indole hydrochloride

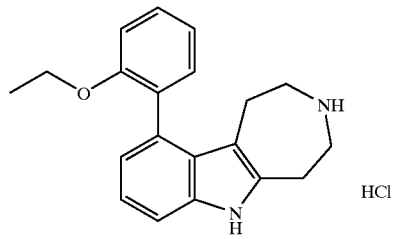

Prepared according to the procedure used to prepare 9-(4-methoxyphenyl)-1,2,3,4,5,6-haxahydroazepino[4,5-b]indole hydrochloride, the title compound was obtained: 0.29 (60%); MS (ESI+) m/z 307.3 (MH+).

EXAMPLE 333

3-benzyl-10-(2-ethoxyphenyl)-1,2,3,4,5,6-hexahydroazepino[4,5-b]indole

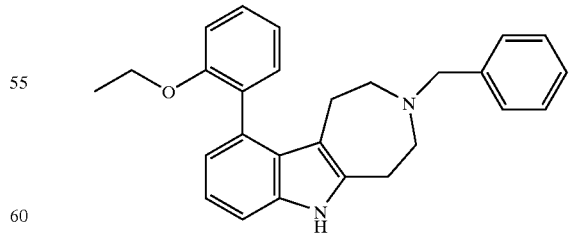

Prepared according to the procedure used to prepare 3-benzyl-7-phenyl-1,2,3,4,5,6-hexahydroazepino[4,5-b]indole, the title compound was obtained: 0.84 (89%); $^1$H NMR 3400 MHz, CDCl$_3$) δ 7.80, 7.40–7.27, 7.22, 7.14, 7.02, 6.94, 3.98, 3.75, 2.90, 2.68, 2.45, 1.19.

EXAMPLE 334

9-pyridin-4-yl-1,2,3,4,5,6-hexahydroazepino[4,5-b]indole formate

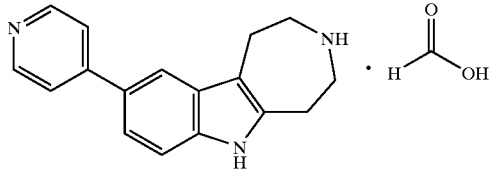

In a 20 mL vial a solution of MeOH/dioxane (10%, 1.5 mL, degassed with $N_2$) was added to a mixture of 3-(tert-butyloxycarbonyl)-9-(4,4,5,5-tetramethyl-1,3,2-dioxaborolan-2-yl)-1,2,3,4,5,6-hexahydroazepino[4,5-b]indole (0.097 g, 0.235 mmol), cesium carbonate (0.115 g, 0.35 mmol), and 4-bromopyridine hydrochloride (0.137g, 0.70 mmol) and diphenylphosphinoferrocene (0.07 g, 5 mol %) were added. The mixture was flushed with argon and tris(dibenzylideneacetone)dipalladium (0) (0.06 g, 3 mol %) was added and the vial was placed on a shaker heated at 90° C. for 18 h. Equivalent amounts of cesium carbonate and the palladium catalyst were added with a small amount of MeOH for solubility, and the vial was returned to the shaker and heated at 90° C. for 48 h. MeOH and Bio-Rad Ag. 50W-X2 resin (0.8 g, 5.2 meq, 18 equivalents) were added and heated on the shaker at 65° C. for 2 h. The mixture was rinsed into a fritted plastic syringe and was washed with: MeOH, water, 2 N pyridine in MeOH, THF, MeOH, THF and finally $CH_2Cl_2$. The resulting cake of resin was then washed with 4 M $NH_4OH$/MeOH and THF successively into tared vials, which were concentrated down on a Genevac for 18 h. The product was purified on a reverse phase HPLC system to give 4.3 mg (7%) of the title compound as the formate salt. MS (EI) m/z 264 (MH+).

EXAMPLE 335

10-(2-Butoxyphenyl)-1,2,3,4,5,6-hexahydroazepino[4,5-b]indole

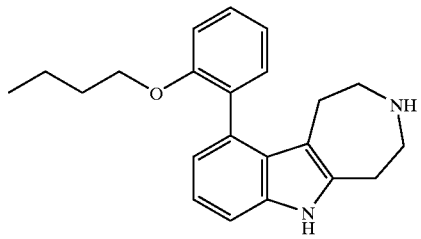

Following the procedure for 10-(2-propoxyphenyl)-1,2,3,4,5,6-hexahydroazepino[4,5-b]indole and substituting 1-iodobutane for 1-iodopropane while making non-critical variations the title compound was obtained as 128 mg (50%) of a brown oil: $^1$H NMR (400 MHz, $CDCl_3$) δ 7.94 (br s, 1 H), 7.37–7.30 (m, 2 H), 7.25 (dd, J=8.0 Hz, 0.9 Hz, 1 H), 7.17–7.13 (m, 1 H), 7.05–7.04 (m, 1 H), 6.99 (d, J=8.2 Hz, 1 H), 6.95–6.93 (m, 1 H), 3.96–3.87 (m, 2 H), 3.11–3.00 (m, 2 H), 2.96–2.81 (m, 4 H), 2.44–2.39 (m, 2 H), 1.59–1.51 (m, 2 H), 1.27–1.17 (m, 2 H), 0.80 (t, J=7.4 Hz, 3 H); HRMS (FAB) calcd for $C_{22}H_{26}N_2O+H_1$: 335.2123 found 335.2137.

EXAMPLE 336

10-[2-(Cyclopropylmethoxy)phenyl]-1,2,3,4,5,6-hexahydroazepino[4,5-b]indole

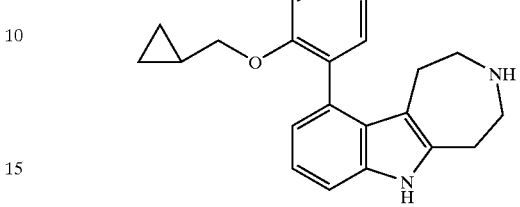

Following the procedure for the preparation of 10-(2-propoxyphenyl)-1,2,3,4,5,6-hexahydroazepino[4,5-b]indole and substituting (bromomethyl)cyclopropane for 1-iodopropane while making non-critical variations the title compound was obtained as 74 mg (14%) of a brown oil: $^1$H NMR (400 MHz, $CDCl_3$) δ 7.92 (br s, 1 H), 7.29–7.21 (m, 2 H), 7.12 (d, J=8.0 Hz, 1 H), 7.07–7.03 (m, 1 H), 6.98–6.94 (m, 1 H), 6.92 (d, J=8.2 Hz, 1 H), 6.86 (d, J=7.1 Hz, 1 H), 3.70 (d, J=6.3 Hz, 2 H), 3.01–2.95 (m, 2 H), 2.85–2.73 (m, 4 H), 2.37–2.31 (m, 2 H), 0.95–0.93 (m, 1 H), 0.30–0.25 (m, 2 H), 0.00-(-0.03) (m, 2 H); HRMS (FAB) calcd for $C_{22}H_{24}N_2O+H_1$: 333.1967 found 333.1955.

EXAMPLE 337

10-[2-(Pentyloxy)phenyl]-1,2,3,4,5,6-hexahydroazepino[4,5-b]indole

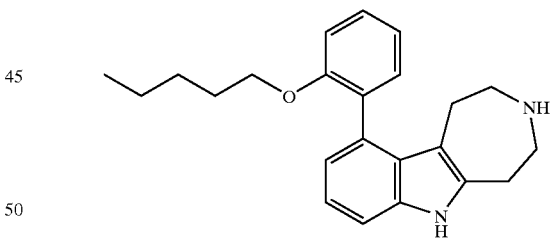

Following the procedure for the preparation of 10-(2-propoxyphenyl)-1,2,3,4,5,6-hexahydroazepino[4,5-b]indole and substituting 1-iodopentane for 1-iodopropane while making non-critical variations the title compound was obtained as 361 mg (71%) of a brown oil: $^1$H NMR (400 MHz, $CDCl_3$) δ 7.83 (br s, 1 H), 7.36–7.28 (m, 3 H), 7.17–7.13 (m, 1 H), 7.05–7.01 (m, 1 H), 6.97 (d, J=8.2 Hz, 1 H), 6.93 (d, J=7.2 Hz, 1 H), 3.95–3.85 (m, 2 H), 3.12–3.10 (m, 1 H), 3.06–3.04 (m, 1 H), 2.98–2.93 (m, 2 H), 2.88–2.85 (m, 1 H), 2.81–2.79 (m, 1 H), 2.42–2.37 (m, 2 H), 1.59–1.52 (m, 2 H), 1.21–1.13 (m, 4 H), 0.79 (t, J=7.0 Hz, 3 H); HRMS (FAB) calcd for $C_{23}H_{28}N_2O+H_1$: 349.2280 found 349.2280.

EXAMPLE 338
10-[2-(Hexyloxy)phenyl]-1,2,3,4,5,6-hexahydroazepino[4,5-b]indole

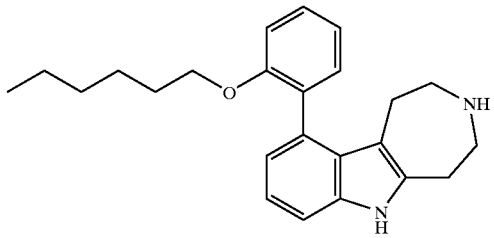

Following the procedure for the preparation of 10-(2-propoxyphenyl)-1,2,3,4,5,6-hexahydroazepino[4,5-b]indole and substituting 1-iodohexane for 1-iodopropane while making non-critical variations the title compound was obtained as 360 mg (66%) of a yellow foam: $^1$H NMR (400 MHz, CDCl$_3$) δ 7.83 (br s, 1 H), 7.36–7.27 (m, 3 H), 7.17–7.13 (m, 1 H), 7.05–7.01 (m, 1 H), 6.98 (d, J=8.2 Hz, 1 H), 6.93 (d, J=7.2 Hz, 1 H), 3.95–3.85 (m, 2 H), 3.12–3.10 (m, 1 H), 3.06–3.01 (m, 1 H), 2.98–2.93 (m, 2 H), 2.90–2.85 (m, 1 H), 2.82–2.79 (m, 1 H), 2.42–2.37 (m, 2 H), 1.57–1.51 (m, 2 H), 1.22–1.16 (m, 6 H), 0.83 (t, J=6.9 Hz, 3 H); HRMS (FAB) calcd for C$_{24}$H$_{30}$N$_2$O+H$_1$: 363.2436 found 363.2444.

EXAMPLE 339
10-(2-Isopropoxyphenyl)-1,2,3,4,5,6-hexahydroazepino[4,5-b]indole

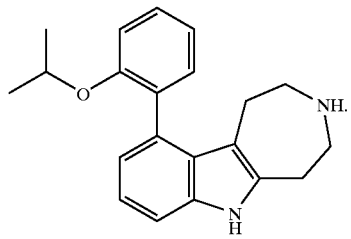

Following the procedure for the preparation of 10-(2-propoxyphenyl)-1,2,3,4,5,6-hexahydroazepino[4,5-b]indole and substituting 2-iodopropane for 1-iodopropane while making non-critical variations the title compound was obtained as 236 mg (56%) of a brown oil: $^1$H NMR (400 MHz, CDCl$_3$) δ 7.88 (br s, 1 H), 7.36–7.26 (m, 3 H), 7.16–7.12 (m, 1 H), 7.05–7.00 (m, 2 H), 6.95 (d, J=7.2 Hz, 1 H), 4.33–4.27 (m, 1 H), 3.11–3.03 (m, 2 H), 2.96–2.94 (m, 2 H), 2.87–2.81 (m, 2 H), 2.48–2.35 (m, 2 H), 1.15–1.08 (m, 6 H); HRMS (FAB) calcd for C$_{21}$H$_{24}$N$_2$O+H$_1$: 321.1967 found 321.1949.

Preparation 113
Preparation of 3-Benzoyl-10-[2-(cyclopentyloxy)phenyl)-1,2,3,4,5,6-hexahydroazepino[4,5-b]indole A 0° C. solution of 2-(3-benzoyl-1,2,3,4,5,6-hexahydroazepino[4,5-b]indol-10-yl)phenol (0.88 mg, 2.30 mmol) in THF (5 mL) was treated with triphenylphosphine (1.03 g, 3.93 mmol) and cyclopentanol (0.32 g, 3.67 mmol). After stirring for 10 minutes, di-tert-butyl azodicarboxylate (0.80 g, 3.45 mmol) was added dropwise and the reaction was stirred at room temperature for 16.5 hours. The reaction mixture was concentrated in vacuo, dissolved in CH$_2$Cl$_2$ and passed through a column of silica gel with 50% ethyl acetate/hexane to give 741 mg (72%) of a yellow solid as the title compound: mp 187.0–189.2° C. MS m/z 451.3 (M$^+$+H).

EXAMPLE 340
10-[2-(Cyclopentyloxy)phenyl]-1,2,3,4,5,6-hexahydroazepino[4,5-b]indole

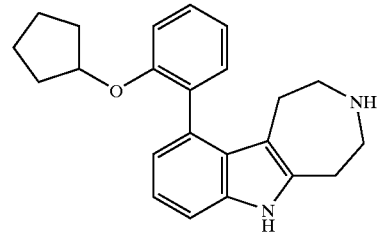

The 3-benzoyl-10-[2-(cyclopentyloxy)phenyl]-1,2,3,4,5,6-hexahydroazepino[4,5-b]indole (0.73 g, 1.6 mmol), potassium hydroxide (2.07 g, 32.1 mmol), and ethylene glycol (15 mL) were heated to 170° C. for 2.67 hours. The reaction was diluted with water and extracted with ethyl acetate (233). The organic layers were combined, washed with brine, dried over MgSO$_4$ and concentrated in vacuo to give a brown oil which was passed through a column of silica gel with 3% methanol/chloroform with 1% NH$_4$OH to give 419 mg (74%) of a white foam as the title compound: $^1$H NMR (400 MHz, CDCl$_3$) δ 7.83 (br s, 1 H), 7.35–7.26 (m, 3 H), 7.15–7.11 (m, 1 H), 7.03–6.96 (m, 2 H), 6.91 (d, J=7.2 Hz, 1 H), 4.69–4.65 (m, 1 H), 3.11–3.07 (m, 2 H), 2.99–2.95 (m, 2 H), 2.87–2.81 (m, 2 H), 2.45–2.39 (m, 2 H), 1.73–1.67 (m, 4 H), 1.48–1.45 (m, 4 H); HRMS (FAB) calcd for C$_{23}$H$_{26}$N$_2$O+H$_1$: 347.2123 found 321.2134.

EXAMPLE 341
10-[2-(Cyclohexyloxy)phenyl]-1,2,3,4,5,6-hexahydroazepino[4,5-b]indole

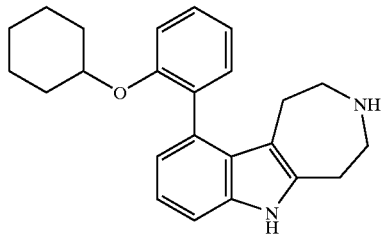

Following the procedure for the preparation of (5aS*, 10bS*)-10-[2-(cyclopentyloxy)phenyl]-1,2,3,4,5,5a,6,10b-octahydroazepino[4,5-b]indole and substituting cyclohexanol for cyclopentanol while making non-critical variations the title compound was obtained as 278 mg (32%) of a white foam: $^1$H NMR (400 MHz, CDCl$_3$) δ 7.84 (br s, 1 H), 7.35–7.26 (m, 3 H), 7.15–7.11 (m, 1 H), 7.04–7.01 (m, 2 H), 6.95 (d, J=7.2 Hz, 1 H), 4.08–4.06 (m, 1 H), 3.09–3.07 (m, 2 H), 2.97–2.96 (m, 2 H), 2.85–2.83 (m, 2 H), 2.47–2.37 (m, 2 H), 1.90 (m, 2 H) 1.71 (m, 2 H), 1.51 (m, 2 H), 1.41 (m, 2 H), 1.15 (m, 3 H); HRMS (FAB) calcd for C$_{24}$H$_{28}$N$_2$O+H$_1$: 361.2280 found 361.2270.

EXAMPLE 342

10-[2-(Cyclobutyloxy)phenyl]-1,2,3,4,5,6-hexahydroazepino[4,5-b]indole

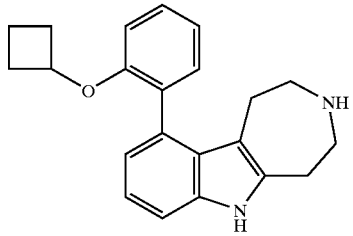

Following the procedure for the preparation of (5aS*, 10bS*)-10-[2-(cyclopentyloxy)phenyl]-1,2,3,4,5,5a,6,10b-octahydroazepino[4,5-b]indole and substituting cyclobutanol for cyclopentanol while making non-critical variations the title compound was obtained as 193 mg (37%) of a tan solid: mp 182.0–184.5° C. $^1$H NMR (400 MHz, CDCl$_3$) δ 7.85 (br s, 1 H), 7.35–7.28 (m, 3 H), 7.18–7.14 (m, 1 H), 7.04–7.00 (m, 1 H), 6.94 (d, J=7.2 Hz, 1 H), 6.84 (d, J=8.2 Hz, 1 H), 4.63–4.56 (m, 1 H), 3.10–3.07 (m, 2 H), 2.98–2.95 (m, 2 H), 2.87–2.84 (m, 2 H), 2.47–2.41 (m, 2 H), 2.37–2.32 (m, 2 H), 2.02–2.00 (m, 2 H), 1.74–1.72 (m, 1 H), 1.64–1.59 (m, 1 H); HRMS (FAB) calcd for C$_{22}$H$_{24}$N$_2$O+H$_1$: 333.1967 found 333.1960.

Preparation 114

Preparation of tert-butyl 10-(4,4,5,5-tetramethyl-1,3,2-dioxaborolan-2-yl)-1,4,5,6-tetrahydroazepino[4,5-b]indole-3(2H)-carboxylate tert-Butyl 10-bromo-1,4,5,6-tetrahydroazepino[4,5-b]indole-3(2H)-carboxylate (1.51 g, 4.12 mmol) and dioxane (26 mL) were combined at rt under N$_2$. Et$_3$N (3.43 mL, 2.49 g, 24.6 mmol) and 4,4,5,5-tetramethyl-1,3,2-dioxaborolan (1.28 mL, 1.05 g, 8.21 mmol) were added to the mixture by syringe. trans-Dichlorobis(triphenylphosphine)palladium (II) (0.147 g, 0.209 mmol) was added and Ar was bubbled through the reaction mixture for 15 min. The reaction mixture was refluxed under N$_2$ for 16 h. The cooled reaction mixture was concentrated and the residue was combined with toluene (50 mL), brine (20 mL) and H$_2$O (100 mL). The layers were separated and the aqueous layer was extracted with toluene (2×50 mL). The combined organic extracts were washed with brine (40 mL), dried over MgSO$_4$, filtered and concentrated. The crude product (1.90 g) was chromatographed (SiO$_2$ 60 g, eluted with 2:2:1 heptane:CH$_2$Cl$_2$:Et$_2$O) to give tert-butyl 10-(4,4,5,5-tetramethyl-1,3,2-dioxaborolan-2-yl)-1,4,5,6-tetrahydroazepino[4,5-b]indole-3(2H)-carboxylate (1.57 g) in 93% yield. MS (ESI+) for C$_{23}$H$_{33}$BN$_2$O$_4$ m/z 413.2 (M+H)$^+$.

Preparation 115

Preparation of tert-butyl 10-(2,6-difluorophenyl)-1,4,5,6-tetrahydroazepino[4,5-b]indole-3(2H)-carboxylate Prepared according to the procedure used to prepare tert-butyl 9-(2,6-difluorophenyl)-1,4,5,6-tetrahydroazepino[4,5-b]indole-3(2H)-carboxylate in 58% yield. MS (ESI+) for C$_{23}$H$_{24}$F$_2$N$_2$O$_3$ m/z 399.0 (M+H)$^+$.

EXAMPLE 343

10-(2,6-difluorophenyl)-1,2,3,4,5,6-hexahydroazepino[4,5-b]indole

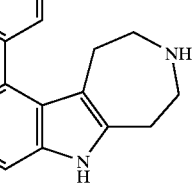

tert-Butyl 10-(2,6-difluorophenyl)-1,4,5,6-tetrahydroazepino[4,5-b]indole-3(2H)-carboxylate (0.700 g, 1.76 mmol) was dissolved in CF$_3$CO$_2$H (4 mL) and CH$_2$Cl$_2$ (14 mL) and the reaction mixture was stirred at rt for 3 h. The reaction mixture was cooled in an ice bath and quenched with cold 1N NaOH (100 mL). The resulting mixture was extracted with 3% CH$_3$OH in CH$_2$Cl$_2$ (3×50 mL). The combined organic extracts were dried over Na$_2$SO$_4$, filtered and concentrated. The crude product (0.51 g) was chromatographed (SiO$_2$ 30 g, eluted with 90:10:1 CH$_2$Cl$_2$:CH$_3$OH:conc. NH$_4$OH) to yield 10-(2,6-difluorophenyl)-1,2,3,4,5,6-hexahydroazepino[4,5-b]indole (0.458 g) in 87% yield. $^1$H NMR (400 MHz, Acetone-d$_6$) δ 2.35–2.38, 2.74–2.77, 2.95–2.98, 6.84, 7.08, 7.12, 7.36, 7.50; MS (ESI+) for C$_{18}$H$_{16}$F$_2$N$_2$ m/z 299.1 (M+H)$^+$.

Preparation 116

Preparation of 3-benzoyl-10-[2-(trifluoromethoxy)phenyl]-1,2,3,4,5,6-hexahydroazepino[4,5-b]indole 3-Benzoyl-10-bromo-1,2,3,4,5,6-hexahydroazepino[4,5-b]indole (4.00 g, 10.8 mmol) was suspended in benzene (170 mL). 2-(Trifluoromethoxy)-phenylboronic acid (4.48 g, 21.7 mmol), trans-dichlorobis(triphenylphosphine)palladium(II) (0.433 g, 0.617 mmol) and 2M Na$_2$CO$_3$ (17.6 mL) were added to the reaction mixture. Ar was bubbled through the reaction mixture for 20 min. The reaction mixture was heated at reflux for 11 h. After cooling, the reaction mixture was concentrated. The residue was combined with EtOAc (250 mL) and H$_2$O (400 mL). The layers were separated and the aqueous layer was extracted with EtOAc (2×100 mL). The combined organic layers were dried over MgSO$_4$, filtered and concentrated. The crude product (7.95 g) was recrystallized from CH$_3$OH to yield 3-benzoyl-10-[2-(trifluoromethoxy)phenyl]-1,2,3,4,5,6-hexahydroazepino[4,5-b]indole (1.43 g). The crude product from the mother liquors was chromatographed (SiO$_2$ 250 g, eluted with 2:1 toluene:EtOAc) to give 3-benzoyl-10-[2-(trifluoromethoxy)phenyl]-1,2,3,4,5,6-hexahydroazepino[4,5-b]indole (5.21 g). The yield of the reaction was 87%. IR (diffuse reflectance) 3266, 3227, 3187, 1615, 1574, 1498, 1483, 1464, 1428, 1382, 1354, 1334, 1323, 1288, 1253, 1221, 1202, 1167, 926, 790, 767, 750, 732, 704, 626 cm$^{-1}$; MS (ESI+) for C$_{26}$H$_{21}$F$_3$N$_2$O$_2$ m/z 450.9 (M+H)$^+$; Anal. Calcd for C$_{26}$H$_{21}$F$_3$N$_2$O$_2$: C, 69.32; H, 4.70; N, 6.22; found: C, 69.25; H, 4.78; N, 6.25.

EXAMPLE 344
10-[2-(trifluoromethoxy)phenyl]-1,2,3,4,5,6-hexahydroazepino[4,5-b]indole

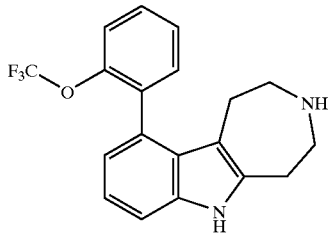

3-Benzoyl-10-[2-(trifluoromethoxy)phenyl]-1,2,3,4,5,6-hexahydroazepino[4,5-b]indole (1.55 g, 3.44 mmol) and ethylene glycol (50 mL) were combined and heated to 170° C. KOH (3.91 g, 69.7 mmol) was added and the reaction mixture was stirred at 170° C. for 1.5 h. The reaction mixture was cooled to rt and was combined with EtOAc (100 mL) and $H_2O$ (300 mL). The layers were separated and the aqueous layer was extracted with EtOAc (2×100 mL). The combined organic layers were dried over $MgSO_4$, filtered and concentrated to give crude product (5.22 g). The crude product was chromatographed ($SiO_2$ 100 g, eluted with 90:10:1 $CH_2Cl_2$:$CH_3OH$:conc. $NH_4OH$) to give 10-[2-(trifluoromethoxy)phenyl]-1,2,3,4,5,6-hexahydroazepino[4,5-b]indole (0.82 g) in 69% yield. $^1H$ NMR (400 MHz, $CD_3OD$) δ 2.24–2.36, 2.70–2.76, 2.95–3.03, 6.75, 7.06, 7.30, 7.36–7.42, 7.46–7.51; MS (ESI+) for $C_{19}H_{17}F_3N_2O$ m/z 347.2 $(M+H)^+$.

Preparation 117
Preparation of 3-benzoyl-10-(4,4,5,5-tetramethyl-1,3,2-dioxaborolan-2-yl)-1,2,3,4,5,6-hexahydroazepino[4,5-b]indole 3-Benzoyl-10-bromo-1,2,3,4,5,6-hexahydroazepino[4,5-b]indole (15.0 g, 40.6 mmol) was combined with dioxane (350 mL) at rt under $N_2$. $Et_3N$ (34.0 mL, 24.7 g, 244 mmol) and 4,4,5,5-tetramethyl-1,3,2-dioxaborolane (11.4 mL, 9.37 g, 73.2mmol) were added to the mixture by syringe. trans-Dichlorobis(triphenylphosphine)palladium(II) (1.44 g, 2.04 mmol) was added and Ar was bubbled through the reaction mixture for 20 min. The reaction mixture was refluxed under $N_2$ for 18 h. The cooled reaction mixture was concentrated and the residue was combined with EtOAc (500 mL) and $H_2O$ (200 mL). The layers were separated and the aqueous layer was extracted with EtOAc (2×100 mL). The combined organic extracts were dried over $MgSO_4$, filtered and concentrated. The crude product (22.9 g) was recrystallized from $CH_3OH$ (50 mL) to give 3-benzoyl-10-(4,4,5,5-tetramethyl-1,3,2-dioxaborolan-2-yl)-1,2,3,4,5,6-hexahydroazepino[4,5-b]indole (11.7 g) in 69% yield. MS (ESI+) for $C_{25}H_{29}BN_2O_3$ m/z 417.2 $(M+H)^+$.

Preparation 118
Preparation of 3-benzoyl-10-[2-(trifluoromethyl)phenyl]-1,2,3,4,5,6-hexahydroazepino[4,5-b]indole 3-Benzoyl-10-(4,4,5,5-tetramethyl-1,3,2-dioxaborolan-2-yl)-1,2,3,4,5,6-hexahydroazepino[4,5-b]indole (2.50 g, 6.00 mmol), triturated potassium phosphate (3.01 g, 14.2 mmol) and tris(dibenzylideneacetone)dipalladium(0) (0.562 g, 0.613 mmol) were combined in dioxane (63 mL) at rt under $N_2$. 2-Bromobenzotrifluoride (0.98 mL, 1.62 g, 7.21 mmol) and trimethylphosphite (0.22 mL, 0.231 g, 1.86 mmol) were added to the reaction mixture by syringe. Ar was bubbled through the reaction mixture for 20 min. The reaction mixture was heated to reflux for 22 h. The reaction mixture was concentrated and the residue was taken up in toluene (150 mL) and $H_2O$ (200 mL). The layers were separated and the aqueous layer was extracted with toluene (1×100 mL, 1×50 mL). The combined organic layers were dried over $MgSO_4$, filtered and concentrated. The crude product (3.90 g) was chromatographed ($SiO_2$ 250 g, eluted with 2:1 toluene:EtOAc) to yield 3-benzoyl-10-[2-(trifluoromethyl)phenyl]-1,2,3,4,5,6-hexahydroazepino[4,5-b]indole (2.48 g) in 95% yield. IR (diffuse reflectance) 3294, 1617, 1575, 1461, 1439, 1423, 1346, 1334, 1316, 1276, 1266, 1259, 1178, 1170, 1126, 1113, 1105, 1058, 1034, 792, 775, 755, 719, 701, 626 $cm^{-1}$; MS (ESI+) for $C_{26}H_{21}F_3N_2O$ m/z 435.0 $(M+H)^+$; Anal. Calcd for $C_{26}H_{21}F_3N_2O$: C, 71.88: H, 4.87: N, 6.45: found: C, 71.94: H, 4.93: N, 6.48.

EXAMPLE 345
10-[2-(trifluoromethyl)phenyl]-1,2,3,4,5,6-hexahydroazepino[4,5-b]indole

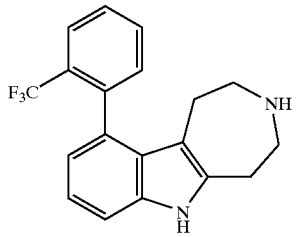

Prepared according to the procedure used to prepare 10-[2-(trifluoromethoxy)phenyl]-1,2,3,4,5,6-hexahydroazepino[4,5-b]indole in 69% yield. $^1H$ NMR (400 MHz, $CD_3OD$) δ 2.02–2.14, 2.64, 2.71, 2.93–3.03, 6.72, 7.02, 7.29, 7.34, 7.56, 7.61, 7.78: MS (ESI+) for $C_{19}H_{17}F_3N_2$ m/z 331.1 $(M+H)^+$.

Preparation 119
Preparation of 3-benzoyl-10-(4-chlorophenyl)-1,2,3,4,5,6-hexahydroazepino[4,5-b]indole 10-bromo-1,4,5,6-tetrahydroazepino[4,5-b]indol-3(2H)-yl](phenyl)methanone (500 mg), 4-chlorophenyl boronic acid (423 mg) and trans-dichlorobis(triphenylphosphine) palladium (II) (52 mg) were dissolved in benzene (42 ml) and 2N $Na_2CO_3$ (3.3 ml). The reaction mixture was heated at 80° C. for 20 h, poured into brine, extracted with EtOAc, dried over $MgSO_4$, filtered and concentrated. Purification via flash chromatography (silica gel, 1:1 hexane:EtOAc) provided 520 mg of the title compound as a solid: $^1H$ NMR (DMSO-$d_6$) δ 1.99, 2.49, 3.12, 3.53, 3.62, 3.84, 6.77, 7.02, 7.4–7.6.

EXAMPLE 346
10-(4-chlorophenyl)-1,2,3,4,5,6-hexahydroazepino[4,5-b]indole dihydrochloride

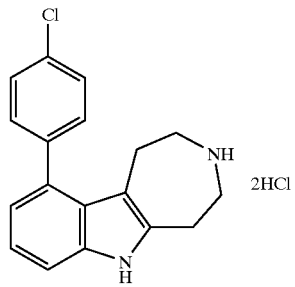

3-benzoyl-10-(4-chlorophenyl)-1,2,3,4,5,6-hexahydroazepino[4,5-b]indole and KOH (3.0 g) were stirred in ethylene glycol (10 ml) and the reaction mixture was heated at 170° C. for 1 h. The reaction mixture was cooled to RT, partitioned between H₂O and EtOAc, separated, dried over MgSO₄, filtered and concentrated. The product was dissolved in EtOAc and HCl (4 ml, 1N in Et₂O) was added. The precipitate was filtered and recrystallized from EtOAc/MeOH to give the title compound as a solid: ¹H NMR (DMSO-d₆) δ 3.09, 3.18, 3.30, 4.48, 6.78, 7.08, 7.32, 7.38, 7.52, 9.60, 11.3. HRMS (FAB) calcd for C₁₈H₁₇ClN₂ (MH⁺) 297.1158, found 297.1137.

Preparation 120
Preparation of 3-benzoyl-10-(3-chlorophenyl)-1,2,3,4,5,6-hexahydroazepino[4,5-b]indole Following the procedure for the preparation of 3-benzoyl-10-(4-chlorophenyl)-1,2,3,4,5,6-hexahydroazepino[4,5-b] indole, making non-critical variations, starting with the appropriate boronic acid, the title compound was obtained. ¹H NMR (DMSO-d₆) δ 2.24, 2.49, 2.89, 3.12, 3.52, 3.59, 3.84, 6.77, 7.06, 7.31–7.47, 11.23. HRMS (FAB) calcd for C₂₅H₂₁ClN₂O (MH⁺) 401.1420, found 401.1396.

EXAMPLE 347
10-(3-chlorophenyl)-1,2,3,4,5,6-hexahydroazepino[4,5-b]indole dihydrochloride

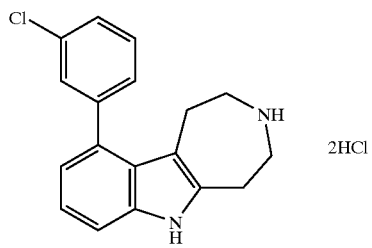

Following the procedure for the preparation of 10-(4-chlorophenyl)-1,2,3,4,5,6-hexahydroazepino[4,5-b]indole hydrochloride, making non-critical variations, starting with 3-benzoyl-10-(3-chlorophenyl)-1,2,3,4,5,6-hexahydroazepino[4,5-b]indole, the title compound was obtained. ¹H NMR (DMSO-d₆) δ 3.05, 3.21, 3.31, 4.51, 6.85, 7.1–7.5, 11.3.

Preparation 121
Preparation of 3-benzoyl-10-(2,4-dichlorophenyl)-1,2,3,4,5,6-hexahydroazepino[4,5-b]indole Following the procedure for the preparation of 3-benzoyl-10-(4-chlorophenyl)-1,2,3,4,5,6-hexahydroazepino[4,5-b] indole, making non-critical variations, starting with the appropriate boronic acid, the title compound was obtained: ¹H NMR (DMSO-d₆) ι1.99, 2.2–2.4, 2.87, 3.11, 3.53, 3.82, 6.69, 7.06, 7.27–7.75, 7.06.

Preparation 122
Preparation of tert-butyl 10-(2,4-dichlorophenyl)-1,4,5,5a,6,10b-hexahydroazepino[4,5-b]indole-3(2H)-carboxylate 10-(2,4-dichlorophenyl)-1,2,3,4,5,6-hexahydroazepino[4,5-b]indole (610 mg) was dissolved in TFA (12 ml), and sodium cyanoborohydride (589 mg)was added portionwise. The reaction mixture stirred 2 h, was quenched with 2N NaOH, extracted with EtOAc, dried over MgSO₄, filtered and concentrated. The crude product was dissolved in THF (14 ml) with 2N Na₂CO₃ (4.6 ml) and Boc₂O (441 mg) was added. The reaction mixture was stirred 1 h, poured into brine, extracted with CH₂Cl₂, dried over MgSO₄, filtered and concentrated. Purification via flash chromatography (silica gel, 3:1 hexanes:EtOAc) provided the title compound (660 mg): ¹H NMR (CD₃OD) δ 1.39, 1.44, 1.99, 3.2–3.6, 6.46, 6.65, 7.05, 7.32, 7.39, 7.41, 7.57.

Preparation 123
Preparation of tert-butyl 10-(2,4-dichlorophenyl)-6-(2-phenoxyethyl)-1,4,5,5a,6,10b-hexahydroazepino[4,5-b]indole-3(2H)-carboxylate To a solution of tert-butyl 10-(2,4-dichlorophenyl)-1,4,5,5a,6,10b-hexahydroazepino[4,5-b]indole-3(2H)-carboxylate (54 mg) in DMF (1.2 ml) was added KH (10 mg) and 2-bromoethyl phenyl ether (30 mg). The reaction mixture was stirred 24 h, poured into satd NaHCO3, extracted with CH₂Cl₂, dried over MgSO₄, filtered and concentrated. Purification via flash chromatography provided the title compound: ¹H NMR (CDCl₃) δ 1.63, 2.30–2.50, 2.92, 3.14, 3.42, 3.75, 4.26, 4.53, 6.84, 6.96, 7.20–7.51.

EXAMPLE 348
10-(2,4-dichlorophenyl)-6-(2-phenoxyethyl)-1,2,3,4,5,6-hexahydroazepino[4,5-b]indole

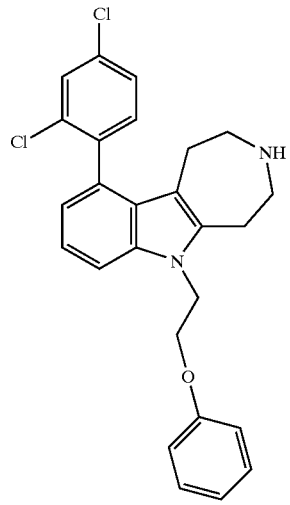

To a solution of 1-tert-butyl 10-(2,4-dichlorophenyl)-1,4,5,5a,6,10b-hexahydroazepino[4,5-b]indole-3(2H)-carboxylate (50 mg) in CH₂Cl₂ (2 ml) was added TFA (0.25 ml). The reaction mixture stirred 2 h, was quenched with 2N NaOH, extracted with EtOAc, dried over MgSO₄, filtered and concentrated. Purification via flash chromatography (silica gel, 9:1 CH₂Cl₂/MeOH with 0.5% NH₄OH) provided the title compound: ¹H NMR (CD₃OD) δ 2.25–2.43, 2.72, 3.03, 3.33, 4.21, 4.55, 6.75, 6.87, 7.14, 7.17. HRMS (FAB) calcd for C₂₆H₂₄Cl₂N₂O₂ (MH⁺) 451.1344, found 451.1340.

EXAMPLE 349
N-phenyl-1,2,3,4,5,6-hexahydroazepino[4,5-b]indol-10-amine

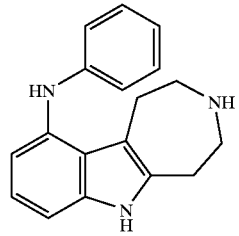

To a solution of tert-butyl 10-bromo-1,4,5,6-tetrahydroazepino[4,5-b]indole-3(2H)-carboxylate (600 mg), sodium t-butoxide (220 mg), tris (dibenzylideneacetone) dipalladium (23 mg), aniline (183 mg) toluene (1.64 ml) was added 2-(di-t-butylphosphino) biphenyl (30 mg) and the reaction mixture was heated at 50° C. The reaction mixture stirred 16 h, was poured into brine, extracted with $CH_2Cl_2$, dried over $MgSO_4$, filtered and concentrated. The crude product was stirred in $CH_2Cl_2$ (8 ml) and TFA (2 ml) was added. The reaction mixture stirred 1 h, was quenched with 2N NaOH, extracted with $CH_2Cl_2$, dried over $MgSO_4$, filtered and concentrated. Purification via flash chromatography (silica gel, $CH_2Cl_2$/MeOH, 9/1 with 0.5% $NH_4OH$) provided the title compound: $^1H$ NMR (DMSO-$d_6$) δ 2.68, 2.83–2.90, 6.58–6.67, 6.89, 7.06, 7.54, 10.71.

EXAMPLE 350

N-(2-chlorophenyl)-1,2,3,4,5,6-hexahydroazepino[4,5-b]indol-10-amine

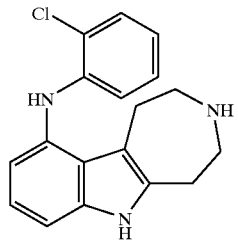

Following the procedure for the preparation of N-phenyl-1,2,3,4,5,6-hexahydroazepino[4,5-b]indol-10-amine, making non-critical variations, starting from tert-butyl 10-bromo-1,4,5,6-tetrahydroazepino[4,5-b]indole-3(2H)-carboxylate the title compound was prepared: $^1H$ NMR (DMSO-$d_6$) δ 2.91, 3.01, 3.06, 3.20, 6.36, 6.65, 6.75, 6.99, 7.17, 7.35, 11.0. HRMS (FAB) calcd for $C_{18}H_{18}ClN_3$ ($MH^+$) 312.1267, found 312.1281.

EXAMPLES 351–465

Preparation 124

Preparation of 8,9-dichloro-1,2,3,4,5,6-hexahydroazepino[4,5-b]indole

A mixture of 3-benzoyl-8,9-dichloro-1,2,3,4,5,6-hexahydroazepino[4,5-b]indole (2.00 g, 5.57 mmol), potassium hydroxide (3.00 g, 53.5 mmol), and ethylene glycol (15 mL) was heated to 170° C. After 2 h, the reaction was cooled to room temperature, diluted with $H_2O$, and extracted with $CH_2Cl_2$. The combined organic extracts were washed with brine, dried over $Na_2SO_4$, decanted, and concentrated under reduced pressure. The crude product was purified by silica gel chromatography with $CH_2Cl_2$/MeOH/$Et_2NH$ (9:1:0 followed by 97:3:1 followed by 95:4:1) to give 1.04 g (73%) of 8,9-dichloro-1,2,3,4,5,6-hexahydroazepino[4,5-b]indole as a dark yellow solid. $^1H$ NMR (d-$CHCl_3$) δ 7.75, 7.50, 7.34, 3.08, 2.92, 2.82, 1.91: MS (ESI) 255.1 ($M^++H$).

EXAMPLE 351
(5aS*,10bS*)-8,9-dichloro-1,2,3,4,5,5a,6,10b-octahydroazepino[4,5-b]indole

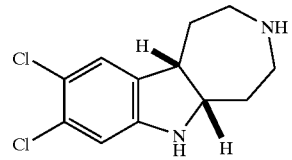

A solution of 8,9-dichloro-1,2,3,4,5,6-hexahydroazepino[4,5-b]indole (0.40 g, 1.6 mmol) in TFA (4.0 mL) was cooled to 0° C., then a freshly prepared solution of Na(CN)BH$_3$ (0.49 g, 7.8 mmol) in MeOH (.1.5 mL) was added dropwise. The ice bath was removed after the addition was complete. After 2.5 h, the reaction was diluted with $H_2O$, made basic with 50% aqueous NaOH, and extracted with EtOAc. The combined organic extracts were washed with brine, dried over $Na_2SO_4$, decanted, and concentrated under reduced pressure. The crude product was purified by silica gel chromatography and prep HPLC to give 0.14 g (36%) of the title compound as pale orange solid. $^1H$ NMR (d-$CHCl_3$) δ 7.00, 6.58, 4.22, 3.81, 3.58, 3.14–2.98, 2.79, 2.07–1.87: IR (drift) 3201, 3170, 3149, 3031, 2927, 2852, 2838, 2750, 1608, 1483, 1450, 1365, 1273, 832, 660 $cm^{-1}$; HRMS (FAB) calcd for $C_{12}H_{14}Cl_2N_2$+H 257.0612, found 257.0614.
Preparation 125
Preparation of 3-benzoyl-8,9-dichloro-1,2,3,4,5,5a,6,10b-octahydroazepino[4,5-b]indole A solution of 3-benzoyl-8,9-dichloro-1,2,3,4,5,6-hexahydroazepino[4,5-b]indole (0.25 g, 0.70 mmol) in TFA (2.0 mL) was cooled to 0° C., then a freshly prepared solution of Na(CN)BH$_3$ (0.22 g, 3.5 mmol) in MeOH (0.75 mL) was added dropwise. The ice bath was removed after the addition was complete. After 3 h, the reaction was diluted with $H_2O$, made basic with 50% aqueous NaOH, and extracted with EtOAc. The combined organic extracts were washed with brine, dried over $Na_2SO_4$, decanted, and concentrated under reduced pressure. The crude product was purified by silica gel chromatography with EtOAc/heptanes (1:1) to give 0.19 g (76%) of 3-benzoyl-8,9-dichloro-1,2,3,4,5,5a,6,10b-octahydroazepino[4,5-b]indole as a yellow foam (mixture of diastereomers). $^1H$ NMR (d-$CHCl_3$) δ 7.42–7.37, 7.04, 6.95, 6.66–6.61, 4.34–3.07, 2.73, 2.49, 2.23–1.52: MS (ESI) 361.1 ($M^++H$).

EXAMPLE 352
(5aR*,10bS*)-8,9-dichloro-1,2,3,4,5,5a,6,10b-octahydroazepino[4,5-b]indole

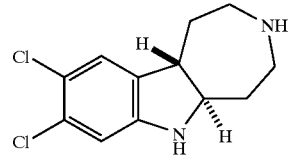

A mixture of 3-benzoyl-8,9-dichloro-1,2,3,4,5,5a,6,10b-octahydroazepino[4,5-b]indole (0.20 g, 0.55), potassium hydroxide (1.0 g, 17.8 mmol), and ethylene glycol (5 mL) was heated to 170° C. Upon the disappearance of starting material, the reaction was cooled to room temperature, diluted with $H_2O$, and extracted with $CH_2Cl_2$. The combined organic extracts were washed with brine, dried over $Na_2SO_4$, decanted, and concentrated under reduced pressure. The crude product was purified by silica gel chromatography and prep HPLC to give the title compound (31 mg, 22%) as a tan solid. $^1$H NMR (d-MeOH) δ 8.54, 7.02, 6.63, 3.73, 3.08–2.88, 2.40, 2.17, 1.81, 1.65: IR (drift) 2934, 2916, 2866, 2850, 2831, 1627, 1608, 1569, 1481, 1466, 1372, 1365, 953, 775, 662 cm$^{-1}$; HRMS (FAB) calcd for $C_{12}H_{14}C_{12}N_2$+H 257.0612, found 257.0619.

EXAMPLE 353

(5aS*,10bS*)-1,2,3,4,5,5a,6,10b-octahydroazepino[4,5-b]indole

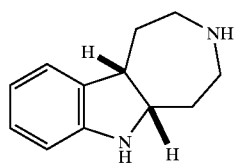

A solution of 1,2,3,4,5,6-hexahydroazepino[4,5-b]indole (0.93 g, 5.0 mmol) in trifluoroacetic acid (17 mL) was cooled to 0° C., and treated with a freshly prepared solution of Na(CN)BH$_3$ (1.57 g, 25 mmol) in MeOH (4 mL). The cooling bath was removed and the reaction mixture was stirred at room temperature for 1 h, then treated with water (75 mL), stirred for an additional 15 minutes before adjusting the pH to 14 with 45% KOH (aqueous). The resulting solution was extracted with EtOAc (3×40 mL), and the combined organic extracts were washed once with brine, dried over MgSO$_4$, filtered, and concentrated in vacuo to give a yellow syrup. The crude product was purified by chromatography and using ethanol:ammonia:dichloromethane (15:1.5:83.5) and trituration of the resulting material gave the title compound (0.64g) as an off-white solid: mp 102–114° C.

EXAMPLE 354

9-(2,6-Difluorophenyl)-1,2,3,4,5,5a,6,10b-octahydroazepino[4,5-b]indole dihydrochloride

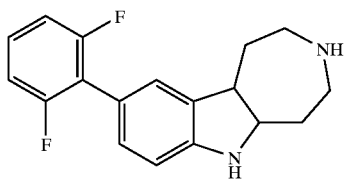

A freshly prepared solution of sodium cyanoborohydride (0.16 g, 2.5 mmol) in MeOH (0.75 mL) was added to a solution of 9-(2,6-difluorophenyl)-1,2,3,4,5,6-hexahydroazepino[4,5-b]indole (0.15 g, 0.50 mmol) in THF (3.0 mL) at 0° C. Upon completion of the addition, the ice bath was removed. After 1 h, the reaction was diluted with H$_2$O, quenched with 50% aqueous NaOH, and extracted with EtOAc (3×10 mL). The combined organic extracts were washed with brine, dried over Na$_2$SO$_4$, decanted, and concentrated. The crude product was purified by column chromatography (Biotage, 40S) with CH$_2$Cl$_2$/MeOH/NH$_4$OH (gradient, 976:21:3 to 960:35:5) to give 98 mg of impure amine. The HCl salt was prepared to give 30 mg of a light pink solid: mp 268.5–271.5° C.; IR (diffuse reflectance) 2858, 2818, 2792, 2774, 2739, 2678, 2641, 2571, 2550, 2494, 2463, 2395, 1464, 990, 800 cm$^{-1}$; MS (EI) m/z 300 (M$^+$), 300, 256, 244, 243, 242, 229, 78, 64, 63, 61: Anal. Calcd for $C_{18}H_{18}F_2N_2$.2HCl: C, 57.92: H, 5.40: N, 7.51: found: C, 57.63; H, 5.58: N, 7.33.

Preparation 126

Preparation of 3-Benzoyl-9-(4-methoxy-2-methylphenyl)-1,2,3,4,5,6-hexahydroazepino[4,5-b]indole.

A solution of 3-benzoyl-9-bromo-1,2,3,4,5,6-hexahydroazepino[4,5-b]indole (1.50 g, 4.06 mmol) in DME (50 mL) was degassed via sonication and vacuum/N$_2$ purge. Then, (PhP$_3$)$_4$Pd (0.235 g, 0.203 mmol) was added and the mixture was stirred for 20 min prior to the addition of a solution of tris(4-methoxy-2-methylphenyl)boroxin (0.900 g, 2.03 mmol) in DME (10 mL) and MeOH (2.5 mL). Next, 2M Na$_2$CO$_3$ (12 mL) was added and the reaction was heated to reflux. After 7 h, additional (PhP$_3$)$_4$Pd (0.235 g, 0.203 mmol) was added. The reaction was cooled to rt after an additional 15 h. The reaction was partitioned between H$_2$O and EtOAc and the layers were separated. The aqueous layer was extracted with additional EtOAc (2×100 mL). The combined organic extracts were washed with brine, dried over Na$_2$SO$_4$, decanted, and concentrated. The crude product was purified by column chromatography (Biotage, 40M) with heptane/EtOAc (gradient, 2:1 to 1:1) to give 0.61 (37%) of the title compound. An analytical sample was prepared, via crystallization from heptane/EtOAc, as an off-white solid: mp 268.5–271.5° C.; IR (diffuse reflectance) 3297, 3250, 3243, 3202, 1608, 1500, 1467, 1430, 1300, 1289, 1276, 1233, 786, 740, 706 cm$^{-1}$; MS (EI) m/z 410 (M$^+$), 290, 289, 288, 276, 105, 86, 77, 51, 50: HRMS (FAB) calcd for $C_{27}H_{26}N_2O_2$+H 411.2072, found 411.2073: % water (KF): 0.23: melt solvate: 1.91% EtOAc, 0.15% heptane; Anal. Calcd for $C_{27}H_{26}N_2O_2$.0.23% H$_2$O.1.91% EtOAc.0.15% heptane: C, 78.36: H, 6.46: N, 6.67: found: C, 78.16: H, 6.47: N, 6.91.

EXAMPLE 355

9-(4-Methoxy-2-methylphenyl)-1,2,3,4,5,5a,6,10b-octahydroazepino[4,5-b]indole dihydrochloride

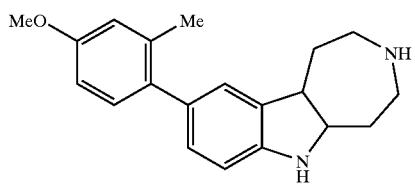

A freshly prepared solution of sodium cyanoborohydride (0.10 g, 1.6 mmol) in MeOH (0.50 mL) was added to a solution of 9-(4-methoxy-2-methylphenyl)-1,2,3,4,5,6-hexahydroazepino[4,5-b]indole (0.10 g, 0.33 mmol) in THF (3.0 mL) at 0° C. After 5 min, the ice bath was removed. After 2 h, the reaction was diluted with H$_2$O, quenched with 50% aqueous NaOH, and extracted with EtOAc (3×10 mL). The combined organic extracts were washed with brine, dried over Na$_2$SO$_4$, decanted, and concentrated. The crude product was purified by column chromatography (Biotage, 40S) with CH$_2$Cl$_2$/MeOH/NH$_4$OH (976:21:3) to give 72 mg of impure amine. The HCl salt was prepared to give 20 mg (16%) of a tan solid: mp 225.5–228° C., IR (diffuse reflectance) 2954, 2849, 2829, 2750, 2687, 2655, 2624, 2526, 2470, 1606, 1485, 1466, 1458, 1289, 1240 cm$^{-1}$; MS (EI) m/z 308 (M$^+$), 306, 278, 265, 264, 251, 250, 78, 63, 56: Anal. Calcd for $C_{20}H_{24}N_2O$.2HCl: C, 62.99: H, 6.87: N, 7.35: found: C, 63.16: H, 7.00: N, 7.31.

EXAMPLE 356

(5aS*, 10bS*)-10-(2-chlorophenyl)-1,2,3,4,5,5a,6,10b-octahydroazepino[4,5-b]indole

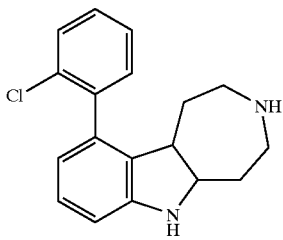

Prepared according to the procedure used to prepare 10-(2,6-difluorophenyl)-1,2,3,4,5,5a,6,10b-octahydroazepino[4,5-b]indole in 78% yield. $^1$H NMR (400 MHz, CD$_3$OD) δ 1.37–1.65, 1.93–2.14, 2.45–2.88, 3.17, 3.66, 4.21, 6.40–6.68, 7.07, 7.25–7.43, 7.50: MS (ESI+) for C$_{18}$H$_{18}$ClN$_2$ m/z 299.1 (M+H)$^+$.

EXAMPLE 357

(5aS*,10bS*)-10-(2-methylphenyl)-1,2,3,4,5,5a,6,10b-octahydroazepino[4,5-b]indole

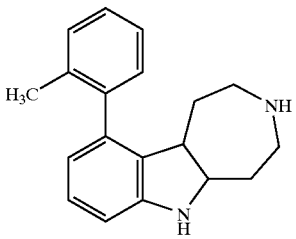

A 0° C. solution of 10-(2-methylphenyl)-1,2,3,4,5,6-hexahydroazepino[4,5-b]indole hydrochloride (268 mg, 0.86 mmol) in trifluoroacetic acid (4 mL) was treated with a solution of sodium cyanoborohydride (280 mg) in methanol (1 mL). The reaction was allowed to slowly warm to room temperature over 3 hours then diluted with water and concentrated in vacuo to remove the majority of acid. The residue was made basic with 15% NaOH, extracted with CH$_2$Cl$_2$ dried over MgSO$_4$ and concentrated in vacuo to give 184 mg of a brown oil which was passed through a column of silica gel with 1:19 methanol/chloroform with 1% NH$_4$OH to give 99 mg (41%) of a white foam as the title compound: $^1$H NMR (400 MHz, Acetone-d$_6$) δ 7.28–7.20 (m, 4 H), 6.97 (m, 1 H), 6.49 (m, 1H), 6.34 (m, 1 H), 5.01 (m, 1 H), 4.19–4.15 (m, 1 H), 3.58 (m, 1H), 2.98 (m, 1 H), 2.61–2.55 (m, 2 H), 2.34–2.28 (m, 1 H), 2.16 (s, 3 H), 2.10–1.85 (in, 2 H), 1.52–1.47 (m, 1 H), 1.25–1.15 (m, 1 H); HRMS (FAB) calcd for C$_{19}$H$_{22}$N$_2$+H$_1$ 279.1861, found 279.1864.

EXAMPLE 358

(5aS*,10bS*)-10-(2-Methoxyphenyl)-1,2,3,4,5,5a,6,10b-octahydroazepino[4,5-b]indole

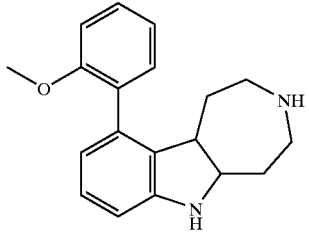

A 0° C. solution of 10-(2-methoxyphenyl)-1,2,3,4,5,6-hexahydroazepino[4,5-b]indole hydrochloride from above (286 mg, 0.87 mmol) in trifluoroacetic acid (4 mL) was treated with a solution of sodium cyanoborohydride (278 mg 4.42 mmol) in methanol (1 mL). The reaction was allowed to slowly warm to room temperature over 3.8 hours then diluted with water and concentrated in vacuo to remove the majority of acid. The residue was made basic with 15% NaOH, extracted with CH$_2$Cl$_2$ dried over MgSO$_4$ and concentrated in vacuo and passed through a column of silica gel with 1:19 methanol/chloroform with 1% NH$_4$OH to give 91 mg (36%) of a white foam as the title compound: $^1$H NMR (400 MHz, Acetone-d$_6$) δ 7.34–7.30 (m, 1 H), 7.17 (dd, J=7.4 Hz, 1.7 Hz, 1 H), 7.06 (d, J=8.3 Hz, 1 H), 7.00–6.92 (m, 2 H), 6.47 (d, J=7.7 Hz, 1 H), 6.42 (d, J=7.6 Hz, 1 H), 4.90 (br s, 1 H), 4.19–4.14 (m, 1 H), 3.78 (s, 3 H), 3.65–3.60 (m, 1 H), 2.97–2.93 (m, 1 H), 2.64–2.56 (m, 2 H) 2.35–2.29 (m, 1 H), 1.98–1.94 (m, 1 H), 1.48–1.44 (m, 1 H), 1.28–1.23 (m, 1 H); HRMS (FAB) calcd for C$_{19}$H$_{22}$N$_2$O$_1$+H$_1$ 295.1810, found 295.1798.

EXAMPLE 359

(5aS*,10bS*)-10-(2-Propoxyphenyl)-1,2,3,4,5,5a,6,10b-octahydroazepino[4,5-b]indole

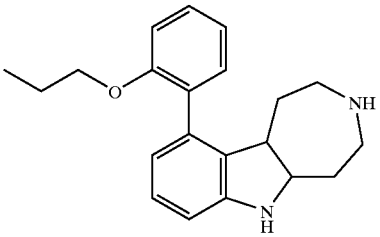

A 0° C. solution of 10-(2-propoxyphenyl)-1,2,3,4,5,6-hexahydroazepino[4,5-b]indole (257 mg, 0.80 mmol) in trifluoroacetic acid (4 mL) was treated with a solution of sodium cyanoborohydride (269 mg 4.28 mmol) in methanol (2 mL). The reaction was allowed to slowly warm to room temperature over 1.6 hours then diluted with water and concentrated in vacuo to remove the majority of acid. The residue was made basic with 15% NaOH, extracted twice with CH$_2$Cl$_2$ dried over MgSO$_4$ and concentrated in vacuo and passed through a column of silica gel with 1:19 methanol/chloroform with 1% NH$_4$OH to give 104 mg (40%) of a brown oil as the title compound: $^1$H NMR (400 MHz, CDCl$_3$) δ 7.32–7.30 (m, 1 H), 7.25 (dd, J=7.4 Hz, 1.7 Hz, 1 H), 7.11–7.07 (m, 1 H), 7.02–6.96 (m, 2 H), 6.65–6.59 (m, 1 H), 4.24–4.21 (m, 1 H), 3.97–3.84 (m, 2 H), 3.73 (dt, J=9.7 Hz, 3.3 Hz, 1 H), 3.13–3.08 (m, 1 H), 2.80–2.76 (m, 1 H), 2.73–2.67 (m, 1 H), 2.47–2.41 (m, 1 H), 2.06–2.04 (m, 1 H), 1.95–1.92 (m, 1 H), 1.75–1.70 (m, 2 H), 1.59–1.55 (m,

EXAMPLES 360 and 361

(5aS,10bS)-10-(2-Propoxyphenyl)-1,2,3,4,5,5a,6,10b-octahydroazepino[4,5-b]indole and (5aR,10bR)-10-(2-Propoxyphenyl)-1,2,3,4,5,5a,6,10b-octahydroazepino[4,5-b]indole

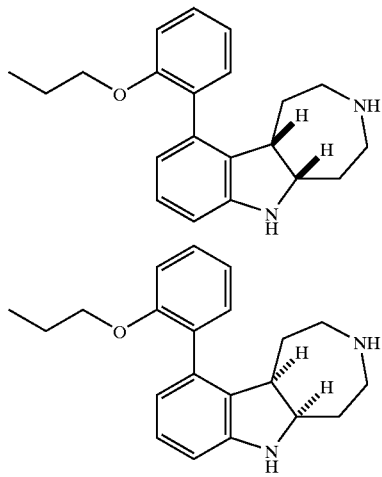

The racemic (5aS*,10bS*)-10-(2-propoxyphenyl)-1,2,3,4,5,5a,6,10b-octahydroazepino[4,5-b]indole from above was resolved by chiral chromatography to give 0.010 g of a brown oil enriched in the more polar enantiomer (72% ee): $^1$H NMR (400 MHz, CDCl$_3$) δ 7.34–7.30 (m, 1 H), 7.25 (dd, J=7.4 Hz, 1.7 Hz, 1 H), 7.11–7.07 (m, 1 H), 7.02–6.96 (m, 2 H), 6.65–6.59 (m, 1 H), 4.27–4.21 (m, 1 H), 3.98–3.89 (m, 2 H), 3.73 (dt, J=9.6 Hz, 3.4 Hz, 1 H), 3.16–3.11 (m, 1 H), 2.80–2.71 (m, 2 H), 2.51–2.45 (m, 1 H), 2.08–2.05 (m, 1 H), 1.98–1.93 (m, 1 H), 1.75–1.70 (m, 2 H), 1.59–1.55 (m, 1 H), 1.40–1.38 (m, 1 H) 0.94 (t, J=7.4 Hz, 3 H); HRMS (FAB) calcd for C$_{21}$H$_{26}$N$_2$O+H$_1$: 323.2123, found 323.21 10. In addition 0.014 g of a brown oil as the less polar enantiomer was obtained: $^1$H NMR (400 MHz, CDCl$_3$) δ 7.34–7.30 (m, 1 H), 7.25 (dd, J=7.4 Hz, 1.7 Hz, 1 H), 7.11–7.07 (m, 1 H), 7.02–6.96 (m, 2 H), 6.65–6.60 (m, 1 H), 4.27–4.21 (m, 1 H), 3.96–3.89 (m, 2 H), 3.72 (dt, J=9.6 Hz, 3.4 Hz, 1 H), 3.15–3.10 (m, 1 H), 2.81–2.69 (m, 2 H), 2.49–2.43 (m, 1 H), 2.08–2.04 (m, 1 H), 1.98–1.92 (m, 1 H), 1.75–1.70 (m, 2 H), 1.59–1.55 (m, 1 H), 1.38–1.36 (m, 1 H) 0.94 (t, J=7.4 Hz, 3 H); HRMS (FAB) calcd for C$_{21}$H$_{26}$N$_2$O+H$_1$: 323.2123, found 323.2117.

Preparation 127

Preparation of (5aS*,10bS*)-tert-Butyl 10-(2-fluorophenyl)-1,4,5,5a,6,10b-hexahydroazepino[4,5-b]indole-3(2H)-carboxylate and (5aS*,10bS*)-di(tert-butyl) 10-(2-fluorophenyl)-1,2,4,5,5a,10b-hexahydroazepino[4,5-b]indole-3,6-dicarboxylate A 0° C. solution of 10-(2-fluorophenyl)-1,2,3,4,5,6-hexahydroazepino[4,5-b]indole (1.14 g, 4.00 mmol) in trifluoroacetic acid (20 mL) was treated with a solution of sodium cyanoborohydride (1.24 g 19.73 mmol) in methanol (5 mL). The reaction was allowed to slowly warm to room temperature over 18.2 hours then diluted with water and concentrated in vacuo to remove the majority of acid. The residue was made basic with 15% NaOH, extracted three times with CH$_2$Cl$_2$ dried over MgSO$_4$ and concentrated in vacuo to give a brown oil (0.86 g). The oil was dissolved in CH$_2$Cl$_2$ (25 mL) and treated with di-tert-butyl dicarbonate (0.75 g, 3.44 mmol) and triethylamine (0.36 g, 3.56 mmol). The reaction was stirred at room temperature for 3 hours. The reaction was concentrated in vacuo and the residue was dissolved in ethyl acetate, washed successively with 2N HCl, saturated NaHCO$_3$, brine, dried over MgSO$_4$ and concentrated in vacuo to give a brown oil (1.0 g) which was passed through a column of silica gel with 20% ethyl acetate/hexane to give (5aS*,10bS*)-di(tert-butyl) 10-(2-fluorophenyl)-1,2,4,5,5a,10b-hexahydroazepino[4,5-b]indole-3,6-dicarboxylate as a white solid 0.32 g (22%): mp 166.0–169.3° C. $^1$H NMR (400 MHz, CDCl$_3$) δ 7.37–7.12 (m, δ 1 H), 6.92 (d, J=7.6 Hz, 1 H), 4.67 (m, 1 H), 4.11 (m, 1 H), 3.41 (m, 2 H), 3.15 (m, 2 H), 2.13 (m, 2 H), 1.62 (s, 9 H), 1.42 (m, 11 H); MS m/z 483.5 (M$^+$+H). A slower fraction from the column gave (5aS*,10bS*)-tert-butyl 10-(2-fluorophenyl)-1,4,5,5a,6,10b-hexahydroazepino[4,5-b]indole-3(2H)-carboxylate as a clear oil 0.41 g (35%): $^1$H NMR (400 MHz, CDCl$_3$) δ 7.37 (m, 2 H), 7.23–7.16 (m, 3 H), 6.78–6.76 (m, 2 H), 4.31–4.26 (m, 1 H), 3.62–3.32 (m, 4 H), 3.12 (m, 1 H), 2.09 (m, 2 H), 1.64 (m, 2 H), 1.43 (s, 9 H); MS m/z 383.4 (M$^+$+H).

EXAMPLE 362

(5aS*,10bS*)-10-(2-Fluorophenyl)-1,2,3,4,5,5a,6,10b-octahydroazepino[4,5-b]indole dihydrochloride

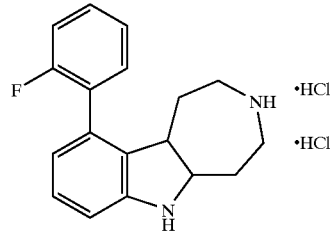

(5aS*,10bS*)-Di(tert-butyl) 10-(2-fluorophenyl)-1,2,4,5,5a,10b-hexahydroazepino[4,5-b]indole-3,6-dicarboxylate (0.094 g, 0.19 mmol) was dissolved in a 4.0 N solution of HCl in dioxane (4 mL) and stirred at room temperature for 26.5 hours. After the reaction mixture was concentrated in vacuo CH$_3$OH was added and the solution was concentrated in vacuo and recrystallized from CH$_3$OH/EtOAc to give 0.054 g (72%) of a white solid as the title compound: mp 248.0–256.7° C. $^1$H NMR (400 MHz, DMSO-d$_6$) δ 9.19 (m, 1 H), 9.05 (m, 1 H), 7.51–7.43 (m, 2 H), 7.36–7.29 (m, 3 H), 7.03–6.98 (m, 2 H) 4.34–4.33 (m, 1 H), 3.85 (m, 1 H), 3.29 (m, 1 H), 3.06 (m, 1 H), 2.90 (m, 1 H), 2.69–2.67 (m, 1 H), 2.27 (m, 2 H), 1.67 (m, 1 H), 1.36–1.34 (m, 1 H); $^{13}$C NMR (100 MHz, DMSO-d$_6$) δ 159.8, 157.3, 132.7, 130.8, 130.7, 130.2, 130.1, 128.6, 126.4, 126.2, 124.8, 124.7, 115.9, 115.7, 59.7, 44.8, 43.9, 41.7, 26.5, 25.7: IR (diffuse reflectance) 2954 (s), 2847 (s), 2817 (s,b), 2755 (s), 2726 (s,b), 2668 (s,b), 2651 (s,b), 2572 (s,b), 2538 (s), 2469 (s), 2350, 2342, 1738, 1474, 771 cm$^{-1}$; HRMS (FAB) calcd for C$_{18}$H$_{19}$FN$_2$+H$_1$: 283.1610 found 283.1612.

EXAMPLES 363 and 364
(5aS,10bS)-10-(2-Fluorophenyl)-1,2,3,4,5,5a,6,10b-octahydroazepino[4,5-b]indole dihydrochloride and (5aR,10bR)-10-(2-Fluorophenyl)-1,2,3,4,5,5a,6,10b-octahydroazepino[4,5-b]indole dihydrochloride

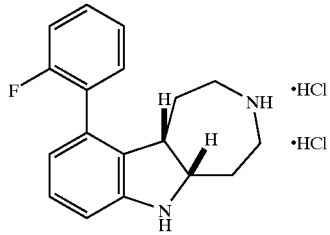

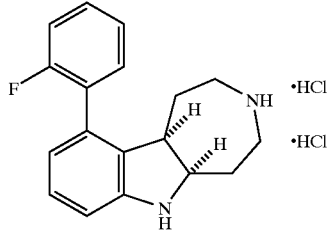

The racemic (5aS*,10bS*)-tert-butyl 10-(2-fluorophenyl)-1,4,5,5a,6,10b-hexahydroazepino[4,5-b]indole-3(2H)-carboxylate from above was resolved by chiral chromatography to give a clear oil (0.149 g) as the more polar enantiomer. This was dissolved in a 4.0 N solution of HCl in dioxane (5 mL) and stirred at room temperature for 5 hours. After the reaction mixture was concentrated in vacuo $CH_3OH$ was added and the solution was concentrated in vacuo and recrystallized from $CH_3OH$/EtOAc to give 0.045 g (33%) of a white solid as the title compound: mp 246.5–250.0° C. $^1$H NMR (400 MHz, DMSO-$d_6$) δ 9.12 (m, 1 H), 9.01 (m, 1 H), 7.50–7.42 (m, 2 H), 7.36–7.29 (m, 3 H), 6.97 (m, 2 H), 4.32–4.31 (m, 1 H), 3.82 (m, 1 H), 3.26 (m, 1 H), 3.06 (m, 1 H), 2.87 (m, 1 H), 2.70 (m, 1 H), 2.24 (m, 2 H), 1.65 (m, 1 H), 1.37 (m, 1 H); $^{13}$C NMR (100 MHz, DMSO-$d_6$) δ 159.8, 157.3, 132.6, 130.8, 130.7, 130.1, 128.5, 126.5, 126.4, 124.7, 124.7, 115.9, 115.7, 59.7, 44.7, 43.8, 41.7, 26.7, 25.7: $^{19}$F NMR (376 MHz, DMSO-$d_6$) δ −116.1 (m); IR (diffuse reflectance) 2954, 2844 (s), 2794 (s), 2750 (s), 2680 (s), 2665 (s), 2651 (s), 2624 (s,b), 2578, 2547 (b), 2537, 2524, 2494 (s), 2468 (s), 763 cm$^{-1}$. HRMS (FAB) calcd for $C_{18}H_{19}FN_2+H_1$: 283.1610 found 283.1603. In addition a clear oil (0.185 g) was obtained as the less polar enantiomer. This was dissolved in a 4.0 N solution of HCl in dioxane (5 mL) and stirred at room temperature for 5 hours. After the reaction mixture was concentrated in vacuo $CH_3OH$ was added and the solution was concentrated in vacuo and recrystallized from $CH_3OH$/EtOAc to give 0.127 g (74%) of a white solid as the title compound: mp 247.6–250.0° C.; $^1$H NMR (400 MHz, DMSO-$d_6$) δ 9.17 (m, 1 H), 9.03 (m, 1 H), 7.51–7.43 (m, 2 H), 7.36–7.29 (m, 3 H), 7.01–6.96 (m, 2 H), 4.34–4.33 (m, 1 H), 3.84 (m, 1 H), 3.29 (m, 1 H), 3.06 (m, 1 H), 2.89 (m, 1 H), 2.69–2.67 (m, 1 H), 2.26 (m, 2 H), 1.67 (m, 1 H), 1.36–1.34 (m, 1 H); $^{13}$C NMR (100 MHz, DMSO-$d_6$) δ 159.8, 157.3, 132.7, 130.8, 130.7, 130.2, 130.1, 128.6, 126.4, 126.3, 124.7, 124.7, 115.9, 115.7, 59.7, 44.8, 43.8, 41.7, 26.6, 25.7: $^{19}$F NMR (376 MHz, DMSO-$d_6$) δ −116.1 (m); IR (diffuse reflectance) 2844, 2834 (b), 2814 (b), 2793 (s), 2751 (s), 2729 (s,b), 2680 (s), 2665 (s), 2651 (s), 2624 (s,b), 2578, 2548, 2494 (s), 2468 (s), 763 (s) cm$^{-1}$; HRMS (FAB) calcd for $C_{18}H_{19}FN_2+H_1$: 283.1610 found 283.1607.

EXAMPLE 365
(5aR*,10bS*)-10-(2-Fluorophenyl)-1,2,3,4,5,5a,6,10b-octahydroazepino[4,5-b]indole

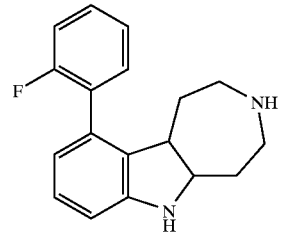

A solution of 10-(2-fluorophenyl)-1,2,3,4,5,6-hexahydroazepino[4,5-b]indole (0.49 g, 1.74 mmol) in THF (6 mL) was added dropwise to 1.5 M borane-THF complex (6 mL, 9 mmol) and stirred at room temperature for 1.25 hours. The excess borane was quenched with $H_2O$ and the mixture was added to TFA at 0° C. After 0.3 hours the reaction was diluted with $H_2O$ and concentrated in vacuo. The residue was diluted with $H_2O$, made basic with 15% NaOH and extracted three times with $CH_2Cl_2$. The extracts were dried over $MgSO_4$ and concentrated in vacuo to give a white solid which was passed through a column of silica gel with 1:19 acetone/$CHCl_3$ with 1% $NH_4OH$ to give 0.25 g (51%) of a light brown solid as the title compound: $^1$H NMR (400 MHz, CDCl$_3$) δ 7.38–7.33 (m, 2 H), 7.21–7.10 (m, 3 H), 6.69 (d, J=7.7 Hz, 2 H), 3.89 (dt, J=11.0 Hz, 3.5 Hz, 1 H), 3.60–3.53 (m, 1 H), 3.18–3.12 (m, 1 H), 2.94–2.88 (m, 1 H), 2.83 (m, 1 H), 2.74–2.72 (m, 1 H), 2.21–2.16 (m, 1 H), 1.97–1.87 (m, 1 H), 1.67 (m, 1 H), 1.26 (m, 1 H); MS m/z 283.2 (M$^+$+H).

EXAMPLES 366 and 367
(5aR,10bS)-10-(2-Fluorophenyl)-1,2,3,4,5,5a,6,10b-octahydroazepino[4,5-b]indole and (5aS,10bR)-10-(2-fluorophenyl)-1,2,3,4,5,5a,6,10b-octahydroazepino[4,5-b]indole

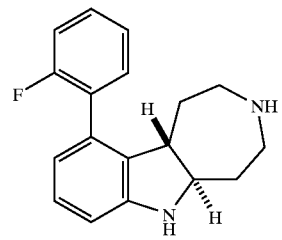

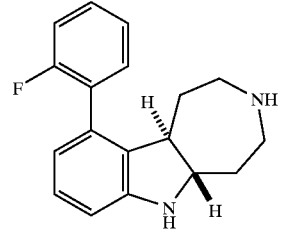

The racemic trans-10-(2-fluorophenyl)-1,2,3,4,5,5 a,6,10b-octahydroazepino[4,5-b]indole from above was resolved by chiral chromatography to, give 0.104 g of a brown oil as the more polar enantiomer: $^1$H NMR (400 MHz, DMSO-$d_6$) δ 7.41–7.37 (m, 1 H), 7.31 (m, 1 H), 7.25–7.21 (m, 2 H), 6.98–6.94 (m, 1 H), 6.49 (d, J=7.7 Hz, 1 H), 6.41 (d, J=7.5 Hz, 1 H), 3.65 (m, 1 H), 3.31 (m, 1 H), 2.96–2.92 (m, 1 H), 2.68 (m, 1 H), 2.63–2.56 (m, 2 H), 2.02–1.98 (m, 1 H), 1.64

(m, 1 H), 1.41 (m, 1 H), 1.00 (m, 1 H); HRMS (FAB) calcd for $C_{18}H_{19}F_1N_2+H_1$: 283.1610 found 283.1620. In addition 0.099 g of a brown oil as the less polar enantiomer was obtained: $^1$H NMR (400 MHz, CDCl$_3$) δ 7.35–7.32 (m, 2 H), 7.19–7.09 (m, 3 H), 6.68 (d, J=7.6 Hz, 2 H), 3.89–3.83 (m, 1 H), 3.59–3.52 (m, 1 H), 3.16–3.10 (m, 1 H), 2.92–2.86 (m, 1 H), 2.80 (m, 1 H), 2.71–2.69 (m, 1 H), 2.19–2.15 (m, 1 H), 1.95–1.85 (m, 1 H), 1.67 (m, 1 H), 1.24 (m, 1 H); IR (diffuse reflectance) 3247, 2938, 2846, 2752 (b), 1591, 1500, 1472, 1439, 1262, 1247, 1214, 819, 789, 758 (s), 737 cm$^{-1}$. HRMS (FAB) calcd for $C_{18}H_{19}F_1N_2+H_1$: 283.1610 found 283.1623.

EXAMPLE 368

(5aR*,10bS*)-10-(2,4-dichlorophenyl)-1,2,3,4,5,5a,6,10b-octahydroazepino[4,5-b]indole maleic acid salt

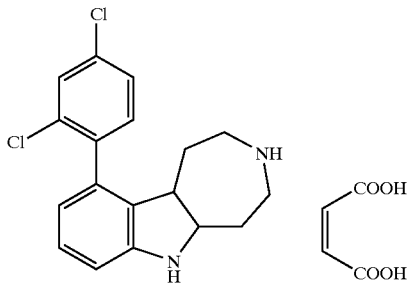

Prepared according to the procedure used to prepare (5aS*,10bS*)-10-(2-methoxyphenyl)-1,2,3,4,5,5a,6,10b-octahydroazepino[4,5-b]indole, the title compound was obtained: MS (ESI+) m/z 333.2 (MH$^+$).

EXAMPLE 369

(5aR*,10bS*)-10-(4-methoxy-2-methylphenyl)-1,2,3,4,5,5a,6,10b-octahydroazepino[4,5-b]indole maleic acid salt

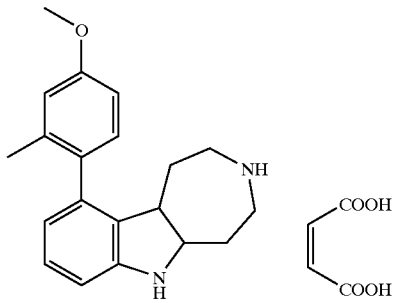

Prepared according to the procedure used to prepare (5aS*,10bS*)-10-(2-methoxyphenyl)-1,2,3,4,5,5a,6,10b-octahydroazepino[4,5-b]indole, the title compound was obtained: mp 142–146° C.; IR (diffuse reflectance) 3022, 3002, 2957, 2833, 1607, 1586, 1533, 1508, 1469, 1453, 1380, 1366, 1291, 1237, 864 cm$^{-1}$; MS (EI) m/z 308 (M+), 264, 263, 252, 251, 250, 236, 84, 56, 54: HRMS (FAB) calcd for $C_{20}H_{24}N_2O+H$ 309.1967, found 309.1958.

EXAMPLE 370

(5aR*,10bS*)-10-(2-ethoxyphenyl)-1,2,3,4,5,5a,6,10b-octahydroazepino[4,5-b]indole

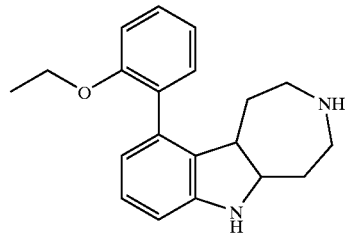

Prepared according to the procedure used to prepare (5aS*,10bS*)-10-(2-methoxyphenyl)-1,2,3,4,5,5a,6,10b-octahydroazepino[4,5-b]indole, the title compound was obtained: 0.14 g (66%), IR (mull) 3023, 1597, 1590, 1578, 1500, 1442, 1414, 1272, 1250, 1233, 1127, 1046, 787, 754, 745 cm$^{-1}$; MS (EI) m/z 308 (M+), 264, 252, 251, 250, 236, 234, 222, 220, 56: HRMS (FAB) calcd for $C_{20}H_{24}N_2O+H$ 309.1967, found 309.1950.

EXAMPLES 371 and 372

(5aS, 10bS)-10-(2-ethoxyphenyl)-1,2,3,4,5,5a,6,10b-octahydroazepino[4,5-b]indole and (5aR, 10bR)-10-(2-ethoxyphenyl)-1,2,3,4,5,5a,6,10b-octahydroazepino[4,5-b]indole

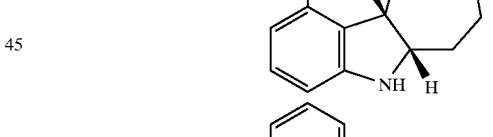

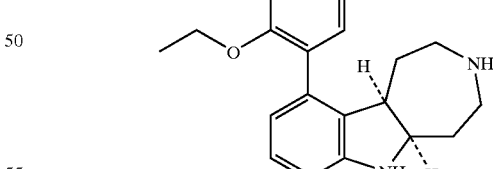

The racemic (5aR*,10bS*)-10-(2-ethoxyphenyl)-1,2,3,4,5,5a,6,10b-octahydroazepino[4,5-b]indole was purified by chiral chromatography (elution with 2–6% MeOH/chloroform+1% ammonium hydroxide) to give 0.038 g of a clear oil which was filtered through a fine fritted funnel to give 0.029 g of a beige foam: MS (EI) m/z 309 (MH+); HPLC retention time 100% 3.24 min. In addition, 0.025 g of a clear oil was obtained: MS (EI) m/z 309 (MH+); HPLC retention time 100% 3.29 min.

EXAMPLE 373

(5aR*,10bS*)-10-phenyl-1,2,3,4,5,5a,6,10b-octahydroazepino[4,5-b]indole maleic acid salt

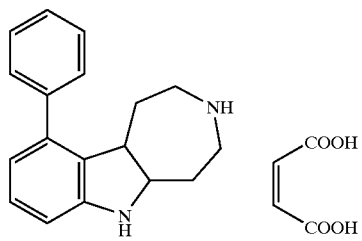

Prepared according to the procedure used to prepare (5aS*,10bS*)-10-(2-methoxyphenyl)-1,2,3,4,5,5a,6,10b-octahydroazepino[4,5-b]indole, the title compound was obtained: 45 mg (42%); IR (diffuse reflectance) 3053, 3028, 1645, 1638, 1588, 1569, 1550, 1532, 1499, 1474, 1457, 1366, 865, 762, 704 cm$^{-1}$; MS (EI) m/z 264 (M+), 264, 220, 219, 218, 208, 207, 206, 204, 193, 165: HRMS (FAB) calcd for $C_{18}H_{20}N_2$+H 265.1704, found 265.1697: Anal. Calcd for $C_{18}H_{20}N_2 \cdot C_4H_4O_4$: C, 69.46: H, 6.36: N, 7.36, found: C, 69.29: H, 6.31: N, 7.34

EXAMPLE 374

(5aS*,10bS*)-10-(3,5-difluorophenyl)-1,2,3,4,5,5a,6,10b-octahydroazepino[4,5-b]indole

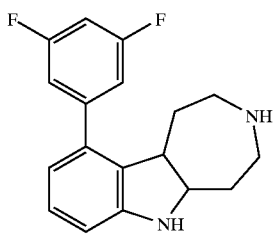

In a 50 mL 2-neck round-bottomed flask 10-(3,5-difluorophenyl)-1,2,3,4,5,6-hexahydroazepino[4,5-b]indole hydrochloride was dissolved in TFA (3 mL) and cooled to 0° C. A solution of sodium cyanoborohydride (0.084 g, 1.34 mmol) in MeOH was added and the mixture was stirred at room temperature for 2 h. Water was added, followed by 15% NaOH until the pH of the mixture was basic, and the mixture was extracted with EtOAc. The organic layer was concentrated to give 0.21 g of a brown oil. Column chromatography (elution with 2–6% MeOH/chloroform) gave 0.060 g (74%) of the title product as a clear oil: MS (EI) m/z 300 (M+), 300, 256, 255, 244, 243, 242, 240, 229, 201, 56: HRMS (FAB) calcd for $C_{18}H_{18}F_2N_2$+H 301.1516, found 301.1500.

EXAMPLE 375

(5aS*,10bS*)-10-(2-Butoxyphenyl)-1,2,3,4,5,5a,6,10b-octahydroazepino[4,5-b]indole

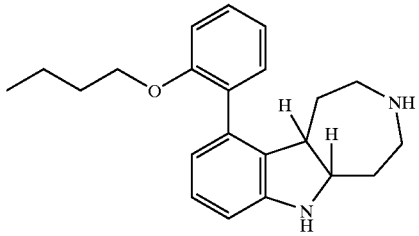

Following the procedure for (5aS*,10bS*)-10-(2-propoxyphenyl)-1,2,3,4,5,5a,6,10b-octahydroazepino[4,5-b]indole, making non-critical variations, the title compound was obtained as 76 mg (61%) of a brown oil: $^1$H NMR (400 MHz, CDCl$_3$) δ 7.34–7.30 (m, 1 H), 7.25 (dd, J=7.4 Hz, 1.6 Hz, 1 H), 7.11–7.07 (m, 1 H), 7.03–6.97 (m, 2 H), 6.65 (d, J=7.5, 1 H), 6.61 (d, J=7.7 Hz, 1 H), 4.26–4.20 (m, 1 H), 4.01–3.92 (m, 2 H), 3.75–3.70 (m, 1 H), 3.14–3.09 (m, 1 H), 2.79–2.76 (m, 1 H), 2.72–2.67 (m, 1 H), 2.47–2.44 (m, 1 H), 2.07–2.04 (m, 1 H), 1.97–1.89 (m, 1 H), 1.71–1.66 (m, 2 H), 1.59–1.56 (m, 1 H), 1.43–1.31 (m, 3 H), 0.92 (t, J=7.4 Hz, 3 H); HRMS (FAB) calcd for $C_{22}H_{28}N_2O$+H$_1$: 337.2280 found 337.2274.

EXAMPLES 376 and 377

(5aS,10bS)-10-(2-Butoxyphenyl)-1,2,3,4,5,5a,6,10b-octahydroazepino[4,5-b]indole and (5aR,10bR)-10-(2-Butoxyphenyl)-1,2,3,4,5,5a,6,10b-octahydroazepino[4,5-b]indole

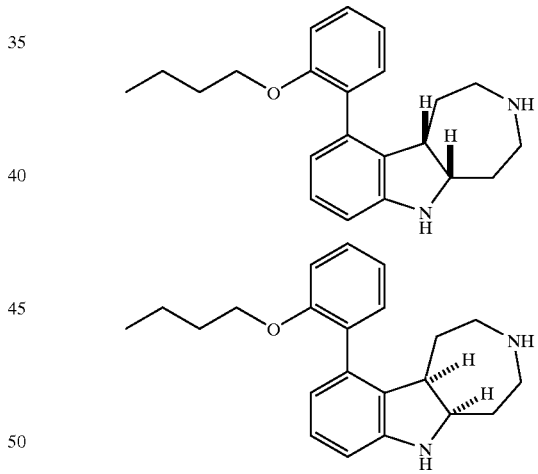

The racemic (5aS*,10bS*)-10-(2-butoxyphenyl)-1,2,3,4,5,5a,6,10b-octahydroazepino[4,5-b]indole from above was resolved by chiral chromatography to give 0.020 g of a clear oil as the more polar enantiomer: $^1$H NMR (400 MHz, CDCl$_3$) δ 7.34–7.30 (m, 1 H), 7.24 (dd, J=7.4 Hz, 1.7 Hz, 1 H), 7.11–7.07 (m, 1 H), 7.02–6.96 (m, 2 H), 6.65 (d, J=7.5, 1 H), 6.61 (d, J=7.7 Hz, 1 H), 4.25–4.20 (m, 1 H), 4.01–3.92 (m, 2 H), 3.72 (dt, J=9.7 Hz, 3.2 Hz, 1 H), 3.15–3.09 (m, 1 H), 2.81–2.76 (m, 1 H), 2.73–2.68 (m, 1 H), 2.47-2.44 (m, 1 H), 2.09–2.05 (m, 1 H), 1.98–1.92 (m, 1 H), 1.71–1.65 (m, 2 H), 1.59-1.55 (m, 1 H), 1.42–1.35 (m, 3 H), 0.92 (t, J=7.4 Hz, 3 H); HRMS (FAB) calcd for $C_{22}H_{28}N_2O$+H$_1$: 337.2280 found 337.2293.

In addition a clear oil (0.019 g) was obtained as the less polar enantiomer: $^1$H NMR (400 MHz, CDCl$_3$) δ 7.34–7.30 (m, 1

H), 7.24 (dd, J=7.4 Hz, 1.7 Hz, 1 H), 7.11–7.07 (m, 1 H), 7.02–6.96 (m, 2 H), 6.65 (d, J=7.5, 1 H), 6.61 (d, J=7.7 Hz, 1 H), 4.25–4.20 (m, 1 H), 4.01–3.92 (m, 2 H), 3.72 (dt, J=9.7 Hz, 3.2 Hz, 1 H), 3.15–3.09 (m, 1 H), 2.81–2.76 (m, 1 H), 2.73–2.68 (m, 1 H), 2.47-2.44 (m, 1 H), 2.09–2.05 (m, 1 H), 1.98–1.92 (m, 1 H), 1.71–1.65 (m, 2 H), 1.59-1.55 (m, 1 H), 1.42–1.35 (m, 3 H), 0.92 (t, J=7.4 Hz, 3 H); HRMS (FAB) calcd for $C_{22}H_{28}N_2O+H_1$: 337.2280 found 337.2279.

EXAMPLE 378

(5aS*,10bS*)-10-[2-(Cyclopropylmethoxy)phenyl]-1,2,3,4,5,5a,6,10b-octahydroazepino[4,5-b]indole

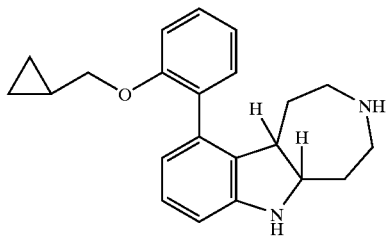

Following the procedure for the preparation of (5aS*,10bS*)-10-(2-propoxyphenyl)-1,2,3,4,5,5a,6,10b-octahydroazepino[4,5-b]indole, making non-critical variations, the title compound was obtained as 17 mg (23%) of a brown oil: $^1$H NMR (400 MHz, CDCl$_3$) δ 7.33–7.26 (m, 2 H), 7.13–7.09 (m, 1 H), 7.04-6.95 (m, 2 H), 6.80–6.61 (m, 2 H), 4.29–4.23 (m, 2 H), 3.86–3.78 (m, 3 H), 3.15–3.09 (m, 1 H), 2.82–2.77 (m, 1 H), 2.73–2.68 (m, 1 H), 2.47–2.42 (m, 1 H), 2.12–2.05 (m, 1 H), 1.98–1.92 (m, 1 H), 1.60–1.56 (m, 1 H), 1.37–1.34 (m, 1 H), 1.23–1.19 (m, 1 H), 0.58–0.55 (m, 2 H), 0.28–0.25 (m, 2 H); HRMS (FAB) calcd for $C_{22}H_{26}N_2O+H_1$: 335.2123 found 335.2115.

EXAMPLE 379

(5aS*,10bS*)-10-[2-(Pentyloxy)phenyl]-1,2,3,4,5,5a,6,10b-octahydroazepino[4,5-b]indole

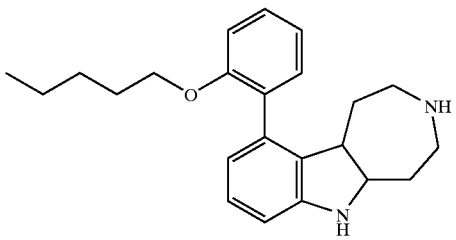

Following the procedure for the preparation of (5aS*,10bS*)-10-(2-propoxyphenyl)-1,2,3,4,5,5a,6,10b-octahydroazepino[4,5-b]indole, making non-critical variations, the title compound was obtained as 144 mg (42%) of a brown oil: $^1$H NMR (400 MHz, CDCl$_3$) δ 7.34–7.24 (m, 2 H), 7.11–7.07 (m, 1 H), 7.02-6.91 (m, 2 H), 6.65 (d, J=7.5 Hz, 1 H), 6.61 (d, J=7.7 Hz, 1 H), 4.26–4.21 (m, 1 H), 4.00–3.90 (m, 2 H), 3.72 (dt, J=9.6 Hz, 3.1 Hz, 1 H), 3.14–3.09 (m, 1 H), 2.81–2.76 (m, 1 H), 2.73–2.68 (m, 1 H), 2.48–2.42 (m, 1 H), 2.09–2.04 (m, 1 H), 1.97–1.92 (m, 1 H), 1.73–1.68 (m, 2 H), ), 1.59–1.56 (m, 1 H), 1.35–1.33 (m, 5 H), 0.90 (t, J=6.9 Hz, 3 H); HRMS (FAB) calcd for $C_{23}H_{30}N_2O+H_1$: 351.2436 found 351.2428.

EXAMPLE 380

(5aS*,10bS*)-10-[2-(Hexyloxy)phenyl]-1,2,3,4,5,5a,6,10b-octahydroazepino[4,5-b]indole

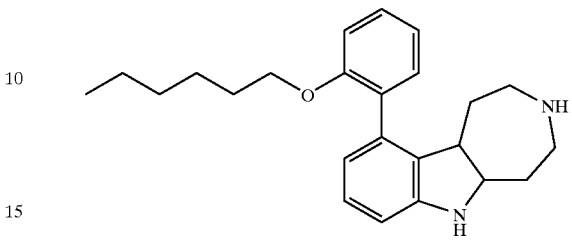

Following the procedure for the preparation of (5aS*,10bS*)-10-(2-propoxyphenyl)-1,2,3,4,5,5a,6,10b-octahydroazepino[4,5-b]indole, making non-critical variations, the title compound was obtained as 136 mg (41%) of a brown oil: $^1$H NMR (400 MHz, CDCl$_3$) δ 7.34–7.30 (m, 2 H), 7.27–7.25 (m, 1 H), 7.10-7.07 (m, 1 H), 7.02–6.96 (m, 2 H), 6.65 (d, J=7.5 Hz, 1 H), 6.61 (d, J=7.7 Hz, 1 H), 4.25–4.21 (m, 1 H), 4.00–3.90 (m, 2 H), 3.73 (dt, J=9.6 Hz, 3.1 Hz, 1 H), 3.14–3.10 (m, 1 H), 2.81–2.68 (m, 2 H), 2.49–2.43 (m, 1 H), 2.09–2.04 (m, 1 H), 1.98–1.92 (m, 1 H), 1.72–1.66 (m, 2 H), ), 1.59–1.55 (m, 1 H), 1.37–1.30 (m, 7 H), 0.90 (t, J=6.8 Hz, 3 H); HRMS (FAB) calcd for $C_{24}H_{32}N_2O+H_1$: 365.2592 found 365.2585.

EXAMPLE 381

(5aS*,10bS*)-10-(2-Isopropoxyphenyl)-1,2,3,4,5,5a,6,10b-octahydroazepino[4,5-b]indole

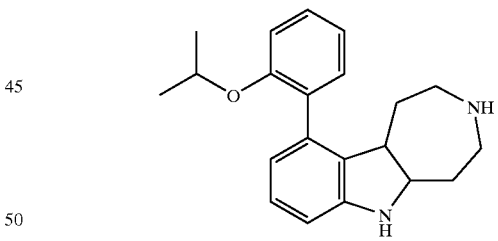

Following the procedure for the preparation of (5aS*,10bS*)-10-(2-propoxyphenyl)-1,2,3,4,5,5a,6,10b-octahydroazepino[4,5-b]indole making non-critical variations, the title compound was obtained as 124 mg (59%) of a brown oil: $^1$H NMR (400 MHz, CDCl$_3$) δ 7.32–7.26 (m, 2 H), 7.10–7.07 (m, 1 H), 7.04–6.97 (m, 2 H), 6.65 (d, J=7.5 Hz, 1 H), 6.61 (d, J=7.7 Hz, 1 H), 4.38–4.33 (m, 1 H), 4.27–4.21 (m, 1 H), 3.80 (dt, J=9.6 Hz, 3.3 Hz, 1 H), 3.14–3.08 (m, 1 H), 2.80–2.69 (m, 2 H), 2.49–2.44 (m, 1 H), 2.10–2.04 (m, 1 H), 1.97–1.92 (m,1 H), 1.58–1.52 (m, 1 H), 1.39–1.32 (m, 1 H), 1.28 (d, J=6.1 Hz, 3 H), 1.15 (d, J=6.8 Hz, 3 H); HRMS (FAB) calcd for $C_{21}H_{26}N_2O+H_1$: 323.2123 found 323.2136.

EXAMPLE 382

(5aS*,10bS*)-10-[2-(cyclopentloxy)phenyl]-1,2,3,4,5,5a,6,10b-octahydroazepino[4,5-b]indole

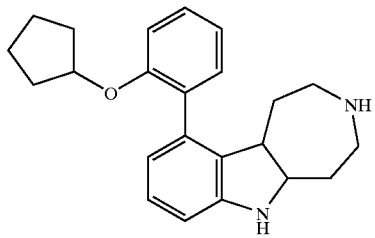

Following the procedure for the preparation of (5aS*,10bS*)-10-(2-propoxyphenyl)-1,2,3,4,5,5a,6,10b-octahydroazepino[4,5-b]indole, making non-critical variations, the title compound was obtained as 255 mg (64%) of a brown oil: $^1$H NMR (400 MHz, CDCl$_3$) δ 7.35–7.23 (m, 2 H), 7.10–7.06 (m, 1 H), 7.03-6.89 (m, 2 H), 6.63–6.59 (m, 2 H), 4.75–4.70 (m, 1 H), 4.26–4.20 (m, 1 H), 3.76–3.70 (m, 1 H), 3.18–3.13 (m, 1 H), 2.79–2.72 (m, 2 H), 2.52–2.47 (m, 1 H), 2.11–2.08 (m, 1 H), 1.96–1.87 (m, 3 H), 1.75–1.69 (m, 3 H), 1.66–1.53 (m, 4 H), 1.39–1.30 (m, 1 H); HRMS (FAB) calcd for C$_{23}$H$_{28}$N$_2$O+H$_1$: 349.2280 found 349.2286.

EXAMPLE 383

(5aS*,10bS*)-10-[2-(Cyclohexyloxy)phenyl]-1,2,3,4,5,5a,6,10b-octahydroazepino[4,5-b]indole

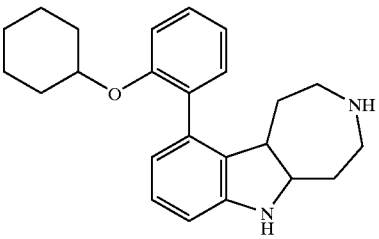

Following the procedure for the preparation of (5aS*,10bS*)-10-(2-propoxyphenyl)-1,2,3,4,5,5a,6,10b-octahydroazepino[4,5-b]indole, making non-critical variations, the title compound was obtained as 125 mg (51%) of a clear oil: $^1$H NMR (400 MHz, CDCl$_3$) δ 7.30–7.27 (m, 2 H), 7.10–7.06 (m, 1 H), 7.02-6.97 (m, 2 H), 6.66 (d, J=7.6 Hz, 1 H), 6.61 (d, J 7.7 Hz, 1 H), 4.26–4.20 (m, 1 H), 4.19–4.09 (m, 1 H), 3.13–3.08 (m, 1 H), 2.81–2.76 (m, 1 H), 2.73–2.68 (m, 1 H), 2.49–2.43 (m, 1 H), 2.06–2.03 (m, 1 H), 1.97–1.89 (m, 2 H), 1.72 (m, 2 H), 1.59–1.48 (m, 3 H), 1.36–1.19 (m, 5 H); HRMS (FAB) calcd for C$_{24}$H$_{30}$N$_2$O+H$_1$: 363.2436 found 363.2421.

EXAMPLE 384

(5aS*,10bS*)-10-[2-(Cyclobutyloxy)phenyl]-1,2,3,4,5,5a,6,10b-octahydroazepino[4,5-b]indole

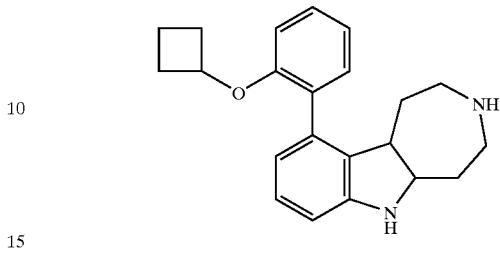

Following the procedure for the preparation of (5aS*,10bS*)-10-(2-propoxyphenyl)-1,2,3,4,5,5a,6,10b-octahydroazepino[4,5-b]indole, making non-critical variations, the title compound was obtained as 85 mg (48%) of a white solid: $^1$H NMR (400 MHz, CDCl$_3$) δ 7.30–7.26 (m, 2 H), 7.12–7.08 (m, 1 H), 7.02–6.98 (m, 1 H), 6.91–6.80 (m, 1 H), 6.65–6.60 (m, 1 H), 4.68–4.61 (m, 1 H), 4.28–4.22 (m, 1 H), 3.83–3.78 (m, 1 H), 3.14–3.08 (m, 1 H), 2.81–2.78 (m, 1 H), 2.73–2.68 (m, 1 H), 2.49–2.38 (m, 3 H), 2.17–2.03 (m, 2 H), 1.98–1.83 (m, 3 H), 1.70–1.57 (m, 2 H), 1.38–1.37 (m, 1 H); HRMS (FAB) calcd for C$_{22}$H$_{26}$N$_2$O+H$_1$: 335.2123 found 335.2121.

EXAMPLE 385

(5aS*, 10bS*)-10-(2,6-difluorophenyl)-1,2,3,4,5,5a,6,10b-octahydroazepino[4,5-b]indole

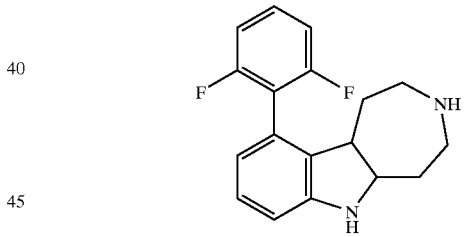

NaCNBH$_3$ (0.223 g, 3.54 mmol) was added to a solution of 10-(2,6-difluorophenyl)-1,2,3,4,5,6-hexahydroazepino[4,5-b]indole (0.336 g, 1.13 mmol) in CF$_3$CO$_2$H (6 mL), which was cooled in an ice-water bath. After stirring for 4 h, the reaction mixture was quenched by adding 6N HCl (6 mL). The resulting mixture was refluxed for 0.45 h. The mixture was cooled and made basic by the addition of 6N NaOH (25 mL). The basic mixture was combined with CHCl$_3$ (30 mL) and H$_2$O (5 mL) and the layers were separated. The aqueous layer was extracted with CHCl$_3$ (2×50 mL). The combined organic layers were dried over Na$_2$SO$_4$, filtered and concentrated. The crude product (0.78 g) was chromatographed (SiO$_2$ 35 g, eluted with 90:10:2 CH$_2$Cl$_2$:CH$_3$OH:conc. NH$_4$OH) to yield 10-(2,6-difluorophenyl)-1,2,3,4,5,5a,6,10b-octahydroazepino[4,5-b]indole (0.232 g) in 69% yield. $^1$H NMR (400 MHz, CD$_3$OD) δ 1.37, 1.61, 1.94, 2.05, 2.44, 2.65–2.73, 3.05, 3.54, 4.19, 6.52, 6.63, 7.03–7.09, 7.41: MS (ESI+) for C$_{18}$H$_{18}$F$_2$N$_2$ m/z 301.2 (M+H)$^+$.

EXAMPLE 386

(5aS*, 10bS*)-10-[2-(trifluoromethoxy)phenyl]-1,2,3,4,5,5a,6,10b-octahydroazepino[4,5-b]indole

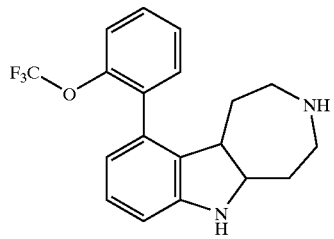

Prepared according to the procedure used to prepare 10-(2,6-difluorophenyl)-1,2,3,4,5,5a,6,10b-octahydroazepino[4,5-b]indole in 88% yield. $^1$H NMR (400 MHz, CD$_3$OD) δ 1.30, 1.52, 1.94, 2.06, 2.40, 2.65, 2.68, 3.07, 3.67, 4.19, 6.53, 6.62, 7.06, 7.38–7.49: MS (ESI+) for C$_{19}$H$_{19}$F$_3$N$_2$O m/z 349.1 (M+H)$^+$.

EXAMPLE 387

(5aS*, 10bS*)-10-[2-(trifluoromethyl)phenyl]-1,2,3,4,5,5a,6,10b-octahydroazepino[4,5-b]indole

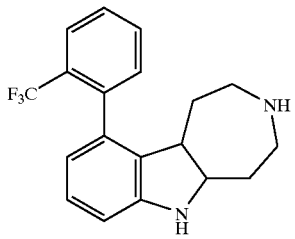

Prepared according to the procedure used to prepare 10-(2,6-difluorophenyl)-1,2,3,4,5,5a,6,10b-octahydroazepino[4,5-b]indole in 67% yield. $^1$H NMR (400 MHz, CD$_3$OD) δ 1.25, 1.37, 1.53, 1.63, 1.90–2.07, 2.37, 2.59–2.74, 3.07, 3.14, 3.35, 3.64, 4.10, 4.21, 6.43, 6.51, 6.61, 6.62, 7.01, 7.02, 7.33, 7.44, 7.54, 7.64, 7.79: MS (ESI+) for C$_{19}$H$_{19}$F$_3$N$_2$ m/z 333.2 (M+H)$^+$.

EXAMPLE 388

(5aS*,10bS*)-10-(4-Chlorophenyl)-1,2,3,4,5,5a,6,10b-octahydroazepino[4,5-b]indole dihydrochloride

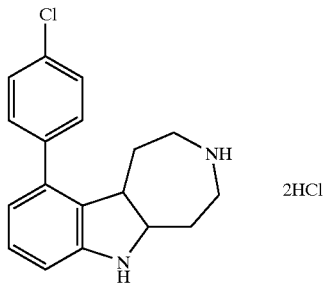

10-(4-Chlorophenyl)-1,2,3,4,5,6-hexahydroazepino[4,5-b]indole hydrochloride (140mg) was dissolved in TFA (3 ml), cool to 0° C. and sodium cyanoborohydride was added portionwise (150 mg). The reaction mixture stirred two hours, was quenched with 2N NaOH, extracted with EtOAc, dried over MgSO$_4$, filtered and concentrated. The product was dissolved in EtOAc and 1N HCl in Et$_2$O was added. The solvent was evaporated and solid recrystallized from EtOAc/MeOH to provide the title compound: $^1$H NMR (DMSO-d$_6$) δ 1.31, 1.66, 2.21, 2.7, 2.91, 3.03, 3.27, 4.1–4.4, 6.88, 7.25, 7.52. HRMS (FAB) calcd for C$_{18}$H$_{21}$ClN$_2$ (MH$^+$) 299.1315, found 299.1321.

EXAMPLE 389

(5aS*,10bS*)-10-(3-chlorophenyl)-1,2,3,4,5,5a,6,10b-octahydroazepino[4,5-b]indole dihydrochloride

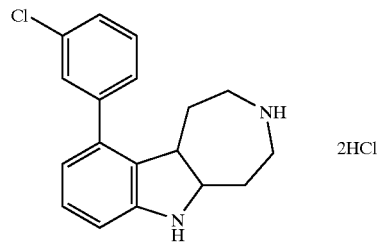

Following the procedure for the preparation of 10-(4-chlorophenyl)-1,2,3,4,5,5a,6,10b-octahydroazepino[4,5-b]indole dihydrochloride, making non-critical variations, starting from 10-(3-chlorophenyl)-1,2,3,4,5,6-hexahydroazepino[4,5-b]indole dihydrochloride the title compound was prepared: $^1$H NMR (DMSO-d$_6$) δ 1.35, 1.55, 2.10, 2.71, 3.05, 3.28, 3.97, 4.20, 6.65, 7.12, 7.4–7.5, 8.8. HRMS (FAB) calcd for C$_{18}$H$_{21}$ClN$_2$ (MH$^+$) 299.1315, found 299.1306.

EXAMPLE 390

(5aS*,10bS*)-10-(2,4-dichlorophenyl)-6-(2-phenoxyethyl)-1,2,3,4,5,5a,6,10b-octahydroazepino[4,5-b]indole

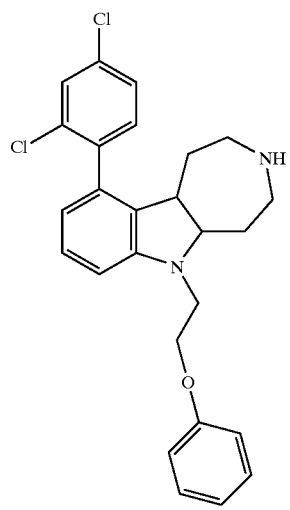

Following the procedure for the preparation of 10-(4-chlorophenyl)-1,2,3,4,5,5a,6,10b-octahydroazepino[4,5-b]indole dihydrochloride, making non-critical variations, starting from 10-(2,4-dichlorophenyl)-6-(2-phenoxyethyl)-1,2,3,4,5,6-hexahydroazepino[4,5-b]indole the title compound was prepared: $^1$H NMR (CD$_3$OD) δ 1.47, 1.55, 2.20, 2.66, 2.90, 3.19, 3.52–3.63, 4.13–4.21, 6.44, 6.50, 6.93, 7.15, 7.25–7.42, 7.57. HRMS (FAB) calcd for C$_{26}$H$_{26}$Cl$_2$N$_2$O$_2$ (MH$^+$) 453.1500, found 453.1520.

Preparation 128

Preparation of di(tert-butyl) 10-(2,4-dichlorophenyl)-1,2,4,5,5a,10b-hexahydroazepino[4,5-b]indole-3,6-dicarboxylate To a solution of 1-tert-butyl 10-(2,4-dichlorophenyl)-1,4,5,5a,6,10b-hexahydroazepino[4,5-b]indole-3(2H)-carboxylate (300 mg) in dioxane (2.30 ml) was added diisopropylethylamine (0.24 ml) and $Boc_2O$ (755 mg). The reaction mixture was heated at 100° C. for 16 h, poured into brine, extracted with $CH_2Cl_2$, dried over $MgSO_4$, filtered and concentrated. Purification via flash chromatography (silica gel, EtOAc/Hexanes 1:15) provided the title compound: $^1$H NMR ($CDCl_3$) δ 1.41, 1.42, 1.47, 5.07, 3.04–3.19, 3.38, 3.85, 4.00, 4.62, 6.73, 6.85, 7.13, 7.22–7.45, 7.45, 7.54, 7.74. HRMS (FAB) calcd for $C_{28}H_{34}Cl_2N_2O_4$ ($MH^+$) 533.1974, found 533.1978.

Preparation 129

Preparation of 1-di(tert-butyl) 9-chloro-10-(2,4-dichlorophenyl)-1,2,4,5,5a,10b-hexahydroazepino[4,5-b]indole-3,6-dicarboxylate To a solution of di(tert-butyl) 10-(2,4-dichlorophenyl)-1,2,4,5,5a,10b-hexahydroazepino[4,5-b]indole-3,6-dicarboxylate (388 mg) in DMF (7.1 ml) was added N-chlorosuccinimide (95 mg). The reaction mixture stirred 48 h, was poured into $H_2O$, extracted with $Et_2O$, dried over $MgSO_4$, filtered and concentrated. Purification via flash chromatography (silica gel, EtOAc:hexanes, 1:15) provided the title compound. $^1$H NMR ($CDCl_3$) δ 1.46, 2.09, 3.11, 3.25, 3.39, 3.52, 3.67, 4.57, 7.07, 7.24, 7.54, 7.71. HRMS (FAB) calcd for $C_{28}H_{33}Cl_3N_2O_4$ ($MH^+$) 567.1584, found 567.1566

EXAMPLE 391

(5aS*,10bS*)-9-chloro-10-(2,4-dichlorophenyl)-1,2,3,4,5,5a,6,10b-octahydroazepino[4,5-b]indole

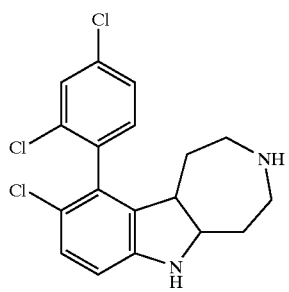

To a solution of 1-di(tert-butyl) 9-chloro-10-(2,4-dichlorophenyl)-1,2,4,5,5a,10b-hexahydroazepino[4,5-b]indole-3,6-dicarboxylate (145 mg) in $CH_2Cl_2$ (5 ml) was added TFA (1 ml). The reaction mixture was stirred 1 h, quenched with 2N NaOH, extracted with $CH_2Cl_2$, dried over $MgSO_4$, filtered and concentrated. Purification via flash chromatography (silica gel, $CH_2Cl_2$:MeOH, 9:1 with 0.5% $NH_4OH$) provided the title compound: $^1$H NMR ($CD_3OD$) δ 1.31, 1.43, 2.05, 2.67, 2.88, 3.24, 3.46, 4.25, 6.60, 7.11, 7.28, 7.45, 7.59. HRMS (FAB) calcd for $C_{18}H_{17}Cl_3N_2$ ($MH^+$) 367.0535, found 367.0525.

EXAMPLE 392

(5aS*,10bS*)-10-[3-(2-chlorophenoxy)propyl]-1,2,3,4,5,5a,6,10b-octahydroazepino[4,5-b]indole

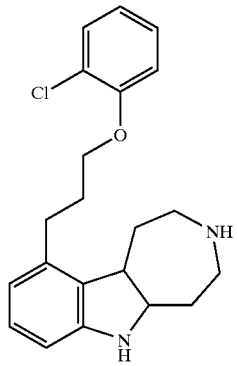

Following the procedure for the preparation of 10-(4-chlorophenyl)-1,2,3,4,5,5a,6,10b-octahydroazepino[4,5-b]indole dihydrochloride, making non-critical variations, starting from 10-[3-(2-chlorophenoxy)propyl]-1,2,3,4,5,6-hexahydroazepino[4,5-b]indole the title compound was prepared: $^1$H NMR ($CDCl_3$) δ 1.99–2.20, 2.27, 2.78, 2.93–3.05, 3.51, 4.11, 6.48, 6.62, 6.92, 7.03, 7.19, 7.38, 7.40. HRMS (FAB) calcd for $C_{21}H_{25}ClN_2O_1$ ($MH^+$) 357.1733, found 357.1749.

EXAMPLE 393

(5aS*,10bS*)-10-(2-phenylethyl)-1,2,3,4,5,5a,6,10b-octahydroazepino[4,5-b]indole

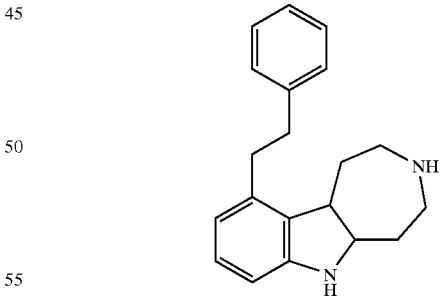

Following the procedure for the preparation of 10-(4-chlorophenyl)-1,2,3,4,5,5a,6,10b-octahydroazepino[4,5-b]indole dihydrochloride, making non-critical variations, starting from 10-(2-phenylethyl)-1,2,3,4,5,6-hexahydroazepino[4,5-b]indole the title compound was prepared: $^1$H NMR ($CDCl_3$) δ 2.02, 2.14, 2.31, 2.79, 2.88, 2.97, 3.15, 3.64, 4.18, 6.52, 6.70, 7.07, 7.16, 7.21, 7.27, 9.5–9.7. HRMS (FAB) calcd for $C_{20}H_{24}N_2$ ($MH^+$) 293.2018, found 293.2013.

EXAMPLE 394

(5aS*,10bS*)-10-[3-(2-naphthyloxy)propyl]-1,2,3,4,5,5a,6,10b-octahydroazepino[4,5-b]indole

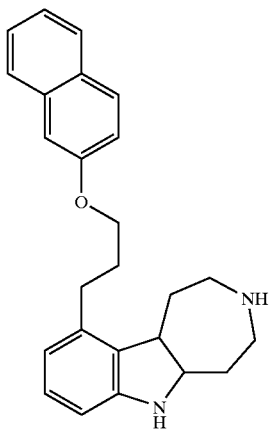

Following the procedure for the preparation of 10-(4-chlorophenyl)-1,2,3,4,5,5a,6,10b-octahydroazepino[4,5-b]indole dihydrochloride, making non-critical variations, starting from 10-[3-(2-naphthyloxy)propyl]-1,2,3,4,5,6-hexahydroazepino[4,5-b]indole the title compound was prepared: $^1$H NMR (CDCl$_3$) δ 1.89–2.08, 2.22, 2.77, 2.91, 3.07, 3.26, 3.51, 3.67, 4.14, 6.47, 6.64, 7.05, 7.12, 7.16, 7.19, 7.35, 7.45, 7.47, 7.78. HRMS (FAB) calcd for C$_{25}$H$_{28}$N$_2$O (MH$^+$) 373.2280, found 373.2288.

EXAMPLE 395

(5aS*,10bS*)-10-(3-phenoxypropyl)-1,2,3,4,5,5a,6,10b-octahydroazepino[4,5-b]indole

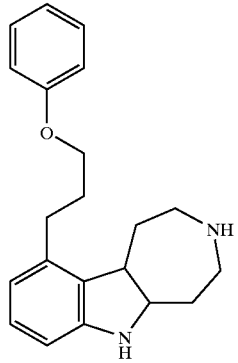

Following the procedure for the preparation of 10-(4-chlorophenyl)-1,2,3,4,5,5a,6,10b-octahydroazepino[4,5-b]indole dihydrochloride, making non-critical variations, starting from 10-(3-phenoxypropyl)-1,2,3,4,5,6-hexahydroazepino[4,5-b]indole the title compound was prepared: $^1$H NMR (CDCl$_3$) δ 2.02–2.14, 2.27, 2.74, 2.90–3.03, 3.45, 3.50, 3.98, 4.14, 4.50, 6.47, 6.63, 6.91, 6.95, 7.03, 7.30. HRMS (FAB) calcd for C$_{21}$H$_{26}$N$_2$O (MH$^+$) 323.2123, found 323.2104.

EXAMPLE 396

(5aS*,10bS*)-N-(2-chlorophenyl)-1,2,3,4,5,5a,6,10b-octahydroazepino[4,5-b]indol-10-amine

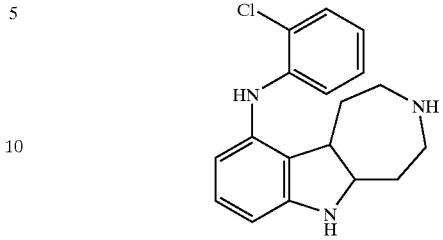

Following the procedure for the preparation of (5aS*,10bS*)-10-(4-chlorophenyl)-1,2,3,4,5,5a,6,10b-octahydroazepino[4,5-b]indole dihydrochloride, making non-critical variations, starting from N-(2-chlorophenyl)-1,2,3,4,5,6-hexahydroazepino[4,5-b]indol-10-amine the title compound was prepared: $^1$H NMR (DMSO-d$_6$) δ 1.68, 1.77, 1.93, 2.58, 2.73, 2.95, 5.62, 6.20, 6.77–6.82, 6.86, 6.94, 7.14, 7.37. HRMS (FAB) calcd for C$_{18}$H$_{20}$ClN$_3$ (MH$^+$) 314.1424, found 314.1422.

Preparation 130

Preparation of 10-bromo-1,2,3,4,5,6-hexahydroazepino[4,5-b]indole

Following the procedure of 9-(4-methoxy-2-methylphenyl)-1,2,3,4,5,6-hexahydroazepino[4,5-b]indole, making non-critical variations, the title compound was obtained. MS (EI) m/z 265.0 (MH$^+$).

EXAMPLE 397

(5aS*,10bS*)-10-Bromo-1,2,3,4,5,5a,6,10b-octahydroazepino[4,5-b]indole

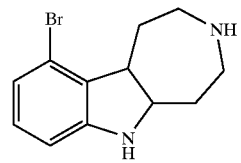

Following the procedure of (5aS*,10bS*)-9-(4-Methoxy-2-methylphenyl)-1,2,3,4,5,5a,6,10b-octahydroazepino[4,5-b]indole dihydrochloride, making non-critical variations, the title compound was obtained. $^1$H NMR (400 MHz, CDCl$_3$) δ 6.87 (m, 1H), 6.80 (d, J=7.9 Hz, 1H), 6.47 (d, J=7.7 Hz, 1H), 4.23 (m, 1H), 3.92 (bs, 1H), 3.50 (m, 1H), 3.21 (m,1H), 3.08 (dt, J=13.5, 4.4 Hz, 1H), 2.86 (m, 1H), 2.78 (dd, J=13.5, 8.9 Hz, 1H), 2.21 (m, 1H), 2.07 (m, 2H), 1.97 (m, 1H); IR (diffuse reflectance) 2926, 2908, 2852, 1602, 1574, 1451, 1370, 1291, 1282, 1260, 1139, 906, 832, 772, 718 cm$^{-1}$; MS (EI) m/z 268, 266 (M+), 224, 222, 212, 185, 144, 143, 129, 128: HRMS (FAB) calcd for C$_{12}$H$_{15}$BrN$_2$+H 267.0497, found 267.0496.

Preparation 131

Preparation of (5aS*,10bS*)-tert-butyl 10-bromo-1,4,5,5a,6,10b-hexahydroazepino[4,5-b]indole-3(2H)-carboxylate Boc$_2$O (2.7 g, 12 mmol) was added to a solution of (5aS*,10bS*)-10-bromo-1,2,3,4,5,6-hexahydroazepino[4,5-b]indole (2.8 g, 12 mmol) in THF (60 mL) followed by 10% aqueous NaOH (15 mL). After 2 h, the reaction was diluted with H$_2$O and extracted with EtOAc (3×100 mL). The combined organic layers were washed with brine, dried over Na$_2$SO$_4$, decanted, and concentrated. The crude orange foam was purified via column chromatography (Biotage, 40M) with heptane/EtOAc (4:1) to give 2.6 g (69%) of a white foam: mp 123.5–124.5° C.; $^1$H NMR (300 MHz, CDCl$_3$) δ 6.85 (m, 2H), 6.50 (d, J=7.4 Hz, 1H), 4.16 (m, 1H), 3.89 (br s, 1H), 3.63 (m, 3H), 3.37 (m, 2H), 2.02 (m, 4H), 1.47 (s, 9H); IR (diffuse reflectance) 3335, 2977, 2929, 1672, 1602, 1465, 1421, 1363, 1322, 1274, 1246, 1175, 1115, 981, 755 cm$^{-1}$; MS (CI) m/z 367 (MH$^+$), 369, 313, 311, 289, 269, 267, 231, 189, 187: Anal. Calcd for C$_{17}$H$_{23}$BrN$_2$O$_2$: C, 55.59: H, 6.31: N, 7.63: found: C, 55.67: H, 6.37: N, 7.57.

Preparation 132

Preparation of (5aS*,10bS*)-di(tert-butyl) 10-bromo-1,2,4,5,5a,10b-hexahydroazepino[4,5-b]indole-3,6-dicarboxylate Boc$_2$O (4.3 g, 20 mmol) was added to a solution of (5aS*,10bS*)-tert-butyl 10-bromo-1,4,5,5a,6,10b-hexahydroazepino[4,5-b]indole-3(2H)-carboxylate (1.5 g, 4.0 mmol) in THF (40 mL) followed by 10% aqueous NaOH (10 mL). After 96 h, the reaction was diluted with H$_2$O and extracted with EtOAc (3×75 mL). The combined organic layers were washed with brine, dried over Na$_2$SO$_4$, decanted, and concentrated. The crude orange foam was purified via column chromatography (Biotage, 40M) with heptane/EtOAc (95:5) to give 2.6 g (69%) of a white foam: $^1$H NMR (300 MHz, CDCl$_3$) δ 7.68 (br s, 1H), 7.06 (m, 2H), 4.56 (m, 1H), 3.75 (m, 1H), 3.46 (m, 4H), 2.22 (m, 4H), 1.56 (s, 9H), 1.45 (s, 9H); IR (diffuse reflectance) 2975, 1694, 1450, 1423, 1391, 1366, 1346, 1324, 1301, 1275, 1253, 1242, 1166, 1148, 775 cm$^{-1}$; MS (EI) m/z(M$^+$), 312, 310, 223, 221, 211, 210, 209, 208, 130, 56: Anal. Calcd for C$_{22}$H$_{31}$BrN$_2$O$_4$: C, 56.53: H, 6.69: N, 5.99: found: C, 56.82: H, 6.72: N, 5.91.

EXAMPLES 398–451

The following general procedure for the parallel synthesis of 10-aryl substituted azepinoindolines was used to prepare the compounds of Examples 402–455. The appropriate boronic acid (0.64 mmol) was added to a 20 mL scintillation vial followed by the addition of a stock solution of the (5aS*,10bS*)-di(tert-butyl) 10-bromo-1,2,4,5,5a,10b-hexahydroazepino[4,5-b]indole-3,6-dicarboxylate (0.10 g, 0.21 mmol) and Pd(Ph$_3$P)$_2$Cl$_2$ (15 mg, 0.021 mmol) in dioxane (1.1 mL). Next, 0.5 mL of a stock solution of 2M aqueous Na$_2$CO$_3$ was added to each vial. Nitrogen was blown over the vials for 1 min, then capped, placed in a J-KEM® heater block attached to a Lab-Line® orbit shaker and shaken (300 RPM) at 100° C. overnight. A subset of the reactions was monitored by LC/MS. After all the starting acid was consumed in these reactions, MeOH (5 mL) and Dowex® 50WX2-400 ion-exchange resin (1.25 g) was added to each vial. The reactions were then shaken (300 RPM) at 60° C. until the product was on the resin, based on LC/MS monitoring. The vials were cooled to rt and transferred with 2×5 mL of CH$_2$Cl$_2$/MeOH (3:1) to disposable fritted syringe barrels on a syringe washing station. The resin was then rinsed with 10 mL of each of the following: MeOH, CH$_2$Cl$_2$ and MeOH. The syringe barrels were then transferred to a vacuum manifold and the product was eluted off the resin into 40 mL scintillation vials with 5×5 mL of MeOH/NH$_4$OH (3:1). Two different methods were used to isolate the products. Method A consisted of removing the solvent in the vacuum oven overnight at 47° C. Method B involved removing the solvent in the vacuum oven overnight at 47° C. followed by purification via prep HPLC. The products were then evaluated by LC/MS.

EXAMPLE 398

(5aS*,10bS*)-10-(1-Naphthyl)-1,2,3,4,5,5a,6,10b-octahydroazepino[4,5-b]indole

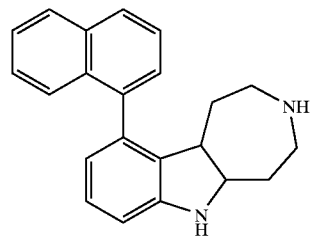

Following the general procedure for the parallel synthesis of 10-aryl substituted azepinoindolines and using isolation method A, the title compound was obtained. MS (ESI+) m/z 315.2 (MH$^+$).

EXAMPLE 399

(5aS*,10bS*)-10-(4-Fluorophenyl)-1,2,3,4,5,5a,6,10b-octahydroazepino[4,5-b]indole

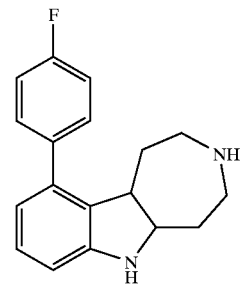

Following the general procedure for the parallel synthesis of 10-aryl substituted azepinoindolines and using isolation method A, the title compound was obtained. MS (ESI+) m/z 283.2 (MH$^+$).

EXAMPLE 400

(5aS*,10bS*)-10-(4-Methylphenyl)-1,2,3,4,5,5a,6,10b-octahydroazepino[4,5-b]indole

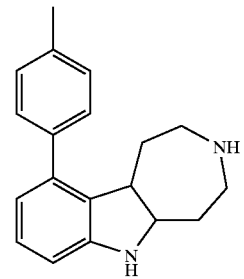

Following the general procedure for the parallel synthesis of 10-aryl substituted azepinoindolines and using isolation method A, the title compound was obtained. MS (ESI+) m/z 279.2 (MH$^+$).

EXAMPLE 401

(5aS*,10bS*)-10-(4-Methoxyphenyl)-1,2,3,4,5,5a,6,10b-octahydroazepino[4,5-b]indole

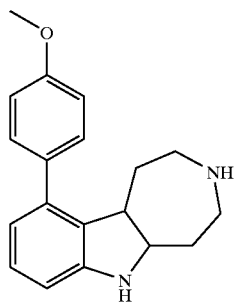

Following the general procedure for the parallel synthesis of 10-aryl substituted azepinoindolines and using isolation method A, the title compound was obtained. MS (ESI+) m/z 295.2 (MH+).

EXAMPLE 402

(5aS*,10bS*)-10-(3-Methylphenyl)-1,2,3,4,5,5a,6,10b-octahydroazepino[4,5-b]indole

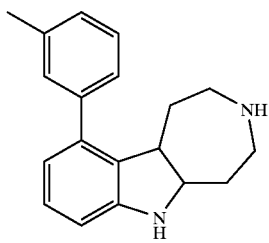

Following the general procedure for the parallel synthesis of 10-aryl substituted azepinoindolines and using isolation method A, the title compound was obtained. MS (ESI+) m/z 279.2 (MH+).

EXAMPLE 403

(5aS*,10bS*)-10-(3-Chloro-4-fluorophenyl)-1,2,3,4,5,5a,6,10b-octahydroazepino[4,5-b]indole

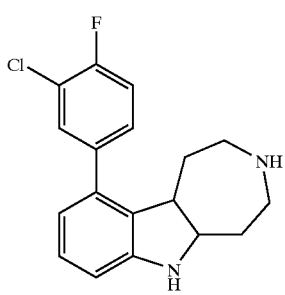

Following the general procedure for the parallel synthesis of 10-aryl substituted azepinoindolines and using isolation method A, the title compound was obtained. MS (ESI+) m/z 317.2 (MH+).

EXAMPLE 404

(5aS*,10bS*)-10-[3,5-Bis(trifluoromethyl)phenyl]-1,2,3,4,5,5a,6,10b-octahydroazepino[4,5-b]indole

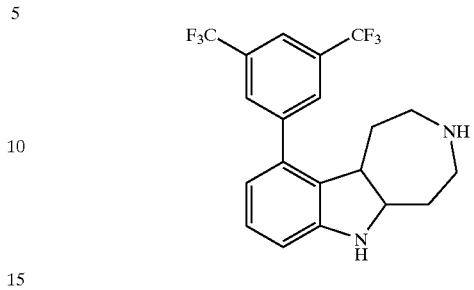

Following the general procedure for the parallel synthesis of 10-aryl substituted azepinoindolines and using isolation method A, the title compound was obtained. MS (ESI+) m/z 401.1 (MH+).

EXAMPLE 405

(5aS*,10bS*)-10-(3,5-Dichlorophenyl)-1,2,3,4,5,5a,6,10b-octahydroazepino[4,5-b]indole

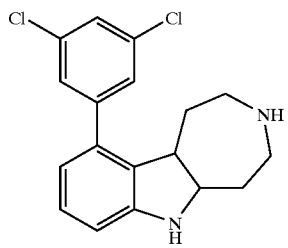

Following the general procedure for the parallel synthesis of 10-aryl substituted azepinoindolines and using isolation method A, the title compound was obtained. MS (ESI+) m/z 333.1 (MH+).

EXAMPLE 406

(5aS*,10bS*)-10-(1,1'-Biphenyl-4-yl)-1,2,3,4,5,5a,6,10b-octahydroazepino[4,5-b]indole

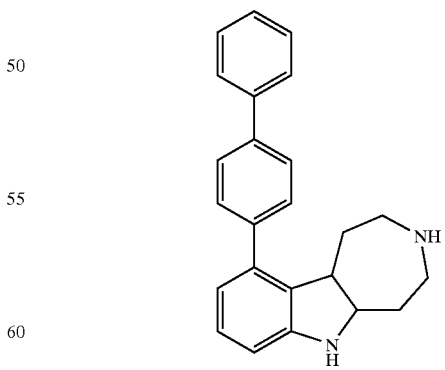

Following the general procedure for the parallel synthesis of 10-aryl substituted azepinoindolines and using isolation method A, the title compound was obtained. MS (ESI+) m/z 341.2 (MH+).

EXAMPLE 407

(5aS*,10bS*)-10-(4-Phenoxyphenyl)-1,2,3,4,5,5a,6,10b-octahydroazepino[4,5-b]indole

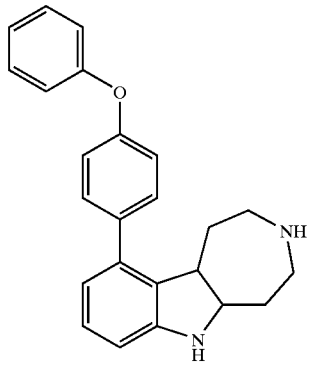

Following the general procedure for the parallel synthesis of 10-aryl substituted azepinoindolines and using isolation method A, the title compound was obtained. MS (ESI+) m/z 357.2 (MH+).

EXAMPLE 408

(5aS*,10bS*)-10-[3-(Trifluoromethyl)phenyl]-1,2,3,4,5,5a,6,10b-octahydroazepino[4,5-b]indole

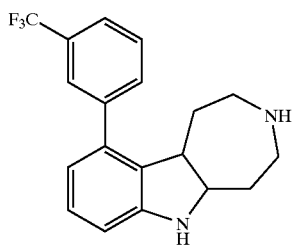

Following the general procedure for the parallel synthesis of 10-aryl substituted azepinoindolines and using isolation method A, the title compound was obtained. MS (ESI+) m/z 333.2 (MH+).

EXAMPLE 409

(5aS*,10bS*)-10-(3-Methoxyphenyl)-1,2,3,4,5,5a,6,10b-octahydroazepino[4,5-b]indole

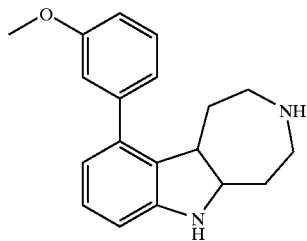

Following the general procedure for the parallel synthesis of 10-aryl substituted azepinoindolines and using isolation method A, the title compound was obtained. MS (ESI+) m/z 295.2 (MH+).

EXAMPLE 410

(5aS*,10bS*)-10-(3,5-Dimethylphenyl)-1,2,3,4,5,5a,6,10b-octahydroazepino[4,5-b]indole

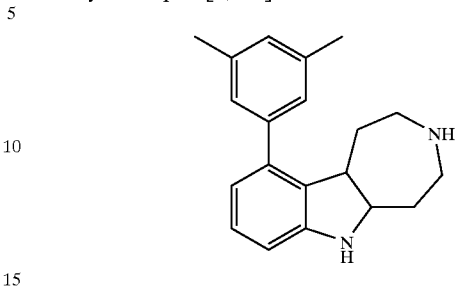

Following the general procedure for the parallel synthesis of 10-aryl substituted azepinoindolines and using isolation method A, the title compound was obtained. MS (ESI+) m/z 293.2 (MH+).

EXAMPLE 411

(5aS*,10bS*)-10-(3-Fluorophenyl)-1,2,3,4,5,5a,6,10b-octahydroazepino[4,5-b]indole

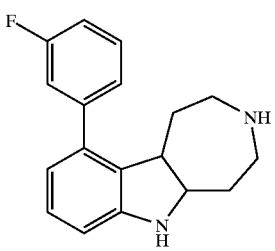

Following the general procedure for the parallel synthesis of 10-aryl substituted azepinoindolines and using isolation method A, the title compound was obtained. MS (ESI+) m/z 283.2 (MH+).

EXAMPLE 412

(5aS*,10bS*)-10-(2-Naphthyl)-1,2,3,4,5,5a,6,10b-octahydroazepino[4,5-b]indole

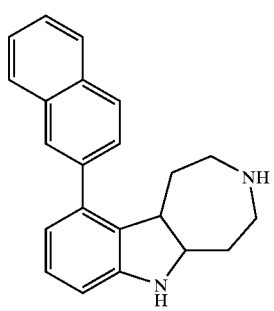

Following the general procedure for the parallel synthesis of 10-aryl substituted azepinoindolines and using isolation method A, the title compound was obtained. MS (ESI+) m/z 315.2 (MH+).

EXAMPLE 413

(5aS*,10bS*)-10-[2-(Trifluoromethyl)phenyl]-1,2,3,4,5,5a,6,10b-octahydroazepino[4,5-b]indole

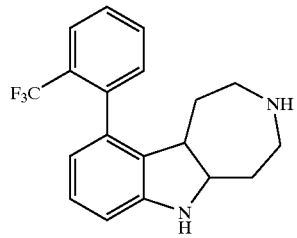

Following the general procedure for the parallel synthesis of 10-aryl substituted azepinoindolines and using isolation method B, the title compound was obtained. MS (ESI+) m/z 333.2 (MH+).

EXAMPLE 414

(5aS*,10bS*)-10-(3-Ethoxyphenyl)-1,2,3,4,5,5a,6,10b-octahydroazepino[4,5-b]indole

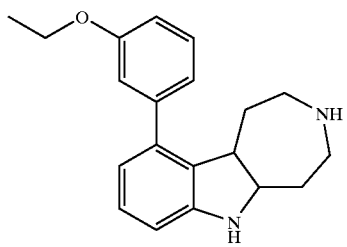

Following the general procedure for the parallel synthesis of 10-aryl substituted azepinoindolines and using isolation method A, the title compound was obtained. MS (ESI+) m/z 309.2 (MH+).

EXAMPLE 415

(5aS*,10bS*)-10-(4-Ethoxyphenyl)-1,2,3,4,5,5a,6,10b-octahydroazepino[4,5-b]indole

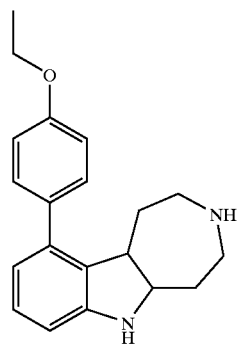

Following the general procedure for the parallel synthesis of 10-aryl substituted azepinoindolines and using isolation method A, the title compound was obtained. MS (ESI+) m/z 309.2 (MH+).

EXAMPLE 416

(5aS*,10bS*)-10-(3,4-Difluorophenyl)-1,2,3,4,5,5a,6,10b-octahydroazepino[4,5-b]indole

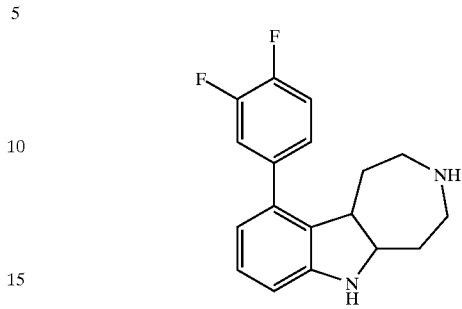

Following the general procedure for the parallel synthesis of 10-aryl substituted azepinoindolines and using isolation method A, the title compound was obtained. MS (ESI+) m/z 301.2 (MH+).

EXAMPLE 417

(5aS*,10bS*)-10-(4-Ethylphenyl)-1,2,3,4,5,5a,6,10b-octahydroazepino[4,5-b]indole

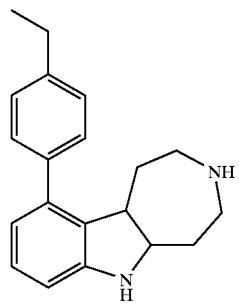

Following the general procedure for the parallel synthesis of 10-aryl substituted azepinoindolines and using isolation method A, the title compound was obtained. MS (ESI+) m/z 293.2 (MH+).

EXAMPLE 418

(5aS*,10bS*)-10-(2-Phenoxyphenyl)-1,2,3,4,5,5a,6,10b-octahydroazepino[4,5-b]indole

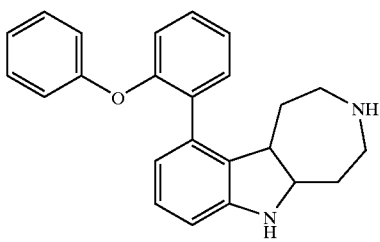

Following the general procedure for the parallel synthesis of 10-aryl substituted azepinoindolines and using isolation method A, the title compound was obtained. MS (ESI+) m/z 357.2 (MH+).

EXAMPLE 419

(5aS*,10bS*)-10-(3,4-Dimethylphenyl)-1,2,3,4,5,5a,6,10b-octahydroazepino[4,5-b]indole

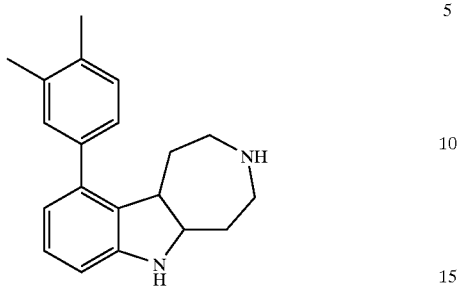

Following the general procedure for the parallel synthesis of 10-aryl substituted azepinoindolines and using isolation method A, the title compound was obtained. MS (ESI+) m/z 293.2 (MH+).

EXAMPLE 420

(5aS*,10bS*)-10-(2,4-Dimethoxyphenyl)-1,2,3,4,5,5a,6,10b-octahydroazepino[4,5-b]indole

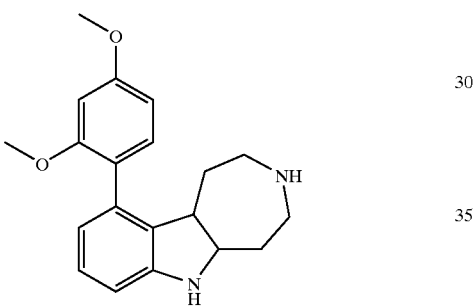

Following the general procedure for the parallel synthesis of 10-aryl substituted azepinoindolines and using isolation method B, the title compound was obtained. MS (ESI+) m/z 325.2 (MH+).

EXAMPLE 421

(5aS*,10bS*)-10-(4-Isopropylphenyl)-1,2,3,4,5,5a,6,10b-octahydroazepino[4,5-b]indole

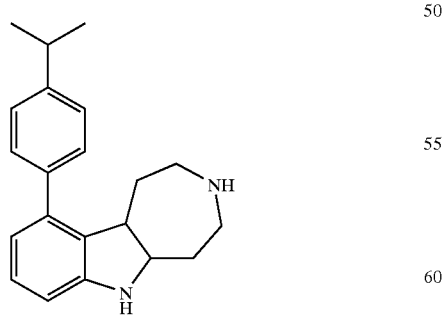

Following the general procedure for the parallel synthesis of 10-aryl substituted azepinoindolines and using isolation method A, the title compound was obtained. MS (ESI+) m/z 307.3 (MH+).

EXAMPLE 422

(5aS*,10bS*)-4-(1,2,3,4,5,5a,6,10b-Octahydroazepino[4,5-b]indol-10-yl)-N,N-dimethyl aniline

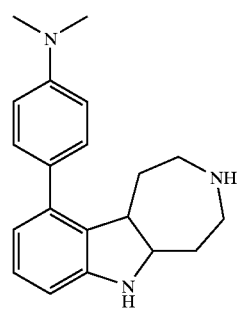

Following the general procedure for the parallel synthesis of 10-aryl substituted azepinoindolines and using isolation method B, the title compound was obtained. MS (ESI+) m/z 308.2 (MH+).

EXAMPLE 423

(5aS*,10bS*)-10-(3,4-Dichlorophenyl)-1,2,3,4,5,5a,6,10b-octahydroazepino[4,5-b]indole

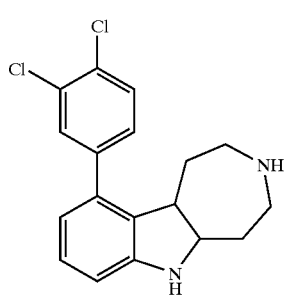

Following the general procedure for the parallel synthesis of 10-aryl substituted azepinoindolines and using isolation method A, the title compound was obtained. MS (ESI+) m/z 333.1 (MH+).

EXAMPLE 424

(5aS*,10bS*)-10-[4-(Trifluoromethoxy)phenyl]-1,2,3,4,5,5a,6,10b-octahydroazepino[4,5-b]indole

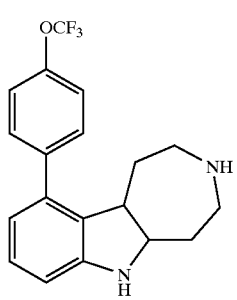

Following the general procedure for the parallel synthesis of 10-aryl substituted azepinoindolines and using isolation method A, the title compound was obtained. MS (ESI+) m/z 349.2 (MH+).

EXAMPLE 425
(5aS*,10bS*)-1-[4-(1,2,3,4,5,5a,6,10b-Octahydroazepino[4,5-b]indol-10-yl)phenyl]ethanone

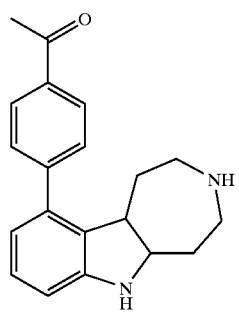

Following the general procedure for the parallel synthesis of 10-aryl substituted azepinoindolines and using isolation method A, the title compound was obtained. MS (ESI+) m/z 307.2 (MH+).

EXAMPLE 426
(5aS*,10bS*)-1-[3-(1,2,3,4,5,5a,6,10b-Octahydroazepino[4,5-b]indol-10-yl)phenyl]ethanone

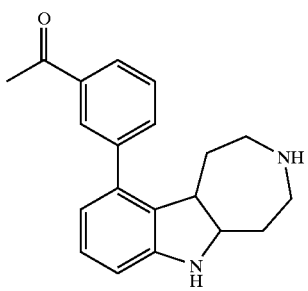

Following the general procedure for the parallel synthesis of 10-aryl substituted azepinoindolines and using isolation method A, the title compound was obtained. MS (ESI+) m/z 307.2 (MH+).

EXAMPLE 427
(5aS*,10bS*)-10-(3,4,5-Trimethoxyphenyl)-1,2,3,4,5,5a,6,10b-octahydroazepino[4,5-b]indole

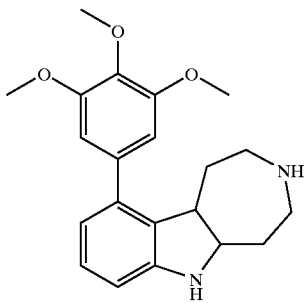

Following the general procedure for the parallel synthesis of 10-aryl substituted azepinoindolines and using isolation method A, the title compound was obtained. MS (ESI+) m/z 355.2 (MH+).

EXAMPLE 428
(5aS*,10bS*)-10-(2,3-Dichlorophenyl)-1,2,3,4,5,5a,6,10b-octahydroazepino[4,5-b]indole

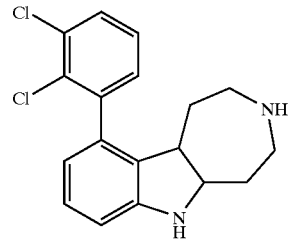

Following the general procedure for the parallel synthesis of 10-aryl substituted azepinoindolines and using isolation method B, the title compound was obtained. MS (ESI+) m/z 333.1 (MH+).

EXAMPLE 429
(5aS*,10bS*)-10-[4-(Benzyloxy)phenyl]-1,2,3,4,5,5a,6,10b-octahydroazepino[4,5-b]indole

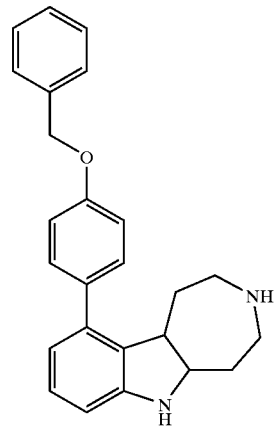

Following the general procedure for the parallel synthesis of 10-aryl substituted azepinoindolines and using isolation method A, the title compound was obtained. MS (ESI+) m/z 371.2 (MH+).

EXAMPLE 430
(5aS*,10bS*)-10-(2-Fluoro-1,1'-biphenyl-4-yl)-1,2,3,4,5,5a,6,10b-octahydroazepino[4,5-b]indole

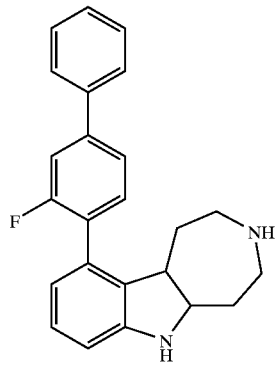

Following the general procedure for the parallel synthesis of 10-aryl substituted azepinoindolines and using isolation method A, the title compound was obtained. MS (ESI+) m/z 359.2 (MH+).

EXAMPLE 431

(5aS*,10bs*)-10-(1,1'-Biphenyl-3-yl)-1,2,3,4,5,5a,6,10b-octahydroazepino[4,5-b]indole

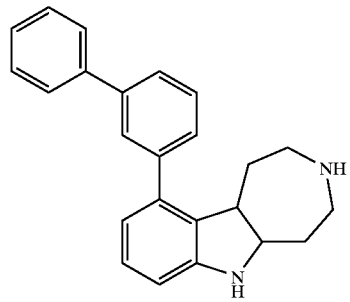

Following the general procedure for the parallel synthesis of 10-aryl substituted azepinoindolines and using isolation method A, the title compound was obtained. MS (ESI+) m/z 341.2 (MH+).

EXAMPLE 432

(5aS*,10bS*)-10-(5-Isopropyl-2-methoxyphenyl)-1,2,3,4,5,5a,6,10b-octahydroazepino[4,5-b]indole

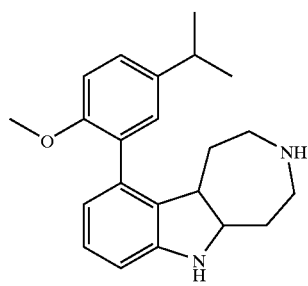

Following the general procedure for the parallel synthesis of 10-aryl substituted azepinoindolines and using isolation method A, the title compound was obtained. MS (ESI+) m/z 337.3 (MH+).

EXAMPLE 433

(5aS*,10bS*)-10-[2-(Methylthio)phenyl]-1,2,3,4,5,5a,6,10b-octahydroazepino[4,5-b]indole

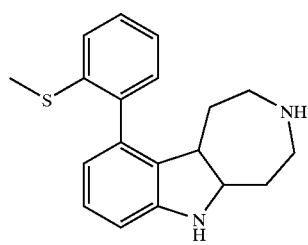

Following the general procedure for the parallel synthesis of 10-aryl substituted azepinoindolines and using isolation method A, the title compound was obtained. MS (ESI+) m/z 311.2 (MH+).

EXAMPLE 434

(5aS*,10bS*)-10-(2,5-Dimethoxyphenyl)-1,2,3,4,5,5a,6,10b-octahydroazepino[4,5-b]indole

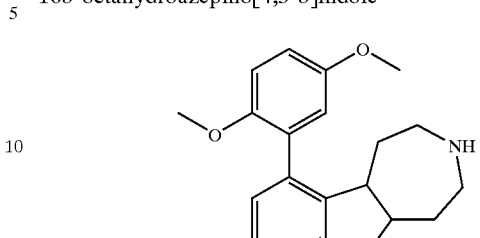

Following the general procedure for the parallel synthesis of 10-aryl substituted azepinoindolines and using isolation method A, the title compound was obtained. MS (ESI+) m/z 325.2 (MH+).

EXAMPLE 435

(5aS*,10bS*)-10-(5-Chloro-2-methoxyphenyl)-1,2,3,4,5,5a,6,10b-octahydroazepino[4,5-b]indole

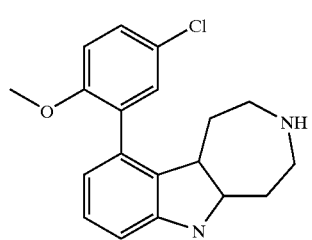

Following the general procedure for the parallel synthesis of 10-aryl substituted azepinoindolines and using isolation method A, the title compound was obtained. MS (ESI+) m/z 329.2 (MH+).

EXAMPLE 436

(5aS*,10bS*)-3-(1,2,3,4,5,5a,6,10b-Octahydroazepino[4,5-b]indol-10-yl)benzonitrile

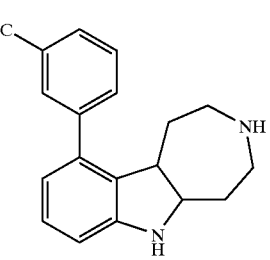

Following the general procedure for the parallel synthesis of 10-aryl substituted azepinoindolines and using isolation method A; the title compound was obtained. MS (ESI+) m/z 290.2 (MH+).

EXAMPLE 437

(5aS*,10bS*)-10-(2,4-Difluorophenyl)-1,2,3,4,5,5a,6,10b-octahydroazepino[4,5-b]indole

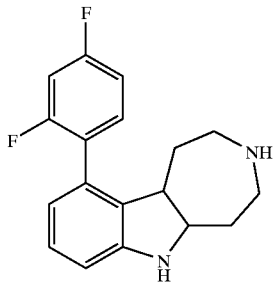

Following the general procedure for the parallel synthesis of 10-aryl substituted azepinoindolines and using isolation method B, the title compound was obtained. MS (ESI+) m/z 301.2 (MH+).

EXAMPLE 438

(5aS*,10bS*)-10-[3-(Trifluoromethoxy)phenyl]-1,2,3,4,5,5a,6,10b-octahydroazepino[4,5-b]indole

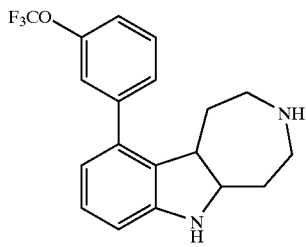

Following the general procedure for the parallel synthesis of 10-aryl substituted azepinoindolines and using isolation method A, the title compound was obtained. MS (ESI+) m/z 349.2 (MH+).

EXAMPLE 439

(5aS*,10bS*)-10-[2-(Benzyloxy)phenyl]-1,2,3,4,5,5a,6,10b-octahydroazepino[4,5-b]indole

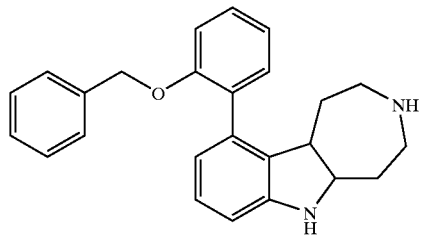

Following the general procedure for the parallel synthesis of 10-aryl substituted azepinoindolines and using isolation method A, the title compound was obtained. MS (ESI+) m/z 371.2 (MH+).

EXAMPLE 440

(5aS*,10bS*)-10-(2,3-Difluorophenyl)-1,2,3,4,5,5a,6,10b-octahydroazepino[4,5-b]indole

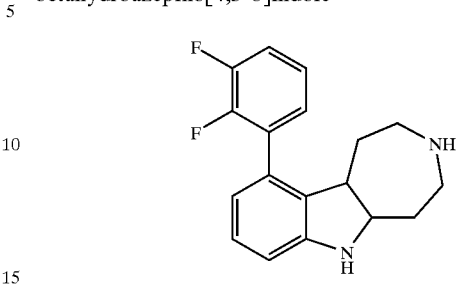

Following the general procedure for the parallel synthesis of 10-aryl substituted azepinoindolines and using isolation method B, the title compound was obtained. MS (ESI+) m/z 301.1 (MH+).

EXAMPLE 441

(5aS*,10bS*)-10-(2,5-Dichlorophenyl)-1,2,3,4,5,5a,6,10b-octahydroazepino[4,5-b]indole

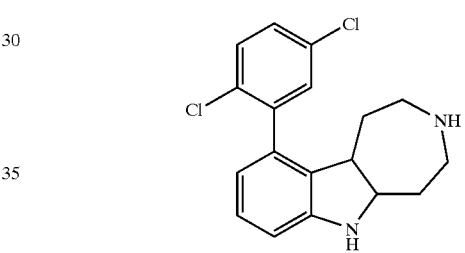

Following the general procedure for the parallel synthesis of 10-aryl substituted azepinoindolines and using isolation method B, the title compound was obtained. MS (ESI+), m/z 333.1 (MH+).

EXAMPLE 442

(5aS*,10bS*)-10-(2,3-Dimethylphenyl)-1,2,3,4,5,5a,6,10b-octahydroazepino[4,5-b]indole

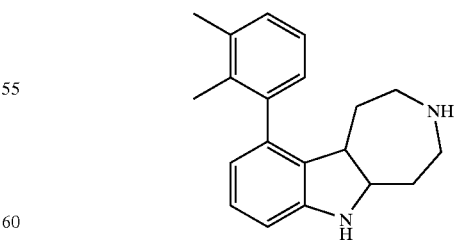

Following the general procedure for the parallel synthesis of 10-aryl substituted azepinoindolines and using isolation method A, the title compound was obtained. MS (ESI+) m/z 293.3 (MH+).

EXAMPLE 443

(5aS*,10bS*)-10-(2,5-Dimethylphenyl)-1,2,3,4,5,5a,6,10b-octahydroazepino[4,5-b]indole

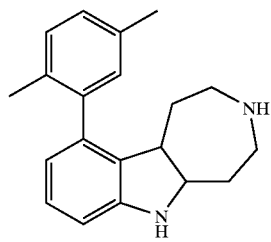

Following the general procedure for the parallel synthesis of 10-aryl substituted azepinoindolines and using isolation method A, the title compound was obtained. MS (ESI+) m/z 293.2 (MH+).

EXAMPLE 444

(5aS*,10bS*)-10-(5-Fluoro-2-methoxyphenyl)-1,2,3,4,5,5a,6,10b-octahydroazepino[4,5-b]indole

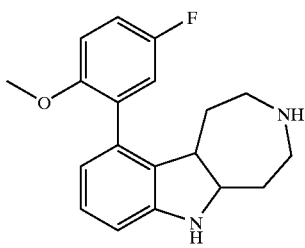

Following the general procedure for the parallel synthesis of 10-aryl substituted azepinoindolines and using isolation method A, the title compound was obtained. MS (ESI+) m/z 313.2 (MH+).

EXAMPLE 445

(5aS*,10bS*)-10-(4-Fluoro-3-methylphenyl)-1,2,3,4,5,5a,6,10 b-octahydroazepino[4,5-b]indole

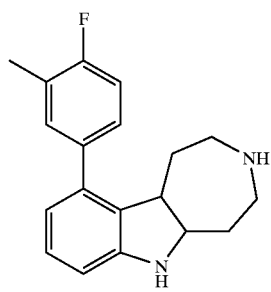

Following the general procedure for the parallel synthesis of 10-aryl substituted azepinoindolines and using isolation method A, the title compound was obtained. MS (ESI+) m/z 297.2 (MH+).

EXAMPLE 446

(5aS*,10bS*)-10-(4-Chloro-2-methylphenyl)-1,2,3,4,5,5a,6,10b-octahydroazepino[4,5-b]indole

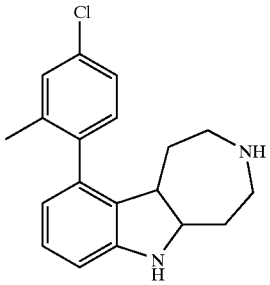

Following the general procedure for the parallel synthesis of 10-aryl substituted azepinoindolines and using isolation method A, the title compound was obtained. MS (ESI+) m/z 313.1 (MH+).

EXAMPLE 447

(5aS*,10bS*)-10-(2-Chloro-4-methoxyphenyl)-1,2,3,4,5,5a,6,10b-octahydroazepino[4,5-b]indole

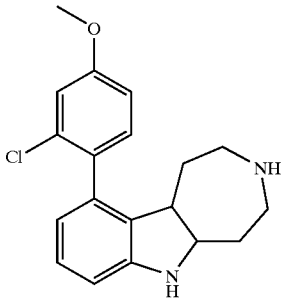

Following the general procedure for the parallel synthesis of 10-aryl substituted azepinoindolines and using isolation method A, the title compound was obtained. MS (ESI+) m/z 329.2 (MH+).

EXAMPLE 448

(5aS*,10bS*)-10-(2-Chloro-4-methylphenyl)-1,2,3,4,5,5a,6,10b-octahydroazepino[4,5-b]indole

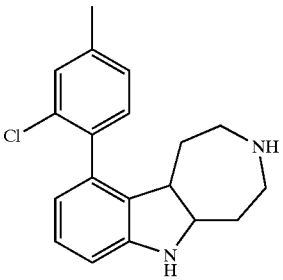

Following the general procedure for the parallel synthesis of 10-aryl substituted azepinoindolines and using isolation method A, the title compound was obtained. MS (ESI+) m/z 313.2 (MH+).

EXAMPLE 449

(5aS*,10bS*)-10-(2-Isopropylphenyl)-1,2,3,4,5,5a,6,10b-octahydroazepino[4,5-b]indole

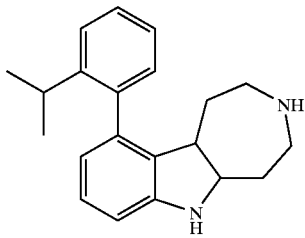

Following the general procedure for the parallel synthesis of 10-aryl substituted azepinoindolines and using isolation method B, the title compound was obtained. MS (ESI+) m/z 307.3 (MH+).

EXAMPLE 450

(5aS*,10bS*)-10-(3-tert-Butyl-5-methylphenyl)-1,2,3,4,5,5a,6,10b-octahydroazepino[4,5-b]indole

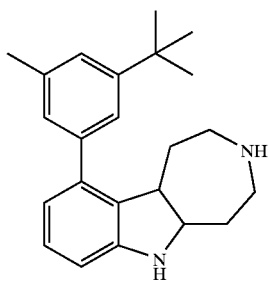

Following the general procedure for the parallel synthesis of 10-aryl substituted azepinoindolines and using isolation method B, the title compound was obtained. MS (ESI+) m/z 335.3 (MH+).

EXAMPLE 451

(5aS*,10bS*)-10-(4-Fluoro-2-methylphenyl)-1,2,3,4,5,5a,6,10b-octahydroazepino[4,5-b]indole

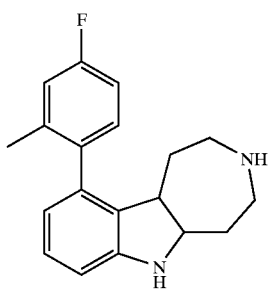

Following the general procedure for the parallel synthesis of 10-aryl substituted azepinoindolines and using isolation method B, the title compound was obtained. MS (ESI+) m/z 297.2 (MH+).

EXAMPLE 452

(5aS*,10bS*)-10-(1-benzofuran-2-yl)-1,2,3,4,5,5a,6,10b-octahydroazepino[4,5-b]indole

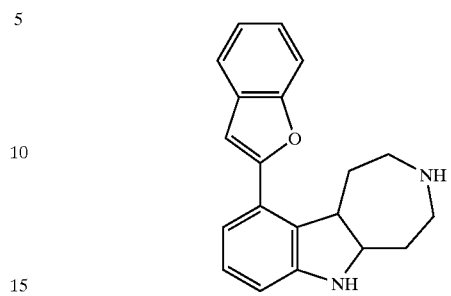

A 30-mL shaker vial was charged with di(tert-butyl) 10-bromo-1,2,4,5,5a,10b-hexahydroazepino[4,5-b]indole-3,6-dicarboxylate (0.10 g, 0.214 mmol), potassium phosphate (0.068 g, 0.32 mmol), benzo[b]furan-2-boronic acid (0.104 g, 0.642 mmol), and DMF (2 mL). The vial was purged with $N_2$, and tetrakis(triphenylphosphine)palladium (0.025 g, 0.02 mmol) was added and the mixture was agitated at 250 RPM with heating at 80° C. overnight. The mixture was filtered through Celite, washing with MeOH (3–5 mL), and sulfonic acid resin (DOWEX®50W-X2, washed and dried, 4.8 meq/g dry weight) was added (1 g). The vial was then purged with $N_2$, capped and agitated at 250 RPM with heating at 65° C. for 36 h. The mixture was filtered through a scintered funnel and the resin was washed 1:1 methylene chloride/methanol and then consecutively washed with MeOH and THF to ensure that all excess reagent was removed from the resin (the methanol and THF washes are alternated to swell and then shrink the resin to help expel reagents from inside the resin). The resin was then washed with 4M ammonium hydroxide in methanol (4×2 ml) and THF (2×2 ml) into an accurately weight round-bottomed flask. The filtrate was concentrated to give 0.042 g (65%) of a beige solid, which was dissolved in methylene chloride and crystallized to give 0.020 g of the title compound as beige solid: MS (EI) m/z 304 (M+), 302, 260, 259, 258, 247, 246, 207, 195, 153; $^1$H NMR (CDCl$_3$) δ 7.64 (d, J=7 Hz, 1 H), 7.53 (d, J=8 Hz, 1 H), 7.35–7.22 (m, 3 H), 7.15 (t, J=8 Hz, 1 H), 6.63 (d, J=8 Hz, 1 H), 4.38–4.27 (m, 1H), 4.16–4.06 (m, 1 H), 3.28–3.22 (m, 1 H), 3.17–3.11 (m, 1 H), 2.95–2.79 (m, 2 H), 2.38–2.26 (m, 1 H), 2.10–1.89 (m, 2 H), 1.81–1.72 (m, 1 H) ppm.

EXAMPLE 453

(5aS*,10bS*)-10-dibenzo[b,d]furan-4-yl-1,2,3,4,5,5a,6,10b-octahydroazepino[4,5-b]indole

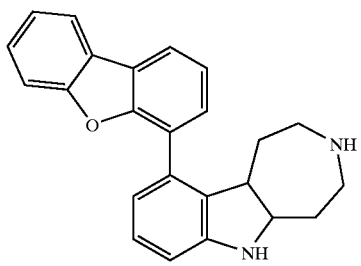

A 30-mL shaker vial was charged with di(tert-butyl) 10-bromo-1,2,4,5,5a,10b-hexahydroazepino[4,5-b]indole-3,6-dicarboxylate (0.10 g, 0.214 mmol), potassium phosphate (0.068 g, 0.32 mmol), 4-dibenzofuranboronic acid (0.136 g, 0.642 mmol), and DMF (2 mL). The vial was purged with N₂, and tetrakis(triphenylphosphine)palladium (0.025 g, 0.02 mmol) was added and the mixture was agitated at 250 RPM with heating at 80° C. overnight. The mixture was filtered through Celite, washing with MeOH (3–5 mL), and sulfonic acid resin (DOWEX®50W-X2, washed and dried, 4.8 meq/g dry weight) was added (1 g). The vial was then purged with N₂, capped and agitated at 250 RPM with heating at 65° C. for 72 h. The mixture was filtered through a scintered funnel and the resin was washed 1:1 methylene chloride/methanol and then consecutively washed with MeOH and THF to ensure that all excess reagent was removed from the resin (the methanol and THF washes are alternated to swell and then shrink the resin to help expel reagents from inside the resin). The resin was then washed with 4M ammonium hydroxide in methanol (4×2 ml) and THF (2×2 ml) into an accurately weight round-bottomed flask. The filtrate was concentrated to give 0.035 g (47%) of a white solid: MS (EI) m/z 355 (MH+); HPLC rt=3.86 min (95%).

EXAMPLE 454

(5aS*,10bS*)-10-thien-3-yl-1,2,3,4,5,5a,6,10b-octahydroazepino[4,5-b]indole

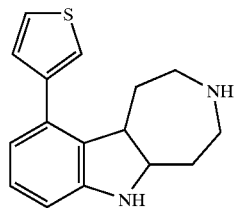

A 30-mL shaker vial was charged with di(tert-butyl) 10-broino-1,2,4,5,5a,10b-hexahydroazepino[4,5-b]indole-3,6-dicarboxylate (0.10 g, 0.214 mmol), potassium phosphate (0.068 g, 0.32 mmol), 3-thiopheneboronic acid (0.82 g, 0.642 mmol), and DMF (2 mL). The vial was purged with N₂, and tetrakis(triphenylphosphine)palladium (0.025 g, 0.02 mmol) was added and the mixture was agitated at 250 RPM with heating at 80° C. overnight. The mixture was filtered through Celite, washing with MeOH (3–5 mL), and sulfonic acid resin (DOWEX®50W-X2, washed and dried, 4.8 meq/g dry weight) was added (1 g). The vial was then purged with N₂, capped and agitated at 250 RPM with heating at 65° C. for 72 h. The mixture was filtered through a scintered funnel and the resin was washed 1:1 methylene chloride/methanol and then consecutively washed with MeOH and THF to ensure that all excess reagent was removed from the resin (the methanol and THF washes are alternated to swell and then shrink the resin to help expel reagents from inside the resin). The resin was then washed with 4M ammonium hydroxide in methanol (4×2 ml) and THF (2×2 ml) into an accurately weight round-bottomed flask. The filtrate was concentrated to give 0.035 g (60%) of a brown oil: MS (EI) m/z 271 (MH+); HPLC rt=2.78 min (100%).

EXAMPLE 455

(5aS*,10bS*)-10-(1-benzothien-2-yl)-1,2,3,4,5,5a,6,10b-octahydroazepino[4,5-b]indole

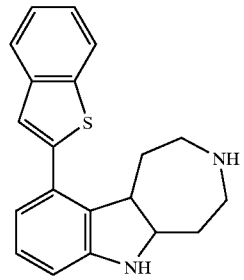

A 30-mL shaker vial was charged with di(tert-butyl) 10-bromo-1,2,4,5,5a,10b-hexahydroazepino[4,5-b]indole-3,6-dicarboxylate (0.10 g, 0.214 mmol), potassium phosphate (0.068 g, 0.32 mmol), benzothiophene-2-boronic acid (0.114 g, 0.642 mmol), and DMF (2 mL). The vial was purged with N₂, and tetrakis(triphenylphosphine)palladium (0.025 g, 0.02 mmol) was added and the mixture was agitated at 250 RPM with heating at 80° C. overnight. The mixture was filtered through Celite, washing with MeOH (3–5 mL), and sulfonic acid resin (DOWEX®50W-X2, washed and dried, 4.8 meq/g dry weight) was added (1 g). The vial was then purged with N₂, capped and agitated at 250 RPM with heating at 65° C. for 72 h. The mixture was filtered through a sintered funnel and the resin was washed 1:1 methylene chloride/methanol and then consecutively washed with MeOH and THF to ensure that all excess reagent was removed from the resin (the methanol and THF washes are alternated to swell and then shrink the resin to help expel reagents from inside the resin). The resin was then washed with 4M ammonium hydroxide in methanol (4×2 ml) and THF (2×2 ml) into an accurately weight round-bottomed flask. The filtrate was concentrated to give 0.040 g (68%) of an amber oil: MS (EI) m/z 321 (MH+); HPLC rt=3.68 min (100%).

EXAMPLE 456

(5aS*,10bS*)-10-Quinolin-3-yl-1,2,3,4,5,5a,6,10b-octahydroazepino[4,5-b]indole

A 30-mL shaker vial was charged with di(tert-butyl) 10-bromo-1,2,4,5,5a,10b-hexahydroazepino[4,5-b]indole-3,6-dicarboxylate (0.10 g, 0.214 mmol), potassium phosphate (0.068 g, 0.32 mmol), 3-quiniline boronic acid (0.111 g, 0.642 mmol), and DMF (2 mL). The vial was purged with N₂, and tetrakis(triphenylphosphine)palladium (0.025 g, 0.02 mmol) was added and the mixture was agitated at 250 RPM with heating at 80° C. overnight. The mixture was filtered through Celite, washing with MeOH (3–5 mL), and sulfonic acid resin (DOWEX®50W-X2, washed and dried, 4.8 meq/g dry weight) was added (1 g). The vial was then purged with $N_2$, capped and agitated at 250 RPM with heating at 65° C. for 72 h. The mixture was filtered through a scintered funnel and the resin was washed 1:1 methylene chloride/methanol and then consecutively washed with MeOH and THF and 2M pyridine/MeOH to ensure that all excess reagent was removed from the resin (the methanol and THF washes are alternated to swell and then shrink the resin to help expel reagents from inside the resin). The resin was then washed with 4M ammonium hydroxide in methanol (4×2 ml) and THF (2×2 ml) into an accurately weight round-bottomed flask. The filtrate was concentrated to give 0.049 g (73%) of an amber oil: MS (EI) m/z 316 (MH+); HPLC rt=2.67 min (85%).

EXAMPLE 457

(5aS*,10bS*)-10-(3-furyl)-1,2,3,4,5,5a,6,10b-octahydroazepino[4,5-b]indole

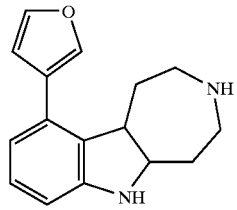

A 30-mL shaker vial was charged with di(tert-butyl) 10-bromo-1,2,4,5,5a,10b-hexahydroazepino[4,5-b]indole-3,6-dicarboxylate (0.10 g, 0.214 mmol), potassium phosphate (0.068 g, 0.32 mmol), furan-3-boronic acid (0.072 g, 0.642 mmol), and DMF (2 mL). The vial was purged with $N_2$, and tetrakis(triphenylphosphine)-palladium (0.025 g, 0.02 mmol) was added and the mixture was agitated at 250 RPM with heating at 80° C. overnight. The mixture was filtered through Celite, washing with MeOH (3–5 mL), and sulfonic acid resin (DOWEX®50W-X2, washed and dried, 4.8 meq/g dry weight) was added (1 g). The vial was then purged with $N_2$, capped and agitated at 250 RPM with heating at 65° C. for 72 h. The mixture was filtered through a scintered funnel and the resin was washed 1:1 methylene chloride/methanol and then consecutively washed with MeOH and THF to ensure that all excess reagent was removed from the resin (the methanol and THF washes are alternated to swell and then shrink the resin to help expel reagents from inside the resin). The resin was then washed with 4M ammonium hydroxide in methanol (4×2 ml) and THF (2×2 ml) into an accurately weight round-bottomed flask. The filtrate was concentrated to give 0.038 g (70%) of a pink oil: MS (EI) m/z 255 (MH+); HPLC rt=2.51 min (100%).

EXAMPLE 458

(5aS*,10bS*)-8,9-Dichloro-6-(2-phenoxyethyl)-1,2,3,4,5,5a,6,10b-octahydroazepino[4,5-b]indole hydrochloride

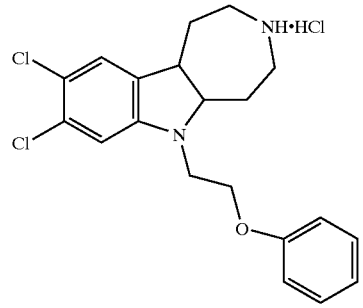

A solution of 8,9-dichloro-6-(2-phenoxyethyl)-1,2,3,4,5,6-hexahydroazepino[4,5-b]indole (1.2 g, 3.1 mmol) in TFA (40 mL) was cooled to 0° C. A fresh solution of $NaCNBH_3$ (4.9 g, 77 mmol) in MeOH (10 mL) was prepared and added dropwise at 0° C. After the addition was complete, the reaction was warmed to rt and then heated to 50° C. After 2 h, the reaction was cooled to rt, diluted with water, made basic with 50% aqueous NaOH, and extracted with EtOAc (3×100 mL). The combined organic layers were washed with brine, dried over $Na_2SO_4$, decanted, and concentrated. The crude material was purified via column chromatography (Biotage, 40M, SIM) with $CH_2Cl_2/MeOH/NH_4OH$ (976:21:3) to give a crude solid. The hydrochloride salt was prepared to give 0.17 g (14%) of a tan solid: mp 223.0–223.5° C.; $^1H$ NMR (DMSO, 300 MHz) δ 8.92 (m, 2H), 7.26 (m, 3H), 6.93 (m, 3H), 6.75 (s, 1H), 4.09 (m, 3H), 3.65 (m, 2H), 3.46 (m, 2H), 3.08 (m, 3H), 2.90 (m, 1H), 2.23 (m 1H), 2.09 (m, 2H); $^{13}C$ NMR (400 MHz, DMSO) δ 158.1, 151.1, 132.2, 130.0, 129.4, 125.2, 120.6, 117.2, 114.3, 107.0, 65.2, 64.7, 44.5, 44.3, 42.3, 42.0, 27.4, 25.6; IR (diffuse reflectance) 2971, 2950, 2857, 2840, 2800, 2750, 2718, 2684, 2656, 1595, 1494, 1467, 1245, 785, 758 cm$^{-1}$; HRMS (FAB) calcd for $C_{20}H_{22}Cl_2N_2O+H$ 377.1187, found 377.1189; Anal. Calcd for $C_{20}H_{22}Cl_2N_2O\cdot HCl$: C, 58.06; H, 5.60; N, 6.77; found: C, 57.81; H, 5.65; N, 6.71.

EXAMPLE 459

(5aS*,10bS*)-9,10-Dichloro-6-(2-phenoxyethyl)-1,2,3,4,5,5a,6,10b-octahydroazepino[4,5-b]indole hydrochloride

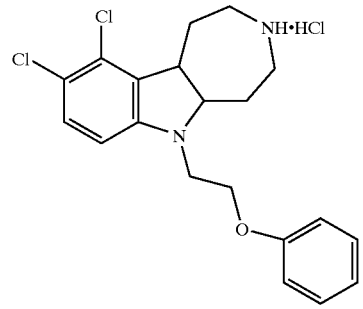

A solution of 9,10-dichloro-6-(2-phenoxyethyl)-1,2,3,4,5,6-hexahydroazepino[4,5-b]indole (0.24 g, 0.64 mmol) in TFA (8 mL) was cooled to 0° C. A fresh solution of NaCNBH$_3$ (1.0 g, 16 mmol) in MeOH (2 mL) was prepared and added dropwise at 0° C. After the addition was complete, the reaction was warmed to rt and then heated to 50° C. After 2.5 h, the reaction was cooled to rt, diluted with water, made basic with 50% aqueous NaOH, and extracted with EtOAc (3×20 mL). The combined organic layers were washed with brine, dried over Na$_2$SO$_4$, decanted, and concentrated. The crude material was purified via column chromatography (Biotage, 40S) with CH$_2$Cl$_2$/MeOH/NH$_4$OH (976:21:3) to give 0.43 g of a crude solid. After the hydrochloride salt was prepared, it was further purified by triturating with ether and recrystallization from MeOH/EtOAc to give 0.16 g (59%) of a white solid: mp 141.6–143.0° C.; $^1$H NMR (DMSO, 300 MHz) δ 8.79 (br s, 2H), 7.28 (m, 3H), 6.93 (m, 3H), 6.63 (d, J=8.5 Hz, 1H), 4.08 (m, 3H), 3.65 (m, 2H), 3.12 (m, 2H), 3.00 (m, 1H), 2.36 (m, 1H), 2.17 (m, 1H), 2.05 (m, 2H); $^{13}$C NMR (DMSO) δ 158.0, 151.7, 130.3, 129.8, 129.4, 127.0, 120.6, 118.1, 114.3, 106.6, 64.9, 64.5, 44.7, 44.7, 43.6, 41.3, 25.3, 24.6; IR (diffuse reflectance) 2971, 2950, 2857, 2840, 2800, 2750, 2718, 2684, 2656, 1595, 1494, 1467, 1245, 785, 758 cm$^{-1}$; HRMS (FAB) calcd for C$_{20}$H$_{22}$Cl$_2$N$_2$O+H 377.1187, found 377.1189; Anal. Calcd for C$_{20}$H$_{22}$Cl$_2$N$_2$O.HCl: C, 58.06; H, 5.60; N, 6.77; found: C, 57.81; H, 5.65; N, 6.71.

Preparation 133

Preparation of tert-butyl (5aS*,10bS*)-9,10-dichloro-6-(2-phenoxyethyl)-1,4,5,5a,6,10b-hexahydroazepino[4,5-b]indole-3(2H)-carboxylate Boc$_2$O (0.59 g, 2.7 mmol) was added to a solution of 9,10-dichloro-6-(2-phenoxyethyl)-1,2,3,4,5,5a,6,10b-octahydroazepino[4,5-b]indole (0.85 g, 2.3 mmol) in THF (32 mL) followed by 10% aqueous NaOH (8 mL). After 2 h, the reaction was diluted with H$_2$O (35 mL) and extracted with EtOAc (3×40 mL). The combined organic layers were washed with brine, dried over Na$_2$SO$_4$, decanted, and concentrated. The crude product was purified via column chromatography (Biotage, 40M) with heptane/EtOAc (4:1) to give 0.60 g of the racemic product that was submitted for separation of the two enantiomers.

Preparation 134

Preparation of tert-butyl (5aS*,10bS*)-9,10-dichloro-6-(2-phenoxyethyl)-1,4,5,5a,6,10b-hexahydroazepino[4,5-b]indole-3(2H)-carboxylate and tert-butyl (5aR,10bR)-9,10-dichloro-6-(2-phenoxyethyl)-1,4,5,Sa,6,10b-hexahydroazepino[4,5-b]indole-3(2H)-carboxylate The racemic tert-butyl (5aS*,10bS*)-9,10-dichloro-6-(2-phenoxyethyl)-1,4,5,5a,6,10b-hexahydroazepino[4,5-b]indole-3(2H)-carboxylate was separated on a Chiralpak AD column (0.46×25 cm; 0.5 mL/min; 5% isopropanol/heptane; 270 nm) to give the faster eluting enantiomer at 17.99 min with 99% ee and the slower eluting at 25.16 min with 97% ee.

EXAMPLE 460

(−)-9,10-Dichloro-6-(2-phenoxyethyl)-1,2,3,4,5,5a,6,10b-octahydroazepino[4,5-b]indole hydrochloride (cis ring fusion)

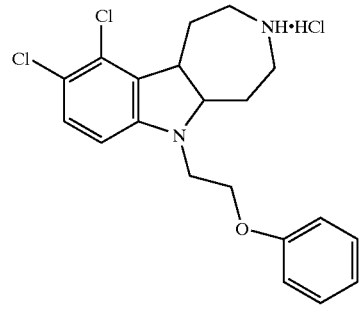

TFA (1.01 ml, 13 mmol) was added to a solution of the faster eluting resolved tert-butyl 9,10-dichloro-6-(2-phenoxyethyl)-1,4,5,5a,6,10b-hexahydroazepino[4,5-b]indole-3(2H)-carboxylate (0.31 g, 0.66 mmol) in CH$_2$Cl$_2$ (7 mL). After 4 h, the reaction was made basic with 10% aqueous NaOH, and extracted with CH$_2$Cl$_2$ (3×25 mL). The combined organic layers were washed with brine, dried over Na$_2$SO$_4$, decanted, and concentrated. The hydrochloride salt was prepared via crystallization from EtOAc/heptane of the crude material and then was further purified by recrystallization from MeOHF/EtOAc to give 18 mg (7%, 100% ee) of a white solid: mp 100.5–104.0° C.; $^1$H NMR (DMSO, 300 MHz) δ 8.92 (br s, 2H), 7.26 (m, 3H), 6.92 (m, 3H), 6.62 (d, J=8.5 Hz, 1H), 4.08 (m, 3H), 3.67 (m, 2H), 3.07 (m, 3H), 2.38 (m, 1H) 2.20 (m, 1H), 2.06 (m, 2H); IR (diffuse reflectance) 2954, 2846, 2778, 2752, 1594, 1497, 1460, 1291, 1273, 1244, 1226, 811, 803, 752, 695 cm$^{-1}$; MS (EI) m/z 376 (M$^+$), 321, 320, 319, 242, 240, 228, 226, 77, 56; HRMS (FAB) calcd for C$_{20}$H$_{22}$Cl$_2$N$_2$O+H 377.1187, found 377.1179.

EXAMPLE 461

(+)-9,10-Dichloro-6-(2-phenoxyethyl)-1,2,3,4,5,5a,6,10b-octahydroazepino[4,5-b]indole hydrochloride (cis ring fusion)

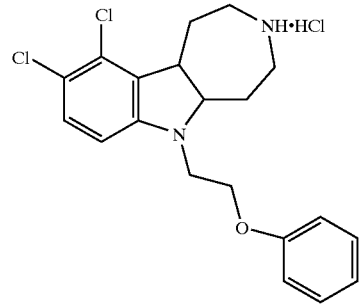

TFA (0.85 ml, 11 mmol) was added to a solution of the slower eluting resolved tert-butyl 9,10-dichloro-6-(2-phenoxyethyl)-1,4,5,5a,6,10b-hexahydroazepino[4,5-b]indole-3(2H)-carboxylate (0.26 g, 0.55 mmol) in CH$_2$Cl$_2$ (7 mL). After 5 h, the reaction was made basic with 10% aqueous NaOH, and extracted with $CH_2Cl_2$ (3×25 mL). The combined organic layers were washed with brine, dried over $Na_2SO_4$, decanted, and concentrated. The hydrochloride salt was prepared via crystallization from EtOAc/heptane of the crude material and then was further purified by recrystallization from MeOH/EtOAc to give 44 mg (19%, 96% ee) of a white solid: mp 110.5–117.0° C.; $^1$H NMR (DMSO, 300 MHz) δ 9.10 (br s, 2H), 7.27 (m, 3H), 6.92 (m, 3H), 6.62 (d, J=8.5 Hz, 1H), 4.08 (m, 3H), 3.63 (m, 2H), 3.41 (m, 1H), 3.27 (m, 3.10 (m, 2H), 3.00 (m, 1H), 2.37 (m, 1H), 2.22 (m, 1H), 2.08 (m, 2H); IR (diffuse reflectance) 2955, 2881, 2850, 2778, 2745, 1595, 1497, 1459, 1291, 1273, 1244, 1226, 811, 752, 695 $cm^{-1}$; MS (EI) m/z 376 (M$^+$), 378, 321, 320, 319, 318, 242, 240, 228, 226; HRMS (FAB) calcd for $C_{20}H_{22}Cl_2N_2O+H$ 377.1187, found 377.1195.

EXAMPLE 462

(SaS*,10bS*)-7,10-Dichloro-6-(2-phenoxyethyl)-1,2,3,4,5,5a,6,10b-octahydroazepino[4,5-b]indole hydrochloride

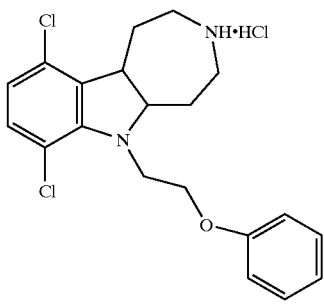

A solution of 7,10-dichloro-6-(2-phenoxyethyl)-1,2,3,4,5,6-hexahydroazepino[4,5-b]indole (0.36 g, 0.96 mmol) in TFA (12 mL) was cooled to 0° C. A fresh solution of $NaCNBH_3$ (1.5 g, 24 mmol) in MeOH (3 mL) was prepared and added dropwise at 0° C. After the addition was complete, the reaction was warmed to rt and then heated to 50° C. After 3 h, the reaction was cooled to rt, diluted with water, made basic with 50% aqueous NaOH, and extracted with $CHCl_3$ (3×30 mL). The combined organic layers were washed with brine, dried over $Na_2SO_4$, decanted, and concentrated. The hydrochloride salt was prepared from the crude solid to give 98 mg (27%) of a white solid: mp 248.5–251.5° C.; $^1$H NMR (DMSO, 300 MHz) δ 8.91 (br s, 2H), 7.27 (m, 2H), 7.12 (d, J=8.7 Hz, 1H), 6.91 (m, 3H), 6.72 (d, J=8.7 Hz, 1H), 4.14 (m, 4H), 3.76 (m, 1H), 3.62 (m, 1H), 3.10 (m, 2H), 2.96 (m, 1H), 2.36 (m, 1H), 2.08 (m, 3H); $^{13}$C NMR (400 MHz, DMSO) δ 158.0, 147.8, 131.8, 131.5, 129.4, 128.0, 120.7, 119.7, 114.2, 112.0, 65.7, 65.4, 45.7, 44.7, 42.9, 41.7, 25.7, 25.0; IR (diffuse reflectance) 2960, 2800, 2779, 2741, 2716, 2694, 2687, 2660, 1590, 1465, 1427, 1246, 1234, 798, 757 $cm^{-1}$; MS (CI) m/z 377 (MH$^+$), 380, 379, 378, 377, 343, 223, 121, 96, 61, 52; % Water (KF): 0.11; Anal. Calcd for $C_{20}H_{22}Cl_2N_2O·HCl$: C, 58.06; H, 5.60; N, 6.77; Cl, 25.70; Found: C, 57.84; H, 5.64; N, 6.73; Found; Cl, 25.07.

EXAMPLE 463

(5aS*,10bS*)-7,8-Dichloro-6-(2-phenoxyethyl)-1,2,3,4,5,5a,6,10b-octahydroazepino[4,5-b]indole hydrochloride

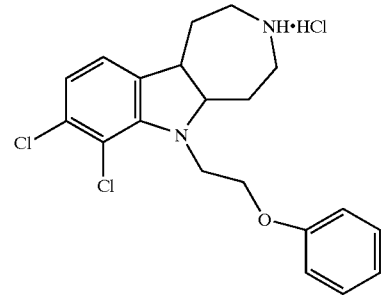

A solution of 7,8-dichloro-6-(2-phenoxyethyl)-1,2,3,4,5,6-hexahydroazepino[4,5-b]indole (0.25 g, 0.67 mmol) in TFA (7.5 mL) was cooled to 0° C. A fresh solution of $NaCNBH_3$ (0.21 g, 3.3 mmol) in MeOH (2.5 mL) was prepared and added dropwise at 0° C. After 2.5 h, the reaction was made basic with 25% aqueous NaOH, and extracted with $CHCl_3$ (3×25 mL). The combined organic layers were washed with brine, dried over $Na_2SO_4$, decanted, and concentrated. The crude material was purified via column chromatography (Biotage, 40S) with $CH_2Cl_2/MeOH/NH_4OH$ (976:21:3) followed by the preparation of the hydrochloride salt to give 0.19 mg (67%) of a white solid: mp 160.5–162.5° C.; $^1$H NMR (DMSO, 300 MHz) δ 8.86 (bs, 1H), 8.74 (bs, 1H), 7.26 (m, 2H), 7.01–6.86 (m, 5H), 4.27–4.04 (m, 4H), 3.84 (td, J=10, 4.3 Hz, 1H), 3.66 (m, 1H), 3.23–2.90 (m, 4H), 2.25–1.91 (m, 4H); IR (diffuse reflectance) 2926, 2908, 2852, 1602, 1574, 1451, 1370, 1291, 1282, 1260, 1139, 906, 832, 772, 718 $cm^{-1}$; MS (EI) m/z 376 (M+), 269, 240, 228, 226, 214, 135, 91, 77, 56, 51; Anal. Calcd for $C_{20}H_{22}Cl_2N_2O·HCl$: C, 58.06; H, 5.60; N, 6.77; Cl, 25.70; found: C, 57.76; H, 5.96; N, 6.59.

EXAMPLE 464

(5aS*,10bS*)-8,10-Dichloro-6-(2-phenoxyethyl)-1,2,3,4,5,5a,6,10b-octahydroazepino[4,5-b]indole hydrochloride

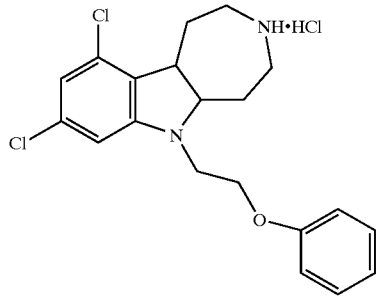

A solution of 8,10-dichloro-6-(2-phenoxyethyl)-1,2,3,4,5,6-hexahydroazepino[4,5-b]indole (0.20 g, 0.53 mmol) in TFA (8 mL) was cooled to 0° C. A fresh solution of $NaCNBH_3$ (0.84 g, 13 mmol) in MeOH (2 mL) was prepared and added dropwise at 0° C. After the addition was complete, the reaction was warmed to rt and then heated to 50° C. After 2.5 h, the reaction was cooled to rt, made basic with 50% aqueous NaOH, and extracted with $CHCl_3$ (3×20 mL). The combined organic layers were washed with brine, dried over $Na_2SO_4$, decanted, and concentrated. The crude material was purified via column chromatography (Biotage, 40S) with $CH_2Cl_2/MeOH/NH_4OH$ (976:21:3) followed by the preparation of the hydrochloride salt to give 0.14 mg (64%) of a beige solid: mp 133.5–135° C.; $^1$H NMR (DMSO, 300 MHz) δ 8.89 (bs, 2H), 7.29 (dd, J=8.6, 7.4 Hz, 2H), 6.91 (m, 3H), 6.68 (d, J=1.7 Hz, 1H), 6.65 (d, J=1.7 Hz, 1H); 4.18 (m, 1H), 4.09 (m, 2H), 3.67 (m, 2H), 3.41 (m, 1H), 3.23 (m, 1H), 3.11 (m, 1H), 2.98 (m, 1H), 2.36 (m, 1H), 2.17 (m, 1H), 2.06 (m, 2H); IR (diffuse reflectance) 2926, 2908, 2852, 1602, 1574, 1451, 1370, 1291, 1282, 1260, 1139, 906, 832, 772, 718 cm$^{-1}$; MS (EI) m/z 390 (M+), 321, 319, 283, 242, 240, 228, 226, 77, 65, 56; HRMS (FAB) calcd for $C_{20}H_{22}Cl_2N_2O$+H 377.1187, found 377.1188.

Preparation 135

Preparation of ethyl (9,10-dichloro-2,3,4,5-tetrahydroazepino[4,5-b]indol-6(1H)-yl)acetate TFA (10.5 mL, 136 mmol) was added to a solution of tert-butyl 9,10-dichloro-6-(2-ethoxy-2-oxoethyl)-1,4,5,6-tetrahydroazepino[4,5-b]indole-3(2H)-carboxylate (3.0 g, 6.8 mmol) in $CH_2Cl_2$ (70 mL). After 5 h, the reaction was made basic with 10% aqueous NaOH and extracted with $CH_2Cl_2$ (3×50 mL). The combined organic layers were washed with brine, dried over $Na_2SO_4$, decanted, and concentrated to give 2.4 g of the crude yellow oil: 1H NMR (300 MHz, $CDCl_3$) δ 7.16 (d, J=8.7 Hz, 1H), 6.97 (d, J=8.7 Hz, 1H), 4.75 (s, 2H), 4.19 (q, J=7.1 Hz, 2H), 3.45 (m, 2H), 3.10 (t, J=5.1 Hz, 4H), 2.87 (m, 2H 2.28 (br s, 1H) 1.25 (m, 3H); IR (diffuse reflectance) 2979, 2958, 2939, 2904, 2837, 2816, 2797, 2766, 2644, 1744, 1449, 1372, 1279, 1204, 1160 cm$^{-1}$;MS (EI) m/z 340 (M$^+$), 305, 300, 298, 270, 226, 224, 154, 149, 127; HRMS (FAB) calcd for $C_{16}H_{18}CL_2N_2O_2$+H 341.0823, found 341.0818.

Preparation 136

Preparation of (5aS*,10bS*)-ethyl (9,10-dichloro-2,3,4,5,5a,10b-hexahydroazepino[4,5-b]indol-6(1H)-yl)acetate A solution of (5aS*, 10bS*)-ethyl (9,10-dichloro-2,3,4,5-tetrahydroazepino[4,5-b]indol-6(1H)-yl)acetate (2.2 g, 6.4 mmol) in TFA (40 mL) was cooled to 0° C. A fresh solution of $NaCNBH_3$ (5.0 g, 80 mmol) in MeOH (10 mL) was prepared and added dropwise at 0° C. After the addition was complete, the reaction was warmed to rt and then heated to 50° C. After 1.5 h, the reaction was cooled to rt, diluted with water, made basic with 50% aqueous NaOH, and extracted with $CHCl_3$. The combined organic layers were washed with brine, dried over $Na_2SO_4$, decanted, and concentrated to a crude yellow foam: $^1$H NMR (300 MHz, $CDCl_3$) δ 8.90 (br s, 1H), 7.18 (m, 1H), 6.23 (m, 1H), 4.20 (m, 3H), 3.91 (m, 1H), 3.67 (m, 2H), 3.45 (m, 1H), 3.25 (m, 1H), 2.86 (m, 1H), 2.30 (m, 5H), 1.25 (t, J=7.1 Hz, 3H); IR (diffuse reflectance) 2983,2959,2866,1739, 1676,1595,1466, 1429,1393,1373, 1305, 1277,1201, 1140, 799 cm$^{-1}$; MS (EI) m/z 342 (M$^+$), 287, 286, 285, 284, 228, 226, 214, 212, 56; HRMS (FAB) calcd for $C_{16}H_{20}CL_2N_2O_2$+H 343.0980, found 343.0970.

Preparation 137

Preparation of tert-butyl (5aS*,10bS*)-9,10-dichloro-6-(2-ethoxy-2-oxoethyl)-1,4,5,5a,6,10b-hexahydroazepino[4,5-b]indole-3(2H)-carboxylate $Boc_2O$ (1.8 g, 8.4 mmol) was added to a solution of ethyl (5aS*,10bS*)-(9,10-dichloro-2,3,4,5,5a,10b-hexahydroazepino[4,5-b]indol-6(1 H)-yl)acetate (2.4 g, 7.0 mmol) in THF (40 mL) followed by 10% aqueous NaOH (10 mL). After 2 h, the reaction was diluted with $H_2O$ (50 mL) and extracted with EtOAc (3×100 mL). The combined organic layers were washed with brine, dried over $Na_2SO_4$, decanted, and concentrated. The crude product was purified via column chromatography (Biotage, 40M) with heptane/EtOAc (4:1) to give 1.2 g of a white foam: $^1$H NMR (300 MHz, $CDCl_3$) δ 7.13 (d, J=8.4 Hz, 1H), 6.19 (d, J=8.4 Hz, 1H), 4.15 (q, J=7.1 Hz, 3H), 3.93 (d, J=17.9 Hz, 1H), 3.71 (d, J=17.9 Hz, 1H), 3.47 (m, 5H), 2.14 (m, 1H), 1.99 (m, 3H), 1.46 (s, 9H), 1.24 (t, J=7.1 Hz, 3H); IR (diffuse reflectance) 1687, 1505, 1468, 1414, 1366, 1296, 1268, 1248, 1218, 1169, 1114, 1105, 865, 827, 746 cm$^{-1}$; MS (ESP) m/z 493 (MH$^+$), 516, 515, 366, 364, 265, 253, 138, 94, 91, 85; Anal. Calcd for $C_{25}H_{27}Cl_2FN_2O_3$: C, 60.86; H, 5.51; N, 5.68; found: C, 60.91; H, 5.61; N, 5.64.

Preparation 138

Preparation of [3-(tert-butoxycarbonyl) (5aS*,10bS*)-9,10-dichloro-2,3,4,5,5a, 10b-hexahydroazepino[4,5-b]indol-6 (1H)-yl]acetic acid A solution of KOH (0.16 g, 2.8 mmol) in $H_2O$ (10 mL) was added to a solution of tert-butyl (5aS*,10bS*)-9,10-dichloro-6-(2-ethoxy-2-oxoethyl)-1,4,5,5a,6,10b-hexahydroazepino[4,5-b]indole-3(2H)-carboxylate (0.96 g, 2.17 mmol) in THF (15 mL). The mixture was heated at 60° C. for 2 h. The reaction was then cooled to rt, acidified with 10% aqueous HCl, and extracted with EtOAc (3×30 mL). The combined organic extracts were washed with brine, dried over $Na_2SO_4$, decanted, and concentrated to give crude white foam (0.90 g): $^1$H NMR (300 MHz, $CDCl_3$) δ 7.14 (d, J=8.3 Hz, 1H), 6.21 (d, J=8.4 Hz, 1H), 4.08 (m, 1H), 3.93 (d, J=18.3 Hz, 1H), 3.76 (d, J=18.3 Hz, 1H), 3.47 (m, 5H), 2.04 (m, 4H), 1.44 (s, 9H); HRMS (FAB) calcd for $Cl_9H_{24}CL_2N_2O_4$+H 415.1191, found 415.1198.

Preparation 139

Preparation of tert-butyl (5aS*, 10bS*)-9,10-dichloro-6-{2-[(2,3-dimethylphenyl)amino]-2-oxoethyl }-1,4,5,5a,6,10b-hexahydroazepino[4,5-b]indole-3(2H)-carboxylate EEDQ (0.57 g, 2.3 mmol) and 2,3-dimethylaniline (0.28 g, 2.3 mmol) were added to a solution of [3-(tert-butoxycarbonyl) (5aS*,10bS*)-9,10-dichloro-2,3,4,5,5a, 10b-hexahydroazepino[4,5-b]indol-6(1H)-yl]acetic acid (0.80 g, 1.9 mmol) in THF (20 mL). The reaction was heated to 50° C., cooled to rt after 6 h, and concentrated. The crude product was purified via column chromatography (Biotage, 40M) with $CH_2Cl_2$/MeOH (99:1) followed by crystallization from EtOAc/heptane to give a white solid: mp 145.5–146.0° C.; $^1$H NMR ($CDCl_3$, 300 MHz) δ 8.49 (br s, 1H), 7.31 (m, 1H), 7.21 (d, J=8.3 Hz, 1H), 7.13 (m, 1H), 7.00 (d, J=7.5 Hz, 1H), 6.37 (d, J=8.4 Hz, 1H), 3.89 (m, 2H), 3.78 (m, 2H), 3.66 (m, 1H), 3.58 (m, 1H), 3.33 (m, 2H), 2.34 (m, 1H), 2.27(s, 3H), 2.17 (m, 1H), 2.02 (s, 3H), 1.90 (m, 2H), 1.45 (s, 9H); IR (diffuse reflectance) 1692, 1661, 1596, 1517, 1499, 1465, 1428, 1365, 1329, 1265, 1252, 1241, 1177, 1142, 795 cm$^{-1}$; MS (EI) m/z 517 (M$^+$), 519, 315, 313, 269, 228, 226, 57, 56, 55; Anal. Calcd for $C_{27}H_{33}Cl_2N_3O_3$: C, 62.55; H, 6.41; N, 8.10; found: C, 62.53; H, 6.43; N, 8.08.

EXAMPLE 465

(5aS*,10bS*)-2-(9,10-dichloro-2,3,4,5,5a,10b-hexahydroazepino[4,5-b]indol-6(1 H)-yl)-N-(2,3-dimethylphenyl)acetamide hydrochloride

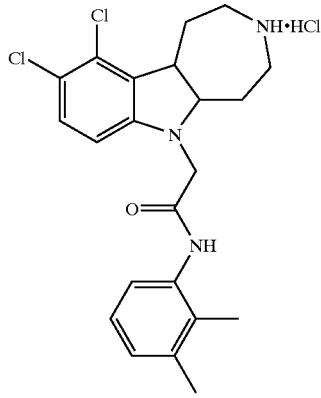

TFA (0.60 mL, 7.7 mmol) was added to a solution of tert-butyl (5aS*,10bS*)-9,10-dichloro-6-{2-[(2,3-dimethylphenyl)amino]-2-oxoethyl }-1,4,5,5a,6,10b-hexahydroazepino[4,5-b]indole-3(2H)-carboxylate (0.20 g, 0.39 mmol) in $CH_2Cl_2$ (7 mL). The reaction was quenched with 10% aqueous NaOH (5 mL) after 2.5 h and extracted with $CH_2Cl_2$ (3×25 mL). The combined organic layers were washed with brine, dried over $Na_2SO_4$, decanted, and concentrated. The crude yellow foam (0.15 g) was purified via column chromatography (Biotage, 40S) with $CH_2Cl_2$/MeOH/$NH_4OH$ (976:21:3) followed by the preparation of the hydrochloride salt to give 67 mg (38%) of an off white solid: mp 238.5–241.0° C.; $^1H$ NMR (DMSO, 300 MHz) δ 9.60 (s, 1H), 8.92 (br s, 2H), 7.30 (d, J=8.4 Hz, 1H), 7.13 (m, 1H), 7.03 (m, 2H), 6.54 (d, J=8.7 Hz, 1H), 4.24 (m, 1H), 4.16 (d, J=17.1 Hz, 1H), 3.87 (d, J=17.1 Hz, 1H), 3.71 (m, 1H), 3.35 (m, 2H 3.08 (m, 3H), 2.34 (m, 1H), 2.24 (m, 3H), 2.12 (m, 5H); IR (diffuse reflectance) 2969, 2955, 2938, 2823, 2796, 2772, 2755, 2727, 1676, 1527, 1464, 1285, 1274, 806, 787 $cm^{-1}$; MS (EI) m/z 417 (M+), 419, 226, 120, 106, 105, 9, 77, 76, 56; HRMS (FAB) calcd for $C_{22}H_{25}CL_2N_3O$+H 418.1453, found 418.1439.

Efficacy Data

The ability of a compound of the invention to act as a 5-HT receptor agonist or antagonist can also be determined using in vitro and in vivo assays that are known in the art. The invention provides compounds of formula (I) that act as either agonists or as antagonists of one or more 5-HT receptor subtypes. The compounds of the invention are 5-HT ligands, which typically displace >50% of a radiolabeled test ligand from one or more 5-HT receptor subtype at a concentration of 1 μM. The procedures used for testing such displacement are well known and would be readily available to one skilled in the art. For example, see L. W. Fitzgerald et al., Mol. Pharmacol, 2000, 57, 1, 75–81; and D. B. Wainscott, et al., J. Pharmacol Exp Ther, 1996, 276, 2, 720–727.

All cited publications, patents, and patent documents are incorporated by reference herein, as though individually incorporated by reference. The invention has been described with reference to various specific and preferred embodiments and techniques. However, it should be understood that many variations and modifications;may be made while remaining within the spirit and scope of the invention.

What is claimed is:
1. A compound of Formula (I):

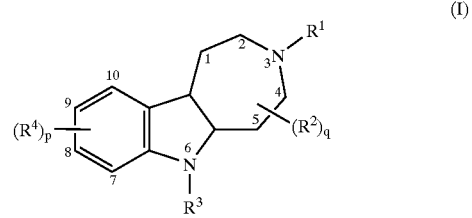

wherein:

$R^1$ is selected from the group consisting of hydrogen, $C_{1-8}$alkyl, and $C_{1-8}$hydrocarbyleneAr;

each $R^2$, independently, is selected from the group consisting of $C_{1-8}$alkyl, and OH;

$R^3$ is hydrogen, $C_{1-8}$alkyl, Ar, Het, $R^7C(=O)$—, $R^7OC(=O)$—, $R^5R^6NC(=O)$—, $R^7C(=S)$—, $R^7SC(=O)$—, $R^5R^6NC(=S)$—, $R^7SO_2$—, $R^5R^6NSO_2$—, $R^7S(=O)$—, $R^5R^6NS(=O)$—, $R^cC_{1-8}$hydrocarbylene-, or $R^cC_{1-8}$ hydrocarbyleneC(=O)—;

each $R^4$, independently, is selected from the group consisting of Ar, $C_{1-8}$alkyl, ArO—, $C_{1-8}$alkoxy, Het, halo, OH, CN, $NO_2$, $CF_3$, $CF_3O$, $NR^aR^b$, $N=CR^aR^b$, $R^7S$, $C_{1-8}$hydrocarbyleneAr, and $C_{1-8}$hydrocarbyleneOR$^a$;

each $R^5$ and $R^6$ is independently hydrogen, $C_{1-8}$alkyl, $C_{2-8}$alkenyl, $C_{2-8}$alkynyl, halo$C_{1-8}$ alkyl, $C_{3-8}$cycloalkenyl, Ar, or —$C_{1-8}$hydrocarbyleneAr; or $R^5$ and $R^6$ together with the nitrogen to which they are attached form a pyrrolidino, piperidino, morpholino, or thiomorpholino ring;

each $R^7$ is independently hydrogen, $C_{1-8}$alkyl, $C_{2-8}$alkenyl, $C_{2-8}$alkynyl, halo$C_{1-8}$alkyl, $C_{3-8}$cycloalkenyl, Ar, or —$C_{1-8}$hydrocarbyleneAr;

$R^a$ and $R^b$, independently, are selected from the group consisting of hydrogen, $C_{1-8}$alkyl, Ar, $C_{1-3}$hydrocarbyleneAr, $SO_2$Ar, $SO_2C_{1-4}$ alkyl, $(C_{3-8}$ cycloalkyl)$C_{1-8}$alkylene, and Het;

$R^c$ is Ar, Het, $R^7CO_2$—, $R^7C(=O)$—, $R^7OC(=O)$—, $R^7O$—, $R^7C_{1-8}$alkyleneO—, $R^7S$—, $R^7C(=S)$—, $R^7S(=O)$—, $R^7S(=O)_2$—, $R^7SC(=O)$—, $R^7C(=O)N(R^7)$—, $R^7C(=S)N(R^7)$—, $R^5R^6N$—, $R^5R^6NC(=O)$—, $R^5R^6NC(=S)$—, $R^5R^6NS(=O)$—, $R^5R^6NSO_2$—, $R^7S(=O)N(R^7)$—, $R^7SO_2N(R^7)$—, or $R^7N(R^7)C(=O) N(R^7)$—, each Ar is independently aryl or heteroaryl;

p is 0, 1, 2, 3, or 4; and q is 0, 1, 2, 3, 4, 5, 6, 7, 8, 9, or 10;

wherein any Ar of $R^1$, $R^3$–$R^7$, $R^a$, $R^b$ and $R^c$ is optionally substituted with one or more substituents independently selected from halo, CN, $NO_2$, $OR^e$, methylenedioxy, ethylenedioxy, $CF_3$, $OCF_3$, $SR^e$, $SO_2R^e$, $NR^fR^g$, $CONR^fR^g$, $COR^e$, $R^e$ and $C_{1-8}$hydrocarbyleneR$^d$;

each $R^d$ is independently hydroxy, $C_{1-8}$alkoxy, cyano, $SR^h$, or $C(=O)R^h$;

each $R^e$ is independently selected from the group consisting of hydrogen, $C_{1-8}$alkyl, Ar, $C_{1-3}$hydrocarbyleneAr, $SO_2$Ar, $SO_2C_{1-4}$ alkyl, $(C_{3-8}$ cycloalkyl)$C_{1-8}$alkylene, and Het; wherein any Ar of $R^e$ is optionally substituted with one or more substituents independently selected from halo, CN, $NO_2$, $OR^d$, methylenedioxy, ethylenedioxy, $CF_3$, $OCF_3$, $SR^f$, $SO_2R^f$, $NR^fR^g$, $CONR^fR^g$, $COR^f$, $R^f$, and $C_{1-8}$hydrocarbylene$R^d$;

each $R^f$ and $R^g$, is independently selected from the group consisting of hydrogen, $C_{1-8}$alkyl, Ar, $C_{1-3}$hydrocarbyleneAr, $SO_2$Ar, $SO_2C_{1-4}$ alkyl, $(C_{3-8}$cycloalkyl)$C_{1-8}$alkylene, and Het; and each $R^h$ is independently hydrogen, $C_{1-8}$alkyl, $C_{2-8}$alkenyl, $C_{2-8}$alkynyl, halo$C_{1-8}$alkyl, $C_{3-8}$cycloalkenyl, phenyl, or —$C_{1-8}$hydrocarbylene(phenyl); and each Het is selected from the group consisting of 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholino;

or a pharmaceutically acceptable salt thereof;

provided that when
(a) $R^1$ is hydrogen or $C_{1-8}$alkyl; and
(b) $R^3$ is hydrogen, $C_{1-8}$alkyl, or $C_{1-8}$hydrocarbylene$NR^5R^6$, wherein $R^5$ and $R^6$, are each independently $C_{1-8}$alkyl;

then either
(i) p is not 0 and at least one $R^4$ is Ar, ArO—, $C_{1-8}$alkoxy, Het, halo, OH, CN, $NO_2$, $CF_3$, $CF_3O$, $NR^aR^b$, $N=CR^aR^b$, $R^7S$, $C_{1-8}$hydrocarbyleneAr, and $C_{1-8}$hydrocarbylene$OR^a$; or
(ii) q is not 0 and at least one $R^2$ is OH.

2. The compound of claim 1 wherein $R^3$ is $C_{1-8}$alkyl, $R^5R^6NC(=O)CH_2$— or aryloxy$(CH_2)_2$—.

3. The compound of claim 1 wherein $R^3$ is: 2-(3-methoxyphenoxy)ethyl, 2-(3-nitrophenoxy)ethyl, 2-(3-isopropylphenoxy)ethyl, 2-(4-pyridyloxy)ethyl, 3-phenoxypropyl, 3-(3-chlorophenoxy)propyl, 3-(4-fluorophenoxy)propyl, 2-phenoxyethyl, N-(2,3-dimethylphenyl)amino-carbonylmethyl, N-(3-methylphenyl)aminocarbonylmethyl, N-(2-fluoro-4-methylphenyl)aminocarbonylmethyl, N-mesitylaminocarbonylmethyl, N-(4-methoxyphenyl)aminocarbonylmethyl, N-(phenyl)aminocarbonylmethyl, N-(4-fluorophenyl)aminocarbonylmethyl, N-(3-nitrophenyl)aminocarbonylmethyl, N-(3-methoxyphenyl)aminocarbonylmethyl, N-(4-cyanophenyl)aminocarbonylmethyl, N-(3,5-dimethoxyphenyl)aminocarbonylmethyl, N-(2,4-dimethoxyphenyl)aminocarbonylmethyl, N-(3-chloro-4-fluorophenyl)aminocarbonylmethyl, 2-anilinoethyl, 1H-benzimidazol-2-ylmethyl, isobutoxycarbonylmethyl, carboxymethyl, N,N-dimethylaminocarbonylmethyl, aminocarbonylmethyl, 2-(phenylsulfinyl)ethyl, 2-(phenylsulfonyl)ethyl, 2-hydroxyethyl, 2-(4-chlorophenoxy)ethyl, 2-(4-fluorophenoxy)ethyl, 2-(phenylthio)ethyl, 2-aminoethyl, 2-(anilinocarbonylamino)-ethyl, 2-(benzoylamino)ethyl, 2-(phenylsulfonylamino)ethyl, N-(4-methoxyphenyl)aminocarbonylethyl, N-phenylaminocarbonylmethyl, N-(2-pyridyl)aminocarbonylmethyl, N-(4-methoxyphenyl)aminocarbonylmethyl, N-(2,3-dimethylphenyl)aminocarbonylmethyl, N-(5,6,7,8-tetrahydro-1-naphthalenyl)aminocarbonylmethyl, 3-ethylanilinocarbonylmethyl, 3-isopropylanilinocarbonylmethyl, N-(3-tert-butylphenyl)aminocarbonylmethyl, N-(1,3-benzothiazol-2-yl)aminocarbonylmethyl, N-(4-methyl-1,3-thiazol-2-yl)aminocarbonylmethyl, N-(5-methyl-1,3-thiazol-2-yl)aminocarbonylmethyl, N-(4-tert-butyl-1,3-thiazol-2-yl)aminocarbonylmethyl, N-(4-phenyl-1,3-thiazol-2-yl)aminocarbonylmethyl, 3-phenylpropyl, 2-phenoxyethyl, 2-(4-chlorophenoxy)ethyl, 2-(4-fluorophenoxy)ethyl, 2-(5,7-dibromo-8-quinolinyloxy)ethyl, 2-(8-quinolinyloxy)ethyl, 2-(5-isoquinolinyloxy)ethyl, 2-(5-quinolinyloxy)ethyl, 2-(5,6,7,8-tetrahydro-1-naphthalenyloxy)ethyl, 2-(1,3-benzodioxol-5-yloxy)ethyl, 2-(1H-indol-4-yloxy)ethyl, 2-(5,6,7,8-tetrahydro-2-naphthalenyloxy)ethyl, 2-(7-quinolinyloxy)ethyl, 2-[(5,5-dimethyl-5,6,7,8-tetrahydronaphthalen-1-yl)oxy]ethyl, N-(3-chloro-2-methylphenyl)aminocarbonylmethyl, N-[2-methyl-3-(trifluoromethyl)phenyl]aminocarbonylmethyl, N-(5,6,7,8-tetrahydronaphthalen-1-yl)aminocarbonylmethyl, N-(4-methyl-1,3-thiazol-2-yl)aminocarbonylmethyl, N-(1,3-dihydro-2-benzofuran-4-yl)aminocarbonylmethyl, N-(4-methoxyphenyl)aminocarbonylmethyl, N-(3-pyridyl)aminocarbonylmethyl, N-(4-methyl-1,3-thiazol-2-yl)aminocarbonylmethyl, or 2-(5,6,7,8-tetrahydronaphthalen-1-yloxy)ethyl.

4. The compound of claim 1 wherein $R^4$ is phenyl, optionally substituted at the 2-position of the phenyl.

5. The compound of claim 1 wherein $R^4$ is 2-ethoxyphenyl, or 2-chlorophenyl.

6. The compound of claim 1 wherein $R^4$ is: 5-pyrimidinyl, 3,4-dimethoxyphenyl, 3,5-difluorophenyl, 4-n-butyloxyphenyl, 4-trifluoromethoxyphenyl, 3,4-dichlorophenyl, 2-naphthyl, 4-pyridinyl, bromo, benzhydrilideneamino, amino, N-(phenylsulfonyl)amino, phenoxy, 3-(phenoxy)propyl, 3-(2-naphthyloxy)propyl, 3-(1-naphthyloxy)propyl, 3-([1,1'-biphenyl]-4-yloxy)propyl, 3-(3-methoxyphonoxy)propyl, 3-(4-methoxyphenoxy)propyl, 3-(4-chlorophenoxy)propyl, 3-(3-chlorophenoxy)propyl, 3-(2-chlorophenoxy)propyl, 3-(2,4-dichlorophenoxy)propyl, 3-(2,5-dichlorophenoxy)propyl, 3-(4-fluorophenoxy)propyl, 3-(4-methylphenoxy)propyl, 3-(4-cyanophenoxy)propyl, 3-(pyridin-2-yloxy)propyl, 3-(2-bromophenoxy)propyl, 3-(2-iodophenoxy)propyl, 3-(2-ethylphenoxy)propyl, 3-(2-isopropylphenoxy)propyl, 3-(2-cyanophenoxy)propyl, 3-(pyridin-3yloxy)propyl, 3-(3-fluorophenoxy)propyl, 3-(3-bromophenoxy)propyl, 3-(3-iodophenoxy)propyl, 3-(3-isopropylphenoxy)propyl, 3-[3-(trifluoromethyl)phenoxy]propyl, 3-[3-(trifluoromethoxy)phenoxy]propyl, 3-(3-ethylphenoxy)propyl, 3-(3-tert-butylphenoxy)propyl, 3-(pyridin-4yloxy)propyl, 3-(4-methoxyphenoxy)propyl, 3-[4-(benzyloxy)phenoxy]propyl, 3-(4-bromophenoxy)propyl, 3-(4-iodophenoxy)propyl, 3-(4-ethylphenoxy)propyl, 3-(4-tert-butylphenoxy)propyl, 3-[4'-(bromo[1,1'-biphenyl]-4-yl)oxy]propyl, 3-(2,3-difluorophenoxy)propyl, 3-(2,4-dibromophenoxy)propyl, 3-(2,4-difluorophenoxy)propyl, 3-(2-methoxy-4-methylphenoxy)propyl, 3-(4-iodo-2-methylphenoxy)propyl, 3-(2,5-difluorophenoxy)propyl, 3-(2-chloro-5-methylphenoxy)propyl, 3-(2-isopropyl-5-methylphenoxy)propyl, 3-(2,6-difluorophenoxy)propyl, 3-(2,6-dichlorophenoxy)propyl, 3-(2,6-dimethylphenoxy)propyl, 3-(2-fluoro-6-methylphenoxy)propyl, 3-hydroxypropyl, 3-(2,3,6-trimethylphenoxy)propyl, 3-(mesityloxy)propyl, 3-(2,6-dibromo-4-fluorophenoxy)propyl, 3-(4-chloro-3-fluorophenoxy)propyl, 3-(4-chloro-3-methylphenoxy)propyl, 3-(3-chloro-4-fluorophenoxy)propyl, 3-(1,3-benzodioxol-5-yloxy)propyl, 3-(3,5-dichlorophenoxy)propyl, 3-(3,5-dimethylphenoxy)propyl, 3-(3,5-dimethoxyphenoxy)propyl, 3-(5,6,7,8-tetrahydro-1-naphthalenyloxy)propyl, 3-[(2,4-dichloro-1-naphthyl)oxy]propyl, 3-[4-methoxy-1-naphthyl)oxy]propyl, 3-[4-chloro-1-naphthyl)oxy]propyl, 3-[1,6-dibromo-2-naphthyl)oxy]

propyl, 3-[1-bromo-2-naphthyl)oxy]propyl, 3-(2,3,4,5,6-pentafluorophenoxy)propyl, 3-(5-isoquinolinyloxy)propyl, 2-methyl-4-methoxyphenyl, 2-ethoxyphenyl, phenyl, phenoxy, 4-pyridinyl, 4-methoxyphenyl, 3,5-difluorophenyl, 3-[1,1'-biphenyl]-2-yloxypropyl, chloro, 2,6-difluorophenyl, bromo, 2-methylphenyl, 2-methoxyphenyl, 2-propoxyphenyl, 2-fluorophenyl, 2,4-dichlorophenyl, 3-(2,4-dibromophenoxy)propyl, 3-(5-chloro-8-quinolinyloxy)propyl, fluoro, 2,6-difluorophenyl, 4-methoxy-2-methylphenyl, or 2,4-dichlorophenyl.

7. The compound of claim 1 wherein $R^4$ is 10-(2-ethoxyphenyl).

8. A pharmaceutical composition comprising a compound as described in claim 1 and a pharmaceutically acceptable carrier.

9. A method of treating anxiety, depression, epilepsy, migraine, or obesity in a mammal comprising administering to the mammal a pharmaceutically effective amount of a compound as described in claim 1.

10. The method of claim 9 wherein the disease or disorder is anxiety or depression.

11. A method of treating anxiety, depression, epilepsy, migraine, or obesity in a mammal comprising administering to the mammal a pharmaceutically effective amount of a compound as described in claim 3.

12. A method of treating anxiety, depression, epilepsy, migraine, or obesity in a mammal comprising administering to the mammal a pharmaceutically effective amount of a compound as described in claim 6.

* * * * *

UNITED STATES PATENT AND TRADEMARK OFFICE
CERTIFICATE OF CORRECTION

PATENT NO. : 6,828,314 B2  
DATED : December 7, 2004  
INVENTOR(S) : Frank et al.

Page 1 of 1

It is certified that error appears in the above-identified patent and that said Letters Patent is hereby corrected as shown below:

Title page,  
Item [56], References Cited, FOREIGN PATENT DOCUMENTS, after "2/1969" insert -- A61K/C07D --.

Column 1,  
Line 7, after "09/957,319" insert -- , --.

Column 262,  
Line 33, after "attached" insert -- , --.  
Line 48, delete "," and insert -- ; --, therefor.

Column 263,  
Line 39, delete "amino-carbonylmethyl" and insert -- aminocarbonylmethyl --, therefor.

Column 264,  
Line 32, delete "3-(3-methoxyphonoxy)propyl" and insert -- 3-(3-methoxyphenoxy)propyl --, therefor.  
Line 40, delete "3-(pyridin-3yloxy)propyl" and insert -- 3-(pyridin-3-yloxy)propyl --, therefor.  
Line 45, delete "(pyridin-4yloxy)propyl" and insert -- (pyridin-4-yloxy)propyl --, therefor.

Signed and Sealed this

Tenth Day of May, 2005

JON W. DUDAS  
*Director of the United States Patent and Trademark Office*